United States Patent
Lewis et al.

(10) Patent No.: US 9,556,135 B2
(45) Date of Patent: Jan. 31, 2017

(54) AMINO-DIHYDROTHIAZINE AND AMINO-DIOXIDO DIHYDROTHIAZINE COMPOUNDS AS BETA-SECRETASE ANTAGONISTS AND METHODS OF USE

(71) Applicant: Amgen Inc., Thousand Oaks, CA (US)

(72) Inventors: Richard T. Lewis, Houston, TX (US); Jennifer R. Allen, Newbury Park, CA (US); Yuan Cheng, Newbury Park, CA (US); Deborah Choquette, Medford, MA (US); Oleg Epstein, Belmont, MA (US); Angel Guzman-Perez, Belmont, MA (US); Paul E. Harrington, Camarillo, CA (US); Zihao Hua, Andover, MA (US); Randall W. Hungate, Longmont, CA (US); Jason Brooks Human, Boston, MA (US); Ted Judd, Granada Hills, CA (US); Qingyian Liu, Camarillo, CA (US); Patricia Lopez, Woodland Hills, CA (US); Ana Elena Minatti, Santa Monica, CA (US); Philip Olivieri, Charlestown, MA (US); Karina Romero, Burlington, MA (US); Shannon Rumfelt, Camarillo, CA (US); Robert M. Rzasa, Ventura, CA (US); Laurie Schenkel, Boston, MA (US); John Stellwagen, Beverly, MA (US); Ryan White, Somerville, MA (US); Qiufen Xue, Newbury Park, CA (US); Xiao Mei Zheng, Natick, MA (US); Wenge Zhong, Thousand Oaks, CA (US)

(73) Assignee: Amgen, Inc., Thousand Oaks, CA (US)

(*) Notice: Subject to any disclaimer, the term of this patent is extended or adjusted under 35 U.S.C. 154(b) by 0 days.

(21) Appl. No.: 14/433,769

(22) PCT Filed: Oct. 10, 2013

(86) PCT No.: PCT/US2013/064400
§ 371 (c)(1),
(2) Date: Apr. 6, 2015

(87) PCT Pub. No.: WO2014/059185
PCT Pub. Date: Apr. 17, 2014

(65) Prior Publication Data
US 2015/0259308 A1 Sep. 17, 2015

Related U.S. Application Data

(60) Provisional application No. 61/713,413, filed on Oct. 12, 2012, provisional application No. 61/783,656, filed on Mar. 14, 2013.

(51) Int. Cl.
*C07D 279/12* (2006.01)
*C07D 417/04* (2006.01)
(Continued)

(52) U.S. Cl.
CPC .......... *C07D 279/12* (2013.01); *C07D 213/79* (2013.01); *C07D 239/74* (2013.01); *C07D 241/44* (2013.01);
(Continued)

(58) Field of Classification Search
CPC ... C07D 279/12; C07D 417/04; C07D 471/04; C07D 239/74; C07D 495/04; C07D 213/79; C07D 241/44; C07D 417/12; C07D 417/14; C07D 513/04; C07D 498/04; C07D 279/14; C07D 513/10
(Continued)

(56) References Cited

U.S. PATENT DOCUMENTS

| | | |
|---|---|---|
| 5,441,870 A | 8/1995 | Seubert et al. |
| 5,712,130 A | 1/1998 | Hajko et al. |

(Continued)

FOREIGN PATENT DOCUMENTS

| | | |
|---|---|---|
| WO | WO00/17369 A2 | 3/2000 |
| WO | WO2007/049532 A1 | 5/2007 |

(Continued)

OTHER PUBLICATIONS

Aisen, P. S., "Alzheimer's disease therapeutic research: the path forward," *Alzheimer's Research & Therapy*, 1: 2, pp. 1-6 (2009).
(Continued)

*Primary Examiner* — Kashay Habte
(74) *Attorney, Agent, or Firm* — Bernard P. Friedrichsen; Markus Bergauer

(57) ABSTRACT

The present invention provides a new class of compounds useful for the modulation of beta-secretase enzyme (BACE) activity. The compounds have a general Formula I: wherein variables $A^4$, $A^5$, $A^6$, $A^8$, $R^1$, $R^2$, $R^3$, $R^7$ and n of Formula I, independently, are defined herein. The invention also provides pharmaceutical compositions comprising the compounds, and corresponding uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formula II and sub-formula embodiments thereof, intermediates and processes and methods useful for the preparation of compounds of Formulas I-II.

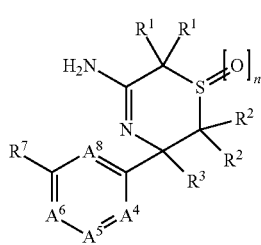

I

38 Claims, No Drawings

(51) Int. Cl.

| | | |
|---|---|---|
| *C07D 471/04* | (2006.01) | |
| *C07D 239/74* | (2006.01) | |
| *C07D 495/04* | (2006.01) | |
| *C07D 213/79* | (2006.01) | |
| *C07D 241/44* | (2006.01) | |
| *C07D 417/12* | (2006.01) | |
| *C07D 417/14* | (2006.01) | |
| *C07D 513/04* | (2006.01) | |
| *C07D 498/04* | (2006.01) | |
| *C07D 513/10* | (2006.01) | |
| *C07D 279/14* | (2006.01) | |
| *C07D 519/00* | (2006.01) | |

(52) U.S. Cl.
CPC ............ *C07D 279/14* (2013.01); *C07D 417/04* (2013.01); *C07D 417/12* (2013.01); *C07D 417/14* (2013.01); *C07D 471/04* (2013.01); *C07D 495/04* (2013.01); *C07D 498/04* (2013.01); *C07D 513/04* (2013.01); *C07D 513/10* (2013.01); *C07D 519/00* (2013.01)

(58) Field of Classification Search
USPC ......... 544/6, 47, 48, 58.2; 514/224.2, 227.5, 514/227.8
See application file for complete search history.

(56) References Cited

U.S. PATENT DOCUMENTS

| | | | |
|---|---|---|---|
| 5,942,400 | A | 8/1999 | Anderson et al. |
| 7,648,983 | B2 | 1/2010 | Audia et al. |
| 8,168,630 | B2 | 5/2012 | Tamura et al. |
| 8,173,642 | B2 | 5/2012 | Kobayashi et al. |
| 8,653,067 | B2 | 2/2014 | Kobayashi et al. |
| 8,999,980 | B2 | 4/2015 | Masui et al. |
| 2012/0022249 | A1 | 1/2012 | Kobayashi et al. |
| 2012/0225858 | A1 | 9/2012 | Hilpert et al. |
| 2012/0238557 | A1 | 9/2012 | Masui et al. |
| 2012/0245154 | A1 | 9/2012 | Anan et al. |
| 2012/0258961 | A1 | 10/2012 | Suzuki et al. |
| 2014/0107109 | A1 | 4/2014 | Lewis et al. |
| 2014/0128382 | A1* | 5/2014 | Wu ................. C07D 417/04 514/228.5 |
| 2014/0200213 | A1* | 7/2014 | Wu ....................... A61K 45/06 514/228.5 |
| 2014/0213581 | A1 | 7/2014 | White et al. |

FOREIGN PATENT DOCUMENTS

| | | | |
|---|---|---|---|
| WO | WO2008/133273 | A1 | 11/2008 |
| WO | WO2008/133274 | A1 | 11/2008 |
| WO | WO2011/009943 | A1 | 1/2011 |
| WO | WO2011/020806 | A1 | 2/2011 |
| WO | WO2011/029803 | A1 | 3/2011 |
| WO | WO2011/058963 | A1 | 5/2011 |
| WO | WO2011/069934 | A1 | 6/2011 |
| WO | WO2011/070029 | A1 | 6/2011 |
| WO | WO2011/070781 | A1 | 6/2011 |
| WO | WO2011/071057 | A1 | 6/2011 |
| WO | WO2011/071135 | A1 | 6/2011 |
| WO | WO2011/077726 | A1 | 6/2011 |
| WO | WO2011/138293 | A1 | 11/2011 |
| WO | WO2011/154431 | A1 | 12/2011 |
| WO | WO2012/006953 | A1 | 1/2012 |
| WO | WO2012/138734 | A1 | 10/2012 |
| WO | WO2012/139425 | A1 | 10/2012 |
| WO | WO2013/028670 | A1 | 2/2013 |
| WO | WO2013/174781 | A1 | 11/2013 |
| WO | WO2014/059185 | A1 | 4/2014 |
| WO | WO2014/099794 | A1 | 6/2014 |
| WO | WO2014/150344 | A1 | 9/2014 |
| WO | WO2015/017407 | A1 | 2/2015 |
| WO | WO2015/038446 | A1 | 3/2015 |

OTHER PUBLICATIONS

Alzforum Networking for a Cure, "Barcelona: Out of Left Field—Hit to the Eye Kills BACE Inhibitor," pp 1-7 (Mar. 31, 2011); access online: www.alzforum.org/news/conference-coverage/barcelona-out-left-field-hit-eye-kills-bace-inhibitor (last accessed Oct. 21, 2015).

Best, J. D. et al., "Quantitative Measurement of Changes in Amyloid-β(40) in the Rat Brain and Cerebrospinal Fluid following Treatment with the κ-Secretase Inhibitor LY-411575 [$N^2$-[(2S)-2-(3,5-Difluorophenyl)-2-hydroxyethanoyl]-$N^1$-[(7S)-5-methyl-6-oxo-6,7-dihydro-5H-dibenzo[b,d]azepin-7-yl]-L-alaninamide]," *Journal of Pharmacology and Experimental Therapeutics*, 313(2): 902-908 (2005).

Citron, M., "β-Secretase inhibition for the treatment of Alzheimer's disease—promise and challenge," *TRENDS in Pharmacological Sciences*, 25(2): 92-97 (2004).

Cole, S. L. and Vasser, R., "The Alzheimer's disease β-secretase enzyme, BACE1," *Molecular Neurodegeneration*, 2: 22, pp. 1-25 (2007).

De Meyer, G. et al., "Diagnosis-Independent Alzheimer Disease Biomarker Signature in Cognitively Normal Elderly People," *Arch Neurol.* 67(8): 949-956 (2010).

Dovey, H. F. et al., "Functional gamma-secretase inhibitors reduce beta-amyloid peptide levels in brain," *Journal of Neurochemistry*, 76: 173-181 (2001).

Follo, C. et al., "Knock-Down of Cathepsin D Affects the Retinal Pigment Epithelium, Impairs Swim-Bladder Ontogenesis and Causes Premature Death in Zebrafish," *PLoS One*. 6(7): e21908, pp. 1-13(2011).

Games, D. et al., "Alzheimer-type neuropathology in transgenic mice overexpressing V717F β-amyloid precursor protein," *Nature*, 373: 523-527 (1995).

Götz, J. et al., "Transgenic animal models of Alzheimer's disease and related disorders: histopathology, behavior and therapy," *Molecular Psychiatry*, 9: 664-683 (2004).

Gulnik, S. V. et al., "Design of sensitive fluorogenic substrates for human cathepsin D," *FEBS Letters*, 413: 379-384 (1997).

Harris, J. A. et al., "Transsynaptic Progression of Amyloid-β-Induced Neuronal Dysfunction within the Entorhinal-Hippocampal Network," *Neuron*, 68: 428-441 (2010).

Henley, D. B., et al., "Development of semagacestat (LY450139), a functional κ-secretase inhibitor, for the treatment of Alzheimer's disease," *Expert Opin. Pharmacother*, 10(10): 1657-1664 (2009).

Hsia, A. Y. et al., "Plaque-independent disruption of neural circuits in Alzheimer's disease mouse models," *PNAS USA*, 96: 3228-3233 (1999).

Hsiao, K. et al., "Correlative Memory Deficits, Aβ Elevation, and Amyloid Plaques in Transgenic Mice," *Science*, 274: 99-102 (1996).

International Search Report for International Patent Application No. PCT/US2013/064400, Applicant: Amgen Inc., mailed Dec. 9, 2013 from the International Searching Authority, pp. 5.

Joachim, C. L. et al., "The Seminal Role of β-Amyloid in the Pathogenesis of Alzheimer Disease," *Alzheimer Disease and Associated. Disorder*, 6: 7-34 (1992).

Koike, M. et al., "Involvement of two different cell death pathways in retinal atrophy of cathepsin D-deficient mice," *Molecular and Cellular Neuroscience*, 22: 146-161 (2003).

Luo, Y. et al., "Mice deficient in BACE1, the Alzheimer's β-secretase, have normal phenotype and abolished β-amyloid generation," *Nature Neuroscience*, 4(3): 231-232 (2001).

May, P. C. et al., "Robust Central Reduction of Amyloid-β in Humans with an Orally Available, Non-Peptidic β-Secretase Inhibitor," *Journal of Neuroscience*, 31(46): 16507-16516 (2011).

Office Action mailed Sep. 15, 2015 for U.S. Appl. No. 14/051,339, Applicant: Amgen Inc., pp. 5.

Palop, J. J. and Mucke, L., "Amyloid-β-induced neuronal dysfunction in Alzheimer's disease: from synapses toward neural networks," *Nature Neuroscience*, 13(7): 812-818 (2010).

Sabbagh, M. N. et al., "β-Amyloid and Treatment Opportunities for Alzheimer's Disease," Alzheimer's Disease Review, 3: 1-19 (1997).

(56) References Cited

OTHER PUBLICATIONS

Selkoe, D. J., "Soluble oligomers of the amyloid β-protein impair synaptic plasticity and behavior," *Behavioural Brain Research*, 192(1): 106-113 (2008).

Selkoe, D. J., "The Molecular Pathology of Alzheimer's Disease," *Neuron*, 6: 487-498 (1991).

Seubert, P. et al., "Isolation and quantification of soluble Alzheimer's β-peptide from biological fluids," Nature, 359: 325-327 (1992).

Shacka, J. J. and Roth, K. A., "Cathepsin D Deficiency and NCL/Batten Disease," *Autophagy*, 3(5): 474-476 (2007).

Shankar, G.M. et al., "Amyloid-β protein dimers isolated directly from Alzheimer's brains impair synaptic plasticity and memory," *Nature Medicine*, 14: 837-842 (2008).

Siemers, E. R et al., "Effects of a κ-secretase inhibitor in a randomized study of patients with Alzheimer disease," *Neurology*, 66: 602-604 (2006).

Siemers, E. R. et al., "Safety, Tolerability, and Effects on Plasma and Cerebrospinal Fluid Amyloid-β After Inhibition of κ-Secretase," *Clinical Neuropharmacology*, 30(6): 317-325 (2007).

Sinha, S. et al., "Purification and cloning of amyloid precursor protein β-secretase from human brain," *Nature*, 402: 537-540 (1999).

Tanzi, R. E. and Bertram, L., "Twenty Years of the Alzheimer's Disease Amyloid Hypothesis: A Genetic Perspective," *Cell*, 120: 545-555 (2005).

Vassar, R. et al., "The β-Secretase Enzyme BACE in Health and Alzheimer's Disease: Regulation, Cell Biology, Function, and Therapeutic Potential," *Journal of Neuroscience*, 29(41): 12787-12794 (2009).

Walsh, D. M. and Selkoe, D. J., "Deciphering the Molecular Basis of Memory Failure in Alzheimer's Disease," *Neuron*, 44: 181-193 (2004).

Written Opinion for International Patent Application No. PCT/US2013/064400, Applicant: Amgen Inc., mailed Dec. 9, 2013 from the International Bureau of WIPO, pp. 6.

Yasuda, Y. et al., "Characterization of New Fluorogenic Substrates for the Rapid and Sensitive Assay of Cathepsin E and Cathepsin D," *J. Biochem.*, 125: 1137-1143 (1999).

\* cited by examiner

AMINO-DIHYDROTHIAZINE AND AMINO-DIOXIDO DIHYDROTHIAZINE COMPOUNDS AS BETA-SECRETASE ANTAGONISTS AND METHODS OF USE

RELATED APPLICATIONS

This application is a national stage application under 35 U.S.C. 371 of International Application No. PCT/US2013/064400, having an international filing date of Oct. 10, 2013, which claims the benefit of U.S. Provisional Patent Application No. 61/713,413, filed on Oct. 12, 2012 and U.S. Provisional Patent Application No. 61/783,656, filed on Mar. 14, 2013, both specifications of which are hereby incorporated herein by reference in their entireties.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million aging people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.,* 6:7-34 (1992).

Several lines of evidence indicate that progressive cerebral deposition of A-beta plays a seminal role in the pathogenisis of AD and can precede cognitive symptoms by years or even decades. Selkoe, *Neuron,* 6:487 (1991). Release of A-beta from neuronal cells grown in culture and the presence of A-beta in cerebrospinal fluid (CSF) of both normal individuals and AD patients has been demonstrated. Seubert et al., *Nature,* 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide comprised of about 39-42 amino acid residues. A-beta 42 (42 amino acids long) is thought to be the major component of these plaque deposits in the brains of Alzheimer's Disease patients. Citron, *Trends in Pharmacological Sciences,* 25-(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature,* 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention, support and commitment from both researchers and investors alike. A small molecule gamma-secretase inhibitor, LY450139 ("Semagacestat"), an A-beta lowering agent, is in phase II clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10 (10); *Clin. Neuropharmacol.* 2007; 30 (pgs 317-325); and *Neurology*, 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. For example, each of the following PCT publications: WO12/006953, WO12/139425, WO12/138734, WO11/069934, WO11/070029, WO11/029803, WO11/020806, WO 11/009943, WO11/138293, WO07/049532, WO08/133273, WO08/133274, WO11/071057, WO11/071135, WO11/070781, WO11/058763, WO11/077726, WO13/028670 and WO11/154431 describe inhibitors of BACE, useful for treating AD and other beta-secretase mediated disorders. For Example, WO2011009943 describes BACE inhibitors for the treatment of neurological disorders of the general formula:

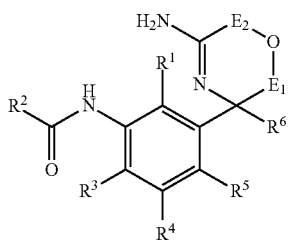

while WO2011138293 describes BACE1 and BACE2 inhibiting compounds of the general formula:

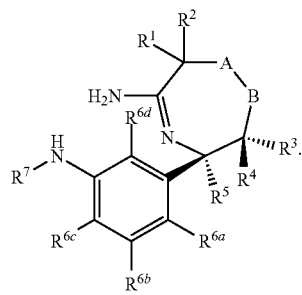

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein Cathepsin D has been implicated in undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by nitrc oxide release from microglial cells. However, in the very same mice, it was also found that no atrophic change was detected in the retina of mice deficient in cathepsin B or L. *Mol. Cell. Neurosci*, 2003, February 22(2):146-161. Further, Animal models of cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy*, 2007, September-October; 3-(5):474-476. Finally, an adverse effect of the inhibition of Cat D is evident from the data presented in *PLoS One*, 2011; 6(7):e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyperpigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human Bace-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities (Alzheimer's Research Forum News, Mar. 31, 2011 reporting on Martin Citron's presentation at the AD/PD Conference 3-2011 in Barcelona, Spain)

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

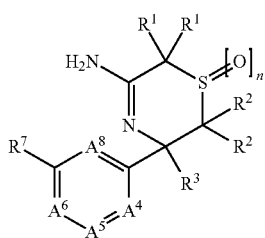

I wherein each of $A^4$, $A^5$, $A^6$, $A^8$, $R^1$, $R^2$, $R^3$, $R^7$ and n of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, there are provided compounds, including stereoisomers, tautomers, hydrates, solvates and pharmaceutically acceptable salts thereof, which are generally defined by Formula I:

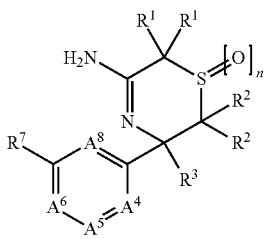

I or a stereoisomer, tautomer, hydrate, solvate or pharmaceutically acceptable salt thereof, wherein $A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H, halo, haloalkyl, haloalkoxy, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$ dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and n is 0, 1 or 2.

In one embodiment of the invention, there are provided compounds, including stereoisomers, tautomers, hydrates, solvates and pharmaceutically acceptable salts thereof, which are generally defined by Formula I:

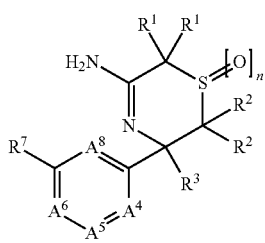

or a stereoisomer, tautomer, hydrate, solvate or pharmaceutically acceptable salt thereof, wherein $A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

each of $R^1$ and $R^2$, independently, is H, F, Cl, $C_{1-6}$-alkyl, $C_{2-4}$alkenyl, $C_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the $C_{1-6}$-alkyl, $C_{2-4}$alkenyl, $C_{2-4}$alkynyl, and $C_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, CH$_2$OC$_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, CH$_2$OC$_{1-2}$alkyl or $C_{1-3}$haloalkyl on the nitrogen atom;

$R^3$ is $C_{1-4}$alkyl, CH$_2$OC$_{1-4}$alkyl, CH$_2$OH, $C_{1-4}$haloalkyl or cyclopropyl, wherein each of the $C_{1-4}$alkyl, CH$_2$OC$_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, CH$_2$OC$_{1-2}$alkyl or $C_{1-3}$haloalkyl on the nitrogen atom;

each of $R^4$, $R^5$, $R^6$ and $R^8$, independently, is H, halo, haloalkyl, haloalkoxyl, $C_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;

$R^7$ is —NH—$R^9$, —NH—C(=O)—$R^9$, —C(=O)NH—$R^9$, —O—$R^9$, —S—$R^9$;

or $R^7$ is

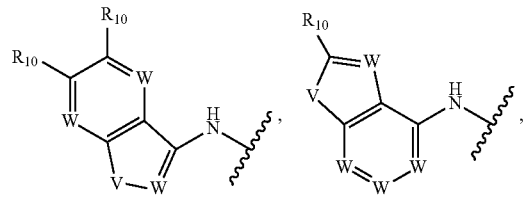

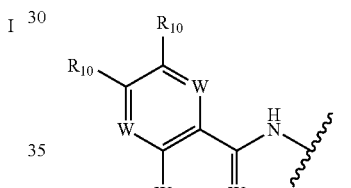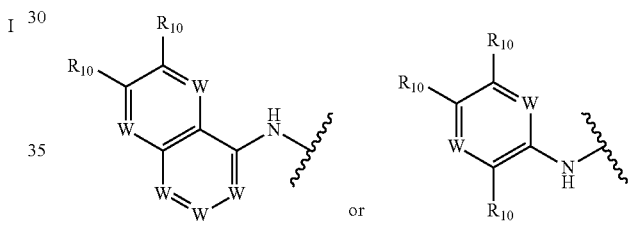

wherein V is $NR^{10}$, O or S; and
each W, independently, is CH, CF, CCl or N;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxyl, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and n is 0, 1 or 2.

In one embodiment of the invention, there are provided compounds, including stereoisomers, tautomers, hydrates, solvates and pharmaceutically acceptable salts thereof, which are generally defined by Formula II:

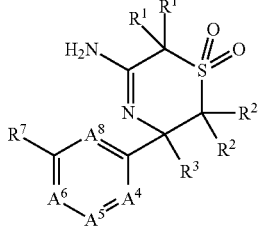

wherein $A^4$ is $CR^4$ or N;

$A^5$ is $CR^5$ or N;

$A^6$ is $CR^6$ or N;

$A^8$ is $CR^8$ or N, provided that no more than two of $A^4$, $A^5$, $A^6$ and $A^8$ is N;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$, —S—$R^9$; or $R^7$ is

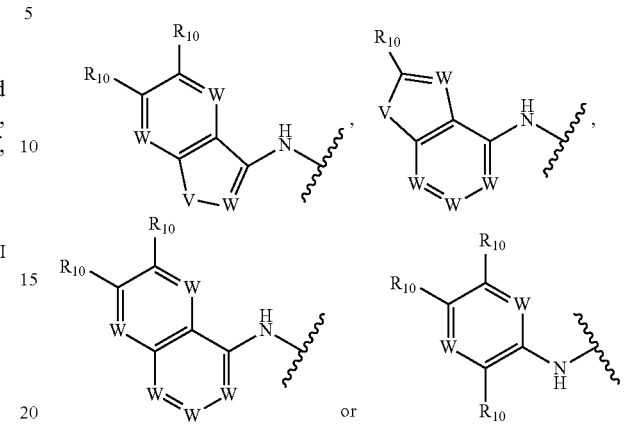

wherein V is $NR^{10}$, O or S; and each W, independently, is CH, CF, CCl or N;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In another embodiment of the invention, there are provided compounds, including stereoisomers, tautomers, hydrates, solvates and pharmaceutically acceptable salts thereof, which are also generally defined by Formula II:

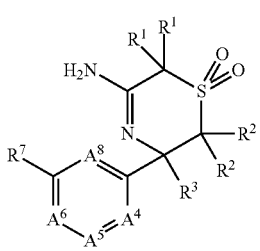

wherein
A⁴ is CR⁴ or N;
A⁵ is CR⁵ or N;
A⁶ is CR⁶ or N;
A⁸ is CR⁸ or N, provided that no more than two of A⁴, A⁵, A⁶ and A⁸ is N;
each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;
$R^7$ is —NH—$R^9$, —NH—C(=O)—$R^9$, —C(=O)NH—$R^9$, —O—$R^9$, —S—$R^9$;
or $R^7$ is wherein V is $NR^{10}$, O or S; and
each W, independently, is CH, CF, CCl or N;
$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In one embodiment of the invention, there are provided compounds, including stereoisomers, tautomers, hydrates, solvates and pharmaceutically acceptable salts thereof, which are generally defined by Formula II-A:

II-A wherein
A⁴ is CR⁴ or N;
A⁵ is CR⁵ or N;
A⁶ is CR⁶ or N;
A⁸ is CR⁸ or N, provided that no more than one of A⁴, A⁵, A⁶ and A⁸ is N;
each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;
alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$ carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H or F;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In one embodiment of the invention, there are provided compounds, including stereoisomers, tautomers, hydrates, solvates and pharmaceutically acceptable salts thereof, which are generally defined by Formula II-B:

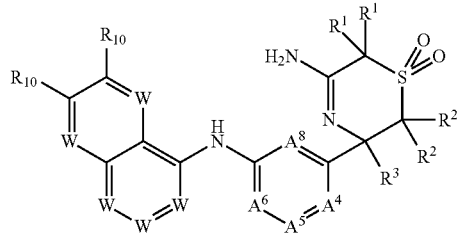

II-B wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, $-CH_2OC_{1-3}$-alkyl, $-OC_{1-3}$-alkyl, wherein each of the $C_{1-4}$-alkyl, $C_{2-4}$alkenyl, $C_2$ 4 alkynyl and $C_{1-4}$-alkyl portion of $-CH_2OC_{1-3}$-alkyl and $-OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$ carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H or F;

each $R^{10}$, independently, is H, halo, haloalkyl, CN, OH, $NO_2$, $NH_2$, acetyl, $-C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and each W, independently, is CH, CF, CCl or N.

In one embodiment of the invention, there are provided compounds, including stereoisomers, tautomers, hydrates, solvates and pharmaceutically acceptable salts thereof, which are generally defined by Formula II-C:

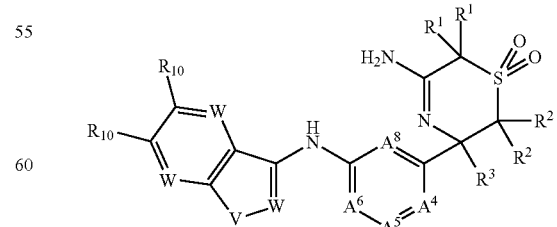

II-C wherein
$A^4$ is $CR^4$ or N;
$A^5$ is $CR^5$ or N;
$A^6$ is $CR^6$ or N;

$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$ carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —$C(O)NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxyl, ethyl, ethoxyl, propyl, propoxyl, isopropyl, isopropoxyl, cyclopropyl, cyclopropylmethoxyl, butyl, butoxyl, isobutoxyl, tert-butoxyl, isobutyl, sec-butyl, tert-butyl, $C_{1-3}$alkylamino-, $C_{1-3}$dialkylamino, $C_{1-3}$thioalkoxyl or oxetan-3yl;

V is $NR^{10}$, O or S; and each W, independently, is CH, CF, CCl or N.

In one embodiment of the invention, there are provided compounds, including stereoisomers, tautomers, hydrates, solvates and pharmaceutically acceptable salts thereof, which are generally defined by Formula III:

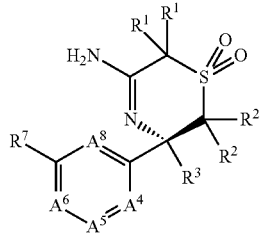

III wherein $A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$, —S—$R^9$;

or $R^7$ is

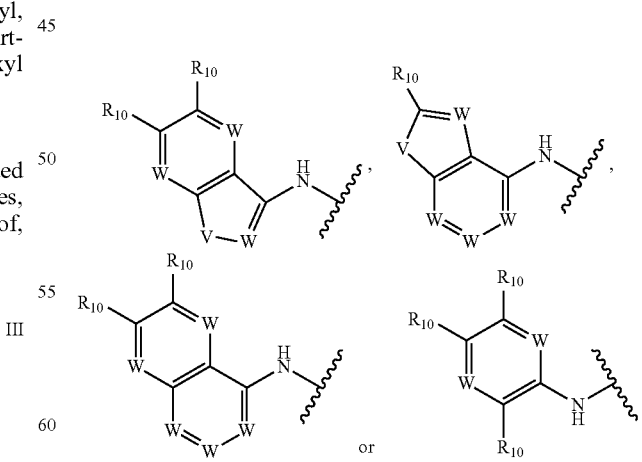

wherein V is $NR^{10}$, O or S; and each W, independently, is CH, CF, CCl or N;

$R^9$ is acetyl, $C_{1-6}$-alkyl, $C_2$ alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_2$ alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

Similarly, the invention provides compounds of subformulas III-A, III-B, III-C and III-D, respectively, as described below.

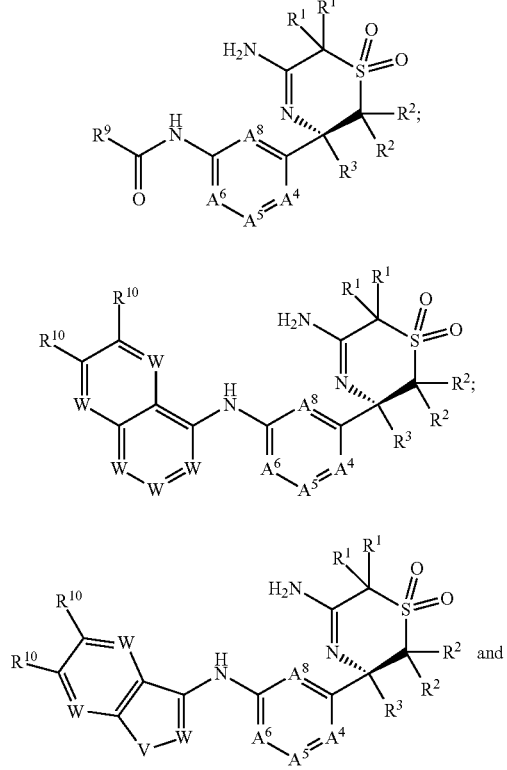

in conjunction with any of the above or below embodiments, including those described in embodiments A, A-1 to A-4, B, B-1 to B-10, C, C-1 to C-10, D, D-1 to D-4, E, E-1 to E-4, F, F-1 to F-4, G, G-1 to G-4, H, H-1 to H-4, I, I-1 to I-9, J, J-1 to J-8, K, K-1 to K-2, L, M, N-1 to N-2, O-1 to O-2 and P-1 to P-2 described herein.

In another embodiment, the invention provides compounds of Formulas III-B, wherein each W, independently, is CH, CF, CCl or N, provided

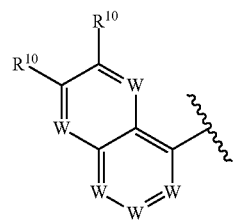

is not

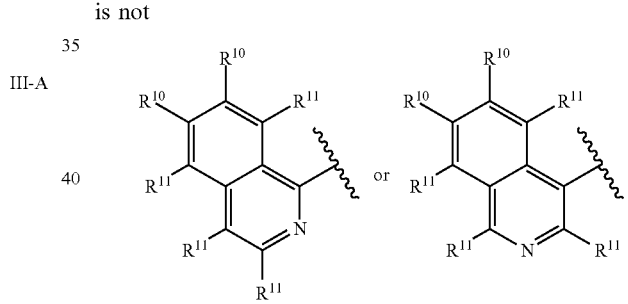

wherein each $R^{11}$, independently, is H, F of Cl.

In one embodiment of the invention, there are provided compounds, including stereoisomers, tautomers, hydrates, solvates and pharmaceutically acceptable salts thereof, which are generally defined by Formula III-B-1:

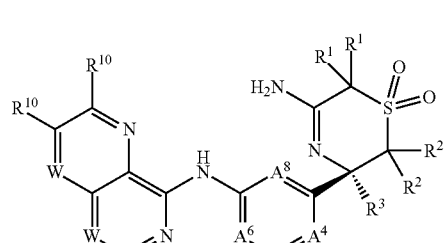

wherein
 $A^4$ is $CR^4$ or N;
 $A^5$ is $CR^5$ or N;
 $A^6$ is $CR^6$ or N;

$A^8$ is $CR^8$ or N, provided that no more than one of $A^4$, $A^5$, $A^6$ and $A^8$ is N; each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and each W, independently, is CH, CF, CCl or N.

In another embodiment, the invention provides compounds of Formulas III-B, III-C and III-D, wherein the sum of the number of heteroatoms, selected from N, O and S, at positions corresponding to each V and W in Formulas III-B, III-C and III-D is at least 4.

In one embodiment of the invention, there are provided compounds, including stereoisomers, tautomers, hydrates, solvates and pharmaceutically acceptable salts thereof, which are generally defined by Formula III-E:

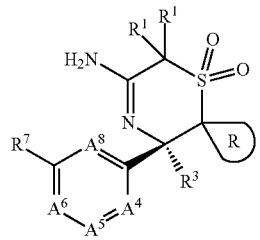

III-E wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
R is a $C_{3-6}$spirocarbocyclic ring optionally including one heteroatom selected from O and N and optionally substituted with 1-4 F atoms on the carbon atoms and/or a substituent of $C_{1-3}$alkyl, $CH_2OC_{1-2}$alkyl or $C_{1-3}$haloalkyl on the nitrogen atom;

each of $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$, —S—$R^9$;

or $R^7$ is

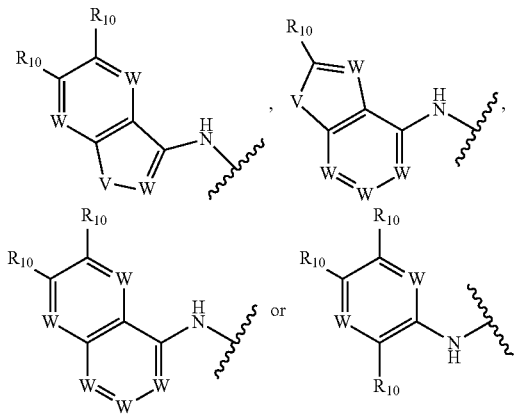

wherein V is NR$^{10}$, O or S; and each W, independently, is CH, CF, CCl or N;

R$^9$ is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_2$ alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxyl or oxetan-3yl.

In another embodiment, the invention includes compounds of Formula III-E, wherein R is a cyclopropyl ring optionally substituted with 1-4 F atoms.

In another embodiment, the invention includes compounds of Formula III-E, wherein R is a cyclobutyl ring optionally substituted with 1-4 F atoms.

In another embodiment, the invention includes compounds of Formula III-E, wherein R is a cyclopentyl ring optionally substituted with 1-4 F atoms.

In one embodiment of the invention, there are provided compounds, including stereoisomers, tautomers, hydrates, solvates and pharmaceutically acceptable salts thereof, which are generally defined by Formula III-E-1:

III-E-1 wherein

A$^4$ is CR$^4$ or N;
A$^5$ is CR$^5$ or N;
A$^6$ is CR$^6$ or N;
A$^8$ is CR$^8$ or N, provided that no more than one of A$^4$, A$^5$, A$^6$ and A$^8$ is N; each R$^a$, independently, is H, F, C$_{1-3}$-alkyl or C$_{1-3}$haloalkyl;

each of R$^1$, independently, is H, F, Cl, CF$_3$, OCF$_3$, methyl, ethyl, CN, OH, OCH$_3$, SCH$_3$, NHCH$_3$, C(O)CH$_3$ or CH$_2$OCHF$_2$;

alternatively, each R$^1$ taken together with the carbon atom to which they are attached form a C$_{3-6}$spirocarbocyclic ring optionally including one heteroatom selected from O and N and optionally substituted with 1-4 F atoms on the carbon atoms and a substituent of C$_{1-3}$alkyl, CH$_2$OC$_{1-2}$alkyl or C$_{1-3}$haloalkyl on the nitrogen atom;

R$^3$ is C$_{1-4}$alkyl, C$_{1-4}$haloalkyl, CH$_2$OH, CH$_2$OCHF$_2$ or cyclopropyl;

each of R$^4$, R$^5$, R$^6$ and R$^8$, independently, is H, F, Cl, CF$_3$, OCF$_3$, methyl, ethyl, CN, OH, OCH$_3$, SCH$_3$, NHCH$_3$ or C(O)CH$_3$;

R$^7$ is —NH—R$^9$, —NH—C(=O)—R$^9$, —C(=O)NH—R$^9$, —O—R$^9$, —S—R$^9$;

or R$^7$ is wherein V is NR$^{10}$, O or S; and each W, independently, is CH, CF, CCl or N;

R$^9$ is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In one embodiment of the invention, there are provided compounds, including stereoisomers, tautomers, hydrates, solvates and pharmaceutically acceptable salts thereof, which are generally defined by Formula III-F:

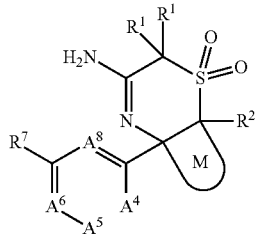

III-F wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

M is a $C_{3-6}$carbocyclic ring optionally including one or two heteroatoms selected from O and N and optionally substituted with 1-4 F atoms on the carbon atoms and/or a substituent of $C_{1-3}$alkyl, $CH_2OC_{1-2}$alkyl or $C_{1-3}$haloalkyl on a nitrogen atom;

each of $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^2$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$, —S—$R^9$;
or $R^7$ is

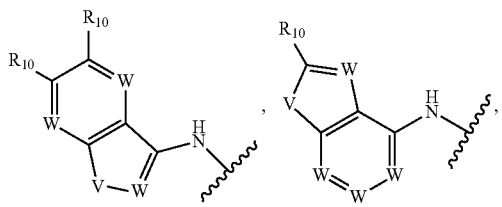

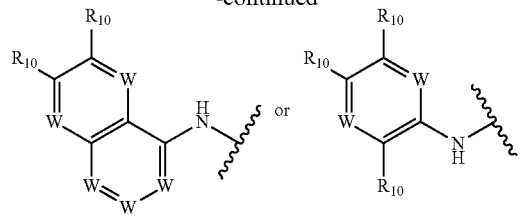

wherein V is $NR^{10}$, O or S; and
each W, independently, is CH, CF, CCl or N;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In another embodiment, the invention includes compounds of Formula III-F, wherein M is a tetrahydrofuran ring optionally substituted with 1-4 F atoms.

In another embodiment, the invention includes compounds of Formula III-F, wherein M is a tetrahydropyran ring optionally substituted with 1-4 F atoms.

In another embodiment, the invention includes compounds of Formula III-F, wherein M is a cyclopentyl ring optionally substituted with 1-4 F atoms.

In one embodiment of the invention, there are provided compounds, including stereoisomers, tautomers, hydrates, solvates and pharmaceutically acceptable salts thereof, which are generally defined by Formula III-F-1:

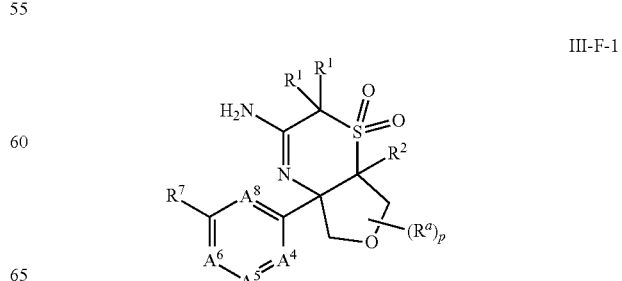

III-F-1 wherein
A⁴ is CR⁴ or N;
A⁵ is CR⁵ or N;
A⁶ is CR⁶ or N;
A⁸ is CR⁸ or N, provided that no more than two of A⁴, A⁵, A⁶ and A⁸ is N; each Rᵃ, independently, is H, F, $C_{1-3}$-alkyl or $C_{1-3}$haloalkyl;

each R¹, independently, is H, F, Cl, $C_{1-6}$-alkyl, $C_{2-4}$alkenyl, $C_{2-4}$alkynyl, CN, —CH₂O$C_{1-6}$-alkyl, —O$C_{1-6}$-alkyl, —S(O)$_o$$C_{1-6}$-alkyl, —NH$C_{1-6}$-alkyl or —C(O)$C_{1-6}$-alkyl, wherein each of the $C_{1-6}$-alkyl, $C_{2-4}$alkenyl, $C_{2-4}$alkynyl, and $C_{1-6}$-alkyl portion of —CH₂O$C_{1-6}$-alkyl, —O$C_{1-6}$-alkyl, —S(O)$_o$$C_{1-6}$-alkyl, —NH$C_{1-6}$-alkyl and —C(O)$C_{1-6}$-alkyl are optionally substituted with 1-4 substituents of F, oxo or OH;

alternatively, each R¹ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, CH₂O$C_{1-2}$alkyl or $C_{1-3}$haloalkyl on the nitrogen atom;

R² is H, F, Cl, $C_{1-6}$-alkyl, $C_{2-4}$alkenyl, $C_{2-4}$alkynyl, CN, —CH₂O$C_{1-6}$-alkyl, —O$C_{1-6}$-alkyl, —S(O)$_o$$C_{1-6}$-alkyl, —NH$C_{1-6}$-alkyl or —C(O)$C_{1-6}$-alkyl, wherein each of the $C_{1-6}$-alkyl, $C_{2-4}$alkenyl, $C_{2-4}$alkynyl, and $C_{1-6}$-alkyl portion of —CH₂O$C_{1-6}$-alkyl, —O$C_{1-6}$-alkyl, —S(O)$_o$$C_{1-6}$-alkyl, —NH$C_{1-6}$-alkyl and —C(O)$C_{1-6}$-alkyl are optionally substituted with 1-4 substituents of F, oxo or OH;

each of R⁴, R⁵, R⁶ and R⁸, independently, is H, halo, haloalkyl, haloalkoxyl, $C_{1-4}$-alkyl, CN, OH, O$C_{1-4}$-alkyl, S(O)$_o$$C_{1-4}$-alkyl, NH$C_{1-4}$-alkyl or C(O)$C_{1-4}$-alkyl;

R⁷ is —NH—R⁹, —NH—C(=O)—R⁹, —C(=O)NH—R⁹, —O—R⁹, —S—R⁹;
or R⁷ is

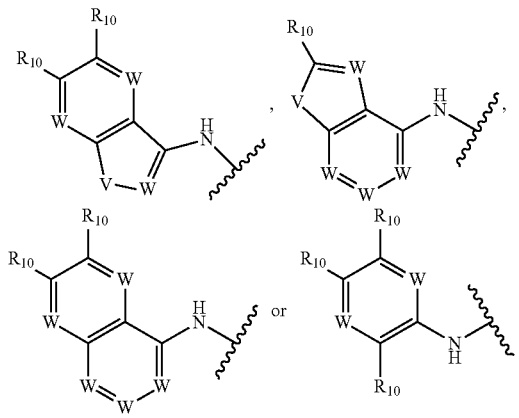

wherein V is NR¹⁰, O or S; and
each W, independently, is CH, CF, CCl or N;

R⁹ is acetyl, $C_{1-6}$-alkyl, $C_2$ alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spirononan-7-yl, cyclopropyl, cyclobutyl, cyclopentyl and cyclohexyl, wherein the $C_{1-6}$-alkyl, $C_2$ alkenyl, $C_{2-4}$alkynyl and ring are optionally substituted, independently, with 1-5 substituents of R¹⁰;

each R¹⁰, independently, is H, halo, haloalkyl, CN, OH, NO₂, NH₂, SF₅, acetyl, —C(O)NHCH₃, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxy or oxetan-3yl; and p is 0, 1, 2 or 3.

In one embodiment of the invention, there are provided compounds, including stereoisomers, tautomers, hydrates, solvates and pharmaceutically acceptable salts thereof, which are generally defined by Formula III-F-2:

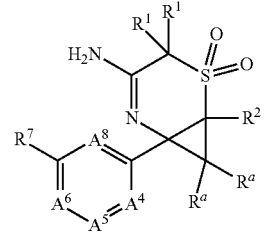

III-F-2 wherein
A⁴ is CR⁴ or N;
A⁵ is CR⁵ or N;
A⁶ is CR⁶ or N;
A⁸ is CR⁸ or N, provided that no more than two of A⁴, A⁵, A⁶ and A⁸ is N;

each Rᵃ, independently, is H, F, $C_{1-3}$-alkyl or $C_{1-3}$haloalkyl;

each R¹, independently, is H, F, Cl, $C_{1-6}$-alkyl, $C_{2-4}$alkenyl, $C_{2-4}$alkynyl, CN, —CH₂O$C_{1-6}$-alkyl, —O$C_{1-6}$-alkyl, —S(O)$_o$$C_{1-6}$-alkyl, —NH$C_{1-6}$-alkyl or —C(O)$C_{1-6}$-alkyl, wherein each of the $C_{1-6}$-alkyl, $C_{2-4}$alkenyl, $C_{2-4}$alkynyl, and $C_{1-6}$-alkyl portion of —CH₂O$C_{1-6}$-alkyl, —O$C_{1-6}$-alkyl, —S(O)$_o$$C_{1-6}$-alkyl, —NH$C_{1-6}$-alkyl and —C(O)$C_{1-6}$-alkyl are optionally substituted with 1-4 substituents of F, oxo or OH;

alternatively, each R¹ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$alkyl, CH₂O$C_{1-2}$alkyl or $C_{1-3}$haloalkyl on the nitrogen atom;

R² is H, F, Cl, $C_{1-6}$-alkyl, $C_{2-4}$alkenyl, $C_{2-4}$alkynyl, CN, —CH₂O$C_{1-6}$-alkyl, —O$C_{1-6}$-alkyl, —S(O)$_o$$C_{1-6}$-alkyl, —NH$C_{1-6}$-alkyl or —C(O)$C_{1-6}$-alkyl, wherein each of the $C_{1-6}$-alkyl, $C_{2-4}$alkenyl, $C_{2-4}$alkynyl, and $C_{1-6}$-alkyl portion of —CH₂O$C_{1-6}$-alkyl, —O$C_{1-6}$-alkyl, —S(O)$_o$$C_{1-6}$-alkyl, —NHC$_{1-6}$-alkyl and —C(O)C$_{1-6}$-alkyl are optionally substituted with 1-4 substituents of F, oxo or OH;

each of R$^4$, R$^5$, R$^6$ and R$^8$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;

R$^7$ is —NH—R$^9$, —NH—C(=O)—R$^9$, —C(=O)NH—R$^9$, —O—R$^9$, —S—R$^9$;

or R$^7$ is

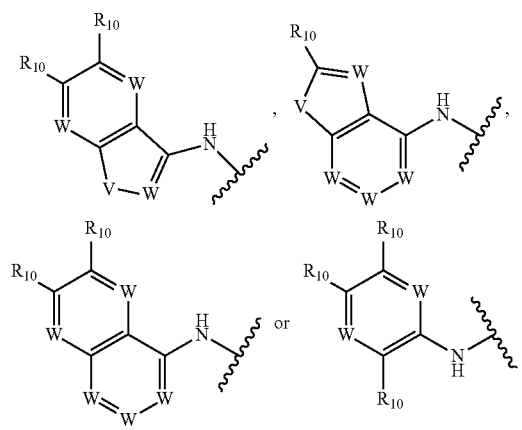

wherein V is NR$^{10}$, O or S; and each W, independently, is CH, CF, CCl or N;

R$^9$ is acetyl, C$_{1-6}$-alkyl, C$_2$ alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_2$ alkenyl, C$_{2-4}$alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-butynyloxy, C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, C$_{1-3}$alkylamino-, C$_{1-3}$dialkylamino, C$_{1-3}$thioalkoxyl or oxetan-3yl.

In yet another embodiment, the invention provides compounds, and tautomers, stereoisomers, hydrates and pharmaceutically acceptable salts thereof, of sub-formula III-G:

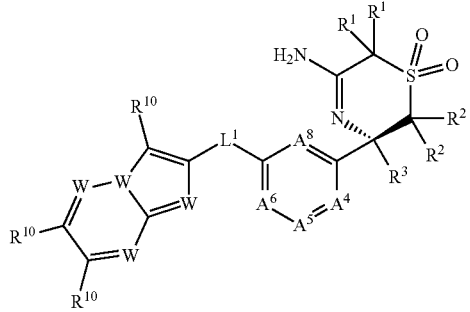

III-G wherein,

A$^4$ is CR$^4$ or N;

A$^5$ is CR$^5$ or N;

A$^6$ is CR$^6$ or N;

A$^8$ is CR$^8$ or N, provided that no more than one of A$^4$, A$^5$, A$^6$ and A$^8$ is N;

L$^1$ is —NH— or —C(=O)NH—;

each of R$^1$ and R$^2$, independently, is H, F, Cl, C$_{1-6}$-alkyl, C$_{2-4}$alkenyl, C$_{2-4}$alkynyl, CN, —CH$_2$OC$_{1-6}$-alkyl, —OC$_{1-6}$-alkyl, —S(O)$_o$C$_{1-6}$-alkyl, —NHC$_{1-6}$-alkyl or —C(O)C$_{1-6}$-alkyl, wherein each of the C$_{1-6}$-alkyl, C$_{2-4}$alkenyl, C$_{2-4}$alkynyl, and C$_{1-6}$-alkyl portion of —CH$_2$OC$_{1-6}$-alkyl, —OC$_{1-6}$-alkyl, —S(O)$_o$C$_{1-6}$-alkyl, —NHC$_{1-6}$-alkyl and —C(O)C$_{1-6}$-alkyl are optionally substituted with 1-4 substituents of F, oxo or OH;

alternatively, each R$^1$ taken together with the carbon atom to which they are attached form a C$_{3-6}$spirocarbocyclic ring optionally including one heteroatom selected from O and N and optionally substituted with 1-4 F atoms on the carbon atoms and a substituent of C$_{1-3}$alkyl, CH$_2$OC$_{1-2}$alkyl or C$_{1-3}$haloalkyl on the nitrogen atom;

alternatively, each R$^2$ taken together with the carbon atom to which they are attached form a C$_{3-6}$ spirocarbocyclic ring optionally including one heteroatom selected from O and N and optionally substituted with 1-4 F atoms on the carbon atoms and a substituent of C$_{1-3}$alkyl, CH$_2$OC$_{1-2}$alkyl or C$_{1-3}$haloalkyl on the nitrogen atom;

R$^3$ is C$_{1-4}$alkyl, CH$_2$OH, CH$_2$OC$_{1-4}$alkyl, C$_{1-4}$haloalkyl or cyclopropyl, wherein each of the C$_{1-4}$alkyl, CH$_2$OC$_{1-4}$alkyl, C$_{1-4}$haloalkyl and cyclopropyl is optionally substituted with 1-4 F atoms;

alternatively, one R$^2$ and R$^3$ taken together with the carbon atoms to which they are attached form a C$_{3-6}$carbocyclic ring optionally including 1-2 heteroatoms selected from O and N and optionally substituted with 1-4 F atoms on the carbon atoms and a substituent of C$_{1-3}$alkyl, CH$_2$OC$_{1-2}$alkyl or C$_{1-3}$haloalkyl on the nitrogen atom;

each of R$^4$, R$^5$, R$^6$ and R$^8$, independently, is H, halo, haloalkyl, haloalkoxyl, C$_{1-4}$-alkyl, CN, OH, OC$_{1-4}$-alkyl, S(O)$_o$C$_{1-4}$-alkyl, NHC$_{1-4}$-alkyl or C(O)C$_{1-4}$-alkyl;

each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-butynyloxy, C$_{1-6}$alkyl, C$_{2-6}$alkenyl, C$_{2-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the C$_{1-6}$alkyl, C$_{2-6}$alkenyl, C$_{2-6}$alkynyl, C$_{3-6}$cycloalkyl, C$_{1-6}$alkylamino-, C$_{1-6}$dialkylamino-, C$_{1-6}$alkoxyl, C$_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl; and each W, independently, is CH, CF, CCl or N.

The present invention contemplates that the various different embodiments of Formulas I, II and III, and sub-Formulas II-A, II-B and II-C thereof, described herein, may comprise the following embodiments with respect to individual variables of $A^4$, $A^5$, $A^6$, $A^8$, $R^1$, $R^2$, $R^3$, $R^7$, V and W, where applicable, as described below. Hence, these embodiments with respect to individual variables $A^4$, $A^5$, $A^6$, $A^8$, $R^1$, $R^2$, $R^3$, $R^7$, V and W where applicable, may be applied "in conjunction with any of the other {above and below} embodiments" to create various embodiments of general Formulas I, II and III, and each sub-formula thereof, which are not literally or identically described herein. More specifically, the term "in conjunction with any of the above or below embodiments" includes embodiments A, A-1 to A-4, B, B-1 to B10, C, C-1 to C-10, D, D-1 to D-4, E, E-1 to E-4, F, F-1 to F-4, G, G-1 to G-4, H, H-1 to H-4, I, I-1 to I-9, J, J-1 to J-9, K, K-1 to K-2, L, M, N-1 to N-2, O-1 to O-2 and P-1 to P-2 described herein, as it applies to general Formulas I and II, and sub-formulas II-A, II-B and II-C, also described herein.

In another embodiment A, the invention includes compounds of Formula I, wherein n is 0, 1 or 2, in conjunction with any of the above or below embodiments.

In another embodiment A-1, the invention includes compounds of Formula I, wherein n is 1 or 2, in conjunction with any of the above or below embodiments.

In another embodiment A-2, the invention includes compounds of Formula I, wherein n is 2, in conjunction with any of the above or below embodiments.

In another embodiment A-3, the invention includes compounds of Formula I, wherein n is 1, in conjunction with any of the above or below embodiments.

In another embodiment A-4, the invention includes compounds of Formula I, wherein n is 0, in conjunction with any of the above or below embodiments.

In another embodiment B, the invention includes compounds wherein each $R^1$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment B-1, the invention includes compounds wherein each $R^1$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment B-2, the invention includes compounds wherein each $R^1$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment B-3, the invention includes compounds wherein each $R^1$, independently, is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment B-4, the invention includes compounds wherein each $R^1$, independently, is H, F, Cl, $CF_3$, $CH_3$, $CF_2H$ or $CH_2F$, in conjunction with any of the above or below embodiments.

In another embodiment B-5, the invention includes compounds wherein each $R^1$, independently, is H, F, $CF_3$, $CH_3$, $CF_2H$ or $CH_2F$, in conjunction with any of the above or below embodiments.

In another embodiment B-6, the invention includes compounds wherein each $R^1$, independently, is H, F, $CF_3$ or $CH_3$, in conjunction with any of the above or below embodiments.

In another embodiment B-7, the invention includes compounds wherein each $R^1$, independently, is H or F, in conjunction with any of the above or below embodiments.

In another embodiment B-8, the invention includes compounds wherein each $R^1$, taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom, in conjunction with any of the above or below embodiments.

In another embodiment B-9, the invention includes compounds wherein each $R^1$, taken together with the carbon atom to which they are attached form a cyclopropyl, cyclobutyl or cyclopentyl ring optionally substituted with 1-4 F atoms on the carbon atoms, in conjunction with any of the above or below embodiments.

In another embodiment B-10, the invention includes compounds wherein each $R^1$, taken together with the carbon atom to which they are attached form a cyclopropyl or cyclopentyl ring optionally substituted with 1-4 F atoms on the carbon atoms, in conjunction with any of the above or below embodiments.

In another embodiment C, the invention includes compounds wherein each $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment C-1, the invention includes compounds wherein each $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment C-2, the invention includes compounds wherein each $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment C-3, the invention includes compounds wherein each $R^2$, independently, is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment C-4, the invention includes compounds wherein each $R^2$, independently, is H, F, Cl, $CF_3$, $CH_3$, $CF_2H$ or $CH_2F$, in conjunction with any of the above or below embodiments.

In another embodiment C-5, the invention includes compounds wherein each $R^2$, independently, is H, F, $CF_3$, $CH_3$, $CF_2H$ or $CH_2F$, in conjunction with any of the above or below embodiments.

In another embodiment C-6, the invention includes compounds wherein each $R^2$, independently, is H, F, $CF_3$ or $CH_3$, in conjunction with any of the above or below embodiments.

In another embodiment C-7, the invention includes compounds wherein each $R^2$, independently, is H or F, in conjunction with any of the above or below embodiments.

In another embodiment C-8, the invention includes compounds wherein each $R^2$, taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom, in conjunction with any of the above or below embodiments.

In another embodiment C-9, the invention includes compounds wherein each $R^2$, taken together with the carbon atom to which they are attached form a cyclopropyl, cyclobutyl or cyclopentyl ring optionally substituted with 1-4 F atoms on the carbon atoms, in conjunction with any of the above or below embodiments.

In another embodiment C-10, the invention includes compounds wherein each $R^2$, taken together with the carbon atom to which they are attached form a cyclopropyl or cyclopentyl ring optionally substituted with 1-4 F atoms on the carbon atoms, in conjunction with any of the above or below embodiments.

In another embodiment D, the invention includes compounds wherein $R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms, in conjunction with any of the above or below embodiments.

In another embodiment D-1, the invention includes compounds wherein $R^3$ is $C_{1-4}$alkyl, $C_{1-4}$haloalkyl, $CH_2OH$, $CH_2OCHF_2$ or cyclopropyl, wherein each of the $C_{1-4}$alkyl, $C_{1-4}$haloalkyl and cyclopropyl is optionally substituted with 1-4 F atoms, in conjunction with any of the above or below embodiments.

In another embodiment D-2, the invention includes compounds wherein $R^3$ is $C_{1-4}$alkyl, $CH_2OH$, $CH_2OCH_2F$, $CH_2OCF_2H$, or cyclopropyl, wherein each of the $C_{1-4}$alkyl and cyclopropyl is optionally substituted with 1-2 F atoms, in conjunction with any of the above or below embodiments.

In another embodiment D-3, the invention includes compounds wherein $R^3$ is $CH_3$, $CF_3$, $C_2H_5$, $CF_2H$ or $CH_2F$, in conjunction with any of the above or below embodiments.

In another embodiment D-4, the invention includes compounds wherein $R^3$ is $CF_3$, $CH_3$, $CF_2H$ or $CH_2F$, in conjunction with any of the above or below embodiments.

In another embodiment E, the invention includes compounds wherein $A^4$ is $CR^4$ wherein $R^4$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment E-1, the invention includes compounds wherein $A^4$ is $CR^4$ wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment E-2, the invention includes compounds wherein $A^4$ is $CR^4$ wherein $R^4$ is H, F, $CF_3$, $CF_2H$, $CH_2F$ or $CH_3$, in conjunction with any of the above or below embodiments.

In another embodiment E-3, the invention includes compounds wherein $A^4$ is $CR^4$ wherein $R^4$ is H or F, in conjunction with any of the above or below embodiments.

In another embodiment E-4, the invention includes compounds wherein $A^4$ is N, in conjunction with any of the above or below embodiments.

In another embodiment F, the invention includes compounds wherein $A^5$ is $CR^5$ wherein $R^5$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment F-1, the invention includes compounds wherein $A^5$ is $CR^5$ wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment F-2, the invention includes compounds wherein $A^5$ is $CR^5$ wherein $R^5$ is H, F, $CF_3$, $CF_2H$, $CH_2F$ or $CH_3$, in conjunction with any of the above or below embodiments.

In another embodiment F-3, the invention includes compounds wherein $A^5$ is $CR^5$ wherein $R^5$ is H or F, in conjunction with any of the above or below embodiments.

In another embodiment F-4, the invention includes compounds wherein $A^5$ is N, in conjunction with any of the above or below embodiments.

In another embodiment G, the invention includes compounds wherein $A^6$ is $CR^6$ wherein $R^6$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment G-1, the invention includes compounds wherein $A^6$ is $CR^6$ wherein $R^6$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment G-2, the invention includes compounds wherein $A^6$ is $CR^6$ wherein $R^6$ is H, F, $CF_3$, $CF_2H$, $CH_2F$ or $CH_3$, in conjunction with any of the above or below embodiments.

In another embodiment G-3, the invention includes compounds wherein $A^6$ is $CR^6$ wherein $R^6$ is H or F, in conjunction with any of the above or below embodiments.

In another embodiment G-4, the invention includes compounds wherein $A^6$ is N, in conjunction with any of the above or below embodiments.

In another embodiment H, the invention includes compounds wherein $A^8$ is $CR^8$ wherein $R^8$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment H-1, the invention includes compounds wherein $A^8$ is $CR^8$ wherein $R^8$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment H-2, the invention includes compounds wherein $A^8$ is $CR^8$ wherein $R^8$ is H, F, $CF_3$, $CF_2H$, $CH_2F$ or $CH_3$, in conjunction with any of the above or below embodiments.

In another embodiment H-3, the invention includes compounds wherein $A^8$ is $CR^8$ wherein $R^8$ is H or F, in conjunction with any of the above or below embodiments.

In another embodiment H-4, the invention includes compounds wherein $A^8$ is N, in conjunction with any of the above or below embodiments.

In another embodiment I, the invention includes compounds wherein no more than two of $A^4$, $A^5$, $A^6$ and $A^8$ is N, in conjunction with any of the above or below embodiments.

In another embodiment I-1, the invention includes compounds wherein no more than one of $A^4$, $A^5$, $A^6$ and $A^8$ is N, in conjunction with any of the above or below embodiments.

In another embodiment I-2, the invention includes compounds wherein $A^4$ is $CR^4$ or N, $A^5$ is $CR^5$ or N, $A^6$ is $CR^6$ or N and $A^8$ is $CR^8$ or N, provided that no more than one of $A^4$, $A^5$, $A^6$ and $A^8$ is N, in conjunction with any of the above or below embodiments.

In another embodiment, the invention includes compounds wherein $A^4$ is $CR^4$ or N, $A^5$ is $CR^5$, $A^6$ is $CR^6$ and $A^8$ is $CR^8$, in conjunction with any of the above or below embodiments.

In another embodiment I-3, the invention includes compounds wherein $A^4$ is N, $A^5$ is $CR^5$, $A^6$ is $CR^6$ and $A^8$ is $CR^8$, in conjunction with any of the above or below embodiments.

In another embodiment I-4, the invention includes compounds wherein $A^4$ is $CR^4$, $A^5$ is N, $A^6$ is $CR^6$, and $A^8$ is $CR^8$, in conjunction with any of the above or below embodiments.

In another embodiment I-5, the invention includes compounds wherein $A^4$ is $CR^4$, $A^5$ is $CR^5$, $A^6$ is N, and $A^8$ is $CR^8$, in conjunction with any of the above or below embodiments.

In another embodiment I-6, the invention includes compounds wherein $A^4$ is $CR^5$, $A^5$ is $CR^5$, $A^6$ is $CR^6$, and $A^8$ is N, in conjunction with any of the above or below embodiments.

In another embodiment I-7, the invention includes compounds wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N; and
each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment I-8, the invention includes compounds wherein
$A^4$ is $CR^4$;
$A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$, in conjunction with any of the above or below embodiments.

In another embodiment I-9, the invention includes compounds wherein $A^4$ is CH, CF or N, $A^5$ is CH, CF or N, $A^6$ is CH, CF or N, $A^8$ is CH, CF or N, one of $A^4$, $A^5$, $A^6$ and $A^8$ is N, in conjunction with any of the above or below embodiments.

In another embodiment J, the invention includes compounds wherein $R^7$ is $NH—R^9$, $—NH—C(=O)—R^9$, $—C(=O)NH—R^9$, $—O—R^9$, $—S—R^9$; or $R^7$ is

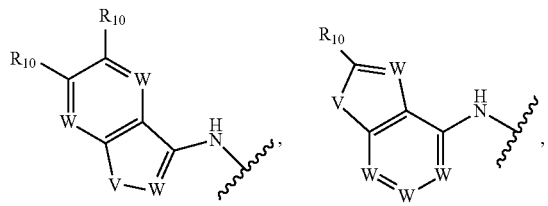

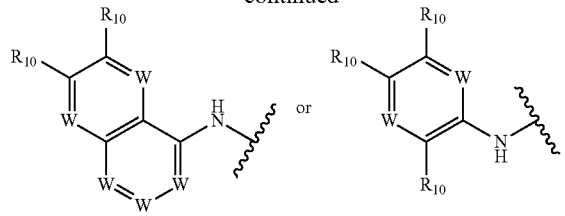

wherein V is $NR^{10}$, O or S; and
each W, independently, is CH, CF, CCl or N, in conjunction with any of the above or below embodiments.

In another embodiment J-1, the invention includes compounds wherein $R^7$ is $—NH—R^9$, $—NH—C(=O)—R^9$ or

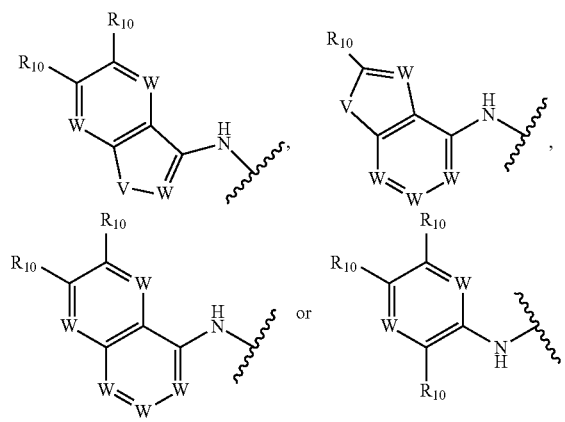

wherein V is $NR^{10}$, O or S; and
each W, independently, is CH, CF, CCl or N, in conjunction with any of the above or below embodiments.

In another embodiment J-2, the invention includes compounds wherein $R^7$ is $—NH—C(=O)—R^9$ or

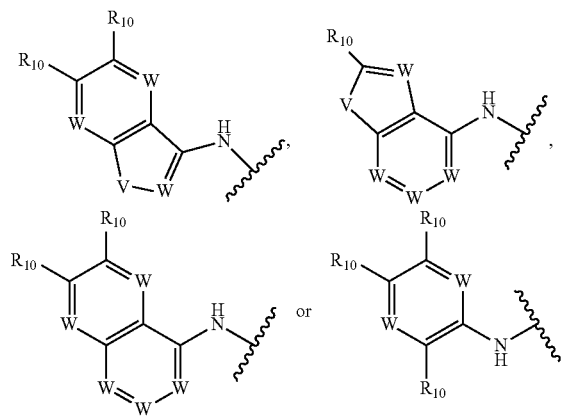

wherein V is $NR^{10}$, O or S; and
each W, independently, is CH, CF, CCl or N, in conjunction with any of the above or below embodiments.

In another embodiment J-3, the invention includes compounds wherein $R^7$ is $—NH—C(=O)—R^9$, in conjunction with any of the above or below embodiments.

In another embodiment J-4, the invention includes compounds wherein $R^7$ is $—NH—R^9$, in conjunction with any of the above or below embodiments.

In another embodiment J-5, the invention includes compounds wherein $R^7$ is

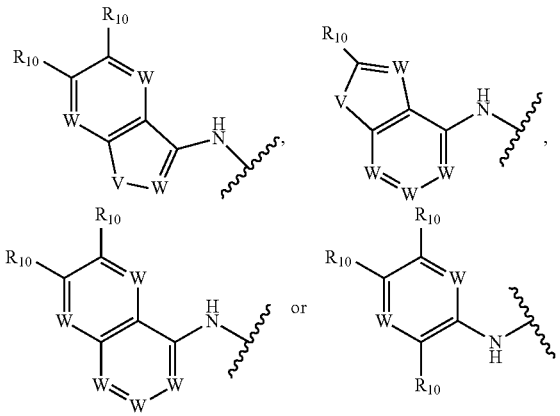

wherein V is $NR^{10}$, O or S; and
each W, independently, is CH, CF, CCl or N, in conjunction with any of the above or below embodiments.

In another embodiment J-6, the invention includes compounds wherein $R^7$ is

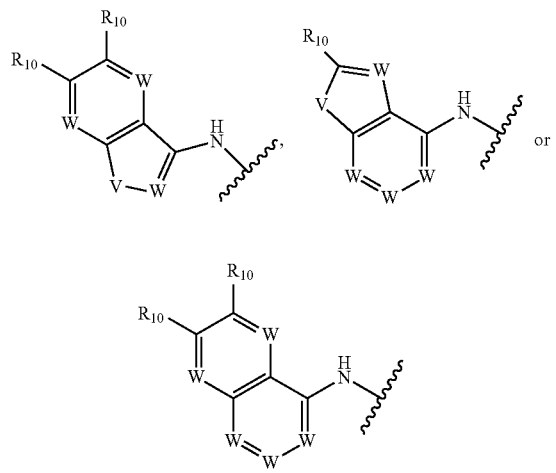

wherein V is $NR^{10}$, O or S; and
each W, independently, is CH, CF, CCl or N, in conjunction with any of the above or below embodiments.

In another embodiment J-7, the invention includes compounds wherein $R^7$ is —NH—$R^9$, —O—$R^9$ or —S—$R^9$, in conjunction with any of the above or below embodiments.

In another embodiment J-8, the invention includes compounds wherein $R^7$ is —O—$R^9$ or —S—$R^9$, in conjunction with any of the above or below embodiments.

In another embodiment J-9, the invention includes compounds wherein $R^7$ is —NH—$R^9$, —NH—C(=O)—$R^9$, —C(=O)NH—$R^9$, —O—$R^9$ or —S—$R^9$, wherein $R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K, the invention includes compounds wherein $R^9$ is acetyl, $C_{1-6}$-alkyl, $C_{2-4}$alkenyl, $C_{2-4}$alkynyl or a fully or partially unsaturated 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K-1, the invention includes compounds wherein each $R^9$, independently, is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$, in conjunction with any of the above or below embodiments.

In another embodiment K-2, the invention includes compounds wherein each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl, in conjunction with any of the above or below embodiments.

In another embodiment L, the present invention provides compounds, and solvates, tautomers, hydrates, stereoisomers and pharmaceutically acceptable salts thereof, as defined by Formulas I, II, II-A, II-B or II-C, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^1$ and $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_3$, $OCF_3$, methyl, ethyl,
CN, OH, $OCH_3$, $SCH_3$, $NHCH_3$ or $C(O)CH_3$, in conjunction with any of the above or below embodiments.

In another embodiment M, the present invention provides compounds, and solvates, tautomers, hydrates, stereoisomers and pharmaceutically acceptable salts thereof, as defined by Formulas I and II, wherein $R^7$ is —NH—$R^9$, —NH—C(=O)—$R^9$ or

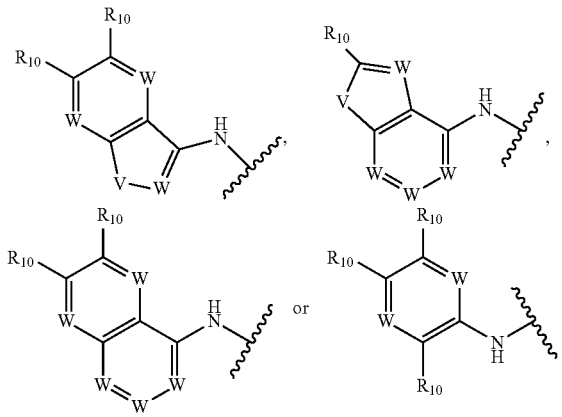

wherein V is $NR^{10}$, O or S; and each W, independently, is CH, CF, CCl or N, in conjunction with any of the above or below embodiments.

In another embodiment N-1, the invention includes compounds of Formula II-A wherein $A^4$ is $CR^4$ or N;

$A^5$ is $CR^5$ or N;

$A^6$ is $CR^6$ or N;

$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$alkenyl, $C_{2-4}$alkynyl, CN, —$CH_2OC_{1-3}$-alkyl, —$OC_{1-3}$-alkyl, wherein each of the $C_{1-4}$-alkyl, $C_{2-4}$alkenyl, $C_{2-4}$alkynyl and $C_{1-4}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

$R^3$ is $C_{1-4}$alkyl, $CH_2OH$, $CH_2OC_{1-4}$alkyl, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

alternatively, one $R^2$ and $R^3$ taken together with the carbon atoms to which they are attached form a $C_{3-6}$ carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;

each of $R^4$, $R^5$, $R^6$ and $R^8$, independently, is H or F;

$R^9$ is acetyl, $C_{1-6}$-alkyl, $C_{2-4}$alkenyl, $C_{2-4}$alkynyl or a ring selected from phenyl, pyridyl, pyrimidyl, pyrazinyl, pyridazinyl, pyrazolyl, isoxazolyl, thiazolyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the $C_{1-6}$-alkyl, $C_{2-4}$alkenyl, $C_{2-4}$alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In another embodiment N-2, the invention includes compounds of Formula II-A wherein $A^4$ is $CR^4$;

$A^5$ is $CR^5$;

$A^6$ is $CR^6$;

$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or C(O)$CH_3$;

each of $R^1$ and $R^2$, independently, is H, $CH_3$, $C_2H_5$, $CF_2H$, $CH_2F$, $CH_2OCH_2F$, $CH_2OCF_2H$ or $CH_2OCF_3$;

alternatively, each $R^1$ taken together with the carbon atom to which they are attached form a $C_{3-6}$ spirocarbocyclic ring optionally including one heteroatom selected from O and N and optionally substituted with 1-3 F atoms;

alternatively, each $R^2$ taken together with the carbon atom to which they are attached form a $C_{3-6}$ spirocarbocyclic ring optionally including one heteroatom selected from O and N and optionally substituted with 1-3 F atoms;

$R^3$ is $CH_3$, $C_2H_5$, $CF_2H$ or $CH_2F$;

$R^9$ is a ring selected from phenyl, pyridyl, pyrimidyl, pyrazinyl, pyridazinyl, pyrazolyl, isoxazolyl, thiazolyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the ring is optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)$NHCH_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In another embodiment O-1, the invention includes compounds of Formula II-B wherein $A^4$ is $CR^4$;
 $A^5$ is $CR^5$;
 $A^6$ is $CR^6$;
 $A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;
 each of $R^1$ and $R^2$, independently, is H, F, $CH_3$, $C_2H_5$, $CF_2H$, $CH_2F$, $CH_2OCH_2F$, $CH_2OCF_2H$ or $CH_2OCF_3$;
 alternatively, each $R^1$ taken together with the carbon atom to which they are attached form a $C_{3-6}$ spirocarbocyclic ring optionally including one heteroatom selected from O and N and optionally substituted with 1-3 F atoms;
 alternatively, each $R^2$ taken together with the carbon atom to which they are attached form a $C_{3-6}$ spirocarbocyclic ring optionally including one heteroatom selected from O and N and optionally substituted with 1-3 F atoms; and
 $R^3$ is $CH_3$, $C_2H_5$, $CF_2H$ or $CH_2F$, in conjunction with any of the above or below embodiments with respect to Formula II-B.

In another embodiment O-2, the invention includes compounds of Formula II-B wherein $A^4$ is $CR^4$ or N;
 $A^5$ is $CR^5$ or N;
 $A^6$ is $CR^6$ or N;
 $A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
 each of $R^1$ and $R^2$, independently, is H, F, Cl, $CF_3$, $CH_3$, $CF_2H$ or $CH_2F$; and
 $R^3$ is $CF_3$, $CH_3$, $CF_2H$ or $CH_2F$, in conjunction with any of the above or below embodiments with respect to Formula II-B.

In another embodiment P-1, the invention includes compounds of Formula II-C wherein $A^4$ is $CR^4$;
 $A^5$ is $CR^5$;
 $A^6$ is $CR^6$;
 $A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;
 each of $R^1$ and $R^2$, independently, is H, F, $CH_3$, $C_2H_5$, $CF_2H$, $CH_2F$, $CH_2OCH_2F$, $CH_2OCF_2H$ or $CH_2OCF_3$;
 alternatively, each $R^1$ taken together with the carbon atom to which they are attached form a $C_{3-6}$ spirocarbocyclic ring optionally including one heteroatom selected from O and N and optionally substituted with 1-3 F atoms;
 alternatively, each $R^2$ taken together with the carbon atom to which they are attached form a $C_{3-6}$ spirocarbocyclic ring optionally including one heteroatom selected from O and N and optionally substituted with 1-3 F atoms; and
 $R^3$ is $CH_3$, $C_2H_5$, $CF_2H$ or $CH_2F$, in conjunction with any of the above or below embodiments with respect to Formula II-C.

In another embodiment P-2, the invention includes compounds of Formula II-C wherein $A^4$ is $CR^4$ or N;
 $A^5$ is $CR^5$ or N;
 $A^6$ is $CR^6$ or N;
 $A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
 each of $R^1$ and $R^2$, independently, is H, F, Cl, $CF_3$, $CH_3$, $CF_2H$ or $CH_2F$; and
 $R^3$ is $CF_3$, $CH_3$, $CF_2H$ or $CH_2F$, in conjunction with any of the above or below embodiments with respect to Formula II-C.

In one embodiment of the invention, there are provided compounds, including stereoisomers, tautomers, hydrates, solvates and pharmaceutically acceptable salts thereof, which are generally defined by Formula II:

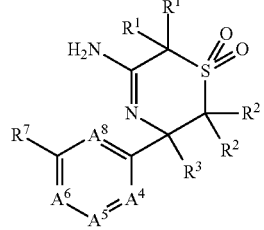

$A^4$ is CH, CF or N;
$A^5$ is CH, CF or N;
$A^6$ is CH, CF or N;
$A^8$ is CH, CF or N, provided that no more than one of $A^4$, $A^5$, $A^6$ and $A^8$ is N;
 each $R^1$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
 alternatively, each $R^1$ taken together with the carbon atom to which they are attached form a spirocyclopropyl, spirocyclobutyl, spirocyclopentyl or spirocyclohexyl ring, said ring optionally substituted with 1-4 F atoms;
 each $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
 alternatively, each $R^2$ taken together with the carbon atom to which they are attached form a spirocyclopropyl, spirocyclobutyl, spirocyclopentyl or spirocyclohexyl ring, said ring optionally substituted with 1-4 F atoms;
 $R^3$ is $C_{1-4}$alkyl, $C_{1-4}$haloalkyl, $CH_2OH$, $CH_2OCHF_2$ or cyclopropyl; and
 alternatively, one $R^2$ and $R^3$ taken together with the carbon atoms to which they are attached form a $C_{3-6}$carbocyclic ring optionally including 1-2 heteroatoms selected from O and N and optionally substituted with 1-4 F atoms on the carbon atoms and a substituent of $C_{1-3}$alkyl, $CH_2OC_{1-2}$alkyl or $C_{1-3}$haloalkyl on the nitrogen atom;
 $R^7$ is $-NH-R^9$, $-NH-C(=O)-R^9$ or $-S-R^9$;
 or $R^7$ is

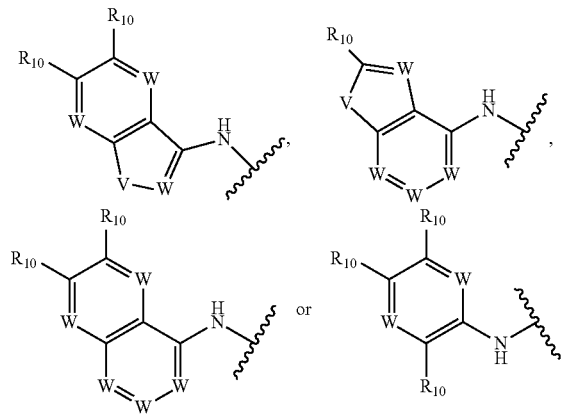

wherein V is NH, $N(CH_3)$, O or S; and
 each W, independently, is CH, CF, CCl or N;
 $R^9$ is a ring selected from phenyl, pyridyl, pyrimidyl, pyrazinyl, pyridazinyl, pyrazolyl, isoxazolyl, thiazolyl, furanyl, thienyl or pyrrolyl, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl or dioxolyl, wherein each of the $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$alkylamino-, $C_{1-3}$dialkylamino, $C_{1-3}$thioalkoxyl or oxetan-3yl.

In another embodiment, the invention provides one or more of the compounds, or a pharmaceutically acceptable salt thereof, of Formulas I and II, and sub-formulas thereof, as taught and described herein.

In another embodiment, the invention provides the compound of Formula I, II or II-A, or a stereoisomer or pharmaceutically acceptable salt thereof, selected from N-(3-((3R)-5-amino-3-methyl-1,1-dioxido-3,6-dihydro-2H-1,4-thiazin-3-yl)-4-fluorophenyl)-5-methoxy-2-pyrazinecarboxamide;

N-(3-((3R)-5-amino-3-methyl-1,1-dioxido-3,6-dihydro-2H-1,4-thiazin-3-yl)-4-fluorophenyl)-5-chloro-2-pyridinecarboxamide;

N-(3-((3R)-5-amino-3-methyl-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-2-pyridinecarboxamide;

Racemic mixture of N-(3-((3R,6R)-5-amino-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide and N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyridinecarboxamide;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-methoxy-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-cyano-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-2-methyl-1,3-thiazole-4-carboxamide;

N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

Racemic mixture of N-(4-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide and N-(4-((3S)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide; and N-(6-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide.

In another embodiment, the invention provides the compound of Formula I, II, II-B, or a stereoisomer or pharmaceutically acceptable salt thereof, selected from N-(3-((3R)-5-amino-3-methyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3-methyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine;
N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine;
8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile;
N-(3-((3R)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine;
Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;
N-(3-((8R)-10-amino-8-methyl-6,6-dioxido-6-thia-9-azaspiro[4.5]dec-9-en-8-yl)-4-fluorophenyl)-3-methoxy-1,7-naphthyridin-8-amine;
N-(3-((6R)-8-amino-6-methyl-4,4-dioxido-4-thia-7-azaspiro[2.5]oct-7-en-6-yl)-4-fluorophenyl)-3-methoxy-1,7-naphthyridin-8-amine;
N-(3-((3R,6R)-5-amino-6-fluoro-3,6-dimethyl-1,1-dioxido-3,6-dihydro-2H-1,4-thiazin-3-yl)-4-fluorophenyl)-3-methoxy-1,7-naphthyridin-8-amine;
N-(3-((3R)-5-amino-3,6,6-trimethyl-1,1-dioxido-3,6-dihydro-2H-1,4-thiazin-3-yl)-4-fluorophenyl)-3-chloro-5-fluoro-1,7-naphthyridin-8-amine;
Racemic mixture of N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine and
N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;
N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;
8-((3-((3R)-5-amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile;
(5R)-5-(2-fluoro-5-(1-naphthalenylsulfanyl)phenyl)-2,2,5-trimethyl-5,6-dihydro-2H-1,4-thiazin-3-amine 1,1-dioxide;
N-(3-((3R,6R)-5-amino-6-fluoro-3,6-dimethyl-1,1-dioxido-3,6-dihydro-2H-1,4-thiazin-3-yl)-4-fluorophenyl)-2-methoxypyrido[3,4-b]pyrazin-5-amine;
8-((3-((3R,6R)-5-amino-6-fluoro-3,6-dimethyl-1,1-dioxido-3,6-dihydro-2H-1,4-thiazin-3-yl)-4-fluorophenyl)amino)-1,7-naphthyridine-3-carbonitrile;
N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine;
N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine;
N-(3-((3R)-5-amino-3,6,6-trimethyl-1,1-dioxido-3,6-dihydro-2H-1,4-thiazin-3-yl)-4-fluorophenyl)-7-chloropyrido[3,2-d]pyrimidin-4-amine;
N-(3-((3R)-5-amino-3,6,6-trimethyl-1,1-dioxido-3,6-dihydro-2H-1,4-thiazin-3-yl)-4-fluorophenyl)-5-fluoro-7-methoxy-4-quinazolinamine;
N-(5-((3R)-5-amino-3,6,6-trimethyl-1,1-dioxido-3,6-dihydro-2H-1,4-thiazin-3-yl)-6-fluoro-3-pyridinyl)-3-methoxy-1,7-naphthyridin-8-amine;
N-(3-((3R)-5-amino-3,6,6-trimethyl-1,1-dioxido-3,6-dihydro-2H-1,4-thiazin-3-yl)-4-fluorophenyl)-2-methoxy-5-quinoxalinamine;
N-(3-((3R)-5-amino-2-fluoro-3,6,6-trimethyl-1,1-dioxido-3,6-dihydro-2H-1,4-thiazin-3-yl)-4-fluorophenyl)-3-methoxy-1,7-naphthyridin-8-amine;
Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine;
N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;
N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;
N-(3-((3R)-5-amino-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine;
5-((3-((3R)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one; and
5-((3-((3S)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one.

In another embodiment, the invention provides the compound of Formula I, II or II-C, or a stereoisomer or pharmaceutically acceptable salt thereof, selected from
Racemic mixture of N-(3-((3R)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine and N-(3-((3S)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine, benzamide; and
3-((3-((3R)-5-amino-3,6,6-trimethyl-1,1-dioxido-3,6-dihydro-2H-1,4-thiazin-3-yl)-4-fluorophenyl)amino)thieno[3,2-b]pyridine-6-carbonitrile.

In another embodiment, the invention provides the compound of Formula II, or a stereoisomer or pharmaceutically acceptable salt thereof, selected from
N-(3-((3R)-5-amino-3-methyl-1,1-dioxido-3,6-dihydro-2H-1,4-thiazin-3-yl)-4-fluorophenyl)-2-methyl[1,3]thiazolo[4,5-c]pyridin-4-amine;
N-(3-((3R)-5-amino-3,6,6-trimethyl-1,1-dioxido-3,6-dihydro-2H-1,4-thiazin-3-yl)-4-fluorophenyl)-2-methyl[1,3]thiazolo[4,5-c]pyridin-4-amine;
N-(3-((3R)-5-amino-3-methyl-1,1-dioxido-3,6-dihydro-2H-1,4-thiazin-3-yl)-4-fluorophenyl)-5-methoxy-2-pyrazinecarboxamide;
N-(3-((3R)-5-amino-3-methyl-1,1-dioxido-3,6-dihydro-2H-1,4-thiazin-3-yl)-4-fluorophenyl)-5-chloro-2-pyridinecarboxamide;
N-(3-((3R)-5-amino-3-methyl-3,6-dihydro-2H-1,4-thiazin-3-yl)-4-fluorophenyl)-5-methoxy-2-pyrazinecarboxamide;
N-(3-((3R)-5-amino-3,6,6-trimethyl-1,1-dioxido-3,6-dihydro-2H-1,4-thiazin-3-yl)-4-fluorophenyl)-5-methoxyl-2-pyrazinecarboxamide;
N-(3-((3R)-5-amino-3,6,6-trimethyl-1,1-dioxido-3,6-dihydro-2H-1,4-thiazin-3-yl)-4-fluorophenyl)-5-fluoro-2-pyridinecarboxamide;
N-(3-((3R)-5-amino-3,6,6-trimethyl-1,1-dioxido-3,6-dihydro-2H-1,4-thiazin-3-yl)-4-fluorophenyl)-5-chloro-2-pyridinecarboxamide;

Racemic mixture of N-(3-((3R,6R)-5-amino-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide and N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyridinecarboxamide;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-methoxy-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-cyano-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-2-methyl-1,3-thiazole-4-carboxamide;

N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

Racemic mixture of N-(4-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide and N-(4-((3S)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide;

N-(6-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide.

N-(3-((3R)-5-amino-3-methyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3-methyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine;

8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile;

N-(3-((3R)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((8R)-10-amino-8-methyl-6,6-dioxido-6-thia-9-azaspiro[4.5]dec-9-en-8-yl)-4-fluorophenyl)-3-methoxy-1,7-naphthyridin-8-amine;

N-(3-((6R)-8-amino-6-methyl-4,4-dioxido-4-thia-7-azaspiro[2.5]oct-7-en-6-yl)-4-fluorophenyl)-3-methoxy-1,7-naphthyridin-8-amine;

N-(3-((3R,6R)-5-amino-6-fluoro-3,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-5-fluoro-1,7-naphthyridin-8-amine;

Racemic mixture of N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine and N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;

8-((3-((3R)-5-amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile;

(5R)-5-(2-fluoro-5-(1-naphthalenylsulfanyl)phenyl)-2,2,5-trimethyl-5,6-dihydro-2H-1,4-thiazin-3-amine 1,1-dioxide;

N-(3-((3R,6R)-5-amino-6-fluoro-3,6-dimethyl-1,1-dioxido-3,6-dihydro-2H-1,4-thiazin-3-yl)-4-fluorophenyl)-2-methoxypyrido[3,4-b]pyrazin-5-amine;

8-((3-((3R,6R)-5-amino-6-fluoro-3,6-dimethyl-1,1-dioxido-3,6-dihydro-2H-1,4-thiazin-3-yl)-4-fluorophenyl)amino)-1,7-naphthyridine-3-carbonitrile;

N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine;

N-(3-((3R)-5-amino-3,6,6-trimethyl-1,1-dioxido-3,6-dihydro-2H-1,4-thiazin-3-yl)-4-fluorophenyl)-7-chloropyrido[3,2-d]pyrimidin-4-amine;

N-(3-((3R)-5-amino-3,6,6-trimethyl-1,1-dioxido-3,6-dihydro-2H-1,4-thiazin-3-yl)-4-fluorophenyl)-5-fluoro-7-methoxy-4-quinazolinamine;

N-(5-((3R)-5-amino-3,6,6-trimethyl-1,1-dioxido-3,6-dihydro-2H-1,4-thiazin-3-yl)-6-fluoro-3-pyridinyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-methoxy-5-quinoxalinamine;

N-(3-((3R)-5-amino-2-fluoro-3,6,6-trimethyl-1,1-dioxido-3,6-dihydro-2H-1,4-thiazin-3-yl)-4-fluorophenyl)-3-methoxy-1,7-naphthyridin-8-amine;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine;

5-((3-((3R)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one;

5-((3-((3S)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one;

Racemic mixture of N-(3-((3R)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine and N-(3-((3S)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine, benzamide; and 3-((3-((3R)-5-amino-3,6,6-trimethyl-1,1-dioxido-3,6-dihydro-2H-1,4-thiazin-3-yl)-4-fluorophenyl)amino)thieno[3,2-b]pyridine-6-carbonitrile.

In another embodiment, the invention provides the compound of Formula II, or a stereoisomer or pharmaceutically acceptable salt thereof, selected from N-(3-((3R)-5-amino-3-methyl-1,1-dioxido-3,6-dihydro-2H-1,4-thiazin-3-yl)-4-fluorophenyl)-5-chloro-2-pyridinecarboxamide;

N-(3-((3R)-5-amino-3-methyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-5-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine;

8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile;

N-(3-((3R,6R)-5-amino-3,6-dimethyl-1,1-dioxido-3,6-dihydro-2H-1,4-thiazin-3-yl)-4-fluorophenyl)-5-methoxy-2-pyrazinecarboxamide;

N-(3-((3R,6S)-5-amino-3,6-dimethyl-1,1-dioxido-3,6-dihydro-2H-1,4-thiazin-3-yl)-4-fluorophenyl)-5-methoxy-2-pyrazinecarboxamide;

N-(3-((6R)-8-amino-6-methyl-4,4-dioxido-4-thia-7-azaspiro[2.5]oct-7-en-6-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide;

N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine;

N-(3-((3R)-5-amino-2-fluoro-3,6,6-trimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((3S)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-cyano-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide; and N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide.

In another embodiment, the invention provides the compound of Formula II, or a stereoisomer or pharmaceutically acceptable salt thereof, selected from 4-(3-((3R)-5-amino-3,6,6-trimethyl-1,1-dioxido-3,6-dihydro-2H-1,4-thiazin-3-yl)-4-fluorophenoxy)benzonitrile;

(5R)-5-(2-fluoro-5-(3-fluoro-5-(trifluoromethyl)phenoxy)phenyl)-2,2,5-trimethyl-5,6-dihydro-2H-1,4-thiazin-3-amine 1,1-dioxide;

(5R)-5-(5-(3-ethylphenoxy)-2-fluorophenyl)-2,2,5-trimethyl-5,6-dihydro-2H-1,4-thiazin-3-amine 1,1-dioxide;

(5R)-5-(5-(4-chloro-3-ethylphenoxy)-2-fluorophenyl)-2,2,5-trimethyl-5,6-dihydro-2H-1,4-thiazin-3-amine 1,1-dioxide;

(5R)-5-(2-fluoro-5-(2-naphthalenyloxyl)phenyl)-2,2,5-trimethyl-5,6-dihydro-2H-1,4-thiazin-3-amine 1,1-dioxide; and (5R)-5-(2-fluoro-5-(2-pyridinyloxyl)phenyl)-2,2,5-trimethyl-5,6-dihydro-2H-1,4-thiazin-3-amine 1,1-dioxide.

In another embodiment, the invention provides the compound of Formula I, II or III, or a stereoisomer or pharmaceutically acceptable salt thereof, selected from N-(3-((3R)-5-amino-3-methyl-1,1-dioxido-3,6-dihydro-2H-1,4-thiazin-3-yl)-4-fluorophenyl)-5-methoxy-2-pyrazinecarboxamide;

N-(3-((3R)-5-amino-3-methyl-1,1-dioxido-3,6-dihydro-2H-1,4-thiazin-3-yl)-4-fluorophenyl)-5-chloro-2-pyridinecarboxamide;

N-(3-((3R)-5-amino-3-methyl-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-2-pyridinecarboxamide;

Racemic mixture of N-(3-((3R,6R)-5-amino-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide and N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyridinecarboxamide;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-methoxy-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-cyano-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-fluoro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-2-methyl-1,3-thiazole-4-carboxamide;

N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide;

N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide;

Racemic mixture of N-(4-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide and N-(4-((3S)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide;

N-(6-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide;

N-(3-((3R)-5-amino-3-methyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3-methyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine;

8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile;

N-(3-((3R)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((8R)-10-amino-8-methyl-6,6-dioxido-6-thia-9-azaspiro[4.5]dec-9-en-8-yl)-4-fluorophenyl)-3-methoxy-1,7-naphthyridin-8-amine;

N-(3-((6R)-8-amino-6-methyl-4,4-dioxido-4-thia-7-azaspiro[2.5]oct-7-en-6-yl)-4-fluorophenyl)-3-methoxy-1,7-naphthyridin-8-amine;

N-(3-((3R,6R)-5-amino-6-fluoro-3,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-5-fluoro-1,7-naphthyridin-8-amine;

Racemic mixture of N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine and N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;

8-((3-((3R)-5-amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile;

(5R)-5-(2-fluoro-5-(1-naphthalenylsulfanyl)phenyl)-2,2,5-trimethyl-5,6-dihydro-2H-1,4-thiazin-3-amine 1,1-dioxide;

N-(3-((3R,6R)-5-amino-6-fluoro-3,6-dimethyl-1,1-dioxido-3,6-dihydro-2H-1,4-thiazin-3-yl)-4-fluorophenyl)-2-methoxypyrido[3,4-b]pyrazin-5-amine;

8-((3-((3R,6R)-5-amino-6-fluoro-3,6-dimethyl-1,1-dioxido-3,6-dihydro-2H-1,4-thiazin-3-yl)-4-fluorophenyl)amino)-1,7-naphthyridine-3-carbonitrile;

N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine;

N-(3-((3R)-5-amino-3,6,6-trimethyl-1,1-dioxido-3,6-dihydro-2H-1,4-thiazin-3-yl)-4-fluorophenyl)-7-chloropyrido[3,2-d]pyrimidin-4-amine;

N-(3-((3R)-5-amino-3,6,6-trimethyl-1,1-dioxido-3,6-dihydro-2H-1,4-thiazin-3-yl)-4-fluorophenyl)-5-fluoro-7-methoxy-4-quinazolinamine;

N-(5-((3R)-5-amino-3,6,6-trimethyl-1,1-dioxido-3,6-dihydro-2H-1,4-thiazin-3-yl)-6-fluoro-3-pyridinyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-methoxy-5-quinoxalinamine;

N-(3-((3R)-5-amino-2-fluoro-3,6,6-trimethyl-1,1-dioxido-3,6-dihydro-2H-1,4-thiazin-3-yl)-4-fluorophenyl)-3-methoxy-1,7-naphthyridin-8-amine;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine;

5-((3-((3R)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one;

5-((3-((3S)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one;

Racemic mixture of N-(3-((3R)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine and N-(3-((3S)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine, benzamide; and 3-((3-((3R)-5-amino-3,6,6-trimethyl-1,1-dioxido-3,6-dihydro-2H-1,4-thiazin-3-yl)-4-fluorophenyl)amino)thieno[3,2-b]pyridine-6-carbonitrile.

In another embodiment, the invention provides the compound of Formula I, II or III, or a stereoisomer or pharmaceutically acceptable salt thereof, selected from N-(5-((3R)-5-amino-3,6,6-trimethyl-1,1-dioxido-3,6-dihydro-2H-1,4-thiazin-3-yl)-6-fluoro-3-pyridinyl)-5-fluoro-3-methoxy-1,7-naphthyridin-8-amine;

N-(5-((3R)-5-amino-3,6,6-trimethyl-1,1-dioxido-3,6-dihydro-2H-1,4-thiazin-3-yl)-6-fluoro-3-pyridinyl)-3-chloro-5-fluoro-1,7-naphthyridin-8-amine;

8-((5-((3R)-5-amino-3,6,6-trimethyl-1,1-dioxido-3,6-dihydro-2H-1,4-thiazin-3-yl)-6-fluoro-3-pyridinyl)amino)-5-fluoro-1,7-naphthyridine-3-carbonitrile;

N-(5-((3R)-5-amino-3,6,6-trimethyl-1,1-dioxido-3,6-dihydro-2H-1,4-thiazin-3-yl)-6-fluoro-3-pyridinyl)-2-methoxypyrido[3,4-b]pyrazin-5-amine;

N-(5-((3R)-5-amino-3,6,6-trimethyl-1,1-dioxido-3,6-dihydro-2H-1,4-thiazin-3-yl)-6-fluoro-3-pyridinyl)-3-chloro-1,7-naphthyridin-8-amine;

N-(5-((3R)-5-amino-3,6,6-trimethyl-1,1-dioxido-3,6-dihydro-2H-1,4-thiazin-3-yl)-6-fluoro-3-pyridinyl)-2-(trifluoromethyl)pyrido[3,4-b]pyrazin-5-amine;

N-(3-((3R,6R)-5-amino-6-fluoro-3,6-dimethyl-1,1-dioxido-3,6-dihydro-2H-1,4-thiazin-3-yl)-4-fluorophenyl)-3-(2-butyn-1-yloxy)-1,7-naphthyridin-8-amine;

N-(3-((3R)-5-amino-2-fluoro-3,6,6-trimethyl-1,1-dioxido-3,6-dihydro-2H-1,4-thiazin-3-yl)-4-fluorophenyl)-7-chloropyrido[3,2-d]pyrimidin-4-amine;

4-((3-((3R)-5-amino-2-fluoro-3,6,6-trimethyl-1,1-dioxido-3,6-dihydro-2H-1,4-thiazin-3-yl)-4-fluorophenyl)amino)pyrido[3,2-d]pyrimidine-7-carbonitrile;

N-(5-((7R)-9-amino-7-methyl-5,5-dioxido-5-thia-8-azaspiro[3.5]non-8-en-7-yl)-6-fluoro-3-pyridinyl)-2-methoxypyrido[3,4-b]pyrazin-5-amine;

N-(3-((7R)-9-amino-7-methyl-5,5-dioxido-5-thia-8-azaspiro[3.5]non-8-en-7-yl)-4-fluorophenyl)-3-chloro-1,7-naphthyridin-8-amine;

N-(3-((7R)-9-amino-6-fluoro-7-methyl-5,5-dioxido-5-thia-8-azaspiro[3.5]non-8-en-7-yl)-4-fluorophenyl)-2-methoxypyrido[3,4-b]pyrazin-5-amine;

N-(3-((3S)-5-amino-3-(fluoromethyl)-6,6-dimethyl-1,1-dioxido-3,6-dihydro-2H-1,4-thiazin-3-yl)-4-fluorophenyl)-3-chloro-5-fluoro-1,7-naphthyridin-8-amine;

N-(3-((3S)-5-amino-3-(fluoromethyl)-6,6-dimethyl-1,1-dioxido-3,6-dihydro-2H-1,4-thiazin-3-yl)-4-fluorophenyl)-7-chloropyrido[3,2-d]pyrimidin-4-amine;

4-((3-((3S)-5-amino-3-(fluoromethyl)-6,6-dimethyl-1,1-dioxido-3,6-dihydro-2H-1,4-thiazin-3-yl)-4-fluorophenyl)amino)pyrido[3,2-d]pyrimidine-7-carbonitrile;

N-(3-((3S)-5-amino-3-(fluoromethyl)-6,6-dimethyl-1,1-dioxido-3,6-dihydro-2H-1,4-thiazin-3-yl)-4-fluorophenyl)-2-ethoxypyrido[3,4-b]pyrazin-5-amine;

N-(3-((7S)-9-amino-7-(fluoromethyl)-5,5-dioxido-5-thia-8-azaspiro[3.5]non-8-en-7-yl)-4-fluorophenyl)-2-ethoxypyrido[3,4-b]pyrazin-5-amine;

N-(3-((7S)-9-amino-7-(fluoromethyl)-5,5-dioxido-5-thia-8-azaspiro[3.5]non-8-en-7-yl)-4-fluorophenyl)-3-methoxy-1,7-naphthyridin-8-amine;

N-(3-((7S)-9-amino-7-(fluoromethyl)-5,5-dioxido-5-thia-8-azaspiro[3.5]non-8-en-7-yl)-4-fluorophenyl)-7-chloropyrido[3,2-d]pyrimidin-4-amine;

8-((3-((7S)-9-amino-7-(fluoromethyl)-5,5-dioxido-5-thia-8-azaspiro[3.5]non-8-en-7-yl)-4-fluorophenyl)amino)-5-fluoro-1,7-naphthyridine-3-carbonitrile;

N-(3-((7S)-9-amino-7-(fluoromethyl)-5,5-dioxido-5-thia-8-azaspiro[3.5]non-8-en-7-yl)-4-fluorophenyl)-7-methoxypyrido[3,2-d]pyrimidin-4-amine;

Mixture of N-(3-((7R)-9-amino-7-(fluoromethyl)-5,5-dioxido-5-thia-8-azaspiro[3.5]non-8-en-7-yl)-4-fluorophenyl)-3-chloro-1,7-naphthyridin-8-amine and N-(3-((7S)-9-amino-7-(fluoromethyl)-5,5-dioxido-5-thia-8-azaspiro[3.5]non-8-en-7-yl)-4-fluorophenyl)-3-chloro-1,7-naphthyridin-8-amine;

N-(3-((7S)-9-amino-7-(fluoromethyl)-5,5-dioxido-5-thia-8-azaspiro[3.5]non-8-en-7-yl)-4-fluorophenyl)-3-chloro-1,7-naphthyridin-8-amine;

N-(3-((7S)-9-amino-7-(fluoromethyl)-5,5-dioxido-5-thia-8-azaspiro[3.5]non-8-en-7-yl)-4-fluorophenyl)-2-methoxypyrido[3,4-b]pyrazin-5-amine;

8-(3-((7R)-9-amino-7-methyl-5,5-dioxido-5-thia-8-azaspiro[3.5]non-8-en-7-yl)-4-fluorophenyl)amino)-1,7-naphthyridine-3-carbonitrile;

8-(3-((7R)-9-amino-6-fluoro-7-methyl-5,5-dioxido-5-thia-8-azaspiro[3.5]non-8-en-7-yl)-4-fluorophenyl)amino)-1,7-naphthyridine-3-carbonitrile;

N-(3-((3R)-5-amino-3,6,6-trimethyl-1,1-dioxido-3,6-dihydro-2H-1,4-thiazin-3-yl)-4-fluorophenyl)-3-(2-butyn-1-yloxy)-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-(cyclopropylmethoxy)-1,7-naphthyridin-8-amine;

8-((3-((3S)-5-amino-3-(fluoromethyl)-6,6-dimethyl-1,1-dioxido-3,6-dihydro-2H-1,4-thiazin-3-yl)-4-fluorophenyl)amino)-1,7-naphthyridine-3-carbonitrile;

N-(3-((3R,6R)-5-amino-6-fluoro-3,6-dimethyl-1,1-dioxido-3,6-dihydro-2H-1,4-thiazin-3-yl)-4-fluorophenyl)-7-methoxypyrido[3,2-d]pyrimidin-4-amine;

N-(3-((3S)-5-amino-3-(fluoromethyl)-6,6-dimethyl-1,1-dioxido-3,6-dihydro-2H-1,4-thiazin-3-yl)-4-fluorophenyl)-5-fluoro-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-(2-fluoroethoxyl)pyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-2-(2,2,2-trifluoroethoxyl)pyrido[3,4-b]pyrazin-5-amine;

((5-((3R)-5-amino-3,6,6-trimethyl-1,1-dioxido-3,6-dihydro-2H-1,4-thiazin-3-yl)-4-fluorophenyl)amino)pyrido[3,4-b]pyrazin-2-yl)oxy)acetonitrile;

N-(3-((3R)-5-amino-3,6,6-trimethyl-1,1-dioxido-3,6-dihydro-2H-1,4-thiazin-3-yl)-4-fluorophenyl)-2-(2,2-difluoroethoxyl)pyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-2-(2-butyn-1-yloxy)pyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-7-(cyclopropylmethoxy)pyrido[3,2-d]pyrimidin-4-amine;

N-(3-((3S)-5-amino-3-(fluoromethyl)-6,6-dimethyl-1,1-dioxido-3,6-dihydro-2H-1,4-thiazin-3-yl)-4-fluorophenyl)-2-methoxypyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-3-bromopyrido[2,3-d]pyridazin-8-amine; and N-(3-((5R,6R)-8-amino-5-fluoro-6-methyl-4,4-dioxido-4-thia-7-azaspiro[2.5]oct-7-en-6-yl)-4-fluorophenyl)-2-methoxypyrido[3,4-b]pyrazin-5-amine.

In another embodiment, the invention provides the compound of Formula I, II or III, or a stereoisomer or pharmaceutically acceptable salt thereof, selected from N-(3-((4aR,7aR)-3-amino-2,2-dimethyl-1,1-dioxido-7,7a-dihydro-2H-furo[3,4-b][1,4]thiazin-4a(5H)-yl)-4-fluorophenyl)-2-methoxypyrido[3,4-b]pyrazin-5-amine;

N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-2-methoxypyrido[3,4-b]pyrazin-5-amine;

5-((3-((4aS,7aS)-3-amino-2,2-dimethyl-1,1-dioxido-7,7a-dihydro-2H-furo[3,4-b][1,4]thiazin-4a(5H)-yl)-4-fluorophenyl)amino)pyrido[3,4-b]pyrazin-2(1H)-one;

N-(3-((8R)-6-amino-5,5,8-trimethyl-4,4-dioxido-4-thia-7-azaspiro[2.5]oct-6-en-8-yl)-4-fluorophenyl)-2-methoxypyrido[3,4-b]pyrazin-5-amine;

N-(3-((8R)-6-amino-5,5,8-trimethyl-4,4-dioxido-4-thia-7-azaspiro[2.5]oct-6-en-8-yl)-4-fluorophenyl)-5-chloro-3-methyl-2-pyridinecarboxamide;

N-(3-((8R)-6-amino-5,5,8-trimethyl-4,4-dioxido-4-thia-7-azaspiro[2.5]oct-6-en-8-yl)-4-fluorophenyl)-5-(difluoromethoxy)-3-methyl-2-pyridinecarboxamide;

N-(3-((1R,6R)-4-amino-3,3-dimethyl-2,2-dioxido-2-thia-5-azabicyclo[4.1.0]hept-4-en-6-yl)-4-fluorophenyl)-5-chloro-3-methyl-2-pyridinecarboxamide;

Mixture of N-(3-((4aR,7aR)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide and N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-chloro-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine;

N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide; and N-(3-((1R,6R)-4-amino-3,3-dimethyl-2,2-dioxido-2-thia-5-azabicyclo[4.1.0]hept-4-en-6-yl)-4-fluorophenyl)-3-chloro-1,7-naphthyridin-8-amine In another embodiment, the invention provides the compound of Formula I, II or III, or a stereoisomer or pharmaceutically acceptable salt thereof, selected from (5R)-5-(2-fluoro-5-((3-fluoro-2-pyridinyl)oxy)phenyl)-2,2,5-trimethyl-5,6-dihydro-2H-1,4-thiazin-3-amine 1,1-dioxide;

2-(3-((3R)-5-amino-3,6,6-trimethyl-1,1-dioxido-3,6-dihydro-2H-1,4-thiazin-3-yl)-4-fluorophenoxy)-4-pyridinecarbonitrile; and (5R)-5-(5-((4-bromo-2-pyridinyl)oxy)-2-fluorophenyl)-2,2,5-trimethyl-5,6-dihydro-2H-1,4-thiazin-3-amine 1,1-dioxide.

In another embodiment, the invention provides the compound of Formula I, II or III, or a stereoisomer or pharmaceutically acceptable salt thereof, selected from N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(2,2-difluoroethoxy)-2-pyrazinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(difluoromethyl)-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-fluoro-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(difluoromethoxy)-3-methyl-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-cyano-3-methyl-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-(difluoromethyl)-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-cyano-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-(methoxymethyl)-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-chloro-3-fluoro-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(difluoromethoxy)-3-methyl-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-chloro-3-methyl-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide N-(3-((3R)-5-amino-2-fluoro-3,6,6-trimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(difluoromethyl)-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-chloro-3-(methoxymethyl)-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-3-chloro-5-methoxy-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-methoxy-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-(1-methylethenyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-ethenyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-ethyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-ethyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-(1-methylethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethoxy)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(5-((3R)-5-amino-3,6,6-trimethyl-1,1-dioxido-3,6-dihydro-2H-1,4-thiazin-3-yl)-6-fluoro-3-pyridinyl)-3-chloro-5-(difluoromethyl)-2-pyridinecarboxamide;

N-(5-((7R)-9-amino-7-methyl-5,5-dioxido-5-thia-8-azaspiro[3.5]non-8-en-7-yl)-6-fluoro-3-pyridinyl)-3-methyl-5-(2,2,2-trifluoroethoxy)-2-pyridinecarboxamide;

N-(3-((3R)-5-amino-3,6,6-trimethyl-1,1-dioxido-3,6-di-hydro-2H-1,4-thiazin-3-yl)-4-fluorophenyl)-3-bromo-5-chloro-2-pyridinecarboxamide;

N-(3-((3R)-5-amino-3,6,6-trimethyl-1,1-dioxido-3,6-di-hydro-2H-1,4-thiazin-3-yl)-4-fluorophenyl)-5-cyano-3-methyl-2-pyridinecarboxamide;

N-(5-((7R)-9-amino-7-methyl-5,5-dioxido-5-thia-8-azaspiro[3.5]non-8-en-7-yl)-6-fluoro-3-pyridinyl)-5-chloro-3-methyl-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-methoxy-3-methyl-2-pyridinecarboxamide;

N-(3-((3R)-5-amino-3,6,6-trimethyl-1,1-dioxido-3,6-di-hydro-2H-1,4-thiazin-3-yl)-4-fluorophenyl)-5-(difluo-romethoxy)-3-methyl-2-pyridinecarboxamide;

N-(3-((7R)-9-amino-2,2-difluoro-7-methyl-5,5-dioxido-5-thia-8-azaspiro[3.5]non-8-en-7-yl)-4-fluorophenyl)-5-chloro-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-(difluoromethoxy)-3-methyl-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-methyl-2-pyridinecarboxamidel;

N-(3-((3S)-5-amino-3-(fluoromethyl)-6,6-dimethyl-1,1-di-oxido-3,6-dihydro-2H-1,4-thiazin-3-yl)-4-fluorophenyl)-5-((4-fluoro-2-butyn-1-yl)oxy)-2-pyridinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-chloro-2-pyridinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-fluoro-2-pyridinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-(dif-luoromethoxy)-3-methyl-2-pyridinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-methoxy-2-pyridinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-(2,2,2-trifluoroethoxy)-2-pyrazinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-cyano-2-pyridinecarboxamide;

N-(5-((3R)-5-amino-3,6,6-trimethyl-1,1-dioxido-3,6-di-hydro-2H-1,4-thiazin-3-yl)-6-fluoro-3-pyridinyl)-5-(dif-luoromethyl)-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-(2,2,2-trifluoroethoxy)-2-pyrazinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-cyano-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-chloro-3-(1-methylethenyl)-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-chloro-3-methyl-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-chloro-3-fluoro-2-pyridinecarboxamide;

Mixture of N-(3-((7R)-9-amino-7-(fluoromethyl)-5,5-di-oxido-5-thia-8-azaspiro[3.5]non-8-en-7-yl)-4-fluorophe-nyl)-5-(difluoromethoxy)-3-methyl-2-pyridinecarboxam-ide and N-(3-((7S)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide;

N-(3-((7S)-9-amino-7-(fluoromethyl)-5,5-dioxido-5-thia-8-azaspiro[3.5]non-8-en-7-yl)-4-fluorophenyl)-5-(difluo-romethoxy)-3-methyl-2-pyridinecarboxamide;

N-(3-((6S,7R)-9-amino-6-fluoro-7-methyl-5,5-dioxido-5-thia-8-azaspiro[3.5]non-8-en-7-yl)-4-fluorophenyl)-5-chloro-2-pyridinecarboxamide;

N-(3-((7R)-9-amino-6-fluoro-7-methyl-5,5-dioxido-5-thia-8-azaspiro[3.5]non-8-en-7-yl)-4-fluorophenyl)-5-(difluo-romethoxy)-3-methyl-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-6-chloro-3-methylimidazo[1,2-a]pyridine-2-carboxam-ide;

N-(5-((3R)-5-amino-3,6,6-trimethyl-1,1-dioxido-3,6-di-hydro-2H-1,4-thiazin-3-yl)-1-methyl-6-oxo-1,6-dihydro-3-pyridinyl)-5-(difluoromethoxy)-3-methyl-2-pyridin-ecarboxamide;

N-(5-((6R)-8-amino-6-methyl-4,4-dioxido-4-thia-7-azaspiro[2.5]oct-7-en-6-yl)-6-fluoro-3-pyridinyl)-5-(dif-luoromethoxy)-3-methyl-2-pyridinecarboxamide;

N-(3-((5S,6R)-8-amino-5-fluoro-6-methyl-4,4-dioxido-4-thia-7-azaspiro[2.5]oct-7-en-6-yl)-4-fluorophenyl)-5-(di-fluoromethyl)-3-methyl-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-methoxy-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-chloro-3-(methoxymethyl)-2-pyridinecarboxamide;

N-(3-((3S)-5-amino-3-(fluoromethyl)-6,6-dimethyl-1,1-di-oxido-3,6-dihydro-2H-1,4-thiazin-3-yl)-4-fluorophenyl)-5-chloro-2-pyridinecarboxamide; and N-(3-((6S)-8-amino-6-(fluoromethyl)-4,4-dioxido-4-thia-7-azaspiro[2.5]oct-7-en-6-yl)-4-fluorophenyl)-5-chloro-3-methyl-2-pyridinecarboxamide.

In another embodiment, the invention provides the compound of Formula III-F, or a stereoisomer or pharmaceutically acceptable salt thereof, selected from N-(3-((4aR,7aR)-3-amino-2,2-dimethyl-1,1-dioxido-7,7a-dihydro-2H-furo[3,4-b][1,4]thiazin-4a(5H)-yl)-4-fluoro-phenyl)-2-methoxypyrido[3,4-b]pyrazin-5-amine;

N-(3-((4aS,7aS)-3-amino-2,2-dimethyl-1,1-dioxido-7,7a-dihydro-2H-furo[3,4-b][1,4]thiazin-4a(5H)-yl)-4-fluoro-phenyl)-2-methoxypyrido[3,4-b]pyrazin-5-amine;

5-((3-((4aS,7aS)-3-amino-2,2-dimethyl-1,1-dioxido-7,7a-dihydro-2H-furo[3,4-b][1,4]thiazin-4a(5H)-yl)-4-fluoro-phenyl)amino)pyrido[3,4-b]pyrazin-2(1H)-one;

N-(3-((1R,6R)-4-amino-3,3-dimethyl-2,2-dioxido-2-thia-5-azabicyclo[4.1.0]hept-4-en-6-yl)-4-fluorophenyl)-5-chloro-3-methyl-2-pyridinecarboxamide;

Racemic mixture of N-(3-((4aR,7aR)-3-amino-2,2-dim-ethyl-1,1-dioxido-7,7a-dihydro-2H-furo[3,4-b][1,4]thi-azin-4a(5H)-yl)-4-fluorophenyl)-5-(difluoromethoxy)-3-methyl-2-pyridinecarboxamide and N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide;

Racemic mixture of N-(3-((4aR,7aS)-3-amino-2,2-dim-ethyl-1,1-dioxido-7,7a-dihydro-2H-furo[3,4-b][1,4]thi-azin-4a(5H)-yl)-4-fluorophenyl)-5-chloro-2-pyridinecar-boxamide and N-(3-((4aS,7aR)-3-amino-2,2-dimethyl-1, 1-dioxido-7,7a-dihydro-2H-furo[3,4-b][1,4]thiazin-4a (5H)-yl)-4-fluorophenyl)-5-chloro-2-pyridinecarboxamide;

Racemic mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide;

Racemic mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide;

Racemic mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine;

N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide; and N-(3-((1R,6R)-4-amino-3,3-dimethyl-2,2-dioxido-2-thia-5-azabicyclo[4.1.0]hept-4-en-6-yl)-4-fluorophenyl)-3-chloro-1,7-naphthyridin-8-amine All of the possible embodiments described herein for various of the R groups of the compounds of Formula I may be applied, as appropriate, to compounds of Formula II and any sub-formulas thereof.

In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

DEFINITIONS

The following definitions should assist in understanding the metes and bounds of the invention.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having $\alpha$ to $\beta$ number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from $\alpha$ and $\beta$. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from $\alpha$ and $\beta$. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)$_2$ and N" embraces linear or branched radicals wherein one or more of the carbon atoms may be replaced with a heteroatom. Examples of such "alkyl" radicals include —O-methyl, —O— ethyl, —CH$_2$—O—CH$_3$, —CH$_2$CH$_2$—O—CH$_3$, —NH—CH$_2$, —CH$_2$CH$_2$—N(CH$_3$)—CH$_3$, —S—(CH$_2$)$_3$CH$_2$, —CH$_2$CH$_2$—S—CH$_3$ and the like. Accordingly, such radicals also include radicals encompassed by —OR$^7$ where R$^7$ may be defined as a $C_{\alpha-\beta}$-alkyl. Examples of such "alkenyl" radicals include —NH—CH$_2$CH=CH$_2$, —S—CH$_2$CH$_2$CH=CHCH$_3$ and the like. Similar examples exist for such "alkynyl" radicals, as appreciated by those skilled in the art.

The term "$C_{\alpha-\beta}$alkoxyl" or "—O$C_{\alpha-\beta}$alkyl" when used alone or in combination, embraces linear or branched oxygen-containing alkyl radicals each having $\alpha$ to $\beta$ number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydroisoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N, N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like. The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:
ACN, MeCN—acetonitrile
Aq., aq.—aqueous
Ar—argon (gas)
BOC—tert-butoxycarbonyl
BOP—benzotriazol-1-yl-oxy Hexafluorophosphate
BuLi—Butyllithium
$Cs_2CO_3$—cesium carbonate
$CHCl_3$—chloroform
$CH_2Cl_2$, DCM—dichloromethane, methylene chloride
Cu(1)I—copper(1) iodide
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide
$Et_2O$—diethyl ether
EtOAc—ethyl acetate
g, gm—gram
h, hr—hour
$H_2$—hydrogen (gas)
$H_2O$—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
$K_2CO_3$—potassium carbonate
KI—potassium iodide
LG—leaving group
LDA—Lithium diisopropylamide
LiOH—lithium hydroxide
$MgSO_4$—magnesium sulfate
MS—mass spectrum
MeOH—methanol
$N_2$—nitrogen (gas)
NaCNB $H_3$—sodium cyanoborohydride
$Na_2CO_3$—sodium carbonate
$NaHCO_3$—sodium bicarbonate
NaH—sodium hydride
NaI—sodium iodide
$NaBH_4$—sodium borohydride
NaOH—sodium hydroxide
$Na_2SO_4$—sodium sulfate
$NH_4Cl$—ammonium chloride
$NH_4OH$—ammonium hydroxide
$P(t-bu)_3$—tri(tert-butyl)phosphine
$Ph_3P$—triphenylphosphine
Pd/C—palladium on carbon
$Pd(PPh_3)_4$—palladium(0)triphenylphosphine tetrakis
$Pd(dppf)Cl_2$—palladium(1,1-bisdiphenylphosphinoferrocene) II chloride
$Pd(PhCN)_2Cl_2$—palladium di-cyanophenyl dichloride
$Pd(OAc)_2$—palladium acetate
$Pd_2(dba)_3$—tris(dibenzylideneacetone)dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography
TBAF—Tetrabutylammonium flouride
TBTU—O-benzotriazol-1-yl-N,N,N,N'-tetramethyluronium tetrafluoroborate
TEA, $Et_3N$—triethylamine
TFA—trifluoroacetic acid
THF—tetrahydrofuran
UV—ultraviolet light

Scheme 1-A

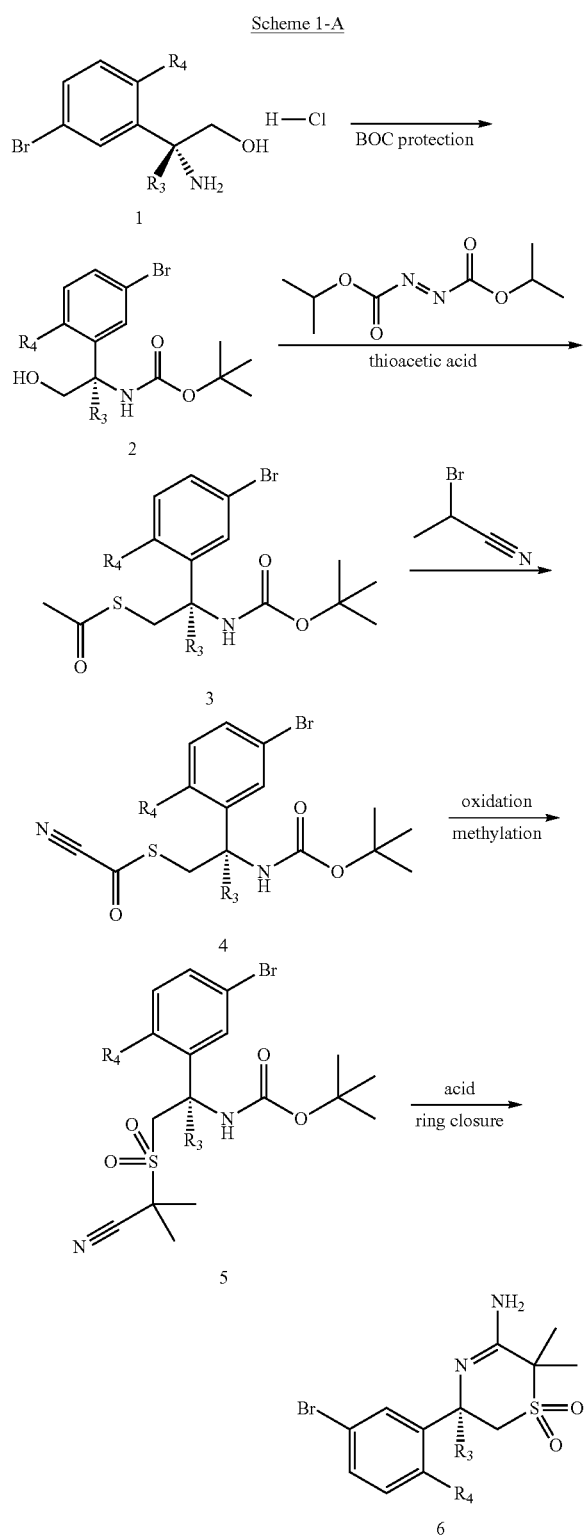

Scheme 1-B

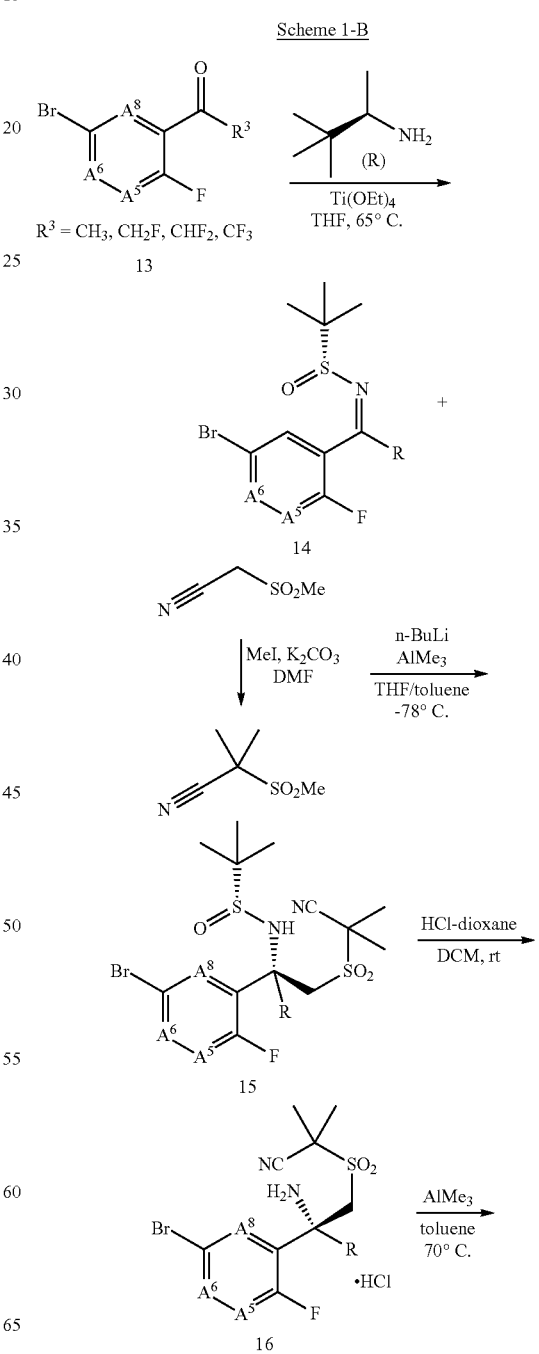

known in the art, as described herein, under suitable conditions, to afford carbamate compound 2. The alcohol group of the carbamate 2 may be converted to the corresponding thio-acetyl using thioacetic acid under suitable conditions as described hereinabove, to generate compound intermediate 3. The thiol group liberated from intermediate 3 may be used to displace the bromide of the cyano-reagent shown above, to afford the corresponding methyl-cyano thio-intermediate 4. Intermediate 4 may be oxidized and methylated under appropriate conditions, to provide compounds 5. Intermediate 5 can then be treated with a suitable acid under appropriate conditions to provide the ring closed desired intermediate 6.

Scheme 1-A describes an exemplary method for preparing racemic compounds 6 of Formulas I, II and III, wherein n is 2, $A^4$ is $CR^4$, each of $A^5$, $A^6$ and $A^8$ is, independently, CH and each $R^1$, independently, is $CH_3$. Beginning with compound 1, one of ordinary skill in the art may BOC protect the amino group via conventional techniques and reagents

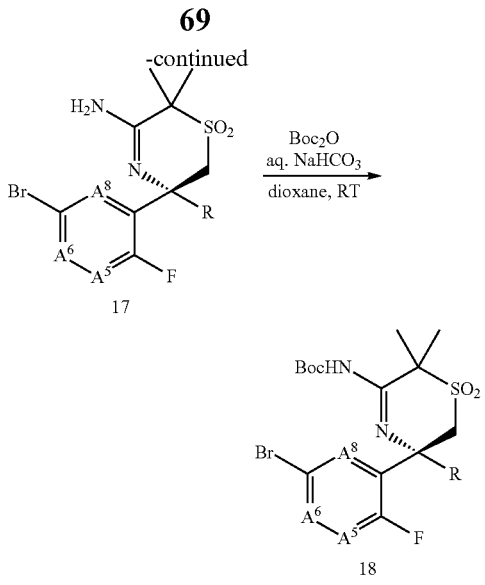

Scheme 1-B describes an exemplary, alternative method for preparing stereospecific, boc-protected compounds 18 of Formulas I, II and III, wherein n is 2, $A^4$ is $CR^4$ and $R^4$ is F, each of $A^5$, $A^6$ and $A^8$ is as defined, such as CH, and each $R^1$, independently, is $CH_3$. Beginning with compound 13 (may be commercially available depending upon $R^3$) one of ordinary skill in the art may generate the corresponding sulfinamide 14 via known techniques and reagents such as Ellman chemistry, or as described herein (see also Example 7 herein), under suitable conditions. The intermediate 15 can be generated using conditions as described hereinabove, followed by deprotection of the amine with acid, such as HCl, to provide intermediate 16. Intermediate 16 may be treated with trimethyl aluminum, or other suitable metal reagent, to effectively close the ring and afford the corresponding stereospecific intermediate 17. The primary amine of intermediate 17 may be protected with Boc under appropriate conditions, to provide useful intermediates 18, as shown. Intermediate 18 may be reacted in synthesis taught herein to provide desired compounds of Formulas I, II, III and sub-Formulas thereof.

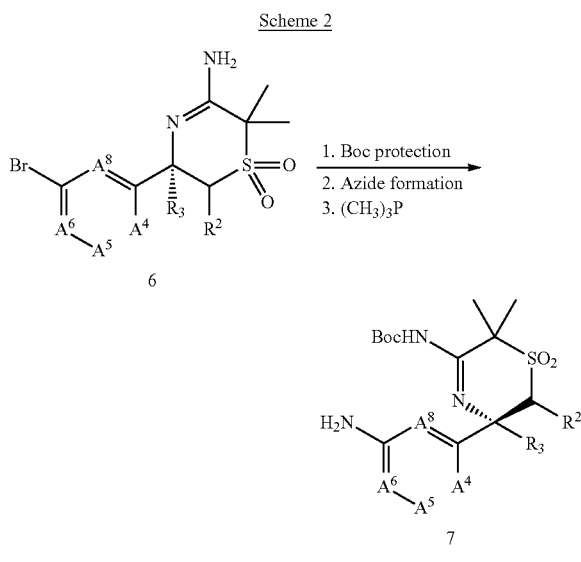

The bromide of compound 6 can be used as the handle by which desired $R^7$ groups, of Formulas I, II and III and sub-formulas thereof, may be introduced to afford the finally desired compounds of the invention, as shown in scheme 2 and described below. Specifically, primary amino group of bromide 6 can be protected with BOC using known methods. The bromide of the boc-protected intermediate can be converted to the corresponding azide using conventional techniques, such as those described herein. The azido intermediate (not shown) can be reduced to the corresponding amine compound 7 by treatment with a suitable phosphine, such as trimethylphosphine under suitable conditions.

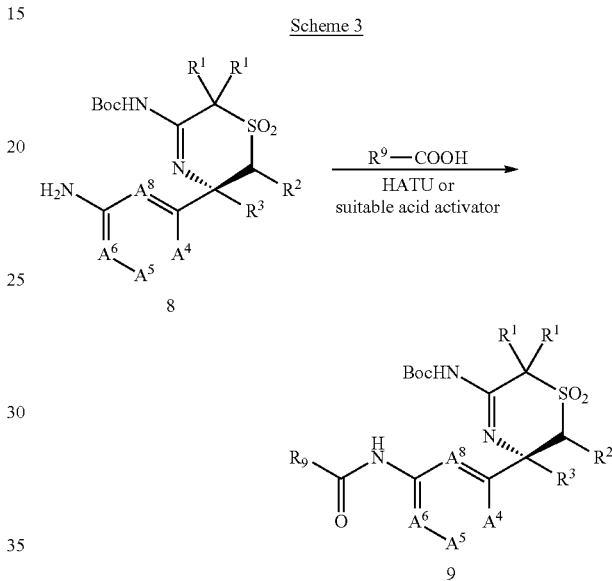

As shown, desired $R^9$-amide-linked compounds 9 can be prepared as desired, such as by treatment with an activated acid in conjunction with an activating reagent, such as HATU or DMTMM (see Method A and B for Examples 17-35 in Table 1) to afford the desired boc-protected amide-linked adduct. Compound 9 can be deprotected using known conditions, such as with an acid, like TFA, to afford final compounds of Formula II-A.

Acid activating groups convert the OH of the acid into a strong leaving group "LG." A "leaving group" which may be a halide such as an iodide, bromide, chloride or fluoride. LG may also be a non-halide moiety such as an alkylsulfonate or other known groups which generally form an electrophilic species (E Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

Scheme 4

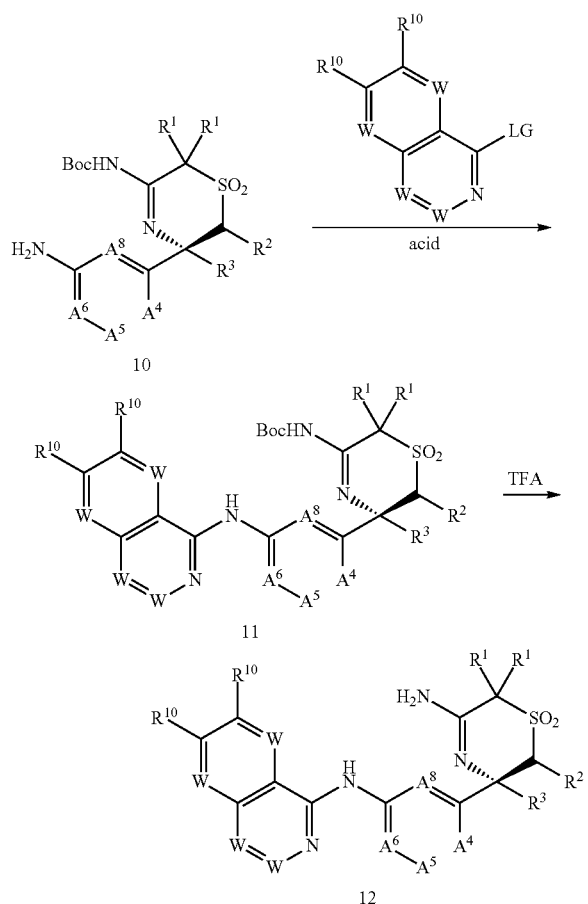

As shown, desired compounds 12 of Formula II-B can be prepared by treatment of intermediate amine 10 with a desired bicyclic $R^7$ group having a suitable leaving group, such as a chloride (Cl) or other aromatic leaving group, in the presence of a suitable acid, such as in the presence of sulfuric acid. This allows coupling of the bicyclic heteroaromatic R7 group to the amine to form boc-protected intermediate 11. Intermediate 11 can then be treated with acid, such as TFA, to afford the desired amine-linked compounds of Formula II.

Scheme 5

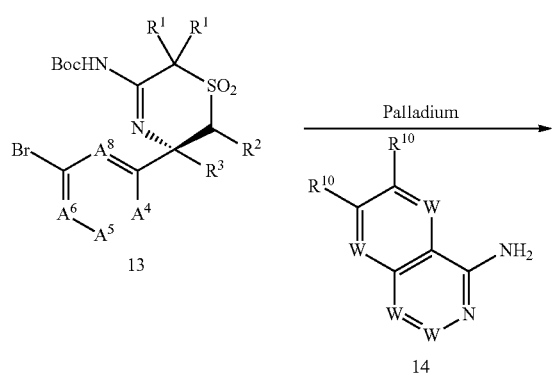

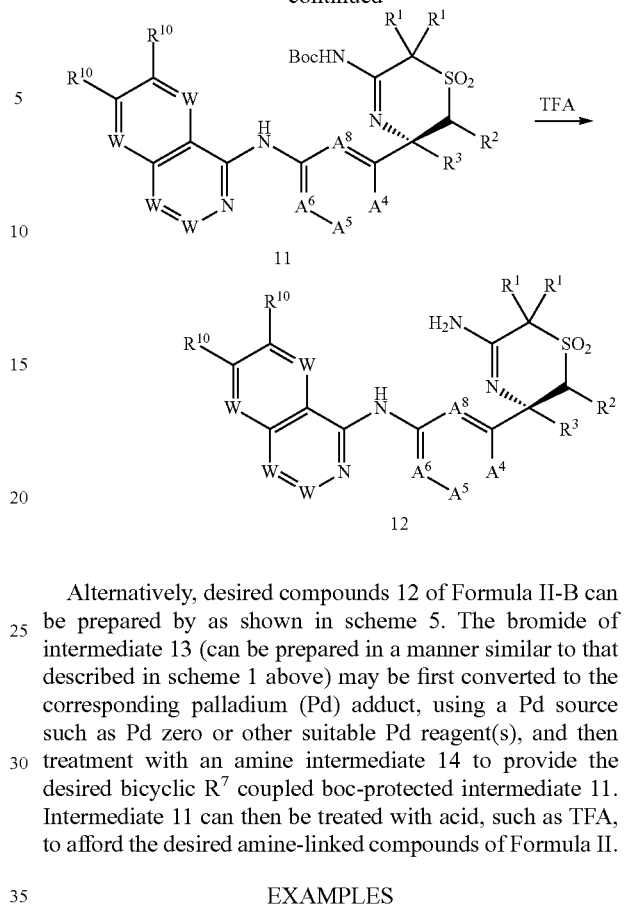

Alternatively, desired compounds 12 of Formula II-B can be prepared by as shown in scheme 5. The bromide of intermediate 13 (can be prepared in a manner similar to that described in scheme 1 above) may be first converted to the corresponding palladium (Pd) adduct, using a Pd source such as Pd zero or other suitable Pd reagent(s), and then treatment with an amine intermediate 14 to provide the desired bicyclic $R^7$ coupled boc-protected intermediate 11. Intermediate 11 can then be treated with acid, such as TFA, to afford the desired amine-linked compounds of Formula II.

EXAMPLES

The Examples, described herein below, represent various exemplary starting materials, intermediates and compounds of Formulas I-III, and sub-formulas thereof, which should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with $SiO_2$) and eluting the product off the column with a solvent gradient as indicated. For example a description of (330 g $SiO_2$, 0-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100%

MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

Example 1

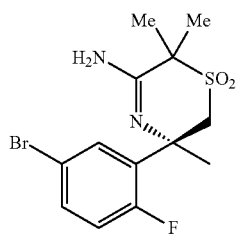 [SMILES: CC1(C)C(N)=N[C@](C)(c2cc(Br)ccc2F)CS1(=O)=O]

Synthesis of (R)-5-Amino-3-(5-bromo-2-fluorophenyl)-3,6,6-trimethyl-3,6-dihydro-2H-1,4-thiazine 1,1-dioxide Step 1: (R)-tert-Butyl (2-(5-bromo-2-fluorophenyl)-1-hydroxypropan-2-yl)carbamate To a suspension of (R)-2-amino-2-(5-bromo-2-fluorophenyl)propan-1-ol HCl (25 g, 88 mmol) in dioxane (150 mL) was added a solution of sodium bicarbonate (22.1 g, 264 mmol) in water (100 mL), followed by di-tert-butyl dicarbonate (21.1 g, 97 mmol). The reaction was stirred overnight at ambient temperature. After 16 hours, the reaction mixture was partitioned between water and ether. The organic layer was washed with water and brine, dried over anhydrous magnesium sulfate, filtered, and concentrated to generate the title intermediate as a white solid (35.5 g, quantitative yield).

Step 2: (R)—S-(2-(5-Bromo-2-fluorophenyl)-2-((tert-butoxycarbonyl)amino)propyl) ethanethioate To a solution of triphenylphosphine (9.0 g, 34.5 mmol) in THF (100 mL) at 0° C. was added diisopropyl azodicarboxylate (6.8 mL, 34.5 mmol) dropwise. The mixture was stirred for 30 minutes at 0° C., and then a solution of (R)-tert-butyl (2-(5-bromo-2-fluorophenyl)-1-hydroxypropan-2-yl)carbamate (10 g, 29 mmol) in THF (30 mL) and thioacetic acid (2.5 mL, 34.5 mmol) were added. The reaction was allowed to warm slowly to ambient temperature and stirred overnight. After 16 hours, the reaction mixture was concentrated, rediluted with DCM (100 mL), and passed through a silica-gel pad, eluting with DCM. The filtrate was concentrated and purified by silica-gel chromatography, eluting with 50-100% dichloromethane in heptanes, to provide the title intermediate (5.2 g, 12.8 mmol, 44% yield) as yellow oil.

Step 3: tert-Butyl ((2R)-2-(5-bromo-2-fluorophenyl)-1-((1-cyanoethyl)thio)propan-2-yl)carbamate To a solution of (R)—S-(2-(5-bromo-2-fluorophenyl)-2-((tert-butoxycarbonyl)amino)propyl)ethanothioate (7.0 g, 17.2 mmol) in ethanol (115 mL) was added a 0.5-M solution of sodium methoxide in MeOH (34.5 mL, 17.2 mmol). The mixture was stirred for 10 minutes at ambient temperature, and then 2-bromopropionitrile (1.8 mL, 20.7 mmol) was added. The reaction was stirred at ambient temperature for 20 minutes, and then concentrated. The crude product was partitioned between water and 1:1 ethyl acetate/heptanes. The organic layer was washed with brine and concentrated to give the title intermediate (7.2 g, 17.2 mmol, quantitative yield), which was used in the next reaction without further purification.

Step 4: (R)-tert-Butyl (2-(5-bromo-2-fluorophenyl)-1-((2-cyanopropan-2-yl)sulfonyl)propan-2-yl)carbamate To a solution of tert-butyl ((2R)-2-(5-bromo-2-fluorophenyl)-1-((1-cyanoethyl)thio)propan-2-yl)carbamate (5.3 g, 12.8 mmol) in MeOH (85 mL) at 0° C. was added a solution of ammonium molybdate tetrahydrate (3.16 g, 2.56 mmol) in 30% aqueous hydrogen peroxide (19.6 mL, 640 mmol). The mixture was stirred at ambient temperature overnight, quenched with saturated aqueous sodium bicarbonate, and extracted with ethyl acetate. The organic layer was washed with water and brine, dried over anhydrous magnesium sulfate, filtered, and concentrated.

The crude product was dissolved in DMF (30 mL). The solution was degassed with nitrogen, and potassium carbonate (2.63 g, 19.1 mmol) and iodomethane (1.18 mL, 19.1 mmol) were added. The reaction was stirred at ambient temperature for one hour. The reaction was diluted with water (200 mL), and the precipitate was collected by vacuum filtration. The precipitate was dissolved in ethyl acetate, washed with brine, dried over anhydrous magnesium sulfate, filtered, and concentrated to provide the title intermediate (3.4 g, 7.3 mmol, 58% yield) as a light-yellow solid.

Step 5: (R)-5-Amino-3-(5-bromo-2-fluorophenyl)-3,6,6-trimethyl-3,6-dihydro-2H-1,4-thiazine 1,1-dioxide A solution of (R)-tert-butyl (2-(5-bromo-2-fluorophenyl)-1-((2-cyanopropan-2-yl)sulfonyl)propan-2-yl)carbamate (3.4 g, 7.3 mmol) in dioxane (25 mL) was transferred to a pressure vessel. To the reaction was added 4 M HCl in dioxane (18.3 mL, 73 mmol), and the vessel was sealed and stirred at 110° C. overnight. After 16 hours, the reaction mixture was concentrated, and the residue was partitioned between ethyl acetate and saturated aqueous sodium bicarbonate. The organic layer was concentrated and purified by silica-gel chromatography, eluting with 0-10% methanol in DCM, to provide the title compound (2.3 g, 6.3 mmol, 86% yield) as an off-white solid. $^1$H-NMR (400 MHz, DMSO-d$_6$): δ 7.61 (dd, J=2.6, 7.2 Hz, 1H), 7.44-7.48 (m, 1H), 7.16 (dd, J=8.6, 12.1 Hz, 1H), 6.20 (bs, 2H), 3.66 (d, J=15.2 Hz, 1H), 3.55 (d, J=15.5 Hz, 1H), 1.57 (s, 6H), 1.44 (s, 3H). LC/MS (ESI$^+$) m/z=363.0, 365.0 (M+H; 2 bromine isotopes).

Intermediate 1

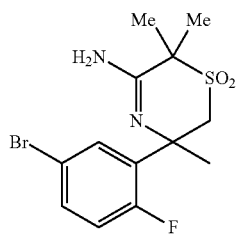 [SMILES: CC1(c2cc(Br)ccc2F)CS(=O)(=O)C(C)(C)C(N)=N1]

Synthesis of R,S-5-Amino-3-(5-bromo-2-fluorophenyl)-3,6,6-trimethyl-3,6-dihydro-2H-1,4-thiazine 1,1-dioxide Step 1: 2-Methyl-2-(methylsulfonyl)propanenitrile To a solution of 2-(methylsulfonyl)acetonitrile (60 g, 504 mmol) in DMF (252 mL) at 0° C. was added potassium carbonate (209 g, 1511 mmol) portion-wise, followed by iodomethane (136 mL, 1511 mmol). After 15 minutes, the ice bath was removed and the reaction was stirred at RT for 48 hours. The reaction mixture was filtered through a Celite® pad, and the filter cake was rinsed with ethyl acetate and ether. The combined filtrates were concentrated and partitioned between ether and water. The organic portion was dried over sodium sulfate, filtered, and concentrated in vacuo to afford the title intermediate (58 g, 78% yield) as an off-white solid. $^1$H NMR (400 MHz, DMSO-d$_6$) δ 3.27 (s, 3H) 1.71 (s, 6H).

Step 2: (E)-N-(1-(5-Bromo-2-fluorophenyl)ethylidene)-2-methylpropane-2-sulfinamide A mixture of 2-methylpropane-2-sulfinamide (14 g, 115 mmol), 1-(5-bromo-2-fluorophenyl)ethanone (25 g, 115 mmol), and titanium (IV) ethoxide (60.3 mL, 288 mmol) in 2-methyltetrahydrofuran (230 mL) was stirred at 65° C. for 16 hours. The reaction was cooled to RT and poured into brine. The resulting mixture was filtered through a Celite® pad, and the filter cake was rinsed with EtOAc. The organic portion was dried over sodium sulfate, filtered, and concentrated in vacuo to afford an oily residue. The crude product was purified by silica-gel chromatography, eluting with 0-100% ethyl acetate in heptanes, to afford the title intermediate (31 g, 84% yield) as a light yellow solid. LC/MS (ESI$^+$) m/z=320 (M+H).

Step 3: N-(2-(5-Bromo-2-fluorophenyl)-1-((2-cyanopropan-2-yl)sulfonyl)propan-2-yl)-2-methylpropane-2-sulfinamide To a solution of 2-methyl-2-(methylsulfonyl)propanenitrile (368 mg, 2.5 mmol) in THF (3.9 mL) at −78° C. was added BuLi (1.6 M in hexane) (1.56 mL, 2.5 mmol) dropwise via syringe. The reaction was stirred for 20 minutes and then a mixture of (E)-N-(1-(5-bromo-2-fluorophenyl)ethylidene)-2-methylpropane-2-sulfinamide (400 mg, 1.25 mmol) and trimethylaluminum (2.0 M in heptane) (0.63 mL, 1.3 mmol) in toluene (3.9 mL) at −78° C. was added. The reaction was stirred at −78° C. for 2 hours, and then partitioned between water and DCM. The organic portion was dried over sodium sulfate, filtered, and concentrated in vacuo to afford a yellow residue. The crude product was purified by silica-gel chromatography, eluting with 10-100% dichloromethane in heptanes, to afford the title intermediate (292 mg, 50% yield) as a white solid. $^1$H NMR (400 MHz, DMSO-d$_6$) δ 7.60-7.67 (m, 2H), 7.16-7.21 (m, 1H), 5.54 (s, 1H), 4.12-4.20 (m, 2H), 2.01 (s, 3H), 1.65 (s, 6H), 1.12 (s, 9H). LC/MS (ESI$^+$) m/z=467 (M+H).

Step 4: 5-Amino-3-(5-bromo-2-fluorophenyl)-3,6,6-trimethyl-3,6-dihydro-2H-1,4-thiazine 1,1-dioxide To a solution of N-(2-(5-bromo-2-fluorophenyl)-1-((2-cyanopropan-2-yl)sulfonyl)propan-2-yl)-2-methylpropane-2-sulfinamide (46.4 mg, 0.1 mmol) in DCM (0.5 mL) and EtOH (0.5 mL) was added 4 N HCl in dioxane (0.1 mL, 0.4 mmol). The reaction was stirred at RT for 1 hour, and then partitioned between aqueous sodium carbonate and DCM. The organic layer was dried over anhydrous sodium sulfate, filtered, and concentrated to provide 2-((2-amino-2-(5-bromo-2-fluorophenyl)propyl)sulfonyl)-2-methylpropanenitrile (36.1 mg, 100% yield). LC/MS (ESI$^+$) m/z=363 (M+H).

A suspension of 2-((2-amino-2-(5-bromo-2-fluorophenyl)propyl)sulfonyl)-2-methylpropanenitrile (36.1 mg, 0.1 mmol) in 4 N HCl in dioxane (0.99 mL, 4.0 mmol) was stirred at 105° C. overnight. The reaction was cooled to RT and poured slowly into a cold solution of aqueous sodium bicarbonate. The mixture was diluted with DCM, and the organic portion was dried over anhydrous sodium sulfate, filtered, and concentrated to give a tan residue. The crude product was suspended in DCM and filtered through a Celite® pad. The filter cake was rinsed with 5% methanol in DCM, and the combined filtrates were concentrated in vacuo to afford the title compound (35 mg, 97% yield) as a tan solid. LC/MS (ESI$^+$) m/z=363, 365 (M+H; 2 bromine isotopes).

Intermediate 2

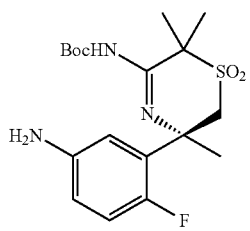 [SMILES: CC(C)(C)OC(=O)NC1=N[C@](C)(c2cc(N)ccc2F)CS(=O)(=O)C1(C)C]

Synthesis of (R)-tert-Butyl (5-(5-amino-2-fluorophenyl)-2,2,5-trimethyl-1,1-dioxido-5,6-dihydro-2H-1,4-thiazin-3-yl)carbamate Step 1: (R)-tert-Butyl (5-(5-bromo-2-fluorophenyl)-2,2,5-trimethyl-1,1-dioxido-5,6-dihydro-2H-1,4-thiazin-3-yl)carbamate To a solution of (R)-5-amino-3-(5-bromo-2-fluorophenyl)-3,6,6-trimethyl-3,6-dihydro-2H-1,4-thiazine 1,1-dioxide (0.34 g, 0.93 mmol) in dioxane (6.2 mL) was added di-tert-butyl dicarbonate (0.323 mL, 1.392 mmol) and a saturated aqueous solution of sodium bicarbonate (6.2 mL). The reaction was stirred at ambient temperature for 16 hours and then partitioned between water and ethyl acetate. The organic layer was concentrated in vacuo to generate the title compound (430 mg, 0.93 mmol, quantitative yield).

Step 2: (R)-tert-Butyl (5-(5-azido-2-fluorophenyl)-2,2,5-trimethyl-1,1-dioxido-5,6-dihydro-2H-1,4-thiazin-3-yl)carbamate To a solution of (R)-tert-butyl (5-(5-bromo-2-fluorophenyl)-2,2,5-trimethyl-1,1-dioxido-5,6-dihydro-2H-1,4-thiazin-3-yl)carbamate (1.85 g, 3.99 mmol) in ethanol (13.91 mL) and water (6.05 mL) were added sequentially copper (I) iodide (0.304 g, 1.60 mmol), sodium azide (2.08 g, 31.9 mmol), (+)-sodium 1-ascorbate (0.32 g, 1.60 mmol) and (1R,2R)—$N^1,N^2$-dimethylcyclohexane-1,2-diamine (0.50 mL, 3.19 mmol). The reaction was stirred at 50° C. for 45 minutes and then partitioned between water and EtOAc. The organic layer was concentrated to generate the title intermediate (1.70 g, 3.99 mmol, quantitative yield), which was used in the next reaction without further purification. LC/MS (ESI$^+$) m/z=426 (M+H).

Step 3: (R)-tert-Butyl (5-(5-amino-2-fluorophenyl)-2,2,5-trimethyl-1,1-dioxido-5,6-dihydro-2H-1,4-thiazin-3-yl)carbamate To a solution of (R)-tert-butyl (5-(5-azido-2-fluorophenyl)-2,2,5-trimethyl-1,1-dioxido-5,6-dihydro-2H-1,4-thiazin-3-yl)carbamate (1.70 g, 3.99 mmol) in THF (26.7 mL) and water (8.91 mL) was added trimethylphosphine (1 M in THF, 4.39 mL, 4.39 mmol). The reaction was stirred at RT for 20 minutes and then partitioned between water and DCM. The organic layer was concentrated to generate a brown residue. The crude product was purified by silica-gel chromatography, eluting with 20-100% EtOAc in heptanes, to generate the title compound (1.25 g, 3.13 mmol, 78% yield) as a tan solid. LC/MS (ESI$^+$) m/z=400 (M+H).

Example 2

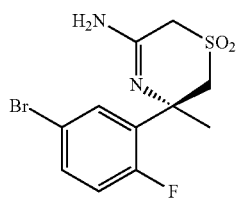 [SMILES: C[C@@]1(c2cc(Br)ccc2F)CS(=O)(=O)CC(N)=N1]

Synthesis of (R)-5-Amino-3-(5-bromo-2-fluorophenyl)-3-methyl-3,6-dihydro-2H-1,4-thiazine 1,1-dioxide Step 1: (R)-tert-Butyl (2-(5-bromo-2-fluorophenyl)-1-((cyanomethyl)thio)propan-2-yl)carbamate In an analogous reaction to that described in Example 1, step 3, (R)—S-(2-(5-bromo-2-fluorophenyl)-2-((tert-butoxycarbonyl)amino)propyl)ethanethioate was condensed with bromoacetonitrile to generate the title intermediate (1.03 g, 2.55 mmol, quantitative yield) as a clear oil.

Step 2: (R)-tert-Butyl (2-(5-bromo-2-fluorophenyl)-1-((cyanomethyl)sulfonyl)propan-2-yl)carbamate In an analogous reaction to that described in Example 1, step 4, (R)-tert-butyl (2-(5-bromo-2-fluorophenyl)-1-((cyanomethyl)thio)propan-2-yl)carbamate was oxidized to generate the title compound (380 mg, 0.87 mmol, quantitative yield) as white foam.

Step 3: (R)-5-Amino-3-(5-bromo-2-fluorophenyl)-3-methyl-3,6-dihydro-2H-1,4-thiazine 1,1-dioxide In an analogous sequence to that described for Example 1, step 5, (R)-tert-butyl (2-(5-bromo-2-fluorophenyl)-1-((cyanomethyl)sulfonyl)propan-2-yl)carbamate was converted to the title compound (294 mg, 0.88 mmol, 76% yield) as an off-white foam. LC/MS (ESI$^+$) m/z=335, 337 (M+H; 2 bromine isotopes).

Intermediate 3

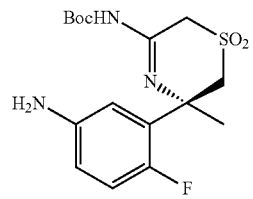 [SMILES: CC(C)(C)OC(=O)NC1=N[C@](C)(c2cc(N)ccc2F)CS(=O)(=O)C1]

Synthesis of (R)-tert-Butyl (5-((5-amino-2-fluorophenyl)-5-methyl-1,1-dioxido-5,6-dihydro-2H-1,4-thiazin-3-yl)carbamate In an analogous sequence of reactions to those described for Intermediate 2, steps 1-3, (R)-5-amino-3-(5-bromo-2-fluorophenyl)-3-methyl-3,6-dihydro-2H-1,4-thiazine 1,1-dioxide was converted to the title compound in 88% overall yield. LC/MS (ESI$^+$) m/z=372 (M+H).

Example 3

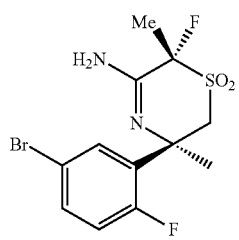 [SMILES: C[C@]1(F)C(N)=N[C@](C)(c2cc(Br)ccc2F)CS1(=O)=O]

Synthesis of (3R,6R)-5-Amino-3-(5-bromo-2-fluorophenyl)-6-fluoro-3,6-dimethyl-3,6-dihydro-2H-1,4-thiazine 1,1-dioxide

Route A

Step 1: (3R)-5-Amino-3-(5-bromo-2-fluorophenyl)-3,6-dimethyl-3,6-dihydro-2H-1,4-thiazine 1,1-dioxide In an analogous sequence of reactions to those described in Example 1, steps 4 and 5, tert-butyl ((2R)-2-(5-bromo-2-fluorophenyl)-1-((1-cyanoethyl)thio)propan-2-yl)carbamate was converted to the title intermediate in 86% overall yield.

Step 2: (3R,6R)-5-Amino-3-(5-bromo-2-fluorophenyl)-6-fluoro-3,6-dimethyl-3,6-dihydro-2H-1,4-thiazine 1,1-dioxide To a solution of (3R)-5-amino-3-(5-bromo-2-fluorophenyl)-3,6-dimethyl-3,6-dihydro-2H-1,4-thiazine 1,1-dioxide (2.28 g, 6.53 mmol) in DMF (32.6 ml) at −40° C. was added N-fluorobenzenesulfonimide (2.26 g, 7.18 mmol) and cesium carbonate (3.19 g, 9.79 mmol). The reaction mixture was stirred at −40° C. for 1.5 hours, and then warmed to RT. The mixture was diluted with water and extracted with EtOAc. The organic layer was washed with water and brine and concentrated. The crude material was purified by silica-gel chromatography, eluting with 20-100% EtOAc in heptane, to provide the title intermediate (2.03 g, 5.53 mmol, 85% yield) as a white solid. LC/MS (ESI+) m/z=367, 369 (M+H; 2 bromine isotopes).

Route B

Step 1: (R)-tert-Butyl 4-(5-bromo-2-fluorophenyl)-4-methyl-1,2,3-oxathiazolidine-3-carboxylate 2,2-dioxide A solution of (R)-tert-butyl (2-(5-bromo-2-fluorophenyl)-1-hydroxypropan-2-yl)carbamate (33.16 g, 95 mmol) in DCM (317 mL) was added dropwise to pre-cooled mixture of pyridine (38.8 ml, 476 mmol) and thionyl chloride (13.89 ml, 190 mmol) at 0° C. The reaction mixture was removed from the ice-water bath and allowed to stir at RT for 2 hours. The reaction was neutralized by the addition of 2 N aqueous HCl (240 mL), the organic phase was separated, and the aqueous phase was extracted with DCM. The combined organic layers were washed with water and brine and concentrated. The residue was dissolved in ACN (300 mL), and ruthenium (III) chloride hydrate (10.73 mg, 0.048 mmol) was added, followed by a solution of sodium metaperiodate (20.37 g, 95 mmol) in water (200 mL). The mixture was stirred for 20 minutes at RT and then diluted with water, and extracted with DCM. The combined extracts were washed with brine, dried over anhydrous sodium sulfate, and concentrated in vacuo to yield (R)-tert-butyl 4-(5-bromo-2-fluorophenyl)-4-methyl-1,2,3-oxathiazolidine-3-carboxylate 2,2-dioxide (33.95 g, 83 mmol, 87% yield) as an off-white solid, which was used without further purification.

Step 2: (R)—S-(2-(5-bromo-2-fluorophenyl)-2-((tert-butoxycarbonyl)amino)propyl) ethanethioate A mixture of potassium ethanethioate (9.98 g, 87 mmol) and (R)-tert-butyl 4-(5-bromo-2-fluorophenyl)-4-methyl-1,2,3-oxathiazolidine-3-carboxylate 2,2-dioxide (32.6 g, 79 mmol) in DMF (306 mL) was stirred at 50° C. for 1 hour. The mixture was cooled, diluted with water and extracted with EtOAc. The combined extracts were washed with 1 N aqueous HCl, water, and brine and concentrated. The residue was purified by silica-gel chromatography, eluting with 5-40% ethyl acetate in heptanes, to afford (R)—S-(2-(5-bromo-2-fluorophenyl)-2-((tert-butoxycarbonyl)amino)propyl) ethanethioate (26.2 g, 64.5 mmol, 81% yield) as an off-white solid.

Step 3: tert-Butyl ((2R)-2-(5-bromo-2-fluorophenyl)-1-((1-cyanoethyl)sulfonyl)propan-2-yl)carbamate To a solution of (R)—S-(2-(5-bromo-2-fluorophenyl)-2-((tert-butoxycarbonyl)amino)propyl) ethanethioate (5.13 g, 12.63 mmol) in ethanol (84 mL) was added sodium methoxide (0.5 M solution in methanol, 25.3 mL, 12.63 mmol). The mixture was stirred at RT for 10 minutes, and then (+/−)-2-bromopropionitrile (1.310 ml, 15.15 mmol) was added. The reaction was stirred at RT for 20 minutes, concentrated, and partitioned between water and 1:1 ethyl acetate/heptane. The aqueous layer was extracted with EtOAc, and the combined organic layers were washed with brine and concentrated.

The residue was dissolved in MeOH (63.2 mL) and cooled in an ice-water bath. To this solution was added a solution of ammonium molybdate (3.12 g, 2.53 mmol) in 30% hydrogen peroxide in water (19.35 mL, 632 mmol). The mixture was stirred at RT for 16 hours, quenched with saturated aqueous sodium bicarbonate, and extracted with DCM. The combined organic layers were washed with water and brine and concentrated. The crude material was purified by silica-gel chromatography, eluting with 20-100% ethyl acetate in heptane, to provide the title intermediate (3.92 g, 8.72 mmol, 69.1% yield) as a white solid.

Step 4: (3R,6R)-5-Amino-3-(5-bromo-2-fluorophenyl)-6-fluoro-3,6-dimethyl-3,6-dihydro-2H-1,4-thiazine 1,1-dioxide The tert-butyl ((2R)-2-(5-bromo-2-fluorophenyl)-1-((1-cyanoethyl)sulfonyl)propan-2-yl)carbamate was converted to the title compound as described in Example 3, steps 2 and 3. LC/MS (ESI+) m/z=367, 369 (M+H; 2 bromine isotopes).

Intermediate 4

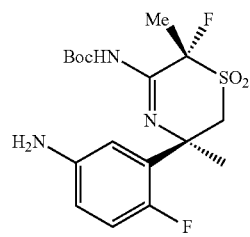 [SMILES: CC(C)(C)OC(=O)NC1=N[C@](C)(c2cc(N)ccc2F)CS(=O)(=O)[C@@]1(C)F]

Synthesis of tert-Butyl ((2R,5R)-5-(5-amino-2-fluorophenyl)-2-fluoro-2,5-dimethyl-1,1-dioxido-5,6-dihydro-2H-1,4-thiazin-3-yl)carbamate In a sequence of reactions analogous to those described for Intermediate 2, steps 1-3, (3R,6R)-5-amino-3-(5-bromo- 2-fluorophenyl)-6-fluoro-3,6-dimethyl-3,6-dihydro-2H-1,4-thiazine 1,1-dioxide was converted to the title compound in 87% overall yield. LC/MS (ESI+) m/z=426 (M+Na).

Example 4

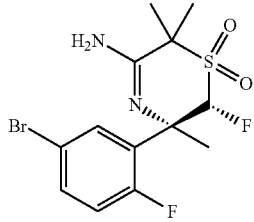 [SMILES: CC1(C)C(N)=N[C@](C)(c2cc(Br)ccc2F)[C@@H](F)S1(=O)=O]

Synthesis of (2S,3R)-5-amino-3-(5-bromo-2-fluorophenyl)-2-fluoro-3,6,6-trimethyl-3,6-dihydro-2H-1,4-thiazine 1,1-dioxide Step 1: tert-Butyl ((5R,6S)-5-(5-bromo-2-fluorophenyl)-6-fluoro-2,2,5-trimethyl-1,1-dioxido-5,6-dihydro-2H-1,4-thiazin-3-yl)carbamate To a solution of potassium 2-methylpropan-2-olate (6.20 g, 55.2 mmol) in tetrahydrofuran (175 ml) at −78° C. was added DIPA (7.87 mL, 55.2 mmol) and the solution was stirred for 15 minutes. A solution of n-butyllithium (2.7 M in heptane) (18.54 ml, 50.1 mmol) was added, and the solution was stirred at −78° C. for 5 minutes, then ((R)-tert-butyl (5-(5-bromo-2-fluorophenyl)-2,2,5-trimethyl-1,1-dioxido-5,6-dihydro-2H-1,4-thiazin-3-yl)carbamate) (8 g, 17.3 mmol) in THF (25 mL) was added dropwise and the solution was stirred at −78° C. for one hour. A solution of N-fluorobenzenesulfonimide (28.3 g, 90 mmol) in THF (100 mL) was then added and the solution was allowed to warm to RT and sonicated for 30 minutes. The solution was quenched with water (250 mL), extracted with ethyl acetate (2×300 mL), and the extracts were concentrated. The product was purified by silica-gel chromatography, eluting with 5-25% ethyl acetate in heptanes, to provide the title intermediate (5.1 g, 12.46 mmol, 61.5% yield). LC/MS (ESI+) m/z=505 (M+Na).

Step 2: (2S,3R)-5-amino-3-(5-bromo-2-fluorophenyl)-2-fluoro-3,6,6-trimethyl-3,6-dihydro-2H-1,4-thiazine 1,1-dioxide To a solution of tert-butyl ((5R,6S)-5-(5-bromo-2-fluorophenyl)-6-fluoro-2,2,5-trimethyl-1,1-dioxido-5,6-dihydro-2H-1,4-thiazin-3-yl)carbamate (312 mg, 0.648 mmol) in DCM (25 mL) was added TFA (1.25 mL, 16.2 mmol). The solution was stirred for 2 hours, quenched with saturated aqueous sodium carbonate, extracted with ethyl acetate, and the extracts were concentrated. The product was purified by silica-gel chromatography, eluting with 0-100% (90/10/1 dichloromethane/methanol/ammonium hydroxide) in dichloromethane, to afford the title compound (125 mg, 0.328 mmol, 50.6% yield).

LC/MS (ESI+) m/z=383, 385 (M+H; 2 bromine isotopes).

Example 5

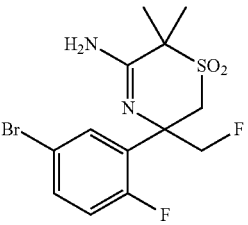 [SMILES: CC1(C)C(N)=NC(CF)(c2cc(Br)ccc2F)CS1(=O)=O]

Synthesis of 5-Amino-3-(5-bromo-2-fluorophenyl)-3-(fluoromethyl)-6,6-dimethyl-3,6-dihydro-2H-1,4-thiazine 1,1-dioxide Step 1: 1-(5-Bromo-2-fluorophenyl)-2-fluoroethanone A 2.0 M solution of LDA in heptane/THF/ethylbenzene (100 mL, 200 mmol) was added dropwise via syringe to a solution of 1-bromo-4-fluorobenzene (20 mL, 182 mmol) in THF (600 mL) at −78° C. After stirring for 2.5 hours at −78° C., ethyl monofluoroacetate (18.47 mL, 191 mmol) was added dropwise via syringe, and the reaction was stirred at −78° C. for 20 minutes and then stirred at −45° C. for 30 minutes before being quenched with saturated aqueous ammonium chloride at −45° C. The mixture was diluted with water and ethyl acetate. The layers were separated and the aqueous layer was extracted with ethyl acetate. The combined organic extracts were washed with saturated aqueous ammonium chloride, water, and saturated aqueous sodium chloride, dried over anhydrous magnesium sulfate, filtered, and concentrated. The crude product was dissolved in a minimal amount of methanol and placed in a −20° C. freezer overnight. The resulting solid was collected and washed with cold methanol to afford the title intermediate (12.07 g, 51.6 mmol, 28% yield) as a white solid.

Step 2: (R,Z)—N-(1-(5-Bromo-2-fluorophenyl)-2-fluoroethylidene)-2-methylpropane-2-sulfinamide Titanium (IV) ethoxide (4.05 mL, 19.6 mmol) was added via syringe to a solution of 1-(5-bromo-2-fluorophenyl)-2-fluoroethanone (2.3 g, 9.79 mmol) and (R)-(+)-2-methyl-2-propanesulfinamide (2.37 g, 19.57 mmol) in tetrahydrofuran (20 ml) at RT. The reaction was stirred for 18 hours and then the reaction was slowly poured into a vigorously stirred water/EtOAc mixture. After stirring 15 minutes, the mixture was filtered through a Celite® pad, which was rinsed with ethyl acetate, and the phases were separated. The aqueous layer was extracted with ethyl acetate; the combined organic extracts were washed with brine, dried over anhydrous sodium sulfate, filtered and concentrated. The crude product was purified by silica-gel chromatography, eluting with 10% EtOAc in hexanes, to provide the title compound (2.81 g, 8.31 mmol, 85% yield) as a yellow oil.

LC/MS (ESI+) m/z=338, 340 (M+H; 2 bromine isotopes).

Step 3: (R)—N-(2-(5-Bromo-2-fluorophenyl)-1-((2-cyanopropan-2-yl)sulfonyl)-3-fluoropropan-2-yl)-2-methylpropane-2-sulfinamide To a solution of 2-methyl-2-(methylsulfonyl)propanenitrile (1.654 g, 11.24 mmol) in THF (14 mL) at −78° C. was added a 2.5 M solution of n-butyllithium in hexanes (4.49 mL, 11.24 mmol) dropwise via syringe. After 30 minutes at −78° C., a 0° C. solution of (R,E)-N-(1-(5-bromo-2-fluorophenyl)-2-fluoroethylidene)-2-methylpropane-2-sulfinamide (1.9 g, 5.62 mmol) in THF (14.00 mL), which had been pretreated with boron trifluoride diethyl etherate (0.693 mL, 5.62 mmol) at 0° C. for 15 minutes, was added dropwise via cannula. The reaction was stirred for 2 hours at −78° C., and then quenched with saturated aqueous ammonium chloride at −78° C. and diluted with water and ethyl acetate. The layers were separated and the aqueous layer was extracted with EtOAc. The combined organic extracts were washed with water and saturated aqueous sodium chloride, and dried over sodium sulfate. The solution was filtered, concentrated, and purified by silica-gel chromatography, eluting with 25% ethyl acetate in hexanes followed by 40% ethyl acetate hexane to provide the title compound. The product was isolated as a 2:1 mixture of diastereomers. LC/MS (ESI+) m/z=485, 487 (M+H; 2 bromine isotopes).

Step 4: 2-((2-Amino-2-(5-bromo-2-fluorophenyl)-3-fluoropropyl)sulfonyl)-2-methylpropanenitrile hydrochloride A 4.0 M solution of hydrogen chloride in 1,4-dioxane (2.4 mL, 9.60 mmol) was added via syringe to a solution of (R)—N-(2-(5-bromo-2-fluorophenyl)-1-((2-cyanopropan-2-yl)sulfonyl)-3-fluoropropan-2-yl)-2-methylpropane-2-sulfinamide (1.14 g, 2.349 mmol) in dichloromethane (12 mL) at RT. After stirring for 2 hours, the reaction was filtered and the solid was washed with DCM and air-dried to afford the title intermediate (0.754 g, 1.805 mmol, 77% yield) as a white solid. LC/MS (ESI+) m/z=381, 383 (M+H; 2 bromine isotopes).

Step 5: 5-Amino-3-(5-bromo-2-fluorophenyl)-3-(fluoromethyl)-6,6-dimethyl-3,6-dihydro-2H-1,4-thiazine 1,1-dioxide A solution of 2-((2-amino-2-(5-bromo-2-fluorophenyl)-3-fluoropropyl)sulfonyl)-2-methylpropanenitrile hydrochloride (0.489 g, 1.171 mmol) in 4 M HCl in 1,4-dioxane (12 mL, 48.0 mmol) was stirred at reflux for 48 hours. After cooling, the solvent was removed and the resulting product was partitioned between DCM and 10% aqueous sodium carbonate. The layers were separated and the aqueous layer was extracted with DCM and then EtOAc. The combined organic extracts were washed with saturated aqueous sodium chloride, dried over anhydrous sodium sulfate, filtered and concentrated. The crude product was purified by silica-gel chromatography, eluting with 40% EtOAc in hexane, to provide the title compound as a white solid. LC/MS (ESI+) m/z=381, 383 (M+H; 2 bromine isotopes).

Intermediate 5

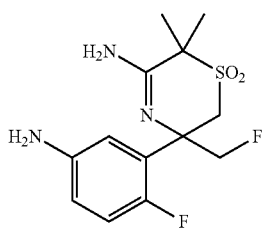 [SMILES: CC1(C)C(N)=NC(CF)(c2cc(N)ccc2F)CS1(=O)=O]

Synthesis of 5-Amino-3-(5-amino-2-fluorophenyl)-3-(fluoromethyl)-6,6-dimethyl-3,6-dihydro-2H-1,4-thiazine 1,1-dioxide 5-Amino-3-(5-bromo-2-fluorophenyl)-3-(fluoromethyl)-6,6-dimethyl-3,6-dihydro-2H-1,4-thiazine 1,1-dioxide (0.183 g, 0.480 mmol) was converted to the title compound using a sequence of reactions analogous to those described in Intermediate 2, steps 2 and 3, as a 2:1 ratio of enantiomers. LC/MS (ESI+) m/z=318 (M+H).

Alternatively, intermediate 5 may be prepared using a different ring closure method, as shown and described

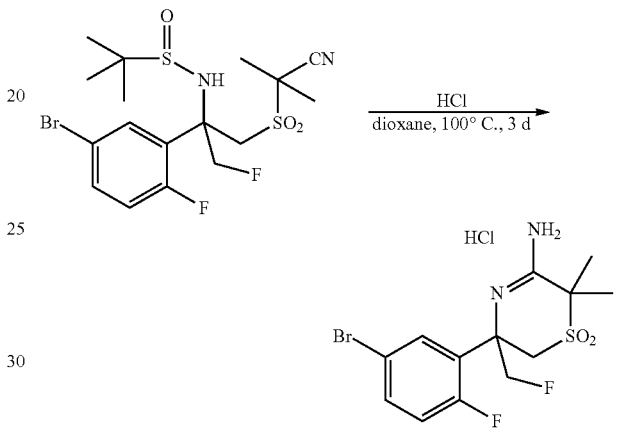

To a solution of N-(2-(5-bromo-2-fluorophenyl)-1-((2-cyanopropan-2-yl)sulfonyl)-3-fluoropropan-2-yl)-2-methylpropane-2-sulfinamide (45 g, 93 mmol) in dioxane (800 mL) was added HCl (4.0 M in 1,4-dioxane, 107 mL, 428 mmol, 4.6 eq.). The reaction mixture was heated to 100° C. for 2 d, cooled to RT, concentrated, and dried under high vacuum to give 5-amino-3-(5-bromo-2-fluorophenyl)-3-(fluoromethyl)-6,6-dimethyl-3,6-dihydro-2H-1,4-thiazine 1,1-dioxide hydrochloride as light brown solid. The product could be resolved into its constituent enantiomers by Chiral supercritical fluid chromatography under the following conditions: Column: Chiralpak AD-H, 30×250 mm, 20 μm; Mobile Phase A: CO2; Mobile Phase B: Methanol (20 mM NH3); Isocratic: 30% B; Flow Rate: 150 g/min; Detection: 270 nm Example 6

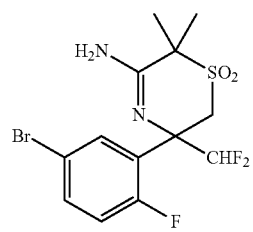 [SMILES: CC1(C)C(N)=NC(c2cc(Br)ccc2F)(C(F)F)CS1(=O)=O]

Synthesis of R,S-5-amino-3-(5-bromo-2-fluorophenyl)-3-(difluoromethyl)-6,6-dimethyl-3,6-dihydro-2H-1,4-thiazine 1,1-dioxide Step 1: R,S—N-(2-(5-Bromo-2-fluorophenyl)-3-((2-cyanopropan-2-yl)sulfonyl)-1,1-difluoropropan-2-yl)-2-methylpropane-2-sulfinamide To a solution of 2-methyl-2-(methylsulfonyl)propanenitrile (0.612 g, 4.15 mmol) in THF (6.5 mL) at −78° C. was added n-butyllithium, 1.6 M solution in hexane (2.60 mL, 4.15 mmol) dropwise. The resulting mixture was stirred for 20 minutes, and a to −78° C. solution of (E)-N-(1-(5-bromo-2-fluorophenyl)-2,2-difluoroethylidene)-2-methylpropane-2-sulfinamide (0.74 g, 2.077 mmol) in toluene (6.49 ml) which had been pretreated with trimethylaluminum, 2.0M solution in toluene (1.039 mL, 2.077 mmol) for 10 minutes, was added dropwise via canula. The resulting mixture was stirred for 2 hours at −78° C., quenched with water at −78° C., and extracted with DCM. The combined organic layers were dried over sodium sulfate, filtered, and concentrated. The crude product was purified by silica-gel chromatography, eluting with a gradient of 0% to 20% 90:10:1 dichloromethane/methanol/ammonium hydroxide in dichloromethane, to provide the title compound (0.936 g, 1.859 mmol, 90% yield) as white solid.

Step 2: R,S-2-((2-Amino-2-(5-bromo-2-fluorophenyl)-3,3-difluoropropyl)sulfonyl)-2-methylpropanenitrile hydrochloride To a solution of R,S—N-(2-(5-bromo-2-fluorophenyl)-3-((2-cyanopropan-2-yl)sulfonyl)-1,1-difluoropropan-2-yl)-2-methylpropane-2-sulfinamide (829 mg, 1.647 mmol) in DCM (8.23 mL) was added HCl (4 N in 1,4-dioxane) (1.65 mL, 6.59 mmol), and the reaction was stirred at RT for 2 hours. The resulting white precipitate was collected by vacuum filtration, washed with DCM, and dried in air to give the title compound (0.66 g, 1.515 mmol, 92% yield) as white solid.

Step 3: R,S-5-amino-3-(5-bromo-2-fluorophenyl)-3-(difluoromethyl)-6,6-dimethyl-3,6-dihydro-2H-1,4-thiazine 1,1-dioxide To a suspension of R,S-2-((2-amino-2-(5-bromo-2-fluorophenyl)-3,3-difluoropropyl)sulfonyl)-2-methylpropanenitrile hydrochloride (0.66 g, 1.515 mmol) in toluene (15.15 mL) was added trimethylaluminum, 2.0M solution in toluene (0.909 ml, 1.818 mmol). The mixture was stirred at 90° C. for 1 hour, cooled to 0° C., and diluted with saturated aqueous sodium carbonate. The aqueous layer was extracted with EtOAc, and the combined organic layers were washed with brine, dried over anhydrous magnesium sulfate, filtered, and concentrated. The crude product was purified by silica-gel chromatography, eluting with a gradient of 0% to 80% 90:10:1 DCM/MeOH/ammonium hydroxide in DCM, to provide the title compound (0.473 g, 1.185 mmol, 78% yield) as white solid. LC/MS (ESI$^+$) m/z=399, 401 (M+H; 2 bromine isotopes).

Intermediate 6

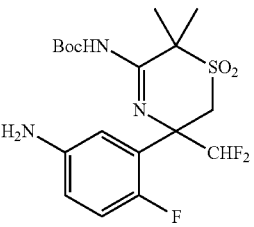 [SMILES: CC(C)(C)OC(=O)NC1=NC(c2cc(N)ccc2F)(C(F)F)CS(=O)(=O)C1(C)C]

Synthesis of R,S-tert-Butyl (5-(5-amino-2-fluorophenyl)-5-(difluoromethyl)-2,2-dimethyl-1,1-dioxido-5,6-dihydro-2H-1,4-thiazin-3-yl)carbamate Using the sequence of steps described for Intermediate 2, R,S-5-amino-3-(5-bromo-2-fluorophenyl)-3-(difluoromethyl)-6,6-dimethyl-3,6-dihydro-2H-1,4-thiazine 1,1-dioxide (0.452 g, 1.132 mmol) was converted to the title compound in 89% yield as a light-yellow solid. LC/MS (ESI$^+$) m/z=484 (M+H).

Example 7

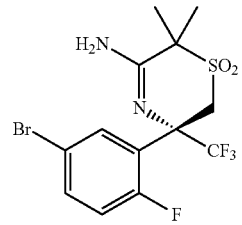 [SMILES: CC1(C)C(N)=N[C@@](c2cc(Br)ccc2F)(C(F)(F)F)CS1(=O)=O]

Synthesis of (S)-5-amino-3-(5-bromo-2-fluorophenyl)-6,6-dimethyl-3-(trifluoromethyl)-3,6-dihydro-2H-1,4-thiazine 1,1-dioxide Step 1: 1-(5-bromo-2-fluorophenyl)-2,2,2-trifluoroethanone To a solution of LDA, 2.0 M in heptane/THF/ethylbenzene (79 ml, 157 mmol) in THF (50 mL) at −78° C. was added a solution of 1-bromo-4-fluorobenzene (15.69 ml, 143 mmol) in THF (50 mL) dropwise. The mixture was stirred at −78° C. for 1 hour, and a solution of ethyl trifluoroacetate (18.70 mL, 157 mmol) in THF (50 mL) was added. The resulting mixture was stirred at 0° C. for 2 hours, quenched with saturated aqueous ammonium chloride, and extracted with ethyl acetate. The combined organics were dried over anhydrous sodium sulfate, filtered, concentrated and purified by silica-gel chromatography, eluting with using 0-30% ethyl acetate in hexanes, to afford the title intermediate (27.6 g, 102 mmol, 71.3% yield) as a brown oil.

Step 2: (R,Z)—N-(1-(5-bromo-2-fluorophenyl)-2,2,2-trifluoroethylidene)-2-methylpropane-2-sulfinamide A mixture of 1-(5-bromo-2-fluorophenyl)-2,2,2-trifluoroethanone (27.6 g, 102 mmol), (R)-2-methylpropane-2- sulfinamide (24.69 g, 204 mmol) and titanium (IV) ethoxide (52.7 mL, 255 mmol) in THF (100 mL) was heated at reflux for 2 hours. The mixture was brought to RT, and brine was added and stirred for 10 min. The suspension was filtered through silica gel; the organic phase was separated and the aqueous phase was extracted with ethyl acetate. The combined organics were washed with brine, dried over anhydrous sodium sulfate, filtered, and concentrated. The crude product was purified by silica-gel chromatography, eluting with 0-5% ethyl acetate in hexanes, to provide the title compound (20.66 g, 55.2 mmol, 54.2% yield) as a yellow oil.

Step 3: N—((S)-2-(5-bromo-2-fluorophenyl)-3-((2-cyanopropan-2-yl)sulfonyl)-1,1,1-trifluoropropan-2-yl)-2-methylpropane-2-sulfinamide To a −78° C. solution of 2-methyl-2-(methylsulfonyl)propanenitrile (11.53 g, 78 mmol) in THF (100 mL) was added a 2.5 M solution of n-butyllithium in hexanes (31.3 ml, 78 mmol) dropwise. The resulting mixture was stirred at −78° C. for 40 minutes, and then a solution of (R,Z)—N-(1-(5-bromo-2-fluorophenyl)-2,2,2-trifluoroethylidene)-2-methylpropane-2-sulfinamide (19.54 g, 52.2 mmol) in THF (100 mL) was added dropwise. The resulting mixture was stirred at −78° C. for 1 hour, quenched with saturated aqueous ammonium chloride, and extracted with EtOAc. The combined organics were dried over anhydrous sodium sulfate, filtered, concentrated and purified by silica-gel chromatography, eluting with 0-10% EtOAc in hexanes, to afford the title intermediate (27 g, 51.8 mmol) as a pale yellow oil. LC/MS (ESI$^+$) m/z=417, 419 (M+H).

Step 4: (5)-5-amino-3-(5-bromo-2-fluorophenyl)-6,6-dimethyl-3-(trifluoromethyl)-3,6-dihydro-2H-1,4-thiazine 1,1-dioxide To a solution of N—((S)-2-(5-bromo-2-fluorophenyl)-3-((2-cyanopropan-2-yl)sulfonyl)-1,1,1-trifluoropropan-2-yl)-2-methylpropane-2-sulfinamide (27 g, 51.8 mmol) in methanol (100 mL) was added a 4 M solution of HCl in 1,4-dioxane (64.7 ml, 259 mmol). The reaction was stirred at ambient temperature for 2 hours, concentrated, and diluted with DCM. The organic phase was washed with 10% aqueous sodium carbonate and 1 N aqueous sodium hydroxide, dried over anhydrous sodium sulfate, filtered and concentrated.

The crude product was dissolved in DCM (100 mL) and a 2 M solution of trimethylaluminum in toluene (41.4 ml, 83 mmol) was added dropwise. The resulting mixture was stirred at ambient temperature for 17 hours, cooled to 0° C., and 1 N HCl (21.40 mL, 21.40 mmol) was added dropwise. After stirring at ambient temperature, the aqueous solution was extracted with DCM. The pH of the aqueous phase was adjusted to pH>10 with 10 N aqueous sodium hydroxide and extracted with DCM. The combined organic extracts were washed with brine, dried over anhydrous sodium sulfate, filtered, and concentrated. The crude product was purified by silica-gel chromatography to afford the title compound (15.83 g, 37.9 mmol, 73.3% yield) as a pale yellow solid.

Example 8

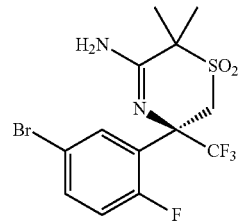 [SMILES: CC1(C)C(N)=N[C@](c2cc(Br)ccc2F)(C(F)(F)F)CS1(=O)=O]

Synthesis of (R)-5-amino-3-(5-bromo-2-fluorophenyl)-6,6-dimethyl-3-(trifluoromethyl)-3,6-dihydro-2H-1,4-thiazine 1,1-dioxide The title compound was prepared as described for Example 7, substituting (S)-2-methylpropane-2-sulfinamide for the (R) isomer in step 2. LC/MS (ESI$^+$) m/z=417, 419 (M+H; 2 bromine isotopes).

Example 9

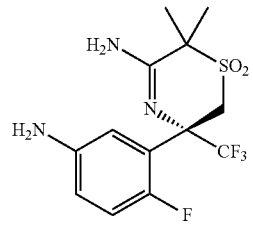 [SMILES: CC1(C)C(N)=N[C@@](c2cc(N)ccc2F)(C(F)(F)F)CS1(=O)=O]

Synthesis of (S)-5-amino-3-(5-amino-2-fluorophenyl)-6,6-dimethyl-3-(trifluoromethyl)-3,6-dihydro-2H-1,4-thiazine 1,1-dioxide To a mixture of (S)-5-amino-3-(5-bromo-2-fluorophenyl)-6,6-dimethyl-3-(trifluoromethyl)-3,6-dihydro-2H-1,4-thiazine 1,1-dioxide (7.0 g, 16.8 mmol), sodium azide (3.27 g, 50.3 mmol), copper (I) iodide (0.639 g, 3.36 mmol) and (+)-sodium 1-ascorbate (0.33 g, 1.68 mmol), under a nitrogen atmosphere, were added (1R,2R)-(−)-N,N'-dimethylcyclohexane-1,2-diamine (0.794 mL, 5.03 mmol), ethanol (40 mL), and water (20 mL). The resulting mixture was stirred at reflux for 2 hours, quenched with a mixture of 9:1 saturated aqueous ammonium chloride/ammonium hydroxide, and extracted with ethyl acetate. The combined organic layers were washed with a 9:1 mixture of saturated aqueous ammonium chloride/ammonium hydroxide, dried over anhydrous sodium sulfate, filtered, and concentrated.

The crude product was dissolved in methanol (50 mL), and sodium borohydride (1.90 g, 50.3 mmol) was added in small portions. The reaction was stirred at RT for 1 hour, carefully quenched with saturated aqueous ammonium chloride, and extracted with DCM. The organic layer was dried over anhydrous sodium sulfate, filtered, concentrated, and purified by silica-gel chromatography, eluting with 0-4% MeOH in DCM, to afford the title compound (2.0 g, 5.66 mmol, 33.7% yield) as an off-white solid. $^1$H NMR (300 MHz, DMSO-d$_6$) δ ppm 1.42 (s, 3H) 1.63 (s, 3H) 3.81-4.05

(m, 2H) 4.93 (s, 2H) 6.45-6.57 (m, 1H) 6.68 (br. s., 2H) 6.75-6.88 (m, 2H). LC/MS (ESI⁺) m/z=354 (M+H).

Example 10

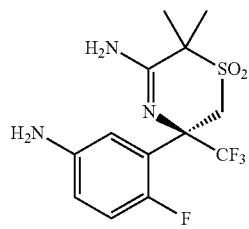 [SMILES: CC1(C)C(N)=N[C@](c2cc(N)ccc2F)(C(F)(F)F)CS1(=O)=O]

Synthesis of (R)-5-amino-3-(5-amino-2-fluorophenyl)-6,6-dimethyl-3-(trifluoromethyl)-3,6-dihydro-2H-1,4-thiazine 1,1-dioxide The title compound was prepared from (S)-5-amino-3-(5-bromo-2-fluorophenyl)-6,6-dimethyl-3-(trifluoromethyl)-3,6-dihydro-2H-1,4-thiazine 1,1-dioxide as described for Example 9. $^1$H NMR (300 MHz, DMSO-$d_6$) δ ppm 1.42 (s, 3H) 1.63 (s, 3H) 3.80-4.06 (m, 2H) 4.93 (s, 2H) 6.52 (m, J=8.60, 3.40, 3.40 Hz, 1H) 6.67 (br. s., 2H) 6.76-6.88 (m, 2H). LC/MS (ESI⁺) m/z=354 (M+H).

Example 11

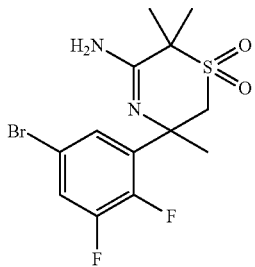 [SMILES: CC1(c2cc(Br)cc(F)c2F)CS(=O)(=O)C(C)(C)C(N)=N1]

Synthesis of R,S-5-Amino-3-(5-bromo-2,3-difluorophenyl)-3,6,6-trimethyl-3,6-dihydro-2H-1,4-thiazine 1,1-dioxide Step 1: 5-Bromo-2,3-difluoro-N-methoxy-N-methylbenzamide To a solution of 5-bromo-2,3-difluorobenzoic acid (5.00 g, 21.10 mmol) in DCM (68 mL) and DMF (0.686 mL, 8.86 mmol), cooled to 0° C., was added oxalyl chloride (5.54 mL, 63.3 mmol) dropwise via syringe, and the reaction mixture was stirred at 0° C. for 15 minutes then warmed to 18° C. and stirred for 1 hour. The reaction mixture was concentrated, and the residue was dissolved in DCM (58 mL). To this solution was added N,O-dimethyl hydroxylamine HCl (4.12 g, 42.2 mmol). The mixture was cooled to 0° C., and TEA (14.70 mL, 105 mmol) and 4-dimethylaminopyridine (0.103 g, 0.844 mmol) were added. The reaction was stirred for 1.5 hours at 0° C., and then quenched with 1 N aq. HCl (20 mL) at 0° C. The mixture was diluted with DCM, washed with water and brine, dried over anhydrous sodium sulfate, filtered, and concentrated to yield the title intermediate (5.91 g, 21.10 mmol, 100% yield) as a light orange crystalline solid. LC/MS (ESI⁺) m/z=280, 282 (M+H; 2 bromine isotopes).

Step 2: 1-(5-Bromo-2,3-difluorophenyl)ethanone

To a solution of 5-bromo-2,3-difluoro-N-methoxy-N-methylbenzamide (5.91 g, 21.10 mmol) in THF (75 mL) at −78° C. was added 3 M methylmagnesium bromide in diethyl ether (21.10 mL, 63.3 mmol) dropwise via an addition funnel. The mixture was slowly warmed to 0° C. then stirred for 30 minutes. The reaction mixture was quenched with 1 N aq. HCl (40 mL) at 0° C. and diluted with water and ethyl acetate. The mixture was filtered through a pad of Celite®, and the filtrate was washed with 1 N aq. HCl and brine. The organic layer was dried over sodium sulfate and concentrated to yield the title compound (4.70 g, 20.0 mmol, 95% yield) as a yellow crystalline solid. LC/MS (ESI⁺) m/z=235, 237 (M+H; 2 bromine isotopes).

Step 3: (E)-N-(1-(5-Bromo-2,3-difluorophenyl)ethylidene)-2-methylpropane-2-sulfinamide To a solution of 1-(5-bromo-2,3-difluorophenyl)ethanone (4.70 g, 20.00 mmol) in 2-methyltetrahydrofuran (40 mL) was added 2-methyl-2-propanesulfinamide (2.67 g, 22.00 mmol) and titanium (IV) ethoxide (10.48 mL, 50.0 mmol). The reaction mixture was heated at 70° C. for 4.5 hours, cooled to room temperature, and poured onto ice. DCM was added and the slurry was stirred vigorously at RT until the ice melted. The mixture was filtered through a pad of Celite®, which was rinsed with DCM. The combined organic filtrates were washed with water and brine and concentrated. The crude product was purified by silica gel chromatography, eluting with 1-100% ethyl acetate in heptane, to afford the title intermediate (5.85 g, 17.30 mmol, 86% yield) as a yellow oil. LC/MS (ESI⁺) m/z=338, 340 (M+H; 2 bromine isotopes).

Step 4: N-(2-(5-bromo-2,3-difluorophenyl)-1-((2-cyanopropan-2-yl)sulfonyl)propan-2-yl)-2-methylpropane-2-sulfinamide To a solution of 2-methyl-2-(methylsulfonyl)propanenitrile (4.13 g, 28.1 mmol) in THF (50 mL) at −78° C. was added a solution of 1.6 M n-butyllithium in hexane (17.56 mL, 28.1 mmol) dropwise via an addition funnel. The mixture was stirred at −78° C. for 45 minutes. A separate solution of (E)-N-(1-(5-bromo-2,3-difluorophenyl)ethylidene)-2-methylpropane-2-sulfinamide (4.75 g, 14.04 mmol) in toluene (50 mL) was cooled to −78° C. and 2.0M trimethylaluminum in toluene (7.02 mL, 14.04 mmol) was added dropwise via syringe. After stirring for 10 minutes, this solution was added to the 2-methyl-2-(methylsulfonyl) propanenitrile solution dropwise via cannula. The final reaction mixture was stirred at −78° C. for 2.5 hours. The reaction was quenched with water (40 mL) at −78° C. then warmed to room temperature. The mixture was diluted with ethyl acetate and washed with water and brine. The organic layer was concentrated, and the crude was purified by silica gel chromatography, eluting with 0-100% ethyl acetate in heptanes, to afford the title compound (5.94 g, 12.24 mmol, 87% yield) as a white waxy solid.

LC/MS (ESI+) m/z=485, 487 (M+H; 2 bromine isotopes).

Step 5: 2-((2-Amino-2-(5-bromo-2,3-difluorophenyl)propyl)sulfonyl)-2-methylpropanenitrile hydrochloride To a solution of N-(2-(5-bromo-2,3-difluorophenyl)-1-((2-cyanopropan-2-yl)sulfonyl)propan-2-yl)-2-methylpropane-2-sulfinamide (5.94 g, 12.24 mmol) in methanol (24 mL) at 0° C. was added 4 N HCl in dioxane (18.36 mL, 73.4 mmol). The reaction mixture was warmed to 18° C. and stirred for 2 hours. The resulting precipitate was collected by vacuum filtration, washed with ethyl acetate, and dried under high vacuum to yield the title intermediate (4.07 g, 9.74 mmol, 80% yield) as a white solid. LC/MS (ESI+) m/z=381, 383 (M+H; 2 bromine isotopes).

Step 6: 5-Amino-3-(5-bromo-2,3-difluorophenyl)-3,6,6-trimethyl-3,6-dihydro-2H-1,4-thiazine 1,1-dioxide To a suspension of 2-((2-amino-2-(5-bromo-2,3-difluorophenyl)propyl)sulfonyl)-2-methylpropanenitrile hydrochloride (4.84 g, 11.59 mmol) in toluene (40 mL) was added 2 M trimethylaluminum in toluene (6.95 mL, 13.90 mmol). The mixture was heated at 100° C. for 2 hours, cooled to 0° C., and quenched with saturated aqueous sodium carbonate (8 mL). The reaction was diluted with ethyl acetate and extracted with EtOAc and DCM. The combined organic layers were dried over sodium sulfate, filtered and concentrated to yield the title compound (3.75 g, 9.84 mmol, 85% yield) as a pale yellow solid. LC/MS (ESI+) m/z=381, 383 (M+H; 2 bromine isotopes).

Intermediate 7

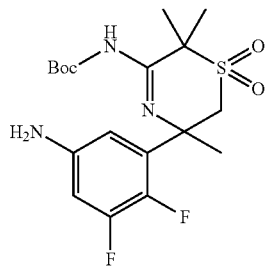 [SMILES: CC(C)(C)OC(=O)NC1=NC(C)(c2cc(N)cc(F)c2F)CS(=O)(=O)C1(C)C]

Synthesis of tert-Butyl (5-(5-amino-2,3-difluorophenyl)-2,2,5-trimethyl-1,1-dioxido-5,6-dihydro-2H-1,4-thiazin-3-yl)carbamate Using the sequence of steps described for Intermediate 2, 5-amino-3-(5-bromo-2,3-difluorophenyl)-3,6,6-trimethyl-3,6-dihydro-2H-1,4-thiazine 1,1-dioxide (0.100 g, 0.262 mmol) was converted to the title compound in 65% yield as a white solid. LC/MS (ESI+) m/z=418 (M+H).

Example 12

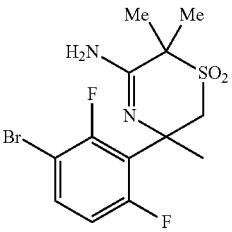 [SMILES: CC1(c2c(F)ccc(Br)c2F)CS(=O)(=O)C(C)(C)C(N)=N1]

Synthesis of R,S-5-Amino-3-(3-bromo-2,6-difluorophenyl)-3,6,6-trimethyl-3,6-dihydro-2H-1,4-thiazine 1,1-dioxide

Step 1: 1-(3-Bromo-2,6-difluorophenyl)ethanol

To a solution of 3-bromo-2,6-difluorobenzaldehyde (6.70 g, 30.3 mmol) in THF (100 mL) at −78° C. was added an ether solution of methylmagnesium bromide (3.0 M, 14.15 mL, 42.4 mmol) dropwise over 5 minutes. The reaction was stirred at −78° C. for 30 minutes, then at 0° C. for 1.5 hours. The reaction was quenched with 50 mL of saturated aqueous ammonium chloride and diluted with 600 mL of 7:3 EtOAc/hexane. The organic layer was separated and extracted with brine, dried over anhydrous magnesium sulfate and concentrated to afford the crude title intermediate (7.2 g, quantitative), which was used in the next step without further purification. $^1$H NMR in CDCl$_3$ δ: 7.43 (ddd, 1H, J=8.9, 7.8, 5.7), 6.82 (td, 1H, J=9.3, 9.3, 1.8), 5.26 (quintet, 1H, J=7.6), 2.20 (m, 1H), 1.64 (d, 3H, J=6.7).

Step 2: 1-(3-Bromo-2,6-difluorophenyl)ethanone

To a solution of 1-(3-bromo-2,6-difluorophenyl)ethanol (7.20 g, 30.4 mmol) in DCM (250 mL) was added water (0.657 mL, 36.4 mmol), followed by Dess-Martin periodinane (19.32 g, 45.6 mmol) in portions over 3 minutes. The resulting thick white suspension was stirred at RT for 2 hours. The reaction was filtered through a Celite pad, which was rinsed with dichloromethane. The filtrate was extracted with 1 M aqueous sodium carbonate and 10% aqueous sodium sulfite, dried over anhydrous magnesium sulfate, and concentrated. The residue was purified by silica gel chromatography, eluting with 11% ethyl acetate in hexanes, to afford the title compound (6.198 g, 26.4 mmol). $^1$H NMR in CDCl3 δ: 7.61 (ddd, 1H, J=8.9, 7.6, 5.8), 6.90 (td, 1H, J=8.9, 8.9, 1.6), 2.61 (s, 3H).

Step 3: (±)-(E)-N-(1-(3-Bromo-2,6-difluorophenyl)ethylidene)-2-methylpropane-2-sulfinamide To a solution of 1-(3-bromo-2,6-difluorophenyl)ethanone (6.198 g, 26.4 mmol) and 2-methylpropane-2-sulfinamide (3.36 g, 27.7 mmol) in THF (60 mL) was added titanium (IV) ethoxide (13.67 mL, 65.9 mmol), and the reaction was stirred at 70° C. for 2 days. The reaction was poured into saturated brine (250 mL), and the resulting suspension was filtered through a Celite pad, which was rinsed with ethyl acetate. The phases of the filtrate were separated, and the organic layer was washed with brine, dried over anhydrous magnesium sulfate, and concentrated. The crude product was purified by silica gel chromatography, eluting with 16% ethyl acetate in hexanes, to provide the title compound (5.927 g, 17.52 mmol). MS m/z=338, 340 (M+H; 2 bromine isotopes). ¹H NMR in CDCl₃ showed an approximately 1:1 ratio of (E) and (Z)-isomers δ: 7.53 (m, 1H), 6.86 (m, 1H), 2.70 (s, 1.5H), 2.48 (s, 1.5H), 1.31 (s, 4.5H), 1.25 (s, 4.5H).

Step 4: N-(2-(3-bromo-2,6-difluorophenyl)-1-((2-cyanopropan-2-yl)sulfonyl)propan-2-yl)-2-methyl-propane-2-sulfinamide To a solution of 2-methyl-2-(methylsulfonyl)propanenitrile (1.78 g, 12.09 mmol) in THF in (13 mL) at −78° C. was added 2,2,6,6-tetramethylpiperidinylmagnesium chloride lithium chloride complex (1 M in tetrahydrofuran, 12.0 mL, 12.0 mmol) dropwise. Immediately after the addition, a solution of (E)-N-(1-(3-bromo-2,6-difluorophenyl)ethylidene)-2-methylpropane-2-sulfinamide (2.27 g, 6.71 mmol) in toluene (15 mL) at −78° C. was added dropwise. The reaction mixture was stirred at −78° C. for 1 hour and quenched with saturated ammonium chloride. The mixture was warmed to room temperature and partitioned between EtOAc and water. The aqueous phase was extracted with ethyl acetate, and the combined organic extracts were washed with brine, dried over anhydrous magnesium sulfate, filtered, and concentrated. The crude product was purified by silica-gel chromatography, eluting with 30-70% ethyl acetate in heptanes, to provide the title intermediate (2.27 g, 6.71 mmol, 24% yield) as a white solid.

Step 5: 2-((2-amino-2-(3-bromo-2,6-difluorophenyl) propyl)sulfonyl)-2-methylpropanenitrile hydrochloride To a solution of N-(2-(3-bromo-2,6-difluorophenyl)-1-((2-cyanopropan-2-yl)sulfonyl)propan-2-yl)-2-methylpropane-2-sulfinamide (0.392 g, 0.808 mmol) in DCM (3 mL) at RT was added hydrogen chloride (1 M in diethyl ether, 3.0 mL, 3.0 mmol). The reaction mixture was stirred at RT for 20 min, diluted with hexanes, and partially concentrated until a precipitate formed. The precipitate was collected by filtration, washed with hexanes, and dried under high vacuum to give the title intermediate (0.321 g, 0.768 mmol, 95% yield) as a white solid.

Step 6: 5-amino-3-(3-bromo-2,6-difluorophenyl)-3,6,6-trimethyl-3,6-dihydro-2H-1,4-thiazine 1,1-dioxide To a suspension of 2-((2-amino-2-(3-bromo-2,6-difluorophenyl)propyl)sulfonyl)-2-methylpropanenitrile hydrochloride (0.310 g, 0.742 mmol) in toluene (3.7 mL) at RT was added trimethylaluminum (2 M in toluene, 0.450 mL, 0.900 mmol). The reaction mixture was stirred at RT for 30 minutes and then heated to 70° C. After 40 minutes, the solution was cooled to 0° C., quenched with saturated aqueous sodium bicarbonate, and partitioned between ethyl acetate and water. The aqueous phase was extracted with ethyl acetate, and the combined organic extracts were washed with brine, dried over anhydrous magnesium sulfate, filtered, and concentrated. The crude product was purified by silica-gel chromatography, eluting with 3.5% methanol in dichloromethane, to provide the title compound (0.184 g, 0.483 mmol, 65% yield) as a white solid. ¹H-NMR (400 MHz, DMSO-d₆): δ 7.66 (ddd, J=8.8, 7.7, 5.5 Hz, 1H), 7.03 (ddd, J=11.9, 8.8, 1.3 Hz, 1H), 5.93 (s br, 2H), 3.64 (d, J=15.0 Hz, 1H), 3.55 (d, J=15.1 Hz, 1H), 1.75 (s, 3H), 1.58 (s, 3H), 1.51 (s, 3H). LC/MS (ESI⁺) m/z=383, 385 (M+H; 2 bromine isotopes).

Example 13

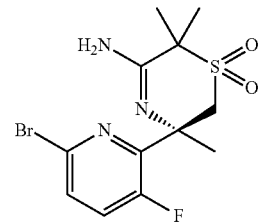 [SMILES: CC1(C)C(N)=N[C@](C)(c2nc(Br)ccc2F)CS1(=O)=O]

Synthesis of (R)-5-Amino-3-(6-bromo-3-fluoropyridin-2-yl)-3,6,6-trimethyl-3,6-dihydro-2H-1,4-thiazine 1,1-dioxide Step 1. 1-(6-Bromo-3-fluoropyridin-2-yl)ethanol To a solution of 6-bromo-3-fluoro-2-formylpyridine (1.05 g, 5.15 mmol) in THF (15 mL) at −78 C was added dropwise methylmagnesium bromide, 3 M solution in diethyl ether (2.5 mL). The reaction was allowed to gradually warm up to RT and stirred overnight. To this was added solid ammonium chloride (5 g) and water (0.5 mL). The slurry was dried over Na₂SO₄, filtered, and concentrated to give the title intermediate (1.13 g, 5.14 mmol).

Step 2. 1-(6-Bromo-3-fluoropyridin-2-yl)ethanone

To a solution of 1-(6-bromo-3-fluoropyridin-2-yl)ethanol (1.13 g, 5.14 mmol) in dichloromethane (20 mL) was added manganese (IV) oxide (2.68 g, 30.8 mmol). After stirring at RT overnight, the solvent was evaporated. The residue was redissolved in toluene (15 mL), manganese (IV) oxide (2 g) was added, and the reaction was heated at 100° C. for 1 hour. The mixture was then filtered through a silica gel pad, which was washed with ethyl acetate. The filtrate was concentrated to provide the title compound (1.2 g) as a yellow oil which was used directly in the next step.

Step 3. (R)—N-(1-(6-Bromo-3-fluoropyridin-2-yl) ethylidene)-2-methylpropane-2-sulfinamide To a solution of 1-(6-bromo-3-fluoropyridin-2-yl)ethanone (1.1 g, 5.05 mmol) and (R)-2-methylpropane-2-sulfinamide (1.223 g, 10.09 mmol) in THF (30 mL) was added titanium (IV) ethoxide (2.61 mL, 12.61 mmol) and the reaction was stirred at 80° C. for 4 hours. After cooling to RT, 5 g of solid sodium bicarbonate was added, followed by 0.5 mL of water. After stirring at RT for 30 minutes, the resulting slurry was filtered, and the precipitate was rinsed with EtOAc. The filtrate was concentrated and the residue was purified by silica-gel chromatography, eluting with 0-25% ethyl acetate in DCM, to give the title intermediate (850 mg, 2.65 mmol). ¹H NMR (400 MHz, CDCl₃) δ 7.54 (dd, J=3.0, 8.5 Hz, 1H), 7.37 (t, J=9.1 Hz, 1H), 2.81 (s, 3H), 1.32 (s, 9H)

Step 4. (R)-2-((2-Amino-2-(6-bromo-3-fluoropyridin-2-yl)propyl)sulfonyl)-2-methylpropanenitrile To a solution of 2-methyl-2-(methylsulfonyl)propanenitrile (532 mg, 3.62 mmol) (azeotroped with toluene) in THF (10 mL) at −78° C. was added n-butyllithium, 1.6 M in hexanes (1.45 mL, 3.62 mmol). The reaction was stirred −78° C. for 20 minutes, and then a solution of (R)—N-(1-(6-bromo-3-fluoropyridin-2-yl)ethylidene)-2-methylpropane-2-sulfinamide (830 mg, 2.58 mmol) in toluene (10 mL) at −78° C., which had been pretreated with a 2 M solution of trimethylaluminum in toluene (1.29 mL, 2.58 mmol) for 10 minutes, was added dropwise. The reaction was stirred at −78° C. for 3 hours, and then quenched with saturated aqueous ammonium chloride and extracted with ethyl acetate. The combined organics were dried over sodium sulfate, filtered, concentrated, and purified by silica-gel chromatography, eluting with 10-20% ethyl acetate in dichloromethane. The isolated product was dissolved in methanol (5 mL) of and treated with 4 N hydrogen chloride in dioxane (2 mL, 8 mmol). After stirring overnight, the solvents were evaporated, and the residue was redissolved in ethyl acetate and washed with saturated aqueous sodium bicarbonate, dried over sodium sulfate, filtered and evaporated to provide the title intermediate (190 mg, 0.522 mmol).

Step 5. (R)-5-amino-3-(6-bromo-3-fluoropyridin-2-yl)-3,6,6-trimethyl-3,6-dihydro-2H-1,4-thiazine 1,1-dioxide To a solution of (R)-2-((2-amino-2-(6-bromo-3-fluoropyridin-2-yl)propyl)sulfonyl)-2-methylpropanenitrile (160 mg, 0.439 mmol) in toluene (10 mL) was added a 2 M solution of trimethylaluminum in toluene (439 μL, 0.879 mmol) and the reaction was stirred at RT overnight. The solvent was evaporated, and the residue was purified by silica-gel chromatography, eluting with 2-5% methanol in DCM, to provide the title compound (80 mg, 0.22 mmol). LC/MS (ESI$^+$) m/z 364, 366 (M+H; 2 bromine isotopes).

Example 14

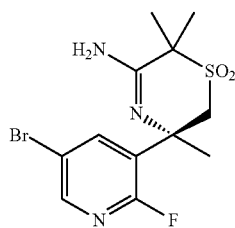 [SMILES: CC1(C)C(N)=N[C@](C)(c2cc(Br)cnc2F)CS1(=O)=O]

Synthesis of (R)-5-Amino-3-(5-bromo-2-fluoropyridin-3-yl)-3,6,6-trimethyl-3,6-dihydro-2H-1,4-thiazine 1,1-dioxide Step 1: 1-(5-Bromo-2-fluoropyridin-3-yl)ethanol To a solution of 5-bromo-2-fluoronicotinaldehyde (10 g, 49.0 mmol) in tetrahydrofuran (100 mL) at −78° C. was added a 3 M solution of methylmagnesium bromide in diethyl ether (24.51 ml, 73.5 mmol) dropwise. After the addition, the reaction was warmed slowly to RT and stirred for 17 hours. The mixture was quenched with saturated aqueous ammonium chloride and extracted with EtOAc. The combined organic layers were washed with brine, dried over anhydrous sodium sulfate, filtered, and concentrated. The crude product was purified by silica-gel chromatography, eluting with 0-10% EtOAc in hexanes, to afford the title compound (10.80 g, 49.1 mmol) as a yellow oil.

Step 2: 1-(5-Bromo-2-fluoropyridin-3-yl)ethanone

To a solution of pyridinium dichromate (55.4 g, 147 mmol) in dichloromethane (100 mL) at 0° C. was added of 1-(5-bromo-2-fluoropyridin-3-yl)ethanol (10.80 g, 49.1 mmol) in dichloromethane (30 mL). The reaction was allowed to warm up to RT and stirred for two days. The mixture was filtered through Celite®, washed with DCM, and concentrated to afford the title intermediate (11 g) as a light yellow solid.

Step 3: (R)-5-Amino-3-(5-bromo-2-fluoropyridin-3-yl)-3,6,6-trimethyl-3,6-dihydro-2H-1,4-thiazine 1,1-dioxide In an analogous sequence of reactions to those described for Example 7, steps 1-4, 1-(5-bromo-2-fluoropyridin-3-yl)ethanone (11 g, 50.5 mmol) was converted to the title compound in 20% yield. LC/MS (ESI$^+$) m/z=364, 366 (M+H; 2 bromine isotopes).

Example 15

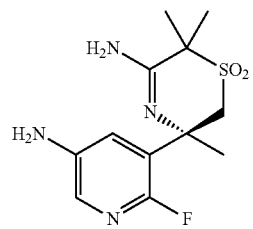 [SMILES: CC1(C)C(N)=N[C@](C)(c2cc(N)cnc2F)CS1(=O)=O]

Synthesis of (R)-5-Amino-3-(5-amino-2-fluoropyridin-3-yl)-3,6,6-trimethyl-3,6-dihydro-2H-1,4-thiazine 1,1-dioxide In an analogous reaction to that described for Example 9, (R)-5-amino-3-(5-bromo-2-fluoropyridin-3-yl)-3,6,6-trimethyl-3,6-dihydro-2H-1,4-thiazine 1,1-dioxide (1.0 g, 2.75 mmol) was converted to the title compound (0.172 g, 0.573 mmol) as a yellow-green oil. LC/MS (ESI$^+$) m/z=301 (M+H).

Example 16

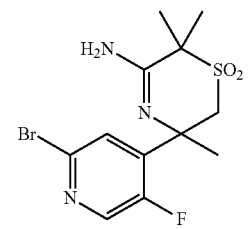 [SMILES: CC1(c2cc(Br)ncc2F)CS(=O)(=O)C(C)(C)C(N)=N1]

Synthesis of 5-amino-3-(2-bromo-5-fluoropyridin-4-yl)-3,6,6-trimethyl-3,6-dihydro-2H-1,4-thiazine 1,1-dioxide In an analogous sequence of reactions to those described for Example 7, steps 1-4, 1-(2-bromo-5-fluoropyridin-4-yl)ethanone (11.63 g, 53.3 mmol) was converted to the title compound in 40% yield. $^1$H NMR (400 MHz, CDCl$_3$) δ 8.19 (d, J=2.93 Hz, 1H), 7.61 (s, 1H), 4.70 (br. s., 2H), 3.44-3.61 (m, 2H), 1.68-1.82 (m, 6H), 1.61 (s, 3H). LC/MS (ESI$^+$) m/z=364, 366 (M+H; 2 bromine isotopes).

Intermediate 8

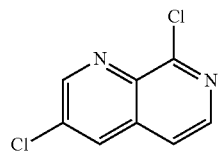 [SMILES: Clc1cnc2c(Cl)nccc2c1]

Synthesis of 3,8-Dichloro-1,7-naphthyridine

Step 1: 3-Bromo-5-chloropicolinonitrile

A microwave vial was charged with copper (I) cyanide (1.089 g, 12.16 mmol), 2,3-dibromo-5-chloropyridine (3 g, 11.06 mmol), and propionitrile (15 mL). The vial was capped and irradiated in a microwave reactor at 150° C. for 2.5 hours. The solution was concentrated, diluted with DCM (25 mL), and filtered. The filtrate was concentrated, and the residue was purified by silica gel chromatography, eluting with 0-30% EtOAc in heptanes, to afford the title compound (2 g, 9.20 mmol). MS m/z=219 (M+H).

Step 2: 5-Chloro-3-((trimethylsilyl)ethynyl)picolinonitrile

A pressure vessel was charged with triethylamine (7.65 mL, 55.2 mmol), ethynyltrimethylsilane (2.32 mL, 16.6 mmol), copper (I) iodide (0.263 g, 1.380 mmol), palladium (0) tetrakis(triphenylphosphine) (0.558 g, 0.483 mmol), 3-bromo-5-chloropicolinonitrile (3.0 g, 13.8 mmol), and N,N-dimethylformamide (50 ml). The vessel was flushed with argon, sealed, stirred at ambient temperature for 15 minutes, and then heated at 50° C. for 4 hours. The solution was diluted with water and extracted with ethyl acetate. The combined organic layers were concentrated, and the residue was purified by silica-gel chromatography, eluting 0-50% ethyl acetate in hexane, to afford the title compound (1.3 g, 5.5 mmol). MS m/z=235 (M+H).

Step 3: 5-Chloro-3-(2,2-dimethoxyethyl)picolinonitrile

A pressure vessel was charged with 5-chloro-3-((trimethylsilyl)ethynyl)picolinonitrile (2 g, 8.52 mmol) and sodium methoxide (0.5 M in methanol, 42.6 mL, 21.30 mmol), sealed, and stirred at 55° C. for one hour. The solution was concentrated, and the residue was purified via silica gel chromatography, eluting with 10% methanol in DCM to afford the title compound (1.7 g, 7.50 mmol). MS m/z=227 (M+H).

Step 4: 3-Chloro-1,7-naphthyridin-8(7H)-one

To a solution of 5-chloro-3-(2,2-dimethoxyethyl)picolinonitrile (1.7 g, 7.50 mmol) in acetone (50 mL) and water (150 mL) was added aqueous saturated sodium carbonate (37.5 mL, 113 mmol) and 30% aqueous hydrogen peroxide (38.3 mL, 375 mmol). The reaction was stirred at RT for one hour, concentrated to remove most of the acetone, and extracted with dichloromethane. The combined organic layers were concentrated.

To a solution of this intermediate (1.8 g, 7.36 mmol) in benzene (20 mL) was added p-toluenesulfonic acid (0.350 g, 1.839 mmol) and the reaction was sonicated for 10 minutes. The solution was stirred overnight at 80° C. and concentrated. The crude product was purified via silica gel, eluting with 0-100% (80/20/1 ethyl acetate/methanol/ammonium hydroxide) in ethyl acetate, to the title intermediate (1.1 g, 6.1 mmol). MS m/z=181 (M+H).

Step 5: 3,8-Dichloro-1,7-naphthyridine

A suspension of -chloro-1,7-naphthyridin-8(7H)-one (250 mg, 1.384 mmol) in phosphorus oxychloride (1.94 mL, 20.8 mmol) was stirred at 95° C. for one hour. The solution was concentrated to afford the title compound (276 mg, 1.39 mmol). MS m/z=199 (M+H).

Intermediate 9

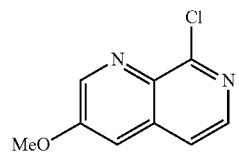 [SMILES: COc1cnc2c(Cl)nccc2c1]

Synthesis of 8-Chloro-3-methoxy-1,7-naphthyridine

Step 1: 3-chloro-5-methoxypicolinonitrile

To a solution of 3,5-dichloropicolinonitrile (22.5 g, 130 mmol) in DMF (500 mL) at 0° C. was added sodium methoxide (6.67 g, 124 mmol) slowly. The reaction was stirred for 5 minutes at 0° C., then allowed to warm to RT and stir for 30 minutes. The solution was partitioned between water and EtOAc. The organic layer was washed with water and concentrated. The crude product was purified via silica gel chromatography, eluting with 0-75% ethyl acetate in heptanes, to afford a 1:1 ratio of the desired isomer 3-chloro-5-methoxypicolinonitrile and 5-chloro-3-methoxypicolinonitrile (7.0 g, 41.5 mmol). The material was used without further purification. MS m/z=169 (M+H).

Step 2: 5-Methoxy-3-((triethylsilyl)ethynyl)picolinonitrile

A sealed vessel was charged with bis(acetonitrile)palladium (II) chloride (0.154 g, 0.593 mmol), dicyclohexyl(2',4',6'-triisopropyl-[1,1'-biphenyl]-2-yl)phosphine (0.848 g, 1.780 mmol), cesium carbonate (25.1 g, 77 mmol), the product of Intermediate 9, step 1 (5 g, 29.7 mmol), and ACN (60 mL). The vessel was flushed with argon, sealed, and stirred at RT for 25 minutes. To the reaction was added triethyl(ethynyl)silane (5.41 g, 38.6 mmol), and the vessel was resealed and stirred at 90° C. for 3 hours. The solution was concentrated, and the residue was purified via silica gel chromatography, eluting with 0-50% ethyl acetate in heptanes, to afford the title compound (3.8 g, 13.9 mmol). MS m/z=273 (M+H).

Step 3: 3-(2,2-Dimethoxyethyl)-5-methoxypicolinonitrile

A pressure vessel was charged with 5-methoxy-3-((triethylsilyl)ethynyl)picolinonitrile (3.8 g, 13.95 mmol) and sodium methoxide (0.5 M in methanol, 69.7 mL, 34.9 mmol). The vessel was sealed and stirred at 55° C. for 2 hours. The reaction was concentrated to afford the title intermediate (3.1 g, 13.95 mmol).

Step 4: 8-chloro-3-methoxy-1,7-naphthyridine

Using an analogous sequence of reactions to those described in Intermediate 8, steps 4-5, 3-(2,2-dimethoxyethyl)-5-methoxypicolinonitrile (3.4 g, 15.30 mmol) was converted to the title compound (552 mg, 2.84 mmol). MS m/z=195 (M+H).

Intermediate 10

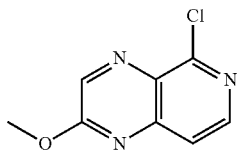

Synthesis of 5-Chloro-2-methoxypyrido[3,4-b]pyrazine

Step 1: 5-Chloropyrido[3,4-b]pyrazin-2(1H)-one

A suspension 2-chloropyridine-3,4-diamine (2.5 g, 17.41 mmol) and a 50% solution of ethyl glyoxalate in toluene (3.45 mL, 17.41 mmol) in ethanol (34.8 mL) was stirred at reflux for 24 hours. The solution was cooled to −20° C. for 16 hours, and the resulting precipitate was collected by vacuum filtration and rinsed with ethanol. The crude product was purified via reverse-phase HPLC, eluting with 5-50% acetonitrile/0.1% trifluoroacetic acid in water/0.1% trifluoroacetic acid, to afford the title compound (570 mg, 3.14 mmol). MS m/z=182 (M+H).

Step 2: 2,5-Dichloropyrido[3,4-b]pyrazine

A suspension of 5-chloropyrido[3,4-b]pyrazin-2(1H)-one (0.57 g, 3.14 mmol) in phosphorus oxychloride (10.24 mL, 110 mmol) was stirred at 110° C. for two hours, and then concentrated. The residue was dissolved in dichloromethane, washed with saturated sodium bicarbonate, dried over anhydrous sodium sulfate, filtered, and concentrated to afford the title compound (580 mg, 2.90 mmol). MS m/z=200 (M+H).

Step 3: 5-Chloro-2-methoxypyrido[3,4-b]pyrazine

To a solution of 2,5-dichloropyrido[3,4-b]pyrazine (580 mg, 2.90 mmol) in N,N-dimethylformamide (10 mL) was added a 0.5-M solution of sodium methoxide in methanol (6.09 mL, 3.04 mmol), and the reaction was stirred at room temperature for 5 minutes. The solution was diluted with water and extracted with ethyl acetate. The organic layer was dried with sodium sulfate, filtered and concentrated to afford the title compound (550 mg, 2.81 mmol). MS m/z=196 (M+H).

Intermediate 11

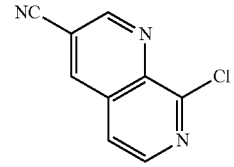 [SMILES: N#Cc1cnc2c(Cl)nccc2c1]

Synthesis of 8-Chloro-1,7-naphthyridine-3-carbonitrile

A screw-cap vial was charged with 3-chloro-1,7-naphthyridin-8(7H)-one (100 mg, 0.554 mmol), zinc cyanide (52.7 µL, 0.831 mmol), 2-dicyclohexylphosphino-2',6'-dimethoxybiphenyl (45.5 mg, 0.111 mmol), tris(dibenzylideneacetone)dipalladium(0) (40.6 mg, 0.044 mmol), DMF (2.74 mL) and water (28 µL). The vial was purged with argon, sealed, and stirred at 110° C. for 1 hour. The mixture was filtered through a pad of Celite, which was rinsed with methanol and dimethylsulfoxide. The combined filtrates were concentrated, and a few drops of water were added. The resulting solids were collected by vacuum filtration, rinsed with water and dried.

The solids were suspended in toluene (3.5 mL), and phosphorus oxychloride (98 µL, 1.052 mmol) and DIPEA (122 µL, 0.701 mmol) were added. The reaction was stirred at 120° C. for 1.5 hours, cooled to RT, diluted with EtOAc, and washed with 2 M aqueous sodium carbonate. The organic portion was dried over anhydrous sodium sulfate, filtered and concentrated. The crude material was purified by silica gel chromatography, eluting with 5-50% EtOAc in heptanes, to provide the title compound (50 mg, 0.264 mmol) as a white solid. LC/MS (ESI⁺) m/z=190 (M+H).

Intermediate 12

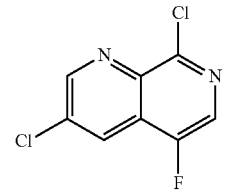 [SMILES: Fc1cnc(Cl)c2ncc(Cl)cc12]

Synthesis of 3,8-Dichloro-5-fluoro-1,7-naphthyridine

Step 1: 3-chloro-5-fluoro-6-methoxy-6,7-dihydro-1,7-naphthyridin-8(5H)-one

A pressure bottle was charged with 3-chloro-1,7-naphthyridin-8(7H)-one (15 g, 83 mmol), methanol (34.6 mL), ACN (173 mL) and 1-chloromethyl-4-fluoro-1,4-diazoniabicyclo [2.2.2]octane bis(tetrafluoroborate) (30.9 g, 87 mmol), and the mixture was heated at 45° C. for 15 hours. Water and ethyl acetate were added, and the layers were separated. The aqueous portion was extracted twice with ethyl acetate and once with DCM, and the combined organic layers were dried with anhydrous sodium sulfate, filtered and concentrated. The crude solid was triturated with a minimum amount of ethyl acetate and filtered. The title intermediate was isolated as an off-white solid (15.34 g, 80%) as a 3:1 mixture of diastereomers.

Step 2: 3,8-dichloro-5-fluoro-1,7-naphthyridine

A vial was charged with 3-chloro-5-fluoro-6-methoxy-6,7-dihydro-1,7-naphthyridin-8(5H)-one (7.5 g, 32.5 mmol), acetonitrile (130 mL) and phosphorus oxychloride (9.09 mL, 98 mmol), and the mixture was stirred at 75° C. for 15 hours. The mixture was concentrated, and the crude material was purified by silica gel chromatography, eluting with 0-50% ethyl acetate in heptanes, to provide the title compound (5.57 g, 25.7 mmol, 79% yield) as a white solid. LC/MS (ESI$^+$) m/z=217 (M+H).

Intermediate 13

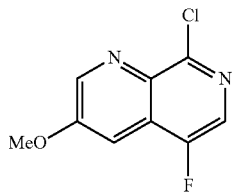 [SMILES: COc1cnc2c(Cl)ncc(F)c2c1]

Synthesis of
8-Chloro-5-fluoro-3-methoxy-1,7-naphthyridine

Using an analogous sequence of reactions to those described for Intermediate 12, 3-chloro-1,7-naphthyridin-8(7H)-one was converted to the title compound. LC/MS (ESI$^+$) m/z=213 (M+H).

Intermediate 14

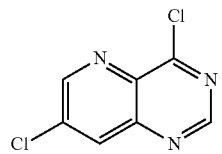 [SMILES: Clc1cnc2c(Cl)ncnc2c1]

Synthesis of 4,7-Dichloropyrido[3,2-d]pyrimidine

Step 1: 3-Amino-5-chloropicolinamide

To a suspension of 5-chloro-2-cyano-3-nitropyridine (1.274 mL, 10.9 mmol) in water (22 mL) was added 28% aqueous ammonium hydroxide (3.94 mL, 28.3 mmol), and the reaction was stirred at RT for 20 minutes. Sodium hydrosulfite (2.68 mL, 32.7 mmol) was added, and the reaction mixture was stirred at RT for 70 minutes. The yellow precipitate was collected by vacuum filtration to provide the title compound (1.097 g, 6.39 mmol) as yellow solid. $^1$H-NMR (400 MHz, DMSO-d$_6$): δ 7.88 (br. s, 1H), δ 7.73 (s, 1H), δ 7.39 (br. s, 1H), δ 7.23 (s, 1H), δ 7.06 (br. s, 2H). LC/MS (ESI$^+$) m/z=172 (M+H).

Step 2: 7-Chloropyrido[3,2-d]pyrimidin-4(1H)-one

A suspension of 3-amino-5-chloropicolinamide (1.1 g, 6.41 mmol) in triethyl orthoformate (15.99 mL, 96 mmol) was stirred at 155° C. for 22 hours. After cooling to RT, the yellow precipitate was collected by vacuum filtration and washed with hexanes to yield the title intermediate (1.03 g, 5.67 mmol) as a yellow solid. $^1$H NMR (400 MHz, DMSO-d$_6$) δ ppm 8.20 (s, 1H) 8.27 (d, J=2.35 Hz, 1H) 8.80 (d, J=2.25 Hz, 1H) 12.68 (br. s., 1H). LC/MS (ESI$^+$) m/z=182 (M+H).

Step 3: 4,7-Dichloropyrido[3,2-d]pyrimidine

To a mixture of 7-chloropyrido[3,2-d]pyrimidin-4(1H)-one (250 mg, 1.377 mmol) in toluene (12 mL) were added DIPEA (0.73 mL, 4.20 mmol) and phosphorus oxychloride (0.391 mL, 4.27 mmol), and the reaction was stirred at reflux for 1 hour. After cooling to RT, the reaction mixture was concentrated to provide the title compound. LC/MS (ESI$^+$) m/z=200 (M+H).

Intermediate 15

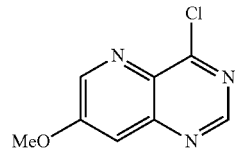 [SMILES: COc1cnc2c(Cl)ncnc2c1]

Synthesis of
4-Chloro-7-methoxypyrido[3,2-d]pyrimidine

Step 1:
7-Methoxypyrido[3,2-d]pyrimidin-4(1H)-one

A microwave vial was charged with 7-chloropyrido[3,2-d]pyrimidin-4(1H)-one (110 mg, 0.606 mmol), a 0.5 M solution of sodium methoxide in methanol (3.65 mL, 1.817 mmol) and sodium methoxide (327 mg, 6.06 mmol). The vial was capped and irradiated in a microwave reactor at 145° C. for 30 minutes. The reaction was neutralized with saturated aqueous ammonium chloride (3 mL), concentrated, and diluted with cold water. The resulting precipitate was collected by vacuum filtration and dried in vacuo to provide the title compound (107 mg, 0.604 mmol) as pink solid. $^1$H NMR (400 MHz, DMSO-d$_6$) δ ppm 3.95 (s, 3H) 7.49 (d, J=2.74 Hz, 1H) 8.11 (s, 1H) 8.47 (d, J=2.74 Hz, 1H). LC/MS (ESI$^+$) m/z=178 (M+H).

Step 2: 4-Chloro-7-methoxypyrido[3,2-d]pyrimidine

Using an analogous reaction to that described for Intermediate 14, step 3, 7-methoxypyrido[3,2-d]pyrimidin-4(1H)-one was converted to the title compound. LC/MS (ESI$^+$) m/z=196 (M+H).

Intermediate 16

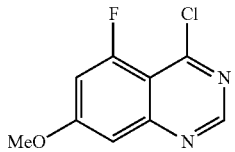 [SMILES: COc1cc(F)c2c(Cl)ncnc2c1]

Synthesis of
4-Chloro-5-fluoro-7-methoxyquinazoline

Step 1: 2-Amino-6-fluoro-4-methoxybenzonitrile

Ammonia gas was bubbled through a solution of 2,6-difluoro-4-methoxybenzonitrile (1.0 g, 5.91 mmol) in dimethylsulfoxide (11.83 mL) for 10 minutes. The reaction was then sealed and stirred at 90° C. for 24 hours. The reaction mixture was cooled to ambient temperature and concentrated in vacuo to afford a tan residue. The residue was triturated with water, collected be vacuum filtration, and dried in vacuo to afford the title intermediate (0.9 g, 5.42 mmol) as a white solid. LC/MS (ESI+) m/z=167 (M+H).

Step 2: 5-Fluoro-7-methoxyquinazolin-4-ol

To a mixture of formic acid (11.43 mL, 298 mmol) and sulfuric acid (0.866 mL, 16.25 mmol) was added 2-amino-6-fluoro-4-methoxybenzonitrile (0.9 g, 5.42 mmol) in portions. The reaction mixture was stirred at 100° C. for 1 hour, cooled to ambient temperature, and poured into 80 mL of an ice-water mixture. The resulting precipitate was collected by vacuum filtration and dried in vacuo to provide the title intermediate (0.8 g, 4.12 mmol) as an off-white solid. LC/MS (ESI+) m/z=195 (M+H).

Step 3: 4-Chloro-5-fluoro-7-methoxyquinazoline

To a suspension of 5-fluoro-7-methoxyquinazolin-4-ol (0.125 g, 0.644 mmol) in thionyl chloride (1.410 mL, 19.31 mmol) was added N,N-dimethylformamide (0.028 mL, 0.361 mmol). The reaction was stirred at 80° C. for 6 hours and concentrated in vacuo. The residue was suspended in saturated aqueous sodium bicarbonate and extracted with dichloromethane. The organic layer was concentrated in vacuo to generate the title compound (0.13 g, 0.611 mmol) as a yellow solid. LC/MS (ESI+) m/z=213 (M+H).

Intermediate 17

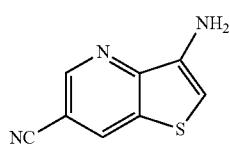 [SMILES: N#Cc1cnc2c(N)csc2c1]

Synthesis of
3-Aminothieno[3,2-b]pyridine-6-carbonitrile

Step 1: Sodium
(E)-2-cyano-3,3-dimethoxyprop-1-en-1-olate

To a suspension of NaH (60% dispersion in mineral oil, 2.52 g, 63.0 mmol) in diethylether (75 mL) was added 3,3-dimethoxypropanenitrile (6.17 mL, 55.0 mmol) followed by methyl formate (6.74 mL, 110 mmol). The solution was stirred for 3 days at RT. The resulting solid was collected by vacuum filtration and washed with ether to afford sodium (E)-2-cyano-3,3-dimethoxyprop-1-en-1-olate (4.2 g, 25.4 mmol).

Step 2: 3-Aminothieno[3,2-b]pyridine-6-carbonitrile

To a solution of sodium (E)-2-cyano-3,3-dimethoxyprop-1-en-1-olate (1012 mg, 6.13 mmol) in methanol (12 mL) was added concentrated hydrochloric acid (503 µL 6.13 mmol). The solution was stirred for 5 minutes, and then a solution of thiophene-3,4-diamine (700 mg, 6.13 mmol) in methanol (12 mL) was added. The solution was stirred at reflux for 3 hours, and then a solution of concentrated HCl (1.0 mL) in methanol (2 mL) was added. The reaction was stirred at reflux for an additional two hours, quenched with TEA (3 mL), and concentrated. The crude product was purified via silica gel chromatography, eluting with 0-100% ethyl acetate in heptanes, to provide the title compound (250 mg, 1.427 mmol). MS m/z=176 (M+H).

Intermediate 18

Synthesis of 3-Methoxy-1,7-naphthyridin-8-amine

Step 1: 3-Methoxy-N-(4-methoxybenzyl)-1,7-naphthyridin-8-amine

To a solution of 8-chloro-3-methoxy-1,7-naphthyridine (1 g, 5.14 mmol) in N,N-dimethylformamide (10.28 mL) was added potassium carbonate (1.42 g, 10.28 mmol) followed by 4-methoxybenzylamine (1.47 ml, 11.3 mmol). The reaction was stirred at 100° C. for 24 hours and then concentrated to generate a brown residue. This was partitioned between ethyl acetate and water. The organic layer was concentrated and purified by silica-gel chromatography, eluting with 1-5% methanol in DCM, to provide the title compound (1.37 g, 4.63 mmol) as a tan solid. LC/MS (ESI+) m/z=296 (M+H).

Step 2: 3-methoxy-1,7-naphthyridin-8-amine

To a solution of N-(4-methoxybenzyl)-1,7-naphthyridin-8-amine (340 mg, 1.15 mmol) in 1,2-dichloroethane (5.80 mL) was added TFA (2.67 mL, 34.5 mmol). The reaction was stirred at 75° C. for 8 hours and then concentrated. The residue was partitioned between DCM and aqueous sodium bicarbonate. The organic layer was concentrated and purified by silica-gel chromatography, eluting with 50-100% EtOAc in DCM, to provide the title compound (171.7 mg, 0.98 mmol) as an off-white solid. LC/MS (ESI⁺) m/z=176 (M+H).

Intermediate 19

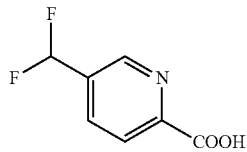 [SMILES: O=C(O)c1ccc(C(F)F)cn1]

Synthesis of 5-(Difluoromethyl)picolinic acid

Step 1: 5-Formylpicolinonitrile

A suspension of 2-bromo-5-formylpyridine (940 mg, 5.05 mmol) and copper (I) cyanide (233 μL, 7.58 mmol) in DMF (8.4 mL) was stirred at 120° C. for 1.5 hours, cooled to RT, and partitioned between water and EtOAc. The solids were removed from the aqueous layer by filtration, and the filtrate was extracted with ethyl acetate. The combined organic layers were washed with brine, dried over anhydrous magnesium sulfate, filtered and concentrated. The crude product was purified by silica-gel chromatography, eluting with a gradient of 40%-60% (40% ethyl acetate in heptane) in heptane, to provide the title compound (236 mg, 1.786 mmol) as white solid. LC/MS (ESI⁺) m/z=133 (M+H).

Step 2: 5-(Difluoromethyl)picolinonitrile

To a solution of 5-formylpicolinonitrile (74 mg, 0.560 mmol) in toluene (0.25 mL) was added bis(2-methoxyethyl)aminosulfur trifluoride (0.258 mL, 1.400 mmol), and the reaction was stirred at RT overnight. The reaction mixture was carefully quenched with saturated aqueous sodium bicarbonate, diluted with water, and extracted with DCM. The organic layer was washed with brine, dried over anhydrous magnesium sulfate, filtered, and concentrated. The crude material was purified by silica-gel chromatography, eluting with a gradient of 40% to 60% (40% ethyl acetate/heptane) in heptane, to provide the title compound (48 mg, 0.311 mmol) as white solid. LC/MS (ESI⁺) m/z=155 (M+H).

Step 3: 5-(difluoromethyl)picolinic acid

A suspension of 5-(difluoromethyl)picolinonitrile (48 mg, 0.311 mmol) in 12 N aqueous hydrochloric acid (4.3 mL, 140 mmol) was stirred at 110° C. for 1.5 hours. After cooling to ambient temperature, the reaction mixture was concentrated and treated with DIPEA (2 mL). The mixture was concentrated and dried in vacuo to provide the title compound in quantitative yield. LC/MS (ESI⁺) m/z=174 (M+H).

Intermediate 20

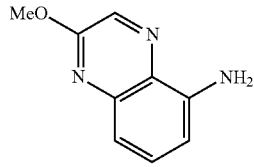 [SMILES: COc1cnc2c(N)cccc2n1]

Synthesis of 2-Methoxyquinoxalin-5-amine

To a suspension of 5-aminoquinoxalin-2(1H)-one (440 mg, 2.73 mmol) in methanol (1 mL), DCM (8 mL) and acetonitrile (8 mL), at 0° C., was added TEA (1.14 mL, 8.19 mmol), followed by (trimethylsilyl)diazomethane (2 mL, 4.10 mmol; 2.0M in hexanes). The reaction mixture was allowed to warm to RT and stirred for additional 3 hours. The suspension was filtered, and the filtrate was concentrated under reduced pressure. The crude product was purified by silica gel chromatography, eluting with 10%-50% ethyl acetate in hexane, to provide the title compound (167 mg, 0.953 mmol) as a light-yellow powder. LC/MS (ESI⁺) m/z=176 (M+H).

General amidation procedures: The following two (2) methods were used to couple the amine core intermediates (see examples and intermediates 1-15; note that the bromide need to be converted to the corresponding amine to be used in the methods below).

Method A: HATU Procedure

To a solution of the aniline (1 equivalent) and the carboxylic acid (1.1 equivalent) in DCM were added triethylamine (1.5 eq) and 1-[bis(dimethylamino)methylene]-1H-1,2,3-triazolo[4,5-b]pyridinium 3-oxide hexafluorophosphate (HATU, 1.1 equivalent). The reaction mixture was stirred at RT for 3 hours, diluted with DCM, and washed with water and brine. The organic layer was concentrated.

The residue was redissolved in DCM, and TFA (10 equivalents) was added. The reaction was stirred at RT for 1 hour, diluted with DCM, and washed with saturated aqueous sodium bicarbonate and brine, and concentrated. The crude product was purified by silica-gel chromatography to provide the title compound.

Method B: DMTMM Procedure

To a solution of the aniline (1 equivalent) and the carboxylic acid (1.1 equivalent) in 2:1 tetrahydrofuran/methanol was added 4-(4,6-dimethoxy-1,3,5-triazin-2-yl)-4-methylmorpholinium chloride (DMTMM, 1.5 equivalents). After about ten minutes, water and saturated aqueous sodium bicarbonate were added, and the mixture was extracted with DCM. The organic extract was washed with brine and concentrated.

The residue was redissolved in DCM, and TFA (10 equivalents) was added. The reaction was stirred at RT for 1 hour, diluted with dichloromethane, and washed with saturated aqueous sodium bicarbonate and brine, and concentrated. The crude product was purified by silica-gel chromatography to provide the title compound.

Examples 17-35

Using procedures similar to one of the general amidation procedures described above, the appropriate aniline and carboxylic acid were combined to provide the examples listed in Table 1:

TABLE 1

| Example # | Method | Product | Structure | Analytical Data |
|---|---|---|---|---|
| 17 | HATU Method | N-(3-((3R)-5-amino-3,6,6-trimethyl-1,1-dioxido-3,6-dihydro-2H-1,4-thiazin-3-yl)-4-fluorophenyl)-5-methoxy-2-pyrazinecarboxamide | 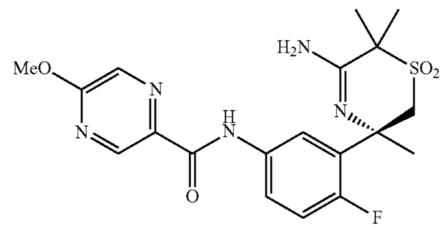 [SMILES: COc1cnc(C(=O)Nc2ccc(F)c([C@]3(C)CS(=O)(=O)C(C)(C)C(N)=N3)c2)cn1] | LC/MS (ESI+) m/z = 436 (M + H). $^1$H NMR (400 MHz, DMSO-d$_6$) δ ppm 10.41 (s, 1 H) 8.88 (d, J = 1.27 Hz, 1 H) 8.40 (d, J = 1.37 Hz, 1 H) 7.75-7.89 (m, 2 H) 7.13 (dd, J = 11.98, 8.85 Hz, 1 H) 6.00 (br. s., 2 H) 4.01 (s, 3 H) 3.47-3.67 (m, 2 H) 1.61 (s, 3 H) 1.56 (s, 3 H) 1.46 (s, 3 H) |
| 18 | HATU Method | N-(3-((3R)-5-amino-3,6,6-trimethyl-1,1-dioxido-3,6-dihydro-2H-1,4-thiazin-3-yl)-4-fluorophenyl)-5-fluoro-2-pyridinecarboxamide | 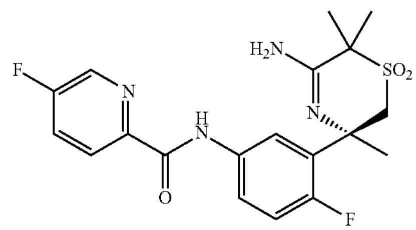 [SMILES: CC1(C)C(N)=N[C@](C)(c2cc(NC(=O)c3ccc(F)cn3)ccc2F)CS1(=O)=O] | LC/MS (ESI+) m/z = 423 (M + H). $^1$H NMR (400 MHz, DMSO-d$_6$) δ ppm 10.53 (br. s., 1 H) 8.74 (d, J = 2.84 Hz, 1 H) 8.24 (dd, J = 8.95, 4.55 Hz, 1 H) 7.99 (td, J = 8.71, 2.84 Hz, 1 H) 7.80-7.91 (m, 2 H) 7.08-7.20 (m, 1 H) 6.02 (br. s., 2 H) 3.49-3.65 (m, 2 H) 1.63 (s, 3 H) 1.58 (s, 3 H) 1.49 (s, 3 H) |
| 19 | HATU Method | N-(3-((3R)-5-amino-3,6,6-trimethyl-1,1-dioxido-3,6-dihydro-2H-1,4-thiazin-3-yl)-4-fluorophenyl)-5-chloro-2-pyridinecarboxamide | 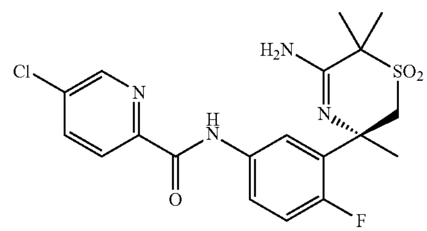 [SMILES: CC1(C)C(N)=N[C@](C)(c2cc(NC(=O)c3ccc(Cl)cn3)ccc2F)CS1(=O)=O] | LC/MS (ESI+) m/z = 439 (M + H). $^1$H NMR (400 MHz, DMSO-d$_6$) δ ppm 10.67 (s, 1 H) 8.85 (dd, J = 2.30, 0.73 Hz, 1 H) 8.12-8.30 (m, 2 H) 7.83-8.01 (m, 2 H) 7.12-7.28 (m, 1 H) 6.09 (br. s., 2 H) 3.45-3.86 (m, 2 H) 1.71 (s, 3 H) 1.66 (s, 3 H) 1.56 (s, 3 H) |
| 20 | DMTMM Method | N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide | 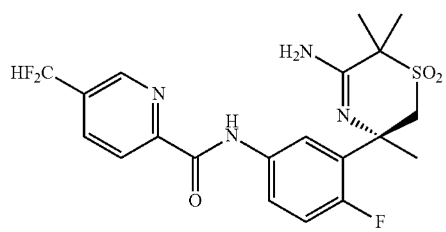 | LC/MS (ESI+) m/z = 455 (M + H). $^1$H NMR (400 MHz, DMSO-d$_6$) δ ppm 1.48 (s, 3 H) 1.58 (s, 3 H) 1.63 (s, 3 H) 3.53-3.64 (m, 2 H) 6.02 (br. s., 2 H) 7.13-7.29 (m, 2 H) 7.82-7.95 (m, 2 H) 8.28 (d, J = 1.37 Hz, 2 H) 8.94 (t, J = 1.22 Hz, 1 H) 10.68 (s, 1 H). |
| 21 | HATU Method | N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyrazinecarboxamide | 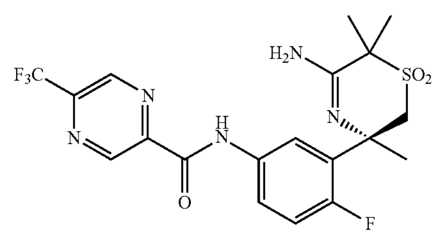 | LC/MS (ESI+) m/z = 479 (M + H). |
| 22 | HATU Method | N-(3-((3R)-5-amino-3,6,6-trimethyl-1,1-dioxido-3,6-dihydro-2H-1,4-thiazin-3-yl)-4-fluorophenyl)-5-methoxy-2-pyridinecarboxamide | 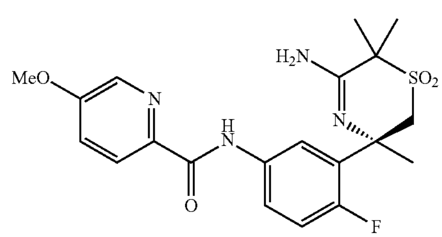 [SMILES: COc1ccc(C(=O)Nc2ccc(F)c([C@]3(C)CS(=O)(=O)C(C)(C)C(N)=N3)c2)nc1] | LC/MS (ESI+) m/z = 435 (M + H). $^1$H NMR (500 MHz, DMSO-d$_6$) δ 10.34 (s, 1 H), 8.38 (d, J = 2.63 Hz, 1 H), 8.12 (d, J = 8.71 Hz, 1 H), 7.75-7.99 (m, 2 H), 7.60 (dd, J = 2.86, 8.71 Hz, 1 H), 7.13 (dd, J = 8.71, 11.80 Hz, 1 H), 6.03 (br. s., 2 H), 3.93 (s, 3 H), 3.62 (d, J = 14.78 Hz, 1 H), 3.52 (d, J = 14.66 Hz, 1 H), 1.63 (s, 3 H), 1.57 (s, 3 H), 1.48 (s, 3 H). |

TABLE 1-continued

| Example # | Method | Product | Structure | Analytical Data |
|---|---|---|---|---|
| 23 | HATU Method | N-(3-((3R)-5-amino-3,6,6-trimethyl-1,1-dioxido-3,6-dihydro-2H-1,4-thiazin-3-yl)-4-fluorophenyl)-5-cyano-2-pyridinecarboxamide | 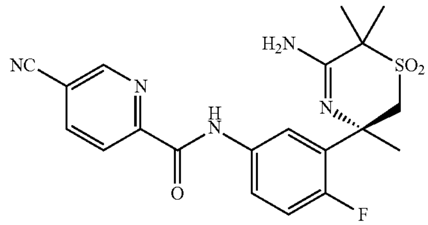 [SMILES: CC1(C)C(N)=N[C@](C)(c2cc(NC(=O)c3ccc(C#N)cn3)ccc2F)CS1(=O)=O] | LC/MS (ESI+) m/z = 430 (M + H). $^1$H NMR (500 MHz, DMSO-d$_6$) δ 10.73 (s, 1 H), 9.08-9.30 (m, 1 H), 8.57 (dd, J = 1.95, 8.13 Hz, 1 H), 8.27 (d, J = 8.02 Hz, 1 H), 7.90 (d, J = 7.33 Hz, 1 H), 7.74-7.87 (m, 1 H), 7.15 (dd, J = 8.88, 11.97 Hz, 1 H), 6.02 (br. s., 2 H), 3.63 (d, J = 15.12 Hz, 1 H), 3.52 (d, J = 15.01 Hz, 1 H), 1.62 (s, 3 H), 1.57 (s, 3 H), 1.47 (s, 3 H). |
| 24 | HATU Method | N-(3-((3R)-5-amino-3,6,6-trimethyl-1,1-dioxido-3,6-dihydro-2H-1,4-thiazin-3-yl)-4-fluorophenyl)-5-chloro-3-fluoro-2-pyridinecarboxamide | 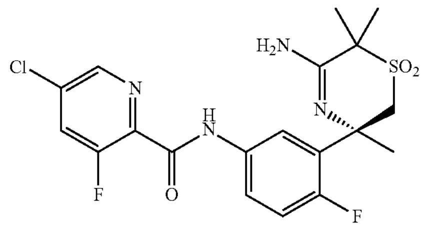 | LC/MS (ESI+) m/z = 457 (M + H). $^1$H NMR (500 MHz, DMSO-d$_6$) δ 10.61 (s, 1 H), 8.64 (s, 1 H), 8.31 (dd, J = 1.78, 10.14 Hz, 1 H), 7.66-7.90 (m, 2 H), 7.14 (dd, J = 8.82, 11.91 Hz, 1 H), 6.02 (br. s., 2 H), 3.63 (d, J = 14.66 Hz, 1 H), 3.52 (d, J = 15.12 Hz, 1 H), 1.62 (s, 3 H), 1.57 (s, 3 H), 1.46 (s, 3 H). |
| 25 | HATU Method | N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide | 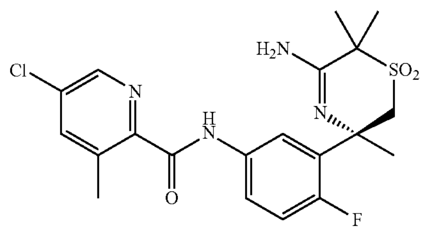 | LC/MS (ESI+) m/z = 453 (M + H). $^1$H NMR (500 MHz, DMSO-d$_6$) δ 10.48 (s, 1 H), 8.56 (d, J = 1.83 Hz, 1 H), 7.94-8.09 (m, 1 H), 7.78-7.92 (m, 1 H), 7.70 (d, J = 5.04 Hz, 1 H), 7.13 (dd, J = 9.11, 11.86 Hz, 1 H), 6.00 (br. s., 2 H), 3.62 (d, J = 15.01 Hz, 1 H), 3.52 (d, J = 15.12 Hz, 1 H), 2.54 (s, 3 H), 1.62 (s, 3 H), 1.57 (s, 3 H), 1.47 (s, 3 H). |
| 26 | HATU Method | N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide | 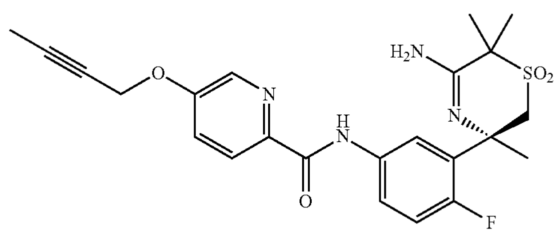 [SMILES: CC#CCOc1ccc(C(=O)Nc2ccc(F)c([C@]3(C)CS(=O)(=O)C(C)(C)C(N)=N3)c2)nc1] | LC/MS (ESI+) m/z = 474 (M + H). $^1$H NMR (500 MHz, DMSO-d$_6$) δ 10.41 (s, 1 H), 8.88 (s, 1H), 8.44 (s, 1 H), 7.88 (dd, J = 2.46, 7.39 Hz, 1 H), 7.69-7.84 (m, 1 H), 7.13 (dd, J = 8.88, 11.86 Hz, 1 H), 6.01 (br. s., 2 H), 5.08 (d, J = 2.29 Hz, 2 H), 3.62 (d, J = 15.12 Hz, 1 H), 3.51 (d, J = 15.12 Hz, 1 H), 1.85 (t, J = 2.23 Hz, 3 H), 1.62 (s, 3 H), 1.57 (s, 3 H), 1.47 (s, 3 H). |
| 27 | HATU Method | N-(3-((3R)-5-amino-3,6,6-trimethyl-1,1-dioxido-3,6-dihydro-2H-1,4-thiazin-3-yl)-4-fluorophenyl)-2-methyl-1,3-thiazole-4-carboxamide | 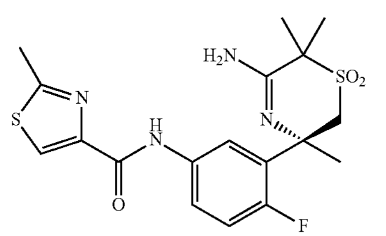 [SMILES: Cc1nc(C(=O)Nc2ccc(F)c([C@]3(C)CS(=O)(=O)C(C)(C)C(N)=N3)c2)cs1] | LC/MS (ESI+) m/z = 425 (M + H). $^1$H NMR (500 MHz, DMSO-d$_6$) δ 10.09 (s, 1 H), 8.25 (s, 1 H), 7.83 (d, J = 5.04 Hz, 1 H), 7.65-7.80 (m, 1 H), 7.11 (dd, J = 8.88, 11.86 Hz, 1 H), 6.00 (br. s., 2 H), 3.61 (d, J = 14.89 Hz, 1 H), 3.51 (d, J = 15.01 Hz, 1 H), 2.76 (s, 3 H), 1.62 (s, 3 H), 1.57 (s, 3H), 1.48 (s, 3 H) |

TABLE 1-continued

| Example # | Method | Product | Structure | Analytical Data |
|---|---|---|---|---|
| 28 | HATU Method | N-(3-((3R)-5-amino-3-methyl-1,1-dioxido-3,6-dihydro-2H-1,4-thiazin-3-yl)-4-fluorophenyl)-5-methoxy-2-pyrazinecarboxamide | 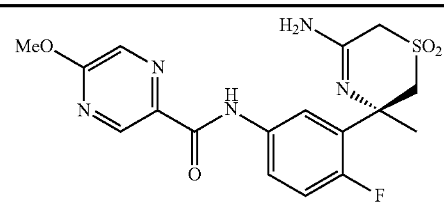 | LC/MS (ESI+) m/z = 408 (M + H). |
| 29 | HATU Method | N-(3-((3R)-5-amino-3-methyl-1,1-dioxido-3,6-dihydro-2H-1,4-thiazin-3-yl)-4-fluorophenyl)-5-chloro-2-pyridinecarboxamide | 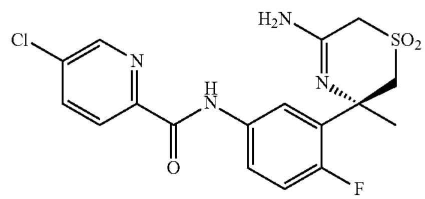 [SMILES: C[C@@]1(c2cc(NC(=O)c3ccc(Cl)cn3)ccc2F)CS(=O)(=O)CC(N)=N1] | LC/MS (ESI+) m/z = 411 (M + H). |
| 30 | HATU Method | N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide | 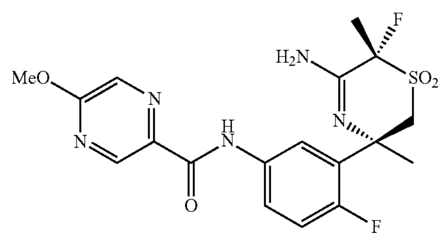 [SMILES: COc1cnc(C(=O)Nc2ccc(F)c([C@]3(C)CS(=O)(=O)[C@@](C)(F)C(N)=N3)c2)cn1] | LC/MS (ESI+) m/z = 440 (M + H). |
| 31 | DMTMM Method | N-(3-(-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide | 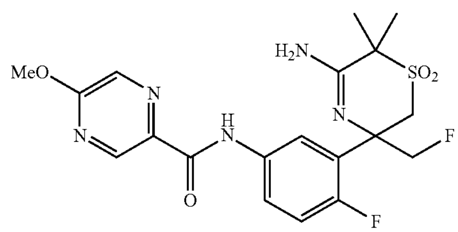 [SMILES: COc1cnc(C(=O)Nc2ccc(F)c(C3(CF)CS(=O)(=O)C(C)(C)C(N)=N3)c2)cn1] | LC/MS (ESI+) m/z = 454 (M + H). |
| 32 | HATU Method | N-(3-(-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide | 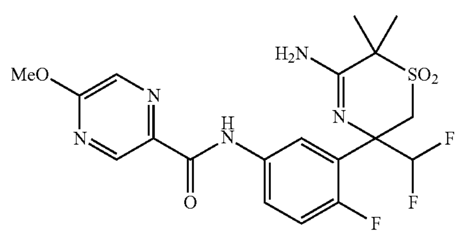 [SMILES: COc1cnc(C(=O)Nc2ccc(F)c(C3(C(F)F)CS(=O)(=O)C(C)(C)C(N)=N3)c2)cn1] | LC/MS (ESI+) m/z = 472 (M + H). |
| 33 | DMTMM Method | N-(3-((3S)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide | 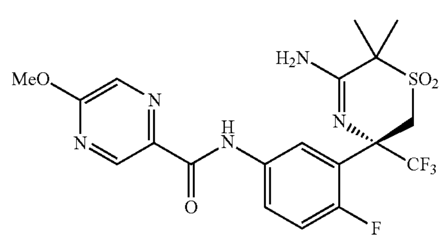 [SMILES: COc1cnc(C(=O)Nc2ccc(F)c([C@]3(C(F)(F)F)CS(=O)(=O)C(C)(C)C(N)=N3)c2)cn1] | LC/MS (ESI+) m/z = 490 (M + H). |
| 34 | DMTMM Method | N-(3-((3R)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide | 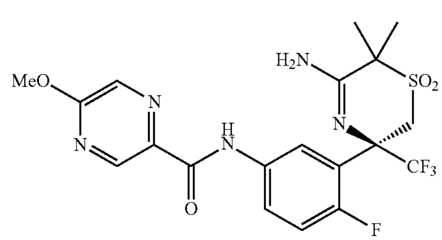 [SMILES: COc1cnc(C(=O)Nc2ccc(F)c([C@@]3(C(F)(F)F)CS(=O)(=O)C(C)(C)C(N)=N3)c2)cn1] | LC/MS (ESI+) m/z = 490 (M + H). |

TABLE 1-continued

| Example # | Method | Product | Structure | Analytical Data |
|---|---|---|---|---|
| 35 | HATU Method | N-(3-(-5-amino-3,6,6-trimethyl-1,1-dioxido-3,6-dihydro-2H-1,4-thiazin-3-yl)-4,5-difluorophenyl)-5-chloro-2-pyridinecarboxamide | 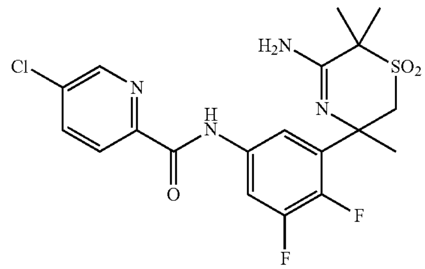 [SMILES: CC1(c2cc(NC(=O)c3ccc(Cl)cn3)cc(F)c2F)CS(=O)(=O)C(C)(C)C(N)=N1] | LC/MS (ESI⁺) m/z = 457 (M + H). |

Example 36

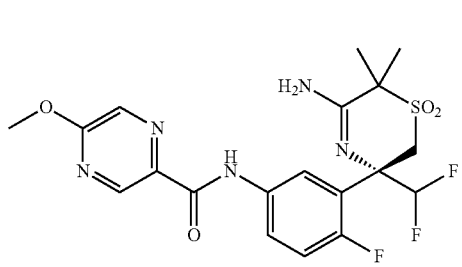 [SMILES: COc1cnc(C(=O)Nc2ccc(F)c([C@]3(C(F)F)CS(=O)(=O)C(C)(C)C(N)=N3)c2)cn1]

Synthesis of (S)—N-(3-(5-amino-3-(difluoromethyl)-6,6-dimethyl-1,1-dioxido-3,6-dihydro-2H-1,4-thiazin-3-yl)-4-fluorophenyl)-5-methoxypyrazine-2-carboxamide The product of Example 32 was purified by chiral SFC, using an AD-H column and eluting with 30% methanol/0.2% diethylamine in $CO_2$, to provide the title compound. LC/MS (ESI⁺) m/z=472 (M+H).

Example 37

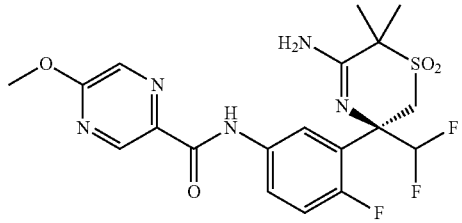 [SMILES: COc1cnc(C(=O)Nc2ccc(F)c([C@@]3(C(F)F)CS(=O)(=O)C(C)(C)C(N)=N3)c2)cn1]

Synthesis of (R)—N-(3-(5-amino-3-(difluoromethyl)-6,6-dimethyl-1,1-dioxido-3,6-dihydro-2H-1,4-thiazin-3-yl)-4-fluorophenyl)-5-methoxypyrazine-2-carboxamide The title compound is the other enantiomer recovered from the chiral SFC purification of the product of Example 32, using an AD-H column and eluting with 30% methanol/0.2% diethylamine in $CO_2$. LC/MS (ESI⁺) m/z=472 (M+H).

Example 38

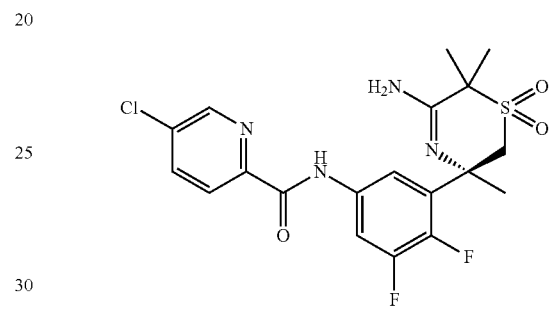

Synthesis of (R)—N-(3-(5-amino-3,6,6-trimethyl-1,1-dioxido-3,6-dihydro-2H-1,4-thiazin-3-yl)-4,5-difluorophenyl)-5-chloropicolinamide The product of Example 35 was separated by chiral SFC, using a ChiralPak IC column and eluting with 50% methanol/0.2% diethylamine in $CO_2$, to provide the title compound as an off-white solid. LC/MS (ESI⁺) m/z=457 (M+H).

Example 39

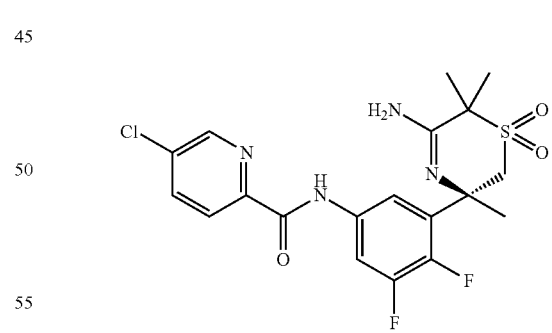

Synthesis of (S)—N-(3-(5-amino-3,6,6-trimethyl-1,1-dioxido-3,6-dihydro-2H-1,4-thiazin-3-yl)-4,5-difluorophenyl)-5-chloropicolinamide The title compound is the other enantiomer recovered from the chiral SFC purification of the product of Example 35, using a ChiralPak column and eluting with 50% methanol/0.2% diethylamine in $CO_2$. LC/MS (ESI⁺) m/z=457 (M+H).

Example 40

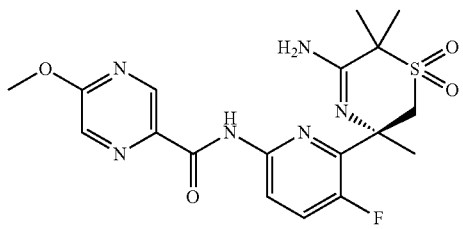 [SMILES: COc1cnc(C(=O)Nc2ccc(F)c([C@]3(C)CS(=O)(=O)C(C)(C)C(N)=N3)n2)cn1]

Synthesis of (R)—N-(6-(5-amino-3,6,6-trimethyl-1,1-dioxido-3,6-dihydro-2H-1,4-thiazin-3-yl)-5-fluoropyridin-2-yl)-5-methoxypyrazine-2-carboxamide A microwave vial was charged with (R)-5-amino-3-(6-bromo-3-fluoropyridin-2-yl)-3,6,6-trimethyl-3,6-dihydro-2H-1,4-thiazine 1,1-dioxide (38 mg, 0.104 mmol), 5-methoxypyrazine-2-carboxamide (23.97 mg, 0.156 mmol), 9,9-dimethyl-4,5-bis(diphenylphosphino)xanthene (6.04 mg, 10.43 µmol), tris(dibenzylideneacetone)dipalladium (0) (4.78 mg, 5.22 µmol), cesium carbonate (0.365 mmol) and dioxane (1 mL). The vial was purged with argon, sealed, and irradiated in a microwave reactor at 110° C. for 1 hour. After cooling to RT, the reaction mixture was diluted with water and extracted with EtOAc. The organic layer was concentrated, and the crude product was purified by silica-gel chromatography, eluting with 2-8% MeOH in ethyl acetate, to provide the title compound (18 mg, 0.041 mmol) as an off-white solid. LC/MS (ESI+) m/z 437 (M+H). $^1$H NMR (400 MHz, DMSO-$d_6$) δ ppm=9.97 (s, 1H), 9.02 (d, J=1.2 Hz, 1H), 8.35 (dd, J=2.9, 8.8 Hz, 1H), 8.22 (d, J=1.2 Hz, 1H), 7.48 (dd, J=8.9, 10.7 Hz, 1H), 4.15 (d, J=13.1 Hz, 1H), 4.08 (s, 3H), 3.37 (d, J=14.9 Hz, 1H), 1.84 (s, 3H), 1.71 (s, 3H), 1.67 (s, 3H).

Example 41

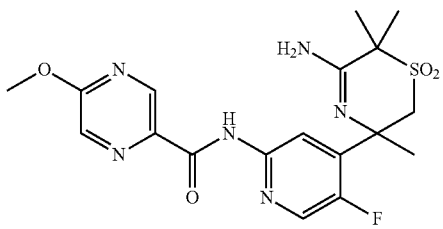 [SMILES: COc1cnc(C(=O)Nc2cc(C3(C)CS(=O)(=O)C(C)(C)C(N)=N3)c(F)cn2)cn1]

Synthesis of N-(4-(5-amino-3,6,6-trimethyl-1,1-dioxido-3,6-dihydro-2H-1,4-thiazin-3-yl)-5-fluoropyridin-2-yl)-5-methoxypyrazine-2-carboxamide In an analogous reaction to that described for Example 40, 5-amino-3-(2-bromo-5-fluoropyridin-4-yl)-3,6,6-trimethyl-3,6-dihydro-2H-1,4-thiazine 1,1-dioxide (0.070 g, 0.192 mmol) was converted to the title compound (0.038 g) as a tan solid. $^1$H NMR (400 MHz, DMSO-$d_6$) δ ppm 10.09 (s, 1H), 8.95 (d, J=1.37 Hz, 1H), 8.44 (s, 1H), 8.38 (d, J=6.26 Hz, 1H), 8.28 (d, J=3.13 Hz, 1H), 6.23 (br. s., 2H), 4.02 (s, 3H), 3.68-3.79 (m, 1H), 3.58-3.67 (m, 1H), 1.61 (br. s., 6H), 1.45 (s, 3H). LC/MS (ESI+) m/z=437 (M+H).

Example 42

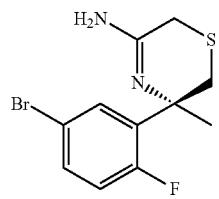 [SMILES: C[C@@]1(c2cc(Br)ccc2F)CSCC(N)=N1]

Synthesis of (R)-5-(5-bromo-2-fluorophenyl)-5-methyl-5,6-dihydro-2H-1,4-thiazin-3-amine In an analogous reaction to that described for Example 1, step 5, (R)-tert-butyl (2-(5-bromo-2-fluorophenyl)-1-((cyanomethyl)thio)propan-2-yl)carbamate was converted to the title compound in 80% yield as an off-white foam. LC/MS (ESI+) m/z=303, 305 (M+H; 2 bromine isotopes).

Example 43

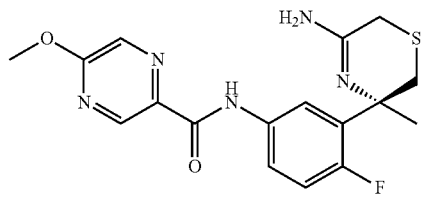 [SMILES: COc1cnc(C(=O)Nc2ccc(F)c([C@]3(C)CSCC(N)=N3)c2)cn1]

Synthesis of (R)—N-(3-(5-amino-3-methyl-3,6-dihydro-2H-1,4-thiazin-3-yl)-4-fluorophenyl)-5-methoxypyrazine-2-carboxamide (R)-tert-butyl (5-(5-amino-2-fluorophenyl)-5-methyl-5,6-dihydro-2H-1,4-thiazin-3-yl)carbamate) was converted to the title compound as described in the HATU procedure as a yellow oil. LC/MS (ESI+) m/z=376 (M+H). $^1$H NMR (400 MHz, methanol-$d_4$) δ ppm 8.93 (d, J=1.27 Hz, 1H) 8.31 (d, J=1.37 Hz, 1H) 7.88 (dd, J=7.38, 2.69 Hz, 1H) 7.77-7.81 (m, 1H) 7.17 (dd, J=12.08, 8.85 Hz, 1H) 4.09 (s, 3H) 3.32-3.38 (m, 4H) 1.83 (s, 3H).

Example 44

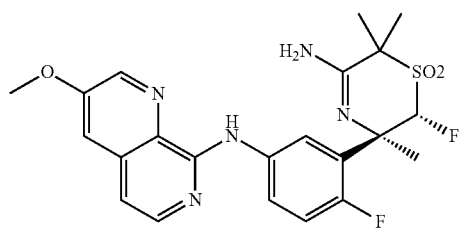 [SMILES: COc1cnc2c(Nc3ccc(F)c([C@@]4(C)N=C(N)C(C)(C)S(=O)(=O)[C@@H]4F)c3)nccc2c1]

Synthesis of (2S,3R)-5-Amino-2-fluoro-3-(2-fluoro-5-((3-methoxy-1,7-naphthyridin-8-yl)amino)phenyl)-3,6,6-trimethyl-3,6-dihydro-2H-1,4-thiazine 1,1-dioxide Step 1: tert-Butyl ((5R,6S)-6-fluoro-5-(2-fluoro-5-((3-methoxy-1,7-naphthyridin-8-yl)amino)phenyl)-2,2,5-trimethyl-1,1-dioxido-5,6-dihydro-2H-1,4-thiazin-3-yl)carbamate To a solution of tert-butyl ((5R)-5-(5-amino-2-fluorophenyl)-6-fluoro-2,2,5-trimethyl-1,1-dioxido-5,6-dihydro-2H-1,4-thiazin-3-yl)carbamate (75 mg, 0.180 mmol) and 8-chloro-3-methoxy-1,7-naphthyridine (38.5 mg, 0.198 mmol) in 2-propanol (4 mL) was added sulfuric acid (9.58 μL, 0.180 mmol). The reaction was stirred at 100° C. for one hour, diluted with water, and neutralized with saturated aqueous sodium bicarbonate. The aqueous layer was extracted with ethyl acetate and the combined organic layers were washed with brine and dried over anhydrous sodium sulfate, filtered and concentrated.

Step 2: (2S,3R)-5-Amino-2-fluoro-3-(2-fluoro-5-((3-methoxy-1,7-naphthyridin-8-yl)amino)phenyl)-3,6,6-trimethyl-3,6-dihydro-2H-1,4-thiazine 1,1-dioxide To a solution of tert-butyl ((5R,6S)-6-fluoro-5-(2-fluoro-5-((3-methoxy-1,7-naphthyridin-8-yl)amino)phenyl)-2,2,5-trimethyl-1,1-dioxido-5,6-dihydro-2H-1,4-thiazin-3-yl)carbamate in DCM (10 mL) was added TFA (1.38 mL, 18.0 mmol). The reaction was stirred at RT for 30 minutes, and then neutralized with saturated aqueous sodium bicarbonate. The aqueous layer was extracted with DCM, and the combined organic layers were concentrated and purified via silica gel chromatography, eluting with 20-100% EtOAC in heptanes, to afford the title compound (50 mg, 0.105 mmol). MS m/z=476 (M+H).

Examples 45-66

In a similar sequence of reactions to those described for Example 44, the appropriate aniline and chloro-substituted heterocycle were combined to provide the compounds listed in Table 2:

TABLE 2

| Example # | Product | Structure | Analytical Data |
|---|---|---|---|
| 45 | N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine | 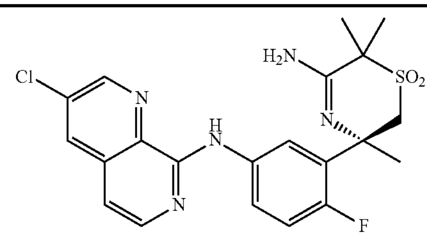 | LC/MS (ESI$^+$) m/z = 462 (M + H). $^1$H NMR (400 MHz, DMSO-d$_6$) δ ppm 9.48 (s, 1 H) 8.90 (d, J = 2.35 Hz, 1 H) 8.51 (d, J = 2.45 Hz, 1 H) 8.08-8.12 (m, 2 H) 7.96-8.02 (m, 1 H) 7.08-7.17 (m, 2 H) 6.03 (br. s, 2 H) 3.40-3.73 (m, 2 H) 1.64 (s, 3 H) 1.57 (s, 3 H) 1.48 (s, 3 H) |
| 46 | N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine | 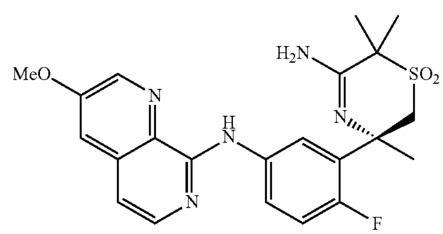 [SMILES: COc1cnc2c(Nc3ccc(F)c([C@]4(C)CS(=O)(=O)C(C)(C)C(N)=N4)c3)nccc2c1] | LC/MS (ESI$^+$) m/z = 458 (M + H). $^1$H NMR (400 MHz, DMSO-d$_6$) δ ppm 9.29 (s, 1 H) 8.63 (d, J = 2.84 Hz, 1 H) 8.14-8.21 (m, 1 H) 8.04 (d, J = 5.67 Hz, 1 H) 7.92 (m, H) 7.71 (d, J = 2.84 Hz, 1 H) 7.09-7.15 (m, 2 H) 6.07 (br. s., 2 H) 3.98 (s, 3 H) 3.45-3.74 (m, 2 H) 1.66 (s, 3 H) 1.59 (s, 3 H) 1.50 (s, 3 H) |
| 47 | N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine | 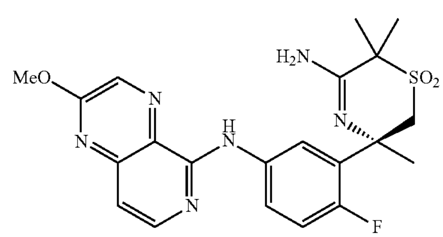 [SMILES: COc1cnc2c(Nc3ccc(F)c([C@]4(C)CS(=O)(=O)C(C)(C)C(N)=N4)c3)nccc2n1] | LC/MS (ESI$^+$) m/z = 459 (M + H). $^1$H NMR (400 MHz, DMSO-d$_6$) δ ppm 9.35 (s, 1 H) 8.54 (s, 1 H) 8.21 (d, J = 5.77 Hz, 1 H) 7.94-8.08 (m, 2 H) 7.01-7.17 (m, 2 H) 6.02 (br. s., 2 H) 4.06 (s, 3 H) 3.43-3.69 (m, 2 H) 1.64 (s, 3 H) 1.57 (s, 3 H) 1.48 (s, 3 H). |
| 48 | 8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile | 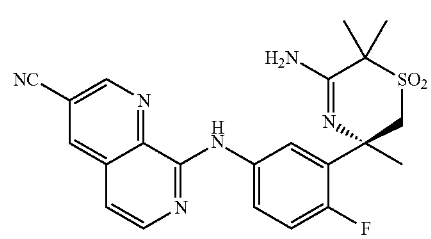 [SMILES: CC1(C)C(N)=N[C@](C)(c2cc(Nc3nccc4cc(C#N)cnc34)ccc2F)CS1(=O)=O] | LC/MS (ESI$^+$) m/z = 453 (M + H). $^1$H NMR (400 MHz, DMSO-d$_6$) δ ppm 9.64 (s, 1 H) 9.23 (d, J = 1.96 Hz, 1 H) 8.99 (d, J = 1.96 Hz, 1 H) 8.22 (d, J = 5.67 Hz, 1 H) 8.01-8.13 (m, 2 H) 7.23 (d, J = 5.77 Hz, 1 H) 7.11-7.18 (m, 1 H) 6.06 (br. s., 2 H) 3.47-3.68 (m, 2 H) |

TABLE 2-continued

| Example # | Product | Structure | Analytical Data |
|---|---|---|---|
| | | | 1.66 (s, 3 H) 1.59 (s, 3 H) 1.50 (s, 3 H). |
| 49 | N-(3-((3R)-5-amino-3,6,6-trimethyl-1,1-dioxido-3,6-dihydro-2H-1,4-thiazin-3-yl)-4-fluorophenyl)-3-chloro-5-fluoro-1,7-naphthyridin-8-amine | 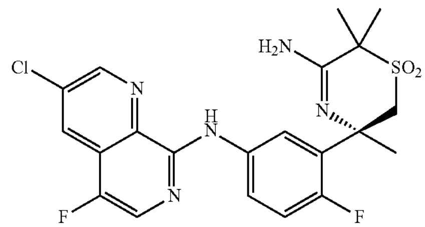 [SMILES: CC1(C)C(N)=N[C@](C)(c2cc(Nc3ncc(F)c4cc(Cl)cnc34)ccc2F)CS1(=O)=O] | ¹H-NMR (400 MHz, DMSO-d₆): δ 9.47 (s, 1 H), 9.00 (d, J = 4 Hz, 1 H), 8.58 (d, J = 4 Hz, 1 H), 8.15 (d, J = 4 Hz, 1 H), 8.07-8.05 (m, 1 H), 8.02-7.98 (m, 1 H), 7.12 (dd, J = 8 Hz, 12 Hz, 1 H), 6.11 (br s, 2 H), 3.64 (d, J = 16 Hz, 1 H), 3.52 (d, J = 16 Hz, 1 H), 1.65 (s, 3 H), 1.58 (s, 3 H), 1.48 (s, 3 H). LC/MS (ESI⁺) m/z = 480 (M + H). |
| 50 | N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine | 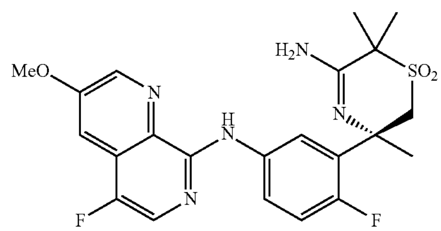 [SMILES: COc1cnc2c(Nc3ccc(F)c([C@]4(C)CS(=O)(=O)C(C)(C)C(N)=N4)c3)ncc(F)c2c1] | ¹H-NMR (400 MHz, DMSO-d₆): δ 9.25 (s, 1 H), 8.70 (d, J = 4 Hz, 1 H), 8.08-8.05 (m, 2 H), 8.00-7.98 (m, 1 H), 7.70 (d, J = 12 Hz, 1 H), 7.10 (dd, J = 4 Hz, 12 Hz, 1 H), 6.08 (br s, 2 H), 4.03 (s, 3 H), 3.64 (d, J = 16 Hz, 1 H), 3.52 (d, J = 16 Hz, 1 H), 1.65 (s, 3H), 1.58 (s, 3 H), 1.48 (s, 3 H). LC/MS (ESI⁺) m/z = 476 (M + H). |
| 51 | N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine | 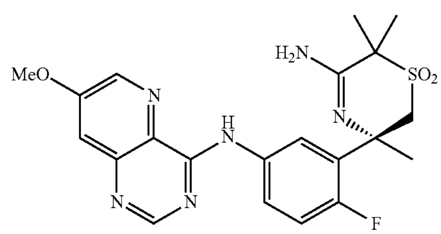 [SMILES: COc1cnc2c(Nc3ccc(F)c([C@]4(C)CS(=O)(=O)C(C)(C)C(N)=N4)c3)ncnc2c1] | ¹H NMR (400 MHz, DMSO-d₆) δ ppm 1.48 (s, 3 H) 1.57 (s, 3 H) 1.64 (s, 3 H) 3.50-3.66 (m, 2 H) 3.99 (s, 3 H) 6.04 (br. s., 2 H) 7.15 (dd, J = 11.98, 8.85 Hz, 1 H) 7.60 (d, J = 2.84 Hz, 1 H) 7.91-8.00 (m, 1 H) 8.08 (dd, J = 7.43, 2.64 Hz, 1 H) 8.63 (d, J = 2.8 Hz, 1 H) 8.59 (m, 1 H) 10.04 (s, 1 H). LC/MS (ESI⁺) m/z = 459 (M + H). |
| 52 | N-(3-((3R)-5-amino-3,6,6-trimethyl-1,1-dioxido-3,6-dihydro-2H-1,4-thiazin-3-yl)-4-fluorophenyl)-7-chloropyrido[3,2-d]pyrimidin-4-amine | 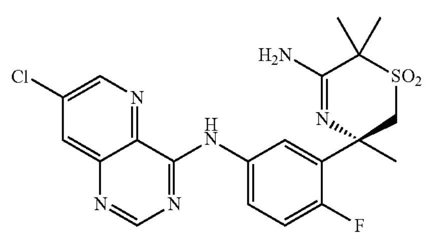 [SMILES: CC1(C)C(N)=N[C@](C)(c2cc(Nc3ncnc4cc(Cl)cnc34)ccc2F)CS1(=O)=O] | ¹H NMR (400 MHz, DMSO-d₆) δ ppm 1.48 (s, 3 H) 1.57 (s, 3 H) 1.64 (s, 3 H) 3.50-3.66 (m, 2 H) 6.04 (br. s., 2 H) 7.18 (dd, J = 11.93, 8.90 Hz, 1 H) 7.87-7.97 (m, 1 H) 8.12 (dd, J = 7.48, 2.59 Hz, 1 H) 8.40 (d, J = 2.25 Hz, 1 H) 8.65 (s, 1 H) 8.93 (d, J = 2.35 Hz, 1 H) 10.37 (s, 1 H). LC/MS (ESI⁺) m/z +32 463 (M + H). |
| 53 | N-(3-((3R)-5-amino-3,6,6-trimethyl-1,1-dioxido-3,6-dihydro-2H-1,4-thiazin-3-yl)-4-fluorophenyl)-5-fluoro-7-methoxy-4-quinazolinamine | 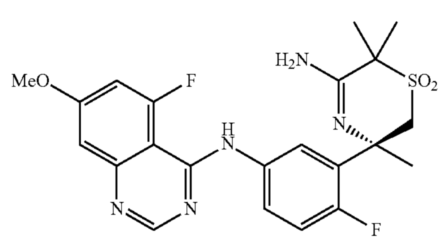 [SMILES: COc1cc(F)c2c(Nc3ccc(F)c([C@]4(C)CS(=O)(=O)C(C)(C)C(N)=N4)c3)ncnc2c1] | LC/MS (ESI⁺) m/z = 476 (M + H). |

| Example # | Product | Structure | Analytical Data |
|---|---|---|---|
| 54 | N-(3-((3R)-5-amino-3,6,6-trimethyl-1,1-dioxido-3,6-dihydro-2H-1,4-thiazin-3-yl)-4-fluorophenyl)-2-methyl[1,3]thiazolo[4,5-c]pyridin-4-amine | 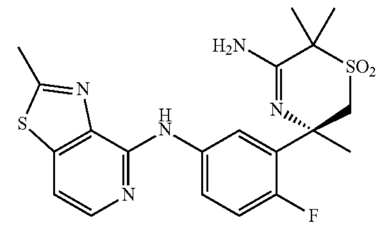 [SMILES: Cc1nc2c(Nc3ccc(F)c([C@]4(C)CS(=O)(=O)C(C)(C)C(N)=N4)c3)nccc2s1] | LC/MS (ESI+) m/z = 448 (M + H). 1H NMR (400 MHz, DMSO-d6) δ 9.00 (s, 1H), 7.86-8.09 (m, 3H), 7.42 (d, J = 5.58 Hz, 1H), 7.07 (dd, J = 8.90, 12.03 Hz, 1H), 5.99 (br. s., 2H), 3.62 (d, J = 15.16 Hz, 1H), 3.50 (d, J = 14.87 Hz, 1H), 2.87 (s, 3H), 1.66 (s, 3H), 1.58 (s, 3H), 1.50 (s, 3H). |
| 55 | N-(3-((3R)-5-amino-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine | 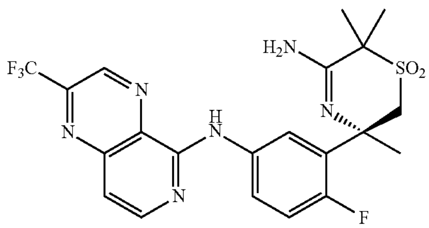 [SMILES: CC1(C)C(N)=N[C@](C)(c2cc(Nc3nccc4nc(C(F)(F)F)cnc34)ccc2F)CS1(=O)=O] | 1H NMR (400 MHz, DMSO-d6) δ ppm 1.49 (s, 3 H) 1.58 (s, 3 H) 1.66 (s, 3 H) 3.47-3.69 (m, 2 H) 6.04 (br. s., 2 H) 7.15 (dd, J = 11.84, 9.10 Hz, 1 H) 7.36 (d, J = 5.97 Hz, 1 H) 7.98-8.19 (m, 2 H) 8.40 (d, J = 5.97 Hz, 1 H) 9.36 (s, 1 H) 9.96 (s, 1 H). LC/MS (ESI+) m/z = 497 (M + H). |
| 56 | N-(3-((3R)-5-amino-3-methyl-1,1-dioxido-3,6-dihydro-2H-1,4-thiazin-3-yl)-4-fluorophenyl)-3-methoxy-1,7-naphthyridin-8-amine | 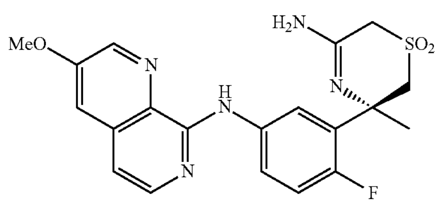 [SMILES: COc1cnc2c(Nc3ccc(F)c([C@]4(C)CS(=O)(=O)CC(N)=N4)c3)nccc2c1] | LC/MS (ESI+) m/z = 430 (M + H). |
| 57 | N-(3-((3R)-5-amino-3-methyl-1,1-dioxido-3,6-dihydro-2H-1,4-thiazin-3-yl)-4-fluorophenyl)-3-chloro-1,7-naphthyridin-8-amine | 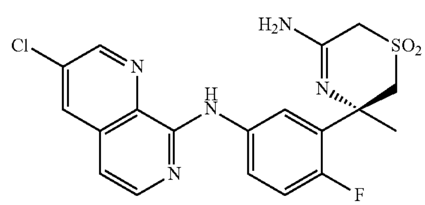 [SMILES: C[C@@]1(c2cc(Nc3nccc4cc(Cl)cnc34)ccc2F)CS(=O)(=O)CC(N)=N1] | LC/MS (ESI+) m/z = 434 (M + H) |
| 58 | N-(3-((3R)-5-amino-3-methyl-1,1-dioxido-3,6-dihydro-2H-1,4-thiazin-3-yl)-4-fluorophenyl)-2-methyl[1,3]thiazolo[4,5-c]pyridin-4-amine | 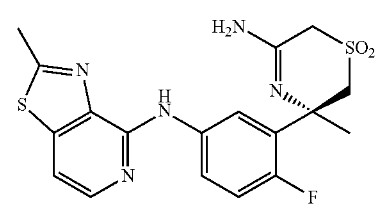 [SMILES: Cc1nc2c(Nc3ccc(F)c([C@]4(C)CS(=O)(=O)CC(N)=N4)c3)nccc2s1] | LC/MS (ESI+) m/z = 420 (M + H) |
| 59 | N-(3-((3R,6R)-5-amino-6-fluoro-3,6-dimethyl-1,1-dioxido-3,6-dihydro-2H-1,4-thiazin-3-yl)-4-fluorophenyl)-2-methoxypyrido[3,4-b]pyrazin-5-amine | 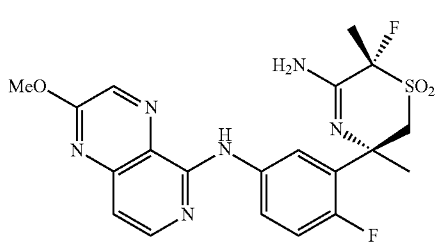 [SMILES: COc1cnc2c(Nc3ccc(F)c([C@]4(C)CS(=O)(=O)[C@@](C)(F)C(N)=N4)c3)nccc2n1] | LC/MS (ESI+) m/z = 463 (M + H) |
| 60 | 8-((3-((3R,6R)-5-amino-6-fluoro-3,6-dimethyl-1,1-dioxido-3,6-dihydro-2H-1,4-thiazin-3-yl)-4-fluorophenyl)amino)-1,7-naphthyridine-3-carbonitrile | 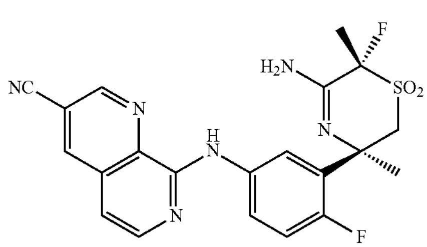 [SMILES: C[C@]1(F)C(N)=N[C@](C)(c2cc(Nc3nccc4cc(C#N)cnc34)ccc2F)CS1(=O)=O] | LC/MS (ESI+) m/z = 457 (M + H) |

TABLE 2-continued

| Example # | Product | Structure | Analytical Data |
|---|---|---|---|
| 61 | N-(3-(5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine | 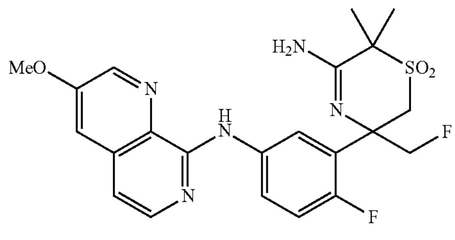 [SMILES: COc1cnc2c(Nc3ccc(F)c(C4(CF)CS(=O)(=O)C(C)(C)C(N)=N4)c3)nccc2c1] | LC/MS (ESI⁺) m/z = 476 (M + H) |
| 62 | N-(3-(5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine | 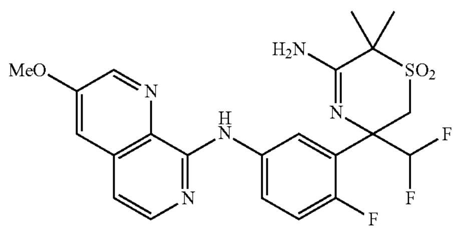 [SMILES: COc1cnc2c(Nc3ccc(F)c(C4(C(F)F)CS(=O)(=O)C(C)(C)C(N)=N4)c3)nccc2c1] | LC/MS (ESI⁺) m/z = 494 (M + H). ¹H NMR (400 MHz, DMSO-d₆) δ 9.37 (s, 1H), 8.70 (d, J = 2.74 Hz, 1H), 8.24-8.37 (m, 1H), 8.01-8.23 (m, 2H), 7.79 (d, J = 2.84 Hz, 1H), 7.14-7.26 (m, 2H), 6.68 (br. s., 2H), 6.04 (t, J = 56.0 Hz, 1H), 4.05 (s, 3H), 3.90 (d, J = 4.30 Hz, 2H), 1.70 (s, 3H), 1.54 (s, 3H) |
| 63 | N-(3-((3S)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine | 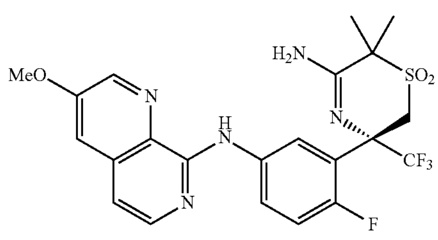 [SMILES: COc1cnc2c(Nc3ccc(F)c([C@]4(C(F)(F)F)CS(=O)(=O)C(C)(C)C(N)=N4)c3)nccc2c1] | ¹H NMR (300 MHz, DMSO-d₆) δ ppm 1.43 (s, 3 H) 1.66 (s, 3 H) 3.85-4.08 (m, 5 H) 5.76 (s, 1 H) 6.81 (br. s., 2 H) 7.10-7.18 (m, 1 H) 7.72 (d, J = 2.78 Hz, 1 H) 8.06 (d, J = 5.70 Hz, 1 H) 8.18 (dt, J = 8.77, 3.43 Hz, 1 H) 8.27 (dd, J = 7.45, 2.78 Hz, 1 H) 8.63 (d, J = 2.92 Hz, 1 H) 9.36 (s, 1 H). LC/MS (ESI⁺) m/z = 512 (M + H). |
| 64 | N-(3-((3R)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine | 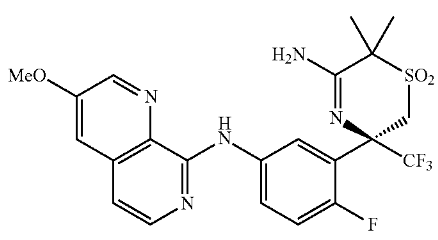 [SMILES: COc1cnc2c(Nc3ccc(F)c([C@@]4(C(F)(F)F)CS(=O)(=O)C(C)(C)C(N)=N4)c3)nccc2c1] | ¹H NMR (300 MHz, DMSO-d₆) δ ppm 1.44 (s, 3 H) 1.66 (s, 3 H) 3.90-4.08 (m, 5 H) 6.82 (br. s., 2 H) 7.11-7.19 (m, 2 H) 7.72 (d, J = 2.78 Hz, 1 H) 8.06 (d, J = 5.85 Hz, 1 H) 8.14-8.23 (m, 1 H) 8.27 (dd, J = 7.38, 2.85 Hz, 1 H) 8.63 (d, J = 2.78 Hz, 1 H) 9.36 (s, 1 H). LC/MS (ESI⁺) m/z = 512 (M + H) |
| 65 | N-(3-(5-amino-3,6,6-trimethyl-1,1-dioxido-3,6-dihydro-2H-1,4-thiazin-3-yl)-4,5-difluorophenyl)-3-chloro-1,7-naphthyridin-8-amine | 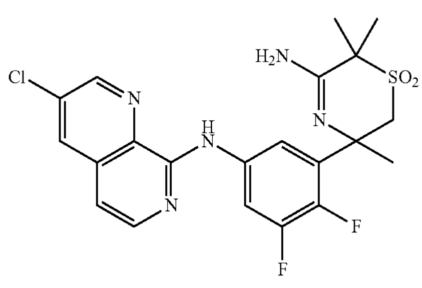 [SMILES: CC1(c2cc(Nc3nccc4cc(Cl)cnc34)cc(F)c2F)CS(=O)(=O)C(C)(C)C(N)=N1] | LC/MS (ESI⁺) m/z = 480 (M + H) |

TABLE 2-continued

| Example # | Product | Structure | Analytical Data |
|---|---|---|---|
| 66 | N-(5-((3R)-5-amino-3,6,6-trimethyl-1,1-dioxido-3,6-dihydro-2H-1,4-thiazin-3-yl)-6-fluoro-3-pyridinyl)-3-methoxy-1,7-naphthyridin-8-amine | 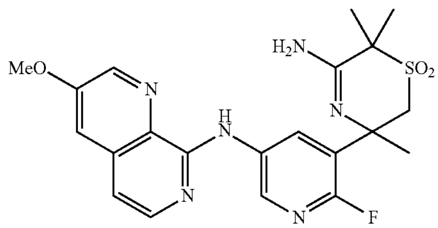 [SMILES: COc1cnc2c(Nc3cnc(F)c(C4(C)CS(=O)(=O)C(C)(C)C(N)=N4)c3)nccc2c1] | $^1$H NMR (400 MHz, DMSO-$d_6$) δ ppm 1.50 (s, 3 H) 1.63 (d, J = 16.82 Hz, 6 H) 3.54-3.71 (m, 2 H) 4.00 (s, 3 H) 6.13 (br. s., 2 H) 7.19 (d, J = 5.67 Hz, 1 H) 7.74 (d, J = 2.93 Hz, 1 H) 8.07 (d, J = 5.67 Hz, 1 H) 8.59-8.68 (m, 2 H) 8.83 (t, J = 2.25 Hz, 1 H) 9.70 (s, 1 H). LC/MS (ESI$^+$) m/z = 459 (M + H) |

Example 67

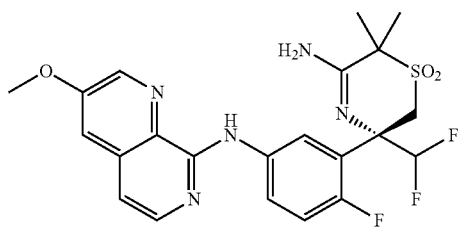 [SMILES: COc1cnc2c(Nc3ccc(F)c([C@]4(C(F)F)CS(=O)(=O)C(C)(C)C(N)=N4)c3)nccc2c1]

Synthesis of (S)-5-Amino-3-(difluoromethyl)-3-(2-fluoro-5-((3-methoxy-1,7-naphthyridin-8-yl)amino)phenyl)-6,6-dimethyl-3,6-dihydro-2H-1,4-thiazine 1,1-dioxide Example 62 was purified by chiral SFC, using an AD-H column and eluting with 35% methanol/0.2% diethylamine in CO$_2$, to provide the title compound. LC/MS (ESI$^+$) m/z=494 (M+H). $^1$H NMR (400 MHz, DMSO-$d_6$) δ 9.37 (s, 1H), 8.70 (d, J=2.74 Hz, 1H), 8.24-8.37 (m, 1H), 8.01-8.23 (m, 2H), 7.79 (d, J=2.84 Hz, 1H), 7.14-7.26 (m, 2H), 6.68 (br. s., 2H), 6.04 (t, J=56.0 Hz, 1H), 4.05 (s, 3H), 3.90 (d, J=4.30 Hz, 2H), 1.70 (s, 3H), 1.54 (s, 3H).

Example 68

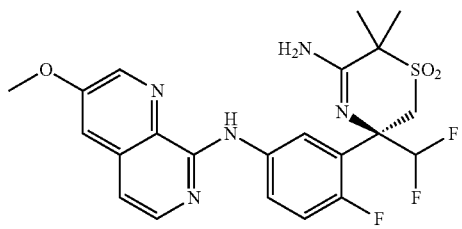 [SMILES: COc1cnc2c(Nc3ccc(F)c([C@@]4(C(F)F)CS(=O)(=O)C(C)(C)C(N)=N4)c3)nccc2c1]

Synthesis of (R)-5-Amino-3-(difluoromethyl)-3-(2-fluoro-5-((3-methoxy-1,7-naphthyridin-8-yl)amino)phenyl)-6,6-dimethyl-3,6-dihydro-2H-1,4-thiazine 1,1-dioxide The title compound is the other enantiomer recovered from the chiral SFC purification of Example 62, using an AD-H column and eluting with 35% methanol/0.2% diethylamine in CO$_2$. LC/MS (ESI$^+$) m/z=494 (M+H). $^1$H NMR (400 MHz, DMSO-$d_6$) δ 9.37 (s, 1H), 8.70 (d, J=2.74 Hz, 1H), 8.24-8.37 (m, 1H), 8.01-8.23 (m, 2H), 7.79 (d, J=2.84 Hz, 1H), 7.14-7.26 (m, 2H), 6.68 (br. s., 2H), 6.04 (t, J=56.0 Hz, 1H), 4.05 (s, 3H), 3.90 (d, J=4.30 Hz, 2H), 1.70 (s, 3H), 1.54 (s, 3H).

Example 69

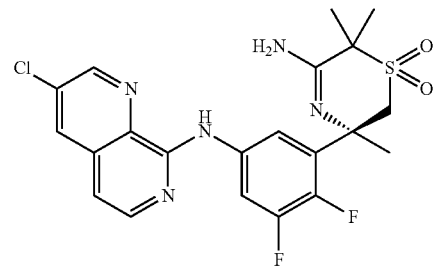 [SMILES: CC1(C)C(N)=N[C@](C)(c2cc(Nc3nccc4cc(Cl)cnc34)cc(F)c2F)CS1(=O)=O]

Synthesis of (R)-5-Amino-3-(5-((3-chloro-1,7-naphthyridin-8-yl)amino)-2,3-difluorophenyl)-3,6,6-trimethyl-3,6-dihydro-2H-1,4-thiazine 1,1-dioxide Example 65 was purified by chiral SFC, using a Chiralpak IC column and eluting with 60% methanol/0.2% diethylamine in CO$_2$, to provide the title compound. LC/MS (ESI$^+$) m/z=480 (M+H).

Example 70

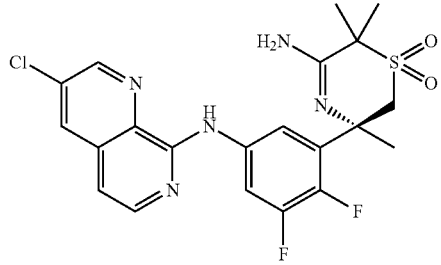 [SMILES: CC1(C)C(N)=N[C@](C)(c2cc(Nc3nccc4cc(Cl)cnc34)cc(F)c2F)CS1(=O)=O]

Synthesis of (S)-5-Amino-3-(5-((3-chloro-1,7-naph-thyridin-8-yl)amino)-2,3-difluorophenyl)-3,6,6-trimethyl-3,6-dihydro-2H-1,4-thiazine 1,1-dioxide The title compound is the other enantiomer recovered from the chiral SFC purification of Example 65, using a Chiralpak IC column and eluting with 60% methanol/0.2% diethylamine in CO$_2$. LC/MS (ESI$^+$) m/z=480 (M+H).

Example 71

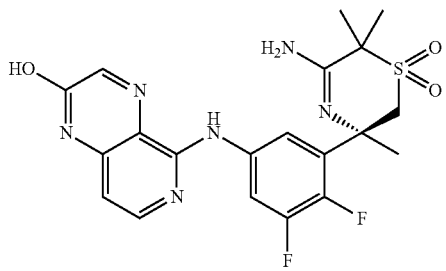 [SMILES: CC1(C)C(N)=N[C@](C)(c2cc(Nc3nccc4nc(O)cnc34)cc(F)c2F)CS1(=O)=O]

Synthesis of (R)-5-Amino-3-(2,3-difluoro-5-((2-hydroxypyrido[3,4-b]pyrazin-5-yl)amino)phenyl)-3,6,6-trimethyl-3,6-dihydro-2H-1,4-thiazine 1,1-dioxide In an analogous reaction sequence described for Example 44, tert-butyl (5-(5-amino-2,3-difluorophenyl)-2,2,5-trimethyl-1,1-dioxido-5,6-dihydro-2H-1,4-thiazin-3-yl)carbamate and 5-chloro-2-methoxypyrido[3,4-b]pyrazine were combined to provide the racemic product, which was purified by chiral SFC, using a ChiralPak IC column and eluting with 50% methanol/0.2% diethylamine in CO$_2$, to provide the title compound. LC/MS (ESI$^+$) m/z=463 (M+H).

Example 72

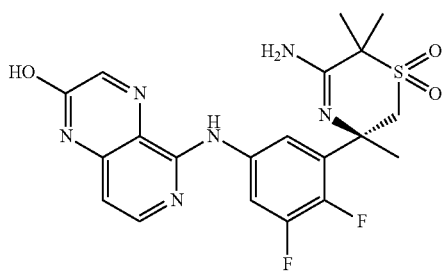 [SMILES: CC1(C)C(N)=N[C@@](C)(c2cc(Nc3nccc4nc(O)cnc34)cc(F)c2F)CS1(=O)=O]

Synthesis of (S)-5-Amino-3-(2,3-difluoro-5-((2-hydroxypyrido[3,4-b]pyrazin-5-yl)amino)phenyl)-3,6,6-trimethyl-3,6-dihydro-2H-1,4-thiazine 1,1-dioxide The title compound is the other enantiomer recovered from the chiral SFC purification of Example 71, using a ChiralPak column and eluting with 50% methanol/0.2% diethylamine in CO$_2$. LC/MS (ESI$^+$) m/z=463 (M+H).

Example 73

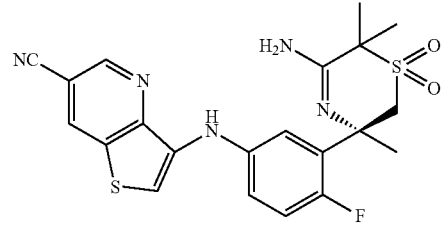 [SMILES: CC1(C)C(N)=N[C@](C)(c2cc(Nc3csc4cc(C#N)cnc34)ccc2F)CS1(=O)=O]

Synthesis of (R)-3-((3-(5-Amino-3,6,6-trimethyl-1,1-dioxido-3,6-dihydro-2H-1,4-thiazin-3-yl)-4-fluorophenyl)amino)thieno[3,2-b]pyridine-6-carbonitrile A microwave vial was charged with (R)-5-amino-3-(5-bromo-2-fluorophenyl)-3,6,6-trimethyl-3,6-dihydro-2H-1,4-thiazine 1,1-dioxide (125 mg, 0.344 mmol), 3-aminothieno[3,2-b]pyridine-6-carbonitrile (90 mg, 0.516 mmol), 2-di-tert-butylphosphino-2',4',6'-triisopropylbiphenyl (43.9 mg, 0.103 mmol), sodium tert-butoxide (93 mg, 0.964 mmol), tris(dibenzylideneacetone)dipalladium(0) (31.5 mg, 0.034 mmol), and toluene (1.72 mL). The vial was purged with argon, sealed, and irradiated in a microwave reactor at 100° C. for 1.5 hours. The reaction was diluted with water and extracted with ethyl acetate; the organic layer was concentrated. The crude product was purified via silica gel chromatography, eluting with 20-100% ethyl acetate in hexane, to the title compound (50 mg, 0.109 mmol, 32% yield). LC/MS (ESI$^+$) m/z=458 (M+H). $^1$H NMR (400 MHz, DMSO-d$_6$) 9.07 (d, J=1.9 Hz, 1H), 9.06 (d, J=1.9 Hz, 1H), 8.46 (s, 1H), 7.52 (dd, J=2.9, 7.2 Hz, 1H), 7.49 (s, 1H), 7.17-7.24 (m, 1H), 7.06 (dd, J=8.8, 11.9 Hz, 1H), 6.09 (br. s., 2H), 3.66 (d, J=15.5 Hz, 1H), 3.51 (d, J=15.5 Hz, 1H), 1.63 (s, 3H), 1.58 (s, 3H), 1.47 (s, 3H).

Example 74

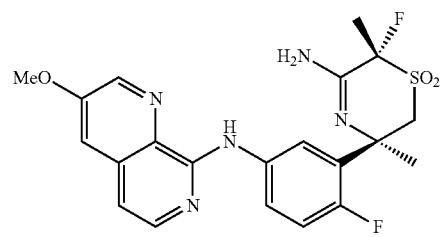 [SMILES: COc1cnc2c(Nc3ccc(F)c([C@]4(C)CS(=O)(=O)[C@@](C)(F)C(N)=N4)c3)nccc2c1]

Synthesis of (3R,6R)-5-Amino-6-fluoro-3-(2-fluorophenyl-5-((3-methoxy-1,7-naphthyridin-8-yl)amino)phenyl)-3,6-dimethyl-3,6-dihydro-2H-1,4-thiazine 1,1-dioxide In an analogous reaction to that described for Example 73, (R)-5-amino-3-(5-bromo-2-fluorophenyl)-3,6,6-trimethyl-3,6-dihydro-2H-1,4-thiazine 1,1-dioxide (50 mg, 0.136 mmol) and 3-methoxy-1,7-naphthyridine-8-amine (29 mg, 0.163 mmol) were converted to the title compound (7 mg, 0.015 mmol, 11% yield) as an off-white solid. LC/MS (ESI$^+$) m/z=462 (M+H).

Example 75

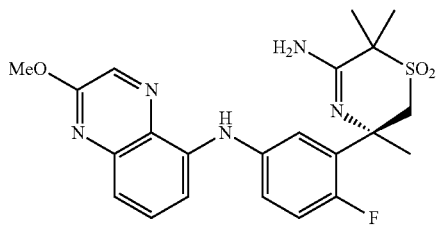 [SMILES: COc1cnc2c(Nc3ccc(F)c([C@]4(C)CS(=O)(=O)C(C)(C)C(N)=N4)c3)cccc2n1]

Synthesis of (R)-5-Amino-3-(2-fluoro-5-((2-methoxyquinoxalin-5-yl)amino)phenyl)-3,6,6-trimethyl-3,6-dihydro-2H-1,4-thiazine 1,1-dioxide A sealable vial was charged with (R)-5-amino-3-(5-bromo-2-fluorophenyl)-3,6,6-trimethyl-3,6-dihydro-2H-1,4-thiazine 1,1-dioxide (34 mg, 0.094 mmol), 2-methoxyquinoxalin-5-amine (18.04 mg, 0.103 mmol) and (2-dicyclohexylphosphino-2',4',6'-triisopropyl-1,1'-biphenyl)[2-(2-aminoethyl)phenyl)]palladium(II) chloride (13.83 mg, 0.019 mmol). The vial was purged with nitrogen, tetrahydrofuran (0.1 mL) was added, followed by lithium bis(trimethylsilyl)amide (234 µL, 0.234 mmol; 1.0M solution in tetrahydrofuran). The reaction mixture was stirred for 2 hours at 65° C., cooled to ambient temperature, and partitioned between 1 M aqueous hydrochloric acid and ethyl acetate. The organic phase was separated and dried over anhydrous magnesium sulfate, filtered, and concentrated. The crude product was purified by reverse-phase preparative HPLC, eluting with 10-100% (0.1% trifluoroacetic acid in acetonitrile) in (0.1% trifluoroacetic acid in water). The product fractions were combined and concentrated, and the residue was redissolved in dichloromethane and washed with 2 M aqueous sodium carbonate. The organic phase was dried over anhydrous magnesium sulfate, filtered, and concentrated to provide the title compound as a greenish-yellow solid.

LC/MS (ESI+) m/z=458 (M+H). $^1$H NMR (400 MHz, CDCl$_3$) δ ppm 1.66 (s, 3H) 1.73 (s, 3H) 1.87 (s, 3H) 3.65 (d, J=4.30 Hz, 2H) 7.07 (dd, J=11.64, 8.71 Hz, 1H) 7.21 (dd, J=15.06, 8.22 Hz, 2H) 7.25-7.30 (m, 4H) 7.40-7.52 (m, 2H) 7.80 (s, 1H) 8.31 (s, 1H).

Example 76

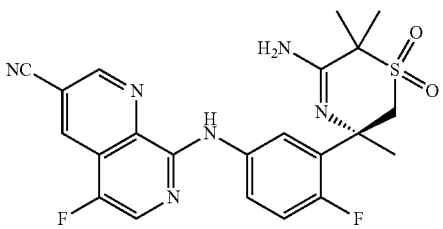 [SMILES: CC1(C)C(N)=N[C@](C)(c2cc(Nc3ncc(F)c4cc(C#N)cnc34)ccc2F)CS1(=O)=O]

Synthesis of (R)-8-((3-(5-Amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile A sealable vial was charged with (R)-5-amino-3-(5-((3-chloro-5-fluoro-1,7-naphthyridin-8-yl)amino)-2-fluorophenyl)-3,6,6-trimethyl-3,6-dihydro-2H-1,4-thiazine 1,1-dioxide (150 mg, 0.313 mmol), 2-dicyclohexylphosphino-2',6'-dimethoxybiphenyl (25.7 mg, 0.063 mmol), tris(dibenzylideneacetone)dipalladium(0) (22.90 mg, 0.025 mmol), ZnCN$_2$ (29.8 µL, 0.469 mmol), N,N-dimethylformamide (1.5 mL), and a drop of water. The vial was purged with argon and the reaction was heated at 110° C. for 1 hour. The reaction was partitioned between water and dichloromethane, and the organic portion was washed with brine, dried with anhydrous sodium sulfate, filtered and concentrated. The crude product was purified by silica gel chromatography, eluting with 5-75% (3:1 ethyl acetate/ethanol, 2% ammonium hydroxide) in heptanes, to provide the title compound (80 mg, 0.170 mmol, 54.4% yield) as a yellow solid. $^1$H-NMR (400 MHz, DMSO-d$_6$): δ (s, 1H), 9.33 (d, J=4 Hz, 1H), 9.14 (d, J=4 Hz, 1H), 8.24 (s, 1H), 8.12-8.10 (m, 1H), 8.00-7.98 (m, 1H), 7.13 (dd, J=8 Hz, 12 Hz, 1H), 6.05 (br s, 2H), 3.64 (d, J=16 Hz, 1H), 3.51 (d, J=16 Hz, 1H), 1.65 (s, 3H), 1.58 (s, 3H), 1.48 (s, 3H). LC/MS (ESI+) m/z=471 (M+H).

Example 77

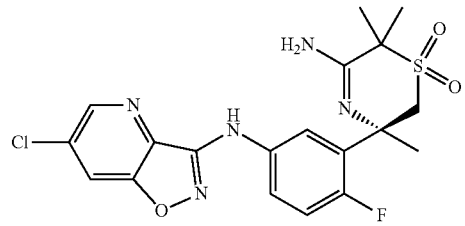 [SMILES: CC1(C)C(N)=N[C@](C)(c2cc(Nc3noc4cc(Cl)cnc34)ccc2F)CS1(=O)=O]

Synthesis of (R)-5-Amino-3-(5-((6-chloroisoxazolo[4,5-b]pyridin-3-yl)amino)-2-fluorophenyl)-3,6,6-trimethyl-3,6-dihydro-2H-1,4-thiazine 1,1-dioxide Step 1:
5-Chloro-3-fluoro-N-methoxy-N-methylpicolinamide To a stirred mixture of 5-chloro-3-fluoropicolinic acid (3.62 g, 20.62 mmol) in dichloromethane (50 mL) were added 1H-benzo[d][1,2,3]triazol-1-ol (0.42 g, 3.09 mmol), N$_1$-((ethylimino)methylene)-N$_3$,N$_3$-dimethylpropane-1,3-diamine HCl (5.93 g, 30.9 mmol), N,O-dimethylhydroxylamine HCl (3.02 g, 30.9 mmol), and TEA (7.19 mL, 51.6 mmol). The reaction mixture was stirred at RT for 2 hours, and then partitioned between ethyl acetate and water. The aqueous layer was extracted with EtOAc, and the combined organic layers were dried over anhydrous sodium sulfate, filtered, and concentrated. The crude product was purified by column chromatography, eluting with 0-100% EtOAc in heptane, to provide the title intermediate (3.71 g) as a white solid.

Step 2: 5-Chloro-3-fluoropicolinaldehyde

To a solution of 5-chloro-3-fluoro-N-methoxy-N-methylpicolinamide (3.71 g, 16.97 mmol) in THF (50 mL) at −78° C. was added a1 M solution of lithium aluminum hydride in THF (7.81 mL, 7.81 mmol). After stirring at −78° C. for 30 minutes, the mixture was quenched with water (35 mL) and brine (30 mL) and allowed to warm to ambient temperature. The aqueous layer was extracted with ethyl acetate, and the combined organic layers were washed with brine, dried over anhydrous sodium sulfate, filtered, and concentrated. The crude product was purified by column chromatography, eluting with 0-50% ethyl acetate in heptane, to afford the title compound as a light yellow oil.

Step 3: (E)-5-Chloro-3-fluoropicolinaldehyde oxime

To a solution of 5-chloro-3-fluoropicolinaldehyde (2.71 g, 17.0 mmol) and hydroxylamine (50 wt % in water, 1.40 g, 21.2 mmol) in MeOH (30 mL) was added 5 N aqueous NaOH (5.10 mL, 25.5 mmol). After 1.5 hours, the mixture was neutralized with concentrated HCl and extracted with DCM. The organic layer was washed with brine, dried over anhydrous sodium sulfate, filtered, and concentrated to afford the title compound (2.61 g) as orange solid. The product was used in next step without further purification.

Step 4: (Z)-5-Chloro-3-fluoro-N-hydroxypicolinimidoyl chloride

To a solution of (E)-5-chloro-3-fluoropicolinaldehyde oxime (0.50 g, 2.86 mmol) in DMF (10 mL) was added N-chlorosuccinimide (0.41 g, 3.08 mmol). The mixture was stirred at 50° C. for 30 minutes, another portion of N-chlorosuccinimide (56 mg) was added, and the reaction was stirred at 50° C. for 30 minutes. The reaction mixture was poured into ice water and extracted with EtOAc. The organic layer was washed with water and brine, dried over anhydrous sodium sulfate, filtered, and concentrated to afford the title compound as a yellow oil.

Step 5: N-(5-(5-Bromo-2-fluorophenyl)-2,2,5-trimethyl-1,1-dioxido-5,6-dihydro-2H-1,4-thiazin-3-yl)benzamide To a solution of (R,S)-5-amino-3-(5-bromo-2-fluorophenyl)-3,6,6-trimethyl-3,6-dihydro-2H-1,4-thiazine 1,1-dioxide (2.42 g, 6.66 mmol) in DMF (40 mL) was added TEA (1.39 mL, 9.99 mmol) and benzoic anhydride (1.66 g, 7.33 mmol). The reaction was stirred at ambient temperature for 1 hour, diluted with saturated aqueous sodium carbonate, and extracted with ethyl acetate. The organic layer was washed with water and brine, dried over anhydrous sodium sulfate, and concentrated. The crude product was purified by column chromatography, eluting with 0-50% ethyl acetate in heptane, to provide the title compound (3.02 g) as a yellow solid.

Step 6: (R)—N-(5-(5-Amino-2-fluorophenyl)-2,2,5-trimethyl-1,1-dioxido-5,6-dihydro-2H-1,4-thiazin-3-yl)benzamide A mixture of N-(5-(5-bromo-2-fluorophenyl)-2,2,5-trimethyl-1,1-dioxido-5,6-dihydro-2H-1,4-thiazin-3-yl)benzamide (3.00 g, 6.42 mmol), sodium azide (1.25 g, 19.26 mmol), (+)-sodium L-ascorbate (0.51 g, 2.57 mmol), (1R, 2R)—$N_1,N_2$-dimethylcyclohexane-1,2-diamine (1.01 mL, 6.42 mmol), and copper (I) iodide (0.49 g, 2.57 mmol) in ethanol (34.5 mL) and water (15 mL) under a nitrogen atmosphere was stirred at 70° C. for 3 hours. The reaction was cooled to RT and partitioned between ethyl acetate and water. The aqueous layer was extracted with ethyl acetate, and the combined organic layers were washed with brine, dried over anhydrous sodium sulfate, filtered, and concentrated. The crude product was resubjected to the reaction conditions and stirred at 80° C. for 5 hours. The reaction was again cooled to RT and partitioned between ethyl acetate and water. The aqueous layer was extracted with ethyl acetate, and the combined organic layers were washed with brine, dried over anhydrous sodium sulfate, filtered, and concentrated. The crude product was purified by column chromatography, eluting with 0-60% ethyl acetate in heptane, to afford the title compound (1.80 g) as an off-white solid.

Step 7: (Z)—N-(5-(5-(5-Chloro-3-fluoro-N-hydroxypicolinimidamido)-2-fluorophenyl)-2,2,5-trimethyl-1,1-dioxido-5,6-dihydro-2H-1,4-thiazin-3-yl)benzamide A mixture of (Z)-5-chloro-3-fluoro-N-hydroxypicolinimidoyl chloride (0.52 g, 2.47 mmol) and N-(5-(5-amino-2-fluorophenyl)-2,2,5-trimethyl-1,1-dioxido-5,6-dihydro-2H-1,4-thiazin-3-yl)benzamide (0.83 g, 2.06 mmol) in THF (8 mL) was stirred at reflux overnight, and then stirred at 75° C. for 4 hours. The cooled reaction mixture was partitioned between ethyl acetate and water. The aqueous phase was extracted with ethyl acetate, and the combined organic layers were washed with brine, dried over anhydrous sodium sulfate, filtered and concentrated. The crude product was purified by column chromatography, eluting with 20-100% ethyl acetate in heptane, to provide the title compound (0.30 g) as an orange solid.

Step 8: N-(5-(5-((6-Chloroisoxazolo[4,5-b]pyridin-3-yl)amino)-2-fluorophenyl)-2,2,5-trimethyl-1,1-dioxido-5,6-dihydro-2H-1,4-thiazin-3-yl)benzamide To a solution of (Z)—N-(5-(5-(5-chloro-3-fluoro-N'-hydroxypicolinimidamido)-2-fluorophenyl)-2,2,5-trimethyl-1,1-dioxido-5,6-dihydro-2H-1,4-thiazin-3-yl)benzamide (0.60 g, 1.05 mmol) in DMF (25 mL) at 0° C. under a nitrogen atmosphere was added 60% NaH in mineral oil (0.15 g, 3.78 mmol). The mixture was gradually warmed to ambient temperature and stirred for 2 hours. The reaction was partitioned between water and EtOac, and the aqueous layer was extracted with EtOAc. The combined organic extracts were washed with water and brine, dried over anhydrous sodium sulfate, filtered, and concentrated. The crude product was purified by column chromatography, eluting with 0-50% ethyl acetate in heptane, to provide the title compound (0.43 g) as an off-white solid.

Step 9: (R)-5-Amino-3-(5-(((6-chloroisoxazolo[4,5-b]pyridin-3-yl)amino)-2-fluorophenyl)-3,6,6-trimethyl-3,6-dihydro-2H-1,4-thiazine 1,1-dioxide A sealed tube was charged with N-(5-(5-((6-chloroisoxazolo[4,5-b]pyridin-3-yl)amino)-2-fluorophenyl)-2,2,5-trimethyl-1,1-dioxido-5,6-dihydro-2H-1,4-thiazin-3-yl)benzamide (0.43 g, 0.77 mmol), tetrahydrofuran (6 mL) and 2.0 M ammonia in methanol (19.33 mL, 38.70 mmol). The tube was sealed and stirred at 60° C. overnight. The reaction was concentrated in vacuo, and the residue was triturated with DCM and then MeOH. The resulting solid was purified by chiral SFC, using a ChiralCel OD-H column and eluting with 55% (20 mM ammonia in MeOH) in $CO_2$, to provide the title compound as a white solid. $^1$H NMR (400 MHz, methanol-$d_4$) δ 8.42 (br. s., 1H), 7.86 (br. s., 1H), 7.74-7.39 (m, 2H), 6.95 (br. s., 1H), 3.65 (br. s., 2H), 2.03-1.44 (m, 9H). LC/MS (ESI$^+$) m/z=452 (M+H).

Example 78

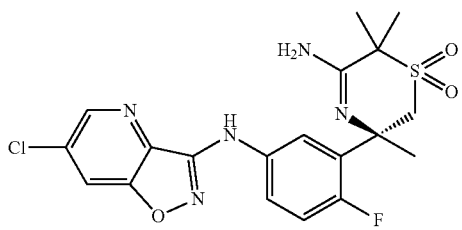 [SMILES: CC1(C)C(N)=N[C@@](C)(c2cc(Nc3noc4cc(Cl)cnc34)ccc2F)CS1(=O)=O]

Synthesis of (S)-5-Amino-3-(5-((6-chloroisoxazolo [4,5-b]pyridin-3-yl)amino)-2-fluorophenyl)-3,6,6-trimethyl-3,6-dihydro-2H-1,4-thiazine 1,1-dioxide The title compound is the other enantiomer recovered from the chiral SFC purification of Example 77, using a ChiralCel OD-H column and eluting with 55% (20 mM ammonia in methanol) in CO$_2$. $^1$H NMR (400 MHz, methanol-$d_4$) δ 8.39 (br. s., 1H), 7.81 (br. s., 1H), 7.69-7.39 (m, 2H), 6.93 (br. s., 1H), 3.65 (br. s., 2H), 1.89-1.52 (m, 9H). LC/MS (ESI$^+$) m/z=452 (M+H).

Example 79

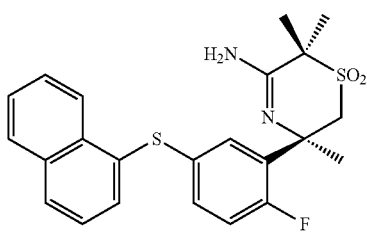

Synthesis of (R)-5-Amino-3-(2-fluoro-5-(naphthalen-1-ylthio)phenyl)-3,6,6-trimethyl-3,6-dihydro-2H-1,4-thiazine 1,1-dioxide To a solution of (R)-5-amino-3-(5-bromo-2-fluorophenyl)-3,6,6-trimethyl-3,6-dihydro-2H-1,4-thiazine 1,1-dioxide (50 mg, 0.138 mmol) and 4,5-bis(diphenylphosphino)-9,9-dimethylxanthene (7.96 mg, 0.014 mmol) in dioxane (1 mL) were added 1-naphthalenethiol (0.021 mL, 0.151 mmol), tris(dibenzylideneacetone)dipalladium(0) (6.30 mg, 6.88 μmol), and DIPEA (0.048 mL, 0.275 mmol). The reaction was flushed with argon, sealed, and stirred at 100° C. for 6 hours. The reaction mixture was partitioned between water and EtOAc; the organic layer was washed with water and brine and concentrated. The crude product was purified by silica-gel chromatography, eluting with 20-100% ethyl acetate in heptane, to provide the title compound (47 mg, 0.106 mmol) as a off-white powder. LC/MS (ESI$^+$) m/z=443 (M+H).

Example 80

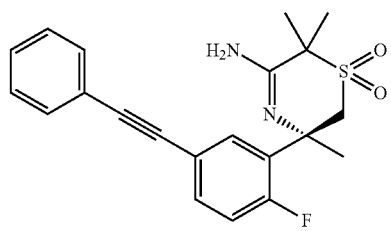 [SMILES: CC1(C)C(N)=N[C@](C)(c2cc(C#Cc3ccccc3)ccc2F)CS1(=O)=O]

Synthesis of (R)-5-amino-3-(2-fluoro-5-(phenylethynyl)phenyl)-3,6,6-trimethyl-3,6-dihydro-2H-1,4-thiazine 1,1-dioxide To a solution of (R)-5-amino-3-(5-bromo-2-fluorophenyl)-3,6,6-trimethyl-3,6-dihydro-2H-1,4-thiazine 1,1-dioxide (100 mg, 0.275 mmol) and ethynylbenzene (0.060 mL, 0.551 mmol) in dioxane (1 mL) was added copper(I) iodide (7.86 mg, 0.041 mmol), bis(triphenylphosphine)palladium (ii) dichloride (19.32 mg, 0.028 mmol), and triethylamine (0.19 mL, 1.38 mmol). The vial was flushed with argon, sealed, and stirred at 100° C. for 5 hours. The reaction was diluted with ethyl acetate, washed with water and brine, dried over anhydrous sodium sulfate, filtered, and concentrated. The crude product was purified by reverse phase HPLC, eluting with a gradient of 15-90% (1% TFA in ACN)/(1% trifluoroacetic acid in water). The product fractions were combined and extracted with EtOAc. The organic layer was washed with aqueous sodium carbonate and water, dried over anhydrous sodium sulfate, filtered, and concentrated to provide the title compound (44 mg, 0.114 mmol) as an off-white solid. $^1$H NMR (400 MHz, CDCl$_3$) δ ppm 1.64 (s, 3H) 1.71 (s, 3H) 1.82 (s, 3H) 3.51-3.66 (m, 2H) 7.05 (dd, J=12.13, 8.41 Hz, 1H) 7.33-7.38 (m, 3H) 7.44 (ddd, J=8.41, 4.74, 2.20 Hz, 1H) 7.50-7.55 (m, 2H) 7.69 (dd, J=7.87, 2.20 Hz, 1H). LC/MS (ESI$^+$) m/z=385 (M+H).

Example 81

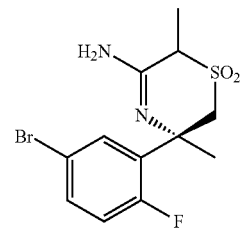

Synthesis of 3R)-5-amino-3-(5-bromo-2-fluorophenyl)-3,6-dimethyl-3,6-dihydro-2H-1,4-thiazine 1,1-dioxide Step 1: tert-butyl ((2R)-2-(5-bromo-2-fluorophenyl)-1-((1-cyanoethyl)sulfonyl)propan-2-yl)carbamate In an analogous oxidation to that described for Example 1, step 4, tert-butyl ((2R)-2-(5-bromo-2-fluorophenyl)-1-

((1-cyanoethyl)thio)propan-2-yl)carbamate was converted to the title compound (0.87 g, 1.94 mmol) as a white foam. LC/MS (ESI$^+$) m/z=471, 473 (M+Na; 2 bromine isotopes).

Step 2: (3R)-5-amino-3-(5-bromo-2-fluorophenyl)-3,6-dimethyl-3,6-dihydro-2H-1,4-thiazine 1,1-dioxide In an analogous reaction to that described for Example 5, step 1, tert-butyl ((2R)-2-(5-bromo-2-fluorophenyl)-1-((1-cyanoethyl)sulfonyl)propan-2-yl)carbamate was converted to the title compound (120 mg, 0.344 mmol) as an off-white foam. LC/MS (ESI$^+$) m/z=349, 351 (M+H; 2 bromine isotopes).

Example 82

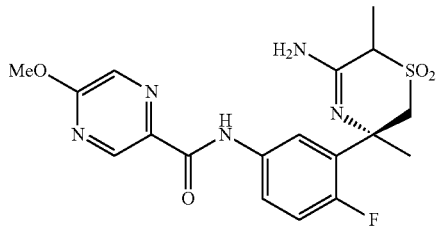

Synthesis of N-(3-((3R)-5-Amino-3,6-dimethyl-1,1-dioxido-3,6-dihydro-2H-1,4-thiazin-3-yl)-4-fluorophenyl)-5-methoxypyrazine-2-carboxamide Step 1: tert-Butyl ((5R)-5-(5-amino-2-fluorophenyl)-2,5-dimethyl-1,1-dioxido-5,6-dihydro-2H-1,4-thiazin-3-yl)carbamate In an analogous sequence of reactions to those described for Intermediate 2, steps 1-3, (3R)-5-amino-3-(5-bromo-2-fluorophenyl)-3,6-dimethyl-3,6-dihydro-2H-1,4-thiazine 1,1-dioxide was converted to the title compound as a tan solid. LC/MS (ESI$^+$) m/z=522 (M+Na).

Step 2: N-(3-((3R)-5-amino-3,6-dimethyl-1,1-dioxido-3,6-dihydro-2H-1,4-thiazin-3-yl)-4-fluorophenyl)-5-methoxypyrazine-2-carboxamide As described in the HATU procedure, tert-butyl ((5R)-5-(5-amino-2-fluorophenyl)-2,5-dimethyl-1,1-dioxido-5,6-dihydro-2H-1,4-thiazin-3-yl)carbamate was converted to the title compound (20 mg, 0.047 mmol) as a tan solid. LC/MS (ESI$^+$) m/z=422 (M+H).

Example 83

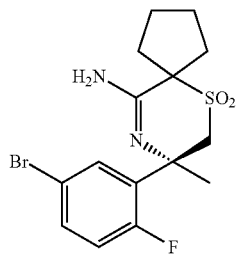 [SMILES: C[C@@]1(c2cc(Br)ccc2F)CS(=O)(=O)C2(CCCC2)C(N)=N1]

Synthesis of (R)-10-Amino-8-(5-bromo-2-fluorophenyl)-8-methyl-6-thia-9-azaspiro[4.5]dec-9-ene 6,6-dioxide Step 1: (R)-tert-Butyl (2-(5-bromo-2-fluorophenyl)-1-((1-cyanocyclopentyl)sulfonyl)propan-2-yl)carbamate To a solution of (R)-tert-butyl (2-(5-bromo-2-fluorophenyl)-1-((cyanomethyl)sulfonyl)propan-2-yl)carbamate (540 mg, 1.24 mmol) in DMF (4.1 mL) were added 1,4-dibromobutane (0.16 mL, 1.37 mmol) and potassium carbonate (377 mg, 2.73 mmol). The reaction was stirred at RT for 3 hours and then at 70° C. for 16 hours. The reaction mixture was cooled to RT and then partitioned between ethyl acetate and water. The organic layer was concentrated and purified by column chromatography, eluting with 0-1% methanol in DCM, to provide the title compound (375 mg, 0.766 mmol). LC/MS (ESI$^+$) m/z=511, 513 (M+Na; 2 bromine isotopes).

Step 2: (R)-10-Amino-8-(5-bromo-2-fluorophenyl)-8-methyl-6-thia-9-azaspiro[4.5]dec-9-ene 6,6-dioxide In an analogous reaction to that described for Example 1, step 5, (R)-tert-butyl (2-(5-bromo-2-fluorophenyl)-1-((1-cyanocyclopentyl)sulfonyl)propan-2-yl)carbamate was converted to the title compound (30 mg, 0.077 mmol) as a tan solid. LC/MS (ESI$^+$) m/z=389, 391 (M+H; 2 bromine isotopes).

Example 84

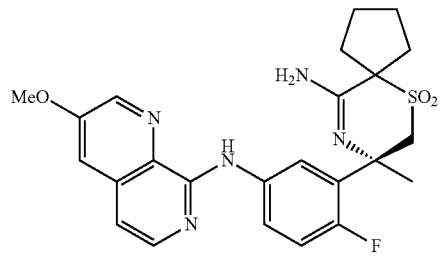 [SMILES: COc1cnc2c(Nc3ccc(F)c([C@]4(C)CS(=O)(=O)C5(CCCC5)C(N)=N4)c3)nccc2c1]

Synthesis of (R)-10-Amino-8-(2-fluoro-5-((3-methoxy-1,7-naphthyridin-8-yl)amino)phenyl)-8-methyl-6-thia-9-azaspiro[4.5]dec-9-ene 6,6-dioxide In an analogous reaction to that described for Example 73, (R)-10-amino-8-(5-bromo-2-fluorophenyl)-8-methyl-6-thia-9-azaspiro[4.5]dec-9-ene 6,6-dioxide (100 mg, 0.26 mmol) and 3-methoxy-1,7-naphthyridin-8-amine (58.5 mg, 0.33 mmol) were converted to the title compound (35 mg, 0.072 mmol) as a tan solid. LC/MS (ESI$^+$) m/z=484 (M+H).

Example 85

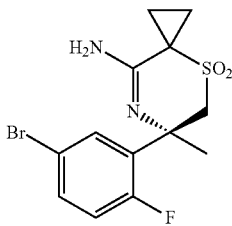 [SMILES: C[C@@]1(c2cc(Br)ccc2F)CS(=O)(=O)C2(CC2)C(N)=N1]

Synthesis of (R)-8-Amino-6-(5-bromo-2-fluorophenyl)-6-methyl-4-thia-7-azaspiro[2.5]oct-7-ene 4,4-dioxide Step 1: (R)-tert-Butyl (2-(5-bromo-2-fluorophenyl)-1-((1-cyanocyclopropyl)sulfonyl)propan-2-yl)carbamate In an analogous reaction to that described in Example 83, step 1, (R)-tert-butyl (2-(5-bromo-2-fluorophenyl)-1-((cyanomethyl)sulfonyl)propan-2-yl)carbamate and 1,2-dibromoethane were combined to provide the title intermediate (140 mg, 0.303 mmol) as a tan solid. LC/MS (ESI$^+$) m/z=483, 485 (M+Na; 2 bromine isotopes).

Step 2: (R)-8-Amino-6-(5-bromo-2-fluorophenyl)-6-methyl-4-thia-7-azaspiro[2.5]oct-7-ene 4,4-dioxide In an analogous reaction to that described in Example 83, step 2, (R)-tert-butyl (2-(5-bromo-2-fluorophenyl)-1-((1-cyanocyclopropyl)sulfonyl)propan-2-yl)carbamate was converted to the title compound (35 mg, 0.097 mmol) as an off-white solid. LC/MS (ESI$^+$) m/z=361, 363 (M+H; 2 bromine isotopes).

Example 86

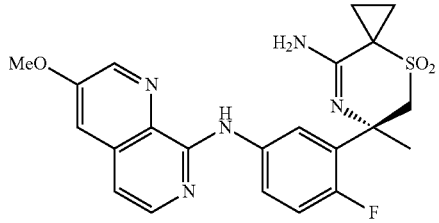 [SMILES: COc1cnc2c(Nc3ccc(F)c([C@]4(C)CS(=O)(=O)C5(CC5)C(N)=N4)c3)nccc2c1]

Synthesis of (R)-8-Amino-6-(2-fluoro-5-((3-methoxy-1,7-naphthyridin-8-yl)amino)phenyl)-6-methyl-4-thia-7-azaspiro[2.5]oct-7-ene 4,4-dioxide In an analogous reaction to that described for Example 73, (R)-8-amino-6-(5-bromo-2-fluorophenyl)-6-methyl-4-thia-7-azaspiro[2.5]oct-7-ene 4,4-dioxide and 3-methoxy-1,7-naphthyridin-8-amine (58.5 mg, 0.33 mmol) were combined to provide the title compound (60 mg, 0.132 mmol) as a tan solid. LC/MS (ESI$^+$) m/z=456 (M+H). $^1$H NMR (400 MHz, DMSO-d$_6$) δ ppm 9.39 (s, 1H) 8.63 (d, J=2.84 Hz, 1H) 8.09-8.17 (m, 1H) 7.98-8.09 (m, 2H) 7.71 (d, J=2.84 Hz, 1H) 7.09-7.18 (m, 2H) 5.88 (br. s., 2H) 3.98 (s, 3H) 3.60-3.77 (m, 2H) 1.85-1.94 (m, 1H) 1.78-1.83 (m, 1H) 1.73 (s, 3H) 1.52-1.60 (m, 1H) 1.48 (m, 1H).

Example 87

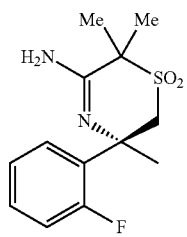 [SMILES: CC1(C)C(N)=N[C@](C)(c2ccccc2F)CS1(=O)=O]

Synthesis of (R)-5-Amino-3-(2-fluorophenyl)-3,6,6-trimethyl-3,6-dihydro-2H-1,4-thiazine 1,1-dioxide To a solution of (R)-5-amino-3-(5-bromo-2-fluorophenyl)-3,6,6-trimethyl-3,6-dihydro-2H-1,4-thiazine 1,1-dioxide (0.6 g, 1.65 mmol) in ethanol (20 mL) was added sodium bicarbonate (139 mg, 1.65 mmol) and 10 wt % palladium on carbon (180 mg, 0.169 mmol). The flask was evacuated and backfilled with hydrogen three times, and stirred at ambient temperature under a hydrogen atmosphere for 1 hour. The reaction mixture was filtered through Celite and concentrated to provide the title compound (0.55 g, 1.934 mmol) as a light-yellow solid. LC/MS (ESI$^+$) m/z=285 (M+H).

Examples 88 and 89

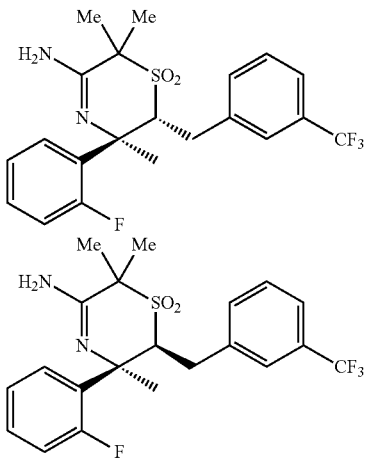

Synthesis of (2R,3R)-5-amino-3-(2-fluorophenyl)-3,6,6-trimethyl-2-(3-(trifluoromethyl)benzyl)-3,6-dihydro-2H-1,4-thiazine 1,1-dioxide and (2S,3R)-5-amino-3-(2-fluorophenyl)-3,6,6-trimethyl-2-(3-(trifluoromethyl)benzyl)-3,6-dihydro-2H-1,4-thiazine 1,1-dioxide Step 1: (R)-tert-Butyl (5-(2-fluorophenyl)-2,5,5-trimethyl-1,1-dioxido-5,6-dihydro-2H-1,4-thiazin-3-yl)carbamate To a suspension of (R)-5-amino-3-(2-fluorophenyl)-3,6,6-trimethyl-3,6-dihydro-2H-1,4-thiazine 1,1-dioxide (0.23 g, 0.809 mmol) in acetonitrile (5 mL) was added di-tert-butyl dicarbonate (0.194 g, 0.890 mmol) and a solution of sodium bicarbonate (0.102 g, 1.213 mmol) in water (1 mL). The reaction was stirred at ambient temperature for 3 hours, and then partitioned between water and ethyl acetate. The organic layer was washed with brine and concentrated. The crude material was purified by silica-gel chromatography, eluting with 0-100% ethyl acetate in dichloromethane, to provide the title compound (0.20 g, 0.520 mmol, 64.3% yield) as a off-white solid. LC/MS (ESI$^+$) m/z=385 (M+H).

Step 2: (R)-tert-Butyl (5-(2-fluorophenyl)-2,5,5-trimethyl-1,1-dioxido-6-(3-(trifluoromethyl)benzyl)-5,6-dihydro-2H-1,4-thiazin-3-yl)carbamate To a solution of (R)-tert-butyl (5-(2-fluorophenyl)-2,2,5-trimethyl-1,1-dioxido-5,6-dihydro-2H-1,4-thiazin-3-yl)carbamate (100 mg, 0.260 mmol) in THF (2 mL) at −78° C. was added a 2.7 M solution of n-butyllithium in heptane (0.241 mL, 0.650 mmol). The reaction was stirred for 5 minutes at −78° C., and then at 0° C. for 30 minutes. To the reaction was added 3-(trifluoromethyl)benzyl bromide (0.079 mL, 0.520 mmol), and the reaction was warmed slowly to RT. The reaction was neutralized with saturated aqueous ammonium chloride and extracted with ethyl acetate. The organic layer was concentrated and purified by silica-gel chromatography, eluting with 20-100% ethyl acetate in heptane, to provide the title compound (45 mg, 0.083 mmol) as a colorless oil.
LC/MS (ESI$^+$) m/z=543 (M+H); ~4:1 ratio of epimers.

Step 3: (2R,3R)-5-Amino-3-(2-fluorophenyl)-3,6,6-trimethyl-2-(3-(trifluoromethyl)benzyl)-3,6-dihydro-2H-1,4-thiazine 1,1-dioxide and (2S,3R)-5-Amino-3-(2-fluorophenyl)-3,6,6-trimethyl-2-(3-(trifluoromethyl)benzyl)-3,6-dihydro-2H-1,4-thiazine 1,1-dioxide To a solution of (R)-tert-butyl (5-(2-fluorophenyl)-2,2,5-trimethyl-1,1-dioxido-6-(3-(trifluoromethyl)benzyl)-5,6-dihydro-2H-1,4-thiazin-3-yl)carbamate (45 mg, 0.083 mmol) in dichloromethane (2 mL) was added TFA (0.128 mL, 1.66 mmol). The reaction was stirred at RT for one hour, diluted with ethyl acetate (10 mL), and neutralized with saturated aqueous sodium bicarbonate. The organic layer was concentrated and purified by silica-gel chromatography, eluting with 20-100% ethyl acetate in heptane. Two isomers with the desired mass were isolated; the major isomer (21 mg, 0.047 mmol, 57.2%) was the (2R,3R) epimer, and the minor isomer (6 mg, 0.014 mmol) was the (2S,3R) epimer. LC/MS (ESI$^+$) m/z=443 (M+H)

Example 90

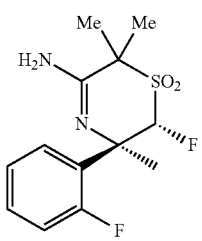 [SMILES: CC1(C)C(N)=N[C@](C)(c2ccccc2F)[C@@H](F)S1(=O)=O]

Synthesis of (2S,3R)-5-Amino-2-fluoro-3-(2-fluorophenyl)-3,6,6-trimethyl-3,6-dihydro-2H-1,4-thiazine 1,1-dioxide Step 1: (R)-tert-Butyl (6-fluoro-5-(2-fluorophenyl)-2,5,5-trimethyl-1,1-dioxido-5,6-dihydro-2H-1,4-thiazin-3-yl)carbamate To a solution of (R)-tert-butyl (5-(2-fluorophenyl)-2,2,5-trimethyl-1,1-dioxido-5,6-dihydro-2H-1,4-thiazin-3-yl)carbamate (100 mg, 0.260 mmol) in THF (2 mL) at −78° C. was added a 2.7 M solution of n-BuLi in heptane (0.289 mL, 0.780 mmol). The reaction was stirred for 5 minutes at −78° C., and then at 0° C. for 30 minutes. To the reaction was added N-fluorobenzenesulfonimide (328 mg, 1.040 mmol), and the reaction was warmed slowly to RT. After 30 minutes, the reaction was neutralized with saturated aqueous ammonium chloride and extracted with EtOAc. The organic layer was concentrated and purified by silica-gel chromatography, eluting with 20-100% EtOAc in heptane, to provide the titled intermediate (45 mg, 0.112 mmol) as a light-yellow oil. LC/MS (ESI$^+$) m/z=403 (M+H).

Step 2: (2S,3R)-5-Amino-2-fluoro-3-(2-fluorophenyl)-3,6,6-trimethyl-3,6-dihydro-2H-1,4-thiazine 1,1-dioxide To a solution of (R)-tert-butyl (6-fluoro-5-(2-fluorophenyl)-2,2,5-trimethyl-1,1-dioxido-5,6-dihydro-2H-1,4-thiazin-3-yl)carbamate (45 mg, 0.112 mmol) in dichloromethane (2 mL) was added TFA (0.172 mL, 2.24 mmol). The reaction was stirred at ambient temperature for 1 hour, diluted with ethyl acetate, and neutralized with saturated aqueous sodium bicarbonate. The organic layer was purified by silica-gel chromatography, eluting with 0-10% methanol in dichloromethane, to provide the title compound (22 mg, 0.073 mmol) as an off-white solid. LC/MS (ESI$^+$) m/z=303 (M+H).

Example 91

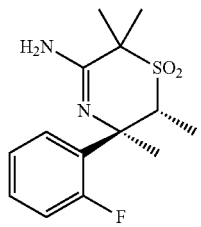 [SMILES: C[C@@H]1[C@@](C)(c2ccccc2F)N=C(N)C(C)(C)S1(=O)=O]

Synthesis of (2R,3R)-5-Amino-3-(2-fluorophenyl)-2,3,6,6-tetramethyl-3,6-dihydro-2H-1,4-thiazine 1,1-dioxide To a solution of (R)-tert-butyl (5-(2-fluorophenyl)-2,2,5-trimethyl-1,1-dioxido-5,6-dihydro-2H-1,4-thiazin-3-yl)carbamate (120 mg, 0.312 mmol) in THF (2 mL) at −78° C. was added a 2.7 M solution of n-BuLi in heptane (0.347 mL, 0.936 mmol). The reaction was stirred for 5 minutes at −78° C., and then at 0° C. for 15 minutes. To the reaction was added iodomethane (0.078 mL, 1.25 mmol), and the reaction was stirred at 0° C. After 30 minutes, the reaction was neutralized with saturated aqueous ammonium chloride and extracted with ethyl acetate. The organic layer was purified by reverse-phase HPLC, using a gradient of 30% to 70% (acetonitrile/0.1% TFA) in (water/0.1% TFA). The product fractions were combined, neutralized with saturated aqueous sodium bicarbonate, and extracted with ethyl acetate. The organic layer was washed with brine, dried over anhydrous magnesium sulfate, filtered, and concentrated to provide the title compound (20 mg, 0.067 mmol) as an off-white solid. LC/MS (ESI$^+$) m/z=299 (M+H).

Example 92

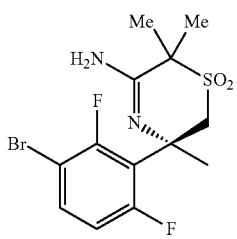 [SMILES: CC1(C)C(N)=N[C@](C)(c2c(F)ccc(Br)c2F)CS1(=O)=O]

Synthesis of (R)-5-Amino-3-(3-bromo-2,6-difluorophenyl)-3,6,6-trimethyl-3,6-dihydro-2H-1,4-thiazine 1,1-dioxide Racemic 5-amino-3-(3-bromo-2,6-difluorophenyl)-3,6,6-trimethyl-3,6-dihydro-2H-1,4-thiazine 1,1-dioxide was purified by chiral SFC, using a ChiralPak IC column and eluting with 25% (20 mM ammonia in methanol) in CO$_2$, to provide the title compound. LC/MS (ESI$^+$) m/z=381, 383 (M+H; 2 bromine isotopes).

Example 93

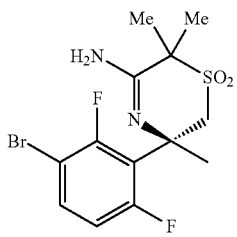 [SMILES: CC1(C)C(N)=N[C@@](C)(c2c(F)ccc(Br)c2F)CS1(=O)=O]

Synthesis of (S)-5-Amino-3-(3-bromo-2,6-difluorophenyl)-3,6,6-trimethyl-3,6-dihydro-2H-1,4-thiazine 1,1-dioxide The title compound is the other enantiomer recovered from the chiral SFC purification described in Example 92, using a ChiralPak IC column and eluting with 25% (20 mM ammonia in methanol) in CO$_2$. LC/MS (ESI$^+$) m/z=381, 383 (M+H; 2 bromine isotopes).

Example 94

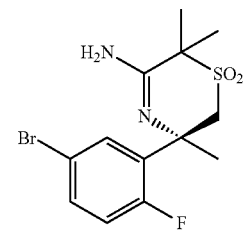 [SMILES: CC1(C)C(N)=N[C@](C)(c2cc(Br)ccc2F)CS1(=O)=O]

Synthesis of (R)-5-Amino-3-(5-amino-2-fluorophenyl)-3,6,6-trimethyl-3,6-dihydro-2H-1,4-thiazine 1,1-dioxide To a solution of (R)-tert-butyl (5-(5-amino-2-fluorophenyl)-2,2,5-trimethyl-1,1-dioxido-5,6-dihydro-2H-1,4-thiazin-3-yl)carbamate (180 mg, 0.45 mmol) in dichloromethane (2.25 mL) was added TFA (0.69 mL, 9.01 mmol). The reaction was stirred at RT for 1 hour. The reaction mixture was concentrated, and the residue was partitioned between DCM and saturated aqueous sodium bicarbonate. The organic layer was concentrated to provide the title compound (65 mg, 0.22 mmol) as a tan solid. LC/MS (ESI$^+$) m/z=300 (M+H).

Example 95

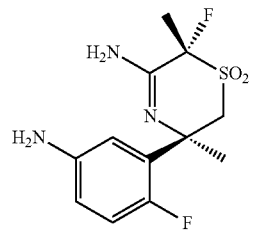 [SMILES: C[C@]1(F)C(N)=N[C@](C)(c2cc(N)ccc2F)CS1(=O)=O]

Synthesis of (3R,6R)-5-Amino-3-(5-amino-2-fluorophenyl)-6-fluoro-3,6-dimethyl-3,6-dihydro-2H-1,4-thiazine 1,1-dioxide In an analogous reaction to that described for Example 94, tert-butyl ((2R,5R)-5-(5-amino-2-fluorophenyl)-2-fluoro-2,5-dimethyl-1,1-dioxido-5,6-dihydro-2H-1,4-thiazin-3-yl)carbamate was converted to the title compound. LC/MS (ESI$^+$) m/z=304 (M+H).

Example 96

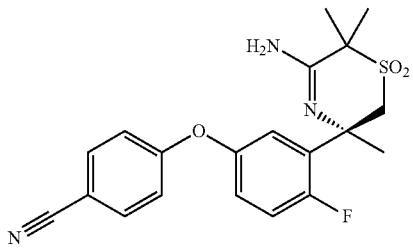 [SMILES: CC1(C)C(N)=N[C@](C)(c2cc(Oc3ccc(C#N)cc3)ccc2F)CS1(=O)=O]

Synthesis of (R)-4-(3-(5-amino-3,6,6-trimethyl-1,1-dioxido-3,6-dihydro-2H-1,4-thiazin-3-yl)-4-fluorophenoxy)benzonitrile To a solution of (R)-5-amino-3-(5-bromo-2-fluorophenyl)-3,6,6-trimethyl-3,6-dihydro-2H-1,4-thiazine 1,1-dioxide (100 mg, 0.28 mmol) in toluene (0.50 mL) and EtOAc (0.05 mL) was added 4-hydroxybenzonitrile (67 mg, 0.55 mmol), copper(I) iodide (63 mg, 0.33 mmol), and cesium carbonate (179 mg, 0.55 mmol). The reaction mixture was stirred at 135° C. for 17 hours. The reaction was diluted with DCM, washed with water and brine, dried over anhydrous sodium sulfate, filtered, and concentrated. The crude mixture was purified by reverse-phase silica-gel chromatography, eluting with a gradient of 0-100% (ACN/1% ammonium hydroxide) in (water/1% ammonium hydroxide) to provide the title compound (6 mg, 0.014 mmol) as a tan solid. LC/MS (ESI$^+$) m/z=402 (M+H).

Example 97

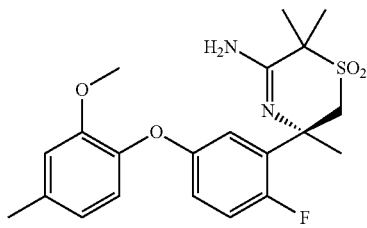 [SMILES: COc1cc(C)ccc1Oc1ccc(F)c([C@]2(C)CS(=O)(=O)C(C)(C)C(N)=N2)c1]

Synthesis of (R)-5-amino-3-(2-fluoro-5-(2-methoxy-4-methylphenoxy)phenyl)-3,6,6-trimethyl-3,6-dihydro-2H-1,4-thiazine 1,1-dioxide In an analogous reaction to that described for Example 96, (R)-5-amino-3-(5-bromo-2-fluorophenyl)-3,6,6-trimethyl-3,6-dihydro-2H-1,4-thiazine 1,1-dioxide (100 mg, 0.28 mmol) was converted to the title compound (0.012 g, 0.029 mmol) as a light yellow solid. LC/MS (ESI$^+$) m/z=421 (M+H).

Example 98

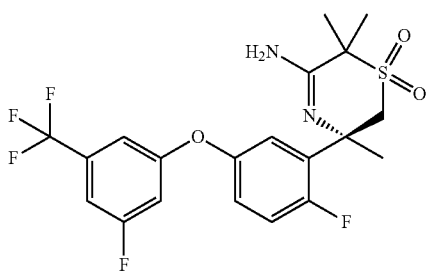 [SMILES: CC1(C)C(N)=N[C@](C)(c2cc(Oc3cc(F)cc(C(F)(F)F)c3)ccc2F)CS1(=O)=O]

Synthesis of (R)-5-amino-3-(2-fluoro-5-(3-fluoro-5-(trifluoromethyl)phenoxy)phenyl)-3,6,6-trimethyl-3,6-dihydro-2H-1,4-thiazine 1,1-dioxide In an analogous reaction to that described for Example 96, (R)-5-amino-3-(5-bromo-2-fluorophenyl)-3,6,6-trimethyl-3,6-dihydro-2H-1,4-thiazine 1,1-dioxide (100 mg, 0.28 mmol) was converted to the title compound (0.018 g, 0.039 mmol) as a tan solid. LC/MS (ESI$^+$) m/z=463 (M+H).

Example 99

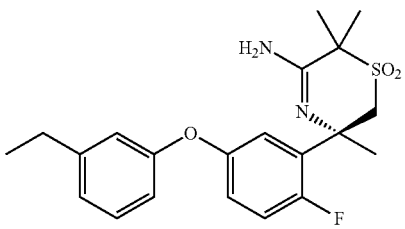 [SMILES: CCc1cccc(Oc2ccc(F)c([C@]3(C)CS(=O)(=O)C(C)(C)C(N)=N3)c2)c1]

Synthesis of (R)-5-amino-3-(5-(3-ethylphenoxy)-2-fluorophenyl)-3,6,6-trimethyl-3,6-dihydro-2H-1,4-thiazine 1,1-dioxide In an analogous reaction to that described for Example 96, (R)-5-amino-3-(5-bromo-2-fluorophenyl)-3,6,6-trimethyl-3,6-dihydro-2H-1,4-thiazine 1,1-dioxide (100 mg, 0.28 mmol) was converted to the title compound (0.022 g, 0.055 mmol) as a tan solid. LC/MS (ESI$^+$) m/z=405 (M+H).

Example 100

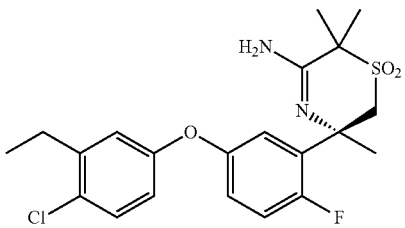 [SMILES: CCc1cc(Oc2ccc(F)c([C@]3(C)CS(=O)(=O)C(C)(C)C(N)=N3)c2)ccc1Cl]

Synthesis of (R)-5-amino-3-(5-(4-chloro-3-ethylphenoxy)-2-fluorophenyl)-3,6,6-trimethyl-3,6-dihydro-2H-1,4-thiazine 1,1-dioxide In an analogous reaction to that described for Example 96, (R)-5-amino-3-(5-bromo-2-fluorophenyl)-3,6,6-trimethyl-3,6-dihydro-2H-1,4-thiazine 1,1-dioxide (100 mg, 0.28 mmol) was converted to the title compound (0.015 g, 0.034 mmol) as a light yellow solid.
LC/MS (ESI$^+$) m/z=439 (M+H).

Example 101

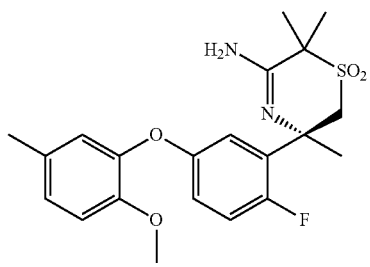 [SMILES: COc1ccc(C)cc1Oc1ccc(F)c([C@]2(C)CS(=O)(=O)C(C)(C)C(N)=N2)c1]

Synthesis of (R)-5-amino-3-(2-fluoro-5-(2-methoxy-5-methylphenoxy)phenyl)-3,6,6-trimethyl-3,6-dihydro-2H-1,4-thiazine 1,1-dioxide In an analogous reaction to that described for Example 96, (R)-5-amino-3-(5-bromo-2-fluorophenyl)-3,6,6-trimethyl-3,6-dihydro-2H-1,4-thiazine 1,1-dioxide (100 mg, 0.28 mmol) was converted to the title compound (0.010 g, 0.025 mmol) as a tan solid. LC/MS (ESI$^+$) m/z=421 (M+H).

Example 102

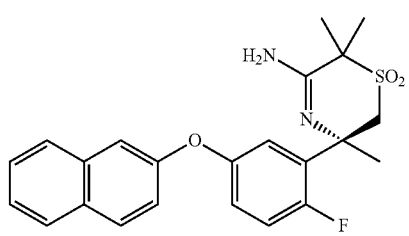 [SMILES: CC1(C)C(N)=N[C@](C)(c2cc(Oc3ccc4ccccc4c3)ccc2F)CS1(=O)=O]

Synthesis of (R)-5-amino-3-(2-fluoro-5-(naphthalen-2-yloxy)phenyl)-3,6,6-trimethyl-3,6-dihydro-2H-1,4-thiazine 1,1-dioxide In an analogous reaction to that described for Example 96, (R)-5-amino-3-(5-bromo-2-fluorophenyl)-3,6,6-trimethyl-3,6-dihydro-2H-1,4-thiazine 1,1-dioxide (100 mg, 0.28 mmol) was converted to the title compound (0.012 g, 0.027 mmol) as a light yellow solid.
LC/MS (ESI$^+$) m/z=427 (M+H).

Example 103

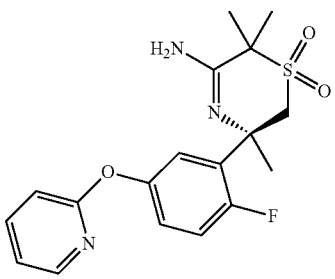 [SMILES: CC1(C)C(N)=N[C@](C)(c2cc(Oc3ccccn3)ccc2F)CS1(=O)=O]

Synthesis of (R)-5-amino-3-(2-fluoro-5-(pyridin-2-yloxy)phenyl)-3,6,6-trimethyl-3,6-dihydro-2H-1,4-thiazine 1,1-dioxide Step 1: (R)—N-(5-(5-bromo-2-fluorophenyl)-2,2,5-trimethyl-1,1-dioxido-5,6-dihydro-2H-1,4-thiazin-3-yl)benzamide To a solution of (R)-5-amino-3-(5-bromo-2-fluorophenyl)-3,6,6-trimethyl-3,6-dihydro-2H-1,4-thiazine 1,1-dioxide (3.00 g, 8.26 mmol) in DMF (16.5 mL) was added benzoic anhydride (2.24 g, 9.91 mmol), and TEA (2.30 mL, 16.5 mmol). The reaction mixture was stirred at RT for 17 hours, diluted with ethyl acetate, and washed with water and brine. The organic layer was dried over anhydrous sodium sulfate, filtered, and concentrated. The crude product was purified by silica-gel chromatography, eluting with 0-50% ethyl acetate in heptanes, to provide the title intermediate (3.47 g, 7.42 mmol, 90% yield) as an off-white solid. LC/MS (ESI$^+$) m/z=467.0, 469.0 (M+H).

Step 2: (R)—N-(5-(2-fluoro-5-(4,4,5,5-tetramethyl-1,3,2-dioxaborolan-2-yl)phenyl)-2,2,5-trimethyl-1,1-dioxido-5,6-dihydro-2H-1,4-thiazin-3-yl)benzamide To a solution of (R)—N-(5-(5-bromo-2-fluorophenyl)-2,2,5-trimethyl-1,1-dioxido-5,6-dihydro-2H-1,4-thiazin-3-yl)benzamide (3.77 g, 8.07 mmol) in degassed 1,4-dioxane (16.1 mL) were added 4,4,4',4',5,5,5',5'-octamethyl-2,2'-bis(1,3,2-dioxaborolane) (3.07 g, 12.10 mmol) and potassium acetate (2.38 g, 24.20 mmol). The flask was purged with nitrogen, 1,1'-bis(diphenylphosphino)ferrocene-palladium(II)dichloride dichloromethane complex (0.590 g, 0.807 mmol) was added, and the flask was purged with nitrogen again, sealed, and heated to 100° C. for 16 hours. The reaction mixture was cooled to ambient temperature and diluted with ethyl acetate. The reaction mixture was washed with water and brine, dried over anhydrous sodium sulfate, filtered, and concentrated. The crude product was purified by silica-gel chromatography, eluting with 0-50% ethyl acetate in heptanes, to provide the title intermediate (3.54 g, 6.88 mmol, 85% yield) as a white solid. LC/MS (ESI$^+$) m/z=515.2 (M+H).

Step 3: (R)—N-(5-(2-fluoro-5-hydroxyphenyl)-2,2,5-trimethyl-1,1-dioxido-5,6-dihydro-2H-1,4-thiazin-3-yl)benzamide To a solution of (R)—N-(5-(2-fluoro-5-(4,4,5,5-tetramethyl-1,3,2-dioxaborolan-2-yl)phenyl)-2,2,5-trimethyl-1,1-dioxido-5,6-dihydro-2H-1,4-thiazin-3-yl)benzamide (3.7 g, 7.19 mmol) in dichloromethane (14.4 mL) was added 30% aqueous hydrogen peroxide (0.882 mL, 8.63 mmol), and the reaction was stirred at ambient temperature for four hours. The reaction was diluted with DCM, washed with water and brine, dried over anhydrous sodium sulfate, filtered, and concentrated. The crude product was purified by silica-gel chromatography, eluting with 0-50% EtOAc in heptanes to provide the title intermediate (2.64 g, 6.53 mmol) as a white solid. LC/MS (ESI$^+$) m/z=405.1 (M+H).

Step 4: (R)-5-amino-3-(2-fluoro-5-hydroxyphenyl)-3,6,6-trimethyl-3,6-dihydro-2H-1,4-thiazine 1,1-dioxide A solution of (R)—N-(5-(2-fluoro-5-hydroxyphenyl)-2,2,5-trimethyl-1,1-dioxido-5,6-dihydro-2H-1,4-thiazin-3-yl)benzamide (1.9 g, 4.70 mmol) in ammonia (2 M in methanol) (23.5 mL, 47.0 mmol) was stirred at 55° C. for 17 hours. The reaction was cooled to ambient temperature and concentrated. The crude product was purified by reverse phase silica-gel chromatography, eluting with 0-100% (acetonitrile/1% trifluoroacetic acid) in (water/1% trifluoroacetic acid) to provide the title intermediate (1.1 g, 3.66 mmol) as an off-white solid. LC/MS (ESI$^+$) m/z=301.0 (M+H).

Step 5: (R)-5-amino-3-(2-fluoro-5-(pyridin-2-yloxy)phenyl)-3,6,6-trimethyl-3,6-dihydro-2H-1,4-thiazine 1,1-dioxide To a solution of (R)-5-amino-3-(2-fluoro-5-hydroxyphenyl)-3,6,6-trimethyl-3,6-dihydro-2H-1,4-thiazine 1,1-dioxide (65 mg, 0.216 mmol) in DMSO (0.43 mL) were added 2-fluoropyridine (0.017 mL, 0.238 mmol) and cesium carbonate (141 mg, 0.433 mmol), and the reaction mixture was stirred at 100° C. for 16 hours. The reaction was cooled to ambient temperature, diluted with ethyl acetate, and washed with water and brine. The organic layer was dried over anhydrous sodium sulfate, filtered, and concentrated. The crude product was purified by silica-gel chromatography, eluting with 1.5-7% methanol in dichloromethane to provide the title compound (23 mg, 0.061 mmol) as an off-white solid. $^1$H NMR (400 MHz, DMSO-$d_6$) δ ppm 1.42 (s, 3H) 1.55 (s, 3H) 1.61 (s, 3H) 3.47-3.72 (m, 2H) 6.08 (br. s., 2H) 6.96 (dt, J=8.34, 0.88 Hz, 1H) 7.01-7.06 (m, 1H) 7.11 (ddd, J=7.19, 4.94, 0.88 Hz, 1H) 7.16-7.23 (m, 2H) 7.83 (ddd, J=8.34, 7.19, 2.05 Hz, 1H) 8.11-8.17 (m, 1H). LC/MS (ESI$^+$) m/z=378.1 (M+H).

The following compounds in Table 3 are examples of compounds of Formulas I, II and III, and sub-formulas thereof, provided by the present invention in Tables 1 and 2 hereinabove. The methods used to prepare the exemplary compounds are included in Tables 1 and 2. Table I further provides the mass and biological data (average nM $IC_{50}$'s for the enzyme and cell assays) for each compound, where available.

TABLE 3

| Example No | Compound Name | BACE1 FRET assay $IC_{50}$ (uM) | HEK cell assay $IC_{50}$ (uM) | CatD IC50 (μM) |
|---|---|---|---|---|
| 28 | N-(3-((3R)-5-amino-3-methyl-1,1-dioxido-3,6-dihydro-2H-1,4-thiazin-3-yl)-4-fluorophenyl)-5-methoxy-2-pyrazinecarboxamide | 0.0149 | 0.068 | 50.9 |
| 29 | N-(3-((3R)-5-amino-3-methyl-1,1-dioxido-3,6-dihydro-2H-1,4-thiazin-3-yl)-4-fluorophenyl)-5-chloro-2-pyridinecarboxamide | 0.006 | 0.0108 | 118 |
| 56 | N-(3-((3R)-5-amino-3-methyl-1,1-dioxido-3,6-dihydro-2H-1,4-thiazin-3-yl)-4-fluorophenyl)-3-methoxy-1,7-naphthyridin-8-amine | 0.0627 | 0.0271 | 69.8 |
| 43 | N-(3-((3R)-5-amino-3-methyl-3,6-dihydro-2H-1,4-thiazin-3-yl)-4-fluorophenyl)-5-methoxy-2-pyrazinecarboxamide | 0.0236 | 0.007 | >400 |
| 57 | N-(3-((3R)-5-amino-3-methyl-1,1-dioxido-3,6-dihydro-2H-1,4-thiazin-3-yl)-4-fluorophenyl)-3-chloro-1,7-naphthyridin-8-amine | 0.0043 | 0.019 | 134 |
| 58 | N-(3-((3R)-5-amino-3-methyl-1,1-dioxido-3,6-dihydro-2H-1,4-thiazin-3-yl)-4-fluorophenyl)-2-methyl[1,3]thiazolo[4,5-c]pyridin-4-amine | 0.19 | 0.292 | 304 |
| 17 | N-(3-((3R)-5-amino-3,6,6-trimethyl-1,1-dioxido-3,6-dihydro-2H-1,4-thiazin-3-yl)-4-fluorophenyl)-5-methoxy-2-pyrazinecarboxamide | .0021 | 0.0022 | >400 |
| 45 | N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine | .00059 | 0.0075 | 90.4 |
| 46 | N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine | 0.0054 | 0.004 | 397 |
| 18 | N-(3-((3R)-5-amino-3,6,6-trimethyl-1,1-dioxido-3,6-dihydro-2H-1,4-thiazin-3-yl)-4-fluorophenyl)-5-fluoro-2-pyridinecarboxamide | 0.0019 | 0.0037 | >400 |
| 19 | N-(3-((3R)-5-amino-3,6,6-trimethyl-1,1-dioxido-3,6-dihydro-2H-1,4-thiazin-3-yl)-4-fluorophenyl)-5-chloro-2-pyridinecarboxamide | .00085 | 0.0014 | 240 |
| 47 | N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine | .0029 | 0.0056 | >400 |
| 48 | 8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile | .00054 | 0.0019 | 66.7 |
| 82 | N-(3-((3R,6R)-5-amino-3,6-dimethyl-1,1-dioxido-3,6-dihydro-2H-1,4-thiazin-3-yl)-4-fluorophenyl)-5-methoxy-2-pyrazinecarboxamide, N-(3-((3R,6S)-5-amino-3,6- | 0.0075 | 0.0125 | >400 |

TABLE 3-continued

| Example No | Compound Name | BACE1 FRET assay IC$_{50}$ (uM) | HEK cell assay IC$_{50}$ (uM) | CatD IC50 (μM) |
|---|---|---|---|---|
| | dimethyl-1,1-dioxido-3,6-dihydro-2H-1,4-thiazin-3-yl)-4-fluorophenyl)-5-methoxy-2-pyrazinecarboxamide | | | |
| 34 | N-(3-((3R)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide | 0.883 | >10.0 | >400 |
| 64 | N-(3-((3R)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine | 8.69 | >10.0 | >400 |
| 32 | N-(3-((3R)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide, N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide | 0.0531 | 1.42 | >400 |
| 62 | N-(3-((3R)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine, N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine | 0.241 | 1.82 | >400 |
| 84 | N-(3-((8R)-10-amino-8-methyl-6,6-dioxido-6-thia-9-azaspiro[4.5]dec-9-en-8-yl)-4-fluorophenyl)-3-methoxy-1,7-naphthyridin-8-amine | 0.0234 | 0.0575 | 283 |
| 86 | N-(3-((6R)-8-amino-6-methyl-4,4-dioxido-4-thia-7-azaspiro[2.5]oct-7-en-6-yl)-4-fluorophenyl)-3-methoxy-1,7-naphthyridin-8-amine | 0.0136 | 0.0082 | 160 |
| 74 | N-(3-((3R,6R)-5-amino-6-fluoro-3,6-dimethyl-1,1-dioxido-3,6-dihydro-2H-1,4-thiazin-3-yl)-4-fluorophenyl)-3-methoxy-1,7-naphthyridin-8-amine | 0.0137 | 0.102 | >400 |
| 78 | N-(3-((3R)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine, N-(3-((3S)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine, benzamide | 0.0138 | 0.0944 | 45.6 |
| 49 | N-(3-((3R)-5-amino-3,6,6-trimethyl-1,1-dioxido-3,6-dihydro-2H-1,4-thiazin-3-yl)-4-fluorophenyl)-3-chloro-5-fluoro-1,7-naphthyridin-8-amine | .00056 | 0.0151 | 27.1 |
| 69 | N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine, N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine | .0014 | 0.0544 | 11.3 |
| 35 | N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide, N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide | 0.0027 | 0.0122 | 99.8 |

TABLE 3-continued

| Example No | Compound Name | BACE1 FRET assay IC$_{50}$ (uM) | HEK cell assay IC$_{50}$ (uM) | CatD IC50 (μM) |
|---|---|---|---|---|
| 36 | N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide | 0.0202 | 0.765 | >400 |
| 67 | N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine | 0.068 | 0.98 | >400 |
| 76 | 8-((3-((3R)-5-amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile | 0.002 | 0.0039 | >44 |
| 30 | N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide, N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide | 0.0031 | 0.0801 | >400 |
| 79 | (5R)-5-(2-fluoro-5-(1-naphthalenylsulfanyl)phenyl)-2,2,5-trimethyl-5,6-dihydro-2H-1,4-thiazin-3-amine 1,1-dioxide | 2.5 | 4.94 | 33.7 |
| 59 | N-(3-((3R,6R)-5-amino-6-fluoro-3,6-dimethyl-1,1-dioxido-3,6-dihydro-2H-1,4-thiazin-3-yl)-4-fluorophenyl)-2-methoxypyrido[3,4-b]pyrazin-5-amine | 0.0033 | 0.178 | 388 |
| 60 | 8-((3-((3R,6R)-5-amino-6-fluoro-3,6-dimethyl-1,1-dioxido-3,6-dihydro-2H-1,4-thiazin-3-yl)-4-fluorophenyl)amino)-1,7-naphthyridine-3-carbonitrile | <0.002 | 0.0808 | 99.9 |
| 20 | N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide | 0.0027 | 0.0039 | 193 |
| 50 | N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine | 0.002 | 0.0053 | 73.3 |
| 51 | N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine | 0.0027 | 0.003 | 81 |
| 52 | N-(3-((3R)-5-amino-3,6,6-trimethyl-1,1-dioxido-3,6-dihydro-2H-1,4-thiazin-3-yl)-4-fluorophenyl)-7-chloropyrido[3,2-d]pyrimidin-4-amine | 0.002 | 0.0023 | 36 |
| 53 | N-(3-((3R)-5-amino-3,6,6-trimethyl-1,1-dioxido-3,6-dihydro-2H-1,4-thiazin-3-yl)-4-fluorophenyl)-5-fluoro-7-methoxy-4-quinazolinamine | 0.739 | 0.399 | 320 |
| 21 | N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyrazinecarboxamide | 0.0074 | 0.011 | >400 |
| 73 | 3-((3-((3R)-5-amino-3,6,6-trimethyl-1,1-dioxido-3,6-dihydro-2H-1,4-thiazin-3-yl)-4-fluorophenyl)amino)thieno[3,2-b]pyridine-6-carbonitrile | 0.002 | 0.0016 | 27.3 |
| 66 | N-(5-((3R)-5-amino-3,6,6-trimethyl-1,1-dioxido-3,6-dihydro-2H-1,4-thiazin-3-yl)-6-fluoro-3-pyridinyl)-3-methoxy-1,7-naphthyridin-8-amine | 0.0043 | 0.0067 | 101 |

TABLE 3-continued

| Example No | Compound Name | BACE1 FRET assay IC$_{50}$ (uM) | HEK cell assay IC$_{50}$ (uM) | CatD IC50 (μM) |
|---|---|---|---|---|
| 75 | N-(3-((3R)-5-amino-3,6,6-trimethyl-1,1-dioxido-3,6-dihydro-2H-1,4-thiazin-3-yl)-4-fluorophenyl)-2-methoxy-5-quinoxalinamine | 0.0114 | 0.212 | 47.6 |
| 31 | N-(3-((3R)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide, N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide | 0.0038 | 0.0279 | >400 |
| 44 | N-(3-((3R)-5-amino-2-fluoro-3,6,6-trimethyl-1,1-dioxido-3,6-dihydro-2H-1,4-thiazin-3-yl)-4-fluorophenyl)-3-methoxy-1,7-naphthyridin-8-amine | 0.0099 | 0.0604 | 357 |
| 61 | N-(3-((3R)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine, N-(3-((3S)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine | 0.0065 | 0.0317 | >400 |
| 54 | N-(3-((3R)-5-amino-3,6,6-trimethyl-1,1-dioxido-3,6-dihydro-2H-1,4-thiazin-3-yl)-4-fluorophenyl)-2-methyl[1,3]thiazolo[4,5-c]pyridin-4-amine | 0.0172 | 0.137 | >400 |
| 22 | N-(3-((3R)-5-amino-3,6,6-trimethyl-1,1-dioxido-3,6-dihydro-2H-1,4-thiazin-3-yl)-4-fluorophenyl)-5-methoxy-2-pyridinecarboxamide | 0.0015 | 0.0031 | >400 |
| 23 | N-(3-((3R)-5-amino-3,6,6-trimethyl-1,1-dioxido-3,6-dihydro-2H-1,4-thiazin-3-yl)-4-fluorophenyl)-5-cyano-2-pyridinecarboxamide | 0.0027 | 0.0027 | 617 |
| 24 | N-(3-((3R)-5-amino-3,6,6-trimethyl-1,1-dioxido-3,6-dihydro-2H-1,4-thiazin-3-yl)-4-fluorophenyl)-5-chloro-3-fluoro-2-pyridinecarboxamide | 0.0006 | 0.0037 | >400 |
| 25 | N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide | 0.0003 | 0.0032 | 263 |
| 26 | N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide | 0.0004 | 5E-05 | 475 |
| 27 | N-(3-((3R)-5-amino-3,6,6-trimethyl-1,1-dioxido-3,6-dihydro-2H-1,4-thiazin-3-yl)-4-fluorophenyl)-2-methyl-1,3-thiazole-4-carboxamide | 0.051 | 0.0609 | >400 |
| 38 | N-(3-((3R)-5-amino-3,6,6-trimethyl-1,1-dioxido-3,6-dihydro-2H-1,4-thiazin-3-yl)-4,5-difluorophenyl)-5-chloro-2-pyridinecarboxamide | 0.001 | 0.0065 | 72.8 |
| 39 | N-(3-((3S)-5-amino-3,6,6-trimethyl-1,1-dioxido-3,6-dihydro-2H-1,4-thiazin-3-yl)-4,5-difluorophenyl)-5-chloro-2-pyridinecarboxamide | 1.18 | 3.27 | 225 |
| 69 | N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine | 0.0004 | 0.0231 | 8.56 |

TABLE 3-continued

| Example No | Compound Name | BACE1 FRET assay IC$_{50}$ (uM) | HEK cell assay IC$_{50}$ (uM) | CatD IC50 (μM) |
|---|---|---|---|---|
| 70 | N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine | 0.83 | 5.04 | 164 |
| 41 | N-(4-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide, N-(4-((3S)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide | 0.252 | 0.935 | 333 |
| 40 | N-(6-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide | 8.2 | 6.98 | >400 |
| 55 | N-(3-((3R)-5-amino-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine | 0.0052 | 0.0346 | >133 |
| 71 | 5-((3-((3R)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one | 0.0037 | 0.0474 | 45.2 |
| 72 | 5-((3-((3S)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one | 0.505 | 5.35 | 175 |
| 96 | 4-(3-((3R)-5-amino-3,6,6-trimethyl-1,1-dioxido-3,6-dihydro-2H-1,4-thiazin-3-yl)-4-fluorophenoxy)benzonitrile | 1.8 | 6.02 | 58.7 |
| 97 | (5R)-5-(2-fluoro-5-(2-methoxy-4-methylphenoxy)phenyl)-2,2,5-trimethyl-5,6-dihydro-2H-1,4-thiazin-3-amine 1,1-dioxide | 11.7 | 6.86 | 182 |
| 98 | (5R)-5-(2-fluoro-5-(3-fluoro-5-(trifluoromethyl)phenoxy)phenyl)-2,2,5-trimethyl-5,6-dihydro-2H-1,4-thiazin-3-amine 1,1-dioxide | 0.135 | 5.04 | 56.3 |
| 99 | (5R)-5-(5-(3-ethylphenoxy)-2-fluorophenyl)-2,2,5-trimethyl-5,6-dihydro-2H-1,4-thiazin-3-amine 1,1-dioxide | 1.43 | 6.68 | 86.8 |
| 100 | (5R)-5-(5-(4-chloro-3-ethylphenoxy)-2-fluorophenyl)-2,2,5-trimethyl-5,6-dihydro-2H-1,4-thiazin-3-amine 1,1-dioxide | 1.55 | >10.0 | 17.7 |
| 101 | (5R)-5-(2-fluoro-5-(2-methoxy-5-methylphenoxy)phenyl)-2,2,5-trimethyl-5,6-dihydro-2H-1,4-thiazin-3-amine 1,1-dioxide | 15.2 | >10.0 | 194 |
| 102 | (5R)-5-(2-fluoro-5-(2-naphthalenyloxy)phenyl)-2,2,5-trimethyl-5,6-dihydro-2H-1,4-thiazin-3-amine 1,1-dioxide | 2.35 | 8.04 | 51.2 |
| 103 | (5R)-5-(2-fluoro-5-(2-pyridinyloxy)phenyl)-2,2,5-tri methyl-5,6-dihydro-2H-1,4-thiazin-3-amine 1,1-dioxide | 0.119 | 0.213 | 246 |

General Amidation Procedures to Prepare Compounds of Formulas I, II and III, and Sub-Formulas Thereof (Unprotected amino-1,1-dioxido-2H-1,4-thiazin-3-yl Cores)

Method C: DMTMM Procedure:

To a solution (0.14 M) of the aniline (1 equivalent; see compounds 7, 8 10 in schemes 2, 3 and 4, respectively, see also the examples herein) in MeOH was added the carboxylic acid (1 equivalent; R$^9$—COOH) and 4-(4,6-dimethoxy-1,3,5-triazin-2-yl)-4-methylmorpholin-4-ium chloride (1 equivalent). After stirring for 1 h at RT, the mixture was diluted with EtOAc, and the organic layer was washed with aqueous sodium bicarbonate, dried over MgSO$_4$, and concentrated. The crude material was purified by silica gel chromatography to furnish the title compound.

Method D: T3P Procedure:

A suspension (0.1 M) of the carboxylic acid (1 equivalent; $R^9$—COOH), Hunig's base (1 equivalent), and the aniline (1 equivalent) in dichloromethane was cooled to 0° C., and an ethyl acetate solution of T3P (50% by weight, 1.40 equivalents) was added. The reaction was allowed to warm naturally to room temperature. After 6 h, the mixture was taken up in 5% MeOH-dichloromethane, washed with aqueous sodium bicarbonate, and the organic layer was dried over MgSO$_4$, and concentrated. The crude material was purified by silica gel chromatography to furnish the title compound.

Method E: CuI Procedure:

A microwave vial was charged with the corresponding bromide (1.0 equivalent), carboxamide (1.2 equivalents; $R^9$—CONH$_2$), CuI (0.20 equivalents) and potassium carbonate (3.0 equivalents). The vial was evacuated and back-filled with nitrogen followed by the addition of dioxane (to give a reaction concentration of 0.2M with respect to bromide) and (1R,2R)-(–)-N,N'-dimethylcyclohexane-1,2-diamine. The resulting mixture was heated at 120° C. for 17 h. The reaction was brought to room temperature, diluted with EtOAc, filtered through celite, concentrated and chromatographed on silica gel to provide the title compound.

Method F: Pd Procedure:

A microwave vial was charged with the corresponding bromide (1.0 equivalent), aniline (1.5 equivalent), tris(dibenzylideneacetone)dipalladium (0) chloroform adduct (0.10 equivalents), 2-di-tert-butylphosphino-2',4',6'-triisopropylbiphenyl (0.30 equivalents) and sodium t-butoxide (2.8 equivalents), purged with nitrogen and toluene added (to give a reaction concentration of 0.2M with respect to bromide). The resulting mixture was sealed, then heated at 100° C. for 1 h, brought to room temperature, diluted with water and extracted with EtOAc. The combined organics were concentrated and chromatographed on silica gel to afford the title compound.

Method G: Amination with CuI Procedure:

A microwave vial was charged with the corresponding bromide (1.0 equivalent), 2,2,2-trifluoroacetamide (2.0 equivalents), potassium carbonate (4.0 equivalents), N,N'-dimethyl ethylenediamine (0.40 equivalents), copper(I) iodide (0.20 equivalents) and 4 A molecular sieves, then purged with nitrogen. Dioxan was added to give a 0.9 M solution with respect to bromide, mixture sealed, and heated at 120° C. for 20 h. The reaction was brought to room temperature, MeOH/water (1:1) was added and the resulting mixture was heated at 80° C. for 1 h. The mixture was diluted with a 9:1 mixture saturated ammonium chloride/ammonium hydroxide, extracted with DCM and chromatographed on silica gel to afford the title compound.

Example 104

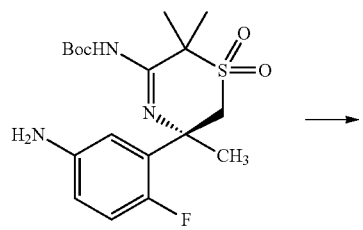

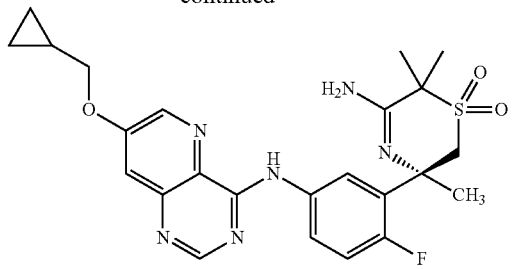

Synthesis of (R)-5-amino-3-(5-((7-(cyclopropylmethoxy)pyrido[3,2-d]pyrimidin-4-yl)amino)-2-fluorophenyl)-3,6,6-trimethyl-3,6-dihydro-2H-1,4-thiazine 1,1-dioxide A reaction vial was charged with (R)-tert-butyl (5-(5-amino-2-fluorophenyl)-2,2,5-trimethyl-1,1-dioxido-5,6-dihydro-2H-1,4-thiazin-3-yl)carbamate (33.9 mg, 0.085 mmol), 4-chloro-7-(cyclopropylmethoxy)pyrido[3,2-d]pyrimidine (20 mg, 0.085 mmol) and 2-propanol (424 µl, 0.085 mmol), followed by p-toluenesulfonic acid monohydrate (32.3 mg, 0.170 mmol). The resulting mixture was stirred at 80° C. for 15 min. The reaction mixture was diluted with saturated aqueous sodium bicarbonate and extracted with EtOAc. The organic extract was washed with brine, dried over MgSO$_4$, filtered and concentrated. The crude material was absorbed onto a plug of silica gel and eluted with a gradient of 20% to 35% to 50% EtOAc/EtOH/Et$_3$N (80/20/2) in (40% EtOAc in Heptane), to provide (R)-5-amino-3-(5-((7-(cyclopropylmethoxy)pyrido[3,2-d]pyrimidin-4-yl)amino)-2-fluorophenyl)-3,6,6-trimethyl-3,6-dihydro-2H-1,4-thiazine 1,1-dioxide (20 mg, 0.040 mmol, 47.3% yield) as off-white solid. LC/MS (ESI$^+$) m/z=499.2 (M+1).

Example 105

Amination Coupling Reaction

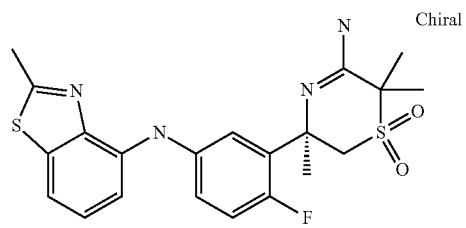

Synthesis of (R)-5-amino-3-(2-fluoro-5-((2-methylbenzo[d]thiazol-4-yl)amino)phenyl)-3,6,6-trimethyl-3,6-dihydro-2H-1,4-thiazine 1,1-dioxide Step 1: Synthesis of (R)-tert-butyl (5-(2-fluoro-5-((2-methylbenzo[d]thiazol-4-yl)amino)phenyl)-2,2,5-trimethyl-1,1-dioxido-5,6-dihydro-2H-1,4-thiazin-3-yl)carbamate To a sealable tube was added 4-bromo-2-methylbenzo[d]thiazole (48.0 mg, 0.210 mmol), (R)-tert-butyl (5-(5-amino-2-fluorophenyl)-2,2,5-trimethyl-1,1-dioxido-5,6-dihydro-2H-1,4-thiazin-3-yl)carbamate (70 mg, 0.175 mmol) and toluene (1.0 mL). It was purged with Argon, then tris (dibenzylideneacetone) dipalladium (0) (16.05 mg, 0.018 mmol), and tBuXphos (18.60 mg, 0.044 mmol) were added and the mixture was purged with Argon. Sodium tert-butoxide (47.2 mg, 0.491 mmol) was added slowly to the mixture. It was stirred at 100° C. for 25 min. The reaction mixture was diluted with sat'd NH₄Cl and extracted with EtOAc. The organic extract was washed with brine and dried over anhydrous MgSO₄. The solution was filtered and concentrated in vacuo to give the crude material as a brown solid. The crude product was used for next step directly. LC/MS (ESI⁺) m/z=547.2 (M+H).

Step 2: Synthesis of (R)-5-amino-3-(2-fluoro-5-((2-methylbenzo[d]thiazol-4-yl)amino)phenyl)-3,6,6-trimethyl-3,6-dihydro-2H-1,4-thiazine 1,1-dioxide To a solution of (R)-tert-butyl (5-(2-fluoro-5-((2-methylbenzo[d]thiazol-4-yl)amino)phenyl)-2,2,5-trimethyl-1,1-dioxido-5,6-dihydro-2H-1,4-thiazin-3-yl)carbamate (95 mg, 0.174 mmol) in DCM (1738 µl) was added TFA (669 µl, 8.69 mmol), and the solution was stirred at RT for 20 min. The reaction mixture was concentrated, diluted with DCM and neutralized with saturated aqueous NaHCO₃. The organic extract was concentrated, and purified by prep reverse phase HPLC using 0.1% NH4OH in ACN and water as mobile phase to yield 32 mg of (R)-5-amino-3-(2-fluoro-5-((2-methylbenzo[d]thiazol-4-yl)amino)phenyl)-3,6,6-trimethyl-3,6-dihydro-2H-1,4-thiazine 1,1-dioxide (41.2% yield, 0.072 mmol). LC/MS (ESI⁺) m/z=447.0 (M+H).

General Cyanation Procedure

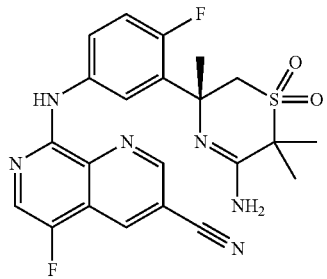 [SMILES: CC1(C)C(N)=N[C@](C)(c2cc(Nc3ncc(F)c4cc(C#N)cnc34)ccc2F)CS1(=O)=O]

Synthesis of (R)-8-((3-(5-Amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile A sealable vial was charged with (R)-5-amino-3-(5-((3-chloro-5-fluoro-1,7-naphthyridin-8-yl)amino)-2-fluorophenyl)-3,6,6-trimethyl-3,6-dihydro-2H-1,4-thiazine 1,1-dioxide (150 mg, 0.313 mmol), 2-dicyclohexylphosphino-2',6'-dimethoxybiphenyl (25.7 mg, 0.063 mmol), tris (dibenzylideneacetone)dipalladium(0) (22.90 mg, 0.025 mmol), ZnCN₂ (55 mg, 0.469 mmol), N,N-dimethylformamide (1.5 mL), and a drop of water. The vial was purged with argon and the reaction was heated at 110° C. for 1 hour. The reaction was partitioned between water and dichloromethane, and the organic portion was washed with brine, dried with anhydrous sodium sulfate, filtered and concentrated. The crude product was purified by silica gel chromatography, eluting with 5-75% (3:1 ethyl acetate/ethanol, 2% ammonium hydroxide) in heptanes, to provide the title compound (80 mg, 0.170 mmol, 54.4% yield) as a yellow solid.

The following intermediates, within the examples, represent various exemplary carboxylic acid, ester, carbamate or amine intermediates as representative R⁹ groups for compounds of the present invention.

Intermediate BY 001

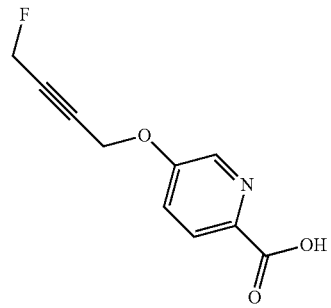 [SMILES: O=C(O)c1ccc(OCC#CCF)cn1]

Synthesis of 5-((4-fluorobut-2-yn-1-yl)oxy)picolinic acid

Step 1: methyl 5-((4-hydroxybut-2-yn-1-yl)oxy)picolinate

In a 500-mL flask, but-2-yne-1,4-diol (5.62 g, 65.3 mmol), methyl 5-hydroxypicolinate (5.00 g, 32.7 mmol) and triphenylphosphine (12.85 g, 49.0 mmol) were suspended in THF (100 mL). The suspension was cooled to 0° C., and (E)-diisopropyl diazene-1,2-dicarboxylate (9.52 mL, 49.0 mmol) was added over 1 minute. The reaction was stirred at 0° C. for 2 h, then at RT for 2 h. The reaction was filtered through Celite, rinsing with DCM (500 mL). The filtrate was concentrated and the residue was chromatographed on silica gel (600 mL), eluent 2% to 3% MeOH-DCM to afford the title compound (3.43 g, 48%). MS: m/z=222 (M+H).

Step 2: methyl 5-((4-fluorobut-2-yn-1-yl)oxy)picolinate

In a 250-mL flask, methyl 5-((4-hydroxybut-2-yn-1-yl)oxy)picolinate (1.77 g, 8.00 mmol, 1 equiv) was suspended in DCM (50 mL). The suspension was cooled to −78° C., and Deoxo Fluor (2.21 mL, 12 mmol, 1.5 equiv) was added dropwise. The mixture was allowed to warm naturally, to RT overnight. The mixture was cooled to 0° C., and quenched with 50 mL of saturated aqueous NaHCO₃. The mixture was filtered through Celite, rinsing with 5% MeOH-DCM (100 mL). The resulting filtrate's aqueous layer was separated and extracted with 5% MeOH-DCM (50 mL). The combined organics were dried over MgSO₄ and concentrated. The residue was chromatographed on silica gel (80 mL) using 50% EtOAc-hexane to afford the title compound (180 mg, 0.81 mmol, 10% yield). MS: m/z=224 (M+H).

Step 3: 5-((4-fluorobut-2-yn-1-yl)oxy)picolinic acid

Methyl 5-((4-fluorobut-2-yn-1-yl)oxy)picolinate (97 mg, 0.435 mmol, 1 equiv) was dissolved in a mixture of THF (1.5 mL) and MeOH (1 mL). The solution was cooled to 0°

C., and aqueous LiOH (1.0 M, 475 microliters, 0.475 mmol, 1.1 equiv) was added. The reaction was warmed to RT and stirred for 5 h. The reaction was neutralized with a dioxane solution of HCl (4.0 M, 0.119 mL, 0.475 mmol, 1.1 equiv). The mixture was concentrated, and azeotropically dried by evaporation from toluene at reduced pressure, to give the title compound (0.435 mmol, 91 mg).

Intermediate BY 002

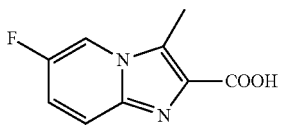

Synthesis of 6-fluoro-3-methylimidazo[1,2-a]pyridine-2-carboxylic acid

Step 1: methyl 3-bromo-2-oxobutanoate

Methyl 2-oxobutanoate (6.73 g, 58.0 mmol) was dissolved in DCM (60 mL). The solution was cooled to 0° C., and bromine (3.02 mL, 58.5 mmol) was added. The flask was stirred for 5 min at 0° C., and the ice-water bath was removed. After 2 h, the mixture was taken up in DCM (300 mL). The organic layer was extracted with saturated aqueous NaHCO₃ (60 mL), then with half-saturated aqueous NaHCO₃ (60 mL), dried over MgSO₄ and concentrated to afford the title compound, which was used without further purification (10.64 g, 54.6 mmol, 94%).

Step 2: methyl 6-fluoro-3-methylimidazo[1,2-a]pyridine-2-carboxylate

The methyl 3-bromo-2-oxobutanoate (1.502 g, 7.70 mmol) was dissolved in DME (9 mL). The solution was cooled in an ice-water bath. 5-Fluoropyridin-2-amine (0.785 g, 7.00 mmol) was added, and the ice bath was removed. The mixture was stirred at RT for 2 days. The thick suspension was filtered through a fine frit, rinsing the solid with DME (15 mL). The recovered solid (1.535 g) was suspended in MeOH (19 mL). The vessel was sealed and heated in an 80° C. oil bath. After 2.5 h, the reaction was cooled and concentrated. The yellow solid was triturated with diethyl ether and dried under vacuum to afford the title compound (777 mg, 48%).

Step 3: 6-fluoro-3-methylimidazo[1,2-a]pyridine-2-carboxylic acid

Methyl 6-fluoro-3-methylimidazo[1,2-a]pyridine-2-carboxylate (679 mg, 3.26 mmol) was suspended in MeOH (10 mL). Aqueous sodium hydroxide (3.0 M, 1.63 mL, 4.89 mmol) was added. The vessel was sealed and heated in a 60° C. oil bath. After 3 h, the mixture was concentrated. The residue was dissolved in a minimum amount of water (10 mL). The mixture was neutralized with aqueous HCl (5.0 M, 0.98 mL, 4.89 mmol). The solution was concentrated on the rotovap. The solid residue was suspended in absolute ethanol (20 mL). The suspension was filtered through a fine frit, and the solid was collected, furnishing the title compound (984 mg).

Intermediate BY 003

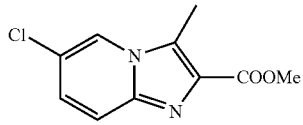

Synthesis of methyl 6-chloro-3-methylimidazo[1,2-a]pyridine-2-carboxylate

The title compound was prepared using the procedure for Step 2 of the preparation of Intermediate BY 002, except that 5-chloropyridin-2-amine was used instead of 5-fluoropyridin-2-amine.

Intermediate BY 004

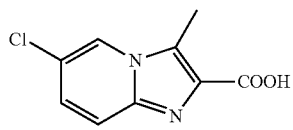

Synthesis of 6-chloro-3-methylimidazo[1,2-a]pyridine-2-carboxylic acid

The title compound was prepared from Intermediate BY 003 using conditions described in Step 3 of the preparation of Intermediate BY 002.

Intermediate BY 005

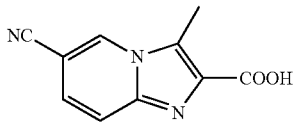

Synthesis of 6-cyano-3-methylimidazo[1,2-a]pyridine-2-carboxylic acid

Step 1: methyl 6-cyano-3-methylimidazo[1,2-a]pyridine-2-carboxylate

The title compound was prepared from Intermediate BY 003 using the general cyanation procedure as described herein.

Step 2: 6-cyano-3-methylimidazo[1,2-a]pyridine-2-carboxylic acid

The title compound was prepared from methyl 6-cyano-3-methylimidazo[1,2-a]pyridine-2-carboxylate using the procedure described in Step 3 of the synthesis of BY 002.

Intermediate BY 006

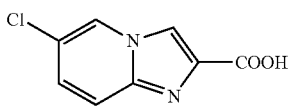 [SMILES: O=C(O)c1cn2cc(Cl)ccc2n1]

Synthesis of 6-chloroimidazo[1,2-a]pyridine-2-carboxylic acid

The title compound was prepared using steps 2 and 3 of the procedure used to prepare Intermediate BY 002, except that the starting materials were 5-chloropyridin-2-amine and ethyl 3-bromo-2-oxopropanoate.

Intermediate BY 007

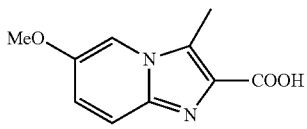

Synthesis of 6-methoxy-3-methylimidazo[1,2-a]pyridine-2-carboxylic acid

The title compound was prepared using steps 2 and 3 of the procedure to prepare Intermediate BY 002, except that the starting material was 5-methoxypyridin-2-amine.

Intermediate BY 008

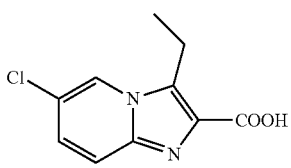

Synthesis of 6-chloro-3-ethylimidazo[1,2-a]pyridine-2-carboxylic acid

The title compound was prepared using steps 1-3 of the procedure to prepare Intermediate BY 002, except that methyl 2-oxopentanoate was used in step 1, and 5-chloropyridin-2-amine was used in step 2.

Intermediate BY 009

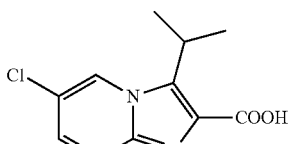

Synthesis of 6-chloro-3-isopropylimidazo[1,2-a]pyridine-2-carboxylic acid

The title compound was prepared using steps 1-3 of the procedure to prepare Intermediate BY 002, except that methyl 4-methyl-2-oxopentanoate was used in step 1, and 5-chloropyridin-2-amine was used in step 2.

Intermediate X01

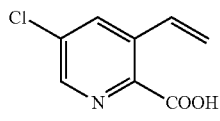

Synthesis of 5-chloro-3-methoxypicolinic acid 5-chloro-3-methoxypicolinonitrile (1 g, 5.45 mmol) was dissolved in EtOH (20 mL) and treated with 5 M NaOH (5 mL). The reaction mixture was heated at 100° C. for 1 h. The reaction mixture was cooled to RT and extracted with EtOAc. The aqueous phase was neutralized with 1 M HCl. The aqueous phase was back-extracted with EtOAc. The organic phase was separated and dried over MgSO$_4$. The solvent was removed under reduced pressure to obtain the title compound as a yellow solid (115 mg). M/S m/z=188.0 [M+H]$^+$. Calculated for C$_7$H$_6$ClNO$_3$: 187.58

Intermediate X02

Synthesis of 5-chloro-3-vinylpicolinic acid

A sealable vial was charged with 3-bromo-5-chloropicolinonitrile (700 mg, 3.22 mmol) and dichlorobis(triphenylphosphine)palladium(II) (271 mg, 0.386 mmol). The vial was evacuated and backfilled with nitrogen. 1,4-dioxane (5 mL) was added, followed by tri-n-butyl(vinyl)tin (1.225 mL, 3.86 mmol). The reaction mixture was heated to 100° C. The reaction mixture was diluted with water and EtOAc. The solvent was removed under reduced pressure. The residue was dissolved in EtOH (3 mL) and NaOH (1M, 6 mL). The cloudy solution was heated to 100° C. for 15 min. The reaction mixture was cooled to RT, the aqueous phase was separated and neutralized with 1 M HCl. The aqueous phase was back-extracted with EtOAc. The organic phase was separated and dried over MgSO$_4$. The solvent was removed under reduced pressure to obtain 5-chloro-3-vinylpicolinic acid (120 mg, 0.654 mmol, 20.30% yield) as a yellow solid. $^1$H NMR (300 MHz, DMSO-d$_6$) δ ppm 5.56 (d, J=11.11 Hz, 1H) 6.07 (d, J=17.54 Hz, 1H) 7.12 (dd, J=17.54, 11.11 Hz, 1H) 8.33 (d, J=2.19 Hz, 1H) 8.58 (d, J=2.19 Hz, 1H)

Intermediate X03

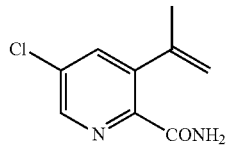

Synthesis of 5-chloro-3-(prop-1-en-2-yl)picolinamide

A sealable vial was charged with tetrakis(triphenylphosphine)palladium (133 mg, 0.115 mmol), sodium carbonate (731 mg, 6.90 mmol) and 3-bromo-5-chloropicolinonitrile (500 mg, 2.3 mmol). The vial was evacuated and backfilled with Nitrogen. 1,4-Dioxane (5 mL) and water (1.5 mL) were added. The reaction mixture was purged with Nitrogen for 2 min. Isopropenylboronic acid pinacol ester (0.474 mL, 2.53 mmol) was added and the reaction mixture was heated at 90° C. overnight. The reaction mixture was cooled to RT and partitioned between water and EtOAc. The organic phase was dried over MgSO$_4$ and concentrated in vacuo. The residue was dissolved in EtOH (5 mL) and NaOH (1M, 10 mL). The cloudy solution was heated at 100° C. for 15 min. The reaction mixture was cooled to RT and partitioned between water and EtOAc. The organic phase was washed with 1 M HCl, dried over MgSO$_4$ and concentrated under reduced pressure. The crude material was absorbed onto a plug of silica gel and purified by chromatography, eluting with a gradient of 10% to 80% EtOAc in hexane, to provide the title compound (268 mg, 1.363 mmol, 59.3% yield) as a white solid. M/S m/z=197.0 [M+H]$^+$. Calculated for C$_9$H$_9$ClN$_2$O: 196.63

R$^9$—Intermediate 1

(6-chloro-3-methylimidazo[1,2-a]pyridin-2-yl)methanamine

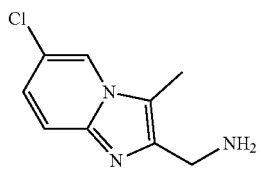

Step 1: (6-chloro-3-methylimidazo[1,2-a]pyridin-2-yl)methanol

To a solution of methyl 6-chloro-3-methylimidazo[1,2-a]pyridine-2-carboxylate (1.00 g, 4.45 mmol) in THF (10 mL) was added lithium borohydride, 2M solution in THF (3.34 ml, 6.68 mmol) at rt. After the addition, the reaction mixture was stirred at 60° C. for 12 h. On cooling the solution was acidified with 2N HCl solution, stirred for 1 h, basified with saturated Na$_2$CO$_3$ solution and extracted with DCM. The organic phase was concentrated and the solid obtained was triturated with ether, filtered and dried to afford the title compound (0.660 g, 3.36 mmol, 75% yield). LC/MS (ESI$^+$) m/z=197.0 (M+1).

Step 2: 6-chloro-2-(chloromethyl)-3-methylimidazo[1,2-a]pyridine

A solution of (6-chloro-3-methylimidazo[1,2-a]pyridin-2-yl)methanol (0.67 g, 3.41 mmol) in DCE (5 mL) was treated with thionyl chloride (0.497 ml, 6.81 mmol) and the resulting mixture stirred at 60° C. for 1 h. The reaction was concentrated, diluted with DCM and washed with 0.5N NaOH solution. The organic was concentrated and residue purified on silica gel eluting with 0-30% EtOAc in hexanes to afford the title compound (0.763 g, 3.55 mmol, 104% yield). LC/MS (ESI$^+$) m/z=215.0 (M+1).

Step 3: (6-chloro-3-methylimidazo[1,2-a]pyridin-2-yl)methanamine

A solution of 6-chloro-2-(chloromethyl)-3-methylimidazo[1,2-a]pyridine (0.763 g, 3.55 mmol) and sodium azide (0.461 g, 7.10 mmol) in DMF (5 mL) was stirred at RT for 18 h. The reaction mixture was diluted with water and extracted with EtOAc. The organic layer was dried over anhydrous magnesium sulfate, filtered, and concentrated. The residue obtained was added to a solution of triphenylphosphine (1.303 g, 4.97 mmol) in THF (10 mL) and water (4 mL). The resulting mixture was stirred overnight at RT and partitioned between EtOAc and 3N aqueous HCl. The aqueous layer was separated and basified to pH 10 with NH$_4$OH solution and extracted with DCM. DCM was dried and concentrated to afford the title compound (0.550 g, 2.81 mmol, 79% yield). The crude product was used without further purification. LC/MS (ESI$^+$) m/z=196.0 (M+1).

R$^9$—Intermediate 2

5-(cyclobutylmethoxy)-3-methylpicolinamide

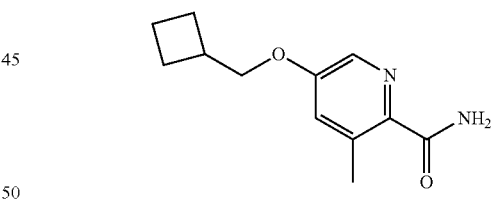

To a solution of 5-hydroxy-3-methylpyridine-2-carbonitrile (0.841 mL, 7.90 mmol), cyclobutylmethanol (0.817 g, 9.48 mmol), and triphenylphosphine (3.11 g, 11.85 mmol) in THF (10 mL) was added diisopropyl azodicarboxylate (2.329 mL, 11.85 mmol) dropwise at rt. After the addition, the reaction mixture was stirred at RT for 12 h, diluted with water and extracted with EtOAc. EtOAc was concentrated and the residue purified on silica gel eluting with 0-50% ethyl acetate/hexanes to give 5-(cyclobutylmethoxy)-3-methylpicolinonitrile. To the 5-(cyclobutylmethoxy)-3-methylpicolinonitrile was added sodium hydroxide 1N (39.5 mL, 39.5 mmol) in EtOH (15 mL). The reaction was refluxed at 100° C. for 18 h. The solid obtained after cooling reaction mixture to RT was filtered, washed with water and dried to afford the title compound (0.63 g, 2.86 mmol, 36.2% yield). LC/MS (ESI$^+$) m/z=221.0 (M+1). 119083-31-2.

$R^9$—Intermediate 3

5-(cyclobutylmethoxy)-3-methylpicolinic acid

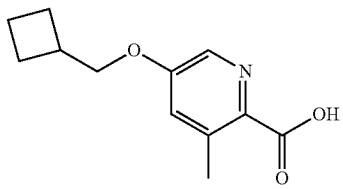 [SMILES: Cc1cc(OCC2CCC2)cnc1C(=O)O]

To a solution of 5-(cyclobutylmethoxy)-3-methylpicolinonitrile was added sodium hydroxide 1N (39.5 mL, 39.5 mmol) in EtOH (15 mL). The reaction was refluxed at 100° C. for 18 h. The reaction mixture was concentrated to half its volume and extracted with EtOAc. The aqueous layer was acidified with 5N HCl to pH 4 and extracted with EtOAc (2×). The organic layer was concentrated to afford the title compound (0.7 g, 3.16 mmol, 40.0% yield). LC/MS (ESI$^+$) m/z=222.1 (M+1). 119083-31-3.

$R^9$—Intermediate 4

5-(2-fluoroethoxy)-3-methylpicolinamide

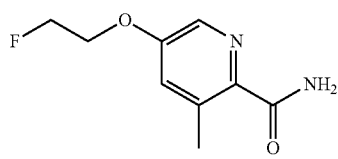

In an analogous reaction to that described for $R^9$—Intermediate 2, 5-(2-fluoroethoxy)-3-methylpicolinonitrile (1.0 g, 5.55 mmol) was converted to the title compound (0.82 g, 4.14 mmol, 74.5% yield),). LC/MS (ESI$^+$) m/z=199.0 (M+1).

$R^9$—Intermediate 5

5-(2-fluoroethoxy)-3-methylpicolinic acid

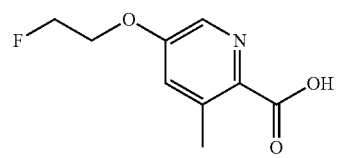

In an analogous reaction to that described for $R^9$—Intermediate 3, 5-(2-fluoroethoxy)-3-methylpicolinonitrile (1.0 g, 5.55 mmol) was converted to the title compound (0.103 g, 0.517 mmol, 9.32% yield). LC/MS (ESI$^+$) m/z=200.0 (M+1).

Step 1 for $R^9$—Intermediates 4 and 5:

5-(2-fluoroethoxy)-3-methylpicolinonitrile

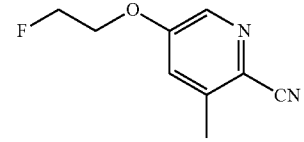

To a solution of 5-hydroxy-3-methylpyridine-2-carbonitrile (0.794 mL, 7.46 mmol), 2-fluoroethanol (0.525 mL, 8.95 mmol), and triphenylphosphine (2.93 g, 11.18 mmol) in THF (10 mL) was added diisopropyl azodicarboxylate (2.198 mL, 11.18 mmol) dropwise keeping temperature at RT. After the addition, the reaction mixture was stirred at RT for 12 h, diluted with water and extracted with EtOAc. EtOAc was concentrated and the residue purified on silica gel eluting with 0-50% ethyl acetate/hexanes to give desired product 5-(2-fluoroethoxy)-3-methylpicolinonitrile (1.2 g, 6.66 mmol, 89% yield)). LC/MS (ESI$^+$) m/z=181.0 (M+1).

$R^9$—Intermediate 6

3-methyl-5-(oxetan-3-yloxy)picolinic acid

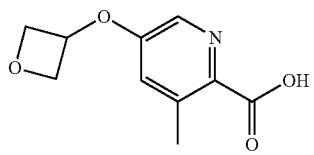

Step 1 for $R^9$—Intermediate 6

3-methyl-5-(oxetan-3-yloxy)picolinonitrile

To a stirred suspension of 5-hydroxy-3-methylpyridine-2-carbonitrile (0.397 mL, 3.73 mmol) and sodium hydride, 60% dispersion in mineral oil (0.194 g, 4.85 mmol) was added 3-oxetanyl tosylate (0.851 g, 3.73 mmol). The resulting mixture was stirred at RT for 6 h, diluted with water, and extracted with EtOAc. EtOAc was concentrated and the residue purified on silica gel eluting with 0-50% ethyl acetate/hexanes to afford the title compound (0.320 g, 1.682 mmol, 45.1% yield). LC/MS (ESI$^+$) m/z=191.0 (M+1).

Step 2: -methyl-5-(oxetan-3-yloxy)picolinic acid

In an analogous reaction to that described for $R^9$—Intermediate 3, -methyl-5-(oxetan-3-yloxy)picolinonitrile (0.320 g, 1.682 mmol) was converted to the title compound (0.21 g, 1.004 mmol, 59.7% yield). LC/MS (ESI$^+$) m/z=210.0 (M+1).

R⁹—Intermediate 7

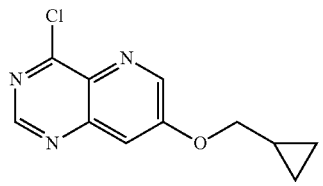 [SMILES: Clc1ncnc2cc(OCC3CC3)cnc12]

Synthesis of 4-chloro-7-(cyclopropylmethoxy)
pyrido[3,2-d]pyrimidine

Step 1: Synthesis of 7-(cyclopropylmethoxy)pyrido
[3,2-d]pyrimidin-4(1H)-one

A glass microwave reaction vessel was charged with cyclopropylmethanol (3123 µl, 38.6 mmol) followed by slow addition of sodium hydride, 60% dispersion in mineral oil (416 mg, 17.35 mmol). The reaction mixture was stirred at RT for several minutes. 7-chloropyrido[3,2-d]pyrimidin-4(1H)-one (350 mg, 1.928 mmol) was added, and the mixture was irradiated in a microwave reactor at 140° C. for 10 min. Then it was quenched with saturated aqueous ammonium chloride and extracted with DCM. The organic extract was washed with brine and dried over anhydrous MgSO₄. The solution was filtered and concentrated in vacuo to give the crude material which was washed with Et₂O and the solid was collected by Buchner funnel to yield 7-(cyclopropylmethoxy)pyrido[3,2-d]pyrimidin-4(1H)-one (50 mg, 0.230 mmol, 11.94% yield) as brown solid. LC/MS (ESI⁺) m/z=218.1 (M+H).

Step 2: Synthesis of 4-chloro-7-(cyclopropylmethoxy)pyrido[3,2-d]pyrimidine

To a mixture of 7-(cyclopropylmethoxy)pyrido[3,2-d]pyrimidin-4(1H)-one (50 mg, 0.230 mmol) in Toluene (1644 µl) were added diisopropylethylamine (122 µl, 0.702 mmol) and phosphorus oxychloride (65.3 µl, 0.714 mmol). The resulting reaction mixture was heated at 130° C. for 15 min. The reaction was concentrated, and the residue was dissolved in DCM and neutralized with saturated aqueous sodium bicarbonate. The aqueous layer was extracted with DCM. The combined organic extract were washed with brine and dried over anhydrous MgSO₄, filtered and concentrated to give the crude material as a dark brown solid. It was used for next step directly. LC/MS (ESI⁺) m/z=236.1 (M+H).

R⁹—Intermediate 8

Synthesis of 2-((5-chloropyrido[3,4-b]pyrazin-2-yl)oxy)acetonitrile

Step 1: Synthesis of
5-chloropyrido[3,4-b]pyrazin-2-ol

A reaction vial was charged with 5-chloro-2-methoxypyrido[3,4-b]pyrazine (70 mg, 0.358 mmol) and boron tribromide, 1.0 M in dichloromethane (1.074 mL, 1.074 mmol) was added slowly. After stirring for 2.5 h at RT, a further 0.3 mL of boron tribromide, 1.0 M in dichloromethane was added and it was stirred for another 2 h. It was then concentrated and aqueous NaHCO₃ was added. The brown solid was collected by filtration, washed with water and dried in-vacuo to yield 5-chloropyrido[3,4-b]pyrazin-2-ol (56 mg, 0.308 mmol, 86% yield) as brown solid. LC/MS (ESI⁺) m/z=182.1 (M+H).

Step 2: Synthesis of
2,5-dichloropyrido[3,4-b]pyrazine

A 100 mL flask was charged with 5-chloropyrido[3,4-b]pyrazin-2-ol (400 mg, 2.203 mmol) and phosphorus oxychloride (8213 µl, 88 mmol). The mixture was stirred at 115° C. for 0.5 h. It was concentrated and diluted with DCM. The black mixture was treated with sat. NaHCO₃ until slightly basic. The reaction mixture was extracted with DCM for several times. The organic extract was dried over anhydrous MgSO₄, filtered through a silica plug and concentrated to give the crude material as a orange solid. LC/MS (ESI⁺) m/z=200.1 (M+H).

Step 3: Synthesis of 2-((5-chloropyrido[3,4-b]
pyrazin-2-yl)oxy)acetonitrile

To reaction vial were added formaldehyde cyanohydrin (244 µl, 4.72 mmol) and sodium hydride, 60% dispersion in mineral oil (12.6 mg, 0.315 mmol) slowly. The mixture was stirred at RT for 10 min. Then 2,5-dichloropyrido[3,4-b]pyrazine (35 mg, 0.157 mmol) was added to the mixture. It was stirred at RT for 10 min. It was quenched by addition of saturated aqueous NH₄Cl, and extracted with EtOAc. The organic extract was washed with Brine and dried over anhydrous MgSO₄, filtered and concentrated to give the crude material as a orange solid. LC/MS (ESI⁺) m/z=221.1 (M+H).

By an analogous procedure, utilizing 2,2-difluoroethanol or 2,2,2-trifluoroethanol instead of formaldehyde cyanohydrin, intermediates 5-chloro-2-(2,2-difluoroethoxyl)pyrido[3,4-b]pyrazine, and 5-chloro-2-(2,2,2-trifluoroethoxyl)pyrido[3,4-b]pyrazine were obtained.

R⁹—Intermediate 9

Synthesis of
5-chloro-2-(2-fluoroethoxy)pyrido[3,4-b]pyrazine

To a reaction vial was added 5-chloropyrido[3,4-b]pyrazin-2-ol (30 mg, 0.165 mmol), 2-fluoroethyl 4-methylbenzenesulfonate (45.1 mg, 0.207 mmol) and cesium carbonate (161 mg, 0.496 mmol) in DMF (1.0 mL). The solution was stirred at 50° C. for 1.25 h. Then the reaction was heated at 60° C. for 3 hr. The reaction mixture was diluted with water and extracted with EtOAc. The organic extract was washed with brine and dried over anhydrous MgSO₄, filtered and concentrated. The crude material was purified by silica-gel chromatography, eluting with a gradient of 20% to 40% to 55% (40% EtOAc in Heptane) in Heptane, to provide 5-chloro-2-(2-fluoroethoxyl)pyrido[3,4-b]pyrazine (19 mg, 0.083 mmol, 50.5% yield) as white solid. LC/MS (ESI⁺) m/z=228.0 (M+H).

R⁹—Intermediate 10

Synthesis of
2-(but-2-yn-1-yloxy)-5-chloropyrido[3,4-b]pyrazine

A microwave reaction vessel was charged with 5-chloropyrido[3,4-b]pyrazin-2-ol (40 mg, 0.220 mmol) and 2-butyn-1-ol (0.046 mL, 0.661 mmol) in THF (0.8 mL) followed by triphenylphosphine (173 mg, 0.661 mmol). The reaction mixture was stirred for 10 min and diisopropyl azodicarboxylate (0.130 mL, 0.661 mmol) was then added slowly. The mixture was stirred at RT for 10 min. It was quenched with water and extracted with EtOAc. The organic extract was washed with brine and dried over anhydrous MgSO$_4$, filtered and concentrated. The crude material was purified by silica gel chromatography to provide 2-(but-2-yn-1-yloxy)-5-chloropyrido[3,4-b]pyrazine (20 mg, 0.086 mmol, 38.9% yield) as light-yellow solid. LC/MS (ESI$^+$) m/z=234.0 (M+H).

Intermediate RR02

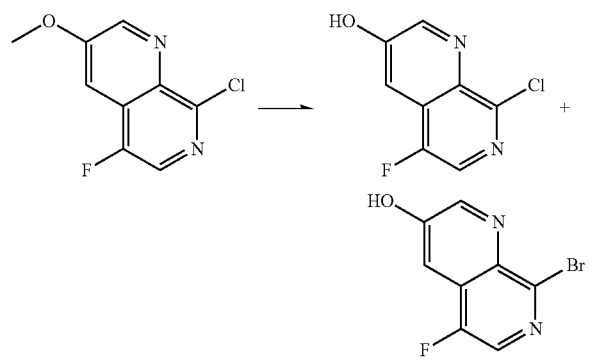

Synthesis of 8-chloro-5-fluoro-1,7-naphthyridin-3-ol & 8-bromo-5-fluoro-1,7-naphthyridin-3-ol To a solution of 8-chloro-5-fluoro-3-methoxy-1,7-naphthyridine (0.879 g, 4.13 mmol) in 1,2-dichloroethane (40 mL) was added boron tribromide, 1.0M in dichloromethane (30 ml, 30.0 mmol) via syringe. Upon completion of addition, the reaction was heated at 70° C. overnight. To the reaction was added boron tribromide, 1.0M in dichloromethane (10 mL). After 15 h the reaction was cooled to RT and the solvent was removed in vacuo. The residue was stirred vigorously with DCM, filtered, washed with water and solvent stripped at reduced pressure to give 658 mg (80%) of a tan crystalline solid, comprised of a mixture of 8-chloro-5-fluoro-1,7-naphthyridin-3-ol: MS m/z=198.9, 200.0 (M+1) and 8-bromo-5-fluoro-1,7-naphthyridin-3-ol: MS m/z=244.9 (M+1).

Intermediate RR03

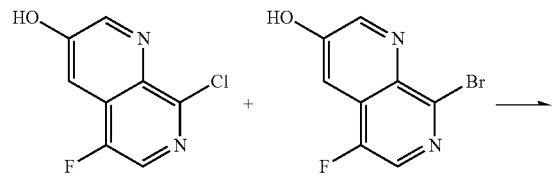

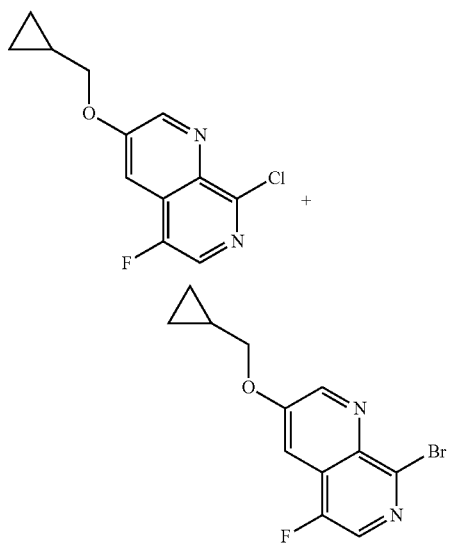

Synthesis of 8-chloro-3-(cyclopropylmethoxy)-5-fluoro-1,7-naphthyridine & 8-bromo-3-(cyclopropylmethoxy)-5-fluoro-1,7-naphthyridine To a cooled (0° C.) mixture of 8-bromo-5-fluoro-1,7-naphthyridin-3-ol & 8-chloro-5-fluoro-1,7-naphthyridin-3-ol (0.200 g, 0.453 mmol) and triphenylphosphine (0.290 g, 1.106 mmol) in THF (5 mL) was added cyclopropanemethanol (0.120 mL, 1.504 mmol) and diisopropyl azodicarboxylate (0.220 mL, 1.120 mmol). The reaction was allowed to warm to RT overnight. The reaction mixture was diluted with EtOAc, evaporated onto silica gel and purified by flash chromatography on silica gel eluting with EtOAc:hexanes (0:1→1:2) to give 175 mg of a white crystalline solid comprised of a mixture of 8-chloro-3-(cyclopropylmethoxy)-5-fluoro-1,7-naphthyridine. MS m/z=258.9 (M+1). & 8-bromo-3-(cyclopropylmethoxy)-5-fluoro-1,7-naphthyridine. MS m/z=298.9 (M+1).

Intermediate RR04

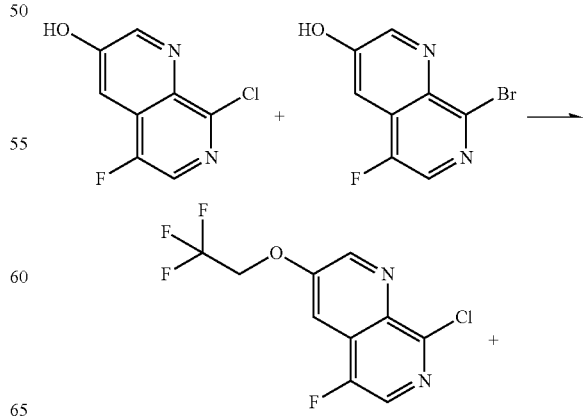

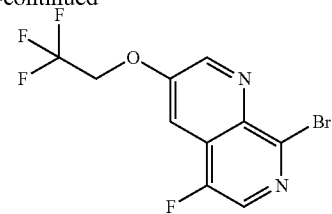

Synthesis of 8-chloro-5-fluoro-3-(2,2,2-trifluoroethoxy)-1,7-naphthyridine & 8-bromo-5-fluoro-3-(2,2,2-trifluoroethoxy)-1,7-naphthyridine To a mixture of 8-bromo-5-fluoro-1,7-naphthyridin-3-ol compound with 8-chloro-5-fluoro-1,7-naphthyridin-3-ol (0.229 g, 0.519 mmol) and cesium carbonate (0.489 g, 1.501 mmol) in DMF (2 mL) was added 2,2,2-trifluoroethyl trifluoromethanesulfonate (0.200 mL, 1.387 mmol) via syringe at RT. After stirring overnight the mixture was diluted with EtOAc and washed with water (1×) and brine (1×). The combined organic layers were dried over MgSO$_4$, were filtered and concentrated in vacuo to give 293 mg (93%) of an off-white crystalline solid comprised of 8-chloro-5-fluoro-3-(2,2,2-trifluoroethoxy)-1,7-naphthyridine: MS m/z=280.9, 283.0 (M+1) and 8-bromo-5-fluoro-3-(2,2,2-trifluoroethoxy)-1,7-naphthyridine: MS m/z=324.8, 326.9 (M+1).

Intermediate RR05

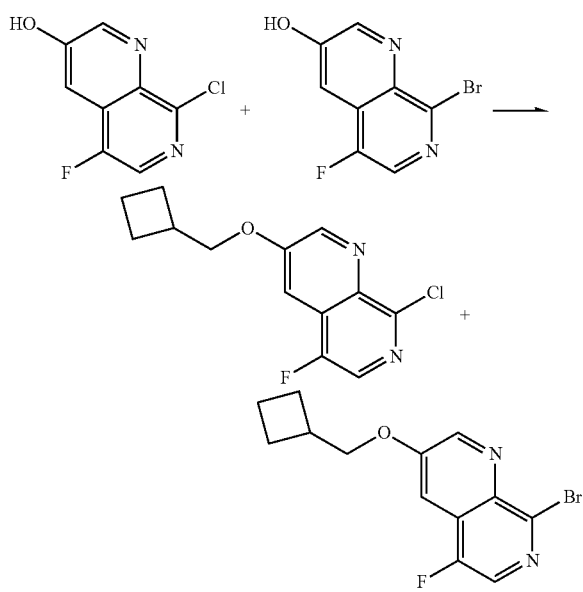

Synthesis of 8-chloro-3-(cyclobutylmethoxy)-5-fluoro-1,7-naphthyridine & 8-bromo-3-(cyclobutylmethoxy)-5-fluoro-1,7-naphthyridine The titled compounds were prepared according to the procedure for Intermediate RR03 using cyclobutanemethanol. 8-Chloro-3-(cyclobutylmethoxy)-5-fluoro-1,7-naphthyridine: MS m/z=267.0 (M+1) and 8-bromo-3-(cyclobutylmethoxy)-5-fluoro-1,7-naphthyridine: MS m/z=313.0 (M+1).

Intermediate RR06

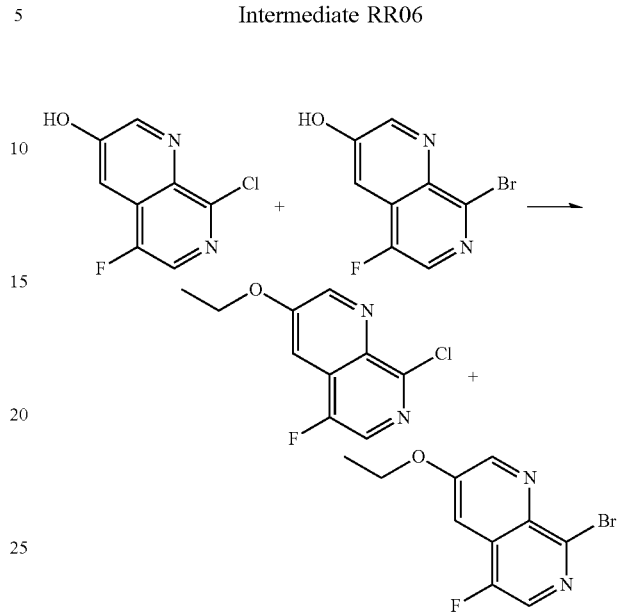

Synthesis of 8-chloro-5-fluoro-3-ethoxy-1,7-naphthyridine & 8-bromo-5-fluoro-3-ethoxy-1,7-naphthyridine The titled compounds were prepared according to the procedure for Intermediate RR04 using ethyl methanesulfonate. 8-Chloro-5-fluoro-3-ethoxy-1,7-naphthyridine: MS m/z=227.0 (M+1) and 8-bromo-5-fluoro-3-ethoxy-1,7-naphthyridine: MS m/z=271.0, 272.9 (M+1).

Intermediate RR07

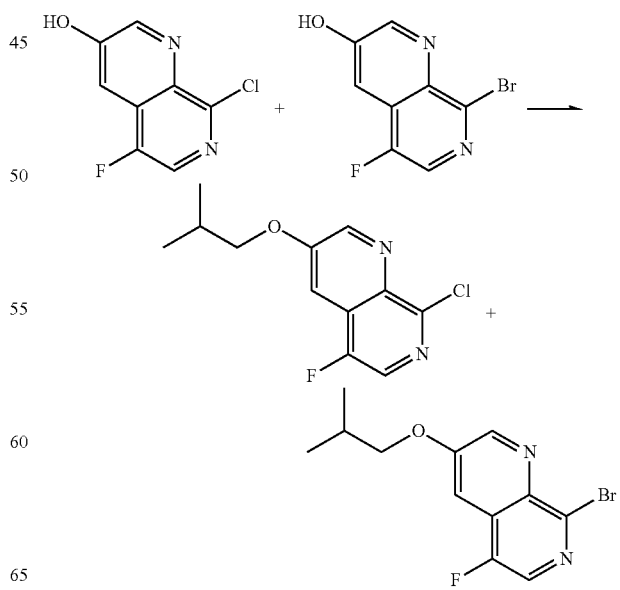

Synthesis of 8-chloro-5-fluoro-3-isobutoxy-1,7-naphthyridine & 8-bromo-5-fluoro-3-isobutoxy-1,7-naphthyridine The titled compounds were prepared according to the procedure for Intermediate RR03 using isobutanol. 8-Chloro-5-fluoro-3-isobutoxy-1,7-naphthyridine: MS m/z=255.1 (M+1). 8-Bromo-5-fluoro-3-isobutoxy-1,7-naphthyridine: MS m/z=298.9 (M+1).

Intermediate RR08

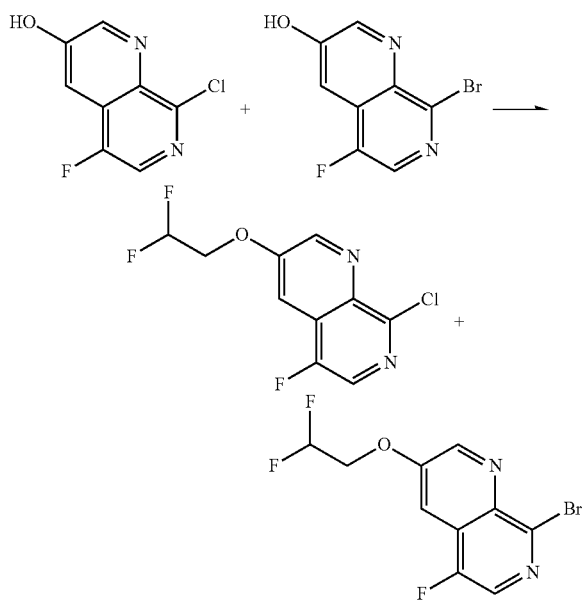

Synthesis of 8-chloro-3-(2,2-difluoroethoxy)-5-fluoro-1,7-naphthyridine & 8-bromo-3-(2,2-difluoroethoxy)-5-fluoro-1,7-naphthyridine The titled compounds were prepared according to the procedure for Intermediate RR04 using 2,2-difluoroethyl trifluoromethanesulfonate. 8-chloro-3-(2,2-difluoroethoxy)-5-fluoro-1,7-naphthyridine: MS m/z=262.9, 265.0 (M+1) and 8-bromo-3-(2,2-difluoroethoxy)-5-fluoro-1,7-naphthyridine: MS m/z=307.0, 308.9 (M+1).

Intermediate KR01

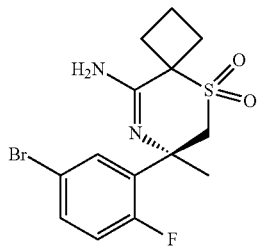 [SMILES: C[C@@]1(c2cc(Br)ccc2F)CS(=O)(=O)C2(CCC2)C(N)=N1]

Synthesis of (R)-9-amino-7-(5-bromo-2-fluorophenyl)-7-methyl-5-thia-8-azaspiro[3.5]non-8-ene 5,5-dioxide Step 1: 1-(methylsulfonyl)cyclobutanecarbonitrile To a solution of 2-(methylsulfonyl)acetonitrile (1.00 g, 8.39 mmol) in acetonitrile (8.4 mL) was added potassium carbonate (3.48 g, 25.2 mmol), followed by 1,3-dibromopropane (0.946 mL, 9.23 mmol). The reaction was stirred at 65° C. for 18 hours. The reaction mixture was cooled to ambient temperature and filtered. The collected solids were rinsed with EtOAc. The filtrate was collected, concentrated in vacuo, and purified by silica-gel chromatography, eluting with 0-50% EtOAc in Heptanes, to provide the title compound (0.80 g, 5.0 mmol, 60% yield) as a colorless oil.

Step 2: (R,E)-N-(1-(5-bromo-2-fluorophenyl)ethylidene)-2-methylpropane-2-sulfinamide In an analogous reaction to that described for Intermediate 1, step 2, 1-(5-bromo-2-fluorophenyl)ethanone (50 g, 230 mmol) was treated with (R)-2-methylpropane-2-sulfinamide (27.9 g, 230 mmol) to give the title compound (54.13 g, 169 mmol, 73% yield). LC/MS (ESI$^+$) m/z=320 (M+H).

Step 3: (R)—N—((R)-2-(5-bromo-2-fluorophenyl)-1-((1-cyanocyclobutyl)sulfonyl)propan-2-yl)-2-methylpropane-2-sulfinamide In an analogous reaction to that described for Intermediate 1, step 3, (R,E)-N-(1-(5-bromo-2-fluorophenyl)ethylidene)-2-methylpropane-2-sulfinamide was converted to the title compound (8.96 g, 18.69 mmol, 60% yield). LC/MS (ESI$^+$) m/z=479 (M+H).

Step 4: (R)-9-amino-7-(5-bromo-2-fluorophenyl)-7-methyl-5-thia-8-azaspiro[3.5]non-8-ene 5,5-dioxide In an analogous sequence of reactions to those described for Example 6, steps 2-3, (R)—N—((R)-2-(5-bromo-2-fluorophenyl)-1-((1-cyanocyclobutyl)sulfonyl)propan-2-yl)-2-methylpropane-2-sulfinamide was converted to the title compound (2.09 g, 5.57 mmol, 67% yield). LC/MS (ESI$^+$) m/z=375 (M+H).

Example 106

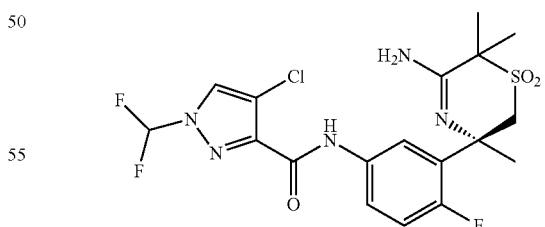

(R)—N-(3-(5-amino-3,6,6-trimethyl-1,1-dioxido-3,6-dihydro-2H-1,4-thiazin-3-yl)-4-fluorophenyl)-4-chloro-1-(difluoromethyl)-1H-pyrazole-3-carboxamide As described in the HATU coupling procedure, (R)-tert-butyl (5-(5-amino-2-fluorophenyl)-2,2,5-trimethyl-1,1-dioxido-5,6-dihydro-2H-1,4-thiazin-3-yl)carbamate and 4-chloro-1-(difluoromethyl)-1H-pyrazole-3-carboxylic acid were combined to provide the title compound (70 mg, 0.146 mmol, 69.7% yield) as an off-white solid. LC/MS (ESI⁺) m/z=478 (M+H). ¹H NMR (400 MHz, DMSO-d₆) δ ppm 10.51 (s, 1H) 8.76 (br. s, 1H) 7.65-8.09 (m, 3H) 7.13 (dd, J=12.08, 8.66 Hz, 1H) 6.02 (br. s., 2H) 3.45-3.69 (m, 2H) 1.62 (s, 3H) 1.58 (s, 3H) 1.47 (s, 3H)

Example 107

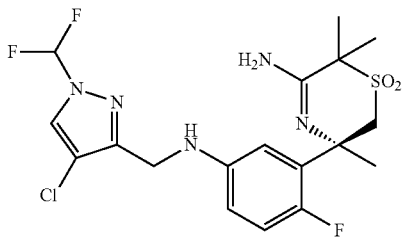 [SMILES: CC1(C)C(N)=N[C@](C)(c2cc(NCc3nn(C(F)F)cc3Cl)ccc2F)CS1(=O)=O]

Synthesis of (R)-5-amino-3-(5-(((4-chloro-1-(difluoromethyl)-1H-pyrazol-3-yl)methyl)amino)-2-fluorophenyl)-3,6,6-trimethyl-3,6-dihydro-2H-1,4-thiazine 1,1-dioxide Step 1: 4-chloro-1-(difluoromethyl)-N-methoxy-N-methyl-1H-pyrazole-3-carboxamide To a solution of 4-chloro-1-(difluoromethyl)-1H-pyrazole-3-carboxylic acid (0.38 g, 1.933 mmol) in DCM (12.89 ml) was added N-methylmorpholine (0.234 ml, 2.127 mmol), 1-(3-dimethylaminopropyl)-3-ethylcarbodiimide hydrochloride (0.408 g, 2.127 mmol), and N,O-dimethylhydroxylamine hydrochloride (0.207 g, 2.127 mmol). The reaction mixture was stirred at ambient temperature overnight. The reaction was then partitioned between ethyl acetate and water. The organic portion was concentrated and the crude product was purified by silica-gel chromatography, eluting with a gradient of 10-40% Ethyl Acetate/Heptanes to give the title compound (270 mg, 1.127 mmol, 58.3% yield) as a white solid. LC/MS (ESI⁺) m/z=240 (M+H).

Step 2: 4-chloro-1-(difluoromethyl)-1H-pyrazole-3-carbaldehyde

To a solution of 4-chloro-1-(difluoromethyl)-N-methoxy-N-methyl-1H-pyrazole-3-carboxamide (0.270 g, 1.127 mmol) in THF (5.6 mL) at 0° C. was added Lithium Aluminium Hydride (1M in THF, 0.563 ml, 0.563 mmol) drop-wise. The reaction mixture was stirred for 45 minutes and then quenched with aqueous NaHSO₄ solution. The crude product was extracted with EtOAc and concentrated in vacuo to give the title compound (0.14 g, 0.775 mmol, 68.8% yield). LC/MS (ESI⁺) m/z=181 (M+H).

Step 3: (R)-5-amino-3-(5-(((4-chloro-1-(difluoromethyl)-1H-pyrazol-3-yl)methyl)amino)-2-fluorophenyl)-3,6,6-trimethyl-3,6-dihydro-2H-1,4-thiazine 1,1-dioxide To a solution of (R)-tert-butyl (5-(5-amino-2-fluorophenyl)-2,2,5-trimethyl-1,1-dioxido-5,6-dihydro-2H-1,4-thiazin-3-yl)carbamate (90 mg, 0.225 mmol) in DCE (0.75 mL) was added 4-chloro-1-(difluoromethyl)-1H-pyrazole-3-carbaldehyde (65.1 mg, 0.360 mmol) followed by acetic acid (64.5 µl, 1.126 mmol). The reaction was stirred for 5 minutes then sodium tri-acetoxy borohydride (71.6 mg, 0.338 mmol) was added. The reaction mixture was stirred for 2 hours. The reaction was then quenched with aqueous sodium bicarbonate solution and extracted with dichloromethane. The organic portion was concentrated, diluted in dichloromethane and treated with TFA (521 µl, 6.76 mmol). The reaction mixture was stirred for 30 minutes and then partitioned between aqueous sodium bicarbonate solution and dichloromethane. The organic portion was concentrated and the crude product was purified by silica-gel chromatography, eluting with a gradient of 10-50% (90/10/1 dichloromethane/methanol/ammonium hydroxide) in dichloromethane to give the title compound (65 mg, 0.140 mmol, 62.2% yield) as a white solid. LC/MS (ESI⁺) m/z=464 (M+H). ¹H NMR (400 MHz, DMSO-d₆) δ ppm 8.52 (s, 1H) 7.74 (t, J=1.22 Hz, 1H,) 6.78-6.90 (m, 2H) 6.45-6.53 (m, 1H) 5.95 (br. s., 1H) 5.93 (br. s., 2H) 4.19 (d, J=5.87 Hz, 2H) 3.36-3.59 (m, 2H) 1.57 (s, 3H) 1.55 (s, 3H) 1.44 (s, 3H)

Example 108

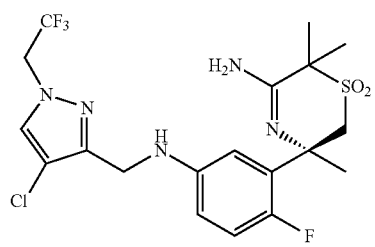 [SMILES: CC1(C)C(N)=N[C@](C)(c2cc(NCc3nn(CC(F)(F)F)cc3Cl)ccc2F)CS1(=O)=O]

(R)-5-amino-3-(5-(((4-chloro-1-(2,2,2-trifluoroethyl)-1H-pyrazol-3-yl)methyl)amino)-2-fluorophenyl)-3,6,6-trimethyl-3,6-dihydro-2H-1,4-thiazine 1,1-dioxide Step 1: (R)-tert-butyl (5-(5-(((4-chloro-1H-pyrazol-3-yl)methyl)amino)-2-fluorophenyl)-2,2,5-trimethyl-1,1-dioxido-5,6-dihydro-2H-1,4-thiazin-3-yl)carbamate To a solution of (R)-tert-butyl (5-(5-amino-2-fluorophenyl)-2,2,5-trimethyl-1,1-dioxido-5,6-dihydro-2H-1,4-thiazin-3-yl)carbamate (150 mg, 0.375 mmol) in DCE (1252 µl) was added acetic acid (107 µl, 1.877 mmol) followed by 4-chloro-1H-pyrazole-3-carbaldehyde (58.8 mg, 0.451 mmol), The reaction mixture was stirred for 5 minutes and then sodium tri-acetoxy borohydride (119 mg, 0.563 mmol) was added. The reaction mixture was stirred for 2 hours. The reaction was quenched with aqueous sodium bicarbonate solution and extracted with DCM. The organic portion was concentrated and the crude product was purified by silica-gel chromatography, eluting with a gradient of 10-50% (90/10/1 DCM/MeOH/ammonium hydroxide) in dichloromethane to give the title compound (120 mg, 0.233 mmol, 62.2% yield). LC/MS (ESI⁺) m/z=514 (M+H).

Step 2: (R)-5-amino-3-(5-(((4-chloro-1-(2,2,2-trifluoroethyl)-1H-pyrazol-3-1,1-dioxide To a solution of (R)-tert-butyl (5-(5-(((4-chloro-1H-pyrazol-3-yl)methyl)amino)-2-fluorophenyl)-2,2,5-trimethyl-1, 1-dioxido-5,6-dihydro-2H-1,4-thiazin-3-yl)carbamate (120 mg, 0.233 mmol) in DMF (0.78 mL) was added potassium carbonate (129 mg, 0.934 mmol) followed by 2,2,2-trifluoroethyl trifluoromethanesulfonate (65.0 µl, 0.280 mmol). The reaction mixture was stirred at 60° C. for 16 hours and then partitioned between water and EtOAc. The organic portion was dried over sodium sulfate and concentrated. The crude product was purified by silica-gel chromatography, eluting with a gradient of 10-50% (90/10/1 dichloromethane/methanol/ammonium hydroxide) in DCM to give the title compound (20 mg, 0.040 mmol) as a yellow solid. LC/MS (ESI+) m/z=496 (M+H).

Example 109

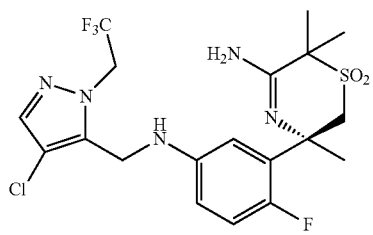 [SMILES: CC1(C)C(N)=N[C@](C)(c2cc(NCc3c(Cl)cnn3CC(F)(F)F)ccc2F)CS1(=O)=O]

(R)-5-amino-3-(5-((4-chloro-1-(2,2,2-trifluoroethyl)-1H-pyrazol-5-yl)methyl)amino)-2-fluorophenyl)-3,6,6-trimethyl-3,6-dihydro-2H-1,4-thiazine 1,1-dioxide To a solution of (R)-tert-butyl (5-(5-(((4-chloro-1H-pyrazol-3-yl)methyl)amino)-2-fluorophenyl)-2,2,5-trimethyl-1,1-dioxido-5,6-dihydro-2H-1,4-thiazin-3-yl)carbamate (120 mg, 0.233 mmol) in DMF (0.78 mL) was added potassium carbonate (129 mg, 0.934 mmol) followed by 2,2,2-trifluoroethyl trifluoromethanesulfonate (65.0 µl, 0.280 mmol). The reaction mixture was stirred at 60° C. for 16 hours and then partitioned between water and ethyl acetate. The organic portion was dried over sodium sulfate and concentrated. The crude product was purified by silica-gel chromatography, eluting with a gradient of 10-50% (90/10/1 dichloromethane/methanol/ammonium hydroxide) in DCM to give the title compound (3 mg, 6.1 umol) as a yellow solid. LC/MS (ESI+) m/z=496 (M+H).

Example 110

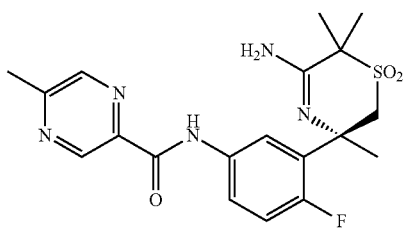 [SMILES: Cc1cnc(C(=O)Nc2ccc(F)c([C@]3(C)CS(=O)(=O)C(C)(C)C(N)=N3)c2)cn1]

(R)—N-(3-(5-amino-3,6,6-trimethyl-1,1-dioxido-3,6-dihydro-2H-1,4-thiazin-3-yl)-4-fluorophenyl)-5-methylpyrazine-2-carboxamide As described in the HATU coupling procedure, (R)-tert-butyl (5-(5-amino-2-fluorophenyl)-2,2,5-trimethyl-1,1-dioxido-5,6-dihydro-2H-1,4-thiazin-3-yl)carbamate (150 mg, 0.375 mmol) and 5-methylpyrazine-2-carboxylic acid (57.1 mg, 0.413 mmol) were combined to provide the title compound (68 mg, 0.162 mmol, 36% yield) as an off-white solid. LC/MS (ESI+) m/z=420 (M+H).

Example 111

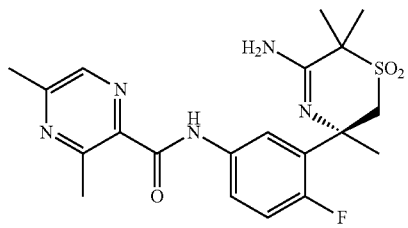 [SMILES: Cc1cnc(C(=O)Nc2ccc(F)c([C@]3(C)CS(=O)(=O)C(C)(C)C(N)=N3)c2)c(C)n1]

®—N-(3-(5-amino-3,6,6-trimethyl-1,1-dioxido-3,6-dihydro-2H-1,4-thiazin-3-yl)-4-fluorophenyl)-3,5-dimethylpyrazine-2-carboxamide As described in the HATU coupling procedure, ®-tert-butyl (5-(5-amino-2-fluorophenyl)-2,2,5-trimethyl-1,1-dioxido-5,6-dihydro-2H-1,4-thiazin-3-yl)carbamate (150 mg, 0.375 mmol) and 3,5-dimethylpyrazine-2-carboxylic acid (62.8 mg, 0.413 mmol) were combined to provide the title compound (80 mg, 0.185 mmol, 47% yield) as an off-white solid. LC/MS (ESI+) m/z=434 (M+H). $^1$H NMR (400 MHz, DMSO-$d_6$) δ ppm 10.55 (s, 1H) 8.50 (s, 1H) 7.80-7.86 (m, 1H) 7.74 (dd, J=7.53, 2.64 Hz, 1H) 7.15 (dd, J=12.13, 8.90 Hz, 1H) 6.02 (br. S, 2H) 3.48-3.70 (m, 2H) 2.74 (s, 3H) 2.57 (s, 3H) 1.63 (s, 3H) 1.58 (s, 3H) 1.48 (s, 3H)

Example 112

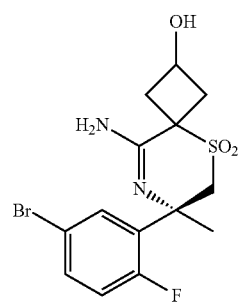

Synthesis of (R)-9-amino-7-(5-bromo-2-fluorophenyl)-2-hydroxy-7-methyl-5-thia-8-azaspiro[3.5]non-8-ene 5,5-dioxide Step 1: (((1,3-dibromopropan-2-yl)oxy)methyl)benzene To a suspension of –2-(benzyloxy)propane-1,3-diol (1 g, 5.49 mmol) in DCM (27.4 ml) at 0° C., was added triphenylphosphine (7.05 g, 26.9 mmol) and carbon tetrabromide (8.74 g, 26.3 mmol). The reaction mixture was brought to ambient temperature and stirred for 16 hours. The reaction mixture was concentrated and the crude solid was rinsed with heptanes. The filtrate was collected and concentrated in vacuo to provide the title compound (0.85 g, 2.76 mmol) as a colorless oil.

Step 2: (R)-tert-butyl (1-((3-(benzyloxy)-1-cyanocyclobutyl)sulfonyl)-2-(5-bromo-2-fluorophenyl)propan-2-yl)carbamate In an analogous reaction to that described in example 83, step 1, (R)-tert-butyl (2-(5-bromo-2-fluorophenyl)-1-((cyanomethyl)sulfonyl)propan-2-yl)carbamate and (((1,3-dibromopropan-2-yl)oxy)methyl)benzene were combined to provide the title compound (0.38 g, 0.65 mmol) as an off-white solid. LC/MS (ESI$^+$) m/z=603 (M+Na).

Step 3: (R)-9-amino-2-(benzyloxy)-7-(5-bromo-2-fluorophenyl)-7-methyl-5-thia-8-azaspiro[3.5]non-8-ene 5,5-dioxide In an analogous reaction to that described in example 83, step 2, (R)-tert-butyl (1-((3-(benzyloxy)-1-cyanocyclobutyl)sulfonyl)-2-(5-bromo-2-fluorophenyl)propan-2-yl)carbamate was converted to the title compound (0.28 g, 0.58 mmol) as a tan solid. LC/MS (ESI$^+$) m/z=481 (M+H).

Step 4: (R)-9-amino-7-(5-bromo-2-fluorophenyl)-2-hydroxy-7-methyl-5-thia-8-azaspiro[3.5]non-8-ene 5,5-dioxide To a solution of (R)-9-amino-2-(benzyloxy)-7-(5-bromo-2-fluorophenyl)-7-methyl-5-thia-8-azaspiro[3.5]non-8-ene 5,5-dioxide (90 mg, 0.187 mmol) in DCM (0.75 mL) at −78° C., was added boron trichloride (1M in DCM, 0.94 mL, 0.94 mmol). The reaction mixture was stirred for 3 hours and then treated with 7N Ammonia in Methanol. The mixture was concentrated and the crude product was purified by silica-gel chromatography, eluting with 20-60% (90/10/1 dichloromethane/methanol/ammonium hydroxide) in dichloromethane, to afford the title compound (70 mg, 0.179 mmol) as a white solid. LC/MS (ESI$^+$) m/z=391 (M+H).

Example 113

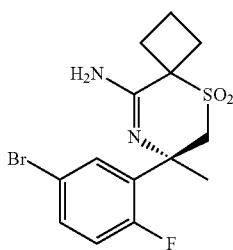

Synthesis of (R)-9-amino-7-(5-bromo-2-fluorophenyl)-7-methyl-5-thia-8-azaspiro[3.5]non-8-ene 5,5-dioxide In an analogous sequence of reactions to those described for example 83, steps 1-2, (R)-tert-butyl (2-(5-bromo-2-fluorophenyl)-1-((cyanomethyl)sulfonyl)propan-2-yl)carbamate was converted to the title compound as a tan solid. LC/MS (ESI$^+$) m/z=375 (M+H).

Example 114

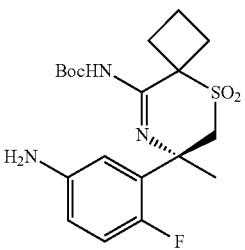 [SMILES: CC(C)(C)OC(=O)NC1=N[C@](C)(c2cc(N)ccc2F)CS(=O)(=O)C12CCC2]

Synthesis of (R)-tert-butyl (7-(5-amino-2-fluorophenyl)-7-methyl-5,5-dioxido-5-thia-8-azaspiro[3.5]non-8-en-9-yl)carbamate In an analogous sequence of reactions to those described for intermediate 2, steps 1-3, (R)-9-amino-7-(5-bromo-2-fluorophenyl)-7-methyl-5-thia-8-azaspiro[3.5]non-8-ene 5,5-dioxide was converted to the title compound as an off-white solid. LC/MS (ESI$^+$) m/z=412 (M+H).

Example 115

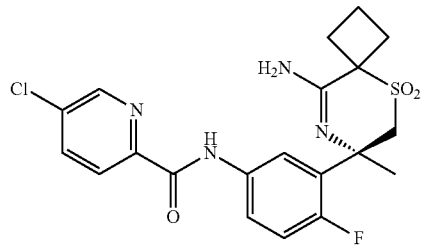 [SMILES: C[C@@]1(c2cc(NC(=O)c3ccc(Cl)cn3)ccc2F)CS(=O)(=O)C2(CCC2)C(N)=N1]

(R)—N-(3-(9-amino-7-methyl-5,5-dioxido-5-thia-8-azaspiro[3.5]non-8-en-7-yl)-4-fluorophenyl)-5-chloropicolinamide As described in the HATU coupling procedure, (R)-tert-butyl (7-(5-amino-2-fluorophenyl)-7-methyl-5,5-dioxido-5-thia-8-azaspiro[3.5]non-8-en-9-yl)carbamate (110 mg, 0.267 mmol) 5-chloro-2-pyridinecarboxylic acid (50.5 mg, 0.321 mmol) were combined to provide the title compound (40 mg, 0.089 mmol, 33% yield) as an off-white solid. LC/MS (ESI$^+$) m/z=451 (M+H).

Example 116

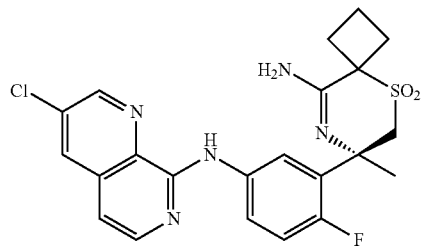 [SMILES: C[C@@]1(c2cc(Nc3nccc4cc(Cl)cnc34)ccc2F)CS(=O)(=O)C2(CCC2)C(N)=N1]

(R)-9-amino-7-(5-((3-chloro-1,7-naphthyridin-8-yl)amino)-2-fluorophenyl)-7-methyl-5-thia-8-azaspiro[3.5]non-8-ene 5,5-dioxide In a similar sequence of reactions to those described for Example 44, (R)-tert-butyl (7-(5-amino-2-fluorophenyl)-7-methyl-5,5-dioxido-5-thia-8-azaspiro[3.5]non-8-en-9-yl)carbamate (350 mg, 0.851 mmol) and 3,8-dichloro-1,7-naphthyridine (152 mg, 0.766 mmol) were combined to provide the title compound (260 mg, 0.549 mmol, 64.5% yield) as a yellow solid. LC/MS (ESI$^+$) m/z=474 (M+H).

Example 117

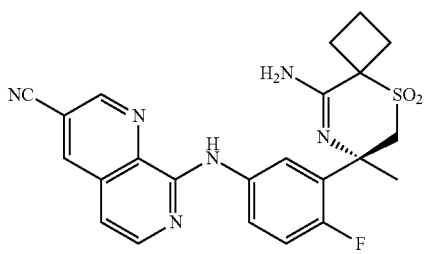 [SMILES: C[C@@]1(c2cc(Nc3nccc4cc(C#N)cnc34)ccc2F)CS(=O)(=O)C2(CCC2)C(N)=N1]

(R)-8-((3-(9-amino-7-methyl-5,5-dioxido-5-thia-8-azaspiro[3.5]non-8-en-7-yl)-4-fluorophenyl)amino)-1,7-naphthyridine-3-carbonitrile In an analogous reaction to that described for Example 76, (R)-9-amino-7-(5-((3-chloro-1,7-naphthyridin-8-yl)amino)-2-fluorophenyl)-7-methyl-5-thia-8-azaspiro[3.5]non-8-ene 5,5-dioxide (150 mg, 0.316 mmol) was converted to the title compound (35 mg, 0.075 mmol, 23.81% yield) as a yellow solid LC/MS (ESI$^+$) m/z=465 (M+H).

Example 118

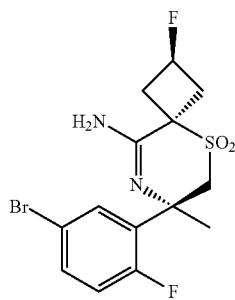 [SMILES: C[C@@]1(c2cc(Br)ccc2F)CS(=O)(=O)[C@]2(C[C@@H](F)C2)C(N)=N1]

(2S,4s,7R)-9-amino-7-(5-bromo-2-fluorophenyl)-2-fluoro-7-methyl-5-thia-8-azaspiro[3.5]non-8-ene 5,5-dioxide Step 1: (R)-tert-butyl (7-(5-bromo-2-fluorophenyl)-2-hydroxy-7-methyl-5,5-dioxido-5-thia-8-azaspiro[3.5]non-8-en-9-yl)carbamate To a solution of (R)-9-amino-7-(5-bromo-2-fluorophenyl)-2-hydroxy-7-methyl-5-thia-8-azaspiro[3.5]non-8-ene 5,5-dioxide (0.070 g, 0.179 mmol) in Dioxane (0.9 mL) was added boc anhydride (0.063 g, 0.286 mmol) and a saturated aqueous solution of sodium bicarbonate (0.9 mL). The resulting mixture was stirred at ambient temperature for 16 hours and then diluted with water and ethyl acetate. The organic layer was collected, dried over anhydrous magnesium sulfate, filtered, and concentrated. The crude product was purified by silica-gel chromatography, eluting with a gradient of 1-3% MeOH in DCM, to provide the title compound (0.060 g, 0.122 mmol) as an off-white solid. LC/MS (ESI$^+$) m/z=491 (M+H).

Step 2: (2S,4s,7R)-9-amino-7-(5-bromo-2-fluorophenyl)-2-fluoro-7-methyl-5-thia-8-azaspiro[3.5]non-8-ene 5,5-dioxide To a solution of (R)-tert-butyl (7-(5-bromo-2-fluorophenyl)-2-hydroxy-7-methyl-5,5-dioxido-5-thia-8-azaspiro[3.5]non-8-en-9-yl)carbamate (0.150 g, 0.305 mmol) in DCM (2.04 mL) was added DAST (0.046 mL, 0.351 mmol). The resulting mixture was stirred at 60° C. for 15 minutes, cooled to RT and poured onto a mixture of ice and aqueous sodium bicarbonate solution. The mixture was then extracted with ethyl acetate. The organic layer was concentrated and passed through a silica plug to give the title compound (0.050 g, 0.127 mmol, 41.7% yield) as an off-white solid. LC/MS (ESI$^+$) m/z=393 (M+H).

Example 119

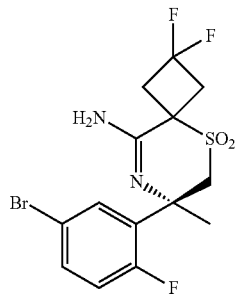 [SMILES: C[C@@]1(c2cc(Br)ccc2F)CS(=O)(=O)C2(CC(F)(F)C2)C(N)=N1]

(R)-9-amino-7-(5-bromo-2-fluorophenyl)-2,2-difluoro-7-methyl-5-thia-8-azaspiro[3.5]non-8-ene 5,5-dioxide Step 1: 2,2-difluoropropane-1,3-diol To a solution of diethyl difluoromalonate (3.77 g, 19.22 mmol) in THF (19.22 ml) at 0° C., was added Lithium Aluminium Hydride (1M in THF, 30.8 ml, 30.8 mmol) drop-wise. The reaction mixture was brought to ambient temperature and then stirred for 16 hours. The reaction mixture was then slowly poured onto an ice-cold suspension of 4 g of Na$_2$SO$_4$.10H$_2$O in 20 mL of THF. This was stirred for 1 h and the resulting slurry was filtered, rinsed with 1:3 MeOH/EtOAc. The filtrate was collected and concentrated to give the title compound (1.7 g, 15.17 mmol, 79% yield) as a white paste.

Step 2: 2,2-difluoropropane-1,3-diyl bis(trifluoromethanesulfonate)

To a suspension of 2,2-difluoropropane-1,3-diol (0.69 g, 6.16 mmol) in Ether (41.0 ml) was added pyridine (2.191 ml, 27.1 mmol). The reaction mixture was cooled to −5° C. and stirred vigorously for 5 minutes. To this was added trifluoromethanesulfonic anhydride (3.12 ml, 18.47 mmol). The reaction mixture was stirred at −5° C. for 30 minutes and then at ambient temperature for 3 hours. The reaction mixture was then filtered through a celite pad and the solids rinsed with ether. The filtrate was concentrated and the residue dried in vacuo to provide the title compound (1.65 g, 4.39 mmol, 71% yield) as a brown oil.

Step 3: (R)-tert-butyl (2-(5-bromo-2-fluorophenyl)-1-((1-cyano-3,3-difluorocyclobutyl)sulfonyl)propan-2-yl)carbamate To a solution of (R)-tert-butyl (2-(5-bromo-2-fluorophenyl)-1-((cyanomethyl)sulfonyl)propan-2-yl)carbamate (1.57 g, 3.61 mmol) and 2,2-difluoropropane-1,3-diyl bis(trifluoromethanesulfonate) (1.438 g, 3.82 mmol) in 1,4-dioxane (36.1 ml) was added cesium carbonate (2.350 g, 7.21 mmol). The reaction mixture was stirred at 55° C. for 3 hours. The reaction was partitioned between water and ethyl acetate. The organic portion was concentrated and the crude product was purified by silica-gel chromatography, eluting with a gradient of 0-1% MeOH in DCM, to provide the title compound (1.2 g, 2.347 mmol, 65.1% yield) as a white solid. LC/MS (ESI$^+$) m/z=533 (M+Na).

Step 4: (R)-9-amino-7-(5-bromo-2-fluorophenyl)-2,2-difluoro-7-methyl-5-thia-8-azaspiro[3.5]non-8-ene 5,5-dioxide A suspension of (R)-tert-butyl (2-(5-bromo-2-fluorophenyl)-1-((1-cyano-3,3-difluorocyclobutyl)sulfonyl)propan-2-yl)carbamate (1.19 g, 2.327 mmol) in HCl (4N in dioxane, 17.45 ml, 69.8 mmol) was heated at reflux for 15 hours. The reaction mixture was then concentrated and partitioned between aqueous sodium bicarbonate solution and DCM. The organic portion was concentrated and passed through a silica gel plug to give the title compound (957 mg, 2.327 mmol, quantitative yield) as a tan solid. LC/MS (ESI$^+$) m/z=411 (M+H).

Example 120

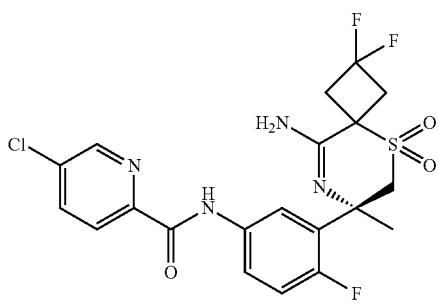 [SMILES: C[C@@]1(c2cc(NC(=O)c3ccc(Cl)cn3)ccc2F)CS(=O)(=O)C2(CC(F)(F)C2)C(N)=N1]

(R)—N-(3-(9-amino-2,2-difluoro-7-methyl-5,5-dioxido-5-thia-8-azaspiro[3.5]non-8-en-7-yl)-4-fluorophenyl)-5-chloropicolinamide Using the standard CuI-driven amidation conditions (R)-9-amino-7-(5-bromo-2-fluorophenyl)-2,2-difluoro-7-methyl-5-thia-8-azaspiro[3.5]non-8-ene 5,5-dioxide (0.105 g, 0.255 mmol) and 5-chloropicolinamide (0.060 g, 0.383 mmol) were combined to give the title compound (20 mg, 0.041 mmol, 16.09% yield) as an off-white solid. LC/MS (ESI$^+$) m/z=487 (M+H). $^1$H NMR (400 MHz, DMSO-d$_6$) δ ppm 10.74 (s, 1H) 8.84 (d, J=1.56 Hz, 1H) 8.13-8.35 (m, 2H) 7.93 (d, J=5.97 Hz, 2H) 7.12-7.35 (m, 1H) 6.31 (br. s., 2H) 3.58-3.89 (m, 2H) 3.06-3.34 (m, 4H) 1.72 (s, 3H)

Example 121

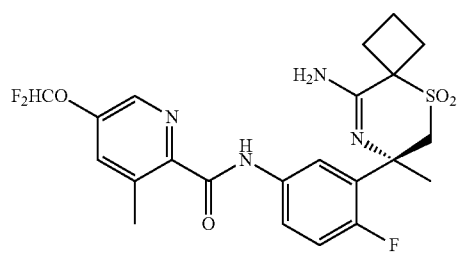 [SMILES: Cc1cc(OC(F)F)cnc1C(=O)Nc1ccc(F)c([C@]2(C)CS(=O)(=O)C3(CCC3)C(N)=N2)c1]

Synthesis of (R)—N-(3-(9-amino-7-methyl-5,5-dioxido-5-thia-8-azaspiro[3.5]non-8-en-7-yl)-4-fluorophenyl)-5-(difluoromethoxy)-3-methylpicolinamide As described in the HATU coupling procedure, (R)-tert-butyl (7-(5-amino-2-fluorophenyl)-7-methyl-5,5-dioxido-5-thia-8-azaspiro[3.5]non-8-en-9-yl)carbamate (100 mg, 0.243 mmol) and 5-(difluoromethoxy)-3-methylpicolinic acid (49.4 mg, 0.243 mmol) were combined to provide the title compound (20 mg, 0.040 mmol, 16.58% yield) as an off-white solid. LC/MS (ESI$^+$) m/z=497 (M+H). $^1$H NMR (400 MHz, DMSO-d$_6$) ppm 10.49 (s, 1H) 8.43 (d, J=2.35 Hz, 1H) 7.80-7.86 (m, 1H) 7.74-7.78 (m, 1H) 7.72 (d, J=2.15 Hz, 1H) 7.44 (t, J=1.00 Hz, 1H) 7.13 (dd, J=12.03, 8.80 Hz, 1H) 6.25 (br. s., 2H) 3.35-3.58 (m, 2H) 2.61-2.77 (m, 2H) 2.59 (s, 3H) 2.53-2.57 (m, 2H) 1.95-2.18 (m, 2H) 1.62 (s, 3H)

Example 122

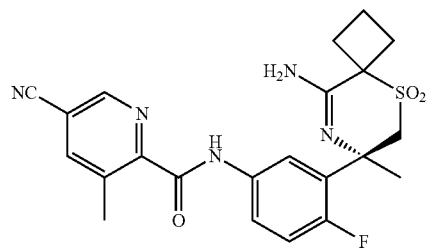 [SMILES: Cc1cc(C#N)cnc1C(=O)Nc1ccc(F)c([C@]2(C)CS(=O)(=O)C3(CCC3)C(N)=N2)c1]

Synthesis of (R)-tert-butyl (7-(5-(5-cyano-3-methylpicolinamido)-2-fluorophenyl)-7-methyl-5,5-dioxido-5-thia-8-azaspiro[3.5]non-8-en-9-yl)carbamate As described in the HATU coupling procedure, (R)-tert-butyl (7-(5-amino-2-fluorophenyl)-7-methyl-5,5-dioxido-5-thia-8-azaspiro[3.5]non-8-en-9-yl)carbamate (100 mg, 0.243 mmol) and 5-cyano-3-methylpicolinic acid (43.3 mg, 0.267 mmol) were combined to provide the title compound (90 mg, 0.162 mmol, 66.7% yield) as an off-white solid. LC/MS (ESI+) m/z=456 (M+H). ¹H NMR (400 MHz, DMSO-d₆) ppm 10.68 (s, 1H) 8.98 (dd, J=1.96, 0.59 Hz, 1H) 8.40 (dd, J=1.96, 0.68 Hz, 1H) 7.79-7.86 (m, 1H) 7.71-7.76 (m, 1H) 7.10-7.20 (m, 1H) 6.26 (br. s., 2H) 3.36-3.62 (m, 2H) 2.56-2.82 (m, 4H) 2.55 (s, 3H) 1.95-2.20 (m, 2H) 1.62 (s, 3H)

Example 123

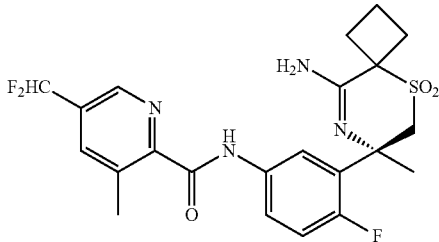 [SMILES: Cc1cc(C(F)F)cnc1C(=O)Nc1ccc(F)c([C@]2(C)CS(=O)(=O)C3(CCC3)C(N)=N2)c1]

Synthesis of (R)—N-(3-(9-amino-7-methyl-5,5-dioxido-5-thia-8-azaspiro[3.5]non-8-en-7-yl)-4-fluorophenyl)-5-(difluoromethyl)-3-methylpicolinamide As described in the HATU coupling procedure, (R)-tert-butyl (7-(5-amino-2-fluorophenyl)-7-methyl-5,5-dioxido-5-thia-8-azaspiro[3.5]non-8-en-9-yl)carbamate (100 mg, 0.243 mmol) and 5-(difluoromethyl)-3-methylpicolinic acid (54.6 mg, 0.292 mmol) were combined to provide the title compound (15 mg, 0.031 mmol, 12.85% yield) as an off-white solid. LC/MS (ESI+) m/z=481 (M+H). ¹H NMR (400 MHz, DMSO-d₆) ppm 10.66 (br. s., 1H) 8.77 (s, 1H) 8.08-8.13 (m, 1H) 7.79-7.93 (m, 2H) 7.12-7.43 (m, 2H) 6.31 (br. s., 2H) 3.42-3.68 (m, 2H) 2.67-2.83 (m, 2H) 2.64 (s, 3H) 2.58-2.62 (m, 2H) 2.01-2.22 (m, 2H) 1.68 (s, 3H)

Example 125

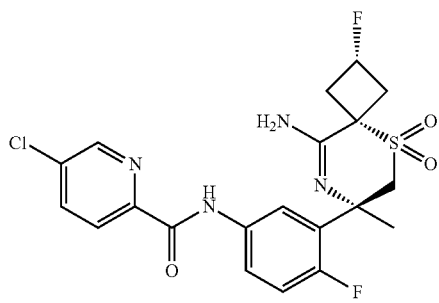 [SMILES: C[C@@]1(c2cc(NC(=O)c3ccc(Cl)cn3)ccc2F)CS(=O)(=O)[C@]2(C[C@@H](F)C2)C(N)=N1]

N-(3-((2S,4s,7R)-9-amino-2-fluoro-7-methyl-5,5-dioxido-5-thia-8-azaspiro[3.5]non-8-en-7-yl)-4-fluorophenyl)-5-chloropicolinamide Using the standard CuI-driven amidation conditions (2S, 4s,7R)-9-amino-7-(5-bromo-2-fluorophenyl)-2-fluoro-7-methyl-5-thia-8-azaspiro[3.5]non-8-ene 5,5-dioxide (0.016 g, 0.041 mmol) and 5-chloropicolinamide (9.56 mg, 0.061 mmol) were combined to give the title compound (8 mg, 0.017 mmol, 41.9% yield) as an off-white solid. LC/MS (ESI+) m/z=469 (M+H).

Example 124

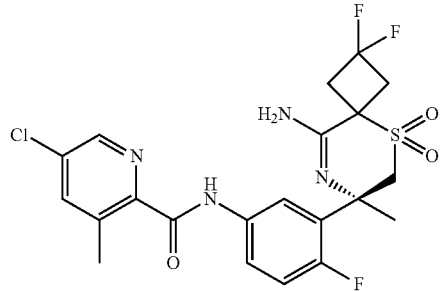 [SMILES: Cc1cc(Cl)cnc1C(=O)Nc1ccc(F)c([C@]2(C)CS(=O)(=O)C3(CC(F)(F)C3)C(N)=N2)c1]

Synthesis of (R)—N-(3-(9-amino-2,2-difluoro-7-methyl-5,5-dioxido-5-thia-8-azaspiro[3.5]non-8-en-7-yl)-4-fluorophenyl)-5-chloro-3-methylpicolinamide Using the standard CuI-driven amidation conditions (R)-9-amino-7-(5-bromo-2-fluorophenyl)-2,2-difluoro-7-methyl-5-thia-8-azaspiro[3.5]non-8-ene 5,5-dioxide (0.075 g, 0.182 mmol) and 5-chloro-3-methylpicolinamide (0.040 g, 0.237 mmol) were combined to give the title compound (0.02 g, 0.040 mmol, 22% yield) as an off-white solid. LC/MS (ESI+) m/z=501 (M+H). ¹H NMR (400 MHz, DMSO-d₆) ppm 10.62 (s, 1H) 8.64 (d, J=1.86 Hz, 1H) 8.07-8.10 (m, 1H) 7.87-7.93 (m, 1H) 7.79 (dd, J=7.24, 2.64 Hz, 1H) 7.21 (dd, J=11.88, 8.95 Hz, 1H) 6.30 (br. s., 2H) 3.63-3.84 (m, 2H) 3.20-3.36 (m, 4H) 2.62 (s, 3H) 1.72 (s, 3H)

Example 126

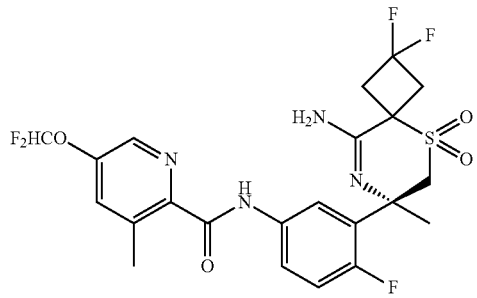 [SMILES: Cc1cc(OC(F)F)cnc1C(=O)Nc1ccc(F)c([C@]2(C)CS(=O)(=O)C3(CC(F)(F)C3)C(N)=N2)c1]

Synthesis of (R)—N-(3-(9-amino-2,2-difluoro-7-methyl-5,5-dioxido-5-thia-8-azaspiro[3.5]non-8-en-7-yl)-4-fluorophenyl)-5-(difluoromethoxy)-3-methylpicolinamide Using the standard CuI-driven amidation conditions (R)-9-amino-7-(5-bromo-2-fluorophenyl)-2,2-difluoro-7-methyl-5-thia-8-azaspiro[3.5]non-8-ene 5,5-dioxide (0.075 g, 0.182 mmol) and 5-(difluoromethoxy)-3-methylpicolinamide (0.048 g, 0.237 mmol) were combined to give the title compound (0.01 g, 0.018 mmol, 10% yield) as an off-white solid. LC/MS (ESI⁺) m/z=533 (M+H).

Example 127

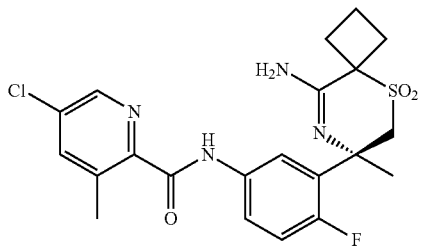

Synthesis of (R)—N-(3-(9-amino-7-methyl-5,5-dioxido-5-thia-8-azaspiro[3.5]non-8-en-7-yl)-4-fluorophenyl)-5-chloro-3-methylpicolinamide Using the standard CuI-driven amidation conditions (R)-9-amino-7-(5-bromo-2-fluorophenyl)-7-methyl-5-thia-8-azaspiro[3.5]non-8-ene 5,5-dioxide (152 mg, 0.405 mmol) and 5-chloro-3-methylpicolinamide (69.1 mg, 0.405 mmol) were combined to give the title compound (38 mg, 0.068 mmol, 17% yield) as an off-white solid. LC/MS (ESI⁺) m/z=465 (M+H).

Example 128

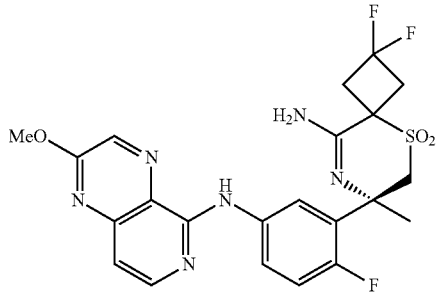 [SMILES: COc1cnc2c(Nc3ccc(F)c([C@]4(C)CS(=O)(=O)C5(CC(F)(F)C5)C(N)=N4)c3)nccc2n1]

Synthesis of (R)-9-amino-2,2-difluoro-7-(2-fluoro-5-((2-methoxypyrido[3,4-b]pyrazin-5-yl)amino)phenyl)-7-methyl-5-thia-8-azaspiro[3.5]non-8-ene 5,5-dioxide In a similar sequence of reactions to those described for Example 44, (R)-tert-butyl (7-(5-amino-2-fluorophenyl)-2,2-difluoro-7-methyl-5,5-dioxido-5-thia-8-azaspiro[3.5]non-8-en-9-yl)carbamate (100 mg, 0.223 mmol) and 5-chloro-2-methoxypyrido[3,4-b]pyrazine (39.3 mg, 0.201 mmol) were combined to provide the title compound (20 mg, 0.039 mmol, 17.67% yield) as a yellow solid. LC/MS (ESI⁺) m/z=507 (M+H).

Example 129

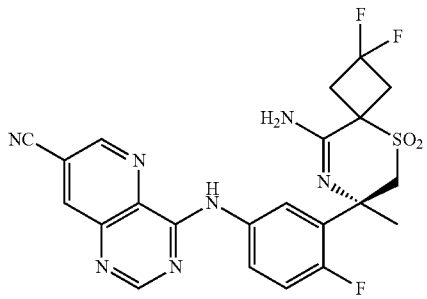 [SMILES: C[C@@]1(c2cc(Nc3ncnc4cc(C#N)cnc34)ccc2F)CS(=O)(=O)C2(CC(F)(F)C2)C(N)=N1]

(R)-4-((3-(9-amino-2,2-difluoro-7-methyl-5,5-dioxido-5-thia-8-azaspiro[3.5]non-8-en-7-yl)-4-fluorophenyl)amino)pyrido[3,2-d]pyrimidine-7-carbonitrile In a similar sequence of reactions to those described for Example 44, (R)-tert-butyl (7-(5-amino-2-fluorophenyl)-2,2-difluoro-7-methyl-5,5-dioxido-5-thia-8-azaspiro[3.5]non-8-en-9-yl)carbamate (100 mg, 0.223 mmol) and 4-chloro-pyrido[3,2-d]pyrimidine-7-carbonitrile (46.9 mg, 0.246 mmol) were combined to provide the title compound (42 mg, 0.084 mmol, 37.5% yield) as a yellow solid. LC/MS (ESI⁺) m/z=502 (M+H).

Example 130

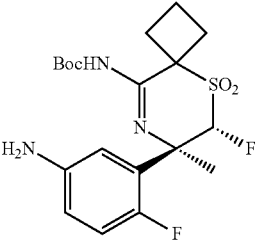 [SMILES: CC(C)(C)OC(=O)NC1=N[C@](C)(c2cc(N)ccc2F)[C@@H](F)S(=O)(=O)C12CCC2]

tert-butyl ((6S,7R)-7-(5-amino-2-fluorophenyl)-6-fluoro-7-methyl-5,5-dioxido-5-thia-8-azaspiro[3.5]non-8-en-9-yl)carbamate Step 1: (R)-tert-butyl (7-(5-bromo-2-fluorophenyl)-7-methyl-5,5-dioxido-5-thia-8-azaspiro[3.5]non-8-en-9-yl)carbamate In an analogous reaction to that described for intermediate 2, step 1, (R)-9-amino-7-(5-bromo-2-fluorophenyl)-7-methyl-5-thia-8-azaspiro[3.5]non-8-ene 5,5-dioxide was converted to the title compound (1.42 g, 2.99 mmol, 93% yield) as a tan solid. LC/MS (ESI⁺) m/z=475 (M+H).

Step 2: tert-butyl ((6S,7R)-7-(5-bromo-2-fluorophenyl)-6-fluoro-7-methyl-5,5-dioxido-5-thia-8-azaspiro[3.5]non-8-en-9-yl)carbamate In an analogous reaction to that described for example 4, step 1, (R)-tert-butyl (7-(5-bromo-2-fluorophenyl)-7- methyl-5,5-dioxido-5-thia-8-azaspiro[3.5]non-8-en-9-yl) carbamate (1.05 g, 2.209 mmol) was converted to the title compound (690 mg, 1.399 mmol, 63.3% yield) as an off-white solid. LC/MS (ESI$^+$) m/z=493 (M+H).

Step 3: tert-butyl ((6S,7R)-7-(5-azido-2-fluorophenyl)-6-fluoro-7-methyl-5,5-dioxido-5-thia-8-azaspiro[3.5]non-8-en-9-yl)carbamate In an analogous reaction to that described for intermediate 2, step 2, tert-butyl ((6S,7R)-7-(5-bromo-2-fluorophenyl)-6-fluoro-7-methyl-5,5-dioxido-5-thia-8-azaspiro[3.5]non-8-en-9-yl)carbamate was converted to the title compound (628 mg, 1.378 mmol, quantitative yield) as a clear oil. LC/MS (ESI$^+$) m/z=478 (M+Na).

Step 4: tert-butyl ((6S,7R)-7-(5-amino-2-fluorophenyl)-6-fluoro-7-methyl-5,5-dioxido-5-thia-8-azaspiro[3.5]non-8-en-9-yl)carbamate In an analogous reaction to that described for intermediate 2, step 3, tert-butyl ((6S,7R)-7-(5-azido-2-fluorophenyl)-6-fluoro-7-methyl-5,5-dioxido-5-thia-8-azaspiro[3.5]non-8-en-9-yl)carbamate (628 mg, 1.378 mmol) was converted to the title compound (420 mg, 0.978 mmol, 71% yield) as a white foam LC/MS (ESI$^+$) m/z=430 (M+H).

Example 131

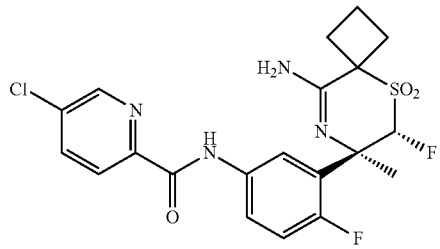 [SMILES: C[C@]1(c2cc(NC(=O)c3ccc(Cl)cn3)ccc2F)N=C(N)C2(CCC2)S(=O)(=O)[C@@H]1F]

N-(3-((6S,7R)-9-amino-6-fluoro-7-methyl-5,5-dioxido-5-thia-8-azaspiro[3.5]non-8-en-7-yl)-4-fluorophenyl)-5-chloropicolinamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (0.15 g, 0.349 mmol) and 5-chloro-2-pyridinecarboxylic acid (0.066 g, 0.419 mmol) were combined to provide the title compound (90 mg, 0.192 mmol, 55.0% yield) as an off-white solid. LC/MS (ESI$^+$) m/z=469 (M+H). $^1$H NMR (400 MHz, DMSO-d$_6$) ppm 10.64 (s, 1H) 8.78 (dd, J=2.35, 0.68 Hz, 1H) 8.12-8.21 (m, 2H) 7.77-7.88 (m, 2H) 7.16 (dd, J=11.93, 8.61 Hz, 1H) 6.56 (br. s., 2H) 5.90 (d, J=1.00 Hz, 1H) 2.59-2.86 (m, 4H) 1.93-2.27 (m, 2H) 1.60 (s, 3H)

Example 132

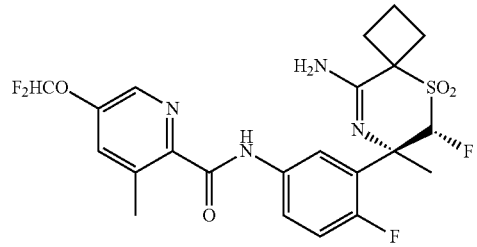 [SMILES: Cc1cc(OC(F)F)cnc1C(=O)Nc1ccc(F)c([C@@]2(C)N=C(N)C3(CCC3)S(=O)(=O)[C@@H]2F)c1]

N-(3-((6S,7R)-9-amino-6-fluoro-7-methyl-5,5-dioxido-5-thia-8-azaspiro[3.5]non-8-en-7-yl)-4-fluorophenyl)-5-(difluoromethoxy)-3-methylpicolinamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (88 mg, 0.205 mmol) and 5-(difluoromethoxy)-3-methylpicolinic acid (41.6 mg, 0.205 mmol) were combined to provide the title compound (45 mg, 0.087 mmol, 42.7% yield) as an off-white solid. LC/MS (ESI$^+$) m/z=515 (M+H). $^1$H NMR (400 MHz, DMSO-d$_6$) ppm 10.56 (s, 1H) 8.47 (d, J=2.45 Hz, 1H) 7.87-7.93 (m, 1H) 7.76 (d, J=2.25 Hz, 1H) 7.67-7.70 (m, 1H) 7.48 (t, J=1.00 Hz, 1H) 7.20 (dd, J=11.98, 8.85 Hz, 1H) 6.63 (br. s., 2H) 5.95 (d, J=1.00 Hz, 1H) 2.65-2.86 (m, 4H) 2.62 (s, 3H) 1.97-2.35 (m, 2H) 1.66 (d, J=3.52 Hz, 3H)

Example 133

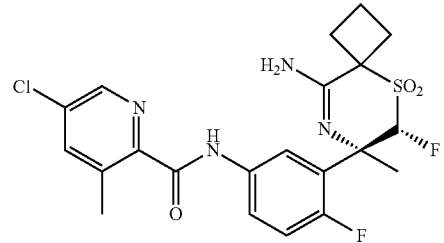 [SMILES: Cc1cc(Cl)cnc1C(=O)Nc1ccc(F)c([C@@]2(C)N=C(N)C3(CCC3)S(=O)(=O)[C@@H]2F)c1]

N-(3-((6S,7R)-9-amino-6-fluoro-7-methyl-5,5-dioxido-5-thia-8-azaspiro[3.5]non-8-en-7-yl)-4-fluorophenyl)-5-chloro-3-methylpicolinamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (113 mg, 0.263 mmol) and 5-chloro-3-methylpyridine-2-carboxylic acid (32.5 μl, 0.263 mmol) were combined to provide the title compound (55 mg, 0.114 mmol, 43.3% yield) as an off-white solid. LC/MS (ESI$^+$) m/z=483 (M+H). $^1$H NMR (400 MHz, DMSO-d$_6$) ppm 10.53 (s, 1H) 8.56 (d, J=1.86 Hz, 1H) 8.01 (d, J=1.66 Hz, 1H) 7.80-7.88 (m, 1H) 7.62 (d, J=4.99 Hz, 1H) 7.16 (dd, J=11.84, 9.00 Hz, 1H) 6.58 (br. s., 2H) 5.90 (d, J=1.00 Hz, 1H) 2.60-2.83 (m, 4H) 2.53 (s, 3H) 1.95-2.27 (m, 2H) 1.60 (d, J=3.23 Hz, 3H)

Example 134

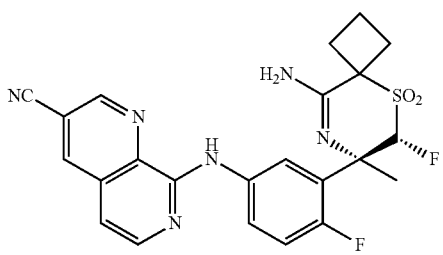 [SMILES: C[C@]1(c2cc(Nc3nccc4cc(C#N)cnc34)ccc2F)N=C(N)C2(CCC2)S(=O)(=O)[C@@H]1F]

8-((3-(((6S,7R)-9-amino-6-fluoro-7-methyl-5,5-di-oxido-5-thia-8-azaspiro[3.5]non-8-en-7-yl)-4-fluoro-phenyl)amino)-1,7-naphthyridine-3-carbonitrile In an analogous reaction to that described for Example 76, (6S,7R)-9-amino-7-(5-((3-chloro-1,7-naphthyridin-8-yl)amino)-2-fluorophenyl)-6-fluoro-7-methyl-5-thia-8-azaspiro[3.5]non-8-ene 5,5-dioxide (0.12 g, 0.244 mmol) was converted to the title compound (35 mg, 0.073 mmol, 29.7% yield) as a yellow solid LC/MS (ESI⁺) m/z=483 (M+H). ¹H NMR (400 MHz, DMSO-d₆) ppm 9.70 (s, 1H) 9.23 (d, J=1.96 Hz, 1H) 8.99 (d, J=2.05 Hz, 1H) 8.24 (d, J=5.67 Hz, 1H) 8.09-8.13 (m, 1H) 8.00-8.06 (m, 1H) 7.24 (d, J=5.87 Hz, 1H) 7.15 (dd, J=11.79, 9.05 Hz, 1H) 6.62 (br. s, 2H) 5.91 (d, J=1.00 Hz, 1H) 2.55-2.82 (m, 4H) 1.92-2.26 (m, 2H) 1.64 (d, J=3.42 Hz, 3H)

Example 135

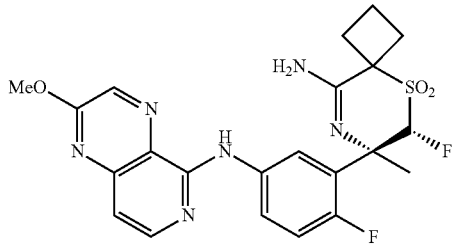 [SMILES: COc1cnc2c(Nc3ccc(F)c([C@@]4(C)N=C(N)C5(CCC5)S(=O)(=O)[C@@H]4F)c3)nccc2n1]

(6S,7R)-9-amino-6-fluoro-7-(2-fluoro-5-((2-methoxypyrido[3,4-b]pyrazin-5-yl)amino)phenyl)-7-methyl-5-thia-8-azaspiro[3.5]non-8-ene 5,5-dioxide In a similar sequence of reactions to those described for Example 44, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (110 mg, 0.256 mmol) and 5-chloro-2-methoxypyrido[3,4-b]pyrazine (52.6 mg, 0.269 mmol) were combined to provide the title compound (45 mg, 0.092 mmol, 36.0% yield) as a yellow solid. LC/MS (ESI⁺) m/z=489 (M+H).

Example 136

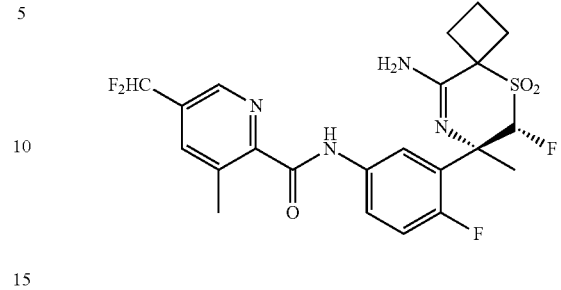

N-(3-((6S,7R)-9-amino-6-fluoro-7-methyl-5,5-di-oxido-5-thia-8-azaspiro[3.5]non-8-en-7-yl)-4-fluoro-phenyl)-5-(difluoromethyl)-3-methylpicolinamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (120 mg, 0.279 mmol) and 5-(difluoromethyl)-3-methylpicolinic acid (62.7 mg, 0.335 mmol) were combined to provide the title compound (67 mg, 0.134 mmol, 48.1% yield) as an off-white solid. LC/MS (ESI⁺) m/z=499 (M+H). ¹H NMR (400 MHz, DMSO-d₆) ppm 10.63 (s, 1H) 8.71 (br. d, J=1.00 Hz, 1H) 8.01-8.08 (m, 1H) 7.82-7.90 (m, 1H) 7.63 (d, J=4.50 Hz, 1H) 7.08-7.37 (m, 2H) 6.58 (br. s., 2H) 5.91 (d, J=1.00 Hz, 1H) 2.60-2.82 (m, 4H) 2.57 (s, 3H) 1.92-2.26 (m, 2H) 1.62 (d, J=3.33 Hz, 3H)

Example 137

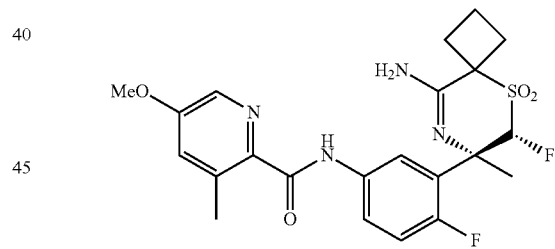

N-(3-((6S,7R)-9-amino-6-fluoro-7-methyl-5,5-di-oxido-5-thia-8-azaspiro[3.5]non-8-en-7-yl)-4-fluoro-phenyl)-5-methoxy-3-methylpicolinamide As described in the HATU coupling procedure, with tert-butyl ((6S,7R)-7-(5-amino-2-fluorophenyl)-6-fluoro-7-methyl-5,5-dioxido-5-thia-8-azaspiro[3.5]non-8-en-9-yl)carbamate (120 mg, 0.279 mmol) and 5-methoxy-3-methylpicolinic acid (56 mg, 0.335 mmol) were combined to provide the title compound (91 mg, 0.190 mmol, 68.1% yield) as an off-white solid. LC/MS (ESI⁺) m/z=479 (M+H). ¹H NMR (400 MHz, DMSO-d₆) ppm 10.36 (s, 1H) 8.22 (d, J=2.45 Hz, 1H) 7.82-7.88 (m, 1H) 7.58-7.64 (m, 1H) 7.40 (d, J=2.64 Hz, 1H) 7.13 (dd, J=11.93, 8.80 Hz, 1H) 6.57 (br. s, 2H) 5.90 (d, J=1.00 Hz, 1H) 3.91 (s, 3H) 2.62-2.82 (m, 4H) 2.61 (s, 3H) 1.95-2.26 (m, 2H) 1.60 (d, J=3.42 Hz, 3H)

Example 138

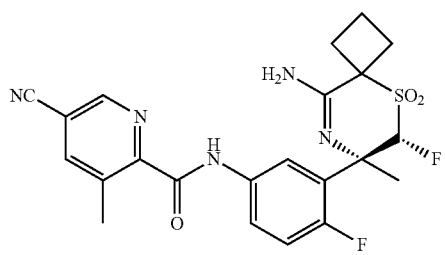 [SMILES: Cc1cc(C#N)cnc1C(=O)Nc1ccc(F)c([C@@]2(C)N=C(N)C3(CCC3)S(=O)(=O)[C@@H]2F)c1]

N-(3-((6S,7R)-9-amino-6-fluoro-7-methyl-5,5-di-oxido-5-thia-8-azaspiro[3.5]non-8-en-7-yl)-4-fluoro-phenyl)-5-cyano-3-methylpicolinamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (120 mg, 0.279 mmol) and 5-cyano-3-methylpicolinic acid (54.4 mg, 0.335 mmol) were combined to provide the title compound (55 mg, 0.116 mmol, 41.6% yield) as an off-white solid. LC/MS (ESI$^+$) m/z=474 (M+H). $^1$H NMR (400 MHz, DMSO-d$_6$) ppm 10.71 (s, 1H) 8.96-8.99 (m, 1H) 8.38-8.42 (m, 1H) 7.82-7.88 (m, 1H) 7.58-7.62 (m, 1H) 7.18 (dd, J=11.98, 8.85 Hz, 1H) 6.59 (br. s., 2H) 5.91 (d, J=1.00 Hz, 1H) 2.55-2.83 (m, 4H) 2.53 (s, 3H) 1.95-2.27 (m, 2H) 1.61 (d, J=3.42 Hz, 3H)

Example 139

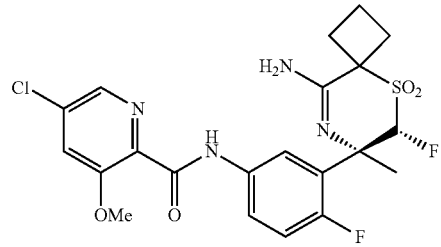 [SMILES: COc1cc(Cl)cnc1C(=O)Nc1ccc(F)c([C@@]2(C)N=C(N)C3(CCC3)S(=O)(=O)[C@@H]2F)c1]

N-(3-((6S,7R)-9-amino-6-fluoro-7-methyl-5,5-di-oxido-5-thia-8-azaspiro[3.5]non-8-en-7-yl)-4-fluoro-phenyl)-5-chloro-3-methoxypicolinamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (120 mg, 0.279 mmol) and 5-chloro-3-methoxypicolinic acid (62.9 mg, 0.335 mmol) were combined to provide the title compound (73 mg, 0.146 mmol, 52% yield) as an off-white solid. LC/MS (ESI$^+$) m/z=499 (M+H).

Example 140

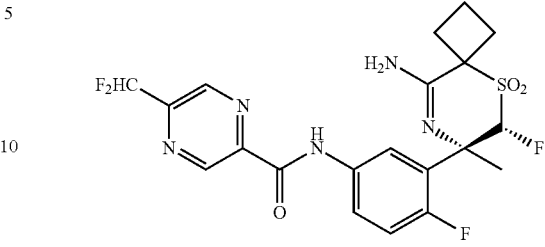

N-(3-((6S,7R)-9-amino-6-fluoro-7-methyl-5,5-di-oxido-5-thia-8-azaspiro[3.5]non-8-en-7-yl)-4-fluoro-phenyl)-5-(difluoromethyl)pyrazine-2-carboxamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (127 mg, 0.296 mmol) and 5-(difluoromethyl)pyrazine-2-carboxylic acid (61.8 mg, 0.355 mmol) were combined to provide the title compound (120 mg, 0.205 mmol, 69.3% yield) as an off-white solid. LC/MS (ESI$^+$) m/z=486 (M+H). $^1$H NMR (400 MHz, DMSO-d$_6$) ppm 10.91 (s, 1H) 9.37-9.39 (m, 1H) 9.08-9.10 (m, 1H) 7.81-7.89 (m, 2H) 7.11-7.42 (m, 2H) 6.59 (br. s., 2H) 5.92 (d, J=1.00 Hz, 1H) 2.58-2.82 (m, 4H) 1.94-2.27 (m, 2H) 1.62 (d, J=3.52 Hz, 3H)

Example 141

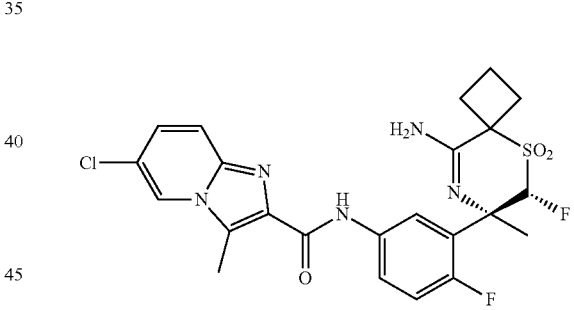

N-(3-((6S,7R)-9-amino-6-fluoro-7-methyl-5,5-di-oxido-5-thia-8-azaspiro[3.5]non-8-en-7-yl)-4-fluoro-phenyl)-6-chloro-3-methylimidazo[1,2-a]pyridine-2-carboxamide As described in the HATU coupling procedure, tert-butyl ((6S,7R)-7-(5-amino-2-fluorophenyl)-6-fluoro-7-methyl-5,5-dioxido-5-thia-8-azaspiro[3.5]non-8-en-9-yl)carbamate (77 mg, 0.179 mmol) and 6-chloro-3-methylimidazo[1,2-a]pyridine-2-carboxylic acid (45.3 mg, 0.215 mmol) were combined to provide the title compound (62 mg, 0.119 mmol, 66% yield) as an off-white solid. LC/MS (ESI$^+$) m/z=522 (M+H). $^1$H NMR (400 MHz, DMSO-d$_6$) ppm 10.20 (s, 1H) 8.68-8.70 (m, 1H) 7.82-7.89 (m, 1H) 7.75 (dd, J=7.34, 2.64 Hz, 1H) 7.70 (dd, J=9.63, 0.83 Hz, 1H) 7.43 (dd, J=9.63, 2.01 Hz, 1H) 7.14 (dd, J=11.98, 8.75 Hz, 1H) 6.58 (br. s, 2H) 5.91 (d, J=1.00 Hz, 1H) 2.81 (s, 3H) 2.58-2.77 (m, 4H) 1.96-2.28 (m, 2H) 1.62 (d, J=3.91 Hz, 3H)

Example 142

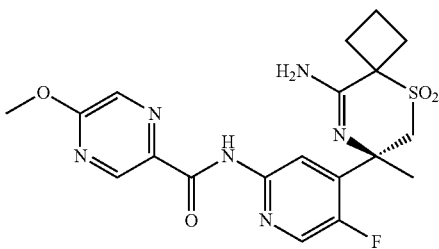 [SMILES: COc1cnc(C(=O)Nc2cc([C@@]3(C)CS(=O)(=O)C4(CCC4)C(N)=N3)c(F)cn2)cn1]

Synthesis of (S)—N-(4-(5-amino-3,6,6-trimethyl-1,1-dioxido-3,6-dihydro-2H-1,4-thiazin-3-yl)-5-fluoropyridin-2-yl)-5-methoxypyrazine-2-carboxamide Using procedure similar to the general CuI amidation procedure, (S)-tert-butyl (5-(2-bromo-5-fluoropyridin-4-yl)-2,2,5-trimethyl-1,1-dioxido-5,6-dihydro-2H-1,4-thiazin-3-yl)carbamate (0.09 g, 0.194 mmol), 5-methoxypyrazine-2-carboxamide (0.036 g, 0.233 mmol), copper(I) iodide (2.0 mg, 9.69 µmol), N,N'-dimethylethylenediamine (2.084 µl, 0.019 mmol), and potassium carbonate (0.080 g, 0.581 mmol) were combined to afford the title compound (0.016 g, 0.037 mmol, 18.91% yield). LC/MS (ESI$^+$) m/z=437.1 (M+H); $^1$H NMR (400 MHz, CHLOROFORM-d) δ ppm: 10.04 (s, 1H), 9.00 (d, J=0.78 Hz, 1H), 8.54 (d, J=6.26 Hz, 1H), 8.01-8.31 (m, 2H), 4.06 (s, 3H), 3.48-3.67 (m, 2H), 1.81 (s, 3H), 1.72 (s, 3H), 1.64 (s, 3H). (NH$_2$ very broad and not accounted for).

Example 143

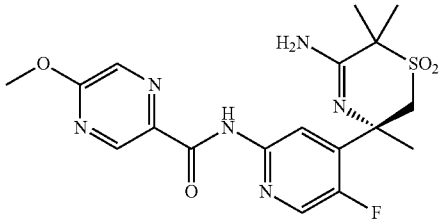 [SMILES: COc1cnc(C(=O)Nc2cc([C@]3(C)CS(=O)(=O)C(C)(C)C(N)=N3)c(F)cn2)cn1]

Synthesis of (R)—N-(4-(5-amino-3,6,6-trimethyl-1,1-dioxido-3,6-dihydro-2H-1,4-thiazin-3-yl)-5-fluoropyridin-2-yl)-5-methoxypyrazine-2-carboxamide A mixture of (R)-tert-butyl (5-(2-bromo-5-fluoropyridin-4-yl)-2,2,5-trimethyl-1,1-dioxido-5,6-dihydro-2H-1,4-thiazin-3-yl)carbamate (0.09 g, 0.194 mmol), 5-methoxypyrazine-2-carboxamide (0.042 g, 0.271 mmol), 4,5-bis(diphenylphosphino)-9,9-dimethyl-xanthene (0.011 g, 0.019 mmol), tris(dibenzylideneacetone) dipalladium (0) (0.018 g, 0.019 mmol), and cesium carbonate (0.189 g, 0.581 mmol) in Dioxane (1.5 mL) contained in a microwave vial was flushed with argon, capped, and heated under microwave irradiation at 120° C. for 1 hr. The reaction mixture was cooled to RT, diluted with water and extracted with EtOAc. The organic phase was concentrated and the residue purified on silica gel eluting with 0-100% ethyl acetate/hexanes to give the tile compound (0.035 g, 0.080 mmol, 41.4% yield).

LC/MS (ESI$^+$) m/z=437.1 (M+H); $^1$H NMR (400 MHz, CHLOROFORM-d) δ ppm: 10.04 (s, 1H), 8.99 (d, J=1.37 Hz, 1H), 8.53 (d, J=6.26 Hz, 1H), 8.04-8.22 (m, 2H), 5.5-4.0 (brs. 2H), 4.06 (s, 3H), 3.46-3.69 (m, 2H), 1.80 (s, 3H), 1.72 (s, 3H), 1.64 (s, 3H).

Example 144

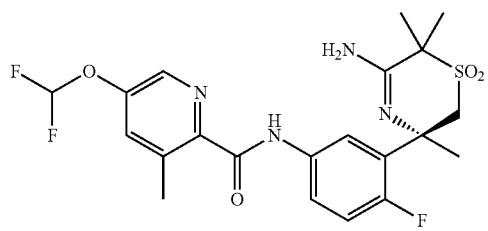 [SMILES: Cc1cc(OC(F)F)cnc1C(=O)Nc1ccc(F)c([C@]2(C)CS(=O)(=O)C(C)(C)C(N)=N2)c1]

Synthesis of (R)—N-(3-(5-amino-3,6,6-trimethyl-1,1-dioxido-3,6-dihydro-2H-1,4-thiazin-3-yl)-4-fluorophenyl)-5-(difluoromethoxy)-3-methylpicolinamide Using procedure similar to the general CuI amidation procedure, (R)-5-amino-3-(5-bromo-2-fluorophenyl)-3,6,6-trimethyl-3,6-dihydro-2H-1,4-thiazine 1,1-dioxide (0.2 g, 0.551 mmol), 5-(difluoromethoxy)-3-methylpicolinamide (0.122 g, 0.606 mmol), copper(I) iodide (0.005 g, 0.026 mmol), N,N'-dimethylethylenediamine (5.92 µl, 0.055 mmol), and potassium carbonate (0.228 g, 1.652 mmol) were combined to afford the title compound (0.182 g, 0.376 mmol, 68.2% yield). LC/MS (ESI$^+$) m/z=485.1 (M+H); $^1$H NMR (400 MHz, CHLOROFORM-d) δ ppm: 10.00 (s, 1H), 8.21 (d, J=1.37 Hz, 1H), 7.84-8.00 (m, 1H), 7.60 (dd, J=7.04, 2.54 Hz, 1H), 7.37 (d, J=2.15 Hz, 1H), 7.08 (dd, J=11.74, 8.80 Hz, 1H), 6.35-6.84 (m, 1H), 4.34-5.21 (m, 2H), 3.39-3.74 (m, 2H), 2.76 (s, 3H), 1.81 (s, 3H), 1.69 (s, 3H), 1.59 (s, 3H).

Example 145

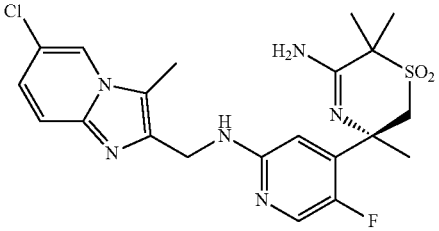 [SMILES: Cc1c(CNc2cc([C@]3(C)CS(=O)(=O)C(C)(C)C(N)=N3)c(F)cn2)nc2ccc(Cl)cn12]

Synthesis of (R)-5-amino-3-(2-(((6-chloro-3-methylimidazo[1,2-a]pyridin-2-yl)methyl)amino)-5-fluoropyridin-4-yl)-3,6,6-trimethyl-3,6-dihydro-2H-1,4-thiazine 1,1-dioxide A mixture of (R)-tert-butyl (5-(2-bromo-5-fluoropyridin-4-yl)-2,2,5-trimethyl-1,1-dioxido-5,6-dihydro-2H-1,4-thiazin-3-yl)carbamate (0.152 g, 0.327 mmol), (6-chloro-3-methylimidazo[1,2-a]pyridin-2-yl)methanamine (0.083 g, 0.426 mmol), Xantphos (0.019 g, 0.033 mmol), palladium (II) acetate (7.35 mg, 0.033 mmol) and sodium t-butoxide (0.063 g, 0.655 mmol) in 1,4-dioxane was microwaved at 100° C. for 40 min, diluted with water and extracted with EtOAc and DCM. The organics were combined, concentrated and residue purified by silica gel chromatography, eluting with 100% EtOAc to give (R)-tert-butyl (5-(2-(((6-chloro-3-methylimidazo[1,2-a]pyridin-2-yl)methyl)amino)-5-fluoropyridin-4-yl)-2,2,5-trimethyl-1,1-dioxido-5,6-dihydro-2H-1,4-thiazin-3-yl)carbamate. The (R)-tert-butyl (5-(2-(((6-chloro-3-methylimidazo[1,2-a]pyridin-2-yl)methyl)amino)-5-fluoropyridin-4-yl)-2,2,5-trimethyl-1,1-dioxido-5,6-dihydro-2H-1,4-thiazin-3-yl)carbamate was dissolved in Dioxane (3 mL) and hydrogen chloride, 4N in 1,4-dioxane (4.09 ml, 16.37 mmol) was added. The reaction mixture was stirred at RT for 12 h. The reaction mixture was concentrated, diluted with water and extracted with DCM. The aqueous phase was basified with 1N NaOH solution and extracted with DCM. The DCM from the second extraction was dried and concentrated to afford the title compound (0.08 g, 0.167 mmol, 51% yield). LC/MS (ESI+) m/z=478.9 (M+); $^1$H NMR (400 MHz, CHLOROFORM-d) δ ppm: 7.78-7.98 (m, 2H), 7.48 (d, J=9.39 Hz, 1H), 7.12 (dd, J=9.49, 1.86 Hz, 1H), 6.64 (d, J=5.28 Hz, 1H), 5.20 (br. s., 1H), 4.62 (d, J=5.09 Hz, 2H), 3.74-3.82 (m, 1H), 3.60-3.68 (m, 1H), 3.43-3.59 (m, 2H), 2.48 (s, 3H), 1.73 (s, 3H), 1.67 (s, 3H), 1.58 (br. s., 3H).

Example 146

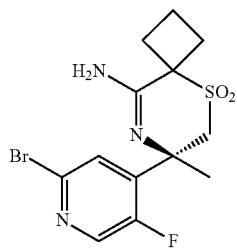 [SMILES: C[C@]1(c2cc(Br)ncc2F)CS(=O)(=O)C2(CCC2)C(N)=N1]

Synthesis of (S)-9-amino-7-(2-bromo-5-fluoropyridin-4-yl)-7-methyl-5-thia-8-azaspiro[3.5]non-8-ene 5,5-dioxide Step 1: 1-(2-bromo-5-fluoropyridin-4-yl)ethanol To a solution of lithium diisopropylamide, 2.0M solution in heptane/THF/ethylbenzene (42.0 mL, 84 mmol) in THF (50 mL), under nitrogen atmosphere at −78° C. was added a solution of 2-bromo-5-fluoropyridine (14.79 g, 84 mmol) in THF (50 mL) dropwise over 15 min. The reaction mixture was stirred at −78° C. for 2 h and acetaldehyde, anhydrous (5.19 mL, 92 mmol) was added dropwise. The reaction mixture was allowed to warm to room temperature over a period of 1 h and stirred at room temperature for 2 h. The reaction mixture was quenched with dropwise addition of H$_2$O (450 mL) and the aqueous layer was extracted with ethyl acetate (3×150 mL). The combined organic extract was dried over sodium sulphate, filtered, and concentrated under reduced pressure to afford a crude product which was purified by silica gel column chromatography eluting with 0-40% EtOAc in hexane to afford the title compound (13.64 g, 62.0 mmol, 73.8% yield). LC/MS (ESI+) m/z=220.0 (M+).

Step 2: (S)-9-amino-7-(2-bromo-5-fluoropyridin-4-yl)-7-methyl-5-thia-8-azaspiro[3.5]non-8-ene 5,5-dioxide In an analogous sequence of reactions to those described for Example 13, steps 2-5, 1-(2-bromo-5-fluoropyridin-4-yl)ethanol was converted to the racemate 9-amino-7-(2-bromo-5-fluoropyridin-4-yl)-7-methyl-5-thia-8-azaspiro[3.5]non-8-ene 5,5-dioxide. The racemate was purified by chiral SFC, using a ChiralPak IC column and eluting with 25% (20 mM ammonia in methanol) in CO$_2$, to provide the title compound in 48%. LC/MS (ESI+) m/z=377.9, 379.9 (M+H; 2 bromine isotopes). $^1$H NMR (400 MHz, CHLOROFORM-d) δ ppm 8.17 (d, J=2.93 Hz, 1H), 7.59 (d, J=6.06 Hz, 1H), 5.07 (br. s., 2H), 3.42-3.52 (m, 1H), 3.29-3.40 (m, 1H), 2.95-3.09 (m, 1H), 2.83-2.94 (m, 1H), 2.43-2.63 (m, 2H), 2.19-2.37 (m, 2H), 1.66-1.75 (m, 3H).

Example 147

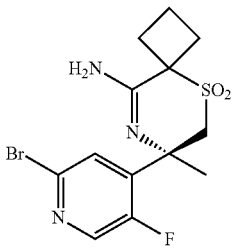 [SMILES: C[C@@]1(c2cc(Br)ncc2F)CS(=O)(=O)C2(CCC2)C(N)=N1]

Synthesis of (R)-9-amino-7-(2-bromo-5-fluoropyridin-4-yl)-7-methyl-5-thia-8-azaspiro[3.5]non-8-ene 5,5-dioxide The title compound is the other enantiomer recovered from the chiral SFC purification described in Example 146 above, using a ChiralPak IC column and eluting with 25% (20 mM ammonia in methanol) in CO$_2$ in 45.2% yield. LC/MS (ESI+) m/z=377.9, 379.9 (M+H; 2 bromine isotopes). $^1$H NMR (400 MHz, CHLOROFORM-d) δ ppm 8.17 (d, J=2.93 Hz, 1H), 7.59 (d, J=6.06 Hz, 1H), 5.07 (br. s., 2H), 3.42-3.52 (m, 1H), 3.29-3.40 (m, 1H), 2.95-3.09 (m, 1H), 2.83-2.94 (m, 1H), 2.43-2.63 (m, 2H), 2.19-2.37 (m, 2H), 1.66-1.75 (m, 3H).

Example 148

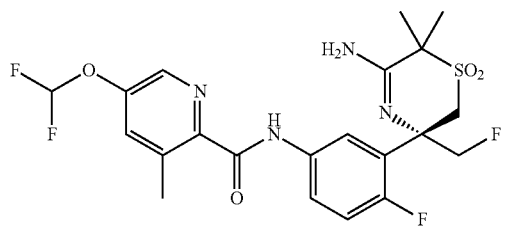 [SMILES: Cc1cc(OC(F)F)cnc1C(=O)Nc1ccc(F)c([C@]2(CF)CS(=O)(=O)C(C)(C)C(N)=N2)c1]

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-(difluoromethoxy)-3-methylpicolinamide Using procedure similar to the general CuI amidation procedure, (S)-5-amino-3-(5-bromo-2-fluorophenyl)-3-

(fluoromethyl)-6,6-dimethyl-3,6-dihydro-2H-1,4-thiazine 1,1-dioxide (0.100 g, 0.262 mmol), 5-(difluoromethoxy)-3-methylpicolinamide (63.6 mg, 0.315 mmol), copper(I) iodide (0.005 g, 0.026 mmol), N,N'-dimethylethylenediamine (40 mg, 0.454 mmol), and potassium carbonate (0.109 g, 0.789 mmol) were combined to afford the title compound (0.073 g, 0.145 mmol, 55.4% yield). LC/MS (ESI$^+$) m/z=503.9 (M+); $^1$H NMR (400 MHz, CHLOROFORM-d) δ ppm 10.00 (s, 1H), 8.21 (s, 1H), 7.89-8.04 (m, 1H), 7.63 (dd, J=7.04, 2.74 Hz, 1H), 7.36 (d, J=1.96 Hz, 1H), 7.09 (dd, J=11.83, 8.90 Hz, 1H), 6.37-6.84 (m, 1H), 5.00-4.4 (br s, 2H), 4.64-4.90 (m, 1H), 4.35-4.62 (m, 1H), 3.60-3.90 (m, 2H), 2.75 (s, 3H), 1.73 (s, 3H), 1.60 (s, 3H).

Example 149

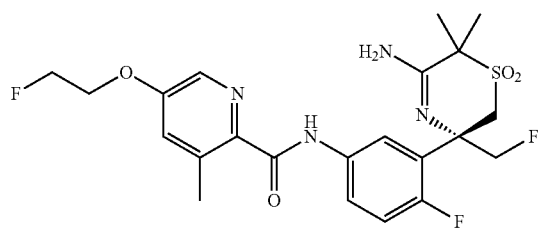 [SMILES: Cc1cc(OCCF)cnc1C(=O)Nc1ccc(F)c([C@]2(CF)CS(=O)(=O)C(C)(C)C(N)=N2)c1]

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-(2-fluoroethoxy)-3-methylpicolinamide Using procedure similar to the Amidation Method D, (S)-5-amino-3-(5-amino-2-fluorophenyl)-3-(fluoromethyl)-6,6-dimethyl-3,6-dihydro-2H-1,4-thiazine 1,1-dioxide (0.053 g, 0.167 mmol) and 5-(2-fluoroethoxy)-3-methylpicolinic acid (0.040 g, 0.200 mmol) and 1-propanephosphonic acid cyclic anhydride (0.159 ml, 0.251 mmol) were combined to afford the title compound (0.067 g, 0.134 mmol, 80% yield). LC/MS (ESI$^+$) m/z=499.1 (M+); $^1$H NMR (400 MHz, CHLOROFORM-d) δ ppm: 10.05 (s, 1H), 8.09 (d, J=2.54 Hz, 1H), 8.02 (ddd, J=8.80, 4.30, 2.93 Hz, 1H), 7.58 (dd, J=7.04, 2.74 Hz, 1H), 7.01-7.14 (m, 2H), 4.67-4.90 (m, 3H), 4.41-4.61 (m, 1H), 4.34 (dd, J=4.79, 3.23 Hz, 1H), 4.27 (dd, J=4.79, 3.23 Hz, 1H), 3.83 (s, 1H), 3.74 (s, 1H), 2.74 (s, 3H), 1.74 (s, 3H), 1.62 (s, 3H).

Example 150

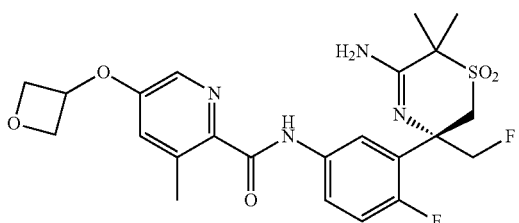

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-3-methyl-5-(oxetan-3-yloxy)picolinamide Using procedure similar to the Amidation Method D, (S)-5-amino-3-(5-amino-2-fluorophenyl)-3-(fluoromethyl)-6,6-dimethyl-3,6-dihydro-2H-1,4-thiazine 1,1-dioxide (0.050 g, 0.158 mmol), 3-methyl-5-(oxetan-3-yloxy)picolinic acid (0.040 g, 0.189 mmol), 1-propanephosphonic acid cyclic anhydride (0.150 ml, 0.236 mmol) were combined to afford the title compound (0.05 g, 0.098 mmol, 62.4% yield). LC/MS (ESI$^+$) m/z=508.9 (M+); $^1$H NMR (400 MHz, CHLOROFORM-d) δ ppm: 10.01 (s, 1H), 8.01 (ddd, J=8.90, 4.21, 2.74 Hz, 1H), 7.87 (d, J=2.74 Hz, 1H), 7.57 (dd, J=6.85, 2.74 Hz, 1H), 7.09 (dd, J=11.83, 8.90 Hz, 1H), 6.83 (d, J=2.35 Hz, 1H), 5.21-5.28 (m, 1H), 4.98 (td, J=6.65, 3.52 Hz, 2H), 4.67-4.87 (m, 3H), 4.39-4.62 (m, 1H), 3.64-3.86 (m, 2H), 2.71 (s, 3H), 1.74 (s, 3H), 1.61 (s, 3H).

Example 151

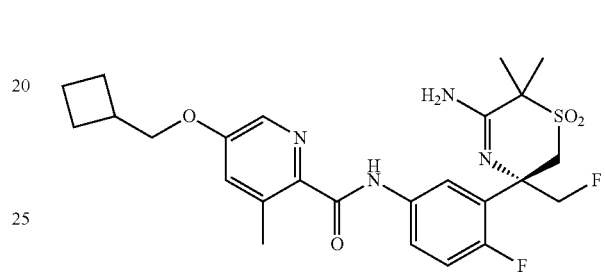

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-(cyclobutylmethoxy)-3-methylpicolinamide Using procedure similar to the general CuI amidation procedure, (S)-5-amino-3-(5-bromo-2-fluorophenyl)-3-(fluoromethyl)-6,6-dimethyl-3,6-dihydro-2H-1,4-thiazine 1,1-dioxide (0,200 mg, 0.525 mmol), 5-(cyclobutylmethoxy)-3-methylpicolinamide (127 mg, 0.577 mmol), copper(I) iodide (19.9 mg, 0.105 mmol), N,N'-dimethylethylenediamine (55 mg, 0.624 mmol), and potassium carbonate (290.0 mg, 2.098 mmol) were combined to afford the title compound (60.0 mg, 0.115 mmol, 21.97% yield). LC/MS (ESI$^+$) m/z=521.0 (M+1); $^1$H NMR (400 MHz, CHLOROFORM-d) δ ppm 10.05 (s, 1H), 7.91-8.11 (m, 2H), 7.59 (dd, J=6.94, 2.64 Hz, 1H), 6.92-7.18 (m, 2H), 4.65-4.88 (m, 1H), 4.41-4.63 (m, 1H), 4.00 (d, J=6.65 Hz, 2H), 3.65-3.85 (m, 2H), 2.76-2.86 (m, 1H), 2.74 (s, 3H), 2.10-2.26 (m, 2H), 1.83-2.03 (m, 4H), 1.73 (s, 3H), 1.62 (s, 3H).

Example 152

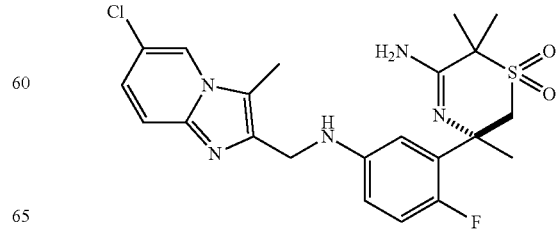

Synthesis of (R)-5-amino-3-(5-(((6-chloro-3-methyl-imidazo[1,2-a]pyridin-2-yl)methyl)amino)-2-fluoro-phenyl)-3,6,6-trimethyl-3,6-dihydro-2H-1,4-thiazine 1,1-dioxide

Step 1: (6-chloro-3-methylimidazo[1,2-a]pyridin-2-yl)methanol

To a solution of methyl 6-chloro-3-methylimidazo[1,2-a]pyridine-2-carboxylate (0.503 g, 2.24 mmol) in THF (4.5 mL) at 0° C. was added lithium borohydride (2.0 M in THF, 1.20 mL, 2.40 mmol). The reaction mixture was warmed to RT and stirred for 15 min, heated to 40° C. for 4 h, then cooled to RT and quenched with saturated NH$_4$Cl. The reaction mixture was diluted with EtOAc and saturated NH$_4$Cl. The aqueous phase was extracted with EtOAc (3×) and the combined organic extracts were washed with brine (1×), dried over MgSO$_4$, filtered, and concentrated. Purification by flash column chromatography on silica gel (10% to 100% EtOAc (10% MeOH) in hexanes) gave (6-chloro-3-methylimidazo[1,2-a]pyridin-2-yl)methanol (0.245 g, 1.25 mmol, 56% yield) as a white solid.

Step 2: 6-chloro-3-methylimidazo[1,2-a]pyridine-2-carbaldehyde

To a solution of (6-chloro-3-methylimidazo[1,2-a]pyridin-2-yl)methanol (0.242 g, 1.23 mmol) in DMSO (4 mL) at room temperature was added TEA (1.00 mL, 7.17 mmol) and sulfur trioxide pyridine complex (0.411 g, 2.58 mmol). The reaction mixture was stirred at RT for 15 min and then diluted with EtOAc and water. The aqueous phase was extracted with EtOAc (4×). The combined organic extracts were washed with brine (1×), dried over MgSO$_4$, filtered, and concentrated. Purification by flash column chromatography on silica gel (70% EtOAc in hexanes) gave 6-chloro-3-methylimidazo[1,2-a]pyridine-2-carbaldehyde (0.221 g, 1.14 mmol, 92% yield) as a white solid.

Step 3: (R)-5-amino-3-(5-(((6-chloro-3-methylimidazo[1,2-a]pyridin-2-yl)methyl)amino)-2-fluorophenyl)-3,6,6-trimethyl-3,6-dihydro-2H-1,4-thiazine 1,1-dioxide To a solution of (R)-tert-butyl (5-(5-amino-2-fluorophenyl)-2,2,5-trimethyl-1,1-dioxido-5,6-dihydro-2H-1,4-thiazin-3-yl)carbamate (0.102 g, 0.255 mmol) and 6-chloro-3-methylimidazo[1,2-a]pyridine-2-carbaldehyde (0.050 g, 0.26 mmol) in DCE (2 mL) at RT was added HOAc (0.015 mL, 0.26 mmol) and sodium triacetoxyborohydride (0.074 g, 0.35 mmol). The reaction mixture was stirred at RT for 25 min and TFA (2 mL) was added. The reaction mixture was stirred at RT for 15 min and then concentrated. The concentrate was diluted with EtOAc and water. The aqueous phase was extracted with EtOAc (2×). The combined organic extracts were washed with brine (1×), dried over MgSO$_4$, filtered, and concentrated. Purification by flash column chromatography on silica gel (20% to 80% EtOAc (10% 2 M NH$_3$ in MeOH) in hexanes) gave (R)-5-amino-3-(5-(((6-chloro-3-methylimidazo[1,2-a]pyridin-2-yl)methyl)amino)-2-fluorophenyl)-3,6,6-trimethyl-3,6-dihydro-2H-1,4-thiazine 1,1-dioxide (0.108 g, 0.226 mmol, 88% yield) as a white solid. LC/MS (ESI$^+$) m/z=478.0 (M+H).

Example 153

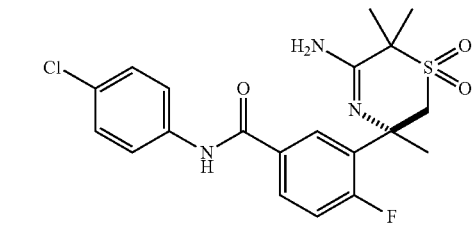

Synthesis of (R)-3-(5-amino-3,6,6-trimethyl-1,1-dioxido-3,6-dihydro-2H-1,4-thiazin-3-yl)-N-(4-chlorophenyl)-4-fluorobenzamide

Step 1: (R)-methyl 3-(5-amino-3,6,6-trimethyl-1,1-dioxido-3,6-dihydro-2H-1,4-thiazin-3-yl)-4-fluorobenzoate To a mixture of 9,9-dimethyl-4,5-bis(bis[3,5-dimethyl-4-methoxyphenyl]phosphino)xanthene (0.104 g, 0.180 mmol), palladium (II) acetate (0.020 g, 0.089 mmol), and (R)-5-amino-3-(5-bromo-2-fluorophenyl)-3,6,6-trimethyl-3,6-dihydro-2H-1,4-thiazine 1,1-dioxide (0.899 g, 2.48 mmol) was added TEA (5.00 mL, 35.9 mmol) and MeOH (1.00 mL, 24.7 mmol). The nitrogen atmosphere was replaced by carbon monoxide from a double balloon and the reaction mixture was heated at 70° C. for 24 h and then cooled to RT. The reaction mixture was diluted with EtOAc and saturated NaHCO$_3$. The aqueous phase was extracted with EtOAc (2×) and the combined organic extracts were washed with brine (1×), dried over MgSO$_4$, filtered, and concentrated. Purification by flash column chromatography on silica gel (70% to 100% EtOAc in hexanes) gave (R)-methyl 3-(5-amino-3,6,6-trimethyl-1,1-dioxido-3,6-dihydro-2H-1,4-thiazin-3-yl)-4-fluorobenzoate (0.594 g, 1.74 mmol, 70% yield) as an off white solid.

Step 2: (R)-methyl 3-(5-((tert-butoxycarbonyl)amino)-3,6,6-trimethyl-1,1-dioxido-3,6-dihydro-2H-1,4-thiazin-3-yl)-4-fluorobenzoate To a mixture of (R)-methyl 3-(5-amino-3,6,6-trimethyl-1,1-dioxido-3,6-dihydro-2H-1,4-thiazin-3-yl)-4-fluorobenzoate (0.079 g, 0.23 mmol) and di-tert-butyl dicarbonate (0.076 g, 0.35 mmol) was added dioxane (2 mL) and saturated NaHCO$_3$ (0.250 mL). The reaction mixture was stirred at RT for 3 h, heated to 40° C. for 3 h, cooled to room temperature, and diluted with DCM. The organic phase was washed with brine (1×), dried over MgSO$_4$, filtered, and concentrated to give (R)-methyl 3-(5-((tert-butoxy carbonyl)amino)-3,6,6-trimethyl-1,1-dioxido-3,6-dihydro-2H-1,4-thiazin-3-yl)-4-fluorobenzoate as a colorless oil that was used without additional purification.

Step 3: (R)-3-(5-((tert-butoxycarbonyl)amino)-3,6,6-trimethyl-1,1-dioxido-3,6-dihydro-2H-1,4-thiazin-3-yl)-4-fluorobenzoic acid To a solution of (R)-methyl 3-(5-((tert-butoxycarbonyl)amino)-3,6,6-trimethyl-1,1-dioxido-3,6-dihydro-2H-1,4-thiazin-3-yl)-4-fluorobenzoate (0.102 g, 0.231 mmol) in MeOH (2 mL) at RT was added potassium hydroxide (0.025 g, 0.45 mmol). The reaction mixture was heated to 40° C. for 15 h and LiOH (10 mg) was added. The reaction mixture was heated at 60° C. for 3 h, cooled to RT, and diluted with EtOAc and brine. The pH was adjusted to pH 5 with 5 M HCl. The aqueous phase was extracted with EtOAc (3×). The combined organic extracts were washed with brine (1×), dried over MgSO$_4$, filtered, and concentrated. Purification by flash column chromatography on silica gel (50% EtOAc (10% MeOH) in hexanes) gave (R)-3-(5-((tert-butoxycarbonyl)amino)-3,6,6-trimethyl-1,1-dioxido-3,6-dihydro-2H-1,4-thiazin-3-yl)-4-fluorobenzoic acid (0.047 g, 0.11 mmol, 48% yield) as a white solid.

Step 4: (R)-tert-butyl (5-(5-((4-chlorophenyl)carbamoyl)-2-fluorophenyl)-2,2,5-trimethyl-1,1-dioxido-5,6-dihydro-2H-1,4-thiazin-3-yl)carbamate To a mixture of (R)-3-(5-((tert-butoxycarbonyl)amino)-3,6,6-trimethyl-1,1-dioxido-3,6-dihydro-2H-1,4-thiazin-3-yl)-4-fluorobenzoic acid (0.047 g, 0.11 mmol) and 4-chloroaniline (0.057 g, 0.45 mmol) was added DMF (1 mL), TEA (0.025 mL, 0.18 mmol), and 1-[bis(dimethylamino)methylene]-1H-benzotriazolium 3-oxide hexafluorophosphate (0.048 g, 0.13 mmol). The reaction mixture was stirred at RT for 18 h and then diluted with EtOAc and water. The aqueous phase was extracted with EtOAc (1×). The combined organic extracts were washed with brine (1×), dried over MgSO$_4$, filtered, and concentrated to give (R)-tert-butyl (5-(5-((4-chlorophenyl)carbamoyl)-2-fluorophenyl)-2,2,5-trimethyl-1,1-dioxido-5,6-dihydro-2H-1,4-thiazin-3-yl)carbamate as a white solid.

Step 5: (R)-3-(5-amino-3,6,6-trimethyl-1,1-dioxido-3,6-dihydro-2H-1,4-thiazin-3-yl)-N-(4-chlorophenyl)-4-fluorobenzamide To a solution of (R)-tert-butyl (5-(5-((4-chlorophenyl)carbamoyl)-2-fluorophenyl)-2,2,5-trimethyl-1,1-dioxido-5,6-dihydro-2H-1,4-thiazin-3-yl)carbamate (0.059 g, 0.11 mmol) in DCM (2 mL) at room temperature was added trifluoroacetic acid (2.0 mL, 0.11 mmol). The reaction mixture was stirred at RT for 15 min and then concentrated. The concentrate was diluted with EtOAc, saturated NaHCO$_3$, and water. The aqueous phase was extracted with EtOAc (2×). The combined organic extracts were washed with brine (1×), dried over MgSO$_4$, filtered, and concentrated. Purification by flash column chromatography on silica gel (30% to 70% EtOAc (10% MeOH) in hexanes) followed by reverse-phase HPLC (Shimadzu; Xbridge, 50 mm×150 mm, 10 µm; eluted with 10% to 60% MeCN in water (0.1% TFA added to mobile phase) at 40 mL/min) Relevant fractions were concentrated, followed by neutralization of the TFA by partitioning between EtOAc and NaHCO$_3$ to give (R)-3-(5-amino-3,6,6-trimethyl-1,1-dioxido-3,6-dihydro-2H-1,4-thiazin-3-yl)-N-(4-chlorophenyl)-4-fluorobenzamide (0.013 g, 0.030 mmol, 27% yield) as a white solid. LC/MS (ESI$^+$) m/z=438.0 (M+H).

Example 154

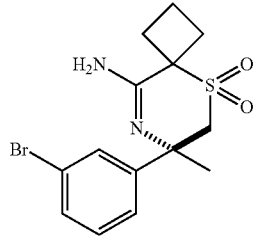

Synthesis of (R)-9-amino-7-(3-bromophenyl)-7-methyl-5-thia-8-azaspiro[3.5]non-8-ene 5,5-dioxide

Step 1: (R,E)-N-(1-(3-bromophenyl)ethylidene)-2-methylpropane-2-sulfinamide

To a solution of 3'-bromoacetophenone (2.00 mL, 15.1 mmol) in 2-methylTHF (30 mL) at room temperature was added (R)-(+)-2-methyl-2-propanesulfinamide (3.47 g, 28.6 mmol) and titanium (IV) ethoxide (8.00 mL, 38.2 mmol). The reaction mixture was heated at 70° C. for 15 h, cooled to room temperature and poured into 100 mL of brine with stirring. The mixture was filtered, and the aqueous phase of the filtrate was discarded. The organic phase was dried over MgSO$_4$, filtered, and concentrated. Purification by flash column chromatography on silica gel (5% to 30% EtOAc in hexanes) gave (R,E)-N-(1-(3-bromophenyl)ethylidene)-2-methylpropane-2-sulfinamide (4.07 g, 13.5 mmol, 89% yield) as a yellow oil.

Step 2: (R)—N—((R)-2-(3-bromophenyl)-1-((1-cyanocyclobutyl)sulfonyl)propan-2-yl)-2-methylpropane-2-sulfinamide To a solution of 1-(methylsulfonyl)cyclobutanecarbonitrile (1.04 g, 6.53 mmol) in THF (7 mL) at −78° C. was added n-butyllithium (1.6 M in hexane, 4.10 mL, 6.56 mmol). The solution was stirred at −78° C. for 15 min and a mixture of (R,E)-N-(1-(3-bromophenyl)ethylidene)-2-methylpropane-2-sulfinamide (1.32 g, 4.37 mmol) and trimethylaluminum (2 M in toluene, 2.20 mL, 4.40 mmol) (AlMe$_3$ was added 10 min before addition to nitrile solution at −78° C.) in PhMe (13 mL) precooled to −78° C., was added dropwise via cannula. The reaction mixture was stirred at −78° C. for 45 min and, quenched with saturated NH$_4$Cl, warmed to room temperature and diluted with saturated NH$_4$Cl, water, and EtOAc. The aqueous phase was discarded and the organic phase was washed with brine (1×), dried over MgSO$_4$, filtered, and concentrated. Purification by flash column chromatography on silica gel (20% to 80% EtOAc in hexanes) gave (R)—N—((R)-2-(3-bromophenyl)-1-((1-cyanocyclobutyl)sulfonyl)propan-2-yl)-2-methylpropane-2-sulfinamide (1.29 g, 2.80 mmol, 64% yield) as a white solid.

Step 3: (R)-9-amino-7-(3-bromophenyl)-7-methyl-5-thia-8-azaspiro[3.5]non-8-ene 5,5-dioxide To a solution of (R)—N—((R)-2-(3-bromophenyl)-1-((1-cyanocyclobutyl)sulfonyl)propan-2-yl)-2-methylpropane-2-sulfinamide (1.29 g, 2.80 mmol) in dioxane (28 mL) at room temperature was added hydrogen chloride (4.0 M solution in 1,4-dioxane, 3.50 mL, 14.00 mmol). The reaction mixture was heated at 100° C. for 15 h, cooled to room temperature, and concentrated. The reaction mixture was diluted with EtOAc and washed with 5 M NaOH (1×), brine (1×), dried over MgSO$_4$, filtered, and concentrated. Purification by flash column chromatography on silica gel (1% to 10% MeOH in DCM) gave (R)-9-amino-7-(3-bromophenyl)-7-methyl-5-thia-8-azaspiro[3.5]non-8-ene 5,5-dioxide (0.634 g, 1.76 mmol, 64% yield) as a white solid. LC/MS (ESI$^+$) m/z=457.0, 359.0 (M+H).

Example 155

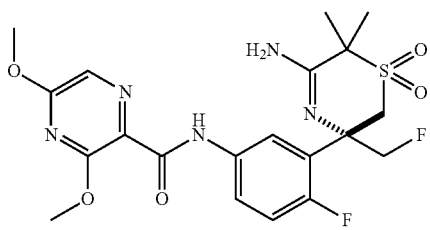

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-3,5-dimethoxypyrazine-2-carboxamide Step 1: 3,5-dichloropyrazine-2-carboxylic acid To a solution of LDA (2.0 M heptane/tetrahydrofuran/ethylbenzene, 11.10 mL, 22.20 mmol) in THF (75 mL) at −78° C. was added a solution of 2,6-dichloropyrazine (1.44 g, 9.67 mmol) in THF (20 mL) at room temperature over 20 min. The reaction mixture was stirred at −78° C. for 1.5 h and was then added via cannula to a 3-neck flask containing dry ice at −78° C. The reaction mixture was warmed from −78° C. to RT over 21 h and then quenched with 5 M HCl. The mixture was partitioned between brine and EtOAc. The aqueous phase was acidified to pH 3.5 with 5 M HCl. The aqueous phase was extracted with EtOAc (6×) and the combined organic extracts were washed with brine (1×), dried over MgSO$_4$, filtered, and concentrated. Purification by flash column chromatography on silica gel (5% to 10% MeOH in DCM) gave 3,5-dichloropyrazine-2-carboxylic acid (0.408 g, 2.11 mmol, 22% yield) as a light brown solid.

Step 2: methyl 3,5-dichloropyrazine-2-carboxylate

To a solution of 3,5-dichloropyrazine-2-carboxylic acid (0.304 g, 1.58 mmol) in MeOH (5 mL) and diethyl ether (5 mL) at RT was added (trimethylsilyl)diazomethane (2.0 M solution in hexanes, 4.00 mL, 8.00 mmol). The reaction mixture was stirred at RT for 30 min and then concentrated. Purification by flash column chromatography on silica gel (5% to 20% EtOAc in hexanes) gave methyl 3,5-dichloropyrazine-2-carboxylate (0.312 g, 1.51 mmol, 96% yield) as a white solid.

Step 3: ethyl 3,5-dimethoxypyrazine-2-carboxylate

To a solution of methyl 3,5-dichloropyrazine-2-carboxylate (0.312 g, 1.51 mmol) in THF (4.5 mL) at room temperature was added sodium hydride (60% wt. dispersion, 0.199 g, 4.98 mmol) and methanol (0.200 mL, 4.94 mmol). The reaction mixture was stirred at room temperature for 30 min, diluted with EtOAc, and quenched with saturated NH$_4$Cl. The reaction mixture was partitioned between brine and EtOAc. The aqueous phase was extracted with EtOAc (3×) and the combined organic extracts were washed with brine (1×), dried over MgSO$_4$, filtered, and concentrated. Purification by flash column chromatography on silica gel (10% to 50% EtOAc in hexanes) gave ethyl 3,5-dimethoxypyrazine-2-carboxylate (0.314 g, 1.48 mmol, 98% yield) as an off white solid.

Step 4: 3,5-dimethoxypyrazine-2-carboxylic acid

To a solution of ethyl 3,5-dimethoxypyrazine-2-carboxylate (0.314 g, 1.48 mmol) in MeOH (5 mL) at RT was added potassium hydroxide (0.135 g, 2.41 mmol). The reaction mixture was stirred at RT for 17 h, quenched with 5 M HCl (0.48 mL), and diluted with EtOAc. The solid was removed by filtration and the filtrate was concentrated. Purification by flash column chromatography on silica gel (10% MeOH in DCM) gave 3,5-dimethoxypyrazine-2-carboxylic acid (0.261 g, 1.42 mmol, 96% yield) as a white solid.

Step 5: (S)—N-(3-(5-amino-3-(fluoromethyl)-6,6-dimethyl-1,1-dioxido-3,6-dihydro-2H-1,4-thiazin-3-yl)-4-fluorophenyl)-3,5-dimethoxypyrazine-2-carboxamide In an analogous reaction to that described in Method C, 3,5-dimethoxypyrazine-2-carboxylic acid was coupled with (S)-5-amino-3-(5-amino-2-fluorophenyl)-3-(fluoromethyl)-6,6-dimethyl-3,6-dihydro-2H-1,4-thiazine 1,1-dioxide to generate the title compound (85 mg, 0.18 mmol, 52% yield) as white solid. $^1$H NMR (400 MHz, CDCl$_3$) δ 9.55 (s br, 1H), 7.95 (m, 1H), 7.75 (s, 1H), 7.68 (dd, J=7.0, 2.7 Hz, 1H), 7.06 (dd, J=11.9, 8.8 Hz, 1H), 4.90 (s br, 2H), 4.75 (dd, J=47.6, 8.6 Hz, 1H), 4.50 (dd, J=47.1, 8.8 Hz, 1H), 4.10 (s, 3H), 4.04 (s, 3H), 3.80 (d, J=15.2 Hz, 1H), 3.70 (d, J=15.4 Hz, 1H), 1.74 (s, 3H), 1.62 (s, 3H). LC/MS (ESI$^+$) m/z=484.0 (M+H).

Example 156

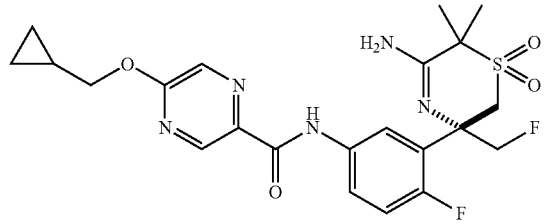

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-(cyclopropylmethoxy)pyrazine-2-carboxamide Step 1: methyl 5-(cyclopropylmethoxy)pyrazine-2-carboxylate and cyclopropylmethyl 5-(cyclopropylmethoxy)pyrazine-2-carboxylate To a suspension of sodium hydride (60% wt. dispersion, 0.562 g, 14.1 mmol) in THF (42 mL) at 0° C. was added (hydroxymethyl)cyclopropane (0.850 mL, 10.5 mmol). The solution was stirred at 0° C. for 30 min and then methyl 5-chloro-2-pyrazinecarboxylate (1.71 g, 9.91 mmol) was added as a solid in one portion. The reaction mixture was stirred at 0° C. for 30 min and then quenched with saturated NH₄Cl. The reaction mixture was partitioned between water and EtOAc. The aqueous phase was extracted with EtOAc (2×) and the combined organic extracts were washed with brine (1×), dried over MgSO₄, filtered, and concentrated to give a 1:1 mixture of methyl 5-(cyclopropylmethoxy)pyrazine-2-carboxylate and cyclopropylmethyl 5-(cyclopropylmethoxy)pyrazine-2-carboxylate which was used in the next step without further purification.

Step 2:
5-(cyclopropylmethoxy)pyrazine-2-carboxylic acid

To a solution of methyl 5-(cyclopropylmethoxy)pyrazine-2-carboxylate and cyclopropylmethyl 5-(cyclopropylmethoxy)pyrazine-2-carboxylate (prepared in the previous step) in THF (15 mL) and water (15 mL). The reaction mixture was stirred at room temperature for 30 min and acidified to pH 5 with 1 M HCl. The reaction mixture was partitioned between water and EtOAc. The aqueous phase was extracted with EtOAc (2×) and the combined organic extracts were washed with brine (1×), dried over MgSO₄, filtered, and concentrated. Purification by flash column chromatography on silica gel (10% MeOH in DCM) gave 5-(cyclopropylmethoxy)pyrazine-2-carboxylic acid (0.489 g, 2.52 mmol, 25% yield) as an off white solid.

Step 3: (S)—N-(3-(5-amino-3-(fluoromethyl)-6,6-dimethyl-1,1-dioxido-3,6-dihydro-2H-1,4-thiazin-3-yl)-4-fluorophenyl)-5-(cyclopropylmethoxy)pyrazine-2-carboxamide In an analogous reaction to that described in Method C, 5-(cyclopropylmethoxy)pyrazine-2-carboxylic acid was coupled with (S)-5-amino-3-(5-amino-2-fluorophenyl)-3-(fluoromethyl)-6,6-dimethyl-3,6-dihydro-2H-1,4-thiazine 1,1-dioxide to generate the title compound (84 mg, 0.17 mmol, 46% yield) as white solid. LC/MS (ESI⁺) m/z=494.0 (M+H).

Example 157

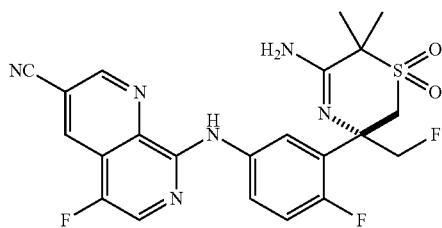

Synthesis of (S)-8-((3-(5-amino-3-(fluoromethyl)-6,6-dimethyl-1,1-dioxido-3,6-dihydro-2H-1,4-thiazin-3-yl)-4-fluorophenyl)amino)-5-fluoro-1,7-naphthyridine-3-carbonitrile To a mixture of 8-chloro-5-fluoro-1,7-naphthyridine-3-carbonitrile (0.061 g, 0.29 mmol) and (S)-5-amino-3-(5-amino-2-fluorophenyl)-3-(fluoromethyl)-6,6-dimethyl-3,6-dihydro-2H-1,4-thiazine 1,1-dioxide (0.075 g, 0.24 mmol) was added a solution of sulfuric acid (0.013 mL, 0.47 mmol) in i-PrOH (1 mL). The reaction mixture was heated at 85° C. for 24 h and then cooled to room temperature. The reaction mixture was partitioned between saturated NaHCO₃ and EtOAc. The aqueous phase was discarded and the organic phase was washed with brine (1×), dried over MgSO₄, filtered, and concentrated. Purification by flash column chromatography on silica gel (70% EtOAc in hexanes) gave (S)-8-((3-(5-amino-3-(fluoromethyl)-6,6-dimethyl-1,1-dioxido-3,6-dihydro-2H-1,4-thiazin-3-yl)-4-fluorophenyl)amino)-5-fluoro-1,7-naphthyridine-3-carbonitrile (0.105 g, 0.215 mmol, 91% yield) as a yellow solid. ¹H NMR (400 MHz, CDCl₃) δ 8.96 (d, J=2.0 Hz, 1H), 8.81 (s br, 1H), 8.64 (d, J=2.0 Hz, 1H), 8.21-8.16 (m, 1H), 8.09 (d, J=1.0 Hz, 1H), 7.73 (dd, J=6.9, 2.7 Hz, 1H), 7.11 (dd, J=11.8, 8.9 Hz, 1H), 4.81 (dd, J=47.3, 7.4 Hz, 1H), 4.80 (s br 2H), 4.52 (dd, J=46.8, 8.6 Hz, 1H), 3.84 (d, J=15.1 Hz, 1H), 3.75 (d, J=15.3 Hz, 1H), 1.77 (s, 3H), 1.65 (s, 3H). LC/MS (ESI⁺) m/z=489.0 (M+H).

Example 158

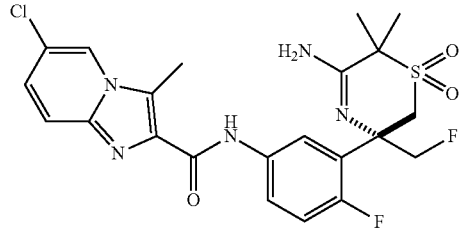

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-6-chloro-3-methylimidazo[1,2-a]pyridine-2-carboxamide In an analogous reaction to that described in Method C, 6-chloro-3-methylimidazo[1,2-a]pyridine-2-carboxylic acid was coupled with (S)-5-amino-3-(5-amino-2-fluorophenyl)-3-(fluoromethyl)-6,6-dimethyl-3,6-dihydro-2H-1,4-thiazine 1,1-dioxide to generate the title compound (37 mg, 0.073 mmol, 21% yield) as white solid. ¹H NMR (400 MHz, CDCl₃) δ 9.32 (s br, 1H), 8.02-7.97 (m, 1H), 7.96 (d, J=1.0 Hz, 1H), 7.67 (dd, J=7.0, 2.7 Hz, 1H), 7.48 (dd, J=9.6, 0.8 Hz, 1H), 7.22 (dd, J=9.6, 2.0 Hz, 1H), 7.08 (dd, J=11.8, 8.9 Hz, 1H), 4.93 (s br, 2H), 4.76 (dd, J=47.7, 8.0 Hz, 1H), 4.58 (dd, J=47.1, 8.8 Hz, 1H), 3.81 (d, J=15.3 Hz, 1H), 3.70 (d, J=15.3 Hz, 1H), 2.81 (s, 3H), 1.74 (s, 3H), 1.63 (s, 3H). LC/MS (ESI⁺) m/z=510.0 (M+H).

Example 159

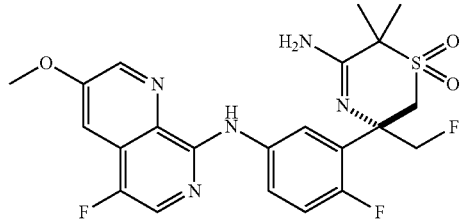

Synthesis of (S)-5-amino-3-(2-fluoro-5-((5-fluoro-3-methoxy-1,7-naphthyridin-8-yl)amino)phenyl)-3-(fluoromethyl)-6,6-dimethyl-3,6-dihydro-2H-1,4-thiazine 1,1-dioxide To a mixture of 8-chloro-5-fluoro-3-methoxy-1,7-naphthyridine (0.102 g, 0.480 mmol) and (S)-5-amino-3-(5-amino-2-fluorophenyl)-3-(fluoromethyl)-6,6-dimethyl-3,6-dihydro-2H-1,4-thiazine 1,1-dioxide (0.150 g, 0.473 mmol) was added a solution of sulfuric acid (0.025 mL, 0.47 mmol) in i-PrOH (2.35 mL). The reaction mixture was heated at 80° C. for 25 h and then cooled to room temperature. The reaction mixture was diluted with EtOAc (3 mL). The solid precipitate was collected by filtration, washed with EtOAc (1×) and partitioned between saturated NaHCO₃ and EtOAc. The aqueous phase was discarded and the organic phase was washed with brine (1×), dried over MgSO₄, filtered, concentrated, and dried under high vacuum to give (S)-5-amino-3-(2-fluoro-5-((5-fluoro-3-methoxy-1,7-naphthyridin-8-yl)amino)phenyl)-3-(fluoromethyl)-6,6-dimethyl-3,6-dihydro-2H-1,4-thiazine 1,1-dioxide (0.184 g, 0.373 mmol, 79% yield) as a pale yellow solid. ¹H NMR (400 MHz, CDCl₃) δ 8.71 (s br, 1H), 8.51 (d, J=2.7 Hz, 1H), 8.23-8.17 (m, 1H), 7.93 (d, J=1.6 Hz, 1H), 7.71 (dd, J=6.9, 2.7 Hz, 1H), 7.45 (d, J=2.7 Hz, 1H), 7.08 (dd, J=11.9, 9.0 Hz, 1H), 4.81 (s br, 2H), 4.80 (dd, J=47.1, 8.4 Hz, 1H), 4.54 (dd, J=47.0, 8.7 Hz, 1H), 4.00 (s, 3H), 3.83 (d, J=15.5 Hz, 1H), 3.73 (d, J=15.3 Hz, 1H), 1.76 (s, 3H), 1.64 (s, 3H). LC/MS (ESI⁺) m/z=494.0 (M+H).

Example 160

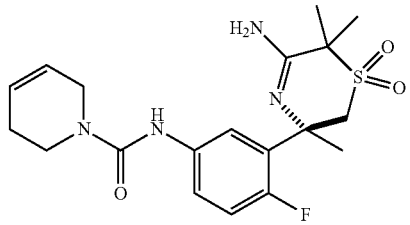

Synthesis of (R)—N-(3-(5-amino-3,6,6-trimethyl-1,1-dioxido-3,6-dihydro-2H-1,4-thiazin-3-yl)-4-fluorophenyl)-5,6-dihydropyridine-1(2H)-carboxamide To a solution of (R)-tert-butyl (5-(5-amino-2-fluorophenyl)-2,2,5-trimethyl-1,1-dioxido-5,6-dihydro-2H-1,4-thiazin-3-yl)carbamate (0.055 g, 0.138 mmol) in DCM (1 mL) was added 4-nitrophenyl chloroformate (0.028 g, 0.138 mmol) as a solid. 1,2,3,6-Tetrahydropyridine (22 mg) was added to the reaction and stirring was continued overnight. To the reaction was added trifluoroacetic acid (0.200 mL, 2.60 mmol). The reaction was evaporated to dryness and the residue was dissolved in MeCN and purified by reverse-phase HPLC (Gilson; Gemini-NX 10 m C18 110A AXIA, 100×50 mm column) eluting with 0.1% TFA-H₂O:0.1% TFA CH₃CN (9:1→1:9). The fractions containing the desired product were combined and concentrated in vacuo. The residue was dissolved in MeOH and loaded onto an Si-propylsulfonic acid (Silicycle) cartridge eluting with MeOH then 2M NH₃ in MeOH to give 28 mg (50%) of a light-yellow crystalline solid. MS m/z=409.0 (M+1).

Example 161

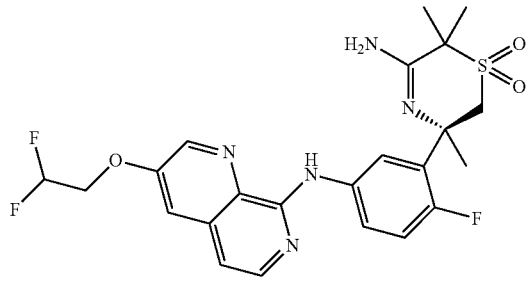 [SMILES: CC1(C)C(N)=N[C@](C)(c2cc(Nc3nccc4cc(OCC(F)F)cnc34)ccc2F)CS1(=O)=O]

Step 1: (R)-5-amino-3-(2-fluoro-5-((3-methoxy-1,7-naphthyridin-8-yl)amino)phenyl)-3,6,6-trimethyl-3,6-dihydro-2H-1,4-thiazine 1,1-dioxide Following the general S$_N$Ar procedure using 8-chloro-3-methoxy-1,7-naphthyridine (2.44 g, 12.52 mmol), (R)-tert-butyl (5-(5-amino-2-fluorophenyl)-2,2,5-trimethyl-1,1-dioxido-5,6-dihydro-2H-1,4-thiazin-3-yl)carbamate (5.00 g, 12.52 mmol), 50 mL iPrOH, and sulfuric acid (0.67 mL, 12.52 mmol), the title compound was isolated as a light yellow solid (4.38 g, 9.57 mmol, 76% yield).

Step 2: (R)-5-amino-3-(2-fluoro-5-((3-hydroxy-1,7-naphthyridin-8-yl)amino)phenyl)-3,6,6-trimethyl-3,6-dihydro-2H-1,4-thiazine 1,1-dioxide A pressure bottle was charged with (R)-5-amino-3-(2-fluoro-5-((3-methoxy-1,7-naphthyridin-8-yl)amino)phenyl)-3,6,6-trimethyl-3,6-dihydro-2H-1,4-thiazine 1,1-dioxide (4.38 g, 9.57 mmol) and DCM (19.15 ml) and was flushed with argon. BBr₃ (1 M in DCM, 19.15 ml, 19.15 mmol) was added, the bottle was sealed, and the reaction was heated at 50° C. for 5 days. The mixture was quenched slowly with saturated NaHCO₃ until basic. Water and EtOAc were added, and the solids were filtered and washed with EtOAc. The aqueous portion was brought to neutral pH with dilute HCl and was extracted with EtOAc/2% iPrOH. The layers were separated and the combined organic portions were dried, filtered and concentrated. The title compound was isolated as a light yellow solid. (1.2 g, 2.71 mmol, 28.3% yield).

Step 3: (R)-5-amino-3-(5-((3-(2,2-difluoroethoxy)-1,7-naphthyridin-8-yl)amino)-2-fluorophenyl)-3,6,6-trimethyl-3,6-dihydro-2H-1,4-thiazine 1,1-dioxide A vial was charged with (R)-5-amino-3-(2-fluoro-5-((3-hydroxy-1,7-naphthyridin-8-yl)amino)phenyl)-3,6,6-trimethyl-3,6-dihydro-2H-1,4-thiazine 1,1-dioxide (125 mg, 0.282 mmol), cesium carbonate (101 mg, 0.310 mmol) and DMSO (1127 μl). 2-bromo-1,1-difluoroethane (23.57 μl, 0.296 mmol) was added, and the mixture was heated at 60° C. for 6 h. Water and EtOAc were added, and the layers were separated. The organic portion was dried with Na₂SO₄, filtered and concentrated. The crude material was purified by silica gel chromatography, 10-70% 75/25 EtOAc/EtOH/2% NH₄OH in heptane to provide the title compound (91 mg, 0.179 mmol, 63.6% yield) as a pale yellow solid. MS m/z=508.2 (M+1).

Example 162

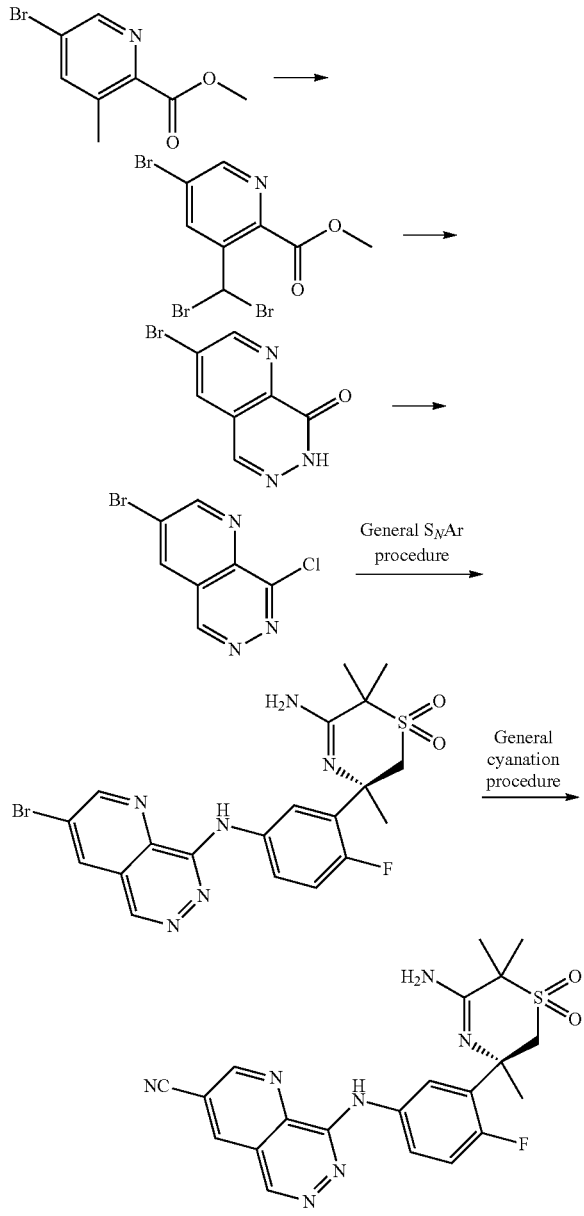

Step 1: Methyl 5-bromo-3-(dibromomethyl)picolinate

A vial was charged with methyl 5-bromo-3-methylpicolinate (2.03 g, 8.82 mmol), carbon tetrachloride (22.06 ml), benzoyl peroxide (0.107 g, 0.441 mmol) and NBS (3.14 g, 17.65 mmol). The mixture was heated at 80° C. for 2 h. Another equivalent of NBS and 50 mg benzoyl peroxide were added, and heating was continued for 16 h. Upon cooling to RT the mixture was filtered through Celite and washed with DCM. The filtrate was concentrated, and the crude material was purified by silica gel, 10-50% EtOAc/heptane to provide the title compound as a yellow oil (3.28 g, 8.46 mmol, 96% yield).

Step 2: 3-Bromopyrido[2,3-d]pyridazin-8(7H)-one

A pressure bottle was charged with methyl 5-bromo-3-(dibromomethyl)picolinate (3.28 g, 8.46 mmol), ethanol (16.91 ml) and hydrazine hydrate (4.19 ml, 85 mmol). The bottle was sealed, and the mixture was heated at 80° C. for 1.5 h. The mixture was heterogeneous upon cooling, so the solids were filtered, washed with MeOH and dried. The filtrate was concentrated and was triturated in MeOH. The solids were filtered, rinsed with MeOH and dried to give a second crop of product. The title compound (1.72 g, 7.61 mmol, 90% yield) was isolated as a yellow solid.

Step 3: 3-bromo-8-chloropyrido[2,3-d]pyridazine

A vial was charged with 3-bromopyrido[2,3-d]pyridazin-8(7H)-one (500 mg, 2.212 mmol) and phosphorus oxychloride (4124 µl, 44.2 mmol). The vial was capped and the mixture was heated at 90° C. for 2 h. The mixture was concentrated and was used without further purification. MS m/z=241 (M+MeOH adduct).

Step 4: (R)-5-amino-3-(5-((3-bromopyrido[2,3-d]pyridazin-8-yl)amino)-2-fluorophenyl)-3,6,6-trimethyl-3,6-dihydro-2H-1,4-thiazine 1,1-dioxide Following the general $S_NAr$ procedure using 3-bromo-8-chloropyrido[2,3-d]pyridazine (500 mg, 2.05 mmol), (R)-tert-butyl (5-(5-amino-2-fluorophenyl)-2,2,5-trimethyl-1,1-dioxido-5,6-dihydro-2H-1,4-thiazin-3-yl)carbamate (817 mg, 2.05 mmol), 5 mL iPrOH, and sulfuric acid (0.11 mL, 2.05 mmol), the title compound was isolated as a tan solid (500 mg, 0.985 mmol, 48.2% yield).

Step 5: (R)-8-((3-(5-amino-3,6,6-trimethyl-1,1-dioxido-3,6-dihydro-2H-1,4-thiazin-3-yl)-4-fluorophenyl)amino)pyrido[2,3-d]pyridazine-3-carbonitrile Following the general cyanation procedure using (R)-5-amino-3-(5-((3-bromopyrido[2,3-d]pyridazin-8-yl)amino)-2-fluorophenyl)-3,6,6-trimethyl-3,6-dihydro-2H-1,4-thiazine 1,1-dioxide (125 mg, 0.25 mmol), ZnCN$_2$ (44 mg, 0.37 mmol), S-Phos (20 mg, 0.049 mmol), Pd$_2$dba$_3$ (18 mg, 0.020 mmol), and 0.985 mL DMF, the title compound was isolated as a yellow solid (12 mg, 0.026 mmol, 10.74% yield).

Step 6: LS Method 3 (General $S_NAr$ with AcOH)

(3R,6R)-5-amino-6-fluoro-3-(2-fluoro-5-((2-(trifluoromethyl)pyrido[3,4-b]pyrazin-5-yl)amino)phenyl)-3,6-dimethyl-3,6-dihydro-2H-1,4-thiazine 1,1-dioxide A vial was charged with 5-chloro-2-(trifluoromethyl)pyrido[3,4-b]pyrazine (48.6 mg, 0.208 mmol), tert-butyl ((2R,5R)-5-(5-amino-2-fluorophenyl)-2-fluoro-2,5-dimethyl-1,1-dioxido-5,6-dihydro-2H-1,4-thiazin-3-yl)carbamate (84 mg, 0.208 mmol), and acetic acid (833 µl, 0.208 mmol). The mixture was stirred at 80° C. for 30 min. The mixture was diluted with EtOAc and washed twice with saturated NaHCO$_3$. The organic portion was dried with Na$_2$SO$_4$, filtered and concentrated. The crude material was purified by silica gel chromatography, 0-50% 75/25/2 EtOAc/EtOH/2% NH$_4$OH in heptane to provide the title compound as an orange solid (50 mg, 0.100 mmol, 48.0% yield). MS m/z=501 (MH+)

Example 163

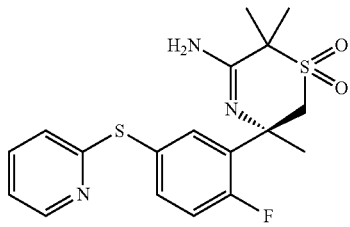 [SMILES: CC1(C)C(N)=N[C@](C)(c2cc(Sc3ccccn3)ccc2F)CS1(=O)=O]

Synthesis of ((R)-5-amino-3-(2-fluoro-5-(pyridin-2-ylthio)phenyl)-3,6,6-trimethyl-3,6-dihydro-2H-1,4-thiazine 1,1-dioxide A sealed tube containing (R)-5-amino-3-(2-fluoro-5-mercaptophenyl)-3,6,6-trimethyl-3,6-dihydro-2H-1,4-thiazine 1,1-dioxide (60 mg, 0.190 mmol), water (0.38 mL) and 2-fluoropyridine (0.016 mL, 0.190 mmol), was stirred at 100° C. for 17 hours. The reaction mixture was diluted with ethyl acetate, washed once with water, once with sodium chloride, dried with sodium sulfate, filtered through a fritted funnel and concentrated. The residue was purified by silica gel chromatography, eluent gradient 25-100% CH2Cl2:MeOH (90:10)/CH2Cl2, to yield (R)-5-amino-3-(2-fluoro-5-(pyridin-2-ylthio)phenyl)-3,6,6-trimethyl-3,6-dihydro-2H-1,4-thiazine 1,1-dioxide (10 mg, 0.025 mmol) as a light yellow solid. LC/MS (ESI$^+$) m/z=394.1 (M+H).

Example 164

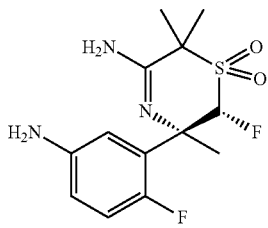 [SMILES: CC1(C)C(N)=N[C@](C)(c2cc(N)ccc2F)[C@@H](F)S1(=O)=O]

Synthesis of (2S,3R)-5-amino-3-(5-amino-2-fluorophenyl)-2-fluoro-3,6,6-trimethyl-3,6-dihydro-2H-1,4-thiazine 1,1-dioxide

Step 1: tert-butyl ((5R,6S)-5-(5-bromo-2-fluorophenyl)-6-fluoro-2,2,5-trimethyl-1,1-dioxido-5,6-dihydro-2H-1,4-thiazin-3-yl)carbamate To potassium t-butoxide (1M in THF) (3.02 ml, 3.02 mmol) in THF (5 ml) at −78° C. was added diisopropylamine (0.431 ml, 3.02 mmol) and the solution was stirred for 15 minutes. Butyllithium (2.7 M in heptane) (0.957 ml, 2.70 mmol) was added and the solution was stirred for 30 min, then (R)-tert-butyl (5-(5-bromo-2-fluorophenyl)-2,2,5-trimethyl-1,1-dioxido-5,6-dihydro-2H-1,4-thiazin-3-yl)carbamate (0.5 g, 1.079 mmol) in 5 ml THF was added dropwise and the solution was stirred at −78° C. for 45 minutes. N-fluoro-N-(phenylsulfonyl)benzenesulfonamide (0.953 g, 3.02 mmol) dissolved in 10 ml of THF was added. The solution was stirred at −78° C. for 15 minutes and allowed to slowly warm to 0° C. and quenched with saturated sodium carbonate. The solution was extracted with ethyl acetate and the extracts were concentrated. The product was purified by silica gel column chromatography (loaded in 50/50 DCM/heptane) eluent 0-20% MTBE in heptane to afford tert-butyl ((5R,6S)-5-(5-bromo-2-fluorophenyl)-6-fluoro-2,2,5-trimethyl-1,1-dioxido-5,6-dihydro-2H-1,4-thiazin-3-yl)carbamate (300 mg, 0.623 mmol, 57.8% yield). MS m/z=503.0 [M+Na]

Step 2: tert-butyl ((5R,6S)-5-(5-azido-2-fluorophenyl)-6-fluoro-2,2,5-trimethyl-1,1-dioxido-5,6-dihydro-2H-1,4-thiazin-3-yl)carbamate A flask was charged with copper(I) iodide (0.158 g, 0.831 mmol), sodium azide (1.080 g, 16.62 mmol), (+)-sodium 1-ascorbate (0.165 g, 0.831 mmol) and tert-butyl ((5R,6S)-5-(5-bromo-2-fluorophenyl)-6-fluoro-2,2,5-trimethyl-1,1-dioxido-5,6-dihydro-2H-1,4-thiazin-3-yl)carbamate (1 g, 2.077 mmol). Trans-N,N'-dimethylcyclohexane-1,2-diamine (0.262 ml, 1.662 mmol), ethanol (7 ml) and water (3 ml) were added, the flask was flushed with nitrogen, capped, and heated at 50° C. for 45 minutes. The reaction mixture was diluted with water and ethyl acetate. The organic layer was collected, dried over sodium sulfate and concentrated to yield tert-butyl ((5R,6S)-5-(5-azido-2-fluorophenyl)-6-fluoro-2,2,5-trimethyl-1,1-dioxido-5,6-dihydro-2H-1,4-thiazin-3-yl)carbamate (0.921 g, 2.077 mmol) as a yellow oil.

Step 3: tert-butyl ((5R,6S)-5-(5-amino-2-fluorophenyl)-6-fluoro-2,2,5-trimethyl-1,1-dioxido-5,6-dihydro-2H-1,4-thiazin-3-yl)carbamate To a solution of tert-butyl ((5R,6S)-5-(5-azido-2-fluorophenyl)-6-fluoro-2,2,5-trimethyl-1,1-dioxido-5,6-dihydro-2H-1,4-thiazin-3-yl)carbamate (0.921 g, 2.077 mmol) in THF (13.91 ml) and water (5 ml) was added trimethylphosphine (1M solution in THF, 2.284 ml, 2.284 mmol), and the reaction was stirred at room temperature for 15 minutes. The reaction was partitioned between water and DCM. The organic layer was concentrated, and the product was purified via silica gel column chromatography (RediSep 40 g column) using 10-50% ethyl acetate in heptane to afford tert-butyl ((5R,6S)-5-(5-amino-2-fluorophenyl)-6-fluoro-2,2,5-trimethyl-1,1-dioxido-5,6-dihydro-2H-1,4-thiazin-3-yl)carbamate (360 mg, 0.862 mmol, 41.5% yield). MS m/z=441 [M+Na].

Step 4: (2S,3R)-5-amino-3-(5-amino-2-fluorophenyl)-2-fluoro-3,6,6-trimethyl-3,6-dihydro-2H-1,4-thiazine 1,1-dioxide Tert-butyl ((5R,6S)-5-(5-amino-2-fluorophenyl)-6-fluoro-2,2,5-trimethyl-1,1-dioxido-5,6-dihydro-2H-1,4-thiazin-3-yl)carbamate (100 mg, 0.240 mmol) was dissolved in 3 ml of DCM and 2 ml of TFA was added. The solution was stirred for one hour at room temperature, then solvent stripped at reduced pressure. The residue was taken up in DCM and was washed with sodium bicarbonate and concentrated. The product was purified via silica gel column chromatography (RediSep 40 g column) using 0 to 100% 90/10 ethyl acetate/MeOH in ethyl acetate to afford (2S, 3R)-5-amino-3-(5-amino-2-fluorophenyl)-2-fluoro-3,6,6-trimethyl-3,6-dihydro-2H-1,4-thiazine 1,1-dioxide (60 mg, 79%). MS m/z=318.2 [M+H].

Intermediate 21

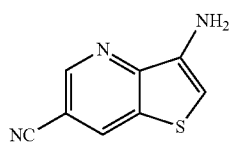 [SMILES: N#Cc1cnc2c(N)csc2c1]

Synthesis of 3-aminothieno[3,2-b]pyridine-6-carbonitrile

Step 1: Sodium (E)-2-cyano-3,3-dimethoxyprop-1-en-1-olate

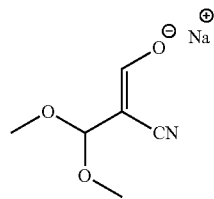

To a suspension of sodium hydride (2.52 g, 63.0 mmol) in ether (75 ml) was added 3,3-dimethoxypropanenitrile (6.17 ml, 55.0 mmol) followed by methyl formate (6.74 ml, 110 mmol). The solution was allowed to stir for 3 days at room temperature. The solid was filtered, washed with ether, and dried under vacuum to afford sodium (E)-2-cyano-3,3-dimethoxyprop-1-en-1-olate (4.2 g, 25.4 mmol, 46.3% yield).

Step 2: 3-Aminothieno[3,2-b]pyridine-6-carbonitrile

Sodium (E)-2-cyano-3,3-dimethoxyprop-1-en-1-olate (1.7 g, 10.27 mmol) was dissolved in 20 ml of MeOH and concentrated hydrochloric acid (844 µl, 10.27 mmol) was added. The solution was stirred for 5 minutes then thiophene-3,4-diamine (1173 mg, 10.27 mmol) in 20 ml MeOH was added. The solution was heated at reflux for 2 hours. Additional concentrated HCl (3 ml) was added in 5 ml MeOH and the solution was refluxed for another hour. The rxn was quenched with 10 ml of TEA and the solution was stirred for 15 minutes then concentrated. Ethyl acetate was added and the mixture was sonicated and stirred. The solid triethylamine hydrochloride was filtered off and washed with ethyl acetate. The filtrates were concentrated. The product was purified via silica gel column chromatography (RediSep 40 g column) using 0-100% ethyl acetate in heptane to afford 3-aminothieno[3,2-b]pyridine-6-carbonitrile (400 mg, 2.283 mmol, 22.22% yield). MS m/z=176.0 [M+H].

Example 165

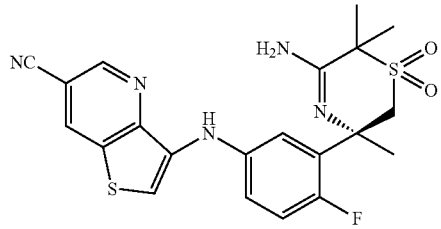 [SMILES: CC1(C)C(N)=N[C@](C)(c2cc(Nc3csc4cc(C#N)cnc34)ccc2F)CS1(=O)=O]

(R)-3-((3-(5-amino-3,6,6-trimethyl-1,1-dioxido-3,6-dihydro-2H-1,4-thiazin-3-yl)-4-fluorophenyl)amino) thieno[3,2-b]pyridine-6-carbonitrile A microwave vial was charged with (R)-5-amino-3-(5-bromo-2-fluorophenyl)-3,6,6-trimethyl-3,6-dihydro-2H-1, 4-thiazine 1,1-dioxide (125 mg, 0.344 mmol), 3-aminothieno[3,2-b]pyridine-6-carbonitrile (125 mg), tert-butyl XPhos (43.9 mg, 0.103 mmol), sodium tert-butoxide (93 mg, 0.964 mmol), Pd$_2$dba$_3$ (31.5 mg, 0.034 mmol), and toluene (2 ml). The vessel was purged with argon and microwaved at 100° C. for 1.5 hours. The mixture was diluted with water and extracted with ethyl acetate. The organic extracts were concentrated and the residue was purified by silica gel column chromatography (RediSep 40 g column), eluent gradient 20-100% ethyl acetate in heptane to afford (R)-3-((3-(5-amino-3,6,6-trimethyl-1,1-dioxido-3, 6-dihydro-2H-1,4-thiazin-3-yl)-4-fluorophenyl)amino) thieno[3,2-b]pyridine-6-carbonitrile (50 mg, 0.109 mmol, 31.8% yield). MS m/z=458.0 [M+H].

Example 166

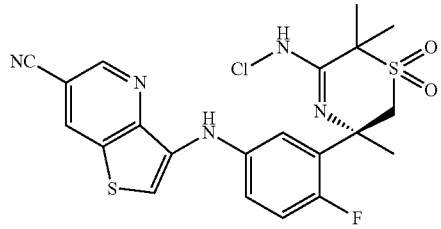 [SMILES: CC1(C)C(NCl)=N[C@](C)(c2cc(Nc3csc4cc(C#N)cnc34)ccc2F)CS1(=O)=O]

(R)-3-((3-(5-(chloroamino)-3,6,6-trimethyl-1,1-dioxido-3,6-dihydro-2H-1,4-thiazin-3-yl)-4-fluorophenyl)amino)thieno[3,2-b]pyridine-6-carbonitrile (R)-3-((3-(5-amino-3,6,6-trimethyl-1,1-dioxido-3,6-dihydro-2H-1,4-thiazin-3-yl)-4-fluorophenyl)amino)thieno[3, 2-b]pyridine-6-carbonitrile (26 mg, 0.057 mmol) was dissolved in DMF (2 ml) and NCS (7.6 mg, 0.057 mmol) was added. The solution was stirred for 30 minutes, quenched with saturated sodium bicarbonate, and extracted with ethyl acetate. The organics were washed with water, dried with sodium sulfate, filtered and concentrated to afford (R)-3-((3-(5-(chloroamino)-3,6,6-trimethyl-1,1-dioxido-3,6-dihydro-2H-1,4-thiazin-3-yl)-4-fluorophenyl)amino)thieno[3,2-b] pyridine-6-carbonitrile (20 mg, 0.041 mmol, 71.5% yield). MS m/z=492.0 [M+H].

Example 167

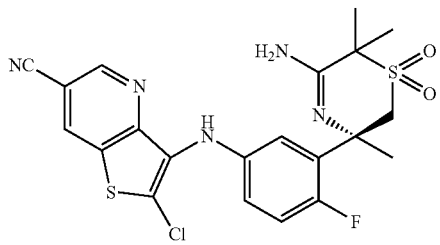 [SMILES: CC1(C)C(N)=N[C@](C)(c2cc(Nc3c(Cl)sc4cc(C#N)cnc34)ccc2F)CS1(=O)=O]

(R)-3-((3-(5-amino-3,6,6-trimethyl-1,1-dioxido-3,6-dihydro-2H-1,4-thiazin-3-yl)-4-fluorophenyl)amino)-2-chlorothieno[3,2-b]pyridine-6-carbonitrile (R)-3-((3-(5-(chloroamino)-3,6,6-trimethyl-1,1-dioxido-3,6-dihydro-2H-1,4-thiazin-3-yl)-4-fluorophenyl)amino)thieno[3,2-b]pyridine-6-carbonitrile (15 mg, 0.030 mmol) was dissolved in acetic acid (2.5 ml) and the solution was stirred at room temperature overnight. The solution was then heated at 50° C. for 24 hours. The solution was concentrated, dissolved in DCM, washed with saturated sodium bicarbonate, water, then dried with sodium sulfate, filtered, and concentrated to afford (R)-3-((3-(5-amino-3,6,6-trimethyl-1,1-dioxido-3,6-dihydro-2H-1,4-thiazin-3-yl)-4-fluorophenyl)amino)-2-chlorothieno[3,2-b]pyridine-6-carbonitrile (14 mg). MS m/z=492 [M+H].

Example 168

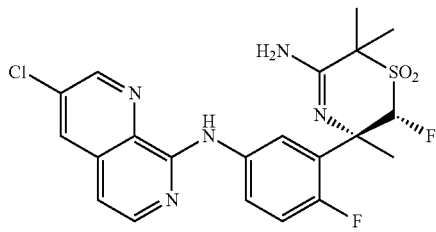 [SMILES: CC1(C)C(N)=N[C@](C)(c2cc(Nc3nccc4cc(Cl)cnc34)ccc2F)[C@@H](F)S1(=O)=O]

(2S,3R)-5-amino-3-(5-((3-chloro-1,7-naphthyridin-8-yl)amino)-2-fluorophenyl)-2-fluoro-3,6,6-trimethyl-3,6-dihydro-2H-1,4-thiazine 1,1-dioxide Tert-butyl ((5R,6S)-5-(5-amino-2-fluorophenyl)-6-fluoro-2,2,5-trimethyl-1,1-dioxido-5,6-dihydro-2H-1,4-thiazin-3-yl)carbamate (3.6 g, 8.62 mmol) and TFA (10 ml, 130 mmol) were combined in 50 ml of DCM and stirred for 30 minutes. The solution was concentrated and dried under vacuum for 30 minutes. 3,8-dichloro-1,7-naphthyridine (1.888 g, 9.49 mmol) and IPA (60 ml) were added and the solution was heated at 80° C. for 1.5 hours. The solution was quenched with 200 ml of saturated sodium bicarbonate and 100 ml of water, extracted once with 250 ml ethyl acetate, and the organic layer was separated and concentrated. The product was purified via silica gel column chromatography (RediSep 120 g column) using 20-100% ethyl acetate/MeOH/NH4OH 90/10/1 in heptane to afford (2S,3R)-5-amino-3-(5-((3-chloro-1,7-naphthyridin-8-yl)amino)-2-fluorophenyl)-2-fluoro-3,6,6-trimethyl-3,6-dihydro-2H-1,4-thiazine 1,1-dioxide (3.3 g, 6.88 mmol, 80% yield). MS m/z=480 [M+H].

Example 169

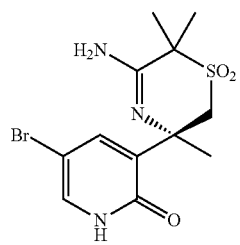 [SMILES: CC1(C)C(N)=N[C@](C)(c2cc(Br)c[nH]c2=O)CS1(=O)=O]

Synthesis of (R)-3-(5-amino-3,6,6-trimethyl-1,1-dioxido-3,6-dihydro-2H-1,4-thiazin-3-yl)-5-bromopyridin-2(1H)-one A microwave vial was charged with (R)-5-amino-3-(5-bromo-2-fluoropyridin-3-yl)-3,6,6-trimethyl-3,6-dihydro-2H-1,4-thiazine 1,1-dioxide (0.500 g, 1.373 mmol) (see example 14 for preparation), hydrogen chloride, 4.0M in dioxane (2.5 ml, 10.00 mmol) and water (1.0 mL). The vial was sealed and heated at 100° C. for 22 hrs. The reaction mixture was concentrated and the residue was neutralized with saturated NaHCO₃ to pH 6-7, then extracted with EtOAc (2×). The organic layers were combined, washed with brine, dried over Na₂SO₄ and filtered. The filtrate was concentrated and purified by silica gel chromatography, eluent gradient (0-10% MeOH/DCM) to afford the title compound (338 mg) as yellow solid. LC/MS (ESI⁺) m/z=362, 364 (M+H; 2 bromine isotopes).

Example 170

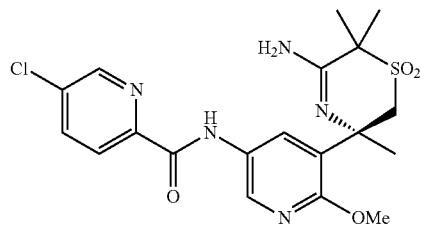 [SMILES: COc1ncc(NC(=O)c2ccc(Cl)cn2)cc1[C@]1(C)CS(=O)(=O)C(C)(C)C(N)=N1]

Synthesis of (R)—N-(5-(5-amino-3,6,6-trimethyl-1,1-dioxido-3,6-dihydro-2H-1,4-thiazin-3-yl)-6-methoxypyridin-3-yl)-5-chloropicolinamide Step 1: (R)-5-amino-3-(5-bromo-2-methoxypyridin-3-yl)-3,6,6-trimethyl-3,6-dihydro-2H-1,4-thiazine 1,1-dioxide (R)-5-amino-3-(5-bromo-2-fluoropyridin-3-yl)-3,6,6-trimethyl-3,6-dihydro-2H-1,4-thiazine 1,1-dioxide (0.586 g, 0.280 mmol) (see example 14 for preparation) was treated with sodium methylate (7.5 ml, 25% wt in MeOH). The mixture was heated at reflux for 45 min. LCMS indicated conversion was completed. The reaction mixture was allowed to cool to RT and quenched with water. The resulted solution was concentrated under reduced pressure to remove MeOH. The aqueous residue was extracted with EtOAc. The organic extracts were washed with brine, dried over Na2SO4 and filtered. The filtrate was concentrated and purified by silica gel column (0-5% MeOH/DCM) to afford the title compound (518 mg) as light brown foam. LC/MS (ESI$^+$) m/z=376, 378 (M+H; 2 bromine isotopes).

Step 2: (R)—N-(5-(5-amino-3,6,6-trimethyl-1,1-dioxido-3,6-dihydro-2H-1,4-thiazin-3-yl)-6-methoxypyridin-3-yl)-5-chloropicolinamide A microwave vial was charged with (R)-5-amino-3-(5-bromo-2-methoxypyridin-3-yl)-3,6,6-trimethyl-3,6-dihydro-2H-1,4-thiazine 1,1-dioxide (0.200 g, 0.532 mmol), 5-chloropicolinamide (0.125 g, 0.797 mmol), copper(i) iodide (0.020 g, 0.106 mmol) and potassium carbonate, powder, particle size −325 mesh (0.220 g, 1.595 mmol). The vial was purged with N$_2$ followed by the addition of 1,4-dioxane (2.0 mL) and trans-n,n'-dimethyl-1,2-cyclohexanediamine (0.084 mL, 0.532 mmol). The vial was sealed and heated at 120° C. for 161 hrs. LCMS indicated reaction went to completion. The reaction mixture was allowed to cool to room temperature and then partitioned between EtOAc and water. The aqueous layer was back extracted with EtOAc. The organic layers were combined, washed with brine, dried over Na2SO4 and filtered. The filtrate was concentrated and purified by Shimadzu HPLC to afford the title compound (0.078 g, 0.173 mmol, 32.5% yield) as off-white solid (free base), LC/MS (ESI$^+$) m/z=452 (M+H).

Example 171

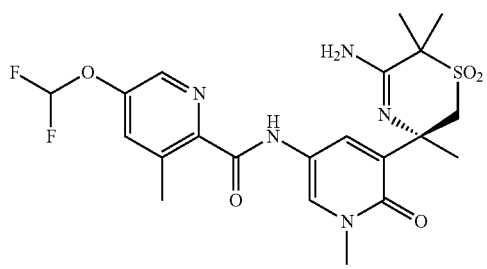 [SMILES: Cc1cc(OC(F)F)cnc1C(=O)Nc1cc([C@]2(C)CS(=O)(=O)C(C)(C)C(N)=N2)c(=O)n(C)c1]

Synthesis of (R)—N-(5-(5-amino-3,6,6-trimethyl-1,1-dioxido-3,6-dihydro-2H-1,4-thiazin-3-yl)-1-methyl-6-oxo-1,6-dihydropyridin-3-yl)-5-(difluoromethoxy)-3-methylpicolinamide Step 1: (R)-tert-butyl (5-(5-bromo-2-oxo-1,2-dihydropyridin-3-yl)-2,2,5-trimethyl-1,1-dioxido-5,6-dihydro-2H-1,4-thiazin-3-yl)carbamate To a solution of (R)-3-(5-amino-3,6,6-trimethyl-1,1-dioxido-3,6-dihydro-2H-1,4-thiazin-3-yl)-5-bromopyridin-2(1H)-one (0.623 g, 1.720 mmol) (see example 311 for preparation) in Dioxane (10.0 mL) was added di-tert-butyl dicarbonate (0.563 g, 2.58 mmol) followed by Saturated sodium bicarbonate (5.0 mL, 1.720 mmol). The mixture was stirred at room temperature for 24 hrs. LCMS indicated full conversion to desired product with MS+=462 plus trace of di-Boc product. The reaction mixture was diluted with EtOAc and water. The separated organic layer was washed with brine, dried over Na2SO4 and filtered. The filtrate was concentrated and dried in vacuo to afford the crude title compound as yellow oil. It was carried on to next step without purification. Assume theoretical yield. LC/MS (ESI$^+$) m/z=462, 464 (M+H; 2 bromine isotopes).

Step 2: (R)-tert-butyl (5-(5-bromo-1-methyl-2-oxo-1,2-dihydropyridin-3-yl)-2,2,5-trimethyl-1,1-dioxido-5,6-dihydro-2H-1,4-thiazin-3-yl)carbamate To a solution of (R)-tert-butyl (5-(5-bromo-2-oxo-1,2-dihydropyridin-3-yl)-2,2,5-trimethyl-1,1-dioxido-5,6-dihydro-2H-1,4-thiazin-3-yl)carbamate (0.795 g, 1.719 mmol) in MeCN (30 mL) was added potassium carbonate (0.356 g, 2.58 mmol) followed by iodomethane (0.534 mL, 8.60 mmol). The mixture was stirred at RT for 24 hrs. LCMS detected starting material and the desired product with MS+=476. The reaction mixture was concentrated to dryness and then diluted with EtOAc and water. The separated organic layer was washed with brine, dried over Na2SO4 and filtered. The filtrate was concentrated and the resulted residue was purified by silica gel chromatography (10-70% EtOAc/hexane) to afford the title compound (0.31 g, 0.651 mmol, 37.8% yield) as yellow solid. LC/MS (ESI$^+$) m/z=476, 478 (M+H; 2 bromine isotopes).

Step 3: (R)-3-(5-amino-3,6,6-trimethyl-1,1-dioxido-3,6-dihydro-2H-1,4-thiazin-3-yl)-5-bromo-1-methylpyridin-2(1H)-one To a solution of (R)-tert-butyl (5-(5-bromo-1-methyl-2-oxo-1,2-dihydropyridin-3-yl)-2,2,5-trimethyl-1,1-dioxido-5,6-dihydro-2H-1,4-thiazin-3-yl)carbamate (0.31 g, 0.651 mmol) in MeOH (2.0 mL) was added hydrogen chloride, 4 m in 1,4-dioxane (2.0 ml, 8.00 mmol). The reaction was stirred at ambient temperature for 24 hrs. LCMS indicated full conversion to the desired product. The reaction mixture was concentrated to dryness. The residue was neutralized with saturated NaHCO3 and then extracted with EtOAc (2×). The organics were washed with brine, dried over Na2SO4 and filtered. The filtrate was concentrated and dried in vacuum to afford the crude title compound (0.23 g, 0.611 mmol, 94% yield) as dark pink solid in about 80% purity. It was carried on without further purification. LC/MS (ESI$^+$) m/z=376, 378 (M+H; 2 bromine isotopes).

Step 4: (R)—N-(5-(5-amino-3,6,6-trimethyl-1,1-dioxido-3,6-dihydro-2H-1,4-thiazin-3-yl)-1-methyl-6-oxo-1,6-dihydropyridin-3-yl)-5-(difluoromethoxy)-3-methylpicolinamide As described in the example 312, step 2, (R)-3-(5-amino-3,6,6-trimethyl-1,1-dioxido-3,6-dihydro-2H-1,4-thiazin-3-yl)-5-bromo-1-methylpyridin-2(1H)-one (173 mg crude) was converted to the title compound (37 mg) as a white solid. LC/MS (ESI$^+$) m/z=498 (M+H).

Example 172

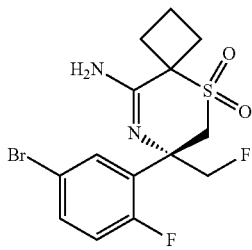 [SMILES: NC1=N[C@](CF)(c2cc(Br)ccc2F)CS(=O)(=O)C12CCC2]

Synthesis of (S)-9-amino-7-(5-bromo-2-fluorophenyl)-7-(fluoromethyl)-5-thia-8-azaspiro[3.5]non-8-ene 5,5-dioxide

Step 1: 1-(methylsulfonyl)cyclobutanecarbonitrile

A mixture of methanesulphonyl acetonitrile (15 g, 126 mmol), 1,3-dibromopropane (13.65 mL, 133 mmol) and potassium carbonate (26.1 g, 189 mmol) in DMF (7.0 mL) was heated at 60° C. for 6 hrs. The reaction was allowed to cool to RT and then diluted with EtOAc and water. The separated aqueous layer was extracted with EtOAc (2×). The organic extracts were combined, washed with brine, dried over $Na_2SO_4$, filtered and concentrated. The residue was purified by silica gel column (0-40% EtOAc/hexane) to afford 1-(methylsulfonyl)cyclobutanecarbonitrile (9.1 g, 57.2 mmol, 45.4% yield) as off-white solid.

Step 2: 1-(5-bromo-2-fluorophenyl)-2-fluoroethanone

In an analogous reaction to that described for example 5, step 1,1-bromo-4-fluorobenzene (22.0 mL, 200 mmol) was converted to the title compound (11.5 g, 24% yield). LC/MS (ESI$^+$) m/z=320 (M+H).

Step 3: (R,Z)—N-(1-(5-Bromo-2-fluorophenyl)-2-fluoroethylidene)-2-methylpropane-2-sulfinamide In an analogous reaction to that described for example 5, step 2, 1-(5-bromo-2-fluorophenyl)-2-fluoroethanone (11.0 g, 46.8 mmol) was converted to the title compound (11.6 g, 34.3 mmol, 73.3% yield) as yellow oil. LC/MS (ESI$^+$) m/z=338, 340 (M+H; 2 bromine isotopes.

Step 4: N-(2-(5-bromo-2-fluorophenyl)-1-((1-cyanocyclobutyl)sulfonyl)-3-fluoropropan-2-yl)-2-methylpropane-2-sulfinamide In an analogous reaction to that described for example 5, step 3, (R,Z)—N-(1-(5-bromo-2-fluorophenyl)-2-fluoroethylidene)-2-methylpropane-2-sulfinamide (5.0 g, 14.78 mmol) was converted to the title compound (3.81 g, 7.66 mmol, 51.8% yield) as yellow oil. LC/MS (ESI$^+$) m/z=497, 499 (M+H; 2 bromine isotopes).

Step 5: 9-amino-7-(5-bromo-2-fluorophenyl)-7-(fluoromethyl)-5-thia-8-azaspiro[3.5]non-8-ene 5,5-dioxide hydrochloride A mixture of N-(2-(5-bromo-2-fluorophenyl)-1-((1-cyanocyclobutyl)sulfonyl)-3-fluoropropan-2-yl)-2-methylpropane-2-sulfinamide (1.8 g, 3.62 mmol) and hydrogen chloride, 4 m in 1,4-dioxane (5.0 ml, 20.00 mmol) was heated at 100° C. for 3 days (over weekend). LCMS indicated full conversion to the desired product. The reaction mixture was concentrated and dried in vacuo to give a brown solid. The solid was stirred in diethyl ether/hexane (1:1) for 15 min, and then filtered. The filter cake was washed with ether and dried in vacuo to afford the title compound as HCL salt. LC/MS (ESI$^+$) m/z=393, 395 (M+H; 2 bromine isotopes).

Step 6: (S)-9-amino-7-(5-bromo-2-fluorophenyl)-7-(fluoromethyl)-5-thia-8-azaspiro[3.5]non-8-ene 5,5-dioxide Racemic 9-amino-7-(5-bromo-2-fluorophenyl)-7-(fluoromethyl)-5-thia-8-azaspiro[3.5]non-8-ene 5,5-dioxide was purified by chiral SFC, using a ChiralPak IC column and eluting with 25% (20 mM ammonia in methanol) in $CO_2$, to provide the title compound. LC/MS (ESI$^+$) m/z=393, 395 (M+H; 2 bromine isotopes).

Example 173

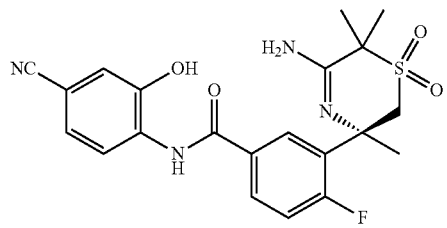 [SMILES: CC1(C)C(N)=N[C@](C)(c2cc(C(=O)Nc3ccc(C#N)cc3O)ccc2F)CS1(=O)=O]

Synthesis of (R)-3-(5-amino-3,6,6-trimethyl-1,1-dioxido-3,6-dihydro-2H-1,4-thiazin-3-yl)-N-(4-cyano-2-hydroxyphenyl)-4-fluorobenzamide

Step 1: (R)-Methyl (5-(5-bromo-2-fluorophenyl)-2,2,5-trimethyl-1,1-dioxido-5,6-dihydro-2H-1,4-thiazin-3-yl)carbamate To a mixture of (R)-5-amino-3-(5-bromo-2-fluorophenyl)-3,6,6-trimethyl-3,6-dihydro-2H-1,4-thiazine 1,1-dioxide (1.00 g, 2.75 mmol) in THF (15 mL) under nitrogen was added triethylamine (0.77 mL, 5.51 mmol) and methyl chloroformate (0.32 mL, 4.13 mmol). The mixture was stirred at room temperature for 18 h. The mixture was diluted with saturated $Na_2CO_3$ solution and extracted with EtOAc (2×). The combined organic extracts were washed with water, brine, dried over $Na_2SO_4$ and concentrated in vacuo.

The crude product was purified by flash column chromatography to afford (R)-methyl (5-(5-bromo-2-fluorophenyl)-2,2,5-trimethyl-1,1-dioxido-5,6-dihydro-2H-1,4-thiazin-3-yl)carbamate as a white solid.

Step 2: (R)-Methyl 4-fluoro-3-(5-((methoxycarbonyl)amino)-3,6,6-trimethyl-1,1-dioxido-3,6-dihydro-2H-1,4-thiazin-3-yl)benzoate The title compound was prepared analogously by following the procedure described in Step 1, PH-2

Step 3: (R)-4-Fluoro-3-(5-((methoxycarbonyl)amino)-3,6,6-trimethyl-1,1-dioxido-3,6-dihydro-2H-1,4-thiazin-3-yl)benzoic acid To a solution of (R)-methyl 4-fluoro-3-(5-((methoxycarbonyl)amino)-3,6,6-trimethyl-1,1-dioxido-3,6-dihydro-2H-1,4-thiazin-3-yl)benzoate (0.2 g, 0.50 mmol) in THF (0.6 ml), MeOH (0.6 ml) and water (0.2 ml) was added lithium hydroxide hydrate (0.57 ml, 0.57 mmol) and the resulting mixture was stirred at room temperature for 20 h. Additional 1N LiOH (0.25 ml) was added, and the reaction was stirred for another 2 h. The reaction mixture was neutralized with 1N HCl and concentrated in vacuo to afford (R)-4-fluoro-3-(5-((methoxycarbonyl)amino)-3,6,6-trimethyl-1,1-dioxido-3,6-dihydro-2H-1,4-thiazin-3-yl)benzoic acid as a white solid that was used without additional purification.

Step 4: (R)-3-(5-Amino-3,6,6-trimethyl-1,1-dioxido-3,6-dihydro-2H-1,4-thiazin-3-yl)-N-(4-cyano-2-hydroxyphenyl)-4-fluorobenzamide A solution of (R)-4-fluoro-3-(5-((methoxycarbonyl)amino)-3,6,6-trimethyl-1,1-dioxido-3,6-dihydro-2H-1,4-thiazin-3-yl)benzoic acid (0.193 g, 0.50 mmol) in thionyl chloride (1.5 ml, 20.6 mmol) was stirred at 80° C. for 1 h. The cooled reaction was concentrated in vacuo, and the resulting white solid (acid chloride) was taken up in dioxane (2 ml) and 4-amino-3-hydroxy-benzonitrile (0.1502 g, 1.120 mmol) was added, followed by methanesulfonic acid (0.097 ml, 1.49 mmol); the mixture was stirred at 100° C. for 1 h. On cooling, the reaction was diluted with $CH_2Cl_2$ and washed with saturated $NaHCO_3$ solution; the aqueous layer was back-extracted with $CH_2Cl_2$ (1x). The combined organic extracts were dried ($MgSO_4$), filtered and concentrated in vacuo. Flash column chromatography (eluent 0% to 5% MeOH/$CH_2Cl_2$) afforded (R)-3-(5-Amino-3,6,6-trimethyl-1,1-dioxido-3,6-dihydro-2H-1,4-thiazin-3-yl)-N-(4-cyano-2-hydroxyphenyl)-4-fluorobenzamide as a tan amorphous solid. LC/MS (ESI$^+$) m/z=445.0 (M+H).

Example 174

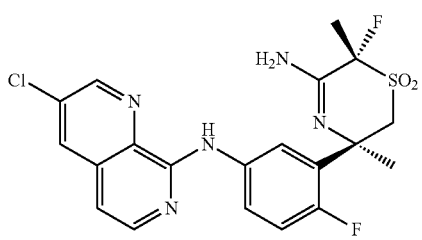 [SMILES: C[C@]1(F)C(N)=N[C@](C)(c2cc(Nc3nccc4cc(Cl)cnc34)ccc2F)CS1(=O)=O]

Synthesis of (3R,6R)-5-Amino-3-(5-((3-chloro-1,7-naphthyridin-8-yl)amino)-2-fluorophenyl)-6-fluoro-3,6-dimethyl-3,6-dihydro-2H-1,4-thiazine 1,1-dioxide Using LS Method 3, tert-butyl ((2R,5R)-5-(5-amino-2-fluorophenyl)-2-fluoro-2,5-dimethyl-1,1-dioxido-5,6-dihydro-2H-1,4-thiazin-3-yl)carbamate (100 mg, 0.25 mmol) and 3,8-dichloro-1,7-naphthyridine (78 mg, 0.25 mmol) were combined to provide the title compound (49 mg, 42% yield) as a light-yellow powder. LC/MS (ESI$^+$) m/z=466 (M+H).

Example 175

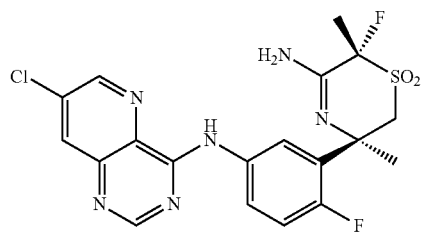 [SMILES: C[C@]1(F)C(N)=N[C@](C)(c2cc(Nc3ncnc4cc(Cl)cnc34)ccc2F)CS1(=O)=O]

Synthesis of (3R,6R)-5-Amino-((7-chloropyrido[3,2-d]pyrimidin-4-yl)amino)-2-fluorophenyl)-6-fluoro-3,6-dimethyl-3,6-dihydro-2H-1,4-thiazine 1,1-dioxide Using LS Method 3, tert-butyl ((2R,5R)-5-(5-amino-2-fluorophenyl)-2-fluoro-2,5-dimethyl-1,1-dioxido-5,6-dihydro-2H-1,4-thiazin-3-yl)carbamate (100 mg, 0.25 mmol) and 4,7-dichloropyrido[3,2-d]pyrimidine (50 mg, 0.25 mmol) were combined to provide the title compound (125 mg, quantitative yield) as an off-white powder. LC/MS (ESI$^+$) m/z=467 (M+H).

Example 176

JS3

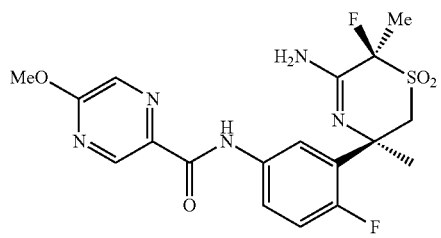 [SMILES: COc1cnc(C(=O)Nc2ccc(F)c([C@]3(C)CS(=O)(=O)[C@](C)(F)C(N)=N3)c2)cn1]

Synthesis of N-(3-(3R,6S)-5-Amino-6-fluoro-3,6-dimethyl-1,1-dioxido-3,6-dihydro-2H-1,4-thiazin-3-yl)-4-fluorophenyl)-5-methoxypyrazine-2-carboxamide

Step 1: (3R,6S)-5-Amino-3-(5-bromo-2-fluorophenyl)-6-fluoro-3,6-dimethyl-3,6-dihydro-2H-1,4-thiazine 1,1-dioxide To a 0° C. solution of (R)-5-amino-3-(5-bromo-2-fluorophenyl)-3-methyl-3,6-dihydro-2H-1,4-thiazine 1,1-dioxide (0.78 g, 2.3 mmol) in N,N-dimethylformamide (15 mL) was added N-fluorobenzenesulfonimide (0.73 g, 2.3 mmol) and cesium carbonate (1.14 g, 3.5 mmol). The reaction was stirred at 0° C. for one hour, and then another portion of cesium carbonate (1.14 g, 3.5 mmol) was added to the reaction, followed by iodomethane (0.145 mL, 2.3 mmol). The reaction was stirred for another 2 hours at 0° C. The reaction mixture was partitioned between water and ethyl acetate; the organic layer was washed with water and brine and concentrated. The two epimers were separated by chiral SFC, using a ChiralCel OD-H column and eluting with 15% (0.1% diethylamine in methanol) in $CO_2$, to provide the title compound (0.26 g, 30% yield) as a white solid. LC/MS (ESI$^+$) m/z=367, 369 (M+H; 2 bromine isotopes).

Step 2: tert-Butyl ((2S,5R)-5-(5-amino-2-fluorophenyl)-2-fluoro-2,5-dimethyl-1,1-dioxido-5,6-dihydro-2H-1,4-thiazin-3-yl)carbamate In an analogous sequence to that described for Intermediate 2, steps 1-3, (3R,6S)-5-amino-3-(5-bromo-2-fluorophenyl)-6-fluoro-3,6-dimethyl-3,6-dihydro-2H-1,4-thiazine 1,1-dioxide (0.26 g, 0.70 mmol) was converted to the title compound (125 mg, 44% yield) as a white solid. LC/MS (ESI$^+$) m/z=404 (M+H).

Step 3: N-(3-(3R,6S)-5-Amino-6-fluoro-3,6-dimethyl-1,1-dioxido-3,6-dihydro-2H-1,4-thiazin-3-yl)-4-fluorophenyl)-5-methoxypyrazine-2-carboxamide Using General Amidation Procedure A, tert-butyl ((2S,5R)-5-(5-amino-2-fluorophenyl)-2-fluoro-2,5-dimethyl-1,1-dioxido-5,6-dihydro-2H-1,4-thiazin-3-yl)carbamate (60 mg, 0.149 mmol) and 5-methoxypyrazine-2-carboxylic acid (24.07 mg, 0.156 mmol) were combined to provide the title compound (49 mg, 0.112 mmol, 79% yield) as a white powder. LC/MS (ESI$^+$) m/z=440 (M+H).

Example 177

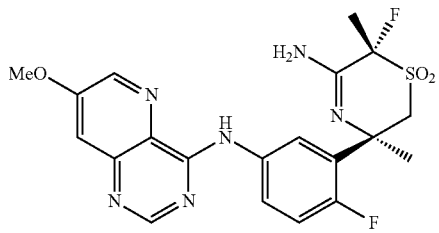 [SMILES: COc1cnc2c(Nc3ccc(F)c([C@]4(C)CS(=O)(=O)[C@@](C)(F)C(N)=N4)c3)ncnc2c1]

Synthesis of (3R,6R)-5-Amino-6-fluoro-3-(2-fluoro-5-((7-methoxypyrido[3,2-d]pyrimidin-4-yl)amino) phenyl)-3,6-dimethyl-3,6-dihydro-2H-1,4-thiazine 1,1-dioxide Using LS Method 3, tert-butyl ((2R,5R)-5-(5-amino-2-fluorophenyl)-2-fluoro-2,5-dimethyl-1,1-dioxido-5,6-dihydro-2H-1,4-thiazin-3-yl)carbamate (100 mg, 0.25 mmol) and 4-chloro-7-methoxypyrido[3,2-d]pyrimidine (49 mg, 0.25 mmol) were combined to provide the title compound (83 mg, 72.4% yield) as a white powder. $^1$H-NMR (400 MHz, DMSO-d$_6$): 10.12 (s, 1H), 8.62 (d, J=2.8 Hz, 1H), 8.59 (s, 1H), 8.06-8.08 (m, 1H), 7.92-7.96 (m, 1H), 7.60 (d, J=2.7 Hz, 1H), 7.16 (dd, J=8.8, 11.9 Hz, 1H), 6.62 (bs, 2H), 4.00 (s, 3H), 3.90 (d, J=15.3 Hz, 1H), 3.81 (d, J=15.8 Hz, 1H), 1.88 (d, J=17.5 Hz, 6H), 1.67 (s, 3H). LC/MS (ESI$^+$) m/z=463 (M+H).

Example 178

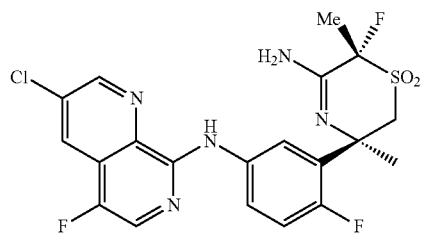 [SMILES: C[C@]1(F)C(N)=N[C@](C)(c2cc(Nc3ncc(F)c4cc(Cl)cnc34)ccc2F)CS1(=O)=O]

Synthesis of (3R,6R)-5-Amino-3-(5-((3-chloro-5-fluoro-1,7-naphthyridin-8-yl)amino)-2-fluorophenyl)-6-fluoro-3,6-dimethyl-3,6-dihydro-2H-1,4-thiazine 1,1-dioxide Step 1: (3R)-5-Amino-3-(5-((3-chloro-5-fluoro-1,7-naphthyridin-8-yl)amino)-2-fluorophenyl)-3,6-dimethyl-3,6-dihydro-2H-1,4-thiazine 1,1-dioxide To a suspension of (3R)-5-amino-3-(5-amino-2-fluorophenyl)-3,6-dimethyl-3,6-dihydro-2H-1,4-thiazine 1,1-dioxide (100 mg, 0.350 mmol) and 3,8-dichloro-5-fluoro-1,7-naphthyridine (84 mg, 0.386 mmol) in 2-propanol (1.7 mL) was added p-toluenesulfonic acid monohydrate (147 mg, 0.771 mmol). The reaction was stirred at 90° C. for 3 hours, and concentrated. The residue was partitioned between dichloromethane and saturated aqueous sodium bicarbonate. The organic layer was concentrated, adsorbed onto a silica-gel loading column, and purified by column chromatography, eluting with 50-100% ethyl acetate in heptane, to provide the title compound (136 mg, 83% yield) as a yellow oil. LC/MS (ESI$^+$) m/z=466 (M+H).

Step 2: (3R,6R)-5-Amino-3-(5-((3-chloro-5-fluoro-1,7-naphthyridin-8-yl)amino)-2-fluorophenyl)-6-fluoro-3,6-dimethyl-3,6-dihydro-2H-1,4-thiazine 1,1-dioxide In an analogous reaction to that described for Example 3, Route A, Step 2, (3R)-5-amino-3-(5-((3-chloro-5-fluoro-1,7-naphthyridin-8-yl)amino)-2-fluorophenyl)-3,6-dimethyl-3,6-dihydro-2H-1,4-thiazine 1,1-dioxide (136 mg, 0.29 mmol) was converted to the title compound (93 mg, 66% yield) as a yellow solid. LC/MS (ESI$^+$) m/z=484 (M+H).

Example 179

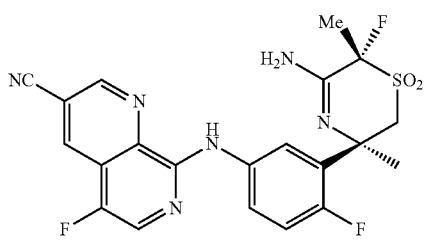 [SMILES: C[C@]1(F)C(N)=N[C@](C)(c2cc(Nc3ncc(F)c4cc(C#N)cnc34)ccc2F)CS1(=O)=O]

Synthesis of 8-((3-((3R,6R)-5-Amino-6-fluoro-3,6-dimethyl-1,1-dioxido-3,6-dihydro-2H-1,4-thiazin-3-yl)-4-fluorophenyl)amino)-5-fluoro-1,7-naphthyridine-3-carbonitrile In an analogous sequence to that described for Example JS5, Steps 1-2, (3R)-5-amino-3-(5-amino-2-fluorophenyl)-3,6-dimethyl-3,6-dihydro-2H-1,4-thiazine 1,1-dioxide (100 mg, 0.35 mmol) and 8-chloro-5-fluoro-1,7-naphthyridine-3-carbonitrile (80 mg, 0.39 mmol) were converted to the title compound (95 mg, 57% yield) as a yellow powder. LC/MS (ESI+) m/z=475 (M+H).

Example 180

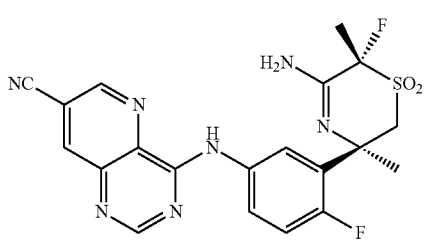 [SMILES: C[C@]1(F)C(N)=N[C@](C)(c2cc(Nc3ncnc4cc(C#N)cnc34)ccc2F)CS1(=O)=O]

Synthesis of 4-((3-((3R,6R)-5-Amino-6-fluoro-3,6-dimethyl-1,1-dioxido-3,6-dihydro-2H-1,4-thiazin-3-yl)-4-fluorophenyl)amino)pyrido[3,2-d]pyrimidine-7-carbonitrile Using LS Method 3, tert-butyl ((2R,5R)-5-(5-amino-2-fluorophenyl)-2-fluoro-2,5-dimethyl-1,1-dioxido-5,6-dihydro-2H-1,4-thiazin-3-yl)carbamate (100 mg, 0.25 mmol) and 4-chloropyrido[3,2-d]pyrimidine-7-carbonitrile (47 mg, 0.25 mmol) were combined to provide the title compound (61 mg, 54% yield) as a yellow powder. LC/MS (ESI+) m/z=475 (M+H).

Example 181

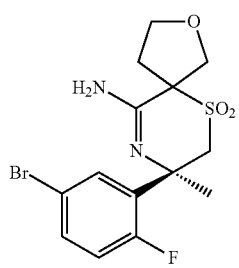 [SMILES: C[C@@]1(c2cc(Br)ccc2F)CS(=O)(=O)C2(CCOC2)C(N)=N1]

Synthesis of (8R)-10-Amino-8-(5-bromo-2-fluorophenyl)-8-methyl-2-oxa-6-thia-9-azaspiro[4.5]dec-9-ene 6,6-dioxide A suspension of (R)-tert-butyl (2-(5-bromo-2-fluorophenyl)-1-((cyanomethyl)sulfonyl)propan-2-yl)carbamate (1.0 g, 2.3 mmol) and cesium carbonate (0.75 g, 2.3 mmol) in 1,4-dioxane (25 mL) was stirred at 90° C. for ten minutes, cooled to ambient temperature, and added to a solution of 2-chloroethyl chloromethyl ether (0.23 mL, 2.3 mmol) in 1,4-dioxane (25 mL). The reaction was stirred at ambient temperature for two hours. Another portion of cesium carbonate (0.75 g, 2.3 mmol) was added to the reaction, and the reaction was stirred overnight at ambient temperature. After 16 hours, the reaction mixture was partitioned between water and ethyl acetate. The organic layer was dried over anhydrous magnesium sulfate, filtered, and concentrated to provide the crude intermediate.

The crude intermediate was dissolved in 4 M hydrochloric acid in 1,4-dioxane (20 mL, 80 mmol), and the reaction was stirred at ambient temperature. After 90 minutes, the reaction mixture was concentrated, and the brown residue was dried under high vacuum. To a suspension of the residue in toluene (20 mL) was added a 2-M solution of trimethylaluminum in toluene (1.04 mL, 2.08 mmol), and the reaction was stirred at 90° C. After 1 hour, the reaction was cooled to ambient temperature and partitioned between ethyl acetate and 10% aqueous ETDA-ol. The organic layer was washed with brine and concentrated. The crude product was purified by reverse-phase silica-gel chromatography, eluting with 10-70% (0.1% trifluoroacetic acid in acetonitrile) in (0.1% trifluoroacetic acid in water). The product fractions were combined, neutralized with saturated aqueous sodium bicarbonate, and extracted with ethyl acetate. The organic layer was dried over anhydrous magnesium sulfate, filtered, and concentrated to provide the title compound (0.18 g, 13% yield) as a 1:1 mixture of diastereomers. LC/MS (ESI+) m/z=391, 393 (M+H; 2 bromine isotopes).

Example 182

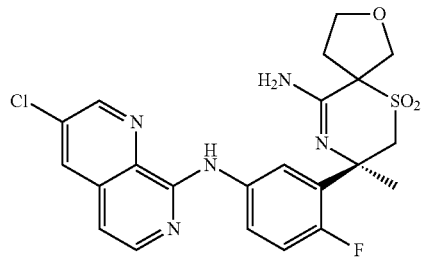 [SMILES: C[C@@]1(c2cc(Nc3nccc4cc(Cl)cnc34)ccc2F)CS(=O)(=O)C2(CCOC2)C(N)=N1]

Synthesis of (8R)-10-Amino-8-(5-((3-chloro-1,7-naphthyridin-8-yl)amino-2-fluorophenyl)-8-methyl-2-oxa-6-thia-9-azaspiro[4.5]dec-9-ene 6,6-dioxide Step 1: (8R)-10-amino-8-(5-amino-2-fluorophenyl)-8-methyl-2-oxa-6-thia-9-azaspiro[4.5]dec-9-ene 6,6-dioxide In an analogous sequence to that described for Intermediate 2, steps 2-3, (8R)-10-amino-845-bromo-2-fluorophenyl)-8-methyl-2-oxa-6-thia-9-azaspiro[4.5]dec-9-ene 6,6-dioxide (140 mg, 0.358 mmol) was converted to the title compound (88 mg, 75% yield) as an off-white solid. LC/MS (ESI+) m/z=328 (M+H).

Step 2: (8R)-10-amino-8-(5-((3-chloro-1,7-naphthyridin-8-yl)amino)-2-fluorophenyl)-8-methyl-2-oxa-6-thia-9-azaspiro[4.5]dec-9-ene 6,6-dioxide In an analogous reaction to that described for Example JS5, Step 1, (8R)-10-amino-8-(5-amino-2-fluorophenyl)-8-methyl-2-oxa-6-thia-9-azaspiro[4.5]dec-9-ene 6,6-dioxide (40 mg, 0.122 mmol) and 3,8-dichloro-1,7-naphthyridine (24.32 mg, 0.122 mmol) were converted to the title compound (25 mg, 0.026 mmol, 20.88% yield) as a 1:1 mixture of diastereomers. $^1$H-NMR (400 MHz, DMSO-d$_6$): δ 9.55 (s, 1H), 8.90 (d, J=2.4 Hz, 1H), 8.51 (d, J=2.4 Hz, 1H), 8.12-8.15 (m, 2H), 8.03-8.04 (m, 1H), 7.11-7.17 (m, 2H), 5.90 (bs, 2H), 4.22 (s, 2H), 4.02-4.11 (m, 1H), 3.56-3.86 (m, 3H), 2.34-2.55 (m, 2H), 1.68 (s, 3H). LC/MS (ESI$^+$) m/z=490 (M+H).

Example 183

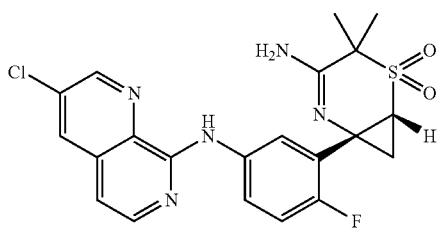 [SMILES: CC1(C)C(N)=N[C@@]2(c3cc(Nc4nccc5cc(Cl)cnc45)ccc3F)C[C@H]2S1(=O)=O]

Synthesis of (1R,6R)-4-amino-6-(5-((3-chloro-1,7-naphthyridin-8-yl)amino)-2-fluorophenyl)-3,3-dimethyl-2-thia-5-azabicyclo[4.1.0]hept-4-ene 2,2-dioxide Step 1: (S)-5-amino-3-(fluoromethyl)-3-(2-fluorophenyl)-6,6-dimethyl-3,6-dihydro-2H-1,4-thiazine 1,1-dioxide To a solution of (S)-5-amino-3-(5-bromo-2-fluorophenyl)-3-(fluoromethyl)-6,6-dimethyl-3,6-dihydro-2H-1,4-thiazine 1,1-dioxide (3.22 g, 8.44 mmol) in ethanol (15 mL) and ethyl acetate (5 mL) was added sodium bicarbonate (138 mg, 1.69 mmol) and 10 wt % palladium on carbon (0.90 g, 8.44 mmol). The flask was evacuated and backfilled with hydrogen three times, and stirred at room temperature under a hydrogen atmosphere for 2 hours. The reaction mixture was filtered through a Celite® pad, and the filter cake was rinsed with ethyl acetate and ethanol. The combined filtrates were concentrated in vacuo and the residue was redissolved in ethyl acetate, washed with saturated aqueous sodium bicarbonate, dried over sodium sulfate, filtered and evaporated to provide the title compound (2.49 g, 8.23 mmol) as an off-white solid. LC/MS (ESI$^+$) m/z=303 (M+H).

Step 2: (S)-5-amino-3-(2-fluoro-5-nitrophenyl)-3-(fluoromethyl)-6,6-dimethyl-3,6-dihydro-2H-1,4-thiazine 1,1-dioxide To a solution of (S)-5-amino-3-(fluoromethyl)-3-(2-fluorophenyl)-6,6-dimethyl-3,6-dihydro-2H-1,4-thiazine 1,1-dioxide (1.98 g, 6.55 mmol) in sulfuric acid (8.73 mL, 0.16 mol) at 0° C. was added potassium nitrate (0.69 g, 6.88 mmol) portionwise. When the addition was completed, the reaction mixture was allowed to warm to room temperature and the mixture was stirred at room temperature for 30 min. The reaction mixture was carefully poured into ice-water (100 mL) and neutralized by the addition of aqueous ammonium hydroxide. The mixture was diluted with water (10 mL) and extracted with ethyl acetate (2×50 mL). The combined organic extracts were washed with brine, dried over sodium sulfate, filtered, and concentrated under vacuum to give the title compound (2.27 g, 6.64 mmol) as an off-white solid. $^1$H NMR (400 MHz, DMSO-d$_6$) 8.43 (dd, J=3.03, 6.75 Hz, 1H), 8.25 (td, J=3.55, 8.95 Hz, 1H), 7.51 (dd, J=9.00, 11.35 Hz, 1H), 6.58 (br. s., 2H), 4.59 (q, J=8.80 Hz, 1H), 4.48 (q, J=8.80 Hz, 1H), 3.68-3.87 (m, 2H), 1.61 (s, 3H), 1.47 (s, 3H). LC/MS (ESI$^+$) m/z=348 (M+H).

Step 3: (S)-tert-butyl (5-(2-fluoro-5-nitrophenyl)-5-(fluoromethyl)-2,2-dimethyl-1,1-dioxido-5,6-dihydro-2H-1,4-thiazin-3-yl)carbamate To a solution of (S)-5-amino-3-(2-fluoro-5-nitrophenyl)-3-(fluoromethyl)-6,6-dimethyl-3,6-dihydro-2H-1,4-thiazine 1,1-dioxide (2.27 g, 6.54 mmol) in dioxane (40 mL) was added saturated aqueous sodium bicarbonate (40 mL), followed by di-tert-butyl dicarbonate (1.85 g, 8.50 mmol). The reaction mixture was stirred at room temperature for 24 h. The mixture was partitioned between water and ethyl acetate. The organic layer was washed with water, brine, dried over anhydrous sodium sulfate, filtered, and concentrated under vacuum. The residue was absorbed onto a plug of silica gel and purified by chromatography through a Redi-Sep pre-packed silica gel column (40 g), eluting with a gradient of 10% to 30% ethyl acetate in hexanes, to provide the title compound (2.21 g, 4.96 mmol) as a white solid. $^1$H NMR (400 MHz, CDCl$_3$) 11.43 (br. s., 1H), 8.26-8.40 (m, 2H), 7.33 (dd, J=9.19, 10.76 Hz, 1H), 4.57-4.95 (m, 2H), 3.77-3.94 (m, 2H), 1.84 (s, 3H), 1.68 (s, 3H), 1.59 (s, 9H). LC/MS (ESI$^+$) m/z=470 (M+Na).

Step 4: tert-butyl ((1R,6R)-6-(2-fluoro-5-nitrophenyl)-3,3-dimethyl-2,2-dioxido-2-thia-5-azabicyclo[4.1.0]hept-4-en-4-yl)carbamate To a solution of (S)-tert-butyl (5-(2-fluoro-5-nitrophenyl)-5-(fluoromethyl)-2,2-dimethyl-1,1-dioxido-5,6-dihydro-2H-1,4-thiazin-3-yl)carbamate (0.79 g, 1.76 mmol) in THF (10 mL) at −78° C. under a nitrogen atmosphere was added lithium bis(trimethylsilyl)amide (4.40 mL, 4.40 mmol; 1.0 M solution in THF). The reaction mixture was stirred at −78° C. for 15 min and quenched by the addition of saturated aqueous ammonium chloride (5 mL). The reaction mixture was warmed to room temperature and partitioned between water and ethyl acetate. The organic phase was separated, washed with water, brine, and dried over anhydrous sodium sulfate, filtered, and concentrated. The title compound was obtained (0.75 g, 1.75 mmol) as a tan solid and used without further purification. $^1$H NMR (400 MHz, CDCl$_3$) 11.19 (br. s., 1H), 8.21-8.38 (m, 2H), 7.36 (t, J=10.00 Hz, 1H), 3.59 (dd, J=6.36, 9.10 Hz, 1H), 2.31 (t, J=6.10 Hz, 1H), 2.23 (q, J=7.00 Hz, 1H), 1.67 (s, 6H), 1.53 (s, 9H). LC/MS (ESI$^+$) m/z=450 (M+Na).

Step 5: tert-butyl ((1R,6R)-6-(5-amino-2-fluorophenyl)-3,3-dimethyl-2,2-dioxido-2-thia-5-azabicyclo[4.1.0]hept-4-en-4-yl)carbamate To a solution of tert-butyl ((1R,6R)-6-(2-fluoro-5-nitrophenyl)-3,3-dimethyl-2,2-dioxido-2-thia-5-azabicyclo[4.1.0]hept-4-en-4-yl)carbamate (0.73 g, 1.72 mmol) in ethanol (21 mL) and ethyl acetate (7 mL) was added 10 wt % palladium on carbon (183 mg, 1.72 mmol). The flask was evacuated and backfilled with hydrogen three times, and stirred at room temperature under a hydrogen atmosphere for 3.5 h. The reaction mixture was filtered through a Celite® pad, and the filter cake was rinsed with ethyl acetate and ethanol. The combined filtrates were concentrated in vacuo to give the title compound (680 mg, 1.71 mmol) as an off-white solid. LC/MS (ESI⁺) m/z=398 (M+H).

Step 6: (1R,6R)-4-amino-6-(5-((3-chloro-1,7-naphthyridin-8-yl)amino)-2-fluorophenyl)-3,3-dimethyl-2-thia-5-azabicyclo[4.1.0]hept-4-ene 2,2-dioxide To a solution of tert-butyl ((1R,6R)-6-(5-amino-2-fluorophenyl)-3,3-dimethyl-2,2-dioxido-2-thia-5-azabicyclo[4.1.0]hept-4-en-4-yl)carbamate (107 mg, 0.27 mmol) and 3,8-dichloro-1,7-naphthyridine (59 mg, 0.30 mmol) in 2-propanol (3 mL) was added 2 of drops of sulfuric acid. The reaction was stirred at 90° C. for one hour, and cooled to room temperature. The mixture was neutralized with NaOH (1N, 5 mL) and extracted with DCM (3×8 mL). The combined organic extracts were dried over anhydrous sodium sulfate, filtered, and concentrated under vacuum. The residue was absorbed onto a plug of silica gel and purified by chromatography through a Redi-Sep pre-packed silica gel column (12 g), eluting with a gradient of 1% to 4% MeOH (2M NH₃) in DCM, to provide the title compound (64 mg, 0.14 mmol) as a yellow solid. ¹H NMR (400 MHz, CDCl₃) 8.92 (s, 1H), 8.70 (d, J=2.35 Hz, 1H), 8.10 (d, J=5.87 Hz, 1H), 7.98-8.07 (m, 2H), 7.86-7.96 (m, 1H), 7.07 (dd, J=8.80, 11.35 Hz, 1H), 6.94 (d, J=5.87 Hz, 1H), 3.41 (dd, J=5.97, 9.10 Hz, 1H), 2.32 (dd, J=6.26, 9.19 Hz, 1H), 1.91 (dt, J=1.56, 6.06 Hz, 1H), 1.66 (s, 3H), 1.65 (s, 3H). LC/MS (ESI⁺) m/z=460 (M+H).
T Judd Example 184

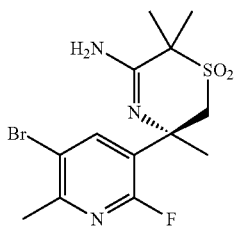 [SMILES: Cc1nc(F)c([C@]2(C)CS(=O)(=O)C(C)(C)C(N)=N2)cc1Br]

Synthesis of (R)-5-Amino-3-(5-bromo-2-fluoro-6-methylpyridin-3-yl)-3,6,6-trimethyl-3,6-dihydro-2H-1,4-thiazine 1,1-dioxide Step 1: 1-(5-bromo-2-fluoro-6-methylpyridin-3-yl)ethanol N-Butyllithium, 2.5 m solution in hexane (17.59 mL, 44.0 mmol) was added dropwise via syringe to a solution of DIPA (6.46 mL, 46.1 mmol) in THF (200 mL) at −78° C. The solution was warmed to 0° C. for 15 minutes and then recooled to −78° C. Next, 3-bromo-6-fluoro-2-methylpyridine (5 mL, 41.9 mmol) was added dropwise via syringe and the resulting solution was stirred 1 hour before acetaldehyde (2.82 mL, 50.3 mmol) was added dropwise. The reaction was quenched with saturated aqueous ammonium chloride at −78° C. and diluted with water and EtOAc. The layers were separated and the aqueous layer was extracted with EtOAc. The combined organic extracts were washed with water, saturated aqueous sodium chloride, and dried over sodium sulfate. The solution was filtered and concentrated in vacuo. The crude material was purified by silica gel chromatography by eluting with 1:9 EtOAc/Hexanes to afford the title compound, 1-(5-bromo-2-fluoro-6-methylpyridin-3-yl)ethanol.

Step 2: 1-(5-bromo-2-fluoro-6-methylpyridin-3-yl)ethanone

Pyridinium dichromate (32.8 g, 87 mmol) was added in portions to a solution of 1-(5-bromo-2-fluoro-6-methylpyridin-3-yl)ethanol (6.8 g, 29.1 mmol) in DCM (60 ml) at 0° C. The resulting mixture was stirred at room temperature and 3 Å sieves were added. After stirring overnight, the reaction was filtered through a pad of magnesium sulfate and celite, washed with DCM. The filtrate was concentrated and then taken up in a 1:1 mixture of diethyl ether and hexanes and filtered. The filtrate was concentrated and the crude material was purified by silica gel chromatography by eluting with 1:20 EtOAc in hexane, to provide 1-(5-bromo-2-fluoro-6-methylpyridin-3-yl)ethanone (4.9 g, 21.12 mmol, 72.7% yield) as a clear solid after drying under vacuum. LC/MS (ESI⁺) m/z=232, 234 (M+H; 2 bromine isotopes).

Step 3: (R)-5-Amino-3-(5-bromo-2-fluoro-6-methylpyridin-3-yl)-3,6,6-trimethyl-3,6-dihydro-2H-1,4-thiazine 1,1-dioxide In an analogous sequence of reactions to those described for Example 11, steps 3-6, 1-(5-bromo-2-fluoro-6-methylpyridin-3-yl)ethanone was converted to the title compound in 42% yield. LC/MS (ESI⁺) m/z=378, 380 (M+H; 2 bromine isotopes).

Example 185 a, b, c & d

Scheme: THF-fused Gem-dimethyl Sulfone

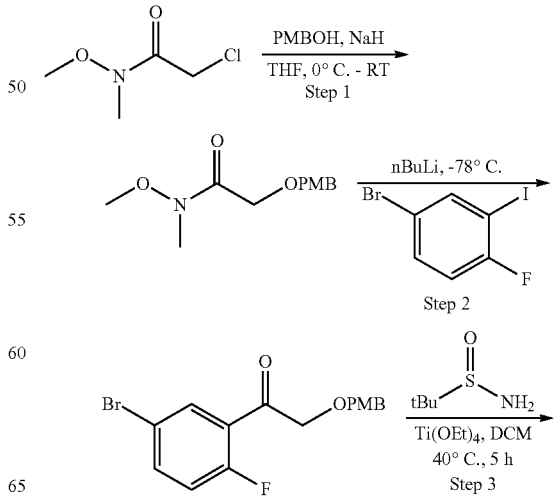

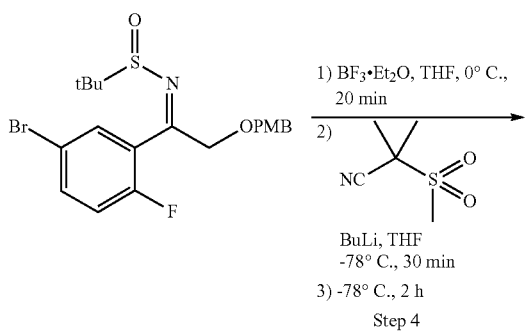

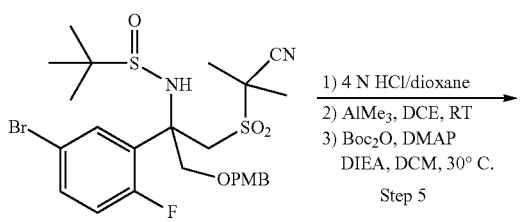

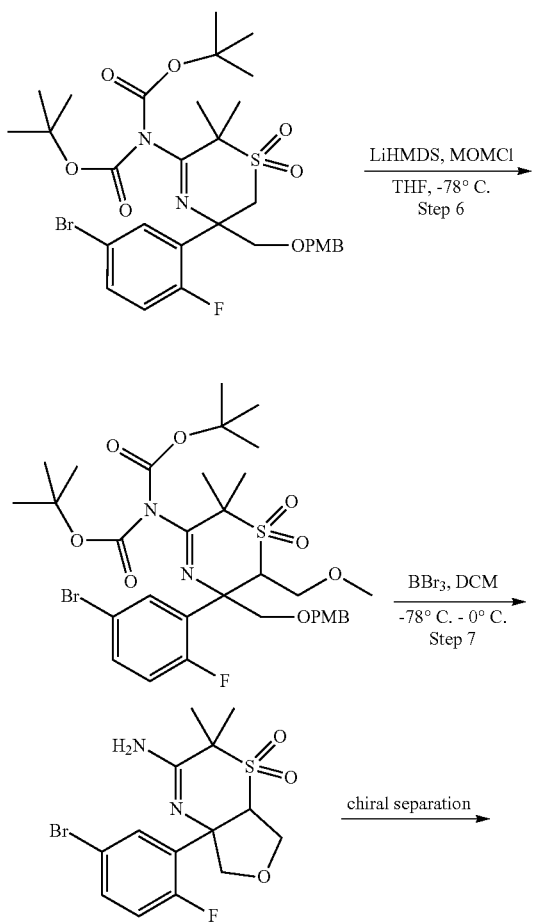

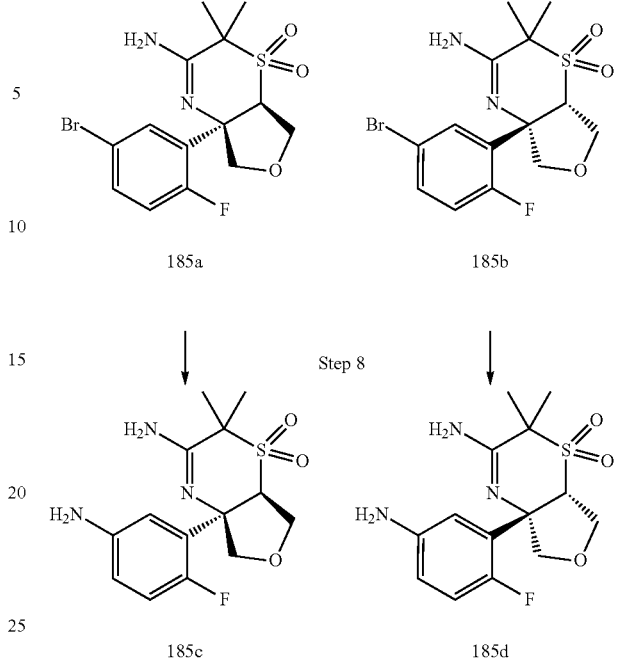

Step 1. N-methoxy-2-((4-methoxybenzyl)oxy)-N-methylacetamide

To a suspension of sodium hydride (1.86 g, 46.5 mmol) in THF (80 ml) at 0° C. was added (4-methoxyphenyl)methyl alcohol (5.80 mL, 46.7 mmol) over 5 min. The reaction mixture was warmed to RT for 1 h, then cooled to 0° C. and a solution of 2-chloro-N-methoxy-N-methylacetamide (6.50 g, 47.3 mmol) in THF (20 mL) was added. The reaction mixture was warmed to room temperature and stirred for 72 hr then quenched with NH$_4$Cl and diluted with EtOAc and water. The aqueous phase was extracted with EtOAc (2x) and the combined organic extracts were washed with brine (1x), dried over MgSO$_4$, filtered, and concentrated. Purification by flash column chromatography on silica gel (120 g, 30% to 80% EtOAc in hexanes) gave N-methoxy-2-((4-methoxybenzyl)oxy)-N-methylacetamide (1.10 g, 4.60 mmol, 9.85% yield) as a yellow oil. ESI (M+Na) 262.1.

Step 2. 1-(5-bromo-2-fluorophenyl)-2-((4-methoxybenzyl)oxy)ethanone

To a solution of 4-bromo-1-fluoro-2-iodobenzene (1.85 g, 6.15 mmol) in THF (12 mL) at −78° C. was added dropwise butyllithium solution, 1.6 m in hexane (3.85 ml, 6.16 mmol). The solution was stirred at −78° C. for 30 min and a solution of N-methoxy-2-((4-methoxybenzyl)oxy)-N-methylacetamide (1.10 g, 4.60 mmol) in THF (10 mL) at −78° C. was added via cannula. The reaction mixture was warmed from −78° C. to −10° C. over 1.5 h and quenched with NH$_4$Cl and diluted with EtOAc and water. The aqueous phase was discarded and the organic phase was washed with brine (1x), dried over MgSO$_4$, filtered, and concentrated. Purification by flash column chromatography on silica gel (40 g, 5% to 10% EtOAc in hexanes) gave 1-(5-bromo-2-fluorophenyl)-2-((4-methoxybenzyl)oxy)ethanone (1.24 g, 3.51 mmol, 76% yield) as a white solid. ESI (M+Na) 377.7.

Step 3. (Z)—N-(1-(5-bromo-2-fluorophenyl)-2-((4-methoxybenzyl)oxy)ethylidene)-2-methylpropane-2-sulfinamide To a mixture of 1-(5-bromo-2-fluorophenyl)-2-((4-methoxybenzyl)oxy)ethanone (9.97 g, 28.2 mmol), titanium (IV) ethoxide (7.95 mL, 38.4 mmol) in DCM (200 mL) at room temperature was added t-butylsulfinamide (8.55 g, 70.6 mmol). The mixture was heated to 40° C. for 5 h. The reaction was quenched with brine (200 mL) and EtOAc. The mixture was filtered through celite and the cake was washed with EtOAc. The two layers were separated. The aqueous layer was extracted with EtOAc and the combined organic layers were washed with brine, dried over $Na_2SO_4$ and concentrated in vacuo. The crude was purified by silica gel chromatography, eluent 0-70% EtOAc-hexanes to give (Z)—N-(1-(5-bromo-2-fluorophenyl)-2-((4-methoxybenzyl)oxy)ethylidene)-2-methylpropane-2-sulfinamide (4.25 g, 33% yield) as yellow oil. ESI (M+Na) 479.8.

Step 4. N-(2-(5-bromo-2-fluorophenyl)-1-((2-cyanopropan-2-yl)sulfonyl)-3-((4-methoxybenzyl)oxy)propan-2-yl)-2-methylpropane-2-sulfinamide N-butyllithium, 2.5 m solution in hexane (2.1 mL, 5.2 mmol) was added dropwise via syringe to a solution of 2-methyl-2-(methylsulfonyl)propanenitrile (0.766 g, 5.21 mmol) in THF (10 mL) at −78° C. After 25 minutes, a solution of (Z)—N-(1-(5-bromo-2-fluorophenyl)-2-((4-methoxybenzyl)oxy)ethylidene)-2-methylpropane-2-sulfinamide (1.32 g, 2.89 mmol) (azetroped with 5 mL of toluene before use) in THF (10 mL) cooled to 0° C. and pretreated with boron trifluoride diethyl etherate (0.357 ml, 2.89 mmol) at 0° C. for 15 minutes, was added dropwise via syringe. The reaction was stirred at −78° C. for 2 h. The reaction was quenched with saturated aqueous ammonium chloride at −78° C. and diluted with water and EtOAc. The layers were separated and the aqueous layer was extracted with EtOAc (3×). The combined organic extracts were washed with water, saturated aqueous sodium chloride, and dried over sodium sulfate. The crude material was purified by silica gel chromatography by eluting with 0-50% EtOAc in hexane, to provide N-(2-(5-bromo-2-fluorophenyl)-1-((2-cyanopropan-2-yl)sulfonyl)-3-((4-methoxybenzyl)oxy)propan-2-yl)-2-methylpropane-2-sulfinamide (1.24 g, 2.054 mmol, 71% yield) as a off-white solid. ESI (M+Na) 603.0.

Step 5

To a solution of N-(2-(5-bromo-2-fluorophenyl)-1-((2-cyanopropan-2-yl)sulfonyl)-3-((4-methoxybenzyl)oxy)propan-2-yl)-2-methylpropane-2-sulfinamide (1.24 g, 2.054 mmol) in MeOH (17 mL) was added HCl (4M in 1,4-dioxane, 2.57 mL, 10.3 mmol) and stirred at RT for 50 min until SM was consumed. The mixture was concentrated, diluted with DCM and neutralized with 10% $Na_2CO_3$ and 1 N NaOH. The organic phase was dried over $Na_2SO_4$, filtered and concentrated to afford a pale yellow oil. The crude material was dissolved in DCE (17 mL) and trimethylaluminum solution, 2.0 M in toluene (1.65 mL, 3.30 mmol) was added dropwise. The resulting mixture was stirred at RT for 17 h. The mixture was cooled to 0° C., diluted with saturated aqueous sodium carbonate. The aqueous layer was extracted with EtOAc (3×). The combined organic layers were washed with brine, dried over sodium sulfate and concentrated to give a light-yellow solid. A solution of the above crude material, di-tert-butyl dicarbonate (1.80 g, 8.25 mmol), DIPEA (1.44 mL, 8.25 mmol), and DMAP (0.076 g, 0.62 mmol) in DCM (10 mL) was stirred at 30° C. for 18 h. The crude product was concentrated to ~5 mL and chromatographed on silica gel, eluting with EtOAc/hexane (0-20%) to give the product of step 5 (see scheme; 1.19 g, 1.7 mmol, 82% yield) as light-yellow oil. ESI (M+Na) 723.0.

Step 6

To a solution of compound from step 5 (680 mg, 0.97 mmol) in THF (6.7 mL) at −78° C. was added lithium bis(trimethylsilyl)amide, 1.0M solution in THF (1.3 mL, 1.26 mmol) dropwise. The mixture was stirred at −78° C. for 1 h and chloro(methoxy)methane (148 µl, 1.94 mmol) in THF (0.2 mL) was added dropwise. The resulting mixture was stirred at −78° C. for 2 h. The reaction was quenched with saturated aqueous ammonium chloride at −78° C. and diluted with water and EtOAc. The layers were separated and the aqueous layer was extracted with EtOAc (2×). The combined organic extracts were dried over sodium sulfate. The crude material was dissolved in DCM and purified by chromatography on silica gel, eluting with a gradient of 0% to 20% EtOAc in hexane to give the product of step 6 (371 mg, 0.5 mmol, 51% yield) as white solid. ESI (M+Na) 765.0.

Step 7. 3-amino-4a-(5-bromo-2-fluorophenyl)-2,2-dimethyl-4a,5,7,7a-tetrahydro-2H-furo[3,4-b][1,4]thiazine 1,1-dioxide To a solution of compound from step 6 (74 mg, 0.100 mmol) in DCM (1 mL) at −78° C. was added boron tribromide, 1.0 M in dichloromethane (1 mL, 1 mmol) dropwise. The reaction mixture was stirred at −78° C. for 1.5 h, then at 0° C. for 4.5 h. The reaction was kept in refrigerator overnight. Additional $BBr_3$ (0.2 mL, 2 eq) was added and stirring was continued at 0° C. for 1.5 h. The reaction was quenched by slow addition of saturated $NaHCO_3$ solution at 0° C. The aqueous layer was back extracted with DCM (2×) and the combined organics dried ($Na_2SO_4$) and concentrated. The crude material was purified by chromatography on silica gel, eluting with a gradient of 0% to 50% EtOAc in hexane, to provide 3-amino-4a-(5-bromo-2-fluorophenyl)-2,2-dimethyl-4a,5,7,7a-tetrahydro-2H-furo[3,4-b][1,4]thiazine 1,1-dioxide (27 mg, 0.069 mmol, 69% yield) as white solid. ESI (M+1) 391.0.

Enantiomer separation was performed by Supercritical fluid chromatography employing the following conditions: Stationary phase: Chiralpak AD-H (5 um, 21 mm×25 cm, S/N=5271) with 20% organic modifier: 80% carbon dioxide. Organic modifier: Methanol with 20 mM ammonia. F=70 ml/min, T=40 C, BPR=100 bar, P=179 bar, 272 nm

Step 8. 2941851#1, (4aS,7aS)-3-amino-4a-(5-amino-2-fluorophenyl)-2,2-dimethyl-4a,5,7,7a-tetrahydro-2H-furo[3,4-b][1,4]thiazine 1,1-dioxide In an analogous sequence of reactions to those described for Intermediate 2, steps 2-3, (4aS,7aS)-3-amino-4a-(5-bromo-2-fluorophenyl)-2,2-dimethyl-4a,5,7,7a-tetrahydro-2H-furo[3,4-b][1,4]thiazine 1,1-dioxide was converted to the title compound in 61% overall yield. LC/MS (ESI⁺) m/z=328 (M+H).

2941850#1, (4aR,7aR)-3-amino-4a-(5-amino-2-fluorophenyl)-2,2-dimethyl-4a,5,7,7a-tetrahydro-2H-furo[3,4-b][1,4]thiazine 1,1-dioxide In an analogous sequence of reactions to those described for Intermediate 2, steps 2-3, (4aR,7aR)-3-amino-4a-(5- bromo-2-fluorophenyl)-2,2-dimethyl-4a,5,7,7a-tetrahydro-2H-furo[3,4-b][1,4]thiazine 1,1-dioxide was converted to the title compound in 86% overall yield. LC/MS (ESI+) m/z=328 (M+H).

Example 186

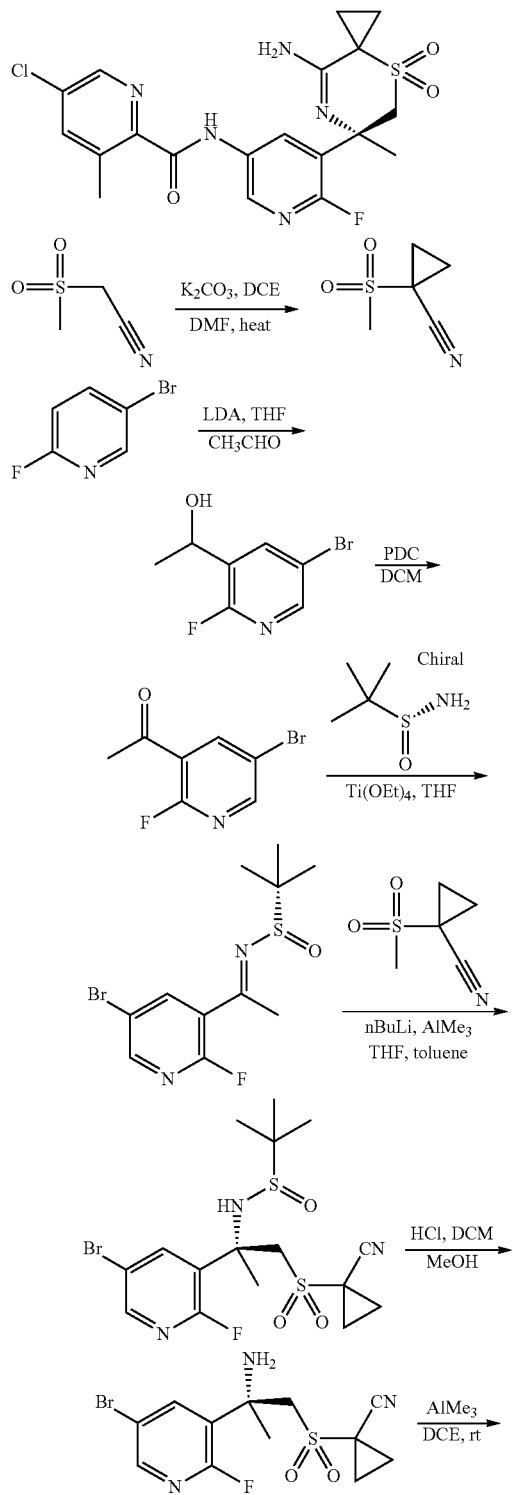

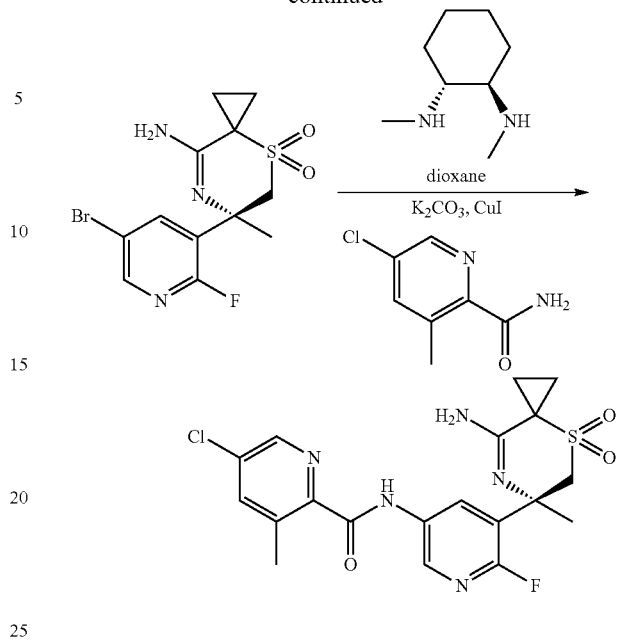

Synthesis of (R)—N-(5-(8-amino-6-methyl-4,4-dioxido-4-thia-7-azaspiro[2.5]oct-7-en-6-yl)-6-fluoropyridin-3-yl)-5-chloro-3-methylpicolinamide Step 1. 1-(methylsulfonyl)cyclopropanecarbonitrile To a solution of (methanesulphonyl) acetonitrile (10.0 g, 84 mmol, aldrich) in DMF (100 mL, aldrich) was added potassium carbonate (15.20 mL, 252 mmol, aldrich) and 1,2-dichloroethane (33.1 mL, 420 mmol). The resulting mixture was then heated at 85° C. for overnight in a pressure tube. Then, the mixture was cooled to RT and H₂O (200 mL) was added. The mixture was extracted with EtOAc (2×200 mL). The combined organic extracts were dried over MgSO₄ and concentrated. The residue was dissolved in DCM (10 mL) and the mixture was then purified by silica gel chromatography, eluent (0%-100% EtOAc/hexane) to give 6.68 g of the title compound as a light yellow solid. $^1$H NMR (400 MHz, CDCl$_3$) δ: 3.18 (s, 3H), 1.84-1.91 (m, 2H), 1.70-1.77 (m, 2H).

Step 2. 1-(5-bromo-2-fluoropyridin-3-yl)ethanol

To a solution of 5-bromo-2-fluoropyridine (9.81 mL, 85 mmol) in THF (150 mL) at −78° C. under N$_2$ was added LDA (2.0M heptane/THF/ethylbenzene (51.1 mL, 102 mmol) dropwise. After addition, the mixture was then stirred at −78° C. for 30 min. Then, a solution of acetaldehyde, anhydrous (14.35 mL, 256 mmol) in THF (50 mL) was added drowpise. After addition, the mixture was then allowed to warm to room temperature and stirred for 2 h. The mixture was quenched with saturated ammonium chloride (30 mL) at 0° C. The organic layer (THF) was collected and aqueous was extracted with EtOAc (1×100 mL). The combined organic extracts were dried over MgSO$_4$ and concentrated. The residue was then dissolved in DCM (50 mL) and combined with another batch (5.0 g scale of 5-bromo-2-fluoropyridine, processed under the same conditions). The mixture was then purified by silica gel chromatography, eluent 0%-80% EtOAc/hexanes, to give 19.19 g of the title compound as a yellow oil. MS (ESI, positive ion) m/z: 219.9. 220.90 (M+H)

Step 3. 1-(5-bromo-2-fluoropyridin-3-yl)ethanone

To a solution of pyridinium dichromate (98 g, 262 mmol) in DCM (200 mL) at 0° C. was added a solution of 1-(5-bromo-2-fluoropyridin-3-yl)ethanol (19.19 g, 87 mmol) in DCM (100 mL). After addition, the mixture was then stirred at RT 72 hr. Pyridinium dichromate (15 g) was added and the mixture was stirred at RT for an additional 12 h. Then, the mixture was filtered through celite and the solid was washed with DCM (3×200 mL). The combined filtrates were concentrated and the residue was dissolved in DCM (10 mL). The mixture was then purified by silica gel chromatography, eluent 0%-100% EtOAc/hexane, to give 11.0 g of the title compound as a white solid. MS (ESI, positive ion) m/z: 218, 219.9 (M+H)

Step 4. (R,E)-N-(1-(5-bromo-2-fluoropyridin-3-yl)ethylidene)-2-methylpropane-2-sulfinamide To a solution of 1-(5-bromo-2-fluoropyridin-3-yl)ethanone (10.93 g, 50.1 mmol) in THF (100 ml) was added (R)-(+)-2-methyl-2-propanesulfinamide (12.15 g, 100 mmol) and titanium (IV)-ethoxide (20.75 mL, 100 mmol). The resulting mixture was then heated at reflux for 1 h. The mixture was cooled to RT and brine (300 mL) was added. The mixture was stirred at RT for 15 min, then filtered and the solid was washed with DCM (2×100 mL). The organic layer was collected and the aqueous layer was dried over MgSO$_4$ and concentrated. The residue was then dissolved in DCM (10 mL) and purified by silica gel chromatography, eluent 0%-100% EtOAc/hexane, to give 14.9 g of the title compound as a yellow solid. MS (ESI, positive ion) m/z: 321, 323 (M+H).

Step 5. N—((R)-2-(5-bromo-2-fluoropyridin-3-yl)-1-((1-cyanocyclopropyl)sulfonyl)propan-2-yl)-2-methylpropane-2-sulfinamide To a solution of 1-(methylsulfonyl)cyclopropanecarbonitrile (6.63 g, 45.7 mmol) in THF (225 mL) under N$_2$ at −78° C. was added butyllithium solution, 1.6 m in hexane (28.5 mL, 45.7 mmol) dropwise. After addition, the mixture was stirred at this temperature for 20 min. Then, a solution of (R,E)-N-(1-(5-bromo-2-fluoropyridin-3-yl)ethylidene)-2-methylpropane-2-sulfinamide (9.0 g, 28.0 mmol) in toluene (90 mL) pre-treated with trimethylaluminum solution, 2.0 m in toluene (14.01 mL, 28.0 mmol) −78° C. was added to the mixture dropwise. After addition, the mixture was stirred at −78° C. for 45 min. Then, the mixture was quenched with saturated ammonium chloride (30 mL) at −78° C. and H$_2$O (100 mL) was added. The mixture was stirred at RT for 15 min. The organic layer was collected and the aqueous layer was extracted with EtOAc (1×200 mL). The combined organic extracts were dried over MgSO$_4$ and concentrated. The residue was then dissolved in MeOH and silica gel was added. The mixture was concentrated and dried in vacuo. The solid mixture was then purified by silica gel chromatography, eluent 0%-100% EtOAc/DCM) to give 6.14 g of title compound as a white solid. MS (ESI, positive ion) m/z: 466, 468 (M+H).

Step 6. (R)-1-((2-amino-2-(5-bromo-2-fluoropyridin-3yl)propyl)sulfonyl)cyclopropanecarbonitrile To a solution of N—((R)-2-(5-bromo-2-fluoropyridin-3-yl)-1-((1-cyanocyclopropyl)sulfonyl)propan-2-yl)-2-methylpropane-2-sulfinamide (5.14 g, 11.02 mmol) in MeOH (45 mL) and DCM (9.00 mL) was added hydrogen chloride, 4.0 m solution in 1,4-dioxane (8.27 mL, 33.1 mmol). After addition, the mixture was the stirred at RT for 45 min. Then, the mixture was concentrated and the crude was dissolved in DCM (100 mL), washed with a solution of NaOH (10 N, 200 mL), dried over MgSO$_4$, concentrated, and dried in vacuo to give the desired product, which was used in the next step without further purification. MS (ESI, positive ion) m/z: 362.0, 364 (M+H).

Step 7. (R)-8-amino-6-(5-bromo-2-fluoropyridin-3-yl)-6-methyl-4-thia-7-azaspiro[2.5]oct-7-ene 4,4-dioxide To a solution of (R)-1-((2-amino-2-(5-bromo-2-fluoropyridin-3yl)propyl)sulfonyl)cyclopropanecarbonitrile (3.99 g, 11.02 mmol, f) in 1,2-dichloroethane (50 mL) under N$_2$ was added trimethylaluminum solution, 2.0M in toluene (11.02 mL, 22.03 mmol) dropwise. After addition, the mixture was then stirred at room temperature for 14 h. Then, the mixture was quenched with 1N HCl solution (30 mL) at 0° C., stirred at RT for 10 min, and concentrated to remove 1,2-dichloroethane. The aqueous was adjusted to pH>10 using NaOH 1.0 N, then, extracted with DCM (2×300 mL). The combined organic extracts were dried over MgSO$_4$ and concentrated in vacuo. The crude product was crystallized using acetone/H$_2$O to give 3.3 g of the title compound as a white solid. MS (ESI, positive ion) m/z: 362.0, 364 (M+H).

Step 8. (R)—N-(5-(8-amino-6-methyl-4,4-dioxido-4-thia-7-azaspiro[2.5]oct-7-en-6-yl)-6-fluoropyridin-3-yl)-5-chloro-3-methylpicolinamide To a solution of (R)-8-amino-6-(5-bromo-2-fluoropyridin-3-yl)-6-methyl-4-thia-7-azaspiro[2.5]oct-7-ene 4,4-dioxide (200 mg, 0.552 mmol) in 1,4-dioxane (1.3 mL) was added potassium carbonate (305 mg, 2.209 mmol), copper(I) iodide (15.77 mg, 0.083 mmol), and trans-N,N'-dimethyl-1,2-cyclohexanediamine (0.013 mL, 0.083 mmol). The resulting mixture was then stirred at RT for 15 min. Then, 5-chloro-3-methylpicolinamide (188 mg, 1.104 mmol) was added and the mixture was then stirred at 105° C. for 14 h. Copper(i) iodide (15.77 mg, 0.083 mmol) and trans-N,N'-dimethyl-1,2-cyclohexanediamine (0.013 mL, 0.083 mmol) were added and the mixture was then heated at 105° C. for 14 h. The mixture was then cooled to RT, saturated NaHCO$_3$ (5 mL) was added and the mixture was extracted with DCM (2×20 mL). The combined organic extracts were dried over MgSO$_4$ and concentrated in vacuo. The residue was purified by silica gel chromatography, eluent 0%-25% MeOH/DCM to give 145 mg of the title compound as yellow solid. MS (ESI, positive ion) m/z: 452.1 (M+H). 1H NMR (DMSO-d6) d: 10.87 (s, 1H), 8.52-8.61 (m, 2H), 8.34 (dd, J=9.3, 2.6 Hz, 1H), 7.99-8.06 (m, 1H), 5.92 (s, 2H), 3.58-3.84 (m, 2H), 2.57 (s, 3H), 1.79 (dd, J=8.0, 4.7 Hz, 1H), 1.67 (s, 3H), 1.55-1.63 (m, 1H), 1.43-1.53 (m, 1H), 1.31-1.42 (m, 1H).

Example 187

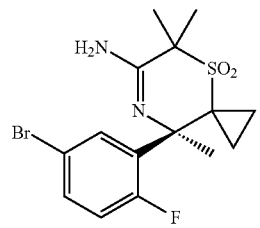 [SMILES: CC1(C)C(N)=N[C@](C)(c2cc(Br)ccc2F)C2(CC2)S1(=O)=O]

Step 1: Tert-butyl ((5R,6R)-6-allyl-5-(5-bromo-2-fluorophenyl)-2,2,5-trimethyl-1,1-dioxido-5,6-dihydro-2H-1,4-thiazin-3-yl)carbamate To (R)-tert-butyl (5-(5-bromo-2-fluorophenyl)-2,2,5-trimethyl-1,1-dioxido-5,6-dihydro-2H-1,4-thiazin-3-yl)carbamate (3.03 g, 6.54 mmol) in THF (1.0 mL) at −78° C. was added lithium diisopropylamide, 2.0M solution in THF/heptane/ethylbenzene (9.81 ml, 19.62 mmol) and the solution was stirred for 15 minutes. allyl bromide (0.849 ml, 9.81 mmol) was added and the mixture was stirred at −78° C. to −60° C. for 2 h. The reaction was quenched with water at this temperature and the mixture was extracted with DCM. The organic extract was washed with satd NaCl (3×10 mL) and dried over $Na_2SO_4$. The crude material was absorbed onto a plug of silica gel and purified by silica gel chromatography, eluting with a gradient of 5% to 40% EtOAc in hexane, to provide tert-butyl ((5R,6R)-6-allyl-5-(5-bromo-2-fluorophenyl)-2,2,5-trimethyl-1,1-dioxido-5,6-dihydro-2H-1,4-thiazin-3-yl)carbamate (1.87 g, 3.71 mmol, 56.8% yield) as white solid.

$^1$H NMR (400 MHz, CHLOδOFORM-d) δ 10.89 (s, 1H), 7.40-7.63 (m, 2H), 7.05 (dd, J=8.71, 12.23 Hz, 1H), 5.53 (dddd, J=5.77, 8.22, 10.03, 16.97 Hz, 1H), 4.80-5.04 (m, 2H), 3.85-4.09 (m, 1H), 2.87-3.10 (m, 1H), 2.22-2.32 (m, 1H), 1.97 (s, 3H), 1.87 (s, 3H), 1.76 (s, 3H), 1.47 (s, 9H).

Step 2: Tert-butyl ((5R,6R)-5-(5-bromo-2-fluorophenyl)-6-(2-hydroxyethyl)-2,2,5-trimethyl-1,1-dioxido-5,6-dihydro-2H-1,4-thiazin-3-yl)carbamate A suspension of tert-butyl ((5R,6R)-6-allyl-5-(5-bromo-2-fluorophenyl)-2,2,5-trimethyl-1,1-dioxido-5,6-dihydro-2H-1,4-thiazin-3-yl)carbamate (1.85 g, 3.67 mmol) and sodium bicarbonate (0.617 g, 7.35 mmol) in DCM and MeOH was cooled in ice-acetone bath. A mixture of $O_3$ in oxygen gas was introduced until the blue color persisted. The excess ozone was removed by purging with oxygen gas for 5 minutes. Sodium borohydride (0.209 g, 5.51 mmol) was added and the mixture was stirred at 0° C. After 30 minutes, the mixture was poured into ice-cold 1 N HCl and extracted with DCM. The extracts were washed with 1N HCl, brine, dried and concentrated to give crude tert-butyl ((5R,6R)-5-(5-bromo-2-fluorophenyl)-6-(2-hydroxyethyl)-2,2,5-trimethyl-1,1-dioxido-5,6-dihydro-2H-1,4-thiazin-3-yl)carbamate as white solid.

Step 3: 2-((2R,3R)-3-(5-bromo-2-fluorophenyl)-5-((tert-butoxycarbonyl)amino)-3,6,6-trimethyl-1,1-dioxido-3,6-dihydro-2H-1,4-thiazin-2-yl)ethyl methanesulfonate To a solution of crude tert-butyl ((5R,6R)-5-(5-bromo-2-fluorophenyl)-6-(2-hydroxyethyl)-2,2,5-trimethyl-1,1-dioxido-5,6-dihydro-2H-1,4-thiazin-3-yl)carbamate (1.862 g, 3.67 mmol) and triethylamine (1.531 ml, 11.01 mmol) in DCM at 0° C. was added methanesulfonyl chloride (0.454 ml, 5.87 mmol). The mixture was allowed to warm to RT slowly with stirring for 16 h. The reaction mixture was diluted with saturated aqueous $NH_4Cl$ and extracted with EtOAc. The organic extract was washed with saturated aqueous NaCl and concentrated in vacuo to give the crude material. The crude material was purified by silica gel chromatography, eluting with a gradient of 0% to 6% MeOH in DCM, to provide 2-((2R,3R)-3-(5-bromo-2-fluorophenyl)-5-((tert-butoxycarbonyl)amino)-3,6,6-trimethyl-1,1-dioxido-3,6-dihydro-2H-1,4-thiazin-2-yl)ethyl methanesulfonate (1.90 g, 3.25 mmol, 88% yield) as off-white solid. $^1$H NMR (400 MHz, CHLOROFORM-d) δ 10.93 (s, 1H), 7.56 (ddd, J=2.40, 4.28, 8.68 Hz, 1H), 7.50 (dd, J=2.35, 7.34 Hz, 1H), 7.10 (dd, J=8.71, 12.23 Hz, 1H), 4.48 (dt, J=3.86, 10.54 Hz, 1H), 4.30 (ddd, J=3.37, 5.70, 10.49 Hz, 1H), 4.21 (d, J=10.07 Hz, 1H), 2.88 (s, 3H), 2.46-2.63 (m, 1H), 1.92 (s, 3H), 1.90 (s, 3H), 1.79-1.87 (m, 1H), 1.76 (s, 3H), 1.47 (s, 9H).

Step 4: (R)-tert-butyl (8-(5-bromo-2-fluorophenyl)-5,5,8-trimethyl-4,4-dioxido-4-thia-7-azaspiro[2.5]oct-6-en-6-yl)carbamate To a solution of 2-((2R,3R)-3-(5-bromo-2-fluorophenyl)-5-((tert-butoxycarbonyl)amino)-3,6,6-trimethyl-1,1-dioxido-3,6-dihydro-2H-1,4-thiazin-2-yl)ethyl methanesulfonate (1.04 g, 1.776 mmol) in THF was added potassium t-butoxide (0.997 g, 8.88 mmol). The mixture was stirred at RT for 0.5 h. The reaction mixture was diluted with water, extracted with ethyl acetate. The combined extracts were washed with brine, dried, filtered and concentrated. The crude material was purified by silica gel chromatography, eluting with a gradient of 10% to 50% EtOAc in hexane, to provide the titled compound (R)-tert-butyl (8-(5-bromo-2-fluorophenyl)-5,5,8-trimethyl-4,4-dioxido-4-thia-7-azaspiro[2.5]oct-6-en-6-yl)carbamate (0.695 g, 1.420 mmol, 80% yield) as white solid. $^1$H NMR (400 MHz, CHLOROFORM-d) δ 11.13 (s, 1H), 7.50 (ddd, J=2.45, 4.16, 8.66 Hz, 1H), 7.42 (dd, J=2.45, 7.14 Hz, 1H), 7.01 (dd, J=8.66, 11.88 Hz, 1H), 2.07 (s, 3H), 1.81 (s, 3H), 1.77 (s, 3H), 1.60-1.66 (m, 2H), 1.50 (s, 9H), 0.79-0.88 (m, 2H).

Example 188

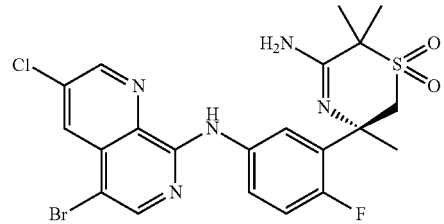 [SMILES: CC1(C)C(N)=N[C@](C)(c2cc(Nc3ncc(Br)c4cc(Cl)cnc34)ccc2F)CS1(=O)=O]

Synthesis of (R)-5-amino-3-(5-((5-bromo-3-chloro-1,7-naphthyridin-8-yl)amino)-2-fluorophenyl)-3,6,6-trimethyl-3,6-dihydro-2H-1,4-thiazine 1,1-dioxide

Step 1

A suspension of 3-chloro-1,7-naphthyridin-8(7H)-one (1.6 g, 8.86 mmol) and N-bromosuccinimide (1.892 g, 10.63 mmol) in 8 mL of DMF was stirred at rt. After 5 h, the reaction was treated with water. The solid precipitate was filtered, washed with water and ether, air-dried to give 5-bromo-3-chloro-1,7-naphthyridin-8(7H)-one (2.18 g, 8.40 mmol, 95% yield) as an off-white solid.

Step 2

A mixture of 5-bromo-3-chloro-1,7-naphthyridin-8(7H)-one (1.82 g, 7.01 mmol) and phosphorus oxychloride (6.42 ml, 70.1 mmol) was heated at 100 C for 2 h. The POCl3 was evaporated under vacuum to give crude 5-bromo-3,8-dichloro-1,7-naphthyridine (2.1 g, 7.56 mmol, 108% yield) as a tan solid which was used directly in the next step.

Step 3

To a solution of (R)-tert-butyl (5-(5-amino-2-fluorophenyl)-2,2,5-trimethyl-1,1-dioxido-5,6-dihydro-2H-1,4-thiazin-3-yl)carbamate (505 mg, 1.264 mmol) and 5-bromo-3,8-dichloro-1,7-naphthyridine (492 mg, 1.770 mmol) in 4 mL of isopropanol was added sulfuric acid, 95% (67.4 µl, 1.264 mmol) and the reaction was sealed and stirred at 95 C for 5 h. The reaction was cooled and extracted with ethyl acetate, washed with sat NaHCO$_3$, dried over Na$_2$SO$_4$, filtered and evaporated to dryness. Chromatography on silica gel (DCM/ethyl acetate=1:1 to 1:2 to ethyl acetate) gave (R)-5-amino-3-(5-((5-bromo-3-chloro-1,7-naphthyridin-8-yl)amino)-2-fluorophenyl)-3,6,6-trimethyl-3,6-dihydro-2H-1,4-thiazine 1,1-dioxide (520 mg, 0.961 mmol, 76% yield) as a light yellow solid. LC/MS (ESI$^+$) m/z=541 (M+H). $^1$H NMR (400 MHz, DMSO-d$_6$) δ=11.29 (s, 1H), 10.12 (s, 1H), 9.65 (br. s., 1H), 9.26 (br. s., 1H), 9.02 (d, J=2.2 Hz, 1H), 8.43 (d, J=2.3 Hz, 1H), 8.35 (s, 1H), 8.25 (dd, J=2.5, 7.6 Hz, 1H), 8.20-8.09 (m, 1H), 7.29 (dd, J=8.9, 12.0 Hz, 1H), 4.36 (d, J=15.5 Hz, 1H), 4.12 (d, J=15.5 Hz, 1H), 1.95 (s, 3H), 1.84 (s, 3H), 1.72 (s, 3H)

Example 189

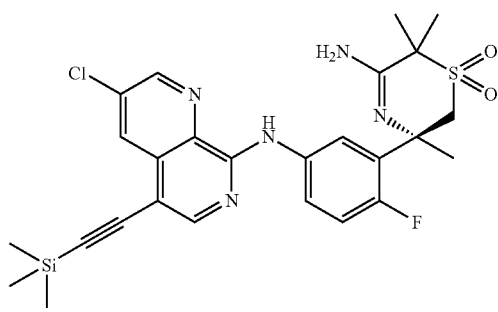 [SMILES: CC1(C)C(N)=N[C@](C)(c2cc(Nc3ncc(C#C[Si](C)(C)C)c4cc(Cl)cnc34)ccc2F)CS1(=O)=O]

Synthesis of (R)-5-amino-3-(5-((3-chloro-5-((trimethylsilyl)ethynyl)-1,7-naphthyridin-8-yl)amino)-2-fluorophenyl)-3,6,6-trimethyl 3,6-dihydro-2H-1,4-thiazine 1,1-dioxide A mixture of (R)-5-amino-3-(5-((5-bromo-3-chloro-1,7-naphthyridin-8-yl)amino)-2-fluorophenyl)-3,6,6-trimethyl-3,6-dihydro-2H-1,4-thiazine 1,1-dioxide (110 mg, 0.203 mmol), bis(triphenylphosphine)palladium(ii) dichloride (14.28 mg, 0.020 mmol), copper(i) iodide (3.87 mg, 0.020 mmol) was evacuated and back filled with N$_2$. To this was added 1 mL of dry dioxane, triethylamine (170 µl, 1.220 mmol) and (trimethylsilyl)-acetylene (43.1 µl, 0.305 mmol). The reaction was sealed and heated at 110 C for 2 h. After cooling, the solvents was evaporated under vacuum and the residue was submitted to flash column (DCM/ethyl acetate=1:1 to 1:2 to ethyl acetate) to give (R)-5-amino-3-(5-((3-chloro-5-((trimethylsilyl)ethynyl)-1,7-naphthyridin-8-yl)amino)-2-fluorophenyl)-3,6,6-trimethyl-3,6-dihydro-2H-1,4-thiazine 1,1-dioxide (80 mg, 0.143 mmol, 70.5% yield) as a light yellow solid. LC/MS (ESI$^+$) m/z=558 (M+H). $^1$H NMR (400 MHz, CHLOROFORM-d)=9.00 (s, 1H), 8.67 (d, J=2.3 Hz, 1H), 8.32 (d, J=2.2 Hz, 1H), 8.28 (s, 1H), 8.04-7.95 (m, 1H), 7.84 (d, J=4.9 Hz, 1H), 7.09 (dd, J=8.8, 11.7 Hz, 1H), 3.70-3.52 (m, 2H), 1.84 (s, 3H), 1.71 (s, 3H), 1.63 (s, 3H), 0.33 (s, 9H)

Example 190

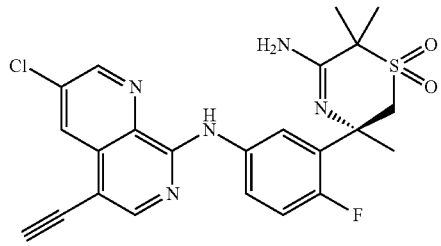 [SMILES: C#Cc1cnc(Nc2ccc(F)c([C@]3(C)CS(=O)(=O)C(C)(C)C(N)=N3)c2)c2ncc(Cl)cc12]

Synthesis of (R)-5-amino-3-(5-((3-chloro-5-ethynyl-1,7-naphthyridin-8-yl)amino)-2-fluorophenyl)-3,6,6-trimethyl-3,6-dihydro-2H-1,4-thiazine 1,1-dioxide To a solution of 70 mg (R)-5-amino-3-(5-((3-chloro-5-((trimethylsilyl)ethynyl)-1,7-naphthyridin-8-yl)amino)-2-fluorophenyl)-3,6,6-trimethyl-3,6-dihydro-2H-1,4-thiazine 1,1-dioxide (80 mg, 0.143 mmol) in 10 mL of MeOH was added potassium carbonate (84 mg, 0.610 mmol) and the reaction was stirred at rt for 2 h. The solvent was evaporated and the residue was chromatographed on silica gel (DCM/ethyl acetate=1:1 to 1:2 to ethyl acetate) to give (R)-5-amino-3-(5-((3-chloro-5-ethynyl-1,7-naphthyridin-8-yl)amino)-2-fluorophenyl)-3,6,6-trimethyl-3,6-dihydro-2H-1,4-thiazine 1,1-dioxide (60 mg, 0.123 mmol, 86% yield) as a light yellow solid. LC/MS (ESI$^+$) m/z=486 (M+H). $^1$H NMR (400 MHz, CHLOROFORM-d)=9.03 (s, 1H), 8.70 (d, J=2.3 Hz, 1H), 8.38 (d, J=2.3 Hz, 1H), 8.33 (s, 1H), 8.10-7.97 (m, 1H), 7.83 (dd, J=2.8, 7.1 Hz, 1H), 7.10 (dd, J=8.8, 11.7 Hz, 1H), 3.70-3.56 (m, 2H), 3.42 (s, 1H), 1.84 (s, 3H), 1.72 (s, 3H), 1.65 (s, 3H)

Example 191

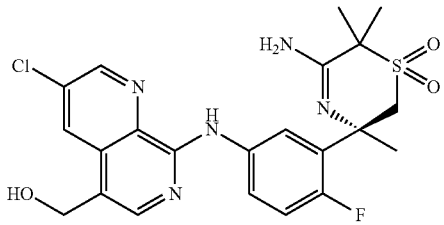 [SMILES: CC1(C)C(N)=N[C@](C)(c2cc(Nc3ncc(CO)c4cc(Cl)cnc34)ccc2F)CS1(=O)=O]

Synthesis of (R)-5-amino-3-(5-((3-chloro-5-(hydroxymethyl)-1,7-naphthyridin-8-yl)amino)-2-fluorophenyl)-3,6,6-trimethyl-3,6-dihydro-2H-1,4-thiazine 1,1-dioxide Step 1: (R)-5-amino-3-(5-((3-chloro-5-vinyl-1,7-naphthyridin-8-yl)amino)-2-fluorophenyl)-3,6,6-trimethyl-3,6-dihydro-2H-1,4-thiazine 1,1-dioxide A mixture of (R)-5-amino-3-(5-((5-bromo-3-chloro-1,7-naphthyridin-8-yl)amino)-2-fluorophenyl)-3,6,6-trimethyl- 3,6-dihydro-2H-1,4-thiazine 1,1-dioxide (150 mg, 0.277 mmol), tributyl(vinyl)tin (114 μl, 0.361 mmol) and 1,1'-bis(diphenylphosphino)ferrocene palladium(II)dichloride dichloromethane adduct (13.59 mg, 0.017 mmol) in 1 mL DMF was flushed with $N_2$ and was sealed and stirred at 110 C for 1 h. After cooling, the solvents were evaporated and the residue was submitted to flash column (DCM to DCM/EtOAc=1:1 to 1:2) to give crude (R)-5-amino-3-(5-((3-chloro-5-vinyl-1,7-naphthyridin-8-yl)amino)-2-fluorophenyl)-3,6,6-trimethyl-3,6-dihydro-2H-1,4-thiazine 1,1-dioxide (95 mg, 0.195 mmol, 70.2% yield) as a yellow gum which was used directly in the next step Step 2: (R)-8-((3-(5-amino-3,6,6-trimethyl-1,1-dioxido-3,6-dihydro-2H-1,4-thiazin-3-yl)-4-fluorophenyl)amino)-3-chloro-1,7-naphthyridine-5-carbaldehyde To a solution of crude (R)-5-amino-3-(5-((3-chloro-5-vinyl-1,7-naphthyridin-8-yl)amino)-2-fluorophenyl)-3,6,6-trimethyl-3,6-dihydro-2H-1,4-thiazine 1,1-dioxide (90 mg, 0.184 mmol) in 3 mL of MeCN and 1.5 mL of water was added 4-methylmorpholine 4-oxide (64.8 mg, 0.553 mmol), osmium tetroxide (1.407 mg, 5.53 μmol), 0.2 mL of pH=7.2 phosphate buffer and sodium periodate (197 mg, 0.922 mmol) and the reaction was stirred at rt overnight. The reaction was diluted with water, extracted with ethyl acetate, dried over $Na_2SO_4$, filtered and evaporated to dryness. Silica gel chromatography (eluent hexanes then hexanes/ethyl acetate=1:1 then 1:2 to ethyl acetate) gave (R)-8-((3-(5-amino-3,6,6-trimethyl-1,1-dioxido-3,6-dihydro-2H-1,4-thiazin-3-yl)-4-fluorophenyl)amino)-3-chloro-1,7-naphthyridine-5-carbaldehyde (50 mg, 0.102 mmol, 55.3% yield) as a yellow solid.

Step 3: (R)-5-amino-3-(5-((3-chloro-5-(hydroxymethyl)-1,7-naphthyridin-8-yl)amino)-2-fluorophenyl)-3,6,6-trimethyl-3,6-dihydro-2H-1,4-thiazine 1,1-dioxide To a solution of (R)-8-((3-(5-amino-3,6,6-trimethyl-1,1-dioxido-3,6-dihydro-2H-1,4-thiazin-3-yl)-4-fluorophenyl)amino)-3-chloro-1,7-naphthyridine-5-carbaldehyde (50 mg, 0.102 mmol) in 5 mL of MeOH was added sodium borohydride (14 mg, 0.369 mmol) and the reaction was stirred at rt overnight. The solvent was evaporated and the residue was submitted to silica gel (ethyl acetate then ethyl acetate/MeOH=10:1) to give (R)-5-amino-3-(5-((3-chloro-5-(hydroxymethyl)-1,7-naphthyridin-8-yl)amino)-2-fluorophenyl)-3,6,6-trimethyl-3,6-dihydro-2H-1,4-thiazine 1,1-dioxide (11 mg, 0.022 mmol, 22% yield) as a light-yellow film. LC/MS (ESI$^+$) m/z=492 (M+H). $^1$H NMR (400 MHz, CHLOROFORM-d) δ=8.87 (s, 1H), 8.62 (d, J=2.3 Hz, 1H), 8.35 (d, J=2.3 Hz, 1H), 8.05-7.95 (m, 2H), 7.83 (dd, J=2.4, 6.9 Hz, 1H), 7.09 (dd, J=8.8, 11.7 Hz, 1H), 4.82 (s, 2H), 3.64 (s, 2H), 1.86 (s, 3H), 1.72 (s, 3H), 1.64 (s, 3H)

Example 192

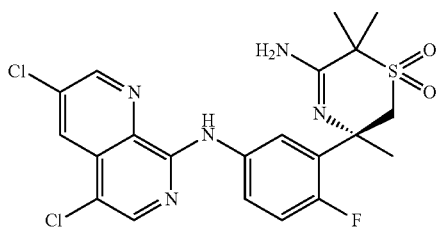 [SMILES: CC1(C)C(N)=N[C@](C)(c2cc(Nc3ncc(Cl)c4cc(Cl)cnc34)ccc2F)CS1(=O)=O]

Synthesis of (R)-5-amino-3-(5-((3,5-dichloro-1,7-naphthyridin-8-yl)amino)-2-fluorophenyl)-3,6,6-trimethyl-3,6-dihydro-2H-1,4-thiazine 1,1-dioxide Step 1: 3,5-dichloro-1,7-naphthyridin-8(7H)-one A suspension of 3-chloro-1,7-naphthyridin-8(7H)-one (540 mg, 2.99 mmol) and N-chlorosuccinimide (479 mg, 3.59 mmol) in 10 mL of MeCN was heated at 80 C. After 2 h, 100 mg more of N-chlorosuccinimide was added. After 2 h, the reaction was cooled, concentrated and was treated with water. The solid precipitate was filtered, washed with water and ether, air-dried to give 3,5-dichloro-1,7-naphthyridin-8(7H)-one (630 mg, 2.93 mmol, 98% yield) as an off-white solid.

Step 2: 3,5,8-trichloro-1,7-naphthyridine

A mixture of 3,5-dichloro-1,7-naphthyridin-8(7H)-one (430 mg, 2.000 mmol) and phosphorus oxychloride (2746 μl, 30.0 mmol) was heated at 100 C for 2 h. The POCl3 was evaporated under vacuum to give 3,5,8-trichloro-1,7-naphthyridine (510 mg, 2.184 mmol, 109% yield) as a brown solid which was used directly in the next step.

Step 3: (R)-5-amino-3-(5-((3,5-dichloro-1,7-naphthyridin-8-yl)amino)-2-fluorophenyl)-3,6,6-trimethyl-3,6-dihydro-2H-1,4-thiazine 1,1-dioxide To a solution of (R)-tert-butyl (5-(5-amino-2-fluorophenyl)-2,2,5-trimethyl-1,1-dioxido-5,6-dihydro-2H-1,4-thiazin-3-yl)carbamate (100 mg, 0.250 mmol) and 3,5,8-trichloro-1,7-naphthyridine (64.3 mg, 0.275 mmol) in 1.5 mL of isopropanol was added sulfuric acid, 95% (13.34 μl, 0.250 mmol) and the reaction was sealed and stirred at 85 C overnight. The reaction was cooled and extracted with ethyl acetate, washed with sat NaHCO3, dried over Na2SO4, filtered and evaporated to dryness. Flash column (DCM/ethyl acetate=1:1 to 1:2 to ethyl acetate) gave (R)-5-amino-3-(5-((3,5-dichloro-1,7-naphthyridin-8-yl)amino)-2-fluorophenyl)-3,6,6-trimethyl-3,6-dihydro-2H-1,4-thiazine 1,1-dioxide (90 mg, 0.181 mmol, 72.4% yield) as a light yellow solid. LC/MS (ESI$^+$) m/z=496 (M+H). $^1$H NMR (400 MHz, CHLOROFORM-d) δ=8.85 (s, 4H), 8.67 (d, J=2.2 Hz, 4H), 8.32 (d, J=2.2 Hz, 1H), 8.11 (s, 1H), 8.05-7.98 (m, 1H), 7.79 (dd, J=2.7, 7.0 Hz, 1H), 7.09 (dd, J=8.9, 11.6 Hz, 1H), 3.71-3.55 (m, 2H), 1.84 (s, 3H), 1.71 (s, 3H), 1.64 (s, 3H).

Example 193

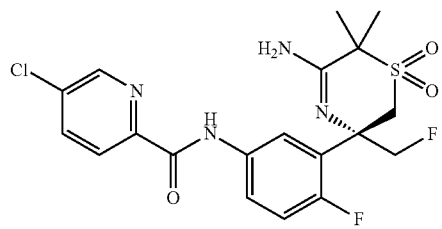 [SMILES: CC1(C)C(N)=N[C@](CF)(c2cc(NC(=O)c3ccc(Cl)cn3)ccc2F)CS1(=O)=O]

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-chloropicolinamide A mixture of (S)-5-amino-3-(5-bromo-2-fluorophenyl)-3-(fluoromethyl)-6,6-dimethyl-3,6-dihydro-2H-1,4-thiazine 1,1-dioxide (100 mg, 0.262 mmol), 5-chloropicolinamide (53.4 mg, 0.341 mmol), copper(I) iodide (9.99 mg, 0.052 mmol) and potassium carbonate (109 mg, 0.787 mmol) contained in a microwave vial was evacuated and purged with N₂ 3 times. To this was added 1.5 mL of dry dioxane under N₂, followed by N,N'-dimethylcyclohexane-1,2-diamine (14.92 mg, 0.105 mmol) and the vial was sealed and heated in an oil bath at 125° C. overnight (16 h). LCMS showed about 30% of desired conversion. It was resealed and heated at 135 C for 24 h. After cooling, the reaction mixture was filtered through a silica gel pad eluted with DCM/MeOH=10:1. After removal of the solvents under vacuum, the residue was chromatographed on silica gel (DCM/ethyl acetate=1:1 to ethyl acetate then ethyl acetate/MeOH=100:1 then 100:2 then 100:3) to give (S)—N-(3-(5-amino-3-(fluoromethyl)-6,6-dimethyl-1,1-dioxido-3,6-dihydro-2H-1,4-thiazin-3-yl)-4-fluorophenyl)-5-chloropicolinamide (40 mg, 0.088 mmol, 33.4% yield) as an off-white solid. LC/MS (ESI⁺) m/z=457 (M+H). ¹H NMR (400 MHz, CHLOROFORM-d) δ=9.82 (br. s., 1H), 8.55 (br. s., 1H), 8.23 (d, J=8.2 Hz, 1H), 8.02-7.92 (m, 1H), 7.87 (d, J=7.8 Hz, 1H), 7.72 (br. s., 1H), 7.11 (dd, J=9.0, 11.7 Hz, 1H), 4.96-4.66 (m, 1H), 4.62-4.40 (m, 1H), 3.91-3.79 (m, 1H), 3.78-3.66 (m, 1H), 1.77 (br. s., 3H), 1.66 (br. s., 3H)

Example 194

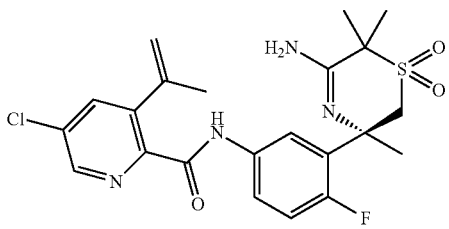 [SMILES: C=C(C)c1cc(Cl)cnc1C(=O)Nc1ccc(F)c([C@]2(C)CS(=O)(=O)C(C)(C)C(N)=N2)c1]

Synthesis of (R)—N-(3-(5-amino-3,6,6-trimethyl-1,1-dioxido-3,6-dihydro-2H-1,4-thiazin-3-yl)-4-fluorophenyl)-5-chloro-3-(prop-1-en-2-yl)picolinamide A sealable vial was charged with (R)-tert-butyl (5-(5-(3-bromo-5-chloropicolinamido)-2-fluorophenyl)-2,2,5-trimethyl-1,1-dioxido-5,6-dihydro-2H-1,4-thiazin-3-yl)carbamate (100 mg, 0.162 mmol), tetrakis(triphenylphosphine)palladium (9.35 mg, 8.09 μmol) and sodium carbonate (51.5 mg, 0.486 mmol). The vial was evacuated and backfilled with nitrogen. 1,4-Dioxane (2 mL) and water (0.6 mL) were added. The reaction mixture was purged with Nitrogen then isopropenylboronic acid pinacol ester (0.030 g, 0.178 mmol) was added and the reaction mixture was heated to 80° C. 1 hr. The reaction temperature was increased to 90° C. for an additional hour. The reaction temperature was increased to 100° C. for an additional hour. The reaction mixture was cooled to rt and partitioned between water and EtOAc. The organic extract was washed with saturated NaCl and dried over MgSO₄. The solution was concentrated under reduced pressure. The residue was purified by reversed-phase HPLC (Gemini Axia 50×250 mm C18, 10-100% CH₃CN, 0.1% TFA/H₂O, 0.1% TFA). The product containing fractions were combined and neutralized with aq. sodium carbonate solution. The product was extracted with DCM. The organic phase was dried over MgSO₄ and the solvent was removed under reduced pressure to give the title compound as yellow solid (20 mg, 0.042 mmol, 25.8% yield). M/S m/z=479.0 [M+H]⁺. Calculated for C₂₂H₂₄ClFN₄O₃S: 478.97: ¹H NMR (300 MHz, DMSO-d₆) δ ppm 1.45 (s, 3H) 1.57 (s, 3H) 1.61 (s, 3H) 2.08 (s, 3H) 3.44-3.57 (m, 1H) 3.57-3.72 (m, 1H) 5.06 (s, 1H) 5.20 (t, J=1.53 Hz, 1H) 6.02 (br. s., 2H) 7.11 (dd, J=12.13, 8.92 Hz, 1H) 7.58 (dd, J=7.45, 2.63 Hz, 1H) 7.76 (dd, J=8.84, 4.46 Hz, 1H) 7.98 (d, J=2.34 Hz, 1H) 8.62 (d, J=2.34 Hz, 1H) 10.54 (s, 1H)

Example 195

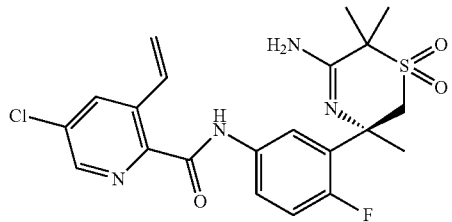 [SMILES: C=Cc1cc(Cl)cnc1C(=O)Nc1ccc(F)c([C@]2(C)CS(=O)(=O)C(C)(C)C(N)=N2)c1]

Synthesis of (R)—N-(3-(5-amino-3,6,6-trimethyl-1,1-dioxido-3,6-dihydro-2H-1,4-thiazin-3-yl)-4-fluorophenyl)-5-chloro-3-vinylpicolinamide A sealable vial was charged with (R)-tert-butyl (5-(5-(3-bromo-5-chloropicolinamido)-2-fluorophenyl)-2,2,5-trimethyl-1,1-dioxido-5,6-dihydro-2H-1,4-thiazin-3-yl)carbamate (225 mg, 0.364 mmol) and dichlorobis(triphenylphosphine)palladium(II) (30.7 mg, 0.044 mmol). The vial was evacuated and backfilled with nitrogen. 1,4-Dioxane (3 mL) was added, followed by tri-n-butyl(vinyl)tin (0.139 mL, 0.437 mmol). The reaction mixture was heated at 100° C. for 40 min. The reaction mixture was cooled to RT and partitioned between water and EtOAc. The organic phase was separated, dried over MgSO₄ and concentrated under reduced pressure. The residue was dissolved in MeOH and washed with hexanes. The MeOH containing fraction was concentrated under reduced pressure and the residue was purified by reversed-phase HPLC (Gemini Axia 50×250 mm C18, 10-100% CH₃CN, 0.1% TFA/H₂O, 0.1% TFA). The product containing fractions were combined and neutralized with aq. sodium carbonate solution. The product was extracted with DCM. The organic phase was dried over MgSO₄ and the solvent was removed under reduced pressure to give the title compound as a yellow solid (60 mg, 0.129 mmol, 35.4% yield). M/S m/z=465.0 [M+H]⁺. Calculated for C₂₁H₂₂ClFN₄O₃S: 464.9: ¹H NMR (300 MHz, DMSO-d₆) δ ppm 1.40-1.80 (m, 9H) 3.39-3.82 (m, 2H) 5.54 (d, J=11.55 Hz, 1H) 5.94-6.17 (m, 2H) 7.08-7.21 (m, 1H) 7.28 (dd, J=17.61, 11.18 Hz, 1H) 7.61-7.92 (m, 2H) 8.38 (d, J=2.34 Hz, 1H) 8.64 (d, J=2.19 Hz, 1H) 10.61 (br. s., 1H)

Example 196

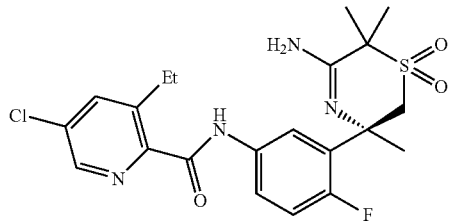 [SMILES: CCc1cc(Cl)cnc1C(=O)Nc1ccc(F)c([C@]2(C)CS(=O)(=O)C(C)(C)C(N)=N2)c1]

Synthesis of (R)—N-(3-(5-amino-3,6,6-trimethyl-1,1-dioxido-3,6-dihydro-2H-1,4-thiazin-3-yl)-4-fluorophenyl)-5-chloro-3-ethylpicolinamide A sealable vial was charged with (R)—N-(3-(5-amino-3,6,6-trimethyl-1,1-dioxido-3,6-dihydro-2H-1,4-thiazin-3-yl)-4-fluorophenyl)-5-chloro-3-vinylpicolinamide (10 mg, 0.022 mmol) and EtOAc (1.5 mL). The solution was purged with nitrogen. Palladium on activated carbon (10% wt., 12 mg, 10.75 µmol) was added. The reaction vessel was evacuated and backfilled with hydrogen. The reaction mixture was stirred at RT for 1 h. The reaction was repeated on a 30 mg scale and the crude reaction mixtures were filtered through a pad of celite. The filtrate was concentrated under reduced pressure, and the residue was purified by reversed-phase HPLC (Gemini Axia 50×250 mm C18, 10-100% $CH_3CN$, 0.1% $TFA/H_2O$, 0.1% TFA). The product containing fractions were combined and neutralized with aq. sodium carbonate solution. The product was extracted with EtOAc. The organic phase was dried over $MgSO_4$ and the solvent was removed under reduced pressure to give the title compound as a light-yellow powder (23 mg). M/S m/z=467.0 $[M+H]^+$. Calculated for $C_{21}H_{24}ClFN_4O_3S$: 466.96: $^1$H NMR (400 MHz, DMSO-$d_6$) δ ppm 1.20 (t, J=7.53 Hz, 4H) 1.46 (br. s., 3H) 1.57 (br. s., 3H) 1.62 (br. s., 3H) 2.90 (q, J=7.50 Hz, 2H) 3.46-3.58 (m, 1H) 3.63 (d, J=14.87 Hz, 1H) 6.03 (br. s., 2H) 7.00-7.25 (m, 1H) 7.66 (d, J=5.09 Hz, 1H) 7.83 (d, J=8.22 Hz, 1H) 8.02 (d, J=2.15 Hz, 1H) 8.57 (d, J=2.35 Hz, 1H) 10.54 (br. s., 1H)

Example 197

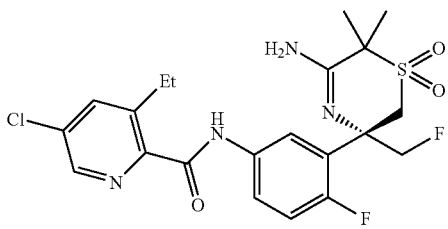 [SMILES: CCc1cc(Cl)cnc1C(=O)Nc1ccc(F)c([C@]2(CF)CS(=O)(=O)C(C)(C)C(N)=N2)c1]

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-chloro-3-ethylpicolinamide A sealable vial was charged with (S)—N-(3-(5-amino-3-(fluoromethyl)-6,6-dimethyl-1,1-dioxido-3,6-dihydro-2H-1,4-thiazin-3-yl)-4-fluorophenyl)-5-chloro-3-vinylpicolinamide (90 mg, 0.186 mmol) and EtOAc (5 mL). The solution was purged with Nitrogen. Palladium on activated carbon (10% wt.; 60 mg) was added. The reaction mixture was evacuated and backfilled with hydrogen. The reaction mixture was stirred at rt for 1 h. The reaction mixture was filtered through a pad of celite to obtain the title product as a light brown solid (65 mg, 0.134 mmol, 72%). M/S m/z=485.0 $[M+H]^+$. Calculated for $C_{21}H_{23}ClF_2N_4O_3S$: 484.9: $^1$H NMR (300 MHz, DMSO-$d_6$) δ ppm 1.21 (t, J=7.45 Hz, 3H) 1.49 (s, 3H) 1.60 (s, 3H) 2.91 (q, J=7.41 Hz, 2H) 3.52-3.66 (m, 1H) 3.67-3.83 (m, 1H) 4.34-4.51 (m, 1H) 4.53-4.76 (m, 1H) 6.32 (s, 2H) 7.17 (dd, J=12.06, 8.99 Hz, 1H) 7.74 (dd, J=7.23, 2.70 Hz, 1H) 7.81-7.94 (m, 1H) 8.02 (d, J=2.34 Hz, 1H) 8.57 (d, J=2.34 Hz, 1H) 10.57 (s, 1H)

Example 198

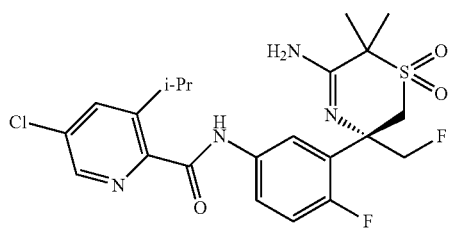 [SMILES: CC(C)c1cc(Cl)cnc1C(=O)Nc1ccc(F)c([C@]2(CF)CS(=O)(=O)C(C)(C)C(N)=N2)c1]

Synthesis of (S)—N-(3-(5-amino-3-(fluoromethyl)-6,6-dimethyl-1,1-dioxido-3,6-dihydro-2H-1,4-thiazin-3-yl)-4-fluorophenyl)-5-chloro-3-isopropylpicolinamide 2,2,2-trifluoroacetate A sealable vial was charged with (S)—N-(3-(5-amino-3-(fluoromethyl)-6,6-dimethyl-1,1-dioxido-3,6-dihydro-2H-1,4-thiazin-3-yl)-4-fluorophenyl)-5-chloro-3-(prop-1-en-2-yl)picolinamide (85 mg, 0.171 mmol) and EtOH (12.5 mL). The solution was purged with Nitrogen. Platinum on activated carbon (10 wt. %; 100 mg, 0.05 mmol) was added, followed by glacial acetic acid (0.1 mL). The reaction mixture was evacuated, backfilled with hydrogen and stirred for 1 h at RT. The reaction mixture was filtered through a pad of celite to obtain the title product as a light-brown solid (62 mg, 0.101 mmol, 59%). M/S m/z=499.1 $[M+H]^+$. Calculated for $C_{22}H_{25}ClF_2N_4O_3S$: 498.9: $^1$H NMR (300 MHz, DMSO-$d_6$) δ ppm 1.24 (d, J=8.04 Hz, 7H) 1.68 (s, 3H) 1.79 (s, 3H) 3.43-3.67 (m, 1H) 4.20 (br. s., 1H) 4.33 (br. s., 1H) 4.88 (br. s., 1H) 5.03 (br. s., 1H) 7.20-7.45 (m, 1H) 7.80 (d, J=4.97 Hz, 1H) 7.96 (d, J=8.62 Hz, 1H) 8.13 (d, J=2.19 Hz, 1H) 8.57 (d, J=2.34 Hz, 1H) 8.98-9.54 (m, 1H) 9.60-10.07 (m, 1H) 10.75 (s, 1H) 10.95-11.34 (m, 1H)

Example 199

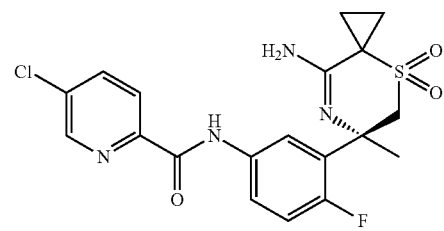 [SMILES: C[C@@]1(c2cc(NC(=O)c3ccc(Cl)cn3)ccc2F)CS(=O)(=O)C2(CC2)C(N)=N1]

Synthesis of (R)—N-(3-(8-amino-6-methyl-4,4-dioxido-4-thia-7-azaspiro[2.5]oct-7-en-6-yl)-4-fluorophenyl)-5-chloropicolinamide Step 1: (R)-tert-butyl (2-(5-bromo-2-fluorophenyl)-1-((1-cyanocyclopropyl)sulfonyl) propan-2-yl)carbamate In an analogous reaction to that described for Example 83, step 1, (R)-tert-butyl (2-(5-bromo-2-fluorophenyl)-1-((cyanomethyl)sulfonyl)propan-2-yl)carbamate (1 g, 2.297 mmol) was treated with 1,2-dibromoethane (0.277 mL, 3.22 mmol) to give the title compound (0.818 g, 1.773 mmol) as a white solid. LC/MS (ESI+) m/z=483 (M+H).

Step 2: (R)-8-amino-6-(5-bromo-2-fluorophenyl)-6-methyl-4-thia-7-azaspiro[2.5]oct-7-ene 4,4-dioxide (R)-tert-Butyl (2-(5-bromo-2-fluorophenyl)-1-((1-cyanocyclopropyl)sulfonyl)propan-2-yl)carbamate (0.660 g, 1.431 mmol) was dissolved in 4N hydrochloric acid in dioxane (7.15 mL, 28.6 mmol). The reaction mixture was stirred at 18° C. for 3 hours. The reaction mixture was concentrated under vacuum then dried further under high vacuum to yield a white solid. This was suspended in toluene (6.6 mL) then 2M trimethylaluminum in toluene (0.858 mL, 1.717 mmol) was added. The mixture was heated at 100° C. for 2 hours. The reaction mixture was cooled to 0° C. and quenched with saturated aqueous sodium carbonate. The mixture was diluted with dichloromethane and the organic layer was washed with saturated aq. sodium carbonate. The organic layer was concentrated under vacuum to yield the title compound as a pale orange foam. The crude material was purified by silica gel chromatography (0-100% 90:10:1 DCM/methanol/NH₄OH) to afford the title compound as a white foam. LC/MS (ESI+) m/z=361 (M+H).

Step 3: (R)-tert-butyl (6-(5-bromo-2-fluorophenyl)-6-methyl-4,4-dioxido-4-thia-7-azaspiro[2.5]oct-7-en-8-yl)carbamate (R)-8-Amino-6-(5-bromo-2-fluorophenyl)-6-methyl-4-thia-7-azaspiro[2.5]oct-7-ene 4,4-dioxide (0.100 g, 0.277 mmol) was dissolved in dioxane (1.0 mL) then di-tert-butyl dicarbonate (0.091 g, 0.415 mmol) and saturated aq. sodium bicarbonate (0.5 mL, 0.277 mmol) were added. The reaction mixture was stirred at 18° C. for 5 hours. The reaction mixture was diluted with ethyl acetate then washed with water and brine. The organic layer was concentrated under vacuum, then purified by silica gel chromatography (eluting with heptane/ethyl acetate, 0-70%) to afford the title compound (0.119 g, 0.258 mmol) as a white foam/colorless oil. LC/MS (ESI+) m/z=461.1 (M+H).

Step 4: (R)—N-(3-(8-amino-6-methyl-4,4-dioxido-4-thia-7-azaspiro[2.5]oct-7-en-6-yl)-4-fluorophenyl)-5-chloropicolinamide In an analogous reaction to that described in Method C, (R)-8-amino-6-(5-bromo-2-fluorophenyl)-6-methyl-4-thia-7-azaspiro[2.5]oct-7-ene 4,4-dioxide (0.050 g, 0.138 mmol) was treated with 5-chloropicolinamide (0.028 g, 0.180 mmol) to give the title compound (0.033 g, 0.076 mmol) as a white solid. LC/MS (ESI+) m/z=437.1 (M+H).

Intermediate 22

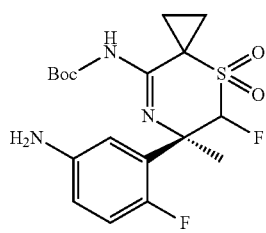 [SMILES: CC(C)(C)OC(=O)NC1=N[C@](C)(c2cc(N)ccc2F)C(F)S(=O)(=O)C12CC2]

Synthesis of Tert-butyl ((6R)-6-(5-amino-2-fluorophenyl)-5-fluoro-6-methyl-4,4-dioxido-4-thia-7-azaspiro[2.5]oct-7-en-8-yl)carbamate Step 1: 1-(methylsulfonyl)cyclopropanecarbonitrile (Methanesulfonyl) acetonitrile (10.00 g, 84 mmol) was dissolved in DMF (24 mL) then cooled to 0° C. Potassium carbonate (24.36 g, 176 mmol) was added followed by dropwise addition of 1,2-dibromoethane (7.16 mL, 83 mmol) via syringe. The mixture was stirred at 0° C. for 15 minutes then warmed to 18° C. and stirred for 3 hours. The reaction mixture was diluted with ethyl acetate then washed with water and brine. The organic layer was dried over sodium sulfate and concentrated under vacuum to yield the title compound (8.48 g, 58.4 mmol) as a brown waxy solid.

Step 2: N—((R)-2-(5-bromo-2-fluorophenyl)-1-((1-cyanocyclopropyl)sulfonyl)propan-2-yl)-2-methylpropane-2-sulfinamide In an analogous reaction to that described for Intermediate 1, step 3, (R,E)-N-(1-(5-bromo-2-fluorophenyl)ethylidene)-2-methylpropane-2-sulfinamide (5.00 g, 15.61 mmol) (from KR01, step 2) was treated with 1-(methylsulfonyl)cyclopropane carbonitrile (4.31 g, 29.7 mmol) to give the title compound (4.03 g, 8.66 mmol) as an off-white foam/oil. LC/MS (ESI+) m/z=465.0 (M+H).

Step 3: (R)-1-((2-amino-2-(5-bromo-2-fluorophenyl)propyl)sulfonyl)cyclopropane carbonitrile hydrochloride N—((R)-2-(5-Bromo-2-fluorophenyl)-1-((1-cyanocyclopropyl)sulfonyl)propan-2-yl)-2-methylpropane-2-sulfinamide (4.03 g, 8.66 mmol) was dissolved in DCM (17 mL) then cooled to 0° C. and 4N HCl in dioxane (12.99 mL, 52.0 mmol) was added. The reaction mixture was warmed to 18° C. and stirred for 4.5 hours. The reaction mixture was concentrated under vacuum and the remaining solid was further dried under high vacuum to give the title compound (3.61 g, 9.08 mmol) as a white solid. LC/MS (ESI+) m/z=361.0 (M+H).

Step 4: (R)-8-amino-6-(5-bromo-2-fluorophenyl)-6-methyl-4-thia-7-azaspiro[2.5]oct-7-ene 4,4-dioxide (R)-1-((2-Amino-2-(5-bromo-2-fluorophenyl)propyl)sulfonyl)cyclopropanecarbonitrile hydrochloride (3.51 g, 8.83 mmol) was suspended in toluene (35 mL) then added 2M trimethylaluminum in toluene (5.30 mL, 10.59 mmol) was added. The mixture was heated at 100° C. for 3 hours. The reaction mixture was cooled to 0° C. and quenched with saturated aqueous sodium carbonate (6.5 mL) and diluted with ethyl acetate then washed with water and brine. The organic layer was concentrated under vacuum then purified by silica gel chromatography (eluting with 0-100% 90:10:1 DCM/methanol/NH₄OH) to afford the title compound as a yellow oil/foam. LC/MS (ESI+) m/z=361.0 (M+H).

Step 5: (R)-tert-butyl (6-(5-bromo-2-fluorophenyl)-6-methyl-4,4-dioxido-4-thia-7-azaspiro[2.5]oct-7-en-8-yl)carbamate (R)-8-Amino-6-(5-bromo-2-fluorophenyl)-6-methyl-4-thia-7-azaspiro[2.5]oct-7-ene 4,4-dioxide (2.64 g, 7.31 mmol) was dissolved in dioxane (26 mL) then di-tert-butyl dicarbonate (2.393 g, 10.96 mmol) and saturated aq. sodium bicarbonate (10.0 mL, 7.31 mmol) were added. The reaction mixture was stirred at 18° C. for 3 hours. The reaction mixture was diluted with ethyl acetate then washed with water and brine. The organic layer was concentrated under vacuum then purified by silica gel chromatography (eluting with heptane/ethyl acetate, 0-70%) to afford the title compound (2.96 g, 6.42 mmol) as a white solid. LC/MS (ESI$^+$) m/z=461.0 (M+H).

Step 6: tert-butyl ((6R)-6-(5-bromo-2-fluorophenyl)-5-fluoro-6-methyl-4,4-dioxido-4-thia-7-azaspiro[2.5]oct-7-en-8-yl)carbamate A solution of 1M potassium tert-butoxide in THF (9.35 mL, 9.35 mmol) was diluted with THF (22 mL), cooled to −78° C. then diisopropylamine (1.332 mL, 9.35 mmol) was added dropwise via syringe. The mixture was stirred at −78° C. for 15 minutes. 2.82M N-Butyllithium in heptane (3.08 mL, 8.68 mmol) was added dropwise to this solution via syringe and the mixture was stirred at −78° C. for 45 minutes. A solution of (R)-tert-butyl (6-(5-bromo-2-fluorophenyl)-6-methyl-4,4-dioxido-4-thia-7-azaspiro[2.5]oct-7-en-8-yl)carbamate (1.54 g, 3.34 mmol) in THF (3 mL) was added dropwise via syringe and the mixture was stirred at −78° C. for 45 minutes. A solution of N-fluorobenzenesulfonimide (2.95 g, 9.35 mmol) in THF (9.5 mL) was added very quickly dropwise via syringe. The mixture was stirred at −78° C. for 2.5 hours. The reaction was quenched with saturated aq. sodium bicarbonate (~12 mL) at −78° C. then warmed to room temperature. The reaction mixture was diluted with ethyl acetate then washed with water and brine. The organic layer was concentrated under vacuum then purified by silica gel chromatography (eluting with heptane/MTBE, 0-60%) to afford the title compound (0.805 g, 1.679 mmol) as a white foam/colorless oil in an ~3:1 mixture of diastereoisomers. LC/MS (ESI$^+$) m/z=422.8 (M+H) as the Boc-acid.

Step 7: tert-butyl ((6R)-6-(5-amino-2-fluorophenyl)-5-fluoro-6-methyl-4,4-dioxido-4-thia-7-azaspiro[2.5]oct-7-en-8-yl)carbamate Tert-Butyl ((6R)-6-(5-bromo-2-fluorophenyl)-5-fluoro-6-methyl-4,4-dioxido-4-thia-7-azaspiro[2.5]oct-7-en-8-yl)carbamate (0.400 g, 0.834 mmol) was dissolved in ethanol (2 mL) and water (0.800 mL) then (+)-sodium 1-ascorbate (0.066 g, 0.334 mmol), sodium azide (0.434 g, 6.68 mmol), copper(I) iodide (0.064 g, 0.334 mmol) and trans-N,N'-dimethylcyclohexane-1,2-diamine (0.105 mL, 0.668 mmol) were added. The reaction mixture was heated at 50° C. in a Biotage microwave reactor for 40 minutes. The reaction mixture was diluted with EtOAc then washed with water and brine. The organic layer was concentrated under vacuum to afford 429 mg of a mixture of azide and aniline as a light orange oil.

A mixture of tert-butyl ((6R)-6-(5-amino-2-fluorophenyl)-5-fluoro-6-methyl-4,4-dioxido-4-thia-7-azaspiro[2.5]oct-7-en-8-yl)carbamate and tert-butyl ((6R)-6-(5-azido-2-fluorophenyl)-5-fluoro-6-methyl-4,4-dioxido-4-thia-7-azaspiro[2.5]oct-7-en-8-yl)carbamate (0.368 g, 0.834 mmol) was dissolved in THF (3.6 mL) and water (1.2 mL) then 1M trimethylphosphine in THF (0.834 mL, 0.834 mmol) was added. The mixture was stirred at 18° C. for 1 hour. The reaction mixture was diluted with ethyl acetate then washed with water and brine. The organic layer was concentrated under vacuum to give 409 mg of crude material as an orange oil which was purified by silica gel chromatography (eluting with heptane/ethyl acetate, 0-80%) to afford the title compound (0.256 g, 0.616 mmol) as a white foam. LC/MS (ESI$^+$) m/z=416.1 (M+H).

Example 200

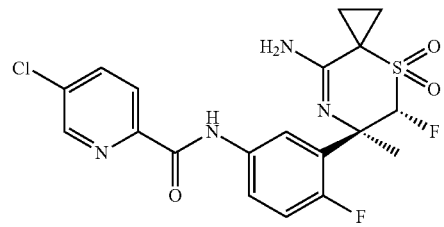 [SMILES: C[C@]1(c2cc(NC(=O)c3ccc(Cl)cn3)ccc2F)N=C(N)C2(CC2)S(=O)(=O)[C@@H]1F]

Synthesis of N-(3-((5S,6R)-8-amino-5-fluoro-6-methyl-4,4-dioxido-4-thia-7-azaspiro[2.5]oct-7-en-6-yl)-4-fluorophenyl)-5-chloropicolinamide Intermediate 22 (0.085 g, 0.205 mmol) and 5-chloro-2-pyridinecarboxylic acid (0.039 g, 0.246 mmol) were dissolved in DMF (1 mL) then pyridine (0.050 mL, 0.614 mmol) was added, followed by HATU (0.117 g, 0.307 mmol). The reaction mixture was stirred at 18° C. for 3 hours. The reaction mixture was cooled to 0° C. then diluted with water. A precipitate formed which was collected on a glass frit, washing well with additional water. The solid was dried under high vacuum. The crude material (117 mg) was dissolved in dichloromethane (1.5 mL) then TFA (0.400 mL) was added. The mixture was stirred for 1 hour at 18° C. The reaction mixture was diluted with dichloromethane then washed with sat. aq. sodium bicarbonate and brine. The organic layer was concentrated under vacuum and was purified and diastereoisomers separated by silica gel chromatography (eluting with 25-100% 90:10:1 dichloromethane/methanol/NH$_4$OH in 3:2 heptane/ethyl acetate) to afford the title compound (0.049 g, 0.108 mmol) as an off-white solid as the major diastereoisomer. LC/MS (ESI$^+$) m/z=455.0 (M+H).

Example 201

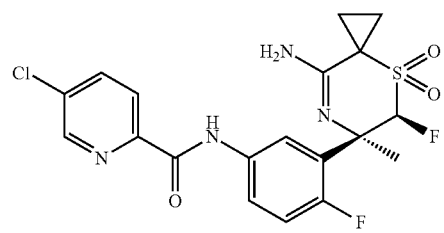 [SMILES: C[C@]1(c2cc(NC(=O)c3ccc(Cl)cn3)ccc2F)N=C(N)C2(CC2)S(=O)(=O)[C@H]1F]

Synthesis of N-(3-((5R,6R)-8-amino-5-fluoro-6-methyl-4,4-dioxido-4-thia-7-azaspiro[2.5]oct-7-en-6-yl)-4-fluorophenyl)-5-chloropicolinamide Purification and separation of Example 200 as previously described afforded the title compound (0.011 g, 0.024 mmol) as a white solid as the minor diastereoisomer. LC/MS (ESI$^+$) m/z=455.0 (M+H).

Example 202

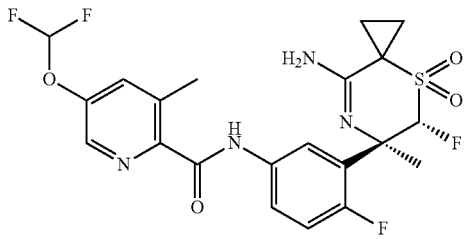 [SMILES: Cc1cc(OC(F)F)cnc1C(=O)Nc1ccc(F)c([C@@]2(C)N=C(N)C3(CC3)S(=O)(=O)[C@@H]2F)c1]

Synthesis of N-(3-((5S,6R)-8-amino-5-fluoro-6-methyl-4,4-dioxido-4-thia-7-azaspiro[2.5]oct-7-en-6-yl)-4-fluorophenyl)-5-(difluoromethoxy)-3-methyl-picolinamide The title compound was prepared as described for Example 200 using Intermediate 22 (0.084 g, 0.202 mmol) and 5-(difluoromethoxy)-3-methylpicolinic acid (0.049 g, 0.243 mmol). The mixture of diastereoisomers was purified and separated by silica gel chromatography (eluting with 15-100% 90:10:1 dichloromethane/methanol/NH$_4$OH in 3:2 heptane/ethyl acetate) to afford the title compound (0.061 g, 0.122 mmol) as an off-white solid as the major diastereoisomer. LC/MS (ESI$^+$) m/z=501.0 (M+H).

Example 203

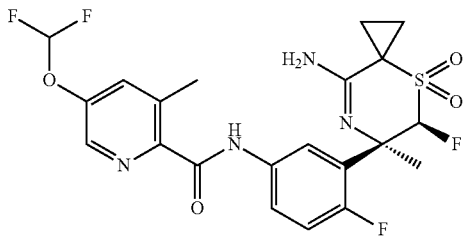 [SMILES: Cc1cc(OC(F)F)cnc1C(=O)Nc1ccc(F)c([C@@]2(C)N=C(N)C3(CC3)S(=O)(=O)[C@H]2F)c1]

Synthesis of N-(3-((5R,6R)-8-amino-5-fluoro-6-methyl-4,4-dioxido-4-thia-7-azaspiro[2.5]oct-7-en-6-yl)-4-fluorophenyl)-5-(difluoromethoxy)-3-methyl-picolinamide Purification and separation of Example 202 as previously described afforded the title compound (0.016 g, 0.032 mmol) as a pale yellow solid as the minor diastereoisomer. LC/MS (ESI$^+$) m/z=501.0 (M+H).

Example 204

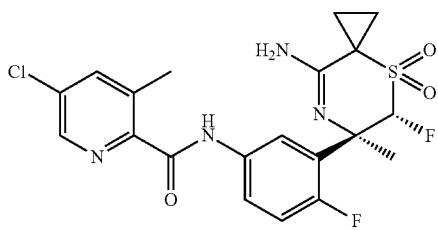 [SMILES: Cc1cc(Cl)cnc1C(=O)Nc1ccc(F)c([C@@]2(C)N=C(N)C3(CC3)S(=O)(=O)[C@@H]2F)c1]

Synthesis of N-(3-((5S,6R)-8-amino-5-fluoro-6-methyl-4,4-dioxido-4-thia-7-azaspiro[2.5]oct-7-en-6-yl)-4-fluorophenyl)-5-chloro-3-methylpicolinamide

Step 1: (6R)-8-amino-6-(5-bromo-2-fluorophenyl)-5-fluoro-6-methyl-4-thia-7-azaspiro[2.5]oct-7-ene 4,4-dioxide Intermediate 22 (0.077 g, 0.161 mmol) was dissolved in DCM (1.0 mL) then trifluoroacetic acid (0.012 mL, 0.161 mmol) was added. The reaction mixture was stirred at 18° C. for 2 hours. Added more trifluoroacetic acid (0.25 mL) and continued stirring at 18° C. overnight. The reaction mixture was diluted with dichloromethane then washed with sat. aq. sodium bicarbonate and water. The organic layer was dried over sodium sulfate and concentrated under vacuum to afford the title compound (0.062 g, 0.163 mmol) as a pale yellow solid. LC/MS (ESI$^+$) m/z=378.9 (M+H).

Step 2: N-(3-((5S,6R)-8-amino-5-fluoro-6-methyl-4,4-dioxido-4-thia-7-azaspiro[2.5]oct-7-en-6-yl)-4-fluorophenyl)-5-chloro-3-methylpicolinamide The title compound was prepared as described in Method C using (6R)-8-amino-6-(5-bromo-2-fluorophenyl)-5-fluoro-6-methyl-4-thia-7-azaspiro[2.5]oct-7-ene 4,4-dioxide (0.062 g, 0.163 mmol) and 5-chloro-3-methylpicolinamide (0.031 g, 0.180 mmol). The mixture of diastereomers was separated by chiral SFC (OJ-H column(2×25 cm), eluent CO$_2$, modified with 17% methanol w/0.2% diethylamine as the eluent) to afford the title compound (0.0088 g, 0.019 mmol) as an off-white solid as the major diastereoisomer. LC/MS (ESI$^+$) m/z=469.0 (M+H). $^1$H NMR (400 MHz, CHLOROFORM-d) δ ppm 1.59-1.81 (m, 3H) 1.84 (d, J=3.23 Hz, 3H) 1.90 (m, J=11.90, 4.10 Hz, 1H) 2.78 (s, 3H) 5.88 (dd, J=48.00, 4.00 Hz, 1H) 7.11 (dd, J=11.88, 8.85 Hz, 1H) 7.52 (dd, J=6.36, 2.05 Hz, 1H) 7.64 (d, J=1.76 Hz, 1H) 7.95 (ddd, J=8.88, 4.23, 2.54 Hz, 1H) 8.38 (d, J=2.15 Hz, 1H) 10.00 (br. s, 1H).

Example 205

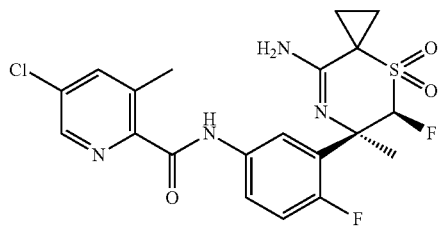 [SMILES: Cc1cc(Cl)cnc1C(=O)Nc1ccc(F)c([C@@]2(C)N=C(N)C3(CC3)S(=O)(=O)[C@H]2F)c1]

Synthesis of N-(3-((5R,6R)-8-amino-5-fluoro-6-methyl-4,4-dioxido-4-thia-7-azaspiro[2.5]oct-7-en-6-yl)-4-fluorophenyl)-5-chloro-3-methylpicolinamide Purification and separation of Example 204 as previously described afforded the title compound (0.0055 g, 0.012 mmol) as an off-white solid as the minor diastereoisomer. LC/MS (ESI$^+$) m/z=469.0 (M+H). $^1$H NMR (400 MHz, CHLOROFORM-d) δ ppm 1.59-1.70 (m, 2H) 1.80-1.92 (m, 2H) 1.94 (s, 3H) 2.80 (s, 3H) 5.75 (d, J=44.00 Hz, 1H) 7.11 (dd, J=11.74, 8.90 Hz, 1H) 7.65 (dd, J=2.15, 0.59 Hz, 1H)

7.72 (dd, J=6.94, 2.64 Hz, 1H) 7.98 (ddd, J=8.80, 4.25, 2.79 Hz, 1H) 8.38 (d, J=2.15 Hz, 1H) 10.02 (br. s, 1H).

Example 206

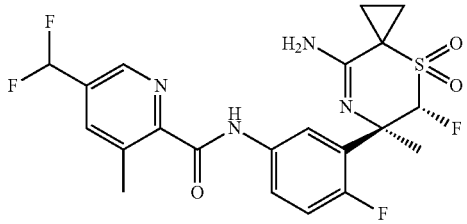 [SMILES: Cc1cc(C(F)F)cnc1C(=O)Nc1ccc(F)c([C@@]2(C)N=C(N)C3(CC3)S(=O)(=O)[C@@H]2F)c1]

Synthesis of N-(3-((5S,6R)-8-amino-5-fluoro-6-methyl-4,4-dioxido-4-thia-7-azaspiro[2.5]oct-7-en-6-yl)-4-fluorophenyl)-5-(difluoromethyl)-3-methylpicolinamide The title compound was prepared as described for Example 199 using Intermediate 22 (0.080 g, 0.193 mmol) and 5-(difluoromethyl)-3-methylpicolinic acid (0.043 g, 0.231 mmol). The mixture of diastereoisomers was purified and separated by silica gel chromatography (eluting with 15-100% 90:10:1 dichloromethane/methanol/NH$_4$OH in 3:2 heptane/ethyl acetate) to afford the title compound (0.058 g, 0.120 mmol) as a white solid and the major diastereoisomer. LC/MS (ESI$^+$) m/z=485.0 (M+H). $^1$H NMR (400 MHz, CHLOROFORM-d) δ ppm 1.58-1.78 (m, 3H), 1.84 (dd, J=3.91, 0.98 Hz, 3H), 1.86-1.93 (m, 1H), 2.79-2.89 (m, 3H), 5.87 (dd, J=44.00, 4.00 Hz, 1H), 6.76 (t, J=56.00 Hz, 1H), 7.12 (dd, J=11.88, 8.85 Hz, 1H), 7.50-7.59 (m, 1H), 7.77 (s, 1H), 7.94 (ddd, J=8.83, 4.28, 2.84 Hz, 1H), 8.57 (s, 1H), 10.12 (s, 1H).

Example 207

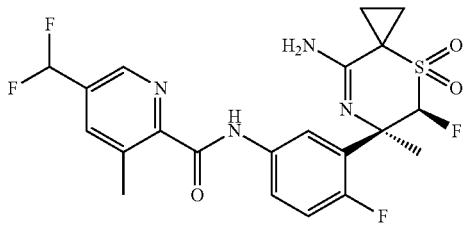 [SMILES: Cc1cc(C(F)F)cnc1C(=O)Nc1ccc(F)c([C@@]2(C)N=C(N)C3(CC3)S(=O)(=O)[C@H]2F)c1]

Synthesis of N-(3-((5R,6R)-8-amino-5-fluoro-6-methyl-4,4-dioxido-4-thia-7-azaspiro[2.5]oct-7-en-6-yl)-4-fluorophenyl)-5-(difluoromethyl)-3-methylpicolinamide Purification and separation of Example 206 as previously described afforded the title compound (0.019 g, 0.039 mmol) as a white solid as the minor diastereoisomer. LC/MS (ESI$^+$) m/z=485.0 (M+H). $^1$H NMR (400 MHz, CHLOROFORM-d) δ ppm 1.63-1.71 (m, 1H) 1.73-1.82 (m, 1H) 1.82-1.95 (m, 2H) 1.96 (s, 3H) 2.86 (s, 3H) 5.74 (d, J=44.00 Hz, 1H) 6.76 (t, J=56.00 Hz, 1H) 7.13 (dd, J=11.74, 8.80 Hz, 1H) 7.72-7.83 (m, 2H) 8.00 (ddd, J=8.80, 4.30, 2.84 Hz, 1H) 8.58 (s, 1H) 10.17 (br. s, 1H).

Example 208

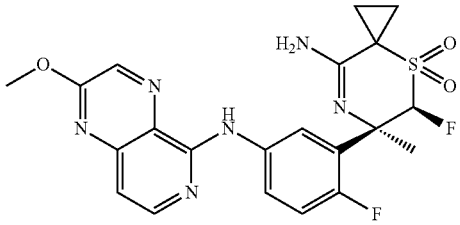 [SMILES: COc1cnc2c(Nc3ccc(F)c([C@@]4(C)N=C(N)C5(CC5)S(=O)(=O)[C@H]4F)c3)nccc2n1]

Synthesis of (5R,6R)-8-amino-5-fluoro-6-(2-fluoro-5-((2-methoxypyrido[3,4-b]pyrazin-5-yl)amino)phenyl)-6-methyl-4-thia-7-azaspiro[2.5]oct-7-ene 4,4-dioxide Intermediate 22 (0.050 g, 0.120 mmol) was suspended in 2,2,2-trifluoroethanol (1 mL) then Intermediate 10 (0.024 g, 0.120 mmol), p-toluenesulfonic acid monohydrate (0.023 g, 0.120 mmol) and silver trifluoromethanesulfonate (0.031 g, 0.120 mmol) were added. The reaction mixture was heated at 90° C. for 2.5 hours. The mixture was diluted with dichloromethane then washed with sat. aq. sodium bicarbonate. The organic layer was concentrated under vacuum, and was purified and separated by silica gel chromatography (eluting with 15-100% 90:10:1 dichloromethane/methanol/NH$_4$OH in 3:2 heptane/ethyl acetate) to afford the title compound (0.0053 g, 0.011 mmol) as a yellow solid and the minor diastereoisomer. LC/MS (ESI$^+$) m/z=475.2

$^1$H NMR (400 MHz, CHLOROFORM-d) δ ppm 1.59-1.63 (m, 2H) 1.81-1.86 (m, 1H) 1.86-1.92 (m, 1H) 1.95 (s, 3H) 4.13 (s, 3H) 5.76 (d, J=48.00 Hz, 1H) 7.05 (d, J=5.87 Hz, 1H) 7.12 (dd, J=11.74, 8.90 Hz, 1H) 7.81 (dd, J=6.85, 2.84 Hz, 1H) 8.16-8.26 (m, 2H) 8.29 (s, 1H) 8.61 (br. s, 1H).

Example 209

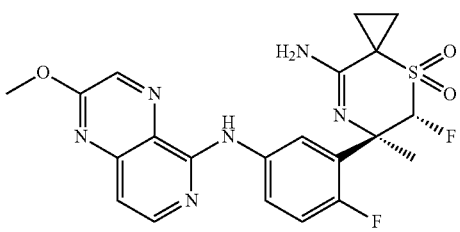 [SMILES: COc1cnc2c(Nc3ccc(F)c([C@@]4(C)N=C(N)C5(CC5)S(=O)(=O)[C@@H]4F)c3)nccc2n1]

Synthesis of (5S,6R)-8-amino-5-fluoro-6-(2-fluoro-5-((2-methoxypyrido[3,4-b]pyrazin-5-yl)amino)phenyl)-6-methyl-4-thia-7-azaspiro[2.5]oct-7-ene 4,4-dioxide Purification and separation of Example 208 as previously described afforded impure material that was further purified by preparative TLC (Whatman 20×20 cm plate; 1000 microns), eluting with 1:1 90/10/1 dichloromethane/methanol/NH$_4$OH: 3:2 heptane/ethyl acetate. The title compound (0.0081 g, 0.017 mmol) was isolated as a yellow solid as the major diastereoisomer. LC/MS (ESI$^+$) m/z=475.2 (M+H). $^1$H NMR (400 MHz, CHLOROFORM-d) δ ppm 1.69-1.88

(m, 3H) 1.91 (d, J=3.23 Hz, 3H) 1.92-1.97 (m, 1H) 4.11 (s, 3H) 5.95 (dd, J=48.00, 4.00 Hz, 1H) 7.03 (d, J=5.97 Hz, 1H) 7.12 (dd, J=11.84, 8.90 Hz, 1H) 7.84-7.93 (m, 1H) 7.99-8.07 (m, 1H) 8.22 (d, J=5.97 Hz, 1H) 8.27 (s, 1H) 8.61 (br. s, 1H).

Example 210

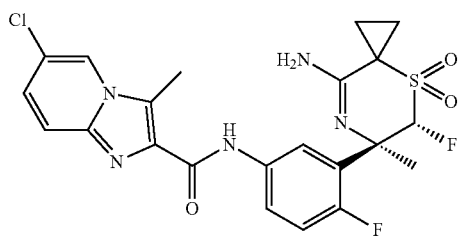 [SMILES: Cc1c(C(=O)Nc2ccc(F)c([C@@]3(C)N=C(N)C4(CC4)S(=O)(=O)[C@@H]3F)c2)nc2ccc(Cl)cn12]

Synthesis of N-(3-((5S,6R)-8-amino-5-fluoro-6-methyl-4,4-dioxido-4-thia-7-azaspiro[2.5]oct-7-en-6-yl)-4-fluorophenyl)-6-chloro-3-methylimidazo[1,2-a]pyridine-2-carboxamide The title compound was prepared as described for Example 199 using Intermediate 22 (0.052 g, 0.125 mmol) and 6-chloro-3-methylimidazo[1,2-a]pyridine-2-carboxylic acid (0.029 g, 0.138 mmol). The mixture of diastereoisomers was purified and separated by silica gel chromatography (eluting with 15-100% 90:10:1 dichloromethane/methanol/NH$_4$OH in 3:2 heptane/ethyl acetate) to afford the title compound (0.024 g, 0.047 mmol) as a white solid and the major diastereoisomer. LC/MS (ESI$^+$) m/z=508.0 (M+H). $^1$H NMR (400 MHz, CHLOROFORM-d) δ ppm 1.61-1.76 (m, 3H) 1.78-1.93 (m, 4H) 2.82 (s, 3H) 5.86 (dd, J=44.00, 4.00 Hz, 1H) 7.10 (dd, J=11.88, 8.85 Hz, 1H) 7.22 (dd, J=9.63, 1.91 Hz, 1H) 7.43-7.50 (m, 1H) 7.61 (dd, J=7.04, 2.74 Hz, 1H) 7.88 (ddd, J=8.85, 4.21, 2.79 Hz, 1H) 7.96 (dd, J=1.81, 0.73 Hz, 1H) 9.34 (br. s, 1H).

Example 211

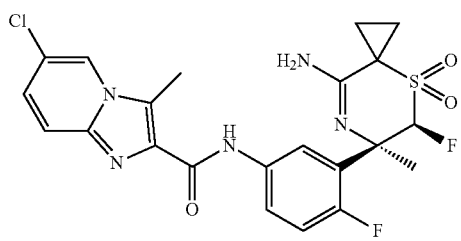 [SMILES: Cc1c(C(=O)Nc2ccc(F)c([C@@]3(C)N=C(N)C4(CC4)S(=O)(=O)[C@H]3F)c2)nc2ccc(Cl)cn12]

Synthesis of N-(3-((5R,6R)-8-amino-5-fluoro-6-methyl-4,4-dioxido-4-thia-7-azaspiro[2.5]oct-7-en-6-yl)-4-fluorophenyl)-6-chloro-3-methylimidazo[1,2-a]pyridine-2-carboxamide Purification and separation of Example 210 as previously described afforded impure material that was further purified by reverse phase prep HPLC eluting with 0.1% NH$_4$OH in ACN and water. The title compound (0.00469 g, 9.23 µmol) was isolated as a white solid and the minor diastereoisomer. LC/MS (ESI$^+$) m/z=508.0 (M+H). $^1$H NMR (500 MHz, DMSO-d$_6$) δ ppm 1.44-1.58 (m, 3H) 1.75 (s, 3H) 2.07-2.12 (m, 1H) 2.80 (s, 3H) 5.92-6.11 (m, 3H) 7.16 (dd, J=11.51, 8.90 Hz, 1H) 7.42 (dd, J=9.64, 1.84 Hz, 1H) 7.68 (d, J=9.67 Hz, 1H) 7.88-7.92 (m, 1H) 7.94-7.97 (m, 1H) 8.68 (br. s, 1H) 10.12 (s, 1H).

Example 212

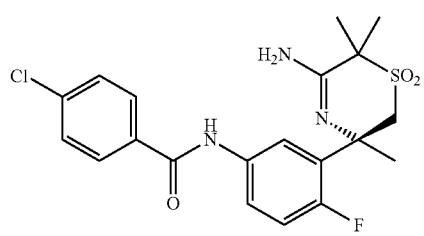

Synthesis of (R)—N-(3-(5-amino-3,6,6-trimethyl-1,1-dioxido-3,6-dihydro-2H-1,4-thiazin-3-yl)-4-fluorophenyl)-4-chlorobenzamide To (R)-tert-butyl (5-(5-amino-2-fluorophenyl)-2,2,5-trimethyl-1,1-dioxido-5,6-dihydro-2H-1,4-thiazin-3-yl)carbamate (0.1037 g, 0.260 mmol) in DCM at RT, were added pyridine (63.5 ml, 779 mmol), and 4-pyrrolidinopyridine (3.85 mg, 0.026 mmol). 4-Chlorobenzoyl chloride (0.037 ml, 0.286 mmol) was added and the mixture was allowed to stir for 1.5 h, then volatiles stripped at reduced pressure. The residue was taken up in DCM, trifluoroacetic acid (6.00 µl, 0.078 mmol) was added, and the mixture was stirred at RT for 1.5 h. The product was adsorbed onto a plug of silica gel and chromatographed on silica gel, eluting with a gradient of 0.5% to 10% MeOH in DCM, to provide (R)—N-(3-(5-amino-3,6,6-trimethyl-1,1-dioxido-3,6-dihydro-2H-1,4-thiazin-3-yl)-4-fluorophenyl)-4-chlorobenzamide (0.0370 g, 0.084 mmol, 32.5% yield). LC/MS (ESI$^+$) m/z=(M+H=437.9). $^1$H NMR (300 MHz, CHLOROFORM-d) δ ppm 1.62 (s, 3H) 1.71 (s, 3H) 1.80 (s, 3H) 3.62 (s, 2H) 7.09 (dd, J=11.69, 8.77 Hz, 1H) 7.40-7.49 (m, 2H) 7.62 (dd, J=7.16, 2.63 Hz, 1H) 7.69-7.75 (m, 1H) 7.75-7.82 (m, 2H) 7.90 (s, 1H)

Example 213

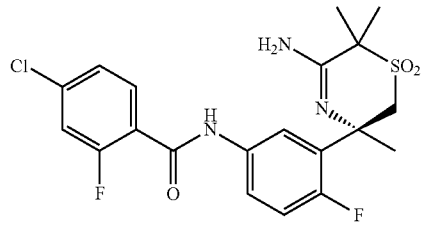 [SMILES: CC1(C)C(N)=N[C@](C)(c2cc(NC(=O)c3ccc(Cl)cc3F)ccc2F)CS1(=O)=O]

Synthesis of (R)—N-(3-(5-amino-3,6,6-trimethyl-1,1-dioxido-3,6-dihydro-2H-1,4-thiazin-3-yl)-4-fluorophenyl)-4-chloro-2-fluorobenzamide (R)—N-(3-(5-amino-3,6,6-trimethyl-1,1-dioxido-3,6-dihydro-2H-1,4-thiazin-3-yl)-4-fluorophenyl)-4-chloro-2- fluorobenzamide was synthesized using the same procedure as described for (R)—N-(3-(5-amino-3,6,6-trimethyl-1,1-dioxido-3,6-dihydro-2H-1,4-thiazin-3-yl)-4-fluorophenyl)-4-chlorobenzamide utilizing 4-chloro-2-fluorobenzoyl chloride instead of 4-chlorobenzoyl chloride.

Examples 214a and 214b

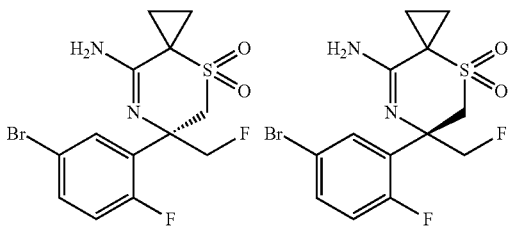

Synthesis of (R)-8-amino-6-(5-bromo-2-fluorophenyl)-6-(fluoromethyl)-4-thia-7-azaspiro[2.5]oct-7-ene 4,4-dioxide (214a) and (S)-8-amino-6-(5-bromo-2-fluorophenyl)-6-(fluoromethyl)-4-thia-7-azaspiro[2.5]oct-7-ene 4,4-dioxide (214b Step 1: 1-(Methylsulfonyl)cyclopropanecarbonitrile A mixture of 2-(methylsulfonyl)acetonitrile (1.3 g, 10.91 mmol), potassium carbonate (3.77 g, 27.3 mmol), and 1,2-dichloroethane (4.31 ml, 54.6 mmol) in DMF (20 mL) was heated at 80° C. for 24 h, the mixture was cooled, $H_2O$ added, extracted with DCM (3×). The extracts dried over $Na_2SO_4$, concentrated and purified by silica gel chromatography (0-45% EtOAc/DCM) to give the light yellow product. $^1H$ NMR (400 MHz, CHLOROFORM-d) δ ppm 3.13-3.23 (3H, m), 1.82-1.94 (2H, m), 1.66-1.78 (2H, m).

Step 2: N-(2-(5-bromo-2-fluorophenyl)-1-((1-cyanocyclopropyl)sulfonyl)-3-fluoropropan-2-yl)-2-methylpropane-2-sulfinamide To a stirred solution of 1-(methylsulfonyl)cyclopropanecarbonitrile (9.01 g, 62.1 mmol) in THF (100 mL) at −78° C. was added butyllithium 2.5 M (22.35 ml, 55.9 mmol) dropwise. After the addition, the mixture was stirred for 2 h at −78 C. In a separate flask, a mixture of (Z)—N-(1-(5-bromo-2-fluorophenyl)-2-fluoroethylidene)-2-methylpropane-2-sulfinamide (10.50 g, 31.0 mmol) and borontrifluoride etherate (4.41 g, 31.0 mmol) in THF (100 mL) was stirred at 0° C. for 30 min, this mixture was then added to the previous mixture by canula. After the addition, the reaction mixture was stirred at −78° C. in 2 h, quenched with saturated $NH_4Cl$, warmed to RT, extracted with EtOAc (3×). The combined extracts were dried over $MgSO_4$, concentrated and purified by silica gel chromatography (0-50% EtOAc/Hexane) to give the title compound (6.74 g, 45%).
LC/MS (ESI$^+$) m/z: 483, 485 (M+H, 2 bromine isotopes).

Step 3: N-(2-amino-2-(5-bromo-2-fluorophenyl)-3-fluoropropyl)sulfonyl)cyclopropanecarbonitrile To a stirred solution of N-(2-(5-bromo-2-fluorophenyl)-1-((2-cyanopropan-2-yl)sulfonyl)-3-fluoropropan-2-yl)-2-methylpropane-2-sulfinamide (5.09 g, 10.49 mmol) in dioxane (30 mL) was added HCl (26.2 ml, 105 mmol). After the addition, the mixture was stirred for 2 h, the mixture was concentrated, added $H_2O$, cooled in an ice bath, neutralized with aqueous saturated $NaHCO_3$, extracted with DCM (3×). The extracts were dried over $Na_2SO_4$, concentrated and purified by silica gel chromatography (30% EtOAc/Hexanes) to give the title compound as a brown oil (3.25 g, 82%). LC/MS (ESI$^+$) m/z: 379, 381 (M+H, 2 bromine isotopes).

Step 4: (R)-8-amino-6-(5-bromo-2-fluorophenyl)-6-(fluoromethyl)-4-thia-7-azaspiro[2.5]oct-7-ene 4,4-dioxide (214-a) and (S)-8-amino-6-(5-bromo-2-fluorophenyl)-6-(fluoromethyl)-4-thia-7-azaspiro[2.5]oct-7-ene 4,4-dioxide (214-b To a stirred solution of 1-(2-amino-2-(5-bromo-2-fluorophenyl)-3-fluoropropyl)sulfonyl)cyclopropanecarbonitrile (1.8 g, 4.75 mmol) in toluene (10 mL) at 0° C. was added trimethylaluminum (2.85 ml, 5.70 mmol) dropwise. After the addition, the mixture was gradually warmed to RT and stirred for 16 h; the mixture was cooled in an ice bath, slowly quenched with Rochelle's salt. The resulting mixture was stirred for 30 min., extracted with EtOAc, (3×), dried over $MgSO_4$, concentrated and purified by silica gel chromatography (0-50% EtOAc/hexanes) to give the racemic mixture which was then separated by chiral phase chromatography (ADH-20-MeOH(NH3) to give the compound 1 (440 mg, 25%) and compound 2 (430 mg, 24%). LC/MS (ESI$^+$) m/z: 379, 381 (M+H, 2 bromine isotopes).

Peak #1 (compound 1): $^1H$ NMR (400 MHz, DMSO-$d_6$) ppm 7.70 (1H, dd, J=7.0, 2.7 Hz), 7.47-7.60 (1H, m), 7.20 (1H, dd, J=11.9, 8.8 Hz), 6.24 (2H, br. s.), 4.61 (1H, d, J=2.9 Hz), 4.49 (1H, d, J=2.5 Hz), 3.81 (1H, d, J=14.7 Hz), 3.71 (1H, d, J=14.7 Hz), 1.57-1.77 (2H, m), 1.34-1.56 (2H, m).

Peak #2 (compound 2): $^1H$ NMR (400 MHz, DMSO-$d_6$) ppm 7.70 (1H, dd, J=7.0, 2.7 Hz), 7.55 (1H, ddd, J=8.6, 4.1, 2.7 Hz), 7.20 (1H, dd, J=11.9, 8.8 Hz), 6.24 (2H, br. s.), 4.61 (1H, d, J=2.9 Hz), 4.49 (1H, d, J=2.5 Hz), 3.81 (1H, d, J=14.7 Hz), 3.71 (1H, d, J=14.7 Hz), 1.57-1.79 (2H, m), 1.34-1.55 (2H, m).

Example 215

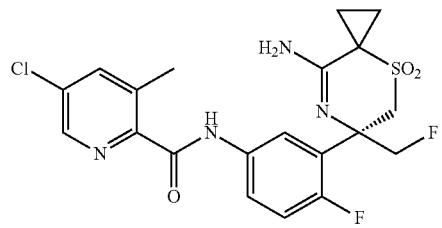 [SMILES: Cc1cc(Cl)cnc1C(=O)Nc1ccc(F)c([C@@]2(CF)CS(=O)(=O)C3(CC3)C(N)=N2)c1]

Synthesis of (R)—N-(3-(8-amino-6-(fluoromethyl)-4,4-dioxido-4-thia-7-azaspiro[2.5]oct-7-en-6-yl)-4-fluorophenyl)-5-chloro-3-methylpicolinamide Step 1: (R)-8-amino-6-(5-azido-2-fluorophenyl)-6-(fluoromethyl)-4-thia-7-azaspiro[2.5]oct-7-ene 4,4-dioxide A mixture of (R)-8-amino-6-(5-bromo-2-fluorophenyl)-6-(fluoromethyl)-4-thia-7-azaspiro[2.5]oct-7-ene 4,4-dioxide (0.430 g, 1.134 mmol), sodium (R)-2-((S)-1,2-dihydroxyethyl)-4-hydroxy-5-oxo-2,5-dihydrofuran-3-olate (0.045 g, 0.227 mmol), sodium azide (0.221 g, 3.40 mmol), (1R, 2R)—N1,N2-dimethylcyclohexane-1,2-diamine (0.040 g, 0.283 mmol), copper(I) iodide (0.054 g, 0.283 mmol) in EtOH/H₂O (4:1, 2.5 mL) was heated at 90° C. for 16 h; the reaction mixture was cooled, added saturated NH₄Cl, extracted with EtOAc (3×). The extracts were dried over MgSO₄, concentrated to give the title product (389 mg, 101%) which was used in the next step without further purification. LC/MS (ESI⁺) m/z: 342 (M+H).

Step 2: (R)-8-amino-6-(5-amino-2-fluorophenyl)-6-(fluoromethyl)-4-thia-7-azaspiro[2.5]oct-7-ene 4,4-dioxide To a stirred solution of ((R)-8-amino-6-(5-azido-2-fluorophenyl)-6-(fluoromethyl)-4-thia-7-azaspiro[2.5]oct-7-ene 4,4-dioxide (0.389 g, 1.140 mmol) THF/H₂O (4 mL, 3:1) was added trimethylphosphine (0.208 g, 1.368 mmol). After the addition, the mixture was stirred for 1 h, added more H₂O, extracted with EtOAc (3×). The extracts were dried over MgSO₄, concentrated and purified by silica gel chromatography (5% MeOH/DCM) to give the tan solid (150 mg, 42%). LC/MS (ESI⁺) m/z: 316 (M+H).

Step 3: (R)—N-(3-(8-amino-6-(fluoromethyl)-4,4-dioxido-4-thia-7-azaspiro[2.5]oct-7-en-6-yl)-4-fluorophenyl)-5-chloro-3-methylpicolinamide To a stirred mixture of (R)-8-amino-6-(5-amino-2-fluorophenyl)-6-(fluoromethyl)-4-thia-7-azaspiro[2.5]oct-7-ene 4,4-dioxide (0.0625 g, 0.198 mmol) and 5-chloro-3-methylpicolinic acid (0.036 g, 0.208 mmol) in DCM (3 mL) was added 2,4,6-tripropyl-1,3,5,2,4,6-trioxatriphosphinane 2,4,6-trioxide (0.378 g, 0.595 mmol). After the addition, the mixture was stirred at RT for 16 h, saturated aqueous NaHCO₃ was added, layers were separated, organic phase dried over Na₂SO₄, concentrated and purified by silica gel chromatography (30% EtOAc/DCM) to give the title compound as an off white solid (51 mg, 55%). LC/MS (ESI⁺) m/z: 469 (M+H). ¹H NMR (400 MHz, CHLOROFORM-d) ppm 10.01 (1H, s), 8.35-8.43 (1H, m), 7.96 (1H, ddd, J=8.8, 4.3, 2.8 Hz), 7.63-7.68 (2H, m), 7.09 (1H, dd, J=11.7, 8.8 Hz), 4.82 (1H, dd, J=14.7, 8.8 Hz), 4.55 (1H, dd, J=14.7, 8.8 Hz), 4.45 (2H, br. s.), 3.77 (2H, dd, J=14.5, 8.8 Hz), 2.79 (3H, s), 1.73-1.86 (2H, m), 1.56 (2H, m).

Example 216

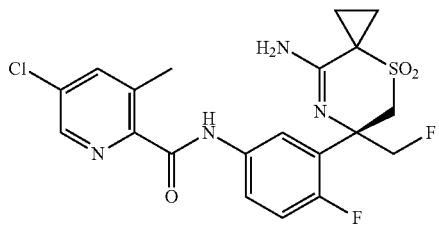 [SMILES: Cc1cc(Cl)cnc1C(=O)Nc1ccc(F)c([C@]2(CF)CS(=O)(=O)C3(CC3)C(N)=N2)c1]

Synthesis of (S)—N-(3-(8-amino-6-(fluoromethyl)-4,4-dioxido-4-thia-7-azaspiro[2.5]oct-7-en-6-yl)-4-fluorophenyl)-5-chloro-3-methylpicolinamide The title compound (46 mg, 48%) was prepared by the method of Example 215. LC/MS (ESI⁺) m/z: 469 (M+H). ¹H NMR (400 MHz, CHLOROFORM-d) δ ppm 10.01 (1H, s), 8.35-8.43 (1H, m), 7.96 (1H, ddd, J=8.8, 4.3, 2.8 Hz), 7.63-7.68 (2H, m), 7.09 (1H, dd, J=11.7, 8.8 Hz), 4.82 (1H, dd, J=14.7, 8.8 Hz), 4.55 (1H, dd, J=14.7, 8.8 Hz), 4.45 (2H, br. s.), 3.77 (2H, dd, J=14.5, 8.8 Hz), 2.79 (3H, s), 1.73-1.86 (2H, m), 1.56 (2H, m).

Example 217

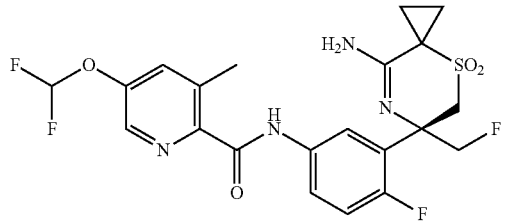 [SMILES: Cc1cc(OC(F)F)cnc1C(=O)Nc1ccc(F)c([C@]2(CF)CS(=O)(=O)C3(CC3)C(N)=N2)c1]

Synthesis of (S)—N-(3-(8-amino-6-(fluoromethyl)-4,4-dioxido-4-thia-7-azaspiro[2.5]oct-7-en-6-yl)-4-fluorophenyl)-5-(difluoromethoxy)-3-methyl picolinamide The title compound (110 mg, 79%) was prepared by the method of Example 215. LC/MS (ESI⁺) m/z: 501 (M+H). ¹H NMR (400 MHz, DMSO-d₆) δ ppm 10.55 (1H, s), 8.42 (1H, d, J=2.5 Hz), 7.80-7.94 (2H, m), 7.71 (1H, d, J=2.3 Hz), 7.24-7.61 (1H, m), 7.17 (1H, dd, J=11.9, 8.6 Hz), 6.16 (2H, s), 4.59-4.75 (1H, m), 4.37-4.59 (1H, m), 3.84 (1H, d, J=14.3 Hz), 3.67 (1H, d, J=14.7 Hz), 2.58 (3H, s), 1.75-1.87 (1H, m), 1.51-1.63 (1H, m), 1.39-1.51 (1H, m), 1.26-1.39 (1H, m).

Example 218

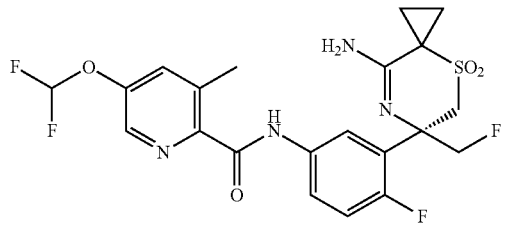 [SMILES: Cc1cc(OC(F)F)cnc1C(=O)Nc1ccc(F)c([C@@]2(CF)CS(=O)(=O)C3(CC3)C(N)=N2)c1]

Synthesis of (R)—N-(3-(8-amino-6-(fluoromethyl)-4,4-dioxido-4-thia-7-azaspiro[2.5]oct-7-en-6-yl)-4-fluorophenyl)-5-(difluoromethoxy)-3-methyl picolinamide The title compound (29 mg, 28%) was prepared by the method of Example 217. LC/MS (ESI⁺) m/z: 501 (M+H). ¹H NMR (400 MHz, DMSO-d₆) ppm 10.55 (1H, s), 8.42 (1H, d, J=2.5 Hz), 7.80-7.94 (2H, m), 7.71 (1H, d, J=2.3 Hz), 7.24-7.61 (1H, m), 7.17 (1H, dd, J=11.9, 8.6 Hz), 6.16 (2H, s), 4.59-4.75 (1H, m), 4.37-4.59 (1H, m), 3.84 (1H, d, J=14.3

Hz), 3.67 (1H, d, J=14.7 Hz), 2.58 (3H, s), 1.75-1.87 (1H, m), 1.51-1.63 (1H, m), 1.39-1.51 (1H, m), 1.26-1.39 (1H, m)

Intermediate 23

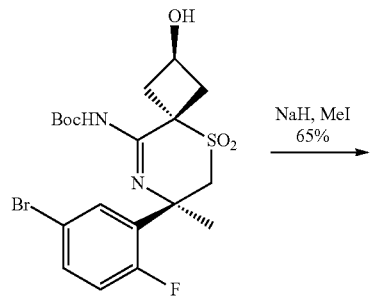

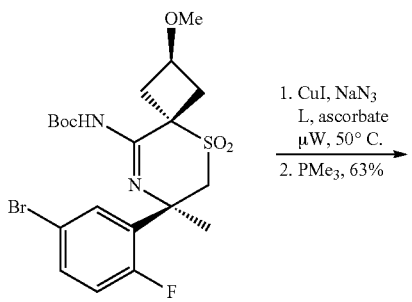

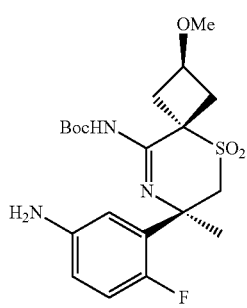

Step 1: Tert-butyl ((2R,4r,7R)-7-(5-bromo-2-fluorophenyl)-2-methoxy-7-methyl-5,5-dioxido-5-thia-8-azaspiro[3.5]non-8-en-9-yl)carbamate To a solution of tert-butyl ((2R,4r,7R)-7-(5-bromo-2-fluorophenyl)-2-hydroxy-7-methyl-5,5-dioxido-5-thia-8-azaspiro[3.5]non-8-en-9-yl)carbamate (0.23 g, 0.468 mmol) in THF at 0° C. was added sodium hydride (60% in oil, 0.094 g, 2.34 mmol). After stirring the reaction mixture for 30 min, iodomethane (0.030 ml, 0.477 mmol) was added and the mixture was stirred at RT overnight. The mixture was diluted with sat. NH₄Cl and extracted with ethyl acetate. The organic extracts were concentrated and the resulting crude material was absorbed onto a plug of silica gel and purified by chromatography through a Redi-Sep pre-packed silica gel column (12 g), eluting with a gradient of 10% to 70% EtOAc in hexane, to provide crude tert-butyl ((2R,4r,7R)-7-(5-bromo-2-fluorophenyl)-2-methoxy-7-methyl-5,5-dioxido-5-thia-8-azaspiro[3.5]non-8-en-9-yl)carbamate (0.154 g, 0.305 mmol, 65.1% yield) as white solid.

Step 2: Tert-butyl ((2R,4r,7R)-7-(5-amino-2-fluorophenyl)-2-methoxy-7-methyl-5,5-dioxido-5-thia-8-azaspiro[3.5]non-8-en-9-yl)carbamate In a manner analogous to the synthesis described for example 83, steps 1-2, ((2R,4r,7R)-7-(5-bromo-2-fluorophenyl)-2-methoxy-7-methyl-5,5-dioxido-5-thia-8-azaspiro[3.5]non-8-en-9-yl)carbamate was converted to the title compound as a white solid. LC/MS (ESI⁺) m/z=442.0 (M+H).

Example 461

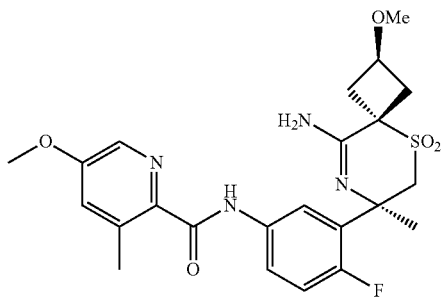 [SMILES: COc1cnc(C(=O)Nc2ccc(F)c([C@]3(C)CS(=O)(=O)[C@]4(C[C@H](OC)C4)C(N)=N3)c2)c(C)c1]

Synthesis of N-(3-((2S,4s,7R)-9-amino-2-fluoro-7-methyl-5,5-dioxido-5-thia-8-azaspiro[3.5]non-8-en-7-yl)-4-fluorophenyl)-5-methoxy-3-methylpicolinamide N-(3-((2R,4r,7R)-9-amino-2-methoxy-7-methyl-5,5-dioxido-5-thia-8-azaspiro[3.5]non-8-en-7-yl)-4-fluorophenyl)-5-methoxy-3-methylpicolinamide was prepared using the HATU coupling procedure in conjunction with intermediate 23 and methoxy-methyl picolinic acid. LC/MS (ESI⁺) m/z=491.0 (M+H). ¹H NMR (400 MHz, DMSO-d₆) δ 10.80 (br. s., 1H), 9.47 (br. s., 1H), 9.15 (br. s., 1H), 8.24 (d, J=2.64 Hz, 1H), 7.98 (d, J=7.83 Hz, 1H), 8.02 (d, J=8.02 Hz, 1H), 7.44 (d, J=2.64 Hz, 1H), 7.30 (dd, J=9.10, 11.93 Hz, 1H), 4.01-4.16 (m, 1H), 3.92 (s, 3H), 3.23 (s, 3H), 3.20 (d, J=6.55 Hz, 1H), 2.95-3.09 (m, 1H), 2.65-2.75 (m, 4H), 2.63 (s, 3H), 1.94 (s, 3H).

Example 460

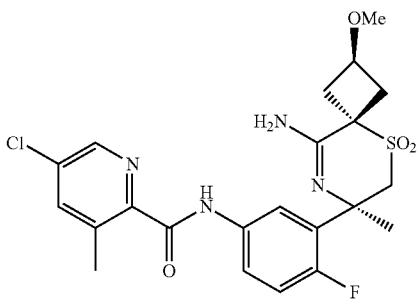 [SMILES: CO[C@H]1C[C@]2(C1)C(N)=N[C@](C)(c1cc(NC(=O)c3ncc(Cl)cc3C)ccc1F)CS2(=O)=O]

Example 460, N-(3-((2R,4r,7R)-9-amino-2-methoxy-7-methyl-5,5-dioxido-5-thia-8-azaspiro[3.5]non-8-en-7-yl)-4-fluorophenyl)-5-chloro-3-methylpicolinamide was prepared using the HATU coupling procedure in conjunction with intermediate 23 and chloro-methyl picolinic acid. LC/MS (ESI⁺) m/z=495.0 (M+H). ¹H NMR (400 MHz, DMSO-d$_6$) δ 10.85 (s, 1H), 9.48 (br. s., 1H), 9.24 (br. s., 1H), 8.60 (d, J=1.86 Hz, 1H), 8.06 (dd, J=0.64, 2.30 Hz, 1H), 7.97-8.02 (m, 1H), 7.94 (dd, J=2.25, 7.63 Hz, 1H), 7.32 (dd, J=8.95, 11.98 Hz, 1H), 4.33 (d, J=15.55 Hz, 1H), 4.23 (d, J=15.65 Hz, 1H), 4.08 (quin, J=6.94 Hz, 1H), 3.15-3.26 (m, 5H), 2.95-3.09 (m, 1H), 2.63 (dd, J=6.85, 13.20 Hz, 1H), 2.58 (s, 3H), 1.94 (s, 3H).

Example 464

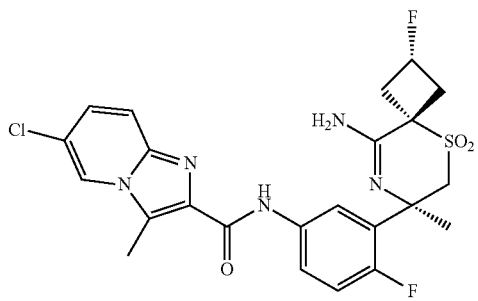 [SMILES: Cc1c(C(=O)Nc2ccc(F)c([C@]3(C)CS(=O)(=O)[C@]4(C[C@@H](F)C4)C(N)=N3)c2)nc2ccc(Cl)cn12]

Example 464, N-(3-((2 S,4s,7R)-9-amino-2-fluoro-7-methyl-5,5-dioxido-5-thia-8-azaspiro[3.5]non-8-en-7-yl)-4-fluorophenyl)-6-chloro-3-methylimidazo[1,2-a]pyridine-2-carboxamide was prepared using the HATU coupling procedure in conjunction with intermediate 23 and chloro-methyl imidazo-pyridine carboxylic acid. LC/MS (ESI⁺) m/z=522.0 (M+H). ¹H NMR (400 MHz, DMSO-d$_6$) δ 10.99 (br. s., 1H), 10.50 (br. s., 1H), 9.51 (br. s., 1H), 9.32 (br. s., 1H), 8.71 (br. s., 1H), 8.10 (br. s., 1H), 8.01 (br. s., 1H), 7.68 (br. s., 1H), 7.45 (d, J=9.29 Hz, 1H), 7.30 (br. s., 1H), 4.33 (br. s., 1H), 4.13 (d, J=12.62 Hz, 1H), 3.10 (br. s., 5H), 2.82 (br. s., 3H), 1.95 (br. s., 3H).

Example 463

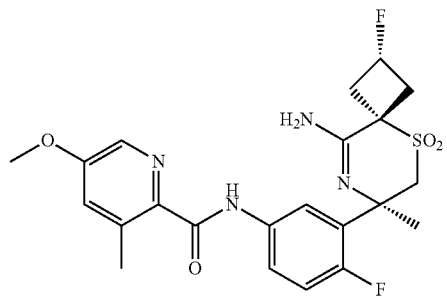 [SMILES: COc1cnc(C(=O)Nc2ccc(F)c([C@]3(C)CS(=O)(=O)[C@]4(C[C@@H](F)C4)C(N)=N3)c2)c(C)c1]

Example 463, N-(3-((2S,4s,7R)-9-amino-2-fluoro-7-methyl-5,5-dioxido-5-thia-8-azaspiro[3.5]non-8-en-7-yl)-4-fluorophenyl)-5-methoxy-3-methylpicolinamide was prepared using the HATU coupling procedure in conjunction with intermediate 23 and methoxy-methyl picolinic acid. LC/MS (ESI⁺) m/z=479.0 (M+H). ¹H NMR (400 MHz, DMSO-d$_6$) δ 10.96 (br. s., 1H), 9.50 (br. s., 1H), 9.28 (br. s., 1H), 8.24 (d, J=2.64 Hz, 1H), 7.99-8.13 (m, 1H), 7.95 (d, J=5.09 Hz, 1H), 7.45 (d, J=2.35 Hz, 1H), 7.30 (dd, J=9.24, 11.69 Hz, 1H), 5.35 (t, J=6.46 Hz, 1H), 4.35 (d, J=14.28 Hz, 1H), 4.12 (d, J=15.55 Hz, 1H), 3.92 (s, 3H), 3.08 (d, J=14.97 Hz, 3H), 3.01 (d, J=1.47 Hz, 1H), 2.64 (s, 3H), 1.94 (br. s., 3H).

The following compounds in Table II are examples of compounds of Formulas I, II and III, and sub-formulas thereof, provided by the present invention hereinabove. The Mass spectrometer data (mass found as measured by M+H⁺) and methods used to prepare the exemplary compounds are also included in Table II. Table II further provides the biological data (average nM IC$_{50}$'s for the enzyme and cell assays) for each compound, where available.

TABLE II

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 146 | (7S)-7-(2-bromo-5-fluoro-4-pyridinyl)-7-methyl-5-thia-8-azaspiro[3.5]non-8-en-9-amine 5,5-dioxide | 377.9 | Example 13, steps 2-5 | >40.0 | >15.6 | >400.0 |
| 147 | (7R)-7-(2-bromo-5-fluoro-4-pyridinyl)-7-methyl-5-thia-8-azaspiro[3.5]non-8-en-9-amine 5,5-dioxide | 377.9 | Example 13, steps 2-5 | 17 | >15.6 | 43.5 |
| 219 | N-(5-((3R)-5-amino-3,6,6-trimethyl-1,1-dioxido-3,6-dihydro-2H-1,4-thiazin-3-yl)-6-fluoro-3-pyridinyl)-5-fluoro-3-methoxy-1,7-naphthyridin-8-amine | 476.9 | as in example 44 | 0.00144 | 0.0029 | 39.7 |
| 220 | N-(5-((3R)-5-amino-3,6,6-trimethyl-1,1-dioxido-3,6-dihydro-2H-1,4-thiazin-3-yl)-6-fluoro-3-pyridinyl)-3-chloro-5-fluoro-1,7-naphthyridin-8-amine | 480.9 | as in example 44 | <0.002 | 0.0033 | 15.2 |
| 221 | 8-((5-((3R)-5-amino-3,6,6-trimethyl-1,1-dioxido-3,6-dihydro-2H-1,4-thiazin-3-yl)-6-fluoro-3-pyridinyl)amino)-5-fluoro-1,7-naphthyridine-3-carbonitrile | 471.9 | as in example 44 | 0.00194 | 0.0058 | 43.1 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 222 | N-(5-((3R)-5-amino-3,6,6-trimethyl-1,1-dioxido-3,6-dihydro-2H-1,4-thiazin-3-yl)-6-fluoro-3-pyridinyl)-2-methoxypyrido[3,4-b]pyrazin-5-amine | 460 | as in example 44 | 0.00259 | 0.0036 | 280 |
| 223 | N-(5-((3R)-5-amino-3,6,6-trimethyl-1,1-dioxido-3,6-dihydro-2H-1,4-thiazin-3-yl)-6-fluoro-3-pyridinyl)-3-chloro-1,7-naphthyridin-8-amine | 462.9 | as in example 44 | 0.00082 | 0.0054 | 23.8 |
| 224 | N-(5-((3R)-5-amino-3,6,6-trimethyl-1,1-dioxido-3,6-dihydro-2H-1,4-thiazin-3-yl)-6-fluoro-3-pyridinyl)-2-(trifluoromethyl)pyrido[3,4-b]pyrazin-5-amine | 497.9 | as in example 44 | 0.016 | 0.0399 | 457 |
| 225 | N-(5-((3R)-5-amino-3,6,6-trimethyl-1,1-dioxido-3,6-dihydro-2H-1,4-thiazin-3-yl)-6-fluoro-3-pyridinyl)-7-chloropyrido[3,2-d]pyrimidin-4-amine | 463.9 | as in example 44 | 0.00328 | 0.0122 | 33 |
| 226 | N-(3-((3R,6R)-5-amino-6-fluoro-3,6-dimethyl-1,1-dioxido-3,6-dihydro-2H-1,4-thiazin-3-yl)-4-fluorophenyl)-3-(2-butyn-1-yloxy)-1,7-naphthyridin-8-amine | 500 | Example 44 | 0.00074 | 0.00574 | >400 |
| 227 | N-(3-((3R)-5-amino-2-fluoro-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine | 515.2 | EX 44 | 0.00659 | | >44.4 |
| 228 | N-(3-((3R)-5-amino-2-fluoro-3,6,6-trimethyl-1,1-dioxido-3,6-dihydro-2H-1,4-thiazin-3-yl)-4-fluorophenyl)-7-chloropyrido[3,2-d]pyrimidin-4-amine | 481.1 | EX 44 | 0.00328 | | 58.9 |
| 229 | 4-((3-((3R)-5-amino-2-fluoro-3,6,6-trimethyl-1,1-dioxido-3,6-dihydro-2H-1,4-thiazin-3-yl)-4-fluorophenyl)amino)pyrido[3,2-d]pyrimidine-7-carbonitrile | 472.1 | EX 44 | 0.00101 | | 80.7 |
| 230 | N-(5-((7R)-9-amino-7-methyl-5,5-dioxido-5-thia-8-azaspiro[3.5]non-8-en-7-yl)-6-fluoro-3-pyridinyl)-3-chloro-1,7-naphthyridin-8-amine | 474.9 | as in example 44 | 0.00376 | 0.0188 | 23.2 |
| 231 | N-(5-((7R)-9-amino-7-methyl-5,5-dioxido-5-thia-8-azaspiro[3.5]non-8-en-7-yl)-6-fluoro-3-pyridinyl)-2-methoxypyrido[3,4-b]pyrazin-5-amine | 471.9 | as in example 44 | 0.00641 | 0.0181 | 163 |
| 116 | N-(3-((7R)-9-amino-7-methyl-5,5-dioxido-5-thia-8-azaspiro[3.5]non-8-en-7-yl)-4-fluorophenyl)-3-chloro-1,7-naphthyridin-8-amine | 474 | Ex 44 | 0.00115 | 0.0263 | 38.8 |
| 128 | N-(3-((7R)-9-amino-2,2-difluoro-7-methyl-5,5-dioxido-5-thia-8-azaspiro[3.5]non-8-en-7-yl)-4-fluorophenyl)-2-methoxypyrido[3,4-b]pyrazin-5-amine | 507 | Ex 44 | 0.0259 | 0.199 | 330 |
| 129 | 4-((3-((7R)-9-amino-2,2-difluoro-7-methyl-5,5-dioxido-5-thia-8-azaspiro[3.5]non-8-en-7-yl)-4-fluorophenyl)amino)pyrido[3,2-d]pyrimidine-7-carbonitrile | 502 | Ex 44 | | | |
| 232 | N-(3-((7R)-9-amino-6-fluoro-7-methyl-5,5-dioxido-5-thia-8-azaspiro[3.5]non-8-en-7-yl)-4-fluorophenyl)-2-methoxypyrido[3,4-b]pyrazin-5-amine | 489 | Ex 44 | 0.0131 | 0.0784 | 303 |
| 233 | N-(3-((3S)-5-amino-3-(fluoromethyl)-6,6-dimethyl-1,1-dioxido-3,6-dihydro-2H-1,4-thiazin-3-yl)-4-fluorophenyl)-3-chloro-5-fluoro-1,7-naphthyridin-8-amine | 497.9 | Example 44 Step 1 | 0.00031 | 0.0845 | 143 |
| 234 | N-(3-((3S)-5-amino-3-(fluoromethyl)-6,6-dimethyl-1,1- | 514.8 | Example 44 Step 1 | 0.00203 | 0.105 | >14.8 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| | dioxido-3,6-dihydro-2H-1,4-thiazin-3-yl)-4-fluorophenyl)-2-(trifluoromethyl)pyrido[3,4-b]pyrazin-5-amine | | | | | |
| 235 | N-(3-((3S)-5-amino-3-(fluoromethyl)-6,6-dimethyl-1,1-dioxido-3,6-dihydro-2H-1,4-thiazin-3-yl)-4-fluorophenyl)-7-chloropyrido[3,2-d]pyrimidin-4-amine | 480.9 | Example 44 Step 1 | 0.00326 | 0.0308 | 68.2 |
| 236 | 4-((3-((3S)-5-amino-3-(fluoromethyl)-6,6-dimethyl-1,1-dioxido-3,6-dihydro-2H-1,4-thiazin-3-yl)-4-fluorophenyl)amino)pyrido[3,2-d]pyrimidine-7-carbonitrile | 472 | Example 44 Step 1 | 0.00073 | 0.0407 | 56.1 |
| 237 | N-(3-((3S)-5-amino-3-(fluoromethyl)-6,6-dimethyl-1,1-dioxido-3,6-dihydro-2H-1,4-thiazin-3-yl)-4-fluorophenyl)-2-ethoxypyrido[3,4-b]pyrazin-5-amine | 491 | Example 44 Step 1 | 0.00285 | 0.0409 | 661 |
| 238 | N-(3-((7S)-9-amino-7-(fluoromethyl)-5,5-dioxido-5-thia-8-azaspiro[3.5]non-8-en-7-yl)-4-fluorophenyl)-2-ethoxypyrido[3,4-b]pyrazin-5-amine | 503 | Example 44 Step 1 | 0.00399 | 0.117 | >400.0 |
| 239 | N-(3-((7S)-9-amino-7-(fluoromethyl)-5,5-dioxido-5-thia-8-azaspiro[3.5]non-8-en-7-yl)-4-fluorophenyl)-3-methoxy-1,7-naphthyridin-8-amine | 488 | Example 44 Step 1 | 0.00415 | 0.0237 | 390 |
| 240 | N-(3-((7S)-9-amino-7-(fluoromethyl)-5,5-dioxido-5-thia-8-azaspiro[3.5]non-8-en-7-yl)-4-fluorophenyl)-7-chloropyrido[3,2-d]pyrimidin-4-amine | 493 | Example 44 Step 1 | 0.0017 | 0.0272 | 57.1 |
| 241 | 8-((3-((7S)-9-amino-7-(fluoromethyl)-5,5-dioxido-5-thia-8-azaspiro[3.5]non-8-en-7-yl)-4-fluorophenyl)amino)-5-fluoro-1,7-naphthyridine-3-carbonitrile | 500.9 | Example 44 Step 1 | 0.0009 | 0.0479 | >4.94 |
| 242 | N-(3-((7S)-9-amino-7-(fluoromethyl)-5,5-dioxido-5-thia-8-azaspiro[3.5]non-8-en-7-yl)-4-fluorophenyl)-7-methoxypyrido[3,2-d]pyrimidin-4-amine | 489 | Example 44 Step 1 | 0.00147 | 0.014 | 119 |
| 243 | N-(3-((7R)-9-amino-7-(fluoromethyl)-5,5-dioxido-5-thia-8-azaspiro[3.5]non-8-en-7-yl)-4-fluorophenyl)-3-chloro-1,7-naphthyridin-8-amine,N-(3-((7S)-9-amino-7-(fluoromethyl)-5,5-dioxido-5-thia-8-azaspiro[3.5]non-8-en-7-yl)-4-fluorophenyl)-3-chloro-1,7-naphthyridin-8-amine | 492 | Made by method of example 44 step 1 | 0.00131 | 0.0779 | 363 |
| 244 | N-(3-((7R)-9-amino-7-(fluoromethyl)-5,5-dioxido-5-thia-8-azaspiro[3.5]non-8-en-7-yl)-4-fluorophenyl)-3-chloro-1,7-naphthyridin-8-amine | 492 | Made by method of example 44 step 1 | 3.53 | | 528 |
| 245 | N-(3-((7S)-9-amino-7-(fluoromethyl)-5,5-dioxido-5-thia-8-azaspiro[3.5]non-8-en-7-yl)-4-fluorophenyl)-3-chloro-1,7-naphthyridin-8-amine | 492 | Made by method of example 44 step 1 | 0.00056 | 0.0465 | 290 |
| 246 | N-(3-((7S)-9-amino-7-(fluoromethyl)-5,5-dioxido-5-thia-8-azaspiro[3.5]non-8-en-7-yl)-4-fluorophenyl)-2-methoxypyrido[3,4-b]pyrazin-5-amine | 489 | Made by method of example 44 step 1 | 0.00146 | 0.0216 | 811 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 247 | N-(3-((4aR,7aR)-3-amino-2,2-dimethyl-1,1-dioxido-7,7a-dihydro-2H-furo[3,4-b][1,4]thiazin-4a(5H)-yl)-4-fluorophenyl)-2-methoxypyrido[3,4-b]pyrazin-5-amine | 487 | Example 44, step 1 | 0.704 | 2.8 | 477 |
| 248 | N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-2-methoxypyrido[3,4-b]pyrazin-5-amine | 487 | Example 44, step 1 | 0.00304 | 0.0209 | 199 |
| 249 | 5-((3-((4aS,7aS)-3-amino-2,2-dimethyl-1,1-dioxido-7,7a-dihydro-2H-furo[3,4-b][1,4]thiazin-4a(5H)-yl)-4-fluorophenyl)amino)pyrido[3,4-b]pyrazin-2(1H)-one | 473 | Example 44, step 1 | 0.00636 | 0.153 | 102 |
| 250 | N-(3-((8R)-6-amino-5,5,8-trimethyl-4,4-dioxido-4-thia-7-azaspiro[2.5]oct-6-en-8-yl)-4-fluorophenyl)-2-methoxypyrido[3,4-b]pyrazin-5-amine | 485 | Example 44 | 0.0212 | 0.059 | 113 |
| 117 | 8-((3-((7R)-9-amino-7-methyl-5,5-dioxido-5-thia-8-azaspiro[3.5]non-8-en-7-yl)-4-fluorophenyl)amino)-1,7-naphthyridine-3-carbonitrile | 465 | Ex 76 | 0.00189 | 0.0051 | 28.3 |
| 251 | 8-((3-((7R)-9-amino-6-fluoro-7-methyl-5,5-dioxido-5-thia-8-azaspiro[3.5]non-8-en-7-yl)-4-fluorophenyl)amino)-1,7-naphthyridine-3-carbonitrile | 483 | Ex 76 | 0.00058 | 0.0135 | 42.8 |
| 252 | (5R)-5-(2-fluoro-5-((4-methoxybenzyl)sulfanyl)phenyl)-2,2,5-trimethyl-5,6-dihydro-2H-1,4-thiazin-3-amine 1,1-dioxide | 437.1 | 79 | 1.21 | 1.9 | 35.9 |
| 112 | (2R,4r,7R)-9-amino-2-(5-bromo-2-fluorophenyl)-7-methyl-5-thia-8-azaspiro[3.5]non-8-en-2-ol 5,5-dioxide, (2S,4s,7R)-9-amino-7-(5-bromo-2-fluorophenyl)-7-methyl-5-thia-8-azaspiro[3.5]non-8-en-2-ol 5,5-dioxide | 391 | by method of example 83 | 1.19 | | 37.3 |
| 113 | (7R)-7-(5-bromo-2-fluorophenyl)-7-methyl-5-thia-8-azaspiro[3.5]non-8-en-9-amine 5,5-dioxide | 375 | by method of example 83 | 4.05 | | 30 |
| 118 | (2S,4s,7R)-7-(5-bromo-2-fluorophenyl)-2-fluoro-7-methyl-5-thia-8-azaspiro[3.5]non-8-en-9-amine 5,5-dioxide | 393 | by method of example 83 | 4.09 | >15.6 | 31.1 |
| 119 | (7R)-7-(5-bromo-2-fluorophenyl)-2,2-difluoro-7-methyl-5-thia-8-azaspiro[3.5]non-8-en-9-amine 5,5-dioxide | 411 | by method of example 83 | | | |
| 253 | (5R)-5-(2-fluoro-5-((2-(trifluoromethyl)pyrido[3,4-b]pyrazin-5-yl)oxy)phenyl)-2,2,5-trimethyl-5,6-dihydro-2H-1,4-thiazin-3-amine 1,1-dioxide | 498 | 106 | 0.0276 | 1.03 | |
| 254 | N-(3-((3R)-5-amino-3,6,6-trimethyl-1,1-dioxido-3,6-dihydro-2H-1,4-thiazin-3-yl)-4-fluorophenyl)-3-(2-butyn-1-yloxy)-1,7-naphthyridin-8-amine | 496.1 | 106 | 0.0006 | 0.0006 | 354 |
| 255 | (5R)-5-(2-fluoro-5-((4-(trifluoromethyl)phenyl)-2-pyridinyl)oxy)phenyl)-2,2,5-trimethyl-5,6-dihydro-2H-1,4-thiazin-3-amine 1,1-dioxide | 522 | 106 | 0.663 | 3.99 | 50.5 |
| 256 | (5R)-5-(2-fluoro-5-((3-fluoro-5-(3-methyl-5-isoxazolyl)-2-pyridinyl)oxy)phenyl)-2,2,5-trimethyl-5,6-dihydro-2H-1,4-thiazin-3-amine 1,1-dioxide | 477 | 106 | 0.65 | 1.82 | 195 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 257 | (5R)-5-(5-((5-(2,2-dimethylpropyl)-2-pyridinyl)oxy)-2-fluorophenyl)-2,2,5-trimethyl-5,6-dihydro-2H-1,4-thiazin-3-amine 1,1-dioxide | 448 | 106 | 18.9 | 7.79 | 187 |
| 258 | (5R)-5-(5-((3-chloro-2-pyridinyl)oxy)-2-fluorophenyl)-2,2,5-trimethyl-5,6-dihydro-2H-1,4-thiazin-3-amine 1,1-dioxide | 412 | 106 | 0.0969 | 0.121 | 207 |
| 259 | (5R)-5-(2-fluoro-5-((4-(trifluoromethyl)-2-pyridinyl)oxy)phenyl)-2,2,5-trimethyl-5,6-dihydro-2H-1,4-thiazin-3-amine 1,1-dioxide | 446 | 106 | 0.153 | 0.248 | 1050 |
| 260 | N-(3-((3R)-5-amino-3,6,6-trimethyl-1,1-dioxido-3,6-dihydro-2H-1,4-thiazin-3-yl)-4-fluorophenyl)-3-(cyclopropylmethoxy)-1,7-naphthyridin-8-amine | 498.2 | 106 | 0.0038 | 0.0075 | 250 |
| 261 | (5R)-5-(2-fluoro-5-(2-quinolinyloxy)phenyl)-2,2,5-trimethyl-5,6-dihydro-2H-1,4-thiazin-3-amine 1,1-dioxide | 428.1 | 106 | 0.3 | 0.574 | 58.3 |
| 262 | (5R)-5-(5-((3,5-difluoro-4-(trifluoromethyl)-2-pyridinyl)oxy)-2-fluorophenyl)-2,2,5-trimethyl-5,6-dihydro-2H-1,4-thiazin-3-amine 1,1-dioxide | 482 | 106 | 15.5 | >15.6 | 68.1 |
| 263 | (5R)-5-(2-fluoro-5-((3-methyl-2-pyridinyl)oxy)phenyl)-2,2,5-trimethyl-5,6-dihydro-2H-1,4-thiazin-3-amine 1,1-dioxide | 392 | 106 | 0.65 | 0.624 | 555 |
| 264 | (5R)-5-(2-fluoro-5-((4-methyl-2-pyridinyl)oxy)phenyl)-2,2,5-trimethyl-5,6-dihydro-2H-1,4-thiazin-3-amine 1,1-dioxide | 392 | 106 | 0.18 | 0.126 | 878 |
| 265 | (5R)-5-(2-fluoro-5-((5-methyl-2-pyridinyl)oxy)phenyl)-2,2,5-3-amine 1,1-dioxide trimethyl-5,6-dihydro-2H-1,4-thiazin-3-amine 1,1-dioxide | 392 | 106 | 2.26 | 0.804 | 373 |
| 266 | (5R)-5-(2-fluoro-5-((6-methyl-2-pyridinyl)oxy)phenyl)-2,2,5-trimethyl-5,6-dihydro-2H-1,4-thiazin-3-amine 1,1-dioxide | 392 | 106 | 0.413 | 0.427 | 407 |
| 267 | (5R)-5-(5-((3-chloro-5-(trifluoromethyl)-2-pyridinyl)oxy)-2-fluorophenyl)-2,2,5-trimethyl-5,6-dihydro-2H-1,4-thiazin-3-amine 1,1-dioxide | 480.1 | 106 | 0.603 | 0.874 | 221 |
| 268 | 6-(3-((3R)-5-amino-3,6,6-trimethyl-1,1-dioxido-3,6-dihydro-2H-1,4-thiazin-3-yl)-4-fluorophenoxy)-2,4-pyrimidinediamine | 409 | 106 | 0.318 | 0.305 | 920 |
| 269 | (5R)-5-(2-fluoro-5-((6-(trifluoromethyl)-2-pyridinyl)oxy)phenyl)-2,2,5-trimethyl-5,6-dihydro-2H-1,4-thiazin-3-amine 1,1-dioxide | 446 | 106 | 0.248 | 0.574 | 132 |
| 270 | (5R)-5-(2-fluoro-5-(2-pyrazinyloxy)phenyl)-2,2,5-trimethyl-5,6-dihydro-2H-1,4-thiazin-3-amine 1,1-dioxide | 319 | 106 | 0.0935 | 0.0511 | 222 |
| 271 | 6-(3-((3R)-5-amino-3,6,6-trimethyl-1,1-dioxido-3,6-dihydro-2H-1,4-thiazin-3-yl)-4-fluorophenoxy)-5-methyl-3-pyridinecarbonitrile | 417 | 106 | 0.549 | 0.474 | 540 |
| 272 | 6-(3-((3R)-5-amino-3,6,6-trimethyl-1,1-dioxido-3,6-dihydro-2H-1,4-thiazin-3-yl)-4-fluorophenoxy)-2-methyl-3-pyridinecarbonitrile | 417 | 106 | 2.69 | 2.02 | 217 |
| 273 | (5R)-5-(5-((3-amino-2-pyridinyl)oxy)-2-fluorophenyl)-2,2,5-trimethyl-5,6-dihydro-2H-1,4-thiazin-3-amine 1,1-dioxide | 393 | 106 | 1.5 | 1.01 | >400.0 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 274 | (5R)-5-(2-fluoro-5-((3-fluoro-2-pyridinyl)oxy)phenyl)-2,2,5-trimethyl-5,6-dihydro-2H-1,4-thiazin-3-amine 1,1-dioxide | 396 | 106 | 0.0374 | 0.0348 | 153 |
| 275 | (5R)-5-(2-fluoro-5-((5-fluoro-2-pyridinyl)oxy)phenyl)-2,2,5-trimethyl-5,6-dihydro-2H-1,4-thiazin-3-amine 1,1-dioxide | 396 | 106 | 0.84 | 0.424 | 364 |
| 276 | (5R)-5-(5-((5-chloro-4-methyl-2-pyridinyl)oxy)-2-fluorophenyl)-2,2,5-trimethyl-5,6-dihydro-2H-1,4-thiazin-3-amine 1,1-dioxide | 426 | 106 | 2.71 | 2.63 | 421 |
| 277 | (5R)-5-(2-fluoro-5-((3-fluoro-5-(trifluoromethyl)-2-pyridinyl)oxy)phenyl)-2,2,5-trimethyl-5,6-dihydro-2H-1,4-thiazin-3-amine 1,1-dioxide | 464 | 106 | 1.21 | 1.15 | 331 |
| 278 | (5R)-5-(2-fluoro-5-((3-(trifluoromethyl)-2-pyridinyl)oxy)phenyl)-2,2,5-trimethyl-5,6-dihydro-2H-1,4-thiazin-3-amine 1,1-dioxide | 446 | 106 | 0.341 | 0.359 | 147 |
| 279 | (5R)-5-(2-fluoro-5-((5-(trifluoromethyl)-2-pyridinyl)oxy)phenyl)-2,2,5-trimethyl-5,6-dihydro-2H-1,4-thiazin-3-amine 1,1-dioxide | 446 | 106 | 5.6 | 2.09 | 188 |
| 280 | 2-(3-((3R)-5-amino-3,6,6-trimethyl-1,1-dioxido-3,6-dihydro-2H-1,4-thiazin-3-yl)-4-fluorophenoxy)-4-pyridinecarbonitrile | 403 | 106 | 0.039 | 0.0521 | 395 |
| 281 | (5R)-5-(5-((5-chloro-2,4'-bipyridin-2'-yl)oxy)-2-fluorophenyl)-2,2,5-trimethyl-5,6-dihydro-2H-1,4-thiazin-3-amine 1,1-dioxide | 489 | 106 | 0.807 | 1.12 | 61.2 |
| 282 | 6-(3-((3R)-5-amino-3,6,6-trimethyl-1,1-dioxido-3,6-dihydro-2H-1,4-thiazin-3-yl)-4-fluorophenoxy)-3-pyridinecarbonitrile | 403 | 106 | 1.56 | 1.15 | 227 |
| 283 | 6-(3-((3R)-5-amino-3,6,6-trimethyl-1,1-dioxido-3,6-dihydro-2H-1,4-thiazin-3-yl)-4-fluorophenoxy)-2-pyridinecarbonitrile | 403 | 106 | 0.0919 | 0.0828 | 12.9 |
| 284 | (5R)-5-(2-fluoro-5-((5-fluoro-6-(trifluoromethyl)-2-pyridinyl)oxy)phenyl)-2,2,5-trimethyl-5,6-dihydro-2H-1,4-thiazin-3-amine 1,1-dioxide | 464 | 106 | 0.769 | 1.64 | 79.1 |
| 285 | (5R)-5-(5-((4-bromo-2-pyridinyl)oxy)-2-fluorophenyl)-2,2,5-trimethyl-5,6-dihydro-2H-1,4-thiazin-3-amine 1,1-dioxide | 456, 458.1 | 106 | 0.0375 | 0.0918 | 374 |
| 286 | (5R)-5-(2-fluoro-5-((4-(1-propyn-1-yl)-2-pyridinyl)oxy)phenyl)-2,2,5-trimethyl-5,6-dihydro-2H-1,4-thiazin-3-amine 1,1-dioxide | 416.1 | 106 | 0.228 | 0.787 | 119 |
| 287 | (5R)-5-(2-fluoro-5-((4-methoxy-2-pyridinyl)oxy)phenyl)-2,2,5-trimethyl-5,6-dihydro-2H-1,4-thiazin-3-amine 1,1-dioxide | 408.1 | 106 | 0.1 | | 204 |
| 288 | (5R)-5-(2-fluoro-5-(2-pyrimidinyloxy)phenyl)-2,2,5-trimethyl-5,6-dihydro-2H-1,4-thiazin-3-amine 1,1-dioxide | 379.1 | 106 | 0.125 | | 222 |
| 289 | (5R)-5-(2-fluoro-5-((4-phenyl-2-pyridinyl)oxy)phenyl)-2,2,5-trimethyl-5,6-dihydro-2H-1,4-thiazin-3-amine 1,1-dioxide | 454 | 106 | 0.0509 | 0.568 | 92.7 |
| 290 | (5R)-5-(5-((4,4'-bipyridin-2-yloxy)-2-fluorophenyl)-2,2,5-trimethyl-5,6-dihydro-2H-1,4-thiazin-3-amine 1,1-dioxide | 455 | 106 | 0.328 | 0.318 | 826 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 291 | (5R)-5-(2-fluoro-5-(thieno[2,3-c]pyridin-7-yloxy)phenyl)-2,2,5-trimethyl-5,6-dihydro-2H-1,4-thiazin-3-amine 1,1-dioxide | 434 | 106 | 0.517 | 0.914 | 242 |
| 292 | 4-(3-((3R)-5-amino-3,6,6-trimethyl-1,1-dioxido-3,6-dihydro-2H-1,4-thiazin-3-yl)-4-fluorophenoxy)thieno[3,2-c]pyridine-7-carboxamide | 477 | 106 | 2.01 | 2.23 | 219 |
| 293 | 2-(3-((3R)-5-amino-3,6,6-trimethyl-1,1-dioxido-3,6-dihydro-2H-1,4-thiazin-3-yl)-4-fluorophenoxy)-4-phenyl-3-pyridinecarbonitrile | 479 | 106 | 0.836 | 0.68 | 50.9 |
| 294 | (5R)-5-(2-fluoro-5-(1-isoquinolinyloxy)phenyl)-2,2,5-trimethyl-5,6-dihydro-2H-1,4-thiazin-3-amine 1,1-dioxide | 428 | 106 | 1.05 | 1.14 | 202 |
| 295 | 2-(3-((3R)-5-amino-3,6,6-trimethyl-1,1-dioxido-3,6-dihydro-2H-1,4-thiazin-3-yl)-4-fluorophenoxy)-4,6-dimethyl-3-pyridinecarbonitrile | 431 | 106 | 2.64 | 2.48 | 1690 |
| 296 | 2-(3-((3R)-5-amino-3,6,6-trimethyl-1,1-dioxido-3,6-dihydro-2H-1,4-thiazin-3-yl)-4-fluorophenoxy)-6-methyl-3-pyridinecarbonitrile | 417 | 106 | 0.263 | 0.515 | 232 |
| 297 | (5R)-5-(2-fluoro-5-((3-methoxy-2-pyridinyl)oxy)phenyl)-2,2,5-trimethyl-5,6-dihydro-2H-1,4-thiazin-3-amine 1,1-dioxide | 408 | 106 | 0.202 | 0.219 | 975 |
| 298 | (5R)-5-(2-fluoro-5-((6-methyl-4-(trifluoromethyl)-2-pyridinyl)oxy)phenyl)-2,2,5-trimethyl-5,6-dihydro-2H-1,4-thiazin-3-amine 1,1-dioxide | 460 | 106 | 0.106 | 0.737 | 547 |
| 299 | (5R)-5-(5-((3,5-dichloro-2-pyridinyl)oxy)-2-fluorophenyl)-2,2,5-trimethyl-5,6-dihydro-2H-1,4-thiazin-3-amine 1,1-dioxide | 447 | 106 | 0.174 | 0.796 | 82.4 |
| 300 | 6-(3-((3R)-5-amino-3,6,6-trimethyl-1,1-dioxido-3,6-dihydro-2H-1,4-thiazin-3-yl)-4-fluorophenoxy)-5-fluoro-3-pyridinecarboxamide | 439 | 106 | 0.897 | 1.18 | 717 |
| 301 | (5R)-5-(5-(benzyloxy)-2-fluorophenyl)-2,2,5-trimethyl-5,6-dihydro-2H-1,4-thiazin-3-amine 1,1-dioxide | 391.2 | 106 |  | 1.06 | 184 |
| 302 | (5R)-5-(2-fluoro-5-((2-methyl[1,3]thiazolo[4,5-c]pyridin-4-yl)oxy)phenyl)-2,2,5-trimethyl-5,6-dihydro-2H-1,4-thiazin-3-amine 1,1-dioxide | 449 | 106 | 3.49 | 2.87 | 241 |
| 303 | (5R)-5-(2-fluoro-5-((2-methoxypyrido[3,4-b]pyrazin-5-yl)oxy)phenyl)-2,2,5-trimethyl-5,6-dihydro-2H-1,4-thiazin-3-amine 1,1-dioxide | 460.2 | 106 | 1.22 | 2.54 | 1000 |
| 304 | (5R)-5-(5-((3-chloro-1,7-naphthyridin-8-yl)oxy)-2-fluorophenyl)-2,2,5-trimethyl-5,6-dihydro-2H-1,4-thiazin-3-amine 1,1-dioxide | 463 | 106 | 0.127 | 0.198 | 282 |
| 305 | (5R)-5-(2-fluoro-5-((3-methoxy-1,7-naphthyridin-8-yl)oxy)phenyl)-2,2,5-trimethyl-5,6-dihydro-2H-1,4-thiazin-3-amine 1,1-dioxide | 459 | 106 | 2.07 | 680 | |
| 306 | 2-(3-((3R)-5-amino-3,6,6-trimethyl-1,1-dioxido-3,6-dihydro-2H-1,4-thiazin-3-yl)-4-fluorophenoxy)-3-pyridinecarbonitrile | 403.1 | 106 | 0.256 | 0.241 | 218 |
| 307 | 2-(3-((3R)-5-amino-3,6,6-trimethyl-1,1-dioxido-3,6-dihydro-2H-1,4-thiazin-3-yl)-4-fluorophenoxy)-3-chloro-4-pyridinecarbonitrile | 437.1 | 106 | 0.168 | 0.258 | 298 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 308 | 3-(3-((3R)-5-amino-3,6,6-trimethyl-1,1-dioxido-3,6-dihydro-2H-1,4-thiazin-3-yl)-4-fluorophenoxy)-2-chloro-4-pyridinecarbonitrile | 437 | 106 | 4.16 | 3.27 | 224 |
| 309 | (5R)-5-(2-fluoro-5-((4-methoxy-2-pyrimidinyl)oxy)phenyl)-2,2,5-trimethyl-5,6-dihydro-2H-1,4-thiazin-3-amine 1,1-dioxide | 409.1 | 106 | 0.101 | 0.0751 | 274 |
| 310 | 2-(3-((3R)-5-amino-3,6,6-trimethyl-1,1-dioxido-3,6-dihydro-2H-1,4-thiazin-3-yl)-4-fluorophenoxy)-4-methyl-3-pyridinecarbonitrile | 417.2 | 106 | 1.34 | 0.931 | 444 |
| 311 | (5R)-5-(2-fluoro-5-((3-methyl-4 (trifluoromethyl)-2-pyridinyl)oxy)phenyl)-2,2,5-trimethyl-5,6-dihydro-2H-1,4-thiazin-3-amine 1,1-dioxide | 460.1 | 106 | 2.57 | 2.39 | 401 |
| 312 | 2-(3-((3R)-5-amino-3,6,6-trimethyl-1,1-dioxido-3,6-dihydro-2H-1,4-thiazin-3-yl)-4-fluorophenoxy)-4-(trifluoromethyl)-3-pyridinecarbonitrile | 471.1 | 106 | 2.89 ) | 1.59 | 771 |
| 313 | N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyrazinecarboxamide | 456 | Made by method C of example 94 | 0.00292 | 0.0063 | 887 |
| 314 | N-(3-((3R)-5-amino-3,6,6-trimethyl-1,1-dioxido-3,6-dihydro-2H-1,4-thiazin-3-yl)-4-fluorophenyl)-5-(2,2-difluoroethoxy)-2-pyrazinecarboxamide | 486 | Amidation method A | 0.00058 | 0.005 | 504 |
| 315 | N-(3-((3R)-5-amino-3,6,6-trimethyl-1,1-dioxido-3,6-dihydro-2H-1,4-thiazin-3-yl)-4-fluorophenyl)-2-quinolinecarboxamide | 455 | Mthod A | 0.0376 | 0.0253 | 253 |
| 316 | N-(3-((3R)-5-amino-3,6,6-trimethyl-1,1-dioxido-3,6-dihydro-2H-1,4-thiazin-3-yl)-4-fluorophenyl)-2-quinoxalinecarboxamide | 456 | Mthod A | 0.0412 | 0.018 | 36.6 |
| 317 | N-(3-((3R,6R)-5-amino-6-fluoro-3,6-dimethyl-1,1-dioxido-3,6-dihydro-2H-1,4-thiazin-3-yl)-4-fluorophenyl)-5-(2-butyn-1-yloxy)-2-pyrazinecarboxamide | 478 | Method A | 0.00021 | 0.0036 | >133.0 |
| 318 | N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyridinecarboxamide | 439 | Method A | 0.0018 | 0.0688 | >400.0 |
| 319 | N-(3-((3R,6R)-5-amino-6-fluoro-3,6-dimethyl-1,1-dioxido-3,6-dihydro-2H-1,4-thiazin-3-yl)-4-fluorophenyl)-5-(difluoromethyl)-2-pyridinecarboxamide | 459 | Method A | 0.00162 | 0.07 | >400.0 |
| 320 | N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-fluoro-2-pyridinecarboxamide | 461 | Method A | 0.0008 | 0.0789 | >400.0 |
| 321 | N-(3-((3R,6R)-5-amino-6-fluoro-3,6-dimethyl-1,1-dioxido-3,6-dihydro-2H-1,4-thiazin-3-yl)-4-fluorophenyl)-5-(difluoromethoxy)-3-methyl-2-pyridinecarboxamide | 489 | Method A | 0.00072 | 0.0449 | 387 |
| 322 | N-(3-((3R,6R)-5-amino-6-fluoro-3,6-dimethyl-1,1-dioxido-3,6-dihydro-2H-1,4-thiazin-3-yl)-4-fluorophenyl)-5-fluoro-2-pyridinecarboxamide | 427 | Method A | 0.00195 | 0.134 | 1220 |
| 323 | N-(3-((3R,6R)-5-amino-6-fluoro-3,6-dimethyl-1,1-dioxido-3,6-dihydro-2H-1,4-thiazin-3-yl)-4-fluorophenyl)-5-(trifluoromethyl)-2-pyrazinecarboxamide | 478 | Method A | 0.00386 | 0.288 | 931 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 324 | N-(3-((3R,6R)-5-amino-6-fluoro-3,6-dimethyl-1,1-dioxido-3,6-dihydro-2H-1,4-thiazin-3-yl)-4-fluorophenyl)-5-cyano-3-methyl-2-pyridinecarboxamide | 448 | Method A | 0.00102 | 0.0651 | 1370 |
| 325 | N-(3-((3R,6R)-5-amino-6-fluoro-3,6-dimethyl-1,1-dioxido-3,6-dihydro-2H-1,4-thiazin-3-yl)-4-fluorophenyl)-5-(2,2,2-trifluoroethoxy)-2-pyrazinecarboxamide | 508 | Method A | 0.00042 | 0.0445 | 1260 |
| 326 | N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-(difluoromethyl)-2-pyridinecarboxamide | 493 | Method A | 0.00277 | 0.0597 | 979 |
| 327 | N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-cyano-2-pyridinecarboxamide | 468 | Method A | 0.00074 | 0.0204 | >400.0 |
| 328 | N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-(methoxymethyl)-2-pyridinecarboxamide | 487 | Method A | 0.00051 | 0.0928 | 598 |
| 329 | N-(3-((3R)-5-amino-2-fluoro-3,6,6-trimethyl-1,1-dioxido-3,6-dihydro-2H-1,4-thiazin-3-yl)-4-fluorophenyl)-5-chloro-3-fluoro-2-pyridinecarboxamide | 475.1 | A | 0.00047 | 0.0058 | >400.0 |
| 330 | N-(3-((3R)-5-amino-2-fluoro-3,6,6-trimethyl-1,1-dioxido-3,6-dihydro-2H-1,4-thiazin-3-yl)-4-fluorophenyl)-5-(difluoromethoxy)-3-methyl-2-pyridinecarboxamide | 503.1 | A | 0.00075 | 0.0041 | 136 |
| 331 | N-(3-((3R)-5-amino-2-fluoro-3,6,6-trimethyl-1,1-dioxido-3,6-dihydro-2H-1,4-thiazin-3-yl)-4-fluorophenyl)-5-chloro-3-methyl-2-pyridinecarboxamide | 471 | A | .0003 | 0.0048 | 188 |
| 332 | N-(3-((3R)-5-amino-2-fluoro-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide | 492 | A | 0.00023 | 0.001 | 44.9 |
| 333 | N-(3-((3R)-5-amino-2-fluoro-3,6,6-trimethyl-1,1-dioxido-3,6-dihydro-2H-1,4-thiazin-3-yl)-4-fluorophenyl)-5-(2,2,2-trifluoroethoxy)-2-pyrazinecarboxamide | 522 | A | 0.0015 | 0.016 | 190 |
| 334 | N-(3-((3R)-5-amino-2-fluoro-3,6,6-trimethyl-1,1-dioxido-3,6-dihydro-2H-1,4-thiazin-3-yl)-4-fluorophenyl)-5-(difluoromethyl)-2-pyridinecarboxamide | 473 | A | .0024 | 0.0055 | 307 |
| 335 | N-(3-((3R)-5-amino-2-fluoro-3,6,6-trimethyl-1,1-dioxido-3,6-dihydro-2H-1,4-thiazin-3-yl)-4-fluorophenyl)-5-chloro-3-(methoxymethyl)-2-pyridinecarboxamide | 501 | A | 0.00056 | 0.0068 | 311 |
| 336 | N-(3-((3R)-5-amino-2-fluoro-3,6,6-trimethyl-1,1-dioxido-3,6-dihydro-2H-1,4-thiazin-3-yl)-4-fluorophenyl)-3-chloro-5-methoxy-2-pyridinecarboxamide | 487 | A | 0.0014 | 0.0053 | 533 |
| 337 | N-(3-((3R)-5-amino-2-fluoro-3,6,6-trimethyl-1,1-dioxido-3,6-dihydro-2H-1,4-thiazin-3-yl)-4-fluorophenyl)-5-methoxy-3-methyl-2-pyridinecarboxamide | 467 | A | 0.00313 | 0.0097 | 233 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 338 | N-(3-((2S,4s,7R)-9-amino-2-fluoro-7-methyl-5,5-dioxido-5-thia-8-azaspiro[3.5]non-8-en-7-yl)-4-fluorophenyl)-5-(difluoromethyl)-3-methyl-2-pyridinecarboxamide | 499 | Method A | 0.00294 | 0.0108 | 59 |
| 339 | N-(3-((3R,6R)-5-amino-6-fluoro-2,3,6-trimethyl-1,1-dioxido-3,6-dihydro-2H-1,4-thiazin-3-yl)-4-fluorophenyl)-5-chloro-2-pyridinecarboxamide | 457 | Method A | 0.0181 | 0.196 | 109 |
| 340 | N-(3-((8R)-6-amino-5,5,8-trimethyl-4,4-dioxido-4-thia-7-azaspiro[2.5]oct-6-en-8-yl)-4-fluorophenyl)-5-chloro-3-methyl-2-pyridinecarboxamide | 479 | Method A | 0.0051 | 0.0044 | 20 |
| 341 | N-(3-((8R)-6-amino-5,5,8-trimethyl-4,4-dioxido-4-thia-7-azaspiro[2.5]oct-6-en-8-yl)-4-fluorophenyl)-5-(difluoromethoxy)-3-methyl-2-pyridinecarboxamide | 511.2 | Method A | 0.00599 | 0.0024 | 9.4 |
| 143 | N-(4-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide | 437.1 | AA Example 2 | 0.115 | 0.462 | 221 |
| 145 | (5R)-5-(2-(((6-chloro-3-methylimidazo[1,2-a]pyridin-2-yl)methyl)amino)-5-fluoro-4-pyridinyl)-2,2,5-trimethyl-5,6-dihydro-2H-1,4-thiazin-3-amine 1,1-dioxide | 478.9 | Example | 0.44 | 0.412 | 102 |
| 194 | N-(3-((3R)-5-amino-3,6,6-trimethyl-1,1-dioxido-3,6-dihydro-2H-1,4-thiazin-3-yl)-4-fluorophenyl)-5-chloro-3-(1-methylethenyl)-2-pyridinecarboxamide | 479 | AM 01 | 0.00518 | 0.00342 | 617 |
| 195 | N-(3-((3R)-5-amino-3,6,6-trimethyl-1,1-dioxido-3,6-dihydro-2H-1,4-thiazin-3-yl)-4-fluorophenyl)-5-chloro-3-ethenyl-2-pyridinecarboxamide | 46 | AM 02 | 0.00059 | 0.0039 | 108 |
| 196 | N-(3-((3R)-5-amino-3,6,6-trimethyl-1,1-dioxido-3,6-dihydro-2H-1,4-thiazin-3-yl)-4-fluorophenyl)-5-chloro-3-ethyl-2-pyridinecarboxamide | 467 | AM 03 | 0.00181 | 0.0054 | 200 |
| 197 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-ethyl-2-pyridinecarboxamide | 485 | AM 04 | 0.00146 | 0.208 | 416 |
| 198 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-(1-methylethyl)-2-pyridinecarboxamide | 499.1 | AM 05 | 0.00799 | 0.0914 | 850 |
| 342 | N-(3-((3R)-5-amino-3,6,6-trimethyl-1,1-dioxido-3,6-dihydro-2H-1,4-thiazin-3-yl)-4-fluorophenyl)-5-(trifluoromethyl)-2-pyridinecarboxamide | 473 | Method B | 0.00061 | 0.0007 | 113 |
| 343 | N-(3-((3R)-5-amino-3,6,6-trimethyl-thiazin-3-yl)-4-fluorophenyl)-3-isoquinolinecarboxamide | 455 | Method B | 0.00511 | 0.0107 | 234 |
| 344 | N-(3-((3R)-5-amino-3,6,6-trimethyl-1,1-dioxido-3,6-dihydro-2H-1,4-thiazin-3-yl)-4-fluorophenyl)-5-(difluoromethoxy)-2-pyrazinecarboxamide | 472 | Method B | 0.00053 | 0.0004 | 388 |
| 345 | N-(3-((3R)-5-amino-3,6,6-trimethyl-1,1-dioxido-3,6-dihydro-2H-1,4-thiazin-3-yl)-4-fluorophenyl)-4-chloro-2-methoxybenzamide | 468 | Method B | 0.0313 | 0.0713 | 75.6 |
| 346 | N-(3-((3R)-5-amino-3,6,6-trimethyl-1,1-dioxido-3,6-dihydro-2H-1,4- | 503.9 | B | 0.00045 | 0.0014 | >400.0 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| | thiazin-3-yl)-4-fluorophenyl)-5-(2,2,2-trifluoroethoxy)-2-pyrazinecarboxamide | | | | | |
| 347 | N-(5-((3R)-5-amino-3,6,6-trimethyl-1,1-dioxido-3,6-dihydro-2H-1,4-thiazin-3-yl)-6-fluoro-3-pyridinyl)-5-chloro-3-methyl-2-pyridinecarboxamide | 453.9 | B | 0.0011 | 0.0018 | 71 |
| 348 | N-(5-((3R)-5-amino-3,6,6-trimethyl-1,1-dioxido-3,6-dihydro-2H-1,4-thiazin-3-yl)-6-fluoro-3-pyridinyl)-3-chloro-5-(difluoromethyl)-2-pyridinecarboxamide | 489.9 | B | 0.00589 | 0.00992 | 490 |
| 349 | N-(5-((7R)-9-amino-7-methyl-5,5-dioxido-5-thia-8-azaspiro[3.5]non-8-en-7-yl)-6-fluoro-3-pyridinyl)-5-(2-butyn-1-yloxy)-3-methyl-2-pyridinecarboxamide | 499.9 | B | 0.00078 | 0.0013 | 196 |
| 350 | N-(5-((7R)-9-amino-7-methyl-5,5-dioxido-5-thia-8-azaspiro[3.5]non-8-en-7-yl)-6-fluoro-3-pyridinyl)-3-methyl-5-(2,2,2-trifluoroethoxy)-2-pyridinecarboxamide | 529.9 | B | 0.00606 | 0.0345 | >400.0 |
| 351 | N-(3-((3R)-5-amino-3,6,6-trimethyl-1,1-dioxido-3,6-dihydro-2H-1,4-thiazin-3-yl)-4-fluorophenyl)-5-chloro-3-(methoxymethyl)-2-pyridinecarboxamide | 483 | B | 0.00052 | 0.0027 | >14.8 |
| 352 | N-(3-((3R)-5-amino-3,6,6-trimethyl-1,1-dioxido-3,6-dihydro-2H-1,4-thiazin-3-yl)-4-fluorophenyl)-3-bromo-5-chloro-2-pyridinecarboxamide | 518.9 | B | 0.0008 | 0.0009 | 410 |
| 353 | N-(3-((3R)-5-amino-3,6,6-trimethyl-1,1-dioxido-3,6-dihydro-2H-1,4-thiazin-3-yl)-4-fluorophenyl)-4-chloro-2-methylbenzamide | 452.0 | Method B | 0.00652 | 0.0166 | 708 |
| 354 | N-(3-((3R)-5-amino-3,6,6-trimethyl-1,1-dioxido-3,6-dihydro-2H-1,4-thiazin-3-yl)-4-fluorophenyl)-2-fluoro-4-methoxybenzamide | 452.0 | Method B | 0.0424 | 0.0187 | 1330 |
| 355 | N-(3-((3R)-5-amino-3,6,6-trimethyl-1,1-dioxido-3,6-dihydro-2H-1,4-thiazin-3-yl)-4-fluorophenyl)-5-cyano-3-methyl-2-pyridinecarboxamide | 444 | Method B | 0.0003 | 0.0005 | 283 |
| 356 | N-(3-((3R)-5-amino-3,6,6-trimethyl-1,1-dioxido-3,6-dihydro-2H-1,4-thiazin-3-yl)-4-fluorophenyl)-3-chloro-5-cyano-2-pyridinecarboxamide | 464.1 | Method B | 0.00035 | 0.0012 | 710 |
| 357 | N-(3-((3R)-5-amino-3,6,6-trimethyl-1,1-dioxido-3,6-dihydro-2H-1,4-thiazin-3-yl)-4-fluorophenyl)-5-methoxy-3-methyl-2-pyridinecarboxamide | 449.1 | B | 0.00283 | 0.0025 | 228 |
| 358 | N-(5-((7R)-9-amino-7-methyl-5,5-dioxido-5-thia-8-azaspiro[3.5]non-8-en-7-yl)-6-fluoro-3-pyridinyl)-5-(difluoromethoxy)-3-methyl-2-pyridinecarboxamide | 497.9 | Method B | 0.00642 | 0.0095 | 139 |
| 359 | N-(5-((7R)-9-amino-7-methyl-5,5-dioxido-5-thia-8-azaspiro[3.5]non-8-en-7-yl)-6-fluoro-3-pyridinyl)-5-chloro-3-methyl-2-pyridinecarboxamide | 465.9 | Method B | 0.0022 | .00521 | 105 |
| 360 | N-(3-((3S)-5-amino-3-(fluoromethyl)-6,6-dimethyl-1,1-dioxido-3,6-dihydro-2H-1,4-thiazin-3-yl)-4-fluorophenyl)-3,5-dimethyl-2-pyridinecarboxamide | 451.1 | | 0.00299 | 0.0245 | 636 |
| 361 | N-(3-((3S)-5-amino-3-(fluoromethyl)-6,6-dimethyl-1,1-dioxido-3,6-dihydro-2H-1,4-thiazin- | 473 | Method B | 0.0008 | 0.0193 | 437 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| | 3-yl)-4-fluorophenyl)-5-(difluoromethyl)-2-pyridinecarboxamide | | | | | |
| 362 | N-(3-((3S)-5-amino-3-(fluoromethyl)-6,6-dimethyl-1,1-dioxido-3,6-dihydro-2H-1,4-thiazin-3-yl)-4-fluorophenyl)-5-(difluoromethoxy)-2-pyridinecarboxamide | 489 | Method B | 0.0003 | 0.0035 | 303 |
| 363 | N-(3-((3S)-5-amino-3-(fluoromethyl)-6,6-dimethyl-1,1-dioxido-3,6-dihydro-2H-1,4-thiazin-3-yl)-4-fluorophenyl)-5-fluoro-2-pyridinecarboxamide | 440.9 | B | 0.0017 | 0.0456 | >400.0 |
| 364 | N-(3-((3S)-5-amino-3-(fluoromethyl)-6,6-dimethyl-1,1-dioxido-3,6-dihydro-2H-1,4-thiazin-3-yl)-4-fluorophenyl)-5-(2,2-difluoroethoxy)-2-pyrazinecarboxamide | 504 | Amidation method B | 0.0005 | 0.0214 | 858 |
| 365 | N-(3-((3S)-5-amino-3-(fluoromethyl)-6,6-dimethyl-1,1-dioxido-3,6-dihydro-2H-1,4-thiazin-3-yl)-4-fluorophenyl)-5-(2-fluoroethoxy)-2-pyrazinecarboxamide | 486 | Amidation method B | 0.00097 | 0.0447 | >400.0 |
| 366 | N-(3-((7S)-9-amino-7-(fluoromethyl)-5,5-dioxido-5-thia-8-azaspiro[3.5]non-8-en-7-yl)-4-fluorophenyl)-5-chloro-3-methyl-2-pyridinecarboxamide | 483 | Amidation method B | 0.00079 | 0.0141 | 241 |
| 367 | N-(3-((7S)-9-amino-7-(fluoromethyl)-5,5-dioxido-5-thia-8-azaspiro[3.5]non-8-en-7-yl)-4-fluorophenyl)-6-chloro-3-methylimidazo[1,2-a]pyridine-2-carboxamide | 522 | Amidation method B | 0.00507 | 0.0137 | >400.0 |
| 368 | N-(3-((7S)-9-amino-7-(fluoromethyl)-5,5-dioxido-5-thia-8-azaspiro[3.5]non-8-en-7-yl)-4-fluorophenyl)-5-cyano-3-methyl-2-pyridinecarboxamide | 474 | Amidation method B | 0.00064 | 0.0046 | 222 |
| 369 | N-(3-((7S)-9-amino-7-(fluoromethyl)-5,5-dioxido-5-thia-8-azaspiro[3.5]non-8-en-7-yl)-4-fluorophenyl)-5-(difluoromethyl)-3-methyl-2-pyridinecarboxamide | 499 | Amidation method B | 0.0014 | .0123) | 233 |
| 370 | N-(3-((7S)-9-amino-7-(fluoromethyl)-5,5-dioxido-5-thia-8-azaspiro[3.5]non-8-en-7-yl)-4-fluorophenyl)-5-chloro-3-(methoxymethyl)-2-pyridinecarboxamide | 12.9 | Amidation method B | 0.00081 | 0.0273 | >400.0 |
| 371 | N-(3-((7S)-9-amino-7-(fluoromethyl)-5,5-dioxido-5-thia-8-azaspiro[3.5]non-8-en-7-yl)-4-fluorophenyl)-5-(cyclopropyl methoxy)-3-methyl-2-pyridinecarboxamide | 519 | Amidation method B | 0.00156 | 0.077 | 391 |
| 372 | N-(3-((7S)-9-amino-7-(fluoromethyl)-5,5-dioxido-5-thia-8-azaspiro[3.5]non-8-en-7-yl)-4-fluorophenyl)-3-chloro-5-cyano-2-pyridinecarboxamide | 493.9 | Amidation method B | 0.00072 | 0.0071 | 367 |
| 373 | N-(3-((7S)-9-amino-7-(fluoromethyl)-5,5-dioxido-5-thia-8-azaspiro[3.5]non-8-en-7-yl)-4-fluorophenyl)-5-methoxy-3-methyl-2-pyridinecarboxamide | 479.1 | Amidation method B | 0.00245 | 0.0148 | 197 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 374 | N-(3-((7S)-9-amino-7-(fluoromethyl)-5,5-dioxido-5-thia-8-azaspiro[3.5]non-8-en-7-yl)-4-fluorophenyl)-3-methyl-5-(2,2,2-trifluoroethoxy)-2-pyridinecarboxamide | 547 | Amidation method B | 0.0011 | 0.0616 | 630 |
| 375 | N-(3-((7S)-9-amino-7-(fluoromethyl)-5,5-dioxido-5-thia-8-azaspiro[3.5]non-8-en-7-yl)-4-fluorophenyl)-5-chloro-3-methoxy-2-pyridinecarboxamide | 499 | Amidation method B | 0.0029 | 0.0298 | 781 |
| 376 | N-(3-((3S)-5-amino-3-(fluoromethyl)-6,6-dimethyl-1,1-dioxido-3,6-dihydro-2H-1,4-thiazin-3-yl)-4-fluorophenyl)-5-(difluoromethyl)-2-pyrazinecarboxamide | 474 | Made by method of C of example 5 | 0.00223 | 0.0615 | 172 |
| 377 | N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-3-methyl-2-pyridinecarboxamide | 467 | Made by method of C of example 5 | 0.003 | 0.0098 | 335 |
| 378 | N-(3-((3S)-5-amino-3-(fluoromethyl)-6,6-dimethyl-1,1-dioxido-3,6-dihydro-2H-1,4-thiazin-3-yl)-4-fluorophenyl)-3,5-difluoro-2-pyridinecarboxamide | 459 (M + H) | C | 0.0016 | 0.018 | >400.0 |
| 379 | N-(3-((3S)-5-amino-3-(fluoromethyl)-6,6-dimethyl-1,1-dioxido-3,6-dihydro-2H-1,4-thiazin-3-yl)-4-fluorophenyl)-3-chloro-5-(trifluoromethyl)-2-pyridinecarboxamide | 525 (M + H) | C | 0.00099 | 0.0115 | 775 |
| 380 | N-(3-((3S)-5-amino-3-(fluoromethyl)-6,6-dimethyl-1,1-dioxido-3,6-dihydro-2H-1,4-thiazin-3-yl)-4-fluorophenyl)-3,5-dichloro-2-pyrazinecarboxamide | 492 (M + H) | C | 0.0018 | 0.999 | 282 |
| 381 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-ethenyl-2-pyridinecarboxamide | 483 | C | 0.00086 | 0.0539 | 194 |
| 382 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-methoxy-2-pyridinecarboxamide | 487 | C | 0.0018 | 0.0173 | >400.0 |
| 383 | N-(3-((3S)-5-amino-3-(fluoromethyl)-6,6-dimethyl-1,1-dioxido-3,6-dihydro-2H-1,4-thiazin-3-yl)-4-fluorophenyl)-5-(trifluoromethyl)-2-pyridinecarboxamide | 491 | Method C | 0.00262 | 0.02 | 217 |
| 204 | N-(3-((5S,6R)-8-amino-5-fluoro-6-methyl-4,4-dioxido-4-thia-7-azaspiro[2.5]oct-7-en-6-yl)-4-fluorophenyl)-5-chloro-3-methyl-2-pyridinecarboxamide | 469 | Method C | 0.00087 | 0.0027 | 182 |
| 205 | N-(3-((5R,6R)-8-amino-5-fluoro-6-methyl-4,4-dioxido-4-thia-7-azaspiro[2.5]oct-7-en-6-yl)-4-fluorophenyl)-5-chloro-3-methyl-2-pyridinecarboxamide | 469 | Method C | 0.00044 | 0.0026 | 28 |
| 384 | 4-((5-((3R)-5-amino-3,6,6-trimethyl-1,1-dioxido-3,6-dihydro-2H-1,4-thiazin-3-yl)-6-fluoro-3-pyridinyl)amino)pyrido[3,2-d]pyrimidine-7-carbonitrile | 454.9 | cyanation procedure | 0.00636 | 0.0239 | 47.3 |
| 385 | 8-((5-((3R)-5-amino-3,6,6-trimethyl-1,1-dioxido-3,6-dihydro-2H-1,4-thiazin-3-yl)-6-fluoro-3-pyridinyl)amino)-1,7-naphthyridine-3-carbonitrile | 454 | cyanation procedure | 0.00262 | 0.0037 | 67.6 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 386 | 8-((5-((7R)-9-amino-7-methyl-5,5-dioxido-5-thia-8-azaspiro[3.5]non-8-en-7-yl)-6-fluoro-3-pyridinyl)amino)-1,7-naphthyridine-3-carbonitrile | 465.9 | cyanation procedure | 0.00409 | 0.0141 | 54.7 |
| 387 | 8-((3-((3S)-5-amino-3-(fluoromethyl)-6,6-dimethyl-1,1-dioxido-3,6-dihydro-2H-1,4-thiazin-3-yl)-4-fluorophenyl)amino)-1,7-naphthyridine-3-carbonitrile | 471.0 | General cyanation | 0.00044 | 0.0053 | 117 |
| 142 | N-(4-((3S)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide | 437.1 | CuI Amidation | 10 | 4.36 | >400.0 |
| 144 | N-(3-((3R)-5-amino-3,6,6-trimethyl-1,1-dioxido-3,6-dihydro-2H-1,4-thiazin-3-yl)-4-fluorophenyl)-5-(difluoromethoxy)-3-methyl-2-pyridinecarboxamide | 485.1 | CuI Amidation | 0.0006 | 0.0016 | 96.7 |
| 120 | N-(3-((7R)-9-amino-2,2-difluoro-7-methyl-5,5-dioxido-5-thia-8-azaspiro[3.5]non-8-en-7-yl)-4-fluorophenyl)-5-chloro-2-pyridinecarboxamide | 487 | CuI Amidation | 0.0013 | 0.0272 | 148 |
| 125 | N-(3-((2S,4s,7R)-9-amino-2-fluoro-7-methyl-5,5-dioxido-5-thia-8-azaspiro[3.5]non-8-en-7-yl)-4-fluorophenyl)-5-chloro-2-pyridinecarboxamide | 469 | CuI Amidation | 0.001 | 0.0107 | 42.8 |
| 124 | N-(3-((7R)-9-amino-2,2-difluoro-7-methyl-5,5-dioxido-5-thia-8-azaspiro[3.5]non-8-en-7-yl)-4-fluorophenyl)-5-chloro-3-methyl-2-pyridinecarboxamide | 501 | CuI Amidation | <0.002 | 0.0246 | 96.3 |
| 126 | N-(3-((7R)-9-amino-2,2-difluoro-7-methyl-5,5-dioxido-5-thia-8-azaspiro[3.5]non-8-en-7-yl)-4-fluorophenyl)-5-(difluoromethoxy)-3-methyl-2-pyridinecarboxamide | 533 | CuI Amidation | 0.00376 | 0.0177 | 45.6 |
| 127 | N-(3-((7R)-9-amino-7-methyl-5,5-dioxido-5-thia-8-azaspiro[3.5]non-8-en-7-yl)-4-fluorophenyl)-5-chloro-3-methyl-2-pyridinecarboxamide | 465 | CuI Amidation | 0.0016 | 0.0070 | 84.7 |
| 148 | N-(3-((3S)-5-amino-3-(fluoromethyl)-6,6-dimethyl-1,1-dioxido-3,6-dihydro-2H-1,4-thiazin-3-yl)-4-fluorophenyl)-5-(difluoromethoxy)-3-methyl-2-pyridinecarboxamide | 503.9 | CuI Amidation | 0.00163 | 0.0091 | 213 |
| 151 | N-(3-((3S)-5-amino-3-(fluoromethyl)-6,6-dimethyl-1,1-dioxido-3,6-dihydro-2H-1,4-thiazin-3-yl)-4-fluorophenyl)-5-(cyclobutylmethoxy)-3-methyl-2-pyridinecarboxamide | 521 | CuI Amidation | 0.0017 | 0.1 | 232 |
| 388 | N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-methyl-2-pyridinecarboxamide | 457.1 | General amidation method D | 0.0004 | 0.0479 | 230 |
| 389 | N-(3-((3S)-5-amino-3-(fluoromethyl)-6,6-dimethyl-1,1-dioxido-3,6-dihydro-2H-1,4-thiazin-3-yl)-4-fluorophenyl)-5-((4-fluoro-2-butyn-1-yl)oxy)-2-pyridinecarboxamide | 509 | Method D from intermed late BY 001 | 0.00026 | 0.0014 | 268 |
| 390 | N-(3-((3S)-5-amino-3-(fluoromethyl)-6,6-dimethyl-1,1-dioxido-3,6-dihydro-2H-1,4-thiazin-3-yl)-4-fluorophenyl)-6-cyano-3-methylimidazo[1,2-a]pyridine-2-carboxamide | 501 | Method D from intermed late BY 005 | 0.00485 | 0.0236 | 379 |
| 391 | N-(3-((3S)-5-amino-3-(fluoromethyl)-6,6-dimethyl-1,1-dioxido-3,6-dihydro-2H-1,4-thiazin- | 496 | Method D from | 0.00969 | 0.0361 | 303 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| | 3-yl)-4-fluorophenyl)-6-chloroimidazo[1,2-a]pyridine-2-carboxamide | | Intermediate BY 006 | | | |
| 392 | N-(3-((3S)-5-amino-3-(fluoromethyl)-6,6-dimethyl-1,1-dioxido-3,6-dihydro-2H-1,4-thiazin-3-yl)-4-fluorophenyl)-6-methoxy-3-methylimidazo[1,2-a]pyridine-2-carboxamide | 506 | Method D from Intermediate BY 007 | 0.104 | 0.823 | 97.6 |
| 393 | N-(3-((3S)-5-amino-3-(fluoromethyl)-6,6-dimethyl-1,1-dioxido-3,6-dihydro-2H-1,4-thiazin-3-yl)-4-fluorophenyl)-6-fluoro-3-methylimidazo[1,2-a]pyridine-2-carboxamide | 494 | Method D from Intermediate BY 007 | 0.0117 | 0.0605 | 103 |
| 394 | N-(3-((3S)-5-amino-3-(fluoromethyl)-6,6-dimethyl-1,1-dioxido-3,6-dihydro-2H-1,4-thiazin-3-yl)-4-fluorophenyl)-6-chloro-3-ethylimidazo[1,2-a]pyridine-2-carboxamide | 524 | Method D from Intermediate BY 008 | 0.0083 | 0.0235 | >14.8, |
| 395 | N-(3-((3S)-5-amino-3-(fluoromethyl)-6,6-dimethyl-1,1-dioxido-3,6-dihydro-2H-1,4-thiazin-3-yl)-4-fluorophenyl)-6-chloro-3-(1-methylethyl)imidazo[1,2-a]pyridine-2-carboxamide | 538 | Method D from Intermediate BY 0098 | 0.0377 | 0.125 | 822 |
| 396 | N-(3-((1R,6R)-4-amino-3,3-dimethyl-2,2-dioxido-2-thia-5-azabicyclo[4.1.0]hept-4-en-6-yl)-4-fluorophenyl)-5-chloro-3-methyl-2-pyridinecarboxamide | 451 | Amidation method D | 0.00239 | 0.862 | 187 |
| 397 | N-(5-((3R)-5-amino-3,6,6-trimethyl-1,1-dioxido-3,6-dihydro-2H-1,4-thiazin-3-yl)-6-fluoro-2-methyl-3-pyridinyl)-5-chloro-2-pyridinecarboxamide | 454.0 | E | 3.04 | 3.25 | 523 |
| 398 | N-(5-((3R)-5-amino-3,6,6-trimethyl-1,1-dioxido-3,6-dihydro-2H-1,4-thiazin-3-yl)-6-fluoro-3-pyridinyl)-5-chloro-2-pyridinecarboxamide | 439.9 | E | 0.002 | 0.0114 | 183 |
| 399 | N-(5-((3R)-5-amino-3,6,6-trimethyl-1,1-dioxido-3,6-dihydro-2H-1,4-thiazin-3-yl)-6-fluoro-3-pyridinyl)-5-fluoro-2-pyridinecarboxamide | 423.9 | E | 0.0031 | 0.0393 | 419 |
| 400 | N-(5-((3R)-5-amino-3,6,6-trimethyl-1,1-dioxido-3,6-dihydro-2H-1,4-thiazin-3-yl)-6-fluoro-3-pyridinyl)-5-(difluoromethoxy)-3-methyl-2-pyridinecarboxamide | 485.9 | E | 0.0014 | 0.0089 | 156 |
| 401 | N-(5-((3R)-5-amino-3,6,6-trimethyl-1,1-dioxido-3,6-dihydro-2H-1,4-thiazin-3-yl)-6-fluoro-3-pyridinyl)-5-methoxy-2-pyridinecarboxamide | 436 | E | 0.00398 | 0.0179 | 757 |
| 402 | N-(5-((3R)-5-amino-3,6,6-trimethyl-1,1-dioxido-3,6-dihydro-2H-1,4-thiazin-3-yl)-6-fluoro-3-pyridinyl)-5-(2,2,2-trifluoroethoxy)-2-pyrazinecarboxamide | 504.9 | E | 0.0011 | 0.011 | 2780 |
| 403 | N-(5-((3R)-5-amino-3,6,6-trimethyl-1,1-dioxido-3,6-dihydro-2H-1,4-thiazin-3-yl)-6-fluoro-3-pyridinyl)-5-cyano-2-pyridinecarboxamide | 431 | E | 0.0019 | 0.0146 | 233 |
| 404 | N-(5-((3R)-5-amino-3,6,6-trimethyl-1,1-dioxido-3,6-dihydro-2H-1,4-thiazin-3-yl)-6-fluoro-3-pyridinyl)-5-(difluoromethyl)-2-pyridinecarboxamide | 455.9 | E | 0.011 | 0.0119 | 247 |
| 405 | N-(3-((3S)-5-amino-3-(fluoromethyl)-6,6-dimethyl-1,1-dioxido-3,6-dihydro-2H-1,4-thiazin-3-yl)-4-fluorophenyl)-5-(2,2,2-trifluoroethoxy)-2-pyrazinecarboxamide | 521.9 | E | 0.0006 | 0.027 | 576 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 406 | N-(3-((3S)-5-amino-3-(fluoromethyl)-6,6-dimethyl-1,1-dioxido-3,6-dihydro-2H-1,4-thiazin-3-yl)-4-fluorophenyl)-5-cyano-2-pyridinecarboxamide | 448.1 | E | 0.00054 | 0.0143 | >400.0 |
| 407 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-(1-methylethenyl)-2-pyridinecarboxamide | 497 | E | 0.00354 | 0.057 | 440 |
| 408 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-methyl-2-pyridinecarboxamide | 471 | Method E | 0.0004 | 0.0232 | 136 |
| 409 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-fluoro-2-pyridinecarboxamide | 475 | Method E | 0.0006 | 0.0037 | 363 |
| 410 | N-(3-((7R)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide,N-(3-((7S)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide | 515 | Amidation method E | 0.0023 | 0.0119 | 170 |
| 411 | N-(3-((7R)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide | 515 | Amidation mathod E | 3.51 | >15.6 | 514 |
| 412 | N-(3-((7S)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide | 515 | Amidation method E | 0.00063 | 0.0082 | 78.9 |
| 413 | N-(3-((4aR,7aR)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide,N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide | 513 | Method E | 0.00265 | 0.0103 | 111 |
| 414 | (5R)-5-(5-((2,2-difluoro-1,3-benzodioxol-5-yl)amino)-2-fluoro-3-pyridinyl)-2,2,5-trimethyl-5,6-dihydro-2H-1,4-thiazin-3-amine 1,1-dioxide | 456.9 | F | 3.2 | 2.53 | 33.9 |
| 415 | (7R)-7-(5-amino-2-fluoro-3-pyridinyl)-7-methyl-5-thia-8-azaspiro[3.5]non-8-en-9-amine 5,5-dioxide | 313 | G | 14.5 | >15.6 | 104 |
| 106 | N-(3-((3R)-5-amino-3,6,6-trimethyl-1,1-dioxido-3,6-dihydro-2H-1,4-thiazin-3-yl)-4-fluorophenyl)-4-chloro-1-(difluoromethyl)-1H-pyrazole-3-carboxamide | 478 | Hatu Method | 0.00174 | | 112 |
| 110 | N-(3-((3R)-5-amino-3,6,6-trimethyl-thiazin-3-yl)-4-fluorophenyl)-5-methyl-2-pyrazinecarboxamide | 420 | Hatu Method | 0.0202 | 0.0144 | 1840 |
| 111 | N-(3-((3R)-5-amino-3,6,6-trimethyl-thiazin-3-yl)-4-fluorophenyl)-3,5-dimethyl-2-pyrazinecarboxamide | 434 | Hatu Method | 0.0182 | 0.0244 | >400.0 |
| 416 | N-(3-((7R)-9-amino-7-methyl-5,5-dioxido-5-thia-8-azaspiro[3.5]non-8- | 451 | Hatu Method | 0.00236 | 0.0059 | 59.5 |

TABLE II-continued

| Example | Compound Name | Mass Spec | Method Used | BACE1 FRET assay $IC_{50}$ (uM) | HEK cell assay $IC_{50}$ (uM) | CatD IC50 (μM) |
|---|---|---|---|---|---|---|
| | en-7-yl)-4-fluorophenyl)-5-chloro-2-pyridinecarboxamide | | | | | |
| 121 | N-(3-((7R)-9-amino-7-methyl-5,5-dioxido-5-thia-8-azaspiro[3.5]non-8-en-7-yl)-4-fluorophenyl)-5-(difluoromethoxy)-3-methyl-2-pyridinecarboxamide | 497 | Hatu Method | 0.00311 | 0.0074 | 67.5 |
| 122 | N-(3-((7R)-9-amino-7-methyl-5,5-dioxido-5-thia-8-azaspiro[3.5]non-8-en-7-yl)-4-fluorophenyl)-5-cyano-3-methyl-2-pyridinecarboxamide | 456 | Hatu Method | 0.00076 | 0.00244 | 134 |
| 123 | N-(3-((7R)-9-amino-7-methyl-5,5-dioxido-5-thia-8-azaspiro[3.5]non-8-en-7-yl)-4-fluorophenyl)-5-(difluoromethyl)-3-methyl-2-pyridinecarboxamide | 481 | Hatu Method | 0.00457 | 0.0063 | 150 |
| 131 | N-(3-((6S,7R)-9-amino-6-fluoro-7-methyl-5,5-dioxido-5-thia-8-azaspiro[3.5]non-8-en-7-yl)-4-fluorophenyl)-5-chloro-2-pyridinecarboxamide | 469 | Hatu Method | 0.0016 | 0.00901 | 162 |
| 132 | N-(3-((7R)-9-amino-6-fluoro-7-methyl-5,5-dioxido-5-thia-8-azaspiro[3.5]non-8-en-7-yl)-4-fluorophenyl)-5-(difluoromethoxy)-3-methyl-2-pyridinecarboxamide | 515 | Hatu Method | 0.00297 | 0.0058 | 61.8 |
| 127 | N-(3-((7R)-9-amino-6-fluoro-7-methyl-5,5-dioxido-5-thia-8-azaspiro[3.5]non-8-en-7-yl)-4-fluorophenyl)-5-chloro-3-methyl-2-pyridinecarboxamide | 483 | Hatu Method | 0.001 | 0.0136 | 55.4 |
| 136 | N-(3-((7R)-9-amino-6-fluoro-7-methyl-5,5-dioxido-5-thia-8-azaspiro[3.5]non-8-en-7-yl)-4-fluorophenyl)-5-(difluoromethyl)-3-methyl-2-pyridinecarboxamide | 499 | Hatu Method | 0.0021 | 0.0049 | 236 |
| 137 | N-(3-((7R)-9-amino-6-fluoro-7-methyl-5,5-dioxido-5-thia-8-azaspiro[3.5]non-8-en-7-yl)-4-fluorophenyl)-5-methoxy-3-methyl-2-pyridinecarboxamide | 479 | Hatu Method | 0.00363 | 0.0064 | 81.3 |
| 122 | N-(3-((7R)-9-amino-6-fluoro-7-methyl-5,5-dioxido-5-thia-8-azaspiro[3.5]non-8-en-7-yl)-4-fluorophenyl)-5-cyano-3-methyl-2-pyridinecarboxamide | 474 | Hatu Method | 0.00054 | 0.0019 | 194 |
| 139 | N-(3-((7R)-9-amino-6-fluoro-7-methyl-5,5-dioxido-5-thia-8-azaspiro[3.5]non-8-en-7-yl)-4-fluorophenyl)-5-chloro-3-methoxy-2-pyridinecarboxamide | 499 | Hatu Method | 0.0038 | 0.0118 | 408 |
| 140 | N-(3-((7R)-9-amino-6-fluoro-7-methyl-5,5-dioxido-5-thia-8-azaspiro[3.5]non-8-en-7-yl)-4-fluorophenyl)-5-(difluoromethyl)-2-pyrazinecarboxamide | 486 | Hatu Method | 0.0088 | 0.0146 | 400.0 |
| 141 | N-(3-((7R)-9-amino-6-fluoro-7-methyl-5,5-dioxido-5-thia-8-azaspiro[3.5]non-8-en-7-yl)-4-fluorophenyl)-6-chloro-3-methylimidazo[1,2-a]pyridine-2-carboxamide | 522 | Hatu Method | | | |
| 417 | (7S)-7-(5-amino-2-fluorophenyl)-7-(fluoromethyl)-5-thia-8-azaspiro[3.5]non-8-en-9-amine 5,5-dioxide | 330 | Intermeidate date 2 Step 2-3 | 2.1 | 3.65 | 69.7 |
| 167 | 3-((3-((3R)-5-amino-3,6,6-trimethyl-1,1-dioxido-3,6-dihydro-2H-1,4-thiazin-3-yl)-4-fluorophenyl)amino)-2-chlorothieno[3,2-b]pyridine-6-carbonitrile | 492 | JBH2 | 0.0139 | 1.44 | 11.8 |
| 164 | (5R)-5-(5-amino-2-fluorophenyl)-6-fluoro-2,2,5-trimethyl-5,6-dihydro-2H-1,4-thiazin-3-amine 1,1-dioxide | 318.2 | JBH1 | 3.72 | 3.03 | 190 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 168 | N-(3-((3R)-5-amino-2-fluoro-3,6,6-trimethyl-1,1-dioxido-3,6-dihydro-2H-1,4-thiazin-3-yl)-4-fluorophenyl)-3-chloro-1,7-naphthyridin-8-amine | 480.2 | JBH3 | 0.00092 | 0.0167 | 66.8 |
| 418 | (7R)-7-(5-bromo-2-fluorophenyl)-7-(fluoromethyl)-5-thia-8-azaspiro[3.5]non-8-en-9-amine 5,5-dioxide | 392.8 | KR 001 | >40.0 | >15.6 | >400.0 |
| 107 | (5R)-5-(5-(((4-chloro-1-(difluoromethyl)-1H-pyrazol-3-yl)methyl)amino)-2-fluorophenyl)-2,2,5-trimethyl-5,6-dihydro-2H-1,4-thiazin-3-amine 1,1-dioxide | 464 | KR002 | 0.00227 | | 81.1 |
| 108 | (5R)-5-(5-(((4-chloro-1-(2,2,2-trifluoroethyl)-1H-pyrazol-3-yl)methyl)amino)-2-fluorophenyl)-2,2,5-trimethyl-5,6-dihydro-2H-1,4-thiazin-3-amine 1,1-dioxide | 496 | KR003 | 0.0452 | 0.161 | 49.8 |
| 109 | (5R)-5-(5-(((4-chloro-1-(2,2,2-trifluoroethyl)-1H-pyrazol-5-yl)methyl)amino)-2-fluorophenyl)-2,2,5-trimethyl-5,6-dihydro-2H-1,4-thiazin-3-amine 1,1-dioxide | 496 | KR003 | 0.208 | 0.36 | 12.2 |
| 173 | 3-((3R)-5-amino-3,6,6-trimethyl-1,1-dioxido-3,6-dihydro-2H-1,4-thiazin-3-yl)-N-(4-cyano-2-hydroxyphenyl)-4-fluorobenzamide | 445 | KS-1 | 2.29 | >15.6 | 104 |
| 419 | N-(3-((3R)-5-amino-3,6,6-trimethyl-1,1-dioxido-3,6-dihydro-2H-1,4-thiazin-3-yl)-4-fluorophenyl)-3-(2,2,2-trifluoroethoxy)-1,7-naphthyridin-8-amine | 526.1 | LS1 | 0.00451 | 0.026 | 631 |
| 161 | N-(3-((3R)-5-amino-3,6,6-trimethyl-1,1-dioxido-2H-1,4-thiazin-3-yl)-4-fluorophenyl)-3-(2,2-difluoroethoxy)-1,7-naphthyridin-8-amine | 508.2 | LSI | 0.0143 | 0.0178 | 447 |
| 420 | ((8-((3-((3R)-5-amino-3,6,6-trimethyl-1,1-dioxido-3,6-dihydro-2H-1,4-thiazin-3-yl)-4-fluorophenyl)amino)-1,7-naphthyridin-3-yl)oxy)acetonitrile | 483.2 | 161 | 0.00485 | 0.0054 | 1260 |
| 421 | N-(3-((3R)-5-amino-3,6,6-trimethyl-1,1-dioxido-3,6-dihydro-2H-1,4-thiazin-3-yl)-4-fluorophenyl)-3-(2-fluoroethoxy)-1,7-naphthyridin-8-amine | 490.1 | 161 | 0.031 | 0.0115 | 1450 |
| 422 | N-(3-((3R)-5-amino-3,6,6-trimethyl-1,1-dioxido-3,6-dihydro-2H-1,4-thiazin-3-yl)-4-fluorophenyl)-3-ethoxy-1,7-naphthyridin-8-amine | 472.2 | 161 | 0.0184 | 0.029 | 958 |
| 162 | 8-((3-((3R)-5-amino-3,6,6-trimethyl-1,1-dioxido-3,6-dihydro-2H-1,4-thiazin-3-yl)-4-fluorophenyl)amino)pyrido[2,3-d]pyridazine-3-carbonitrile | 454.1 | LS2 | 0.0023 | 0.0015 | 418 |
| 423 | N-(3-((3R,6R)-5-amino-6-fluoro-3,6-dimethyl-1,1-dioxido-3,6-dihydro-2H-1,4-thiazin-3-yl)-4-fluorophenyl)-2-(trifluoromethyl)pyrido[3,4-b]pyrazin-5-amine | 501 | eg 162 step 6 (General SnAr wth AcOH) | 0.0013 | 0.735 | >133.0 |
| 174 | N-(3-((3R,6R)-5-amino-6-fluoro-3,6-dimethyl-1,1-dioxido-3,6-dihydro-2H-1,4-thiazin-3-yl)-4-fluorophenyl)-3-chloro-1,7-naphthyridin-8-amine | 466.1 (M + H) | eg 162 step 6 | 0.00033 | 0.119 | 101 |
| 175 | N-(3-((3R,6R)-5-amino-6-fluoro-3,6-dimethyl-1,1-dioxido-3,6-dihydro-2H-1,4-thiazin-3-yl)-4-fluorophenyl)-7-chloropyrido[3,2-d]pyrimidin-4-amine | 467.0 (M + H) | eg 162 step 6 | 0.00388 | 0.103 | 75.8 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 177 | N-(3-((3R,6R)-5-amino-6-fluoro-3,6-dimethyl-1,1-dioxido-3,6-dihydro-2H-1,4-thiazin-3-yl)-4-fluorophenyl)-7-methoxypyrido[3,2-d]pyrimidin-4-amine | 463.1 (M + H) | eg 162 step 6 | 0.00268 | 0.0782 | 175 |
| 180 | 4-((3-((3R,6R)-5-amino-6-fluoro-3,6-dimethyl-1,1-dioxido-3,6-dihydro-2H-1,4-thiazin-3-yl)-4-fluorophenyl)amino)pyrido[3,2-d]pyrimidine-7-carbonitrile | 458.1 (M + H) | eg 162 step 6 | 0.0011 | 0.0894 | 65.5 |
| 424 | N-(5-((3R)-5-amino-3,6,6-trimethyl-1,1-dioxido-3,6-dihydro-2H-1,4-thiazin-3-yl)-6-methoxy-3-pyridinyl)-2-pyridinecarboxamide | 418.1 | Made by method of example MX312 | 0.298 | 0.131 | 567 |
| 425 | N-(5-((7R)-9-amino-7-methyl-5,5-dioxido-5-thia-8-azaspiro[3.5]non-8-en-7-yl)-1-methyl-6-oxo-1,6-dihydro-3-pyridinyl)-6-chloro-3-methylimidazo[1,2-a]pyridine-2-carboxamide | 517.1 | Made by method of example MX312 | | | |
| 426 | N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-2-pyridinecarboxamide,N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-chloro-2-pyridinecarboxamide | 467 | Made by method E of example NC 1 | 0.0015 | 0.0136 | 170 |
| 427 | N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide,N-(3-((4aS,7aR)-3-amino-2,2-dimethyl-1,1-dioxido-7,7a-dihydro-2H-furo[3,4-13][1,4]thiazin-4a(5H)-yl)-4-fluorophenyl)-5-chloro-3-methyl-2-pyridinecarboxamide | 481 | Made by method E of example NC 1 | 0.001 | 0.033 | 220 |
| 428 | N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide,N-(3-((4aS,7aR)-3-amino-2,2-dimethyl-1,1-dioxido-7,7a-dihydro-2H-furo[3,4-13][1,4]thiazin-4a(5H)-yl)-4-fluorophenyl)-5-methoxy-3-methyl-2-pyridinecarboxamide | 477.8 | Made by method E of example NC 1 | 0.00971 | 0.0373 | 309 |
| 185 | (4aR,7aS)-4a-(5-bromo-2-fluorophenyl)-2,2-dimethyl-4a,5,7,7a-tetrahydro-2H-furo[3,4-b][1,4]1,1-dioxide, (4aS,7aR)-4a-(5-bromo-2-fluorophenyl)-2,2-dimethyl-4a,5,7,7a-tetrahydro-2H-furo[3,4-b][1,4]1,1-dioxide | 391 | Made in step 7 of example NC 1 | 30.2 | >15.6 | 322 |
| 429 | N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine,N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine | 489.9 | Made by method Ex. 44 step 1 of example NC 1 | 0.0046 | 0.157 | 131 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 185b | (4aS,7aS)-4a-(5-bromo-2-fluorophenyl)-2,2-dimethyl-4a,5,7,7a-tetrahydro-2H-furo[3,4-b][1,4]thiazin-3-amine 1,1-dioxide | 390.8 | Made in step 7 of example NC 1 after chiral separation, compound 1 | >40.0 | >15.6 | >400.0 |
| 185a | (4aR,7aR)-4a-(5-bromo-2-fluorophenyl)-2,2-dimethyl-4a,5,7,7a-tetrahydro-2H-furo[3,4-b][1,4]1,1-dioxide | 390.8 | Made in step 7 of example NC 1 after chiral separation, compound 2 | 4.83 | >15.6 | 70.9 |
| 430 | N-(3-((4aS,7aS)-3-amino-2,2-dimethyl-1,1-dioxido-7,7a-dihydro-2H-furo[3,4-13][1,4]thiazin-4a(5H)-yl)-4-fluorophenyl)-5-methoxy-3-methyl-2-pyridinecarboxamide | 477 | Made in step 7 of example NC 1 after chiral separation, compound 2 | 0.0041 | 0.0117 | 144 |
| 183 | N-(3-((1R,6R)-4-amino-3,3-dimethyl-2,2-dioxido-2-thia-5-azabicyclo[4.1.0]hept-4-en-6-yl)-4-fluorophenyl)-3-chloro-1,7-naphthyridin-8-amine | 460 | | 0.00305 | 4.74 | 87.9 |
| 152 | (5R)-5-(5-(((6-chloro-3-methylimidazo[1,2-a]pyridin-2-yl)methyl)amino)-2-fluorophenyl)-2,2,5-trimethyl-5,6-dihydro-2H-1,4-thiazin-3-amine 1,1-dioxide | 478 (M + H) | PH-1 | 2.94 | 0.302 | 1460 |
| 153 | 3-((3R)-5-amino-3,6,6-trimethyl-1,1-dioxido-3,6-dihydro-2H-1,4-thiazin-3-yl)-N-(4-chlorophenyl)-4-fluorobenzamide | 438 (M + H) | PH-2 | 4.68 | 3.21 | 237 |
| 154 | (7R)-7-(3-bromophenyl)-7-methyl-5-thia-8-azaspiro[3.5]non-8-en-9-amine 5,5-dioxide | 457/459 (M + H) | PH-3 | 6.06 | 2.39 | 31.2 |
| 155 | N-(3-((3S)-5-amino-3-(fluoromethyl)-6,6-dimethyl-1,1-dioxido-3,6-dihydro-2H-1,4-thiazin-3-yl)-4-fluorophenyl)-3,5-dimethoxy-2-pyrazinecarboxamide | 484 (M + H) | PH-4 | 0.0043 | 0.0351 | 470 |
| 156 | N-(3-((3S)-5-amino-3-(fluoromethyl)-6,6-dimethyl-1,1-dioxido-3,6-dihydro-2H-1,4-thiazin-3-yl)-4-fluorophenyl)-5-(cyclopropyl methoxy)-2-pyrazinecarboxamide | 494 (M + H) | PH-5 | 0.0005 | 0.0049 | 835 |
| 157 | 8-((3-((3S)-5-amino-3-(fluoromethyl)-6,6-dimethyl-1,1-dioxido-3,6-dihydro-2H-1,4-thiazin-3-yl)-4-fluorophenyl)amino)-5-fluoro-1,7-naphthyridine-3-carbonitrile | 489 (M + H) | PH-6 | 0.00056 | 0.0271 | >14.8 |
| 158 | N-(3-((3S)-5-amino-3-(fluoromethyl)-6,6-dimethyl-1,1-dioxido-3,6-dihydro-2H-1,4-thiazin-3-yl)-4-fluorophenyl)-6-chloro-3-methylimidazo[1,2-a]pyridine-2-carboxamide | 510.0 (M + H) | PH-7 | 0.00303 | 0.0106 | 4060 |
| 159 | N-(3-((3S)-5-amino-3-(fluoromethyl)-6,6-dimethyl-1,1-dioxido-3,6-dihydro-2H-1,4-thiazin-3-yl)-4-fluorophenyl)-5-fluoro-3-methoxy-1,7-naphthyridin-8-amine | 494.0 | PH-8 | 0.00055 | 0.0285 | 159 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 431 | N-(3-((3S)-5-amino-3-(fluoromethyl)-6,6-dimethyl-1,1-dioxido-3,6-dihydro-2H-1,4-thiazin-3-yl)-4-fluorophenyl)-3-(cyclopropylmethoxy)-5-fluoro-1,7-naphthyridin-8-amine | 534 | PH-8 | 0.0012 | 0.1 | 476 |
| 432 | N-(3-((3S)-5-amino-3-(fluoromethyl)-6,6-dimethyl-1,1-dioxido-3,6-dihydro-2H-1,4-thiazin-3-yl)-4-fluorophenyl)-5-fluoro-3-(2,2,2-trifluoroethoxy)-1,7-naphthyridin-8-amine | 562 | PH-8 | 0.00247 | 0.187 | 312 |
| 433 | 8-((3-((3S)-5-amino-3-(fluoromethyl)-6,6-dimethyl-1,1-dioxido-3,6-dihydro-2H-1,4-thiazin-3-yl)-4-fluorophenyl)amino)-5-fluoro-1,7-naphthyridin-3-ol | 480 | PH-8 | 0.0006 | 0.0314 | 111 |
| 434 | N-(3-((3S)-5-amino-3-(fluoromethyl)-6,6-dimethyl-1,1-dioxido-3,6-dihydro-2H-1,4-thiazin-3-yl)-4-fluorophenyl)-3-(cyclobutylmethoxy)-5-fluoro-1,7-naphthyridin-8-amine | 548 | PH-8 | 0.0015 | 0.341 | 32.3 |
| 435 | N-(3-((3S)-5-amino-3-(fluoromethyl)-6,6-dimethyl-1,1-dioxido-3,6-dihydro-2H-1,4-thiazin-3-yl)-4-fluorophenyl)-3-ethoxy-5-fluoro-1,7-naphthyridin-8-amine | 508 | PH-8 | 0.0016 | 0.049 | >400.0 |
| 436 | N-(3-((3S)-5-amino-3-(fluoromethyl)-6,6-dimethyl-1,1-dioxido-3,6-dihydro-2H-1,4-thiazin-3-yl)-4-fluorophenyl)-5-fluoro-3-(2-methylpropoxy)-1,7-naphthyridin-8-amine | 536 | PH-8 | 0.0043 | 0.626 | 61.6 |
| 437 | N-(3-((3S)-5-amino-3-(fluoromethyl)-6,6-dimethyl-1,1-dioxido-3,6-dihydro-2H-1,4-thiazin-3-yl)-4-fluorophenyl)-3-(2,2-difluoroethoxy)-5-fluoro-1,7-naphthyridin-8-amine | 544 | PH-8 | 0.00223 | 0.0643 | >1.65 |
| 438 | N-(3-((7S)-9-amino-7-(fluoromethyl)-5,5-dioxido-5-thia-8-azaspiro[3.5]non-8-en-7-yl)-4-fluorophenyl)-3-ethoxy-5-fluoro-1,7-naphthyridin-8-amine | 520 | PH-8 | 0.00382 | 0.198 | >1.65 |
| 163 | (5R)-5-(2-fluoro-5-(2-pyridinylsulfanyl)phenyl)-2,2,5-trimethyl-5,6-dihydro-2H-1,4-thiazn-3-amine 1,1-dioxide | 394.1 | P0-01 | 3.25 | 2.36 | 73.5 |
| 439 | (5R)-5-(2-fluoro-5-((3-fluoro-2-pyridinyl)sulfanyl)phenyl)-2,2,5-trimethyl-5,6-dihydro-2H-1,4-thiazin-3-amine 1,1-dioxide | 412 | 163 | 0.375 | 0.99 | 215 |
| 440 | 2-((3-((3R)-5-amino-3,6,6-trimethyl-1,1-dioxido-3,6-dihydro-2H-1,4-thiazin-3-yl)-4-fluorophenyl)sulfanyl)-4-pyridinecarbonitrile | 419 | P0-01 | 0.566 | 0.679 | 218 |
| 441 | N-(3-((3R)-5-amino-3,6,6-trimethyl-1,1-dioxido-3,6-dihydro-2H-1,4-thiazin-3-yl)-4-fluorophenyl)-2-(2-fluoroethoxy)pyrido[3,4-b]pyrazin-5-amine | 491.2 | Rena Method 1 | 0.00534 | 0.0138 | 407 |
| 442 | N-(3-((3R)-5-amino-3,6,6-trimethyl-1,1-dioxido-3,6-dihydro-2H-1,4-thiazin-3-yl)-4-fluorophenyl)-2-(2,2,2-trifluoroethoxy)pyrido[3,4-b]pyrazin-5-amine | 527 | Rena Method 1 | 0.00322 | 0.0319 | 389 |
| 443 | ((5-((3-((3R)-5-amino-3,6,6-trimethyl-1,1-dioxido-3,6-dihydro-2H-1,4-thiazin-3-yl)-4-fluorophenyl)amino)pyrido[3,4-b]pyrazin-2-yl)oxy)acetonitrile | 484 | Rena Method 1 | 0.00287 | 0.004 | 346 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
| --- | --- | --- | --- | --- | --- | --- |
| 444 | N-(3-((3R)-5-amino-3,6,6-trimethyl-1,1-dioxido-3,6-dihydro-2H-1,4-thiazin-3-yl)-4-fluorophenyl)-2-(2,2-difluoroethoxy)pyrido[3,4-b]pyrazin-5-amine | 509 | Rena Method 1 | 0.00454 | .0083) | 242 |
| 445 | N-(3-((3R)-5-amino-3,6,6-trimethyl-1,1-dioxido-3,6-dihydro-2H-1,4-thiazin-3-yl)-4-fluorophenyl)-2-(2-butyn-1-yloxy)pyrido[3,4-b]pyrazin-5-amine | 497.2 | Rena Method 1 | 0.00032 | 0.0002 | 178 |
| 104 | N-(3-((3R)-5-amino-3,6,6-trimethyl-1,1-dioxido-3,6-dihydro-2H-1,4-thiazin-3-yl)-4-fluorophenyl)-7-(cyclopropylmethoxy)pyrido[3,2-d]pyrimidin-4-amine | 499.2 | Rena Method 1 | 0.00154 | 0.0052 | 358 |
| 105 | N-(3-((3R)-5-amino-3,6,6-trimethyl-1,1-dioxido-3,6-dihydro-2H-1,4-thiazin-3-yl)-4-fluorophenyl)-2-methyl-1,3-benzothiazol-4-amine | 447 | Rena Method 1 | 0.184 | 0.742 | 145 |
| 446 | N-(3-((3R)-5-amino-3,6,6-trimethyl-1,1-dioxido-3,6-dihydro-2H-1,4-thiazin-3-yl)-4-fluorophenyl)-3,6-dichloro-8-quinolinamine | 495 | Rena Method 1 | 0.0022 | 0.263 | 13.9 |
| 447 | N-(3-((3S)-5-amino-3-(fluoromethyl)-6,6-dimethyl-1,1-dioxido-3,6-dihydro-2H-1,4-thiazin-3-yl)-4-fluorophenyl)-2-methoxypyrido[3,4-b]pyrazin-5-amine | 477.0 | Step 1 of general SNAr | 0.00088 | 0.0141 | 1120 |
| 448 | N-(3-((3S)-5-amino-3-(fluoromethyl)-6,6-dimethyl-1,1-dioxido-3,6-dihydro-2H-1,4-thiazn-3-yl)-4-fluorophenyl)-3-chloro-1,7-naphthyridin-8-amine | 480.0 | Step 1 of general SNAr | 0.00037 | 0.0285 | 58.4 |
| 449 | N-(3-((3S)-5-amino-3-(fluoromethyl)-6,6-dimethyl-1,1-dioxido-3,6-dihydro-2H-1,4-thiazin-3-yl)-4-fluorophenyl)-6-bromo-1-phthalazinamine | 524.9 | General Bicyclic SNAR (Example 44) | 0.0302 | 0.159 | 375 |
| 450 | N-(3-((3S)-5-amino-3-(fluoromethyl)-6,6-dimethyl-1,1-dioxido-3,6-dihydro-2H-1,4-thiazin-3-yl)-4-fluorophenyl)-6-chloro-1-phthalazinamine | 480.0 | General Bicyclic SNAR (Example 44) | | 0.7 | |
| 149 | N-(3-((3S)-5-amino-3-(fluoromethyl)-6,6-dimethyl-1,1-dioxido-3,6-dihydro-2H-1,4-thiazin-3-yl)-4-fluorophenyl)-5-(2-fluoroethoxy)-3-methyl-2-pyridinecarboxamide | 499.1 | T3P | 0.00271 | 0.0651 | 855 |
| 150 | N-(3-((3S)-5-amino-3-(fluoromethyl)-6,6-dimethyl-1,1-dioxido-3,6-dihydro-2H-1,4-thiazin-3-yl)-4-fluorophenyl)-3-methyl-5-(3-oxetanyloxy)-2-pyridinecarboxamide | 508.9 | T3P | 0.0445 | 0.528 | 622 |
| 184 | (5R)-5-(5-bromo-2-fluoro-6-methyl-3-pyridinyl)-2,2,5-trimethyl-5,6-dihydro-2H-1,4-thiazin-3-amine 1,1-dioxide | 377.9/380.0 | TJ14 | 8.11 | 3.99 | 127 |
| 189 | N-(3-((3R)-5-amino-3,6,6-trimethyl-1,1-dioxido-3,6-dihydro-2H-1,4-thiazin-3-yl)-4-fluorophenyl)-3-chloro-5-((trimethylsilyl)ethynyl)-1,7-naphthyridin-8-amine | 558 | WQ2 | 0.0068 | 0.231 | >4.94 |
| 188 | N-(3-((3R)-5-amino-3,6,6-trimethyl-1,1-dioxido-3,6-dihydro-2H-1,4-thiazin-3-yl)-4-fluorophenyl)-4-bromo-6-chloro-1-isoquinolinamine | 541 | | 0.00083 | 0.0597 | 213 |
| 192 | N-(3-((3R)-5-amino-3,6,6-trimethyl-1,1-dioxido-3,6-dihydro-2H-1,4-thiazin-3-yl)-4-fluorophenyl)-3,5-dichloro-1,7-naphthyridin-8-amine | 496 | | 0.0007 | 0.0366 | 32.4 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 190 | N-(3-((3R)-5-amino-3,6,6-trimethyl-1,1-dioxido-3,6-dihydro-2H-1,4-thiazin-3-yl)-4-fluorophenyl)-3-chloro-5-ethynyl-1,7-naphthyridin-8-amine | 486 | | 0.0013 | 0.0448 | 63.9 |
| 191 | (8-((3-((3R)-5-amino-3,6,6-trimethyl-1,1-dioxido-3,6-dihydro-2H-1,4-thiazin-3-yl)-4-fluorophenyl)amino)-3-chloro-1,7-naphthyridin-5-yl)methanol | 492 | | 0.00447 | 0.0089 | 65 |
| 212 | N-(3-((3R)-5-amino-3,6,6-trimethyl-1,1-dioxido-3,6-dihydro-2H-1,4-thiazin-3-yl)-4-fluorophenyl)-4-chlorobenzamide | 437.9 | See Write up | 0.0102 | 0.0233 | 317 |
| 213 | N-(3-((3R)-5-amino-3,6,6-trimethyl-1,1-dioxido-3,6-dihydro-2H-1,4-thiazin-3-yl)-4-fluorophenyl)-4-chloro-2-fluorobenzamide | 455.9 | See Write up | 0.0123 | 0.029 | 442 |
| 160 | N-(3-((3R)-5-amino-3,6,6-trimethyl-1,1-dioxido-3,6-dihydro-2H-1,4-thiazin-3-yl)-4-fluorophenyl)-3,6-dihydro-1(2H)-pyridinecarboxamide | 409 | see experimental | 0.575 | 0.681 | >14.8 |
| 451 | N-(3-((3R)-5-amino-3,6,6-trimethyl-1,1-dioxido-3,6-dihydro-2H-1,4-thiazin-3-yl)-4-fluorophenyl)-3-bromopyrido[2,3-d]pyridazin-8-amine | 507/509 | | 0.00068 | 0.0006 | 104 |
| 169 | 3-((3R)-5-amino-3,6,6-trimethyl-1,1-dioxido-3,6-dihydro-2H-1,4-thiazin-3-yl)-5-bromo-2(1H)-pyridinone | 361.9 | MX311 | 21.1 | >15.6 | >400.0 |
| 170 | N-(5-((3R)-5-amino-3,6,6-trimethyl-1,1-dioxido-3,6-dihydro-2H-1,4-thiazin-3-yl)-6-methoxy-3-pyridinyl)-5-chloro-2-pyridinecarboxamide | 452 | | 0.0225 | 0.0289 | 305 |
| 452 | N-(5-((3R)-5-amino-3,6,6-trimethyl-1,1-dioxido-3,6-dihydro-2H-1,4-thiazin-3-yl)-6-oxo-1,6-dihydro-3-pyridinyl)-5-chloro-2-pyridinecarboxamide | 438 | Amidation method E | 0.00704 | 0.0159 | 1870 |
| 171 | N-(5-((3R)-5-amino-3,6,6-trimethyl-1,1-dioxido-3,6-dihydro-2H-1,4-thiazin-3-yl)-1-methyl-6-oxo-1,6 dihydro-3-pyridinyl)-5-(difluoromethoxy)-3-methyl-2-pyridinecarboxamide | 498.1 | | 0.00927 | 0.0083 | 186 |
| 176 | N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide | 440.1 (M + H) | | 0.0028 | 0.254 | 650 |
| 178 | N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-fluoro-1,7-naphthyridin-8-amine | 4.84.1 (M + H) | | 0.00038 | 0.379 | 32.1 |
| 179 | 8-((3-((3R,6R)-5-amino-6-fluoro-3,6-dimethyl-1,1-dioxido-3,6-dihydro-2H-1,4-thiazin-3-yl)-4-fluorophenyl)amino)-5-fluoro-1,7-naphthyridine-3-carbonitrile | 475.1 (M + H) | | 0.0008 | 0.157 | >44.4 |
| 453 | (7R)-7-(5-bromo-2-fluorophenyl)-7-methyl-5-thia-8-azaspiro[3.5]non-8-en-9-amine 5,5-dioxide, (7S)-7-(5-bromo-2-fluorophenyl)-7-methyl-5-thia-8-azaspiro[3.5]non-8-en-9-amine 5,5-dioxide | | | | | |
| 454 | N-(5-((6R)-8-amino-6-methyl-4,4-dioxido-4-thia-7-azaspiro[2.5]oct-7-en-6-yl)-6-fluoro-3-pyridinyl)-5-(difluoromethoxy)-3-methyl-2-pyridinecarboxamide | 484 | | 0.0031 | 0.0039 | 106 |
| 455 | (6R)-6-(5-bromo-2-fluoro-3-pyridinyl)-6-methyl-4-thia-7-azaspiro[2.5]oct-7-en-8-amine 4,4-dioxide | 362/364 | | 12.5 | >15.6 | 100 |

TABLE II-continued

| Example | Compound Name | Mass Spec | Method Used | BACE1 FRET assay $IC_{50}$ (uM) | HEK cell assay $IC_{50}$ (uM) | CatD IC50 (μM) |
|---|---|---|---|---|---|---|
| 199 | N-(3-((6R)-8-amino-6-methyl-4,4-dioxido-4-thia-7-azaspiro[2.5]oct-7-en-6-yl)-4-fluorophenyl)-5-chloro-2-pyridinecarboxamide | 437.1 | Example 199 | 0.0019 | 0.0011 | 81 |
| 186 | N-(5-((6R)-8-amino-6-methyl-4,4-dioxido-4-thia-7-azaspiro[2.5]oct-7-en-6-yl)-6-fluoro-3-pyridinyl)-5-chloro-3-methyl-2-pyridinecarboxamide | | | 0.0024 | 0.0043 | 65.7 |
| 181 | (5R,8R)-8-(5-bromo-2-fluorophenyl)-8-methyl-2-oxa-6-thia-9-azaspiro[4.5]dec-9-en-10-amine 6,6-dioxide, (5S,8R)-8-(5-bromo-2-fluorophenyl)-8-methyl-2-oxa-6-thia-9-azaspiro[4.5]dec-9-en-10-amine 6,6-dioxide | 391.0 (M + H) | | 16.3 | >15.6 | 43.3 |
| 182 | N-(3-((5R,8R)-10-amino-8-methyl-6,6-dioxido-2-oxa-6-thia-9-azaspiro[4.5]dec-9-en-8-yl)-4-fluorophenyl)-3-chloro-1,7-naphthyridin-8-amine, N-(3-((5S,8R)-10-amino-8-methyl-6,6-dioxido-2-oxa-6-thia-9-azaspiro[4.5]dec-9-en-8-yl)-4-fluorophenyl)-3-chloro-1,7-naphthyridin-8-amine | 490.1 (M + H) | | .0022 | 0.0306 | 63.6 |
| 200 | N-(3-((5S,6R)-8-amino-5-fluoro-6-methyl-4,4-dioxido-4-thia-7-azaspiro[2.5]oct-7-en-6-yl)-4-fluorophenyl)-5-chloro-2-pyridinecarboxamide | 455 | Example 200 | 0.0013 | 0.0039 | 55.6 |
| 201 | N-(3-((5R,6R)-8-amino-5-fluoro-6-methyl-4,4-dioxido-4-thia-7-azaspiro[2.5]oct-7-en-6-yl)-4-fluorophenyl)-5-chloro-2-pyridinecarboxamide | 455 | Example 200 | 0.00062 | 0.002 | 31.1 |
| 202 | N-(3-((5S,6R)-8-amino-5-fluoro-6-methyl-4,4-dioxido-4-thia-7-azaspiro[2.5]oct-7-en-6-yl)-4-fluorophenyl)-5-(difluoromethoxy)-3-methyl-2-pyridinecarboxamide | 501 | Example 200 | 0.0015 | 0.0036 | 96.7 |
| 203 | N-(3-((5R,6R)-8-amino-5-fluoro-6-methyl-4,4-dioxido-4-thia-7-azaspiro[2.5]oct-7-en-6-yl)-4-fluorophenyl)-5-(difluoromethoxy)-3-methyl-2-pyridinecarboxamide | 501 | Example 200 | 0.00048 | 0.0023 | 30.2 |
| 206 | N-(3-((5S,6R)-8-amino-5-fluoro-6-methyl-4,4-dioxido-4-thia-7-azaspiro[2.5]oct-7-en-6-yl)-4-fluorophenyl)-5-(difluoromethyl)-3-methyl-2-pyridinecarboxamide | 405 | Example 200 | 0.0019 | 0.0054 | 193 |
| 207 | N-(3-((5R,6R)-8-amino-5-fluoro-6-methyl-4,4-dioxido-4-thia-7-azaspiro[2.5]oct-7-en-6-yl)-4-fluorophenyl)-5-(difluoromethyl)-3-methyl-2-pyridinecarboxamide | 485 | Example 200 | 0.00092 | 0.0067 | 56.1 |
| 209 | N-(3-((5S,6R)-8-amino-5-fluoro-6-methyl-4,4-dioxido-4-thia-7-azaspiro[2.5]oct-7-en-6-yl)-4-fluorophenyl)-2-methoxypyrido[3,4-b]pyrazin-5-amine | 475.2 | Example 200 | 0.0085 | 0.0854 | 157 |
| 208 | N-(3-((5R,6R)-8-amino-5-fluoro-6-methyl-4,4-dioxido-4-thia-7-azaspiro[2.5]oct-7-en-6-yl)-4-fluorophenyl)-2-methoxypyrido[3,4-b]pyrazin-5-amine | 475.2 | Example 200 | <0.002 | 0.0107 | 696 |
| 210 | N-(3-((5S,6R)-8-amino-5-fluoro-6-methyl-4,4-dioxido-4-thia-7-azaspiro[2.5]oct-7-en-6-yl)-4-fluorophenyl)-6-chloro-3-methylimidazo[1,2-a]pyridine-2-carboxamide | 508 | Example 210 | | | |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 456 | (5S)-5-(5-amino-2-fluorophenyl)-5-(fluoromethyl)-2,2-dimethyl-5,6-dihydro-2H-1,4-thiazin-3-amine 1,1-dioxide | 318.1 | | 2.53 | >15.6 | 228 |
| 457 | N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyridinecarboxamide | 452.9 | | 0.00065 | 0.0129 | 812 |
| 458 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-(methoxymethyl)-2-pyridinecarboxamide | | | 0.0009 | 0.0239 | 499 |
| 193 | N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-2-pyridinecarboxamide | 457 | | 0.00076 | 0.0161 | 228 |
| 214a | (6R)-6-(5-bromo-2-fluorophenyl)-6-(fluoromethyl)-4-thia-7-azaspiro[2.5]oct-7-en-8-amine 4,4-dioxide | 316 | | >40.0 | >15.6 | >400.0 |
| 214b | (6S)-6-(5-bromo-2-fluorophenyl)-6-(fluoromethyl)-4-thia-7-azaspiro[2.5]oct-7-en-8-amine 4,4-dioxide | 316 | | 2.28 | 10.6 | 78.9 |
| 215 | N-(3-((6R)-8-amino-6-(fluoromethyl)-4,4-dioxido-4-thia-7-azaspiro[2.5]oct-7-en-6-yl)-4-fluorophenyl)-5-chloro-3-methyl-2-pyridinecarboxamide | 469 | | 0.212 | 0.903 | 432 |
| 216 | N-(3-((6S)-8-amino-6-(fluoromethyl)-4,4-dioxido-4-thia-7-azaspiro[2.5]oct-7-en-6-yl)-4-fluorophenyl)-5-chloro-3-methyl-2-pyridinecarboxamide | 469 | | 0.00054 | 0.0044 | 132 |
| 217 | N-(3-((6S)-8-amino-6-(fluoromethyl)-4,4-dioxido-4-thia-7-azaspiro[2.5]oct-7-en-6-yl)-4-fluorophenyl)-5-(difluoromethoxy)-3-methyl-2-pyridinecarboxamide | 501 | | 0.0012 | 0.0061 | 46.8 |
| 218 | N-(3-((6R)-8-amino-6-(fluoromethyl)-4,4-dioxido-4-thia-7-azaspiro[2.5]oct-7-en-6-yl)-4-fluorophenyl)-5-(difluoromethoxy)-3-methyl-2-pyridinecarboxamide | 501 | | 0.15 | 0.83 | 637 |
| 172 | (7S)-7-(5-bromo-2-fluorophenyl)-7-(fluoromethyl)-5-thia-8-azaspiro[3.5]non-8-en-9-amine 5,5-dioxide | 392.9 | MX321 | 3.56 | >15.6 | 45.4 |
| 459 | (2R,5R)-5-(5-bromo-2-fluorophenyl)-2-fluoro-2,5,6-trimethyl-5,6-dihydro-2H-1,4-thiazin-3-amine 1,1-dioxide | 381, 383 | | 2.3 | 5.47 | >400.0 |
| 185c | (4aR,7aR)-4a-(5-amino-2-fluorophenyl)-2,2-dimethyl-4a,5,7,7a-tetrahydro-2H-furo[3,4-b][1,4],1-dioxide | 328 | | >40.0 | >15.6 | >400.0 |
| 185d | (4aS,7aS)-4a-(5-amino-2-fluorophenyl)-2,2-dimethyl-4a,5,7,7a-tetrahydro-2H-furo[3,4-b][1,4],1-dioxide | 328 | | 3.83 | >15.6 | 152 |
| 187 | (8R)-8-(5-bromo-2-fluorophenyl)-5,5,8-trimethyl-4-thia-7-azaspiro[2.5]oct-6-en-6-amine 4,4-dioxide | 389, 391 | ZH001 | 30.7 | >15.6 | >400.0 |
| 460 | N-(3-((2R,4r,7R)-9-amino-2-methoxy-7-methyl-5,5-dioxido-5-thia-8-azaspiro[3.5]non-8-en-7-yl)-4-fluorophenyl)-5-chloro-3-methyl-2-pyridinecarboxamide | 496 | Example 460 herein HATU method | 0.004 | 0.0349 | 466 |

TABLE II-continued

| Example | Compound Name | Mass Spec | Method Used | BACE1 FRET assay IC$_{50}$ (uM) | HEK cell assay IC$_{50}$ (uM) | CatD IC50 (μM) |
|---|---|---|---|---|---|---|
| 461 | N-(3-((2R,4r,7R)-9-amino-2-methoxy-7-methyl-5,5-dioxido-5-thia-8-azaspiro[3.5]non-8-en-7-yl)-4-fluorophenyl)-5-methoxy-3-methyl-2-pyridinecarboxamide | 491 | Example 460 | 0.0157 | 0.028 | 399 |
| 462 | N-(3-((5R,6R)-8-amino-5-fluoro-6-methyl-4,4-dioxido-4-thia-7-azaspiro[2.5]oct-7-en-6-yl)-4-fluorophenyl)-6-chloro-3-methylimidazo[1,2-a]pyridine-2-carboxamide | 508 | Example 211 | 0.0032 | 0.0104 | 60.1 |
| 463 | N-(3-((2S,4s,7R)-9-amino-2-fluoro-7-methyl-5,5-dioxido-5-thia-8-azaspiro[3.5]non-8-en-7-yl)-4-fluorophenyl)-5-methoxy-3-methyl-2-pyridinecarboxamide | 479 | HATU method | 0.0046 | 0.0132 | 76.5 |
| 464 | N-(3-((2S,4s,7R)-9-amino-2-fluoro-7-methyl-5,5-dioxido-5-thia-8-azaspiro[3.5]non-8-en-7-yl)-4-fluorophenyl)-6-chloro-3-methylimidazo[1,2-a]pyridine-2-carboxamide | 523 | HATU method | 0.004 | 0.006 | 67.4 |

The present invention also provides methods for making compounds of Formulas I-III, and sub-formulas therein. For example, the compounds of the present invention and additional examples may be made by the following methods, as similarly described in the literature references mentioned below.

In one embodiment of the invention, there is provided a method of making a compound of Formula II-A having a general structure of

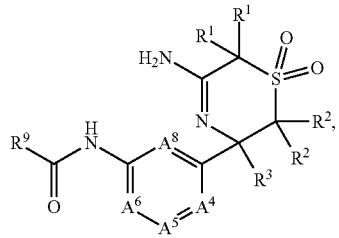

the method comprising the step of reacting a compound 20

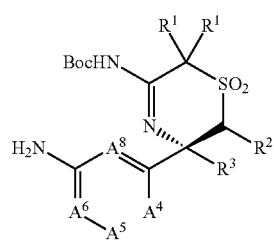

wherein $A^4$, $A^5$, $A^6$, $A^8$, each $R^1$, each $R^2$ and $R^3$ of Formula II-A are as defined herein, with a compound having the structure $R^9$—COOH, wherein $R^9$ is as defined herein, to make a compound of Formula II-A.

In one embodiment of the invention, there is provided a method of making a compound of Formula II-B having a general structure of

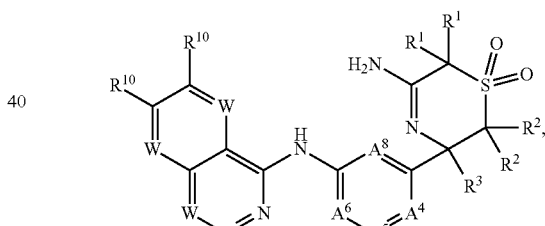

the method comprising the step of reacting a compound 20

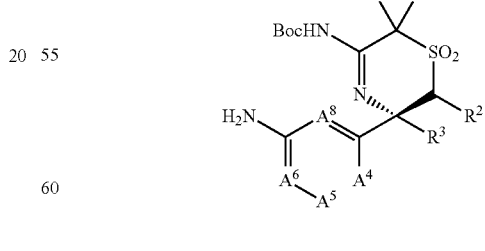

wherein $A^4$, $A^5$, $A^6$, $A^8$, each $R^1$, each $R^2$ and $R^3$ of Formula II-B are as defined herein, with a compound having the structure

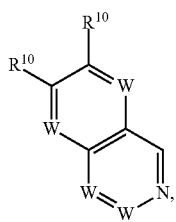

wherein each W and each $R^{10}$ are, independently, as defined herein, in the presence of acid to make a compound of Formula II-B.

In one embodiment of the invention, there is provided a method of making a compound of Formula II-C

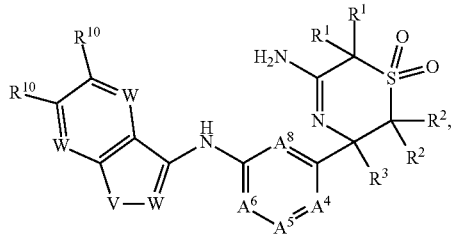

the method comprising the step of reacting a compound 20

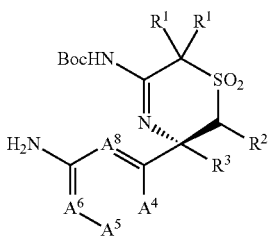

wherein $A^4$, $A^5$, $A^6$, $A^8$, each $R^1$, each $R^2$ and $R^3$ of Formula II-C are as defined herein, with a compound having the structure

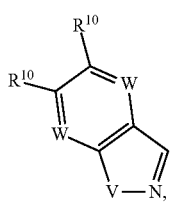

wherein V, each W and each $R^{10}$ are, independently, as defined herein, to make a compound of Formula II-C.

In another embodiment of the invention, there is provided a method of making a compound of Formula III having a general formula of

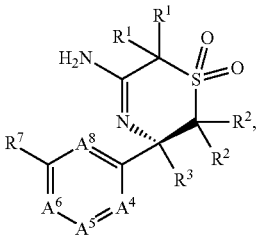

the method comprising the step of reacting a compound 20

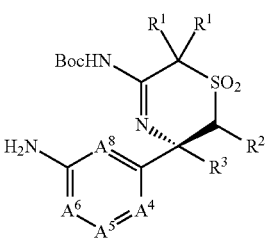

wherein $A^4$, $A^5$, $A^6$, $A^8$, each $R^1$, each $R^2$, $R^3$ and $R^7$ of Formula III are as defined herein, with a compound having either structure of $R^7$—COOH in the presence of a base or $R^7$ in the presence of an acid, wherein $R^7$ is as defined herein, to make a compound of Formula III.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2nd edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The invention provides compounds of Formulas I, II and III, and sub-Formulas thereof, and stereoisomers thereof. For example, as shown in Formula III below, and for purposes of clarity, the following isomers about the central quaternary carbon are deemed equivalent and the same herein:

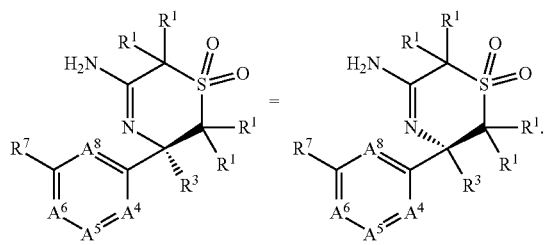

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$ (deuterium), $^3H$ (tritium), $^{13}C$, $^{14}C$, $^{15}N$, $^{16}O$, $^{17}O$, $^{31}F$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Deuterated ($^2H$), Tritiated ($^3H$) and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Tables I and II)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Tables I and II.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 μM or 10 μM. The compounds were diluted from stock solutions in DMSO and the final DMSO concentration of the test compounds on cells was 0.1%. After 24 h of incubation with the test compounds the supernatant conditioned media was collected and the Aβ 40 levels were determined using a sandwich ELISA. The $IC_{50}$ of the compound was calculated from the percent of control or percent inhibition of Aβ 40 as a function of the concentration of the test compound.

The sandwich ELISA to detect Aβ 40 was performed in 96 well microtiter plates, which were pre-treated with goat anti-rabbit IgG (Pierce). The capture and detecting antibody pair that were used to detect Aβ 40 from cell supernatants were affinity purified pAb40 (Biosource) and biotinylated 6E10 (Signet Labs Inc.), respectively. The optimal concentration for the pAb40 antibody was 3 μg/ml in Superblock/TBS (Pierce) that was supplemented with 0.05% Tween 20 (Sigma). Optimal concentration for the detection antibody 6E10-biotinylated was 0.5 μg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Tables I and II.

In Vitro Enzymatic Cathepsin D (Cat D) FRET (Fluorescence Resonance Energy Transfer) Assay Recombinant Cat D was expressed in CHO cells. The assay buffer for CathepsinD is 0.05 M citrate pH 3.5, 10% DMSO final, 5 mM CHAPS. The Cat D enzyme (9 nM) is pre-incubated for one hour with inhibitors, typically in about 1 uL of DMSO according to a serial dilution, is added thereto. The assays are effectively started by the addition of different FRET substrates (20 nM for Cat D) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The Cat D substrate peptide sequence is based on sequence #1 of Table 1 from Gulnik et al. FEBS Letters v413 p 379-384 1997. Proteolytic cleavage of the FRET substrate releases quenching of fluorescence (Cat D excitation 500 nm and emission 580 nm).

Alternatively, a Cat D assay may also be run according to the procedure described in the article, Characterization of new fluorgenic substrates for the rapid and sensitive assay of cathepsin E and cathepsin D, *J. Biochem.*, 125:1137, 1999. In addition, the cathepsin D and cathepsin E assays are described in PCT publication WO2011069934. This WIPO publication describes BACE inhibitor compounds having an amide linker connecting two aromatic groups with extremely poor cathepsin D and/or cathepsin E inhibitory activity (see Table 2).

Where available, the in-vitro Cat D FRET assay data for each of the Examples, conducted by the first procedure, is provided. For example, the compound of example 43 has a Cat D $IC_{50}$ value of >400 uM. As shown by the high micromolar Cat D data (very poorly active or inactive against cat D), the compounds of the present invention possess the unexpected property of little to no ability to inhibit the activity of Cat D. It was surprisingly found that incorporation of an amino- or amido-linker between the core of the compounds and the $R^7$ and $R^9$ groups, respectively, has conferred a significantly reduced, poor or no potency on the protein Cat D. Thus, with this surprising selectivity profile, the compounds of the present invention are believed to minimize, reduce or completely eliminate any risk of retinal atrophy and abnormal development of the eye and of the retinal pigmented epithelium as it relates to the normal function and activity of Cat D.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic mice are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76, 173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2

IV: 5% EtOH, 45% Propylene glycol in 5% Dextrose

The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
| --- | --- | --- |
| 17 | 84 | 71 |
| 45 | 63 | 34 |
| 46 | 76 | 64 |
| 18 | 73 | 57 |
| 19 | 83 | 74 |
| 47 | 82 | 66 |
| 48 | 79 | 59 |
| 76 | 60 | 46 |
| 30 | 56 | 37 |
| 219 | 42 | 9 |
| 222 | 65 | 49 |
| 228 | 67 | 58 |
| 229 | 61 | 43 |
| 233 | 25 | 0 |
| 235 | 38 | 14 |
| 236 | 35 | 1 |
| 317 | 23 | 0 |
| 321 | 44 | 37 |

-continued

| Ex. No. | % reduction of rat CSF levels at 10 pmk | % reduction of rat brain levels at 10 mpk |
|---|---|---|
| 324 | 44 | 29 |
| 329 | 27 | 20 |
| 330 | 78 | 72 |
| 331 | 67 | 59 |
| 332 | 24 | 11 |
| 346 | 69 | 48 |
| 359 | 55 | 24 |
| 377 | 68 | 53 |
| 387 | 43 | 27 |
| 144 | 79 | 72 |
| 120 | 39 | 18 |
| 148 | 68 | 57 |
| 388 | 33 | 7 |
| 398 | 63 | 39 |
| 400 | 58 | 25 |
| 401 | 69 | 48 |
| 402 | 43 | 10 |
| 408 | 62 | 37 |
| 412 | 52 | 33 |
| 131 | 10 | −18 |
| 132 | 31 | 10 |
| 177 | 37 | 24 |
| 430 | 31 | 1 |
| 158 | 11 | −5 |
| 159 | 45 | 31 |
| 447 | 62 | 42 |
| 171 | 1 | 3 |
| 457 | 67 | 50 |
| 458 | 35 | 8 |
| 193 | 57 | 30 |
| 216 | 57 | 14 |

Indications

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. *Arch Neurol.* 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, *Cell*, (120): 545-555, 2005; Walsh and Selkoe, *Neuron*, (44): 181-193, 2004). Although the precise mechanisms of Ab toxicity are unclear, oligomeric forms of Ab may contribute to cognitive decline by altering synaptic structure and function (Palop and Mucke, *Nat. Neuroscience*, (13): 812-818, 2010; Selkoe, *Behavioral Brain Res.*, (192): 106-113, 2008; Shankar et al., *Nat. Medicine* (14): 837-842, 2008). Transgenic mouse models that overexpress mutant APP and produce high levels of Ab show amyloid plaque deposition, synaptic deficits, learning and memory impairments, and other behavioral abnormalities (Games et al., *Nature*, (373): 523-527, 1995; Go tz et al., *Molecular Psychiatry* (9): 664-683, 2004; Hsia et al., *Proc. Natl. Academy of Science USA* (96): 3228-3233, 1999; Hsiao et al., *Science* (274): 99-102, 1996, citing Harris et al, *Neuron* (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

Bapineuzamab, a monoclonal amino-terminus specific anti-amyloid antibody is presently in Phase III clinical trials for the treatment of AD. *Alzheimer's Research & Therapy*, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier and more common. It is firmly believed that by reducing the formation of A-beta, one can begin to pre-treat AD. Vassar et al, *Journal of Neuroscience*, 29 (41):12787-12794, 2009. One published pathway for treatment of AD is inhibition of beta-secretase. Tirrell, *Bloomberg News, The Boston Globe*, Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [(S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from preclinical animal models to man. Because of toxicology findings identified in longer-term preclinical studies, this compound is no longer progressing in clinical development. However, BACE1 remains a viable target because the adverse effects reported here were recapitulated in LY2811376-treated BACE1 KO mice and thus are unrelated to BACE1 inhibition. The magnitude and duration of central Aβ reduction obtainable with BACE1 inhibition positions this protease as a tractable small-molecule target through which to test the amyloid hypothesis in man. *Neuroscience*, 31(46):16507-16515, 2011

The compounds of the invention have been shown to modulate, and specifically inhibit the activity of the beta-secretase enzyme, thereby reducing the A-beta peptide fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneously with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula II-B

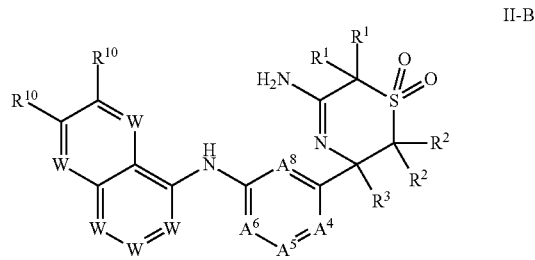

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;

each of $R^1$ and $R^2$, independently, is H, F, Cl, $C_{1-4}$-alkyl, $C_{2-4}$-alkenyl, $C_{2-4}$-alkynyl, CN, —$CH_2OC_{1-3}$-alkyl, —$OC_{1-3}$-alkyl, wherein each of the $C_{1-4}$-alkyl, $C_{2-4}$-alkenyl, $C_{2-4}$-alkynyl and $C_{1-3}$-alkyl portion of —$CH_2OC_{1-3}$-alkyl and —$OC_{1-3}$-alkyl are optionally substituted with 1-4 substituents of F;

alternatively, each $R^1$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

$R^3$ is $C_{1-4}$-alkyl, $CH_2OC_{1-4}$-alkyl, $CH_2OH$, $C_{1-4}$-haloalkyl or cyclopropyl, wherein each of the $C_{1-4}$-alkyl, $CH_2OC_{1-4}$-alkyl, $C_{1-4}$-haloalkyl and cyclopropyl is optionally substituted with 1-4 F atoms;

alternatively, one $R^2$ and $R^3$ taken together with the carbon atoms to which they are attached form a $C_{3-6}$ carbocyclic ring optionally including 1-2 heteroatoms selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

each of $R^4$, $R^5$, $R^6$ and $R^8$, independently, is H or F;

each $R^{10}$, independently, is H, halo, haloalkyl, CN, OH, $NO_2$, $NH_2$, $SF_5$, acetyl, —$C(O)NHCH_3$, oxo, cycloproylmethoxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$-alkylamino-, $C_{1-3}$-dialkylamino, $C_{1-3}$-thioalkoxyl or oxetan-3-yl; and each W, independently, is CH, CF, CCl or N.

2. The compound according to claim 1, or a stereoisomer or pharmaceutically acceptable salt thereof, wherein
$A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H or F;
each of $R^1$ and $R^2$, independently, is H, F, $CH_3$, $C_2H_5$, $CF_2H$, $CH_2F$, $CH_2OCH_2F$, $CH_2OCF_2H$ or $CH_2OCF_3$;
alternatively, each $R^1$ taken together with the carbon atom to which they are attached form a $C_{3-6}$ spirocarbocyclic ring optionally including one heteroatom selected from O and N and optionally substituted with 1-3 F atoms;
alternatively, each $R^2$ taken together with the carbon atom to which they are attached form a $C_{3-6}$ spirocarbocyclic ring optionally including one heteroatom selected from O and N and optionally substituted with 1-3 F atoms; and $R^3$ is $CH_3$, $C_2H_5$, $CF_2H$ or $CH_2F$.

3. The compound according to claim 1, or a stereoisomer or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F, Cl, $CF_3$, $CH_3$, $CF_2H$ or $CH_2F$; and
$R^3$ is $CF_3$, $CH_3$, $CF_2H$ or $CH_2F$.

4. A compound of Formula III-B-1

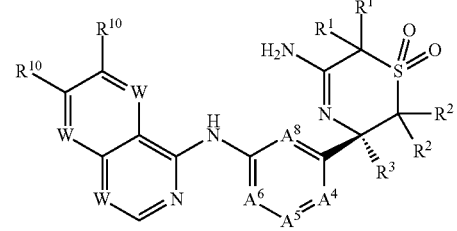

III-B-1 or a stereoisomer or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^1$ and $R^2$, independently, is H, F, Cl, $C_{2-4}$-alkenyl, $C_{2-4}$-alkynyl, CN, —$CH_2OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$-alkenyl, $C_{2-4}$-alkynyl, and $C_{1-6}$-alkyl portion of —$CH_2OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

alternatively, each $R^2$ taken together with the carbon atom to which they are attached form a $C_{3-6}$ spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

$R^3$ is $C_{1-4}$-alkyl, $CH_2OH$, $CH_2OC_{1-4}$-alkyl, $C_{1-4}$-haloalkyl or cyclopropyl, wherein each of the $C_{1-4}$-alkyl, $CH_2OC_{1-4}$-alkyl, $C_{1-4}$-haloalkyl and cyclopropyl is optionally substituted with 1-4 F atoms;

alternatively, one $R^2$ and $R^3$ taken together with the carbon atoms to which they are attached form a $C_{3-6}$-carbocyclic ring optionally including 1-2 heteroatoms selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)C_{1-4}$-alkyl, $NHC_{1-4}$-alkyl or $C(O)C_{1-4}$-alkyl;

each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$-alkylamino-, $C_{1-3}$-dialkylamino, $C_{1-3}$-thioalkoxyl or oxetan-3-yl; and each W, independently, is CH, CF, CCl or N.

5. A compound of Formula III-E

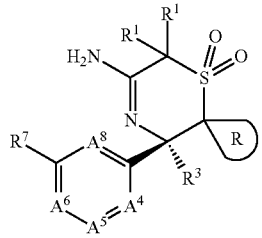

III-E or a stereoisomer or pharmaceutically acceptable salt thereof,
wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

R is a $C_{3-6}$-spirocarbocyclic ring optionally including one heteroatom selected from O and N and optionally substituted with 1-4 F atoms on the carbon atoms and/or a substituent of $C_{1-3}$-alkyl, $CH_2OC_{1-2}$-alkyl or $C_{1-3}$-haloalkyl on the nitrogen atom;

each of $R^1$, independently, is H, F, Cl, $C_{1-6}$-alkyl, $C_{2-4}$-alkenyl, $C_{2-4}$-alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$-alkenyl, $C_{2-4}$-alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;

$R^3$ is $C_{1-4}$-alkyl, $CH_2OH$, $CH_2OC_{1-4}$-alkyl, $C_{1-4}$-haloalkyl or cyclopropyl, wherein each of the $C_{1-4}$-alkyl, $CH_2OC_{1-4}$-alkyl, $C_{1-4}$-haloalkyl and cyclopropyl is optionally substituted with 1-4 F atoms;

each of $R^4$, $R^5$, $R^6$ and $R^8$, independently, is H, halo, haloalkyl, haloalkoxyl,
$C_{1-4}$-alkyl, CN, OH, $OC_{1-4}$-alkyl, $S(O)C_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$, —S—$R^9$;

or $R^7$ is

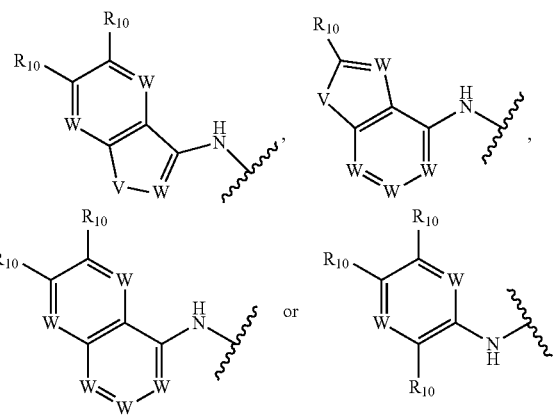

wherein V is $NR^{10}$, O or S; and
each W, independently, is CH, CF, CCl or N;

$R^9$ is acetyl, $C_{1-6}$-alkyl, $C_{2-4}$-alkenyl, $C_{2-4}$-alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, furanyl, dihydrofuranyl, thienyl, and pyrrolyl, wherein the $C_{1-6}$-alkyl, $C_{2-4}$-alkenyl, $C_{2-4}$-alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$-alkylamino-, $C_{1-3}$-dialkylamino-, $C_{1-3}$-thioalkoxyl or oxetan-3-yl.

6. The compound of claim 5, or a stereoisomer or pharmaceutically acceptable salt thereof, as defined by Formula III-E-1

III-E-1

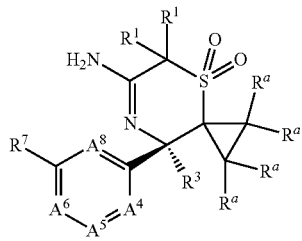

wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each $R^a$, independently, is H or F;
each of $R^1$, independently, is H, F, Cl, $CF_3$, $OCF_3$, methyl, ethyl, CN, $OCH_3$, $NHCH_3$, $C(O)CH_3$ or $CH_2OCHF_2$;
alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;
$R^3$ is $C_{1-4}$-alkyl, $C_{1-4}$-haloalkyl, $CH_2OH$, $CH_2OCHF_2$ or cyclopropyl;
each of $R^4$, $R^5$, $R^6$ and $R^8$, independently, is H, F, Cl, $CF_3$, $OCF_3$, methyl, ethyl, CN, OH, $OCH_3$, $NHCH_3$ or $C(O)CH_3$;
$R^7$ is $-NH-R^9$, $-NH-C(=O)-R^9$, $-C(=O)NH-R^9$, $-O-R^9$, $-S-R^9$;
or $R^7$ is

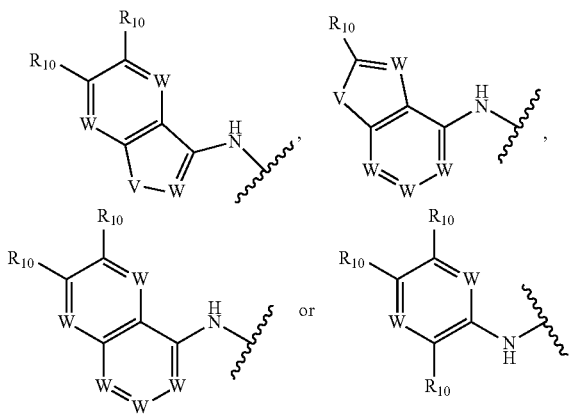

wherein V is $NR^{10}$, O or S; and
each W, independently, is CH, CF, CCl or N;
$R^9$ is acetyl, $C_{1-6}$-alkyl, $C_{2-4}$-alkenyl, $C_{2-4}$-alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, furanyl, dihydrofuranyl, thienyl, and pyrrolyl, wherein the $C_{1-6}$-alkyl, $C_{2-4}$-alkenyl, $C_{2-4}$-alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, $-C(O)NHCH_3$, oxo, cyclopropylmethoxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, $C_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$-alkylamino-, $C_{1-3}$-dialkylamino-, $C_{1-3}$-thioalkoxyl or oxetan-3-yl.

7. A compound of Formula III-F

III-F

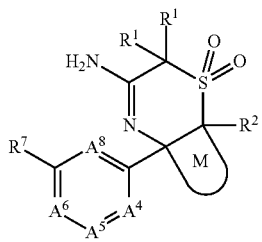

or a stereoisomer or pharmaceutically acceptable salt thereof,
wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
M is a $C_{3-6}$-carbocyclic ring optionally including one or two heteroatoms selected from O and N and optionally substituted with 1-4 F atoms on the carbon atoms and/or a substituent of $C_{1-3}$=alkyl, $CH_2OC_{1-2}$-alkyl or $C_{1-3}$-haloalkyl on a nitrogen atom;
each of $R^1$, independently, is H, F, $C_{2-4}$-alkenyl, $C_{2-4}$-alkynyl, CN, $-CH_2OC_{1-6}$-alkyl, $-OC_{1-6}$-alkyl, $-S(O)C_{1-6}$-alkyl, $-NHC_{1-6}$-alkyl or $-C(O)C_{1-6}$-alkyl, wherein each of the $C_{1-6}$-alkyl, $C_{2-4}$-alkenyl, $C_{2-4}$-alkynyl, and $C_{1-6}$-alkyl portion of $-CH_2OC_{1-6}$-alkyl, $-S(O)C_{1-6}$-alkyl, $-NHC_{1-6}$-alkyl and $-C(O)C_{1-6}$-alkyl are optionally substituted with 1-4 substituents of F, oxo or OH;
alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$-alkyl, $CH_2OC_{1-2}$-alkyl or $C_{1-3}$-haloalkyl on the nitrogen atom;
$R^2$ is H, F, $C_{2-4}$-alkenyl, $C_{2-4}$-alkynyl, CN, $-CH_2OC_{1-6}$-alkyl, $-S(O)C_{1-6}$-alkyl, $-NHC_{1-6}$-alkyl or $-C(O)C_{1-6}$-alkyl, wherein each of the $C_{1-6}$-alkyl, $C_{2-4}$-alkenyl, $C_{2-4}$-alkynyl, and $C_{1-6}$-alkyl portion of $-CH_2OC_{1-6}$-alkyl, $-S(O)C_{1-6}$-alkyl, $-NHC_{1-6}$-alkyl and —C(O)C$_{1-6}$-alkyl are optionally substituted with 1-4 substituents of F, oxo or OH;

each of R$^4$, R$^5$, R$^6$ and R$^8$, independently, is H, halo, haloalkyl, haloalkoxyl, CN, OH, OC$_{1-4}$-alkyl, S(O) C$_{1-4}$-alkyl, NHC$_{1-4}$-alkyl or C(O)C$_{1-4}$-alkyl;

R$^7$ is —NH—R$^9$, —NH—C(=O)—R$^9$, —C(=O)NH— R$^9$, —O—R$^9$, —S—R$^9$;

or R$^7$ is

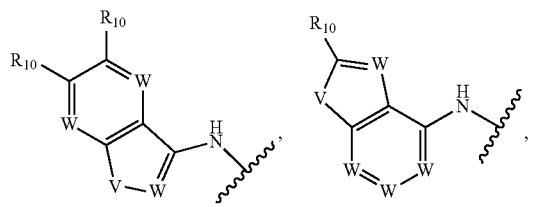

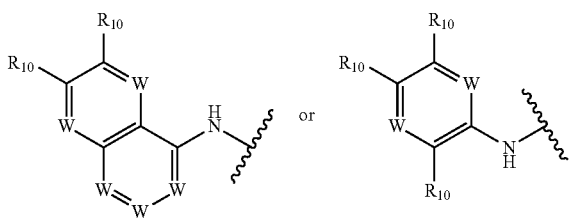

wherein V is NR$^{10}$, O or S; and each W, independently, is CH, CF, CCl or N;

R$^9$ is acetyl, C$_{1-6}$-alkyl, C$_{2-4}$-alkenyl, C$_{2-4}$-alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, furanyl, dihydrofuranyl, thienyl, and pyrrolyl, wherein the C$_{1-6}$-alkyl, C$_{2-4}$-alkenyl, C$_{2-4}$-alkynyl and ring are optionally substituted, independently, with 1-5 substituents of R$^{10}$; and each R$^{10}$, independently, is H, halo, haloalkyl, CN, OH, NO$_2$, NH$_2$, SF$_5$, acetyl, —C(O)NHCH$_3$, oxo, cyclopropylmethoxy, 2-butynyloxy, C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolyl, pyrrolidinyl, piperazinyl, oxetan-3-yl or dioxolyl, wherein each of the C$_{1-6}$-alkyl, C$_{2-6}$-alkenyl, C$_{2-6}$-alkynyl, C$_{3-6}$-cycloalkyl, C$_{1-6}$-alkylamino-, C$_{1-6}$-dialkylamino-, C$_{1-6}$-alkoxyl, C$_{1-6}$-thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO$_2$, NH$_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, C$_{1-3}$-alkylamino-, C$_{1-3}$-dialkylamino-, C$_{1-3}$-thioalkoxyl or oxetan-3-yl.

8. The compound of claim 7, or a stereoisomer or pharmaceutically acceptable salt thereof, as defined by Formula III-F-1

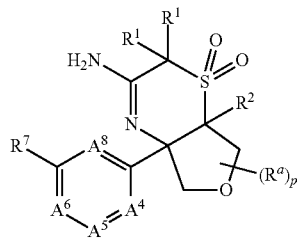

III-F-1 wherein

A$^4$ is CR$^4$ or N;
A$^5$ is CR$^5$ or N;
A$^6$ is CR$^6$ or N;
A$^8$ is CR$^8$ or N, provided that no more than two of A$^4$, A$^5$, A$^6$ and A$^8$ is N;

each R$^a$, independently, is H or F;

each R$^1$, independently, is H, F, C$_{2-4}$-alkenyl, C$_{2-4}$-alkynyl, CN, —CH$_2$OC$_{1-6}$-alkyl, —S(O)C$_{1-6}$-alkyl, —NHC$_{1-6}$-alkyl or —C(O)C$_{1-6}$-alkyl, wherein each of the C$_{1-6}$-alkyl, C$_{2-4}$-alkenyl, C$_{2-4}$-alkynyl, and C$_{1-6}$-alkyl portion of —CH$_2$OC$_{1-6}$-alkyl, —S(O)C$_{1-6}$-alkyl, —NHC$_{1-6}$-alkyl and —C(O)C$_{1-6}$-alkyl are optionally substituted with 1-4 substituents of F, oxo or OH;

alternatively, each R$^1$ taken together with the carbon atom to which they are attached form a C$_{3-6}$spirocarbocyclic ring optionally including one heteroatom selected from O and N and optionally substituted with 1-4 F atoms on the carbon atoms and a substituent of C$_{1-3}$-alkyl, CH$_2$OC$_{1-2}$-alkyl or C$_{1-3}$-haloalkyl on the nitrogen atom;

R$^2$ is H, F, C$_{2-4}$-alkenyl, C$_{2-4}$-alkynyl, CN, —CH$_2$ OC$_{1-6}$-alkyl, —S(O)C$_{1-6}$-alkyl, —NHC$_{1-6}$-alkyl or —C(O)C$_{1-6}$-alkyl, wherein each of the C$_{1-6}$-alkyl, C$_{2-4}$-alkenyl, C$_{2-4}$-alkynyl, and C$_{1-6}$-alkyl portion of —CH$_2$OC$_{1-6}$-alkyl, —S(O)C$_{1-6}$-alkyl, —NHC$_{1-6}$-alkyl and —C(O)C$_{1-6}$-alkyl are optionally substituted with 1-4 substituents of F, oxo or OH;

each of R$^4$, R$^5$, R$^6$ and R$^8$, independently, is H, halo, haloalkyl, haloalkoxyl, CN, OH, OC$_{1-4}$-alkyl, S(O) C$_{1-4}$-alkyl, NHC$_{1-4}$-alkyl or C(O)C$_{1-4}$-alkyl;

R$^7$ is —NH—R$^9$, —NH—C(=O)—R$^9$, —C(=O)NH— R$^9$, —O—R$^9$, —S—R$^9$;

or R$^7$ is

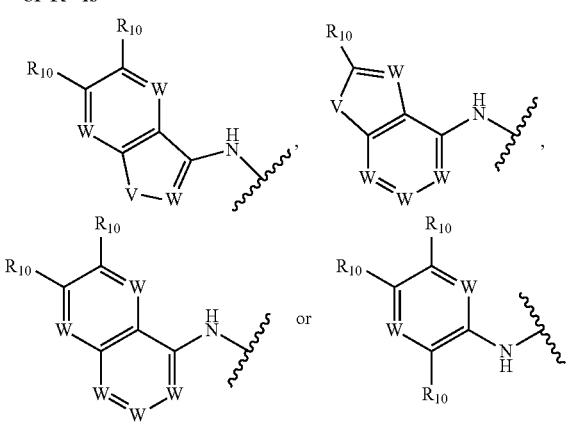

wherein V is NR$^{10}$, O or S; and
each W, independently, is CH, CF, CCl or N;

R$^9$ is acetyl, C$_{1-6}$-alkyl, C$_{2-4}$-alkenyl, C$_{2-4}$-alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, furanyl, dihydrofuranyl, thienyl, and pyrrolyl, wherein the $C_{1-6}$-alkyl, $C_{2-4}$-alkenyl, $C_{2-4}$-alkynyl and ring are optionally substituted, independently, with 1-5 substituents of $R^{10}$;

each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkoxyl, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$-alkylamino-, $C_{1-3}$-dialkylamino-, $C_{1-3}$-thioalkoxyl or oxetan-3-yl; and p is 0, 1, 2 or 3.

9. The compound of claim 7, or a stereoisomer or pharmaceutically acceptable salt thereof, as defined by Formula III-F-2

III-F-2 wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;
each $R^a$, independently, is H or F;
each $R^1$, independently, is H, F, Cl, $C_{1-6}$-alkyl, $C_{2-4}$-alkenyl, $C_{2-4}$-alkynyl, CN, —CH$_2$OC$_{1-6}$-alkyl, —OC$_{1-6}$-alkyl, —S(O)C$_{1-6}$-alkyl, —NHC$_{1-6}$-alkyl or —C(O)C$_{1-6}$-alkyl, wherein each of the $C_{1-6}$-alkyl, $C_{2-4}$-alkenyl, $C_{2-4}$-alkynyl, and $C_{1-6}$-alkyl portion of —CH$_2$OC$_{1-6}$-alkyl, —OC$_{1-6}$-alkyl, —S(O)C$_{1-6}$-alkyl, —NHC$_{1-6}$-alkyl and —C(O)C$_{1-6}$-alkyl are optionally substituted with 1-4 substituents of F, oxo or OH;

alternatively, each $R^1$ taken together with the carbon atom to which they are attached form a $C_{3-6}$spirocarbocyclic ring optionally including one heteroatom selected from O and N and optionally substituted with 1-4 F atoms on the carbon atoms and a substituent of $C_{1-3}$-alkyl, CH$_2$OC$_{1-2}$-alkyl or $C_{1-3}$-haloalkyl on the nitrogen atom;

$R^2$ is H, F, Cl, $C_{1-6}$-alkyl, $C_{2-4}$-alkenyl, $C_{2-4}$-alkynyl, CN, —CH$_2$OC$_{1-6}$-alkyl, —OC$_{1-6}$-alkyl, —S(O)C$_{1-6}$-alkyl, —NHC$_{1-6}$-alkyl or —C(O)C$_{1-6}$-alkyl, wherein each of the $C_{1-6}$-alkyl, $C_{2-4}$-alkenyl, $C_{2-4}$-alkynyl, and $C_{1-6}$-alkyl portion of —CH$_2$OC$_{1-6}$-alkyl, —OC$_{1-6}$-alkyl, —S(O)C$_{1-6}$-alkyl, —NHC$_{1-6}$-alkyl and —C(O)C$_{1-6}$-alkyl are optionally substituted with 1-4 substituents of F, oxo or OH;

each of $R^4$, $R^5$, $R^6$ and $R^8$, independently, is H, halo, haloalkyl, haloalkoxyl, $C_{1-4}$-alkyl, CN, OH, OC$_{1-4}$-alkyl, S(O)C$_{1-4}$-alkyl, NHC$_{1-4}$-alkyl or C(O)C$_{1-4}$-alkyl;

$R^7$ is —NH—$R^9$, —NH—C(=O)—$R^9$, —C(=O)NH—$R^9$, —O—$R^9$, —S—$R^9$;

or $R^7$ is wherein V is $NR^{10}$, O or S; and
each W, independently, is CH, CF, CCl or N;
$R^9$ is acetyl, $C_{1-6}$-alkyl, $C_{2-4}$-alkenyl, $C_{2-4}$-alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, furanyl, dihydrofuranyl, thienyl, and pyrrolyl, wherein the $C_{1-6}$-alkyl, $C_{2-4}$-alkenyl, $C_{2-4}$-alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-butynyloxy, $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, morpholinyl, pyrazolyl, isoxazolyl, dihydropyranyl, pyrrolyl, pyrrolidinyl, piperazinyl, oxetan-3-yl or dioxolyl, wherein each of the $C_{1-6}$-alkyl, $C_{2-6}$-alkenyl, $C_{2-6}$-alkynyl, $C_{3-6}$-cycloalkyl, $C_{1-6}$-alkylamino-, $C_{1-6}$-dialkylamino-, $C_{1-6}$-alkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, methyl, methoxy, ethyl, ethoxy, propyl, propoxy, isopropyl, isopropoxy, cyclopropyl, cyclopropylmethoxy, butyl, butoxy, isobutoxy, tert-butoxy, 2-butynyloxy, isobutyl, sec-butyl, tert-butyl, $C_{1-3}$-alkylamino-, $C_{1-3}$-dialkylamino-, $C_{1-3}$-thioalkoxyl or oxetan-3-yl.

10. The compound of claim 1, or a stereoisomer or pharmaceutically acceptable salt thereof, selected from N-(3-((3R)-5-amino-3-methyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3-methyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-methoxypyrido[3,4-b]pyrazin-5-amine;

8-((3-((3R)-5-amino-3,6,6-trimethyl-1,1-dioxido-3,6-dihydro-2H-1,4-thiazin-3-yl)-4-fluorophenyl)amino)-1,7-naphthyridine-3-carbonitrile;

N-(3-((3R)-5-amino-6,6-dimethyl-1,1-dioxido-3-(trifluoromethyl)-3,6-dihydro-2H-1,4-thiazin-3-yl)-4-fluorophenyl)-3-methoxy-1,7-naphthyridin-8-amine;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((8R)-10-amino-8-methyl-6,6-dioxido-6-thia-9-azaspiro[4.5]dec-9-en-8-yl)-4-fluorophenyl)-3-methoxy-1,7-naphthyridin-8-amine;

N-(3-((6R)-8-amino-6-methyl-4,4-dioxido-4-thia-7-azaspiro[2.5]oct-7-en-6-yl)-4-fluorophenyl)-3-methoxy-1,7-naphthyridin-8-amine;

N-(3-((3R,6R)-5-amino-6-fluoro-3,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-chloro-5-fluoro-1,7-naphthyridin-8-amine;

Racemic mixture of N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine and N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3S)-5-amino-3-(difluoromethyl)-6,6-dimethyl-1,1-dioxido-3,6-dihydro-2H-1,4-thiazin-3-yl)-4-fluorophenyl)-3-methoxy-1,7-naphthyridin-8-amine;

8-((3-((3R)-5-amino-3,6,6-trimethyl-1,1-dioxido-3,6-dihydro-2H-1,4-thiazin-3-yl)-4-fluorophenyl)amino)-5-fluoro-1,7-naphthyridine-3-carbonitrile;

N-(3-((3R,6R)-5-amino-6-fluoro-3,6-dimethyl-1,1-dioxido-3,6-dihydro-2H-1,4-thiazin-3-yl)-4-fluorophenyl)-2-methoxypyrido[3,4-b]pyrazin-5-amine;

8-((3-((3R,6R)-5-amino-6-fluoro-3,6-dimethyl-1,1-dioxido-3,6-dihydro-2H-1,4-thiazin-3-yl)-4-fluorophenyl)amino)-1,7-naphthyridine-3-carbonitrile;

N-(3-((3R)-5-amino-3,6,6-trimethyl-1,1-dioxido-3,6-dihydro-2H-1,4-thiazin-3-yl)-4-fluorophenyl)-5-fluoro-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-7-methoxypyrido[3,2-d]pyrimidin-4-amine;

N-(3-((3R)-5-amino-3,6,6-trimethyl-1,1-dioxido-3,6-dihydro-2H-1,4-thiazin-3-yl)-4-fluorophenyl)-7-chloropyrido[3,2-d]pyrimidin-4-amine;

N-(3-((3R)-5-amino-3,6,6-trimethyl-1,1-dioxido-3,6-dihydro-2H-1,4-thiazin-3-yl)-4-fluorophenyl)-5-fluoro-7-methoxy-4-quinazolinamine;

N-(5-((3R)-5-amino-3,6,6-trimethyl-1,1-dioxido-3,6-dihydro-2H-1,4-thiazin-3-yl)-6-fluoro-3-pyridinyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-methoxy-5-quinoxalinamine;

N-(3-((3R)-5-amino-2-fluoro-3,6,6-trimethyl-1,1-dioxido-3,6-dihydro-2H-1,4-thiazin-3-yl)-4-fluorophenyl)-3-methoxy-1,7-naphthyridin-8-amine;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine and N-(3-((3S)-5-amino-3-(fluoromethyl)-6,6-dimethyl-1,1-dioxido-3,6-dihydro-2H-1,4-thiazin-3-yl)-4-fluorophenyl)-3-methoxy-1,7-naphthyridin-8-amine;

N-(3-((3R)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3S)-5-amino-3,6,6-trimethyl-1,1-dioxido-3,6-dihydro-2H-1,4-thiazin-3-yl)-4,5-difluorophenyl)-3-chloro-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-(trifluoromethyl)pyrido[3,4-b]pyrazin-5-amine;

5-((3-((3R)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one; or 5-((3-((3S)-5-amino-3,6,6-trimethyl-1,1-dioxido-3,6-dihydro-2H-1,4-thiazin-3-yl)-4,5-difluorophenyl)amino)pyrido[3,4-b]pyrazin-2(1H)-one.

11. The compound of claim 1, or a stereoisomer or pharmaceutically acceptable salt thereof, selected from N-(5-((3R)-5-amino-3,6,6-trimethyl-1,1-dioxido-3,6-dihydro-2H-1,4-thiazin-3-yl)-6-fluoro-3-pyridinyl)-5-fluoro-3-methoxy-1,7-naphthyridin-8-amine;

N-(5-((3R)-5-amino-3,6,6-trimethyl-1,1-dioxido-3,6-dihydro-2H-1,4-thiazin-3-yl)-6-fluoro-3-pyridinyl)-3-chloro-5-fluoro-1,7-naphthyridin-8-amine;

8-((5-((3R)-5-amino-3,6,6-trimethyl-1,1-dioxido-3,6-dihydro-2H-1,4-thiazin-3-yl)-6-fluoro-3-pyridinyl)amino)-5-fluoro-1,7-naphthyridine-3-carbonitrile;

N-(5-((3R)-5-amino-3,6,6-trimethyl-1,1-dioxido-3,6-dihydro-2H-1,4-thiazin-3-yl)-6-fluoro-3-pyridinyl)-2-methoxypyrido[3,4-b]pyrazin-5-amine;

N-(5-((3R)-5-amino-3,6,6-trimethyl-1,1-dioxido-3,6-dihydro-2H-1,4-thiazin-3-yl)-6-fluoro-3-pyridinyl)-3-chloro-1,7-naphthyridin-8-amine;

N-(5-((3R)-5-amino-3,6,6-trimethyl-1,1-dioxido-3,6-dihydro-2H-1,4-thiazin-3-yl)-6-fluoro-3-pyridinyl)-2-(trifluoromethyl)pyrido[3,4-b]pyrazin-5-amine;

N-(3-((3R,6R)-5-amino-6-fluoro-3,6-dimethyl-1,1-dioxido-3,6-dihydro-2H-1,4-thiazin-3-yl)-4-fluorophenyl)-3-(2-butyn-1-yloxy)-1,7-naphthyridin-8-amine;

N-(3-((3R)-5-amino-2-fluoro-3,6,6-trimethyl-1,1-dioxido-3,6-dihydro-2H-1,4-thiazin-3-yl)-4-fluorophenyl)-7-chloropyrido[3,2-d]pyrimidin-4-amine;

4-((3-((3R)-5-amino-2-fluoro-3,6,6-trimethyl-1,1-dioxido-3,6-dihydro-2H-1,4-thiazin-3-yl)-4-fluorophenyl)amino)pyrido[3,2-d]pyrimidine-7-carbonitrile;

N-(5-((7R)-9-amino-7-methyl-5,5-dioxido-5-thia-8-azaspiro[3.5]non-8-en-7-yl)-6-fluoro-3-pyridinyl)-2-methoxypyrido[3,4-b]pyrazin-5-amine;

N-(3-((7R)-9-amino-7-methyl-5,5-dioxido-5-thia-8-azaspiro[3.5]non-8-en-7-yl)-4-fluorophenyl)-3-chloro-1,7-naphthyridin-8-amine;

N-(3-((7R)-9-amino-6-fluoro-7-methyl-5,5-dioxido-5-thia-8-azaspiro[3.5]non-8-en-7-yl)-4-fluorophenyl)-2-methoxypyrido[3,4-b]pyrazin-5-amine;

N-(3-((3S)-5-amino-3-(fluoromethyl)-6,6-dimethyl-1,1-dioxido-3,6-dihydro-2H-1,4-thiazin-3-yl)-4-fluorophenyl)-3-chloro-5-fluoro-1,7-naphthyridin-8-amine;

N-(3-((3S)-5-amino-3-(fluoromethyl)-6,6-dimethyl-1,1-dioxido-3,6-dihydro-2H-1,4-thiazin-3-yl)-4-fluorophenyl)-7-chloropyrido[3,2-d]pyrimidin-4-amine;

4-((3-((3S)-5-amino-3-(fluoromethyl)-6,6-dimethyl-1,1-dioxido-3,6-dihydro-2H-1,4-thiazin-3-yl)-4-fluorophenyl)amino)pyrido[3,2-d]pyrimidine-7-carbonitrile;

N-(3-((3S)-5-amino-3-(fluoromethyl)-6,6-dimethyl-1,1-dioxido-3,6-dihydro-2H-1,4-thiazin-3-yl)-4-fluorophenyl)-2-ethoxypyrido[3,4-b]pyrazin-5-amine;

N-(3-((7 S)-9-amino-7-(fluoromethyl)-5, 5-dioxido-5-thia-8-azaspiro[3 5]non-8-en-7-yl)-4-fluorophenyl)-2-ethoxypyrido[3,4-b]pyrazin-5-amine;

N-(3-((7 S)-9-amino-7-(fluoromethyl)-5, 5-dioxido-5-thia-8-azaspiro[3.5]non-8-en-7-yl)-4-fluorophenyl)-3-methoxy-1,7-naphthyridin-8-amine;

N-(3-((7 S)-9-amino-7-(fluoromethyl)-5, 5-dioxido-5-thia-8-azaspiro[3.5]non-8-en-7-yl)-4-fluorophenyl)-7-chloropyrido[3,2-d]pyrimidin-4-amine;

8-((3-((7 S)-9-amino-7-(fluoromethyl)-5,5-dioxido-5-thia-8-azaspiro[3.5]non-8-en-7-yl)-4-fluorophenyl)amino)-5-fluoro-1,7-naphthyridine-3-carbonitrile;

N-(3-((7 S)-9-amino-7-(fluoromethyl)-5, 5-dioxido-5-thia-8-azaspiro[3.5]non-8-en-7-yl)-4-fluorophenyl)-7-methoxypyrido[3,2-d]pyrimidin-4-amine;

Mixture of N-(3-((7R)-9-amino-7-(fluoromethyl)-5,5-dioxido-5-thia-8-azaspiro[3.5]non-8-en-7-yl)-4-fluorophenyl)-3-chloro-1,7-naphthyridin-8-amine and N-(3-((7S)-9-amino-7-(fluoromethyl)-5,5-dioxido-5-thia-8-azaspiro[3 5]non-8-en-7-yl)-4-fluorophenyl)-3-chloro-1,7-naphthyridin-8-amine;

N-(3-((7 S)-9-amino-7-(fluoromethyl)-5, 5-dioxido-5-thia-8-azaspiro[3.5]non-8-en-7-yl)-4-fluorophenyl)-3-chloro-1,7-naphthyridin-8-amine;

N-(3-((7 S)-9-amino-7-(fluoromethyl)-5, 5-dioxido-5-thia-8-azaspiro[3.5]non-8-en-7-yl)-4-fluorophenyl)-2-methoxypyrido[3,4-b]pyrazin-5-amine;

8-((3-((7R)-9-amino-7-methyl-5,5-dioxido-5-thia-8-azaspiro[3.5]non-8-en-7-yl)-4-fluorophenyl)amino)-1, 7-naphthyridine-3-carbonitrile;

8-((3-((7R)-9-amino-6-fluoro-7-methyl-5, 5-dioxido-5-thia-8-azaspiro [3.5]non-8-en-7-yl)-4-fluorophenyl) amino)-1, 7-naphthyridine-3-carbonitrile;

N-(3-((3R)-5-amino-3,6,6-trimethyl-1,1-dioxido-3,6-dihydro-2H-1,4-thiazin-3-yl)-4-fluorophenyl)-3-(2-butyn-1-yloxy)-1, 7-naphthyridin-8-amine;

N-(3-((3R)-5-amino-3,6,6-trimethyl-1,1-dioxido-3,6-dihydro-2H-1,4-thiazin-3-yl)-4-fluorophenyl)-3-(cyclopropylmethoxy)-1,7-naphthyridin-8-amine;

8-((3-((3S)-5-amino-3-(fluoromethyl)-6,6-dimethyl-1,1-dioxido-3,6-dihydro-2H-1,4-thiazin-3-yl)-4-fluorophenyl)amino)-1,7-naphthyridine-3-carbonitrile;

N-(3-((3R,6R)-5-amino-6-fluoro-3,6-dimethyl-1,1-dioxido-3,6-dihydro-2H-1,4-thiazin-3-yl)-4-fluorophenyl)-7-methoxypyrido[3,2-d]pyrimidin-4-amine;

N-(3-((3S)-5-amino-3-(fluoromethyl)-6,6-dimethyl-1,1-dioxido-3,6-dihydro-2H-1,4-thiazin-3-yl)-4-fluorophenyl)-5-fluoro-3-methoxy-1,7-naphthyridin-8-amine;

N-(3-((3R)-5-amino-3,6,6-trimethyl-1,1-dioxido-3,6-dihydro-2H-1,4-thiazin-3-yl)-4-fluorophenyl)-2-(2-fluoroethoxy)pyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-2-(2,2,2-trifluoroethoxy)pyrido[3,4-b]pyrazin-5-amine;

((5-((3-((3R)-5-amino-3,6,6-trimethyl-1,1-dioxido-3,6-dihydro-2H-1,4-thiazin-3-yl)-4-fluorophenyl)amino)pyrido[3,4-b]pyrazin-2-yl)oxy)acetonitrile;

N-(3-((3R)-5-amino-3,6,6-trimethyl-1,1-dioxido-3,6-dihydro-2H-1,4-thiazin-3-yl)-4-fluorophenyl)-2-(2,2-difluoroethoxy)pyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-2-(2-butyn-1-yloxy)pyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-7-(cyclopropylmethoxy)pyrido[3,2-d]pyrimidin-4-amine;

N-(3-((3S)-5-amino-3-(fluoromethyl)-6,6-dimethyl-1,1-dioxido-3,6-dihydro-2H-1,4-thiazin-3-yl)-4-fluorophenyl)-2-methoxypyrido[3,4-b]pyrazin-5-amine;

N-(3-((3R)-5-amino-3,6,6-trimethyl-1,1-dioxido-3,6-dihydro-2H-1,4-thiazin-3-yl)-4-fluorophenyl)-3-bromopyrido[2,3-d]pyridazin-8-amine;

N-(3-((5R,6R)-8-amino-5-fluoro-6-methyl-4,4-dioxido-4-thia-7-azaspiro[2.5]oct-7-en-6-yl)-4-fluorophenyl)-2-methoxypyrido[3,4-b]pyrazin-5-amine;

N-(3-((4aR,7aR)-3-amino-2,2-dimethyl-1,1-dioxido-7, 7a-dihydro-2H-furo[3,4-b][1,4]thiazin-4a(5H)-yl)-4-fluorophenyl)-2-methoxypyrido[3,4-b]pyrazin-5-amine;

N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-2-methoxypyrido[3,4-b]pyrazin-5-amine;

5-((3-((4aS,7aS)-3-amino-2,2-dimethyl-1,1-dioxido-7, 7a-dihydro-2H-furo[3,4-b][1,4]thiazin-4a(5H)-yl)-4-fluorophenyl)amino)pyrido[3,4-b]pyrazin-2(1H)-one;

N-(3-((8R)-6-amino-5,5,8-trimethyl-4,4-dioxido-4-thia-7-azaspiro[2.5]oct-6-en-8-yl)-4-fluorophenyl)-2-methoxypyrido[3,4-b]pyrazin-5-amine;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-3-chloro-1,7-naphthyridin-8-amine; or N-(3-((1R,6R)-4-amino-3,3-dimethyl-2,2-dioxido-2-thia-5-azabicyclo[4.1.0]hept-4-en-6-yl)-4-fluorophenyl)-3-chloro-1,7-naphthyridin-8-amine.

12. The compound of claim 5, or a stereoisomer or pharmaceutically acceptable salt thereof, selected from N-(3-((8R)-6-amino-5,5,8-trimethyl-4,4-dioxido-4-thia-7-azaspiro[2.5]oct-6-en-8-yl)-4-fluorophenyl)-5-chloro-3-methyl-2-pyridinecarboxamide;

N-(3-((8R)-6-amino-5,5,8-trimethyl-4,4-dioxido-4-thia-7-azaspiro[2.5]oct-6-en-8-yl)-4-fluorophenyl)-5-(difluoromethoxy)-3-methyl-2-pyridinecarboxamide;

N-(3-((1R,6R)-4-amino-3,3-dimethyl-2,2-dioxido-2-thia-5-azabicyclo[4.1.0]hept-4-en-6-yl)-4-fluorophenyl)-5-chloro-3-methyl-2-pyridinecarboxamide;

Mixture of N-(3-((4aR,7aR)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide and N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-(difluoromethoxy)-3-methyl-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-2-pyridinecarboxamide and N-(3-((4aS,7aR)-3-amino-2,2-dimethyl-1,1- dioxido-7,7a-dihydro-2H-furo[3,4-b][1,4]thiazin-4a(5H)-yl)-4-fluorophenyl)-5-chloro-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-chloro-3-methyl-2-pyridinecarboxamide;

Mixture of N-(3-((4aR,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide and N-(3-((4aS,7aR)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide;

N-(3-((4aS,7aS)-3-amino-2,2-dimethyl-1,1-dioxido-7,7a-dihydro-2H-furo[3,4-b][1,4]thiazin-4a(5H)-yl)-4-fluorophenyl)-5-methoxy-3-methyl-2-pyridinecarboxamide;

N-(5-47R)-9-amino-7-methyl-5,5-dioxido-5-thia-8-azaspiro[3.5]non-8-en-7-yl)-6-fluoro-3-pyridinyl)-3-methyl-5-(2,2,2-trifluoroethoxy)-2-pyridinecarboxamide;

N-(5-((7R)-9-amino-7-methyl-5,5-dioxido-5-thia-8-azaspiro[3.5]non-8-en-7-yl)-6-fluoro-3-pyridinyl)-5-chloro-3-methyl-2-pyridinecarboxamide;

N-(3-((7R)-9-amino-2,2-difluoro-7-methyl-5,5-dioxido-5-thia-8-azaspiro[3.5]non-8-en-7-yl)-4-fluorophenyl)-5-chloro-2-pyridinecarboxamide;

Mixture of N-(3-((7R)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide and N-(3-((7S)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide;

N-(3-((7S)-9-amino-7-(fluoromethyl)-5,5-dioxido-5-thia-8-azaspiro[3.5]non-8-en-7-yl)-4-fluorophenyl)-5-(difluoromethoxy)-3-methyl-2-pyridinecarboxamide;

N-(3-((6S,7R)-9-amino-6-fluoro-7-methyl-5,5-dioxido-5-thia-8-azaspiro[3.5]non-8-en-7-yl)-4-fluorophenyl)-5-chloro-2-pyridinecarboxamide;

N-(3-((7R)-9-amino-6-fluoro-7-methyl-5,5-dioxido-5-thia-8-azaspiro[3.5]non-8-en-7-yl)-4-fluorophenyl)-5-(difluoromethoxy)-3-methyl-2-pyridinecarboxamide;

N-(5-((6R)-8-amino-6-methyl-4,4-dioxido-4-thia-7-azaspiro[2.5]oct-7-en-6-yl)-6-fluoro-3-pyridinyl)-5-(difluoromethoxy)-3-methyl-2-pyridinecarboxamide;

N-(3-((5 S,6R)-8-amino-5-fluoro-6-methyl-4,4-dioxido-4-thia-7-azaspiro[2.5]oct-7-en-6-yl)-4-fluorophenyl)-5-(difluoromethyl)-3-methyl-2-pyridinecarboxamide; or N-(3-((6S)-8-amino-6-(fluoromethyl)-4,4-dioxido-4-thia-7-azaspiro[2.5]oct-7-en-6-yl)-4-fluorophenyl)-5-chloro-3-methyl-2-pyridinecarboxamide.

13. A compound, or a stereoisomer or pharmaceutically acceptable salt thereof, selected from N-(3-((3R)-5-amino-3,6,6-trimethyl-1,1-dioxido-3,6-dihydro-2H-1,4-thiazin-3-yl)-4-fluorophenyl)-5-(2,2-difluoroethoxy)-2-pyrazinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(difluoromethyl)-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-fluoro-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(difluoromethoxy)-3-methyl-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-cyano-3-methyl-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-(difluoromethyl)-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-3-chloro-5-cyano-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-(methoxymethyl)-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-chloro-3-fluoro-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(difluoromethoxy)-3-methyl-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-chloro-3-methyl-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-(difluoromethyl)-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-chloro-3-(methoxymethyl)-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-3-chloro-5-methoxy-2-pyridinecarboxamide;

N-(3-((3R)-5-amino-2-fluoro-3,6,6-trimethyl-1,1-dioxido-3,6-dihydro-2H-1,4-thiazin-3-yl)-4-fluorophenyl)-5-methoxy-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-(1-methylethenyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-ethenyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-ethyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-ethyl-2-pyridinecarboxamide;

N-(3-((3S)-5-amino-3-(fluoromethyl)-6,6-dimethyl-1,1-dioxido-3,6-dihydro-2H-1,4-thiazin-3yl)-4-fluorophenyl)-5-chloro-3-(1-methylethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethoxy)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(5-((3R)-5-amino-3,6,6-trimethyl-1,1-dioxido-3,6-dihydro-2H-1,4-thiazin-3-yl)-6-fluoro-3-pyridinyl)-3-chloro-5-(difluoromethyl)-2-pyridinecarboxamide;

N-(3-((3R)-5-amino-3,6,6-trimethyl-1,1-dioxido-3,6-dihydro-2H-1,4-thiazin-3-yl)-4-fluorophenyl)-3-bromo-5-chloro-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-cyano-3-methyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethoxy)-3-methyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-(difluoromethoxy)-3-methyl-2-pyridinecarboxamide;

N-(3-((3R,6R)-5-amino-6-fluoro-3,6-dimethyl-1,1-dioxido-3,6-dihydro-2H-1,4-thiazin-3-yl)-4-fluorophenyl)-5-chloro-3-methyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-((4-fluoro-2-butyn-1-yl)oxy)-2-pyridinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-chloro-2-pyridinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-fluoro-2-pyridinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-(difluoromethoxy)-3-methyl-2-pyridinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-methoxy-2-pyridinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-(2,2,2-trifluoroethoxy)-2-pyrazinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-cyano-2-pyridinecarboxamide;

N-(5-((3R)-5-amino-3,6,6-trimethyl-1,1-dioxido-3,6-dihydro-2H-1,4-thiazin-3-yl)-6-fluoro-3-pyridinyl)-5-(difluoromethyl)-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-(2,2,2-trifluoroethoxy)-2-pyrazinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-cyano-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-(1-methylethenyl)-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-methyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-fluoro-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-6-chloro-3-methylimidazo[1,2-a]pyridine-2-carboxamide;

N-(5-((3R)-5-amino-3,6,6-trimethyl-1,1-dioxido-3,6-dihydro-2H-1,4-thiazin-3-yl)-1-methyl-6-oxo-1,6-dihydro-3-pyridinyl)-5-(difluoromethoxy)-3-methyl-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-3-(methoxymethyl)-2-pyridinecarboxamide;

N-(3-((3S)-5-amino-3-(fluoromethyl)-6,6-dimethyl-1,1-dioxido-3,6-dihydro-2H-1,4-thiazin-3-yl)-4-fluorophenyl)-5-chloro-2-pyridinecarboxamide;

N-(3-((3R)-5-amino-3-methyl-1,1-dioxido-3,6-dihydro-2H-1,4-thiazin-3-yl)-4-fluorophenyl)-5-methoxy-2-pyrazinecarboxamide;

N-(3-((3R)-5-amino-3-methyl-1,1-dioxido-3,6-dihydro-2H-1,4-thiazin-3-yl)-4-fluorophenyl)-5-chloro-2-pyridinecarboxamide;

N-(3-((3R)-5-amino-3-methyl-3,6-dihydro-2H-1,4-thiazin-3-yl)-4-fluorophenyl)-5-methoxy-2-pyrazinecarboxamide;

Racemic mixture of N-(3-((3R,6R)-5-amino-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-6,6-dimethyl-1,1-dioxido-3-(trifluoromethyl)-3,6-dihydro-2H-1,4-thiazin-3-yl)-4-fluorophenyl)-5-methoxy-2-pyrazinecarboxamide;

Racemic mixture of N-(3-((3R)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

N-(3-((3S)-5-amino-3-(difluoromethyl)-6,6-dimethyl-1,1-dioxido-3,6-dihydro-2H-1,4-thiazin-3-yl)-4-fluorophenyl)-5-methoxy-2-pyrazinecarboxamide;

Racemic mixture of N-(3-((3R,6R)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide and N-(3-((3R,6S)-5-amino-6-fluoro-3,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-(difluoromethyl)-2-pyridinecarboxamide;

Racemic mixture of N-(3-((3R)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide and N-(3-((3S)-5-amino-3-(fluoromethyl)-6,6-dimethyl-1,1-dioxido-3,6-dihydro-2H-1,4-thiazin-3-yl)-4-fluorophenyl)-5-methoxy-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-5-chloro-3-methyl-2-pyridinecarboxamide;

N-(3-((3R)-5-amino-3,6,6-trimethyl-1,1-dioxido-3,6-dihydro-2H-1,4-thiazin-3-yl)-4-fluorophenyl)-5-(2-butyn-1-yloxy)-2-pyrazinecarboxamide;

N-(3-((3R)-5-amino-3,6,6-trimethyl-1,1-dioxido-3,6-dihydro-2H-1,4-thiazin-3-yl)-4-fluorophenyl)-2-methyl-1,3-thiazole-4-carboxamide;

Racemic mixture of N-(4-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide and N-(4-((3S)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide;

N-(6-((3R)-5-amino-3,6,6-trimethyl-1,1-dioxido-3,6-dihydro-2H-1,4-thiazin-3-yl)-5-fluoro-2-pyridinyl)-5-methoxy-2-pyrazinecarboxamide;

(5R)-5-(2-fluoro-5-(1-naphthalenylsulfanyl)phenyl)-2,2,5-trimethyl-5,6-dihydro-2H-1,4-thiazin-3-amine 1,1-dioxide;

Racemic mixture of N-(3-((3R)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine and N-(3-((3S)-5-amino-3,6,6-trimethyl-1,1-dioxido-3,6-dihydro-2H-1,4-thiazin-3-yl)-4-fluorophenyl)-6-chloroisoxazolo[4,5-b]pyridin-3-amine;

3-((3-((3R)-5-amino-3,6,6-trimethyl-1,1-dioxido-3,6-dihydro-2H-1,4-thiazin-3-yl)-4-fluorophenyl)amino)thieno[3,2-b]pyridine-6-carbonitrile;

(5R)-5-(2-fluoro-5-(3-fluoro-2-pyridinyl)oxy)phenyl)-2,2,5-trimethyl-5,6-dihydro-2H-1,4-thiazin-3-amine 1,1-dioxide;

2-(3-((3R)-5-amino-3,6,6-trimethyl-1,1-dioxido-3,6-dihydro-2H-1,4-thiazin-3-yl)-4-fluorophenoxy)-4-pyridinecarbonitrile; or (5R)-5-(5-(4-bromo-2-pyridinyl)oxy)-2-fluorophenyl)-2,2,5-trimethyl-5,6-dihydro-2H-1,4-thiazin-3-amine 1,1-dioxide.

14. A pharmaceutical composition comprising the compound of claim 1 and a pharmaceutically acceptable excipient.

15. A method of reducing beta amyloid peptide levels in the cerebral spinal fluid of a subject, the method comprising administering to the subject an effective dosage amount of the compound of claim 1.

16. A method of treating Alzheimer's disease, cognitive impairment or a combination thereof in a subject, the method comprising administering to the subject an effective dosage amount of the compound of claim 1.

17. A method of treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of the compound of claim 1.

18. A method of reducing the formation of plaque on the brain of a subject, the method comprising administering to the subject an effective dosage amount of the compound of claim 1.

19. A pharmaceutical composition comprising the compound of claim 4 and a pharmaceutically acceptable excipient.

20. A method of reducing beta amyloid peptide levels in the cerebral spinal fluid of a subject, the method comprising administering to the subject an effective dosage amount of the compound of claim 4.

21. A method of treating Alzheimer's disease, cognitive impairment or a combination thereof in a subject, the method comprising administering to the subject an effective dosage amount of the compound of claim 4.

22. A method of treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of the compound of claim 4.

23. A method of reducing the formation of plaque on the brain of a subject, the method comprising administering to the subject an effective dosage amount of the compound of claim 4.

24. A pharmaceutical composition comprising the compound of claim 5 and a pharmaceutically acceptable excipient.

25. A method of reducing beta amyloid peptide levels in the cerebral spinal fluid of a subject, the method comprising administering to the subject an effective dosage amount of the compound of claim 5.

26. A method of treating Alzheimer's disease, cognitive impairment or a combination thereof in a subject, the method comprising administering to the subject an effective dosage amount of the compound of claim 5.

27. A method of treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of the compound of claim 5.

28. A method of reducing the formation of plaque on the brain of a subject, the method comprising administering to the subject an effective dosage amount of the compound of claim 5.

29. A pharmaceutical composition comprising the compound of claim 7 and a pharmaceutically acceptable excipient.

30. A method of reducing beta amyloid peptide levels in the cerebral spinal fluid of a subject, the method comprising administering to the subject an effective dosage amount of the compound of claim 7.

31. A method of treating Alzheimer's disease, cognitive impairment or a combination thereof in a subject, the method comprising administering to the subject an effective dosage amount of the compound of claim 7.

32. A method of treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of the compound of claim 7.

33. A method of reducing the formation of plaque on the brain of a subject, the method comprising administering to the subject an effective dosage amount of the compound of claim 7.

34. A pharmaceutical composition comprising the compound of claim 13 and a pharmaceutically acceptable excipient.

35. A method of reducing beta amyloid peptide levels in the cerebral spinal fluid of a subject, the method comprising administering to the subject an effective dosage amount of the compound of claim 13.

36. A method of treating Alzheimer's disease, cognitive impairment or a combination thereof in a subject, the method comprising administering to the subject an effective dosage amount of the compound of claim 13.

37. A method of treating a neurological disorder selected from the group consisting of mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of the compound of claim 13.

38. A method of reducing the formation of plaque on the brain of a subject, the method comprising administering to the subject an effective dosage amount of the compound of claim 13.

* * * * *